US012703754B2

(12) United States Patent
Porter-Brown et al.

(10) Patent No.: US 12,703,754 B2
(45) Date of Patent: Aug. 11, 2026

(54) TREATMENT OF ATOPIC DERMATITIS

(71) Applicant: Kymab Limited, Cambridge (GB)

(72) Inventors: Ben Porter-Brown, Paris (FR); Sonia Quaratino, Paris (FR); Richard C A Sainson, Paris (FR); John Powell, Ely (GB)

(73) Assignee: KYMAB LIMITED, Cambridge (GB)

( * ) Notice: Subject to any disclaimer, the term of this patent is extended or adjusted under 35 U.S.C. 154(b) by 0 days.

(21) Appl. No.: 17/818,397

(22) Filed: Aug. 9, 2022

(65) Prior Publication Data

US 2023/0235069 A1 Jul. 27, 2023

(30) Foreign Application Priority Data

Aug. 10, 2021 (GB) .................................... 2111492
Oct. 21, 2021 (GB) .................................... 2115152
Mar. 24, 2022 (GB) .................................... 2204211
Mar. 25, 2022 (GB) .................................... 2204291

(51) Int. Cl.
*C07K 16/28* (2006.01)
*A61K 39/00* (2006.01)
*A61K 39/395* (2006.01)
*A61K 45/06* (2006.01)
*A61P 17/00* (2006.01)
*A61P 37/02* (2006.01)

(52) U.S. Cl.
CPC ...... *C07K 16/2875* (2013.01); *A61K 39/3955* (2013.01); *A61K 45/06* (2013.01); *A61P 17/00* (2018.01); *A61K 2039/505* (2013.01); *A61K 2039/54* (2013.01); *A61K 2039/545* (2013.01)

(58) Field of Classification Search
None
See application file for complete search history.

(56) References Cited

U.S. PATENT DOCUMENTS 4,663,281 A 5/1987 Gillies et al.
4,741,900 A 5/1988 Alvarez et al.
4,816,397 A 3/1989 Boss et al.
4,816,567 A 3/1989 Cabilly et al.
4,997,423 A 3/1991 Okuda et al.
5,219,996 A 6/1993 Bodmer et al.
5,223,409 A 6/1993 Ladner et al.
5,314,995 A 5/1994 Fell, Jr. et al.
5,403,484 A 4/1995 Ladner et al.
5,427,908 A 6/1995 Dower et al.
5,516,637 A 5/1996 Huang et al.
5,545,806 A 8/1996 Lonberg et al.
5,545,807 A 8/1996 Surani et al.
5,569,825 A 10/1996 Lonberg et al.
5,571,698 A 11/1996 Ladner et al.
5,580,717 A 12/1996 Dower et al.
5,585,089 A 12/1996 Queen et al.
5,625,126 A 4/1997 Lonberg et al.
5,633,425 A 5/1997 Lonberg et al.
5,645,835 A 7/1997 Fell, Jr. et al.
5,658,727 A 8/1997 Barbas et al.
5,661,016 A 8/1997 Lonberg et al.
5,677,425 A 10/1997 Bodmer et al.
5,698,426 A 12/1997 Huse
5,712,380 A 1/1998 Kendall et al.
5,733,743 A 3/1998 Johnson et al.
5,750,753 A 5/1998 Kimae et al.
5,766,886 A 6/1998 Studnicka et al.
5,770,429 A 6/1998 Lonberg et al.
5,780,225 A 7/1998 Wigler et al.
5,821,047 A 10/1998 Garrard et al.
5,869,046 A 2/1999 Presta et al.
5,869,619 A 2/1999 Studnicka
5,908,686 A 6/1999 Sudo et al.
5,969,108 A 10/1999 McCafferty et al.
6,011,003 A 1/2000 Charnock-Jones et al.
6,028,176 A 2/2000 Greve et al.
6,100,071 A 8/2000 Davis-Smyth et al.
6,121,022 A 9/2000 Presta et al.
6,286,699 B1 9/2001 Sudo et al.
6,331,415 B1 12/2001 Cabilly et al.
6,407,088 B1 6/2002 Dong et al.
(Continued)

FOREIGN PATENT DOCUMENTS

AU 2020205839 6/2021
CN 101023102 8/2007
(Continued)

OTHER PUBLICATIONS

US 9,382,325 B1, 07/2016, Bland-Ward et al. (withdrawn)
Pan et al. A systematic review of ustekinumab in the treatment of atopic dermatitis. Journal of Dermatological Treatment. 29(6): 539-541; Published: Sep. 1, 2018 (Year: 2018).*
Fernandez-Anton Martinez et al.Ustekinumab in the Treatment of Severe Atopic Dermatitis: A Preliminary Report of Our Experience With 4 Patients. Actas Dermo-Sifiliograficas. 105(3): 312-323; Published: Apr. 2014 (Year: 2014).*
Elsner et al. The OX40 Axis is Associated with Both Systemic and Local Involvement in Atopic Dermatitis. Acta Derm Venereol. 100(6):adv00099; Published: Mar. 31, 2020 (Year: 2020).*
(Continued)

*Primary Examiner* — Juliet C Switzer
*Assistant Examiner* — Katherine Ann Holtzman
(74) *Attorney, Agent, or Firm* — LATHROP GPM LLP; James H. Velema, Esq.; Judith L. Stone-Hulslander

(57) ABSTRACT

The present invention relates to methods of treating Atopic Dermatitis in a human subject comprising administering a therapeutically effective amount of an anti-OX40L antibody, or antigen-binding fragment thereof, wherein the antibody or fragment thereof is administered via injection. Also provided are anti-OX40L antibodies, or antigen-binding fragments thereof, glass vials, drug delivery devices, pre-filled syringes, microinfusors, pen delivery devices, autoinjectors and kits comprising an anti-OX40L antibody, or antigen-binding fragment thereof for use in such methods.

52 Claims, 44 Drawing Sheets

Specification includes a Sequence Listing.

(56) References Cited

U.S. PATENT DOCUMENTS 6,528,055 B2 3/2003 Godfrey et al.
6,528,623 B2 3/2003 Godfrey et al.
6,548,507 B1 4/2003 Bountra et al.
6,599,906 B1 7/2003 Ku et al.
6,629,949 B1 10/2003 Douglas
6,645,635 B2 11/2003 Muraki
6,659,982 B2 12/2003 Douglas et al.
6,803,039 B2 10/2004 Tsuji et al.
6,875,432 B2 4/2005 Liu et al.
6,897,294 B2 5/2005 Davis-Smyth et al.
7,029,895 B2 4/2006 Glucksmann et al.
7,030,225 B1 4/2006 Tamatani et al.
7,045,615 B2 5/2006 Tamatani et al.
7,056,509 B2 6/2006 Thorpe et al.
7,098,184 B2 8/2006 Godfrey et al.
7,125,551 B2 10/2006 Kroczek
7,129,338 B1 10/2006 Ota et al.
7,132,099 B2 11/2006 Kroczek
7,166,283 B2 1/2007 Tsuji et al.
7,196,175 B2 3/2007 Tamatani et al.
7,226,554 B2 6/2007 Sudo et al.
7,226,909 B2 6/2007 Tamatani et al.
7,259,247 B1 8/2007 Kroczek
7,261,893 B2 8/2007 Veldman et al.
7,279,560 B2 10/2007 Tamatani et al.
7,291,331 B1 11/2007 Croft et al.
7,300,754 B2 11/2007 Abi Fadel et al.
7,304,033 B2 12/2007 Larsen
7,306,800 B2 12/2007 Kroczek
7,368,531 B2 5/2008 Rosen et al.
7,411,051 B2 8/2008 Rosen et al.
7,438,905 B2 10/2008 Suzuki et al.
7,456,187 B2 11/2008 Ford et al.
7,456,264 B2 11/2008 Keler et al.
7,465,445 B2 12/2008 Tezuka et al.
7,482,147 B2 1/2009 Glucksmann et al.
7,501,496 B1 3/2009 Endl et al.
7,521,541 B2 4/2009 Eigenbrot et al.
7,572,618 B2 8/2009 Mintier et al.
7,582,288 B2 9/2009 Gillies et al.
7,704,500 B2 4/2010 Papadopoulos et al.
7,722,872 B2 5/2010 Kroczek
7,776,577 B2 8/2010 Kapeller-Libermann et al.
7,794,710 B2 9/2010 Chen et al.
7,812,133 B2 10/2010 Martin
7,868,141 B2 1/2011 Endl et al.
7,892,540 B2 2/2011 Chen
7,932,358 B2 4/2011 Tamatani et al.
7,943,743 B2 5/2011 Korman et al.
7,968,689 B2 6/2011 Rosen et al.
7,972,813 B2 7/2011 McCormack et al.
7,988,965 B2 8/2011 Tsuji et al.
7,998,478 B2 8/2011 Tezuka et al.
8,008,449 B2 8/2011 Korman et al.
8,030,457 B2 10/2011 Jackson et al.
8,062,640 B2 11/2011 Sleeman et al.
8,080,243 B2 12/2011 Liang et al.
8,101,175 B1 1/2012 Croft et al.
8,168,179 B2 5/2012 Honjo
8,168,762 B2 5/2012 Jackson et al.
8,188,233 B2 5/2012 Condra et al.
8,188,234 B2 5/2012 Condra et al.
8,318,905 B2 11/2012 Kroczek
8,344,114 B2 1/2013 Sparrow et al.
8,357,371 B2 1/2013 Sleeman et al.
8,389,690 B2 3/2013 Tamatani et al.
8,399,646 B2 3/2013 Liang et al.
8,420,098 B2 4/2013 Camphausen et al.
8,426,363 B2 4/2013 Liang et al.
8,486,647 B2 7/2013 Haber et al.
8,501,184 B2 8/2013 Sleeman et al.
8,530,414 B2 9/2013 Davies et al.
8,551,477 B1 10/2013 Croft et al.
8,563,698 B2 10/2013 Jackson et al.
8,598,320 B2 12/2013 Hedrick
8,840,889 B2 9/2014 Chen
8,916,155 B2 12/2014 Kroczek
8,956,615 B1 2/2015 Croft et al.
8,962,807 B2 2/2015 Verdonck et al.
9,102,725 B2 8/2015 Korman
9,139,653 B1 * 9/2015 Campbell .......... A61K 39/3955
9,234,043 B1 1/2016 Campbell
9,376,493 B2 6/2016 Faget et al.
9,428,570 B2 8/2016 Lawson
9,512,229 B2 12/2016 Bland-Ward
9,567,399 B1 2/2017 Campbell
9,587,030 B2 * 3/2017 Campbell ............... A61P 37/06
9,617,338 B1 4/2017 Campbell
9,868,789 B2 1/2018 Bland-Ward
9,868,790 B2 1/2018 Bland-Ward
10,118,963 B2 11/2018 Zhou
10,214,586 B2 2/2019 Ludwig et al.
10,604,576 B2 3/2020 Campbell
10,654,935 B2 5/2020 Campbell et al.
10,669,342 B2 6/2020 Campbell et al.
11,396,550 B2 * 7/2022 Campbell ............ C07K 16/241
11,753,479 B2 9/2023 Campbell et al.
11,773,175 B2 * 10/2023 Campbell .............. A61K 39/00
424/130.1
11,779,604 B2 * 10/2023 Bland-Ward ......... C12N 5/0638
424/93.2
2002/0045571 A1 4/2002 Liu et al.
2002/0064555 A1 5/2002 Cullen et al.
2002/0081679 A1 6/2002 Chiang et al.
2002/0082259 A1 6/2002 Ono et al.
2002/0114814 A1 8/2002 Gray
2002/0150576 A1 10/2002 LaRosa et al.
2002/0156242 A1 10/2002 Tamatani et al.
2003/0119038 A1 6/2003 Bingham et al.
2003/0124149 A1 7/2003 Shalaby et al.
2003/0158402 A1 8/2003 Hall
2004/0009553 A1 1/2004 Glucksmann et al.
2004/0023243 A1 2/2004 Henry et al.
2004/0038242 A1 2/2004 Edmonds et al.
2004/0110226 A1 6/2004 Lazar
2004/0191265 A1 9/2004 Schenerman et al.
2004/0248177 A1 12/2004 Abi Fadel et al.
2004/0265309 A1 12/2004 Kandel et al.
2005/0085433 A1 4/2005 Breidenstein et al.
2005/0101529 A1 5/2005 Yue et al.
2005/0118625 A1 6/2005 Mounts
2005/0147612 A1 7/2005 Yayon et al.
2005/0175610 A1 8/2005 Wiegand et al.
2005/0197285 A1 9/2005 Rosen et al.
2005/0260203 A1 11/2005 Wiegand et al.
2005/0271656 A1 12/2005 Huang
2005/0281822 A1 12/2005 Cedarbaum et al.
2005/0281831 A1 12/2005 Davis-Smyth et al.
2006/0002929 A1 1/2006 Khare et al.
2006/0116508 A1 6/2006 Glucksmann et al.
2006/0147945 A1 7/2006 Edmonds et al.
2006/0210566 A1 9/2006 Holash et al.
2006/0223088 A1 10/2006 Rosen et al.
2006/0223090 A1 10/2006 Rosen et al.
2006/0246071 A1 11/2006 Green et al.
2006/0246483 A1 11/2006 Rosen et al.
2007/0015696 A1 1/2007 Rosen et al.
2007/0037206 A1 2/2007 Rosen et al.
2007/0037748 A1 2/2007 Stahl et al.
2007/0041963 A1 2/2007 Rosen
2007/0041972 A1 2/2007 Rother et al.
2007/0055056 A1 3/2007 Rosen et al.
2007/0082345 A1 4/2007 Ota et al.
2007/0122378 A1 5/2007 Freeman et al.
2007/0224663 A1 9/2007 Rosen et al.
2007/0292440 A1 12/2007 Kenyon
2008/0008697 A1 1/2008 Mintier et al.
2008/0069795 A1 3/2008 Rabb
2008/0103090 A1 5/2008 Rosen et al.
2008/0113930 A1 5/2008 Tan et al.
2008/0279862 A1 11/2008 Khare
2009/0053230 A1 2/2009 Martin
2009/0055944 A1 2/2009 Korman et al.
2009/0142352 A1 6/2009 Jackson et al.

(56) References Cited

U.S. PATENT DOCUMENTS

| | | | |
|---|---|---|---|
| 2009/0232795 | A1 | 9/2009 | Condra et al. |
| 2009/0246192 | A1 | 10/2009 | Condra et al. |
| 2009/0252749 | A1 | 10/2009 | Leister |
| 2009/0269350 | A1 | 10/2009 | Glucksmann et al. |
| 2009/0326202 | A1 | 12/2009 | Jackson et al. |
| 2010/0040610 | A1 | 2/2010 | Sitlani et al. |
| 2010/0040611 | A1 | 2/2010 | Sparrow et al. |
| 2010/0041102 | A1 | 2/2010 | Sitlani et al. |
| 2010/0068194 | A1 | 3/2010 | Kim |
| 2010/0068199 | A1 | 3/2010 | Liang et al. |
| 2010/0098712 | A1 | 4/2010 | Adler et al. |
| 2010/0136028 | A1 | 6/2010 | Sparrow et al. |
| 2010/0150937 | A1 | 6/2010 | Sparrow et al. |
| 2010/0166740 | A1 | 7/2010 | Endl et al. |
| 2010/0166768 | A1 | 7/2010 | Sleeman et al. |
| 2010/0183591 | A1 | 7/2010 | Baron |
| 2010/0183612 | A1 | 7/2010 | Peach |
| 2010/0203056 | A1 | 8/2010 | Irving et al. |
| 2010/0233177 | A1 | 9/2010 | Yowe et al. |
| 2010/0291099 | A1 | 11/2010 | Glucksmann et al. |
| 2010/0323359 | A1 | 12/2010 | MacDonald et al. |
| 2011/0027287 | A1 | 2/2011 | Jackson et al. |
| 2011/0033451 | A1 | 2/2011 | Carreno |
| 2011/0033465 | A1 | 2/2011 | Hedrick |
| 2011/0065902 | A1 | 3/2011 | Sleeman et al. |
| 2011/0070239 | A1 | 3/2011 | Endl et al. |
| 2011/0091481 | A1 | 4/2011 | Burnette |
| 2011/0105726 | A1 | 5/2011 | Rosen |
| 2011/0117011 | A1 | 5/2011 | Jackson et al. |
| 2011/0135662 | A1 | 6/2011 | Finney et al. |
| 2011/0142849 | A1 | 6/2011 | Rue |
| 2011/0229489 | A1 | 9/2011 | Pons et al. |
| 2011/0230392 | A1 | 9/2011 | Chiang et al. |
| 2011/0256148 | A1 | 10/2011 | Sleeman et al. |
| 2011/0274702 | A1 | 11/2011 | Lanzavecchia et al. |
| 2011/0307966 | A1 | 12/2011 | MacDonald et al. |
| 2012/0014951 | A1 | 1/2012 | Liang et al. |
| 2012/0015435 | A1 | 1/2012 | Liang et al. |
| 2012/0020975 | A1 | 1/2012 | Jackson et al. |
| 2012/0020976 | A1 | 1/2012 | Jackson et al. |
| 2012/0027751 | A1 | 2/2012 | Rennert |
| 2012/0027765 | A1 | 2/2012 | Jackson et al. |
| 2012/0058906 | A1 | 3/2012 | Smider |
| 2012/0064621 | A1 | 3/2012 | Papadopoulos et al. |
| 2012/0076799 | A1 | 3/2012 | Sparrow et al. |
| 2012/0077964 | A1 | 3/2012 | Sparrow et al. |
| 2012/0082679 | A1 | 4/2012 | Sparrow et al. |
| 2012/0082680 | A1 | 4/2012 | Sitlani et al. |
| 2012/0185956 | A1 | 7/2012 | Gingras et al. |
| 2012/0195910 | A1 | 8/2012 | Wu et al. |
| 2012/0208208 | A1 | 8/2012 | Ni et al. |
| 2012/0208209 | A1 | 8/2012 | Ichetovkin et al. |
| 2012/0213794 | A1 | 8/2012 | Luo et al. |
| 2012/0213797 | A1 | 8/2012 | Jackson et al. |
| 2012/0219558 | A1 | 8/2012 | Ni et al. |
| 2012/0231005 | A1 | 9/2012 | Luo et al. |
| 2012/0244553 | A1 | 9/2012 | Andoh et al. |
| 2012/0251544 | A1 | 10/2012 | Jackson et al. |
| 2012/0269723 | A1 | 10/2012 | Brinkmann et al. |
| 2012/0301461 | A1 | 11/2012 | Condra et al. |
| 2012/0321879 | A1 | 12/2012 | Teutsch et al. |
| 2012/0328616 | A1 | 12/2012 | Li et al. |
| 2013/0018175 | A1 | 1/2013 | Verdonck |
| 2013/0052201 | A1 | 2/2013 | Jackson et al. |
| 2013/0058944 | A1 | 3/2013 | Jackson et al. |
| 2013/0064825 | A1 | 3/2013 | Chan et al. |
| 2013/0064834 | A1 | 3/2013 | Sleeman et al. |
| 2013/0071379 | A1 | 3/2013 | Condra et al. |
| 2013/0071405 | A1 | 3/2013 | Davies et al. |
| 2013/0072665 | A1 | 3/2013 | Jackson et al. |
| 2013/0079501 | A1 | 3/2013 | Jackson et al. |
| 2013/0079502 | A1 | 3/2013 | Jackson et al. |
| 2013/0085265 | A1 | 4/2013 | Jackson et al. |
| 2013/0085266 | A1 | 4/2013 | Sleeman et al. |
| 2013/0095108 | A1 | 4/2013 | Nadler et al. |
| 2013/0095109 | A1 | 4/2013 | Nadler |
| 2013/0115171 | A1 | 5/2013 | McDonough et al. |
| 2013/0115223 | A1 | 5/2013 | Sparrow et al. |
| 2013/0142783 | A1 | 6/2013 | Coyle |
| 2013/0183315 | A1 | 7/2013 | Attinger |
| 2013/0189278 | A1 | 7/2013 | Sitlani |
| 2013/0245235 | A1 | 9/2013 | Jackson et al. |
| 2013/0273069 | A1 | 10/2013 | Liang et al. |
| 2013/0310324 | A1 | 11/2013 | Flinspach et al. |
| 2014/0037648 | A1 | 2/2014 | Corti et al. |
| 2014/0044703 | A1 | 2/2014 | Kato et al. |
| 2014/0086932 | A1 | 3/2014 | Traber et al. |
| 2014/0093497 | A1 | 4/2014 | Reimann |
| 2014/0161794 | A1 | 6/2014 | Lugovskoy et al. |
| 2014/0165219 | A1 | 6/2014 | Leppert et al. |
| 2014/0170157 | A1 | 6/2014 | Agarwal et al. |
| 2014/0286897 | A1 | 9/2014 | Podack |
| 2014/0322132 | A1 | 10/2014 | Vitalis et al. |
| 2015/0203580 | A1 | 7/2015 | Papadopoulos et al. |
| 2015/0239978 | A1 | 8/2015 | Marodon et al. |
| 2015/0307620 | A1 | 10/2015 | Vella et al. |
| 2016/0000909 | A1 | 1/2016 | Eisenbach-Schwartz et al. |
| 2016/0002336 | A1 | 1/2016 | Chen |
| 2016/0024211 | A1 | 1/2016 | Chen |
| 2016/0145344 | A1 | 5/2016 | Akbari |
| 2016/0215059 | A1 | 7/2016 | Liu et al. |
| 2016/0264666 | A1 | 9/2016 | Faget et al. |
| 2016/0264675 | A1 | 9/2016 | Bland-Ward et al. |
| 2016/0304610 | A1 | 10/2016 | Sazinsky et al. |
| 2016/0361364 | A1 | 12/2016 | Corbascio |
| 2016/0368997 | A1 | 12/2016 | Campbell et al. |
| 2017/0002083 | A1 | 1/2017 | Campbell et al. |
| 2017/0037137 | A1 | 2/2017 | Bland-Ward |
| 2017/0044250 | A1 | 2/2017 | Campbell et al. |
| 2017/0260279 | A1 | 9/2017 | Bland-Ward et al. |
| 2017/0327586 | A1 | 11/2017 | Bland-Ward et al. |
| 2017/0327587 | A1 | 11/2017 | Campbell et al. |
| 2018/0305464 | A1 | 10/2018 | Li et al. |
| 2019/0077867 | A1 | 3/2019 | Zhu et al. |
| 2019/0275084 | A1 | 9/2019 | Bland-Ward et al. |
| 2019/0276547 | A1 | 9/2019 | Campbell |
| 2020/0109453 | A1 | 4/2020 | Shanmugam et al. |
| 2020/0231692 | A1 | 7/2020 | Hu et al. |
| 2021/0087287 | A1 | 3/2021 | Campbell et al. |
| 2021/0188986 | A1 | 6/2021 | Rommelaere et al. |
| 2021/0214453 | A1* | 7/2021 | Back ...................... A61P 37/02 |
| 2021/0395378 | A1 | 12/2021 | Campbell et al. |
| 2022/0372153 | A1 | 11/2022 | Bland-Ward et al. |
| 2024/0122985 | A1 | 4/2024 | Bland-Ward et al. |
| 2024/0132605 | A1 | 4/2024 | Campbell et al. |
| 2024/0392021 | A1 | 11/2024 | Zhu et al. |
| 2025/0059289 | A1 | 2/2025 | Bernigaud et al. |
| 2025/0263492 | A1 | 8/2025 | Campbell et al. |

FOREIGN PATENT DOCUMENTS

| | | |
|---|---|---|
| CN | 101248089 | 8/2008 |
| CN | 101374865 | 2/2009 |
| CN | 103221427 | 7/2013 |
| EP | 0438474 | 5/1996 |
| EP | 0463151 | 6/1996 |
| EP | 0546073 | 9/1997 |
| EP | 0984023 | 3/2000 |
| EP | 0996622 | 5/2000 |
| EP | 1067182 | 1/2001 |
| EP | 1125585 | 8/2001 |
| EP | 1158004 | 11/2001 |
| EP | 1374901 | 1/2004 |
| EP | 1502920 | 2/2005 |
| EP | 1514933 | 3/2005 |
| EP | 1286668 | 4/2005 |
| EP | 1618212 | 11/2007 |
| EP | 2481758 | 1/2012 |
| EP | 1740617 | 10/2013 |
| EP | 2650016 | 10/2013 |
| EP | 2691419 | 11/2016 |
| EP | 3369745 | 9/2018 |
| EP | 2812022 | 6/2019 |
| EP | 3495391 | 6/2019 |

(56) References Cited

FOREIGN PATENT DOCUMENTS

EP 4137157 A1 2/2023
JP 2005/130764 5/2005
JP 2009-518005 5/2007
JP 2008-512995 5/2008
JP 2016-555520 6/2017
RU 2540490 2/2015
WO WO 1985/004880 11/1985
WO WO 1990/002809 3/1990
WO WO 1991/004329 4/1991
WO WO 1991/009967 7/1991
WO WO 1991/010737 7/1991
WO WO 1991/013166 9/1991
WO WO 1992/001047 1/1992
WO WO 1992/002551 2/1992
WO WO 1992/008495 5/1992
WO WO 1992/008801 5/1992
WO WO 1992/018619 10/1992
WO WO 1992/022583 12/1992
WO WO 1993/011236 6/1993
WO WO 1993/012227 6/1993
WO WO 1993/020849 10/1993
WO WO 1995/015982 6/1995
WO WO 1995/020401 8/1995
WO WO 1995/021915 8/1995
WO WO 1996/008570 3/1996
WO WO 1997/044453 11/1997
WO WO 1997/049805 12/1997
WO WO 1998/003821 1/1998
WO WO 1998/013071 4/1998
WO WO 1998/020734 5/1998
WO WO 1998/024893 6/1998
WO WO 1998/025971 6/1998
WO WO 1999/003859 1/1999
WO WO 1999/003996 1/1999
WO WO 1999/015553 4/1999
WO WO 1999/029732 6/1999
WO WO 1999/043713 9/1999
WO WO 1999/052562 10/1999
WO WO 1999/053958 10/1999
WO WO 1999/060128 11/1999
WO WO 2000/011033 3/2000
WO WO 2000/040615 7/2000
WO WO 2000/047228 8/2000
WO WO 2000/076310 12/2000
WO WO 2001/007081 2/2001
WO WO 2001/010912 2/2001
WO WO 2001/014424 3/2001
WO WO 2001/031007 5/2001
WO WO 2001/057081 8/2001
WO WO 2001/058957 8/2001
WO WO 2001/087981 11/2001
WO WO 2001/098468 12/2001
WO WO 2002/000243 1/2002
WO WO 2002/002143 1/2002
WO WO 2002/014358 2/2002
WO WO 2002/046383 6/2002
WO WO 2002/057435 7/2002
WO WO 2002/066514 8/2002
WO WO 2002/072605 9/2002
WO WO 2002/079232 10/2002
WO WO 2002/079415 10/2002
WO WO 2002/090526 11/2002
WO WO 2002/090566 11/2002
WO WO 2002/102993 12/2002
WO WO 2002/102994 12/2002
WO WO 2003/015697 2/2003
WO WO 2003/048208 6/2003
WO WO 2003/048334 6/2003
WO WO 2003/050531 6/2003
WO WO 2003/059245 7/2003
WO WO 2004/018649 3/2004
WO WO 2004/051268 6/2004
WO WO 2004/055056 7/2004
WO WO 2004/094613 11/2004
WO WO 2004/097047 11/2004
WO WO 2004/106377 12/2004
WO WO 2005/003169 1/2005
WO WO 2005/003170 1/2005
WO WO 2005/003171 1/2005
WO WO 2005/007121 1/2005
WO WO 2005/016969 2/2005
WO WO 2005/021592 3/2005
WO WO 2005/063808 7/2005
WO WO 2005/063820 7/2005
WO WO 2005/066348 7/2005
WO WO 2005/086751 9/2005
WO WO 2005/086798 9/2005
WO WO 2005/094879 10/2005
WO WO 2005/103081 11/2005
WO WO 2005/103086 11/2005
WO WO 2005/113605 12/2005
WO WO 2005/117984 12/2005
WO WO 2006/029879 3/2006
WO WO 2006/030220 3/2006
WO WO 2006/061219 6/2006
WO WO 2006/091899 8/2006
WO WO 2006/133396 12/2006
WO WO 2007/005874 1/2007
WO WO 2007/023298 3/2007
WO WO 2007/041972 4/2007
WO WO 2007/062245 5/2007
WO WO 2007/109324 9/2007
WO WO 2007/113648 10/2007
WO WO 2007/128121 11/2007
WO WO 2007/133290 11/2007
WO WO 2008/003473 1/2008
WO WO 2008/027338 3/2008
WO WO 2008/038024 4/2008
WO WO 2008/057457 5/2008
WO WO 2008/057458 5/2008
WO WO 2008/057459 5/2008
WO WO 2008/063382 5/2008
WO WO 2008/083174 7/2008
WO WO 2008/086395 7/2008
WO WO 2008/090958 7/2008
WO WO 2008/106116 9/2008
WO WO 2008/109871 9/2008
WO WO 2008/125623 10/2008
WO WO 2008/130704 10/2008
WO WO 2008/133647 11/2008
WO WO 2008/137915 11/2008
WO WO 2009/026558 2/2009
WO WO 2009/033027 3/2009
WO WO 2009/055783 4/2009
WO WO 2009/061853 5/2009
WO WO 2009/070642 6/2009
WO WO 2009/100297 8/2009
WO WO 2009/100318 8/2009
WO WO 2009/126688 10/2009
WO WO 2009/131740 10/2009
WO WO 2009/141239 11/2009
WO WO 2010/029513 3/2010
WO WO 2010/031720 3/2010
WO WO 2010/035012 4/2010
WO WO 2010/036959 4/2010
WO WO 2010/054007 5/2010
WO WO 2010/056804 5/2010
WO WO 2010/073180 7/2010
WO WO 2010/077634 7/2010
WO WO 2010/077854 8/2010
WO WO 2010/089411 8/2010
WO WO 2010/111180 9/2010
WO WO 2010/117448 10/2010
WO WO 2011/004192 1/2011
WO WO 2011/020024 2/2011
WO WO 2011/020783 2/2011
WO WO 2011/025904 3/2011
WO WO 2011/037791 3/2011
WO WO 2011/041613 4/2011
WO WO 2011/051350 5/2011
WO WO 2011/051351 5/2011
WO WO 2011/053665 5/2011
WO WO 2011/053743 5/2011
WO WO 2011/053759 5/2011

(56) References Cited

FOREIGN PATENT DOCUMENTS

| | | | |
|---|---|---|---|
| WO | WO 2011/053783 | 5/2011 | |
| WO | WO 2011/056997 | 5/2011 | |
| WO | WO 2011/066389 | 6/2011 | |
| WO | WO 2011/071871 | 6/2011 | |
| WO | WO 2011/072263 | 6/2011 | |
| WO | WO 2011/073180 | 6/2011 | |
| WO | WO 2011/097477 | 8/2011 | |
| WO | WO 2011/111007 | 9/2011 | |
| WO | WO 2011/158009 | 12/2011 | |
| WO | WO 2012/025536 | 3/2012 | |
| WO | WO 2012/027328 | 3/2012 | |
| WO | WO 2012/054438 | 4/2012 | |
| WO | WO 2012/062228 | 5/2012 | |
| WO | WO 2012/088313 | 6/2012 | |
| WO | WO 2012/088446 | 6/2012 | |
| WO | WO 2012/101251 | 8/2012 | |
| WO | WO 2012/101252 | 8/2012 | |
| WO | WO 2012/101253 | 8/2012 | |
| WO | WO 2012/107416 | 8/2012 | |
| WO | WO 2012/107417 | 8/2012 | |
| WO | WO 2012/109530 | 8/2012 | |
| WO | WO 2012/131004 | 10/2012 | |
| WO | WO 2012/132067 | 10/2012 | |
| WO | WO 2012/145493 | 10/2012 | |
| WO | WO 2012/146628 | 11/2012 | |
| WO | WO 2012/154999 | 11/2012 | |
| WO | WO 2012/162583 | 11/2012 | |
| WO | WO 2012/168491 | 12/2012 | |
| WO | WO 2012/170438 | 12/2012 | |
| WO | WO 2012/170607 | 12/2012 | |
| WO | WO 2012/174338 | 12/2012 | |
| WO | WO 2012/177741 | 12/2012 | |
| WO | WO 2012/178137 | 12/2012 | |
| WO | WO 2013/008171 | 1/2013 | |
| WO | WO 2013/008185 | 1/2013 | |
| WO | WO 2013/016648 | 1/2013 | |
| WO | WO 2013/028231 | 2/2013 | |
| WO | WO 2013/039958 | 3/2013 | |
| WO | WO 2013/039969 | 3/2013 | |
| WO | WO 2013/041844 | 3/2013 | |
| WO | WO 2013/061078 | 5/2013 | |
| WO | WO 2013/061098 | 5/2013 | |
| WO | WO 2013/063298 | 5/2013 | |
| WO | WO 2013/079174 | 6/2013 | |
| WO | WO 2013/148284 | 10/2013 | |
| WO | WO 2013/148350 | 10/2013 | |
| WO | WO 2013/170367 | 11/2013 | |
| WO | WO 2013/172933 | 11/2013 | |
| WO | WO 2013/173223 | 11/2013 | |
| WO | WO 2013/180201 | 12/2013 | |
| WO | WO 2013/181087 | 12/2013 | |
| WO | WO 2013/181634 | 12/2013 | |
| WO | WO 2014/023679 | 2/2014 | |
| WO | WO 2014/023752 | 2/2014 | |
| WO | WO 2014/033327 | 3/2014 | |
| WO | WO 2014/055897 | 4/2014 | |
| WO | WO 2014/089113 | 6/2014 | |
| WO | WO 2014/100079 | 6/2014 | |
| WO | WO 2014/109999 | 7/2014 | |
| WO | WO 2014/116846 | 7/2014 | |
| WO | WO 2014/159562 | 10/2014 | |
| WO | WO 2014/159595 | 10/2014 | |
| WO | WO 2014/165082 | 10/2014 | |
| WO | WO 2014/194111 | 12/2014 | |
| WO | WO 2015/004052 | 1/2015 | |
| WO | WO 2015/036499 | 3/2015 | |
| WO | WO 2015/040401 | 3/2015 | |
| WO | WO 2015/049537 | 4/2015 | |
| WO | WO 2015/061668 | 4/2015 | |
| WO | WO 2015/109124 | 7/2015 | |
| WO | WO 2015/112800 | 7/2015 | |
| WO | WO 2015/112805 | 7/2015 | |
| WO | WO 2015/112900 | 7/2015 | |
| WO | WO 2015/118016 | 8/2015 | |
| WO | WO 2015/132580 | 9/2015 | |
| WO | WO 2015/136541 | 9/2015 | |
| WO | WO-2015132580 A1 * | 9/2015 | ............ A61K 39/00 |
| WO | WO 2015/153514 | 10/2015 | |
| WO | WO 2015/173267 | 11/2015 | |
| WO | WO 2015/179654 | 11/2015 | |
| WO | WO 2015/181342 | 12/2015 | |
| WO | WO 2016/000619 | 1/2016 | |
| WO | WO 2016/007235 | 1/2016 | |
| WO | WO 2016/022468 | 2/2016 | |
| WO | WO 2016/022630 | 2/2016 | |
| WO | WO 2016/028656 | 2/2016 | |
| WO | WO 2016/030350 | 3/2016 | |
| WO | WO 2016/061142 | 4/2016 | |
| WO | WO 2016/106302 | 6/2016 | |
| WO | WO 2016/111645 | 7/2016 | |
| WO | WO 2016/120789 | 8/2016 | |
| WO | WO 2016/139482 | 9/2016 | |
| WO | WO 2016/149201 | 9/2016 | |
| WO | WO 2016/154177 | 9/2016 | |
| WO | WO 2016/160792 | 10/2016 | |
| WO | WO 2016/191643 | 12/2016 | |
| WO | WO 2016/193346 | 12/2016 | |
| WO | WO 2016/193348 | 12/2016 | |
| WO | WO 2016/193352 | 12/2016 | |
| WO | WO 2016/193353 | 12/2016 | |
| WO | WO 2016/193355 | 12/2016 | |
| WO | WO 2016/197367 | 12/2016 | |
| WO | WO 2017/020291 | 2/2017 | |
| WO | WO 2017/020801 | 2/2017 | |
| WO | WO 2017/020802 | 2/2017 | |
| WO | WO 2017/020858 | 2/2017 | |
| WO | WO 2017/030823 | 2/2017 | |
| WO | WO 2017/034916 | 3/2017 | |
| WO | WO 2017/037707 | 3/2017 | |
| WO | WO 2017/053748 | 3/2017 | |
| WO | WO 2017/059095 | 4/2017 | |
| WO | WO 2017/070423 | 4/2017 | |
| WO | WO 2017/087547 | 5/2017 | |
| WO | WO 2017/087587 | 5/2017 | |
| WO | WO 2017/091429 | 6/2017 | |
| WO | WO 2017/118321 | 7/2017 | |
| WO | WO 2017/134292 A1 | 8/2017 | |
| WO | WO 2017/196867 | 11/2017 | |
| WO | WO 2017/213695 | 12/2017 | |
| WO | WO 2017/215590 | 12/2017 | |
| WO | WO 2017/218435 | 12/2017 | |
| WO | WO 2017/220569 | 12/2017 | |
| WO | WO 2017/220988 | 12/2017 | |
| WO | WO 2018/005682 | 1/2018 | |
| WO | WO 2018/009894 | 1/2018 | |
| WO | WO 2018/025221 | 2/2018 | |
| WO | WO 2018/045110 | 3/2018 | |
| WO | WO 2018/047178 | 3/2018 | |
| WO | WO 2018/054940 | 3/2018 | |
| WO | WO 2018/080812 | 5/2018 | |
| WO | WO 2018/085358 | 5/2018 | |
| WO | WO 2018/115859 | 6/2018 | |
| WO | WO 2018/119475 | 6/2018 | |
| WO | WO 2018/136553 | 7/2018 | |
| WO | WO 2018/162749 | 9/2018 | |
| WO | WO 2018/187191 | 10/2018 | |
| WO | WO 2018/187613 | 10/2018 | |
| WO | WO 2018/195226 | 10/2018 | |
| WO | WO 2018/222949 | 12/2018 | |
| WO | WO 2019/028367 | 2/2019 | |
| WO | WO 2019/219978 A1 | 11/2019 | |
| WO | WO 2019/229155 A1 | 12/2019 | |
| WO | WO 2022/075476 A1 | 4/2022 | |
| WO | WO 2022/079036 | 4/2022 | |
| WO | WO 2023/017252 | 2/2023 | |
| WO | WO 2024/261177 | 12/2024 | |
| WO | WO 2024/261192 | 12/2024 | |

OTHER PUBLICATIONS

Weidinger et al. Atopic dermatitis. Nature Reviews Disease Primers. 4:1: Published: Jun. 21, 2018 (Year: 2018).*

(56) References Cited

OTHER PUBLICATIONS

Dupixent (dupilumab; anti-IL-4Rα antibody) Prescribing Information; Published: Mar. 2017 (Year: 2017).*
ClinicalTrials.gov Study NCT03754309. Phase 2a Trial of KY1005 in Patients with Moderate to Severe Atopic Dermatitis; Published: Jun. 5, 2020 (Year: 2020).*
Rivas et al. Regulatory T cells in allergic diseases. Journal of Allergy and Clinical Immunology. 138(3): 639-652; Published: Sep. 2016 (Year: 2016).*
Worm et al. Efficacy and Safety of Multiple Dupilumab Dose Regimens After Initial Successful Treatment in Patients With Atopic Dermatitis A Randomized Clinical Trial. JAMA Dermatology. 156(2): 131-143; Published: Dec. 26, 2019 (Year: 2019).*
Lambert et al. Practical guidance on immunogenicity to biologic agents used in the treatment of psoriasis: What can be learnt from other diseases? Journal of Dermatological Treatment. 26(6): 520-527. Published: Jun. 25, 2015 (Year: 2015).*
Rerknimitr et al. The etiopathogenesis of atopic dermatitis: barrier disruption, immunological derangement, and pruritus. Inflammation and Regeneration. 37: 14; Published: Jun. 5, 2017 (Year: 2017).*
WHO Drug Information, vol. 34, No. 3, 2020; Published: Dec. 2020 (Year: 2020).*
Dupixent (dupilumab; anti-IL-4Ra antibody) Prescribing Information; Published: Mar. 2017 (Year: 2017).*
Lyons et al. Immunology and Allergy Clinics of North America. 35(1): 161-183; Published: Feb. 2015 (Year: 2015).*
FDA Guidance Atopic Dermatitis: Timing of Pediatric Studies During Development of Systemic Drugs Guidance for Industry; Published: Oct. 2018 (Year: 2018).*
U.S. Appl. No. 14/700,896 U.S. Pat. No. 9,139,653, filed Apr. 30, 2015 Sep. 22, 2015, Jamie Campbell.
U.S. Appl. No. 14/811,163 U.S. Pat. No. 9,234,043, filed Jul. 28, 2015 Jan. 12, 2016, Jamie Campbell.
U.S. Appl. No. 14/955,843, filed Dec. 1, 2015, Jamie Campbell.
U.S. Appl. No. 15/122,298 2016/0368997 U.S. Pat. No. 10,669,342, filed Mar. 3, 2015 Dec. 22, 2016 Jun. 2, 2022, Jamie Campbell.
U.S. Appl. No. 15/259,553 2017/0002083 U.S. Pat. No. 9,587,030, filed Sep. 8, 2016 Jan. 5, 2017 Mar. 7, 2017, Jamie Campbell.
U.S. Appl. No. 15/340,497 2017/0044250 U.S. Pat. No. 10,654,935, filed Nov. 1, 2016 Feb. 16, 2017 May 19, 2020, Jamie Campbell.
U.S. Appl. No. 15/661,658 2017/0327587 U.S. Pat. No. 11,396,550, filed Jul. 27, 2017 Nov. 16, 2017 Jul. 26, 2022, Jamie Campbell.
U.S. Appl. No. 16/188,541 2019/00276547, filed Nov. 13, 2018 Sep. 12, 2019, Jamie Campbell.
U.S. Appl. No. 17/115,021 2021/0087287, filed Dec. 8, 2020 Mar. 25, 2021, Jamie Campbell.
U.S. Appl. No. 17/390,413 2021/0395378, filed Jul. 30, 2021 Dec. 23, 2021, Jamie Campbell.
U.S. Appl. No. 14/935,937 U.S. Pat. No. 9,434,785, filed Nov. 9, 2015 Sep. 6, 2016, Philip Bland-Ward.
U.S. Appl. No. 15/142,538 2016/0264675 U.S. Pat. No. 9,512,229, filed Apr. 29, 2016 Sep. 15, 2016 Dec. 6, 2016, Philip Bland-Ward.
U.S. Appl. No. 15/333,517 2017/0037137, filed Oct. 25, 2016 Feb. 9, 2017, Philip Bland-Ward.
U.S. Appl. No. 15/604,495 2017/0260279 U.S. Pat. No. 9,868,789, filed May 24, 2017 Sep. 14, 2017 Jan. 16, 2018, Philip Bland-Ward.
U.S. Appl. No. 15/661,584 2017/0327586 U.S. Pat. No. 9,868,790, filed Jul. 27, 2017 Nov. 16, 2017 Jan. 16, 2018, Philip Bland-Ward.
U.S. Appl. No. 17/725,228, filed Apr. 20, 2022, Philip Bland-Ward.
U.S. Appl. No. 16/346,675 2019/0275084, filed May 1, 2019 Sep. 12, 2019, Philip Bland-Ward.
U.S. Appl. No. 15/211,504 U.S. Pat. No. 9,567,399, filed Jul. 15, 2016 Feb. 14, 2017, Jamie Campbell.
U.S. Appl. No. 15/354,971 U.S. Pat. No. 9,617,338, filed Nov. 17, 2017 Apr. 11, 2017, Jamie Campbell.
U.S. Appl. No. 15/480,525 2017/0362321 U.S. Pat. No. 10,604,576, filed Apr. 6, 2017 Dec. 21, 2017 Mar. 31, 2020, Jamie Campbell.
U.S. Appl. No. 16/311,440 2019/0330351, filed Jun. 20, 2017 Oct. 31, 2019, Jamie Campbell.
U.S. Appl. No. 17/243,372 2021/0380699, filed Apr. 28, 2021 Dec. 9, 2021, Jamie Campbell.
U.S. Appl. No. 15/110,487 2017/0291951 U.S. Pat. No. 10,259,880, filed Jan. 13, 2015 Oct. 12, 2017 Apr. 16, 2019, Jamie Campbell.
U.S. Appl. No. 15/624,765 2017/0320956, filed Jun. 16, 2017 Nov. 9, 2017, Jamie Campbell.
U.S. Appl. No. 14/472,685 U.S. Pat. No. 8,992,927, filed Aug. 29, 2014 Mar. 31, 2015, Jasper Rupert Clube.
U.S. Appl. No. 14/472,698 U.S. Pat. No. 8,986,694, filed Aug. 29, 2014 Mar. 24, 2015, Jasper Rupert Clube.
U.S. Appl. No. 14/536,129 U.S. Pat. No. 9,062,105, filed Nov. 7, 2014 Jun. 23, 2015 Jasper Rupert Clube.
U.S. Appl. No. 14/536,049 U.S. Pat. No. 9,045,545, filed Nov. 7, 2017 Jun. 2, 2015, Jasper Rupert Clube.
U.S. Appl. No. 14/659,910 U.S. Pat. No. 9,109,034, filed Mar. 17, 2015 Aug. 18, 2015, Jasper Rupert Clube.
U.S. Appl. No. 14/537,403 U.S. Pat. No. 9,067,998, filed Nov. 10, 2014 Jun. 30, 2015, Jasper Rupert Clube.
U.S. Appl. No. 14/665,532 U.S. Pat. No. 9,150,660, filed Mar. 23, 2015 Oct. 6, 2015, Jasper Rupert Clube.
U.S. Appl. No. 17/818,397, filed Aug. 9, 2022, Ben Porter-Brown.
U.S. Appl. No. 14/700,896 U.S. Pat. No. 9,139,653, filed Apr. 30, 2015 Sep. 22, 2015, Jamie Campbell, Anti-Human Ox40L Antibodies and Method of Treatment.
U.S. Appl. No. 14/811,163 U.S. Pat. No. 9,234,043, filed Jul. 28, 2015 Jan. 12, 2016, Jamie Campbell, Anti-Human OX40L Antibodies.
U.S. Appl. No. 15/661,658 2017/0327587 U.S. Pat. No. 11,396,550, filed Jul. 27, 2017 Nov. 16, 2017 Jul. 26, 2022, Jamie Campbell, Methods of Treating Comprising Administering Anti-OX40L Antibodies.
U.S. Appl. No. 17/115,021 2021/0087287, filed Dec. 8, 2020 Mar. 25, 2021, Jamie Campbell, Nucleic Acids Encoding Anti OX40L Anitbodies.
U.S. Appl. No. 17/390,413 2021/0395378, filed Jul. 30, 2021 Dec. 23, 2021, Jamie Campbell, Antibodies, Uses & Methods.
U.S. Appl. No. 16/346,675 2019/0275084, filed May 1, 2019 Sep. 12, 2019, Philip Bland-Ward, Antibodies, Combinations Comprising Antibodies, Biomarkers, Uses & Methods.
U.S. Appl. No. 17/818,397, filed Aug. 9, 2022, Ben Porter-Brown, Treatment of Atopic Dermatitis.
U.S. Appl. No. 18/364,906, filed Aug. 3, 2023, Jamie Campbell, Antibodies, Uses & Methods.
U.S. Appl. No. 18/459,995, filed Sep. 1, 2023, Philip Bland-Ward, Antibodies, Combinations Comprising Antibodies, Biomarkers, Uses & Methods.
Diamond et al., "Somatic mutation of the T15 heavy chain gives rise to an antibody with autoantibody specificity", PNAS USA, . Proc. Natl. Acad. Sci. USA, Sep. 1984, 81(18): 5841-5844.
Koenig et al., "Mutational landscape of antibody variable domains reveals a switch modulating the interdomain conformational dynamics and antigen binding", PNAS USA, Jan. 24, 2017, 114(4): E486-E495.
Kyowa Kirin Co., Ltd., "A Phase 1 Study of KHK4083 in subjects with Atopic Dermatitis", Dec. 3, 2018.
Kyowa Kirin Co., Ltd., "Joint Development and Commercial Agreement of KHK4083 with Amgen", Jun. 1, 2021.
Kyowa Kirin Co., Ltd., "Kyowa Kirin Announces Positive Phase 2 Results for KHK4083 in Patients with Moderate to Severe Atopic Dermatitis", Feb. 18, 2021, Tokyo, Japan.
Ohno et al., "Antigen-binding specificities of antibodies are primarily determined by seven residues of VH", PNAS USA, May 1985, 82(9): 2945-2949.
Sanofi, "Positive topline Phase 2b data in atopic dermatitis support amlitelimab as a potential first and best-in-class novel investigational anti-OX40-ligand monoclonal antibody", Press Release of Jun. 27, 2023.
Sher et al., "Telazorlimab in atopic dermatitis: Phase 2b study shows improvement at 16 weeks", Abstracts—Pharmacology and Drug Development, Abstract 472, Apr. 19, 2021, Journal of Investigative Dermatology, 141: 582.
Abboud et al., Proprotein convertase subtilisin/kexin type 9 (PCSK9) gene is a risk factor of large-vessel atherosclerosis stroke PLoS One, 2(10):e1043, (2007).

(56) References Cited

OTHER PUBLICATIONS

Abcam Product Datasheet, Anti-ICOS antibody [C398.4A] ab81459, 2 pages.

Abifadel et al, Human Mutation, vol. 30, No. 4, pp. 520-529, 2009.

Abifadel et al. Mutations in PCSK9 cause autosomal dominant hypercholesterolemia Nat. Genet. 34, 154-156 (2003).

Abiko et al., PD-L1 on tumor cells is induced in ascites and promotes peritoneal dissemination of ovarian cancer through CTL dysfunction, Clin Cancer Res, 19(6):1363-74 (2013).

Abouelnasr et al., Defining the role of sirolimus in the management of graft-versus-host disease: from prophylaxis to treatment, Bioi Blood Marrow Transplant, 19(1):12-21 (2013).

Adebi et al., Ophthalmology 120(1):115-21 (2013). Variants in the VEGFA gene and treatment outcome after anti-VEGF treatment for neovascular age-related macular degeneration2.

Affymetrix eBioscience, Anti-Human CD278 (ICOS) Purified, obtained from url: <https://www.antibodypedia.com/gene/34168/ICOS/antibody/1028742/14-9948-80> on May 10, 2022.

Akers Michael J. et al., Formulation Development of Protein Dosage Forms Pharmaceutical Biotechnology, Kluwer, Dordrecht, NL, vol. 14, Jan. 1, 2002, pp. 47-127.

Akiba et al., CD28-independent costimulation of T cells by OX40 ligand and CD70 on activated B cells, J Immunol, 162(12):7058-66 (1999).

Akimova et al. Differing effects of rapamycin or calcineurin inhibitor on T-regulatory cells in pediatric liver and kidney transplant recipients. Am. J. Transplant. 12, 3449-3461 (2012).

Alborn et al., Serum proprotein convertase subtilisin kexin type 9 is correlated directly with serum LDL cholesterol:, Clin Chem, 53(10):1814-1819, (2007).

Alexandrov et al., Signatures of mutational processes in human cancer. Nature. Aug. 22, 2013;500(7463):415-21.

Alignment of Amgen Publication Heavy Chain Sequence SEQ ID No. 22 and Kymab Application HCDR3 Sequence SEQ ID No. 106. Alignment generated using BLAST on Aug. 10, 2017.

Allard et al., Genetic heterogeneity of autosomal dominant hypercholesterolemia: PCSK9, a third genet involved in the disease:, Current Topics in Genetics, 1, pp. 103-112, 2005.

Allard et al., Novel mutations of the PCSK9 gene cause variable phenotype of autosomal dominant hypercholesterolemia, Human mutation, 26(5), pp. 497, Nov. 2005.

Allard et al., PC9, a new actor in autosomal dominant hypercholesterolemia, Current Genomics, 6(7), pp. 535-543, Nov. 2005.

Alonso, A., et al., Subthreshold Na1-dependent theta-like rhythmicity in stellate cells of entorhinal cortex layer II, Nature, vol. 342,pp. 175-177,1989.

Anderson et al. Activation of the furin endoprotease is a multiple-step process: requirements for acidification and internal propeptide cleavage. EMBO J. 16, 1508-1518., 1997.

Anger, T., et al., Medicinal chemistry of neuronal voltage-gated sodium channel blockers, J. Med. Chem., vol. 44, No. 2 pp. 115-137, 2001.

Attie et al., Dual regulation of the LDL receptor—some clarity and new questions, Cell Metab., 1(5):290-292, (2005).

Attie et al., The mystery of PCSK9, Aterioscler Thromb Vase Biol., 24(8):1337-1339, (2004).

Augood et al., Arch Ophthalmol. 124:529e35 (2006). Prevalence of agerelated maculopathy in older Europeans: the European Eye Study (EUREYE).

Aung, et al, "The proprotein convertase subtilisin/kexin type 9 gene E670G polymorphism and serum lipid levels in the Guangxi Bai Ku Yao and Han populations", Lipids in Health and Disease, vol. 10, No. 5, pp. 1-15, 2011.

Austin et al., Genetic causes of monogenic heterozygous familial hypercholesterolemia: a HuGE prevalence review, American Journal of Epidemiology, 160 (5) pp. 407-420, 2004.

Awata et al., Diabetes. 51(5):1635-9, (2002) A common polymorphism in the 5'-untranslated region of the VEGF gene is associated with diabetic retinopathy in type 2 diabetes.

Babcook, J., et al., A Novel Strategy for generating Monoclonal Antibodies from Single, Isolated Lymphocytes Producing Antibodies of Defined Specificities, Proc. Natl. Acad. Sci. USA, vol. 93, No. 15, pp. 7843-7848, 1996.

Bansal et al., Cord blood lipoproteins and prenatal influences, Current Opinion in Lipidology, 16(4), pp. 400-408, Aug. 2005.

Barbie et al., Systematic RNA interference reveals that oncogenic KRAS-driven cancers require TBK1. Nature, 2009; 462(7269)108-12, plus 22 pages supplemental material.

Barrios et al., Length of the Antibody Heavy Chain Complementarity Determining Region 3 as a Specificity-Determining Factor, J. Mol. Recognit., 2004, pp. 332-338, vol. 17.

Baruch et al. CNS-specific T Cells Shape Brain Function via the Choroid Plexus, Brain Behay. Immun. 34: 11-16 (2013).

Baruch et al., Aging-Induced type I Interferon Response at the Choroid Plexus Negatively Affects Brain Function, Science 346(6205): 89-93 (2014).

Baruch et al., Breaking Immune Tolerance by Targeting Foxp3(+) Regulatory T Cells Mitigates Alzheimer's Disease Pathology, Nat Commun. 6: 7967-7978 (2015).

Baruch et al., Cerebral Nitric Oxide Represses Choroid Plexus NFKB-Dependent Gateway Activity for Leukocyte Trafficking, EMBO J. 34(13): 1816-1828 (2015).

Baruch et al., CNS-Specific Immunity at the Choroid Plexus Shifts Toward Destructive Th2 Inflammation in Brain Aging, Proc. Natl. Acad. Sci. U. S. A. 110 (6): 2264-2269 (2013).

Baruch et al., PD-1 immune checkpoint blockade reduces pathology and improves memory in mouse models of Alzheimer's disease. Nat Med, 2016; 22(2): 135-9, plus 296 pages supplemental material.

Basak, A., Inhibitors of Proprotien Convertases, J Mol Med 83: pp. 844-855, 2005.

Bedi et al., Inhibition of squalene synthase upregulates PCSK9 expression in rat liver, Arch Biochem Biophys., 470 (2):116-119, (2008).

Beer et al., Randomized, Double-Blind, Phase III Trial of Ipilimumab Versus Placebo in Asymptomatic or Minimally Symptomatic Patients with Metastatic Chemotherapy-Naïve Castration-Resistant Prostate Cancer, Journal of Clinical Oncology, 35(1): 40-51 (2019).

Beier et al., Induction, binding specificity and function of human ICOS. Eur J Immunol. Dec. 2000;30(12):3707-17.

Bekele-Arcuri, Z. et al., Generation and Characterization of Subtype-specific Monoclonal Antibodies to K+ Channel a- and 13-subunit Polypeptides, Neuropharmacology, vol. 35, No. 7, pp. 851-865, 1996.

Benes, J., et al., Anticonvulsant and sodium channel-blocking properties of novel 10,11-dihydro-5H-dibenz[b,f] azepine-5-carboxamide derivatives, J. Med. Chem., vol. 42, pp. 2582-2587, 1999.

Benjannet et al. (2006) The Proprotein Convertase (PC) PCSK9 is Inactivated by Furin and/or PC5/6A, J. Biol. Chem. 281(41):30561-30572.

Benjannet et al. NARC-1/PCSK9 and its natural mutants: zymogen cleavage and effects on the low density lipoprotein (LDL) receptor and LDL cholesterol. J Biol Chem, 2004, 279 (47): 48865-48875.

Benn et al, "PCSK9R46L, Low-Density Lipoprotein Cholesterol Levels, and Risk of Ischemic Heart Disease: 3 Independent Studies and Meta-Analyses", Journal of the American College of Cardiology, vol. 55, No. 25, 2010, pp. 2833-2842.

Berge et al. Missense mutations in the PCSK9 gene are associated with hypocholesterolemia and possibly increased response to statin therapy. Arterioscler. Thromb. Vasc. Biol. (2006) 26, 1094-1100.

Biasco et al., In vivo tracking of T cells in humans unveils decade-long survival and activity of genetically modified T memory stem cells, Sci Transl Med, 7(273):273ra13 (2015).

Bingham et al. Proapoptotic Effects of NARC 1 (=PCSK9), the Gene Encoding a Novel Serine Proteinase. Cytometry Part A, 2006, 69A: 1123-1131.

Binnewies et al., Understanding the tumor immune microenvironment (TIME) for effective therapy, Nature Medicine, Published online Apr. 23, 2018 (10 pages).

Black, J.A., et al., Multiple Sodium Channel Isoforms and Mitogens-Activated Protein Kinases Are Present in Painful Human Neromas, American Neurological Association, vol. 64, pp. 664-653, 2008.

(56) References Cited

OTHER PUBLICATIONS

Blank et al., J. Immunol. 171:4574-81 (2013). Absence of programmed death Receptor 1 alters thymic development and enhances generation of CD4/CD8 double-negative TCR-Transgenic T Cells.
Blank et al., PD-L1/B7H-1 inhibits the effector phase of tumor rejection by T cell receptor (TCR) transgenic CD8+ T cells 64(3):1140-5 (2004).
Blazar et al., Ligation of OX40 (CD134) regulates graft-versus-host disease (GVHD) and graft rejection in allogeneic bone marrow transplant recipients, Blood, 101:3741-3748 (2003).
Bos et al., Transient regulatory T cell ablation deters oncogene-driven breast cancer and enhances radiotherapy. J Exp Med 210(11):2434-2446 (2013).
Boschetti et al., Therapy with Anti-TNF.alpha. Antibody Enhances Number and Function of FOXP3+ Regulatory T Cells in Inflammatory Bowel Diseases. AGA Abstracts, S-743 (2010).
Bossu, J.L., et al., Patch-clamp study of the tetrodotoxin-resistant sodium current in group C sensory neurons, Neuroscience Letters, vol. 51, pp. 241-246 1984.
Bottomley et al. Structural and biochemical characterization of the wild type PCSK9/EGF-AB complex and natural FH mutants. J Biol Chem Nov. 2008.
Bourgon et al., Independent filtering increases detection power for high-throughput experiments. Proc. Natl. Acad. Sci. U.S.A. 107, 9546-9551 (2010).
Boyerinas et al., "Antibody-dependent cellular cytotoxicity (ADCC) activity of a novel anti-PD-L1 antibody avelumab (MSB0010718C) on human tumor cells", Cancer Immunol Res., Oct. 2015, 3(10): 1148-1157.
Brahmer et al., Phase I study of single-agent anti-programmed death-1 (MDX-1106) in refractory solid tumors: safety, clinical activity, pharmacodynamics, and immunologic correlates, J Clin Oncol, 28(19):3167-75 (2010).
Brahmer et al., Safety and activity of anti-PD-L1 antibody in patients with advanced cancer, N Engl J Med, 366 (26):2455-65 (2012).
Briskin, Efficacy of Anti-ICOS Agonist Monoclonal Antibodies in Preclinical Models Provides a Rationale for Clinical Development for cancer immunotherapy. Presentation SITC 2015, 22 pages.
Brown et al., Blockade of programmed death-1 ligands on dendritic cells enhances T cell activation and cytokine production, J Immunol, 170(3):1257-66 (2003).
Brown, M.S. & Goldstein, J.L. Lowering LDL—not only how low, but how long? Science 311, 1721-1723 (2006).
Brummell et al., "Probing the combining site of an anti-carbohydrate antibody by saturation-mutagenesis: role of the heavy-chain CDR3 residues", Biochemistry 32:1180-1187, 1993.
Brunger et al., Crystallography & NMR System: A new software suite for macromolecular structure determination, Acta Crystallogr D Biol Crystallogr 54, 905-21 (1998).
Bujotzek et al., VH-VL orientation prediction for antibody humanization candidate selection: A case study. MABS 8 (2):288-305 (2016).
Buonfiglio et al., The T cell activation molecule H4 and the CD28-like molecule ICOS are identical. Eur. J. Immunol., 30:3463-3467 (2000).
Burmeister et al., ICOS Controls the Pool Size of Effector-Memory and Regulatory T Cells. J. Immunol., 180(2): 774-782 (2008).
Burnett et al. New therapies for familial hypercholesterolemia Expert Opin. Ther. Patents 16(3): 349-361, 2006.
Burris III et al., Phase 1 Safety of ICOS Agonist Antibody JTX-2011 Alone and with Nivolumab (Nivo) in Advanced Solid Tumors; Predicted vs. Observed Pharmacokinetics (PK) in Iconic. (2017).
Burrows et al., OX40 blockade inhibits house dust mite driven allergic lung inflammation in mice and in vitro allergic responses in humans, Eur. J. Immunol pp. 1-13 (2015).
Butte et al., Programmed death-1 ligand 1 interacts specifically with the B7-1 costimulatory molecule to inhibit T cell responses, Immunity, 27(1):111-22 (2007).
Cameron et al. Effect of mutations in the PCSK9 gene on the cell surface LDL receptors. Hum. Mol. Genet. 15, 1551-1558 (2006).
Cameron et al., Berberine decreases PCSK9 expression in HepG2 cells, Atherosclerosis, 201(2):266-273, (2008).
Cameron et al., Characterization of novel mutations in the catalytic domain of the PCSK9 gene, J Intern Med., 263 (4):420-431, (2008).
Cameron et al., Investigations on the evolutionary conservation of PCSK9 reveal a functionally important protrusion, The FEBS Journal, pp. 1-13, 2008.
Campbell, Chapter 1, Monoclonal Antibody Technology, 1984 pp. 1-32, Elsevier Science Publishers B.V., The Netherlands.
Camus et al., Coordination of Intratumoral Immune Reaction and Human Colorectal Cancer Recurrence, Cancer Res 69:2685-93 (2009).
Cancer Discovery, "PD-1/PD-L1 Immunotherapy is Effective in Advanced Solid Tumors", 2012, 2(7): 581.
Careskey et al., Atorvastatin increases human serum levels of proprotein convertase subtilisin/kexin type 9, J Lipid Res., 49(2):394-398, (2008).
Carmenate et al., Human IL-2 Mutein with Higher Antitumor Efficacy Than Wild Type IL-2. J Immunol, published online May 15, 2013, http://http//www.jimmunol.org/content/early/2013/05/15/jimmunol.1201895, 10 pages.
Carthon et al., Preoperative CTLA-4 blockade: Tolerability and immune monitoring in the setting of a presurgical clinical trial. Clin. Cancer Res. 16:2861-2871, 2010.
Cassell et al., Therapeutic Enhancement of IL-2 Through Molecular Design. Current Pharmaceutical Design, 2002; 8:2172-2183.
Casset et al., A Peptide Mimetic of an Anti-CD4 Monoclonal Antibody by Rational Design, Biochemical and Biophysical Research Communications, 2003, vol. 307, pp. 198 205.
Cauvin et al. (2015) Advantages and Limitations of Commonly Used Nonhuman Primate Species in Research and Development of Biopharmaceuticals in The Nonhuman Primate, Nonclinical Drug Development and Safety Assessment (Academic Press), 379-395.
Cayman Chemical Company: Material Safety Data Sheet PCSK9 (human) Polyclonal Antibody Jul. 26, 2007, pp. 1-3.
Cayman Chemical Company: Material Safety Data Sheet PCSK9 (murine) Polyclonal Antibody Sep. 5, 2007, pp. 1-4.
Cayman Chemical Company: Product information PCSK9 (mouse) Polyclonal Antibody Catalog No. 10008811, Sep. 5, 2007, pp. 1-4.
Cayman Chemical Company: Product information PCSK9 Polyclonal Antibody Catalog No. 10007185 Dec. 10, 2007, pp. 1-2.
Chamow et al., Immunoadhesins: principles and applications, Trends in Biotechnology, 1996, 14(2): 52-60.
Chan et al. (2009) A proprotein convertase subtilisin/kexin type 9 neutralizing antibody reduces serum cholesterol in mice and non-human primates, Proc Natl Acad Sci USA, 106(24): 9820-9825.
Charbonnier et al. CTLA4-Ig restores rejection of MHC class-II mismatched allografts by disabling IL-2-expanded regulatory T cells. Am. J. Transplant. 12, 2313-2321 (2012).
Chattopadhyay et al., Structural Basis of Inducible Costimulatory Ligand Function: Determination of the Cell Surface Oligomeric State and Functional Mapping of the Receptor Binding Site of the Protein. J. Immunol. 177(6):3920-3929 (2006).
Chemnitz et al., Blood, 110:3226-33 (2007). RNA fingerprints provides direct evidence for the inhibitory role of TGFb and PD-1 on CD.varies.T Cells in Hodgkin lymphoma.
Chen Bei et al. Influence of histidine on the stability and physical properties of a fully human antibody in aqueous and solid forms Pharmaceutical Research, Kluwer Academic Publishers, New York, NY vol. 20, No. 12, Dec. 1, 2003, pp. 1952-1960.
Chen et al. Ox40-ligand has a critical costimulatory role in dendritic cell: T cell interactions, Immunity, 11:689-698 (1999).
Chen et al., "Enhancement and destruction of antibody function by somatic mutation: unequal occurrence is controlled by V gene combinatorial associations", EMBO J., 1995, 14(12): 2784-2794.
Chen et al., "Therapeutic efficacy of an anti-PD-L1 antibody based immunocytokine in a metastatic mouse model of colorectal cancer", Biochemical and Biophysical Research Communications, 2016, 480(2): 160-165.
Chen et al., A common PCSK9 haplotype, encompassing the E670G coding single nucleotide polymorphism, is a novel genetic marker

(56) References Cited

OTHER PUBLICATIONS for plasma low-density lipoprotein cholesterol levels and severity of coronary atherosclerosis, J Am Coll Cardiol. 45(10):1611-1619, (2005).
Chen et al., Asia Pac J Clin Oncol. (2014). Association between single nucleotide polymorphism of PD-L1 gene and non-small cell lung cancer susceptibility in a Chinese population.
Chen et al., Selection and Analysis of an Optimized Anti-VEGF Antibody: Crystal Structure of an Affinity Matured Fab in Complex with Antigen, J. Mol. Biol., 1999, vol. 293, pp. 865-881.
Chen, X. et al. Blockade of interleukin-6 signaling augments regulatory T-cell reconstitution and attenuates the severity of graft-versus-host disease. Blood 114, 891-900 (2009).
Cheung et al., Polymorphic variants of LIGHT (TNF superfamily-14) alter receptor avidity and bioavailability. The Journal of Immunology 185(3):1949-1958 (2010).
Chevalier et al., Phenotype Alterations in Regulatory T-Cell Subsets in Primary HIV Infection and Identification of Tr1-like Cells at the Main Interleukin 10-Producing CD4+ T Cells. JID, 211: 769-779 (2015).
Chioni, A-M. et al., A Novel Polyclonal antibody Specific lor the Nav 1.5 Voltage-Gated Na+ Channel 'Neonatal' Splice Form, Journal of Neuroscience Methods, vol. 147, pp. 88-98, 2005.
Chung et al., Treatment of malignant ascites, Current Treatment Options in Oncology, 2008, 9(2-3): 215-233.
Cieri et al., Generation of human memory stem T cells after haploidentical T-replete hematopoietic stem cell transplantation, Blood, 125(18):2865-2874 (2015).
Cieri et al., IL-7 and IL-15 instruct the generation of human memory stem T cells from naive precursors, Blood, 121 (4):573-584 (2013).
Cohen et al. Sequence variations in PCSK9, low LDL, and protection against coronary heart disease. N. Engl. J. Med. 354, 1264-1272 (2006).
Cohen et al., Erratum: Low LDL cholesterol in African Americans resulting from frequent nonsense mutations in PCSK9, Nature Genetics, 37(3), pp. 328, 2005.
Cohen et al., Low LDL cholesterol in individuals of African descent resulting from frequent nonsense mutations in PCSK9, Nat Genet. 37(2):161-165, (2005).
Colman, Effects of amino acid sequence changes on antibody-antigen interactions, Research in Immunology, 1994, 145(1): 33-36.
Collaborative Computational Project, No. 4 (CCP4), The CCP4 suite: programs for protein crystallography, Acta Crystallogr D. Biol Crystallogr, 50: 760-763 (1994).
Collin, Immune checkpoint inhibitors: a patent review. Expert Opinion on Therapeutic Patents, 26(5): 555-564 (2016).
Collins et al., Identification of specific residues of human interleukin 2 that affect binding to the 70-kDa subunit (p70) of the interleukin 2 receptor. Immunology, 85:7709-7713 (1988).
Conrad et al., Plasmacytoid dendritic cells and regulatory T cells in the tumor microenvironment: A dangerous liaison. Oncolmmunology. May 1, 2013;2(5):e2388.
Costet et al. Hepatic PCSK9 Expression Is Regulated by Nutritional Status via Insulin and Sterol Regulatory Element-binding Protein 1c. Journal of Biological Chemistry, Mar. 2006. 281(10): 6211-6218.
Costet et al., PCSK9 and LDL cholesterol: unraveling the target to design the bullet, Trends Biochem Sci., 33(9):426-434, (2008).
Costet et al., Proprotein Convertase Subtilisin Kexin type 9 is repressed by the peroxisome proliferator activated receptor alpha ligand fenofibric acid. Abstracts from Scientific Sessions 2006, 11-187. Basic Science.
Cox, J.J et al., An SCN9A channelopathy causes congenital inability to experience pain, Nature, vol. 444, No. 7121, pp. 894-898, 2006.
Coyle et al., The CD28-related molecule ICOS is required for effective T cell-dependent immune responses. Immunity. Jul. 2000;13(1):95-105.
Croft et al., Control of Immunity by the TNFR-Related molecule OX40 (CD134), Annu. Rev. Immunol. 28:57-78 (2010).
Crotty, T follicular helper cell differentiation, function, and roles in disease. Immunity. Oct. 16, 2014;41(4):529-42.
Culhane et al. MADE4: An R package for multivariate analysis of gene expression data. BioInformatics 21, 2789-2790 (2005).
Cummins, T. R., et al., Electrophysiological Properties of Mutant Nav1.7 Sodium Channels in a Painful Inherited Neuropathy, The Journal of Neuroscience, 24(38), pp. 8232-8236, 2004.
Cunningham et al., Structural and biophysical studies of PCSK9 and its mutants linked to familiar hypercholesterolemia, Nature Structural & Molecular Biology, vol. 14, No. 5, pp. 413-419 (May 2007).
Curiel et al., Nat. Med. 9:562-67 (2003). Blockade of B7-H1 improves myeloid dendritic cell-mediated antitumor immunity.
Curran et al., PD-1 and CTLA-4 combination blockade expands infiltrating cells and reduces regulatory T and myeloid cells within B16 melanoma tumors. PNAS, 107(9):4275-4280 (2010).
Currie et al., Dual Control of Antitumor CD8 T Cells through the Programmed Death-1/Programmed Death-Ligand 1 Pathway and Immunosuppressive CD4 T Cells: Regulation and Counterregulation. J. Immunol., 183(12): 7898-7908 (2009).
Cutler et al. Tacrolimus/sirolimus vs tacrolimus/methotrexate as GVHD prophylaxis after matched, related donor allogenic HCT. Blood 124, 1372-1377 (2014).
Dai et al., Anti-OX40L monoclonoal antibody prolongs secondary heart allograft survival based on CD40/CD40L and LFA-1/ICAM-1 blockade, Transplant Immunology {2015), http://dx.doi.org/10.1016/j.trim.2015.01.001.
Dall et al., Increasing the affinity of a human lgG1 for the neonatal Fc receptor : Biological consequences. Immunol 2002; 169:5171-5180.
Damayanti et al., Serial OX40 engagement on CD+4 T cells and natural killer T cells causes allergic airway inflammation, Am J Respir Crit Care Med 181(7):688-698 (2010).
Damgaard et al., No genetic linkage or molecular evidence for involvement of the PCSK9, ARH or CYP7A1 genes in the Familial Hypercholesterolemia phenotype in a sample of Danish families without pathogenic mutations in the LDL receptor and apoB genes, Atherosclerosis 177 (2), pp. 415-422, 2004.
Dana Farber Blog, Enhancing Immunotherapy: The Race to Make 'Cold' Tumors 'Hot,' Published Jun. 6, 2018 at https://blog.dana.farber.org/insight/2018/06/enhancing-immunotherapy-race-make-cold-tumors-hot/ (7 pages).
D'Angelo et al., Many Routes to an Antibody Heavy-Chain CDR3: Necessary, Yet Insufficient, for Specific Binding, Front Immunol., 2018, vol. 9, Article 395.
Davignon et al. Erratum to NARC-1: A potential new target for drug therapy of hypercholesterolemia, Atherosclerosis, 176, pp. 429, 2004.
Davignon et al., Narc-1: A Potential New Target for Drug Therapy of Hypercholesterolemia, XIIIth International Symposium on Atherosclerosis, Sep. 28-Oct. 2, 2003, Kyoto, Japan, pp. 182-183.
Davis-Smyth et al., The EMBO Journal 15(18):4919-4927 (1996). The second immunoglobulin-like domain of the VEGF tyrosine kinase receptor Flt-1 determines ligand binding and may initiate a signal transduction cascade.
De Genst, E., et al., Molecular basis for the preferential cleft recognition by dromedary heavy-chain antibodies, PNAS, vol. 103, No. 12, pp. 4586-4591, 2006.
De Haard, Novel Strategies for Identification and Characterization of Human Antibodies Against Nav1.7 Ion Channel Target, Antibodies Against Membrane Protein Targets, 2013, pp. 1-31.
De Pascalis et al., Grafting of 'Abbreviated' Complementarity Determining Regions Containing Specificity Determining Residues Essential for Ligand Contact to Engineer a Less Immunogenic Humanized Monoclonal Antibody, J. Immunol, 2002, vol. 169, pp. 3076-3084.
Declaration of Dr. Anil K. Thotakura submitted with Statement of Opposition filed at European Patent Office against European Patent No. EP2482849 on Mar. 6, 2019 (27 pages).
Declaration of Dr. Gwenoline Borhis submitted with Statement of Opposition filed at European Patent Office against European Patent No. EP2482849 on Mar. 6, 2019 (10 pages).

(56) References Cited

OTHER PUBLICATIONS

Declaration of Dr. Richard C.A. Sainson, submitted with Statement of Opposition filed at European Patent Office against European Patent No. EP2482849 on Mar. 6, 2019 (8 pages).
DeDoussis et al., LDL-receptor mutations in Europe, Human Mutation, 24(6), pp. 443-459, 2004.
Dellemijn, Paul, Are opioids effective in relieving neuropathic pain?, International Association for the Study of Pain, vol. 80, No. 3, pp. 453-462, 1999.
Deng et al., An Agonist Human ICOS Monoclonal Antibody that Induces T Cell Activation and Inhibits Proliferation of a Myeloma Cell Line. Hybridoma and Hybridomics, 23(3): 176-182 (2004).
Deng et al., Extrafollicular CD4+ T-B interactions are sufficient for inducing autoimmune-like chronic graft-versus-host disease, Nature Communications 2017, 18:978, (17 pages).
Devries et al. Science 225:989-991 (1992). , The fms-like tyrosine kinase, a receptor for vascular endothelial growth factor.
Diamond et al. The broad-spectrum antiviral functions of IFIT and IFITM proteins. Nat. Rev. Immunol. 13, 46-57 (2013).
Dib-Hajj et al., Review, 2007, vol. 30, No. 11, pp. 555-563.
Dib-Hajj, et al., Genetics and molecular pathophysiology of Na(v)1. 7-related pain syndromes, Advances in Genetics, vol. 63, pp. 85-110, 2008.
Dib-Hajj, et al., Voltage-gated sodium channels: therapeutic targets for pain, American Academy of Pain Medicine, vol. 10, No. 7, pp. 1260-1269, 2009.
Ding et al., Molecular population genetics of PCSK9: a signature of recent positive selection, Pharmacogenet Genomics. 18(3):169-179, (2008).
Dong et al., Angiogenesis., 17(3):553-62 (2014). Antagonism of PDGF-BB suppresses subretinal neovascularization and enhances the effects of blocking VEGF-A.
Dong et al., B7-H1, a third member of the B7 family, co-stimulates T-cell proliferation and interleukin-10 secretion Nat Med, 5(12):1365-9 (1999).
Dong et al., ICOS co-stimulatory receptor is essential for T-cell activation and function. Nature. 2001; 409(6816):97-101.
Dong et al., Tumor-associated B7-H1 promotes T-cell apoptosis: a potential mechanism of immune evasion, Nat Med, 8(8):793-800 (2002).
Dorfman et al., Am. J. Surg. Pathol. 30:802-10 (2006). Programmed death-1 (PD-1) is a marker of germinal centerassocaited T-cells and angioimmunoblastic T-Cell lymphoma.
Doyle, D.A., et al., The Structure of the Potassium Channel, Molecular Basis of K+ Conduction and Selectivity, Science, vol. 280, No. 5360. pp. 69-77, 1998.
Dranoff et al., Vaccination with irradiated tumor cells engineered to secrete murine granulocyte-macrophage colony-stimulating factor stimulates potent, specific, and long-lasting anti-tumor immunity, Proc. Natl. Acad. Sci. USA 90: 3539-3543 (1993).
Drenth et al. (2001) The primary erythermalgia-susceptibility gene is located on chromosome 2q31-32, Am. J. Hum. Genet., 2001, 68(5): 1277-1282.
Driessens et al., Costimulatory and coinhibitory receptors in anti-tumor immunity. Immunol. Rev. 229(1): 126-144 (2009).
Duan et al. Large scale analysis of positional effects of single-base mismatches on microarray gene expression data. BioData Min. 3, 2 (2010).
Dubuc et al. Statins upregulate PCSK9, the gene encoding the proprotein convertase neural apoptosis-regulated convertase-1 implicated in familial hypercholesterolemia. Arterioscler. Thromb. Vasc. Biol. 24, 1454-1459 (2004).
Duff et al. Antibody-mediated disruption of the interaction between PCSK9 and the low-density lipoprotein receptor. Biochemical Journal. Published online Feb. 5, 2009 as Manuscript BJ20082407.
Dworkin, R. H., An overview of neuropathic pain: syndromes, symptoms, signs, and several mechanisms, The Clinical Journal of Pain, vol. 18, pp. 343-349, 2002.
Eager et al., GM-CSF Gene-Transduced Tumor Vaccines, Molecular Therapy 12(1):18-27 (2005).
EB 06682 Goat Anti-PCSK9 Antibody, Everest Biotech Online Catalogue,.Copyrgt. 2007, auto-generated Sep. 7, 2007.
Edwards et al., (2003) The remarkable flexibility of the human antibody repertoire; isolation of over one thousand different antibodies to a single protein, BLyS, J Mol Biol., 334(1): 103-118.
Ellis et al., Engineered Anti-CD38 Monoclonal Antibodies for Immunotherapy of Multiple Myeloma. The Journal of Immunology 155 (1995): 925-937.
Elpek et al., Abstract A059: Efficacy of anti-ICOS agonist monoclonal antibodies in preclinical tumor models proves a rationale for clinical development as cancer immunotherapeutics. Cancer Immunology Research, (2016).
EuropeanBiotechnology.com, Roche's anti-PD-L1 fails in bladder cancer, Published May 10, 2017 at https://european-biotechnology.com/up-to-date/latest-news/news/roches-anti-pd-11-fails-in-bladder-cancer.html (2 pages).
Evans et al., The E670G SNP in the PCSK9 gene is associated with polygenic hypercholesterolemia in men but not in women, BMC Med Genet., 7:66, (2006).
Faget et al., ICOS—Ligand Expression on Plasmacytoid Dendritic Cells Supports Breast Cancer Progression by Promoting the Accumulation of Immunosuppressive CD4+ T Cells. Cancer Res., 72(23): (2012).
Fan et al. Self-Association of Human PCSK9 Correlates with Its LDLR-Degrading Activity, Biochemistry, 2008, 47:1631-1639.
Fan et al., Engagement of the ICOS pathway markedly enhances efficacy of CTLA-4 blockade in cancer immunotherapy. J Exp Med. Apr. 7, 2014;211(4):715-25.
Fehrenbacher et al., Atezolizumab versus docetaxel for patients with previously treated non-small-cell lung cancer (POPLAR): a multicentre, open-label, phase 2 randomised controlled trial, Lancet, 387(10030):1837-46 (2016).
Feyler et al., Tumour Cell Generation of Inducible Regulatory T-Cells in Multiple Myeloma is Contact-Dependent and Antigen-Presenting Cell-Independent. PLoS One, 7(5): 10 pages (2012).
Findlay et al., OX40L blockade is therapeutic in arthritis despite promoting osteoclastogenesis, PNAS, 111 (6):2289-2294 (2014).
Finger et al., Survey of Ophthalmology, 59(1):1-8 (2014). Predictors of anti-VEGF treatment response in neovascular age-related macular degeneration.
Fisher et al., Effects of pH and low density lipoprotein (LDL) on PCSK9-dependent LDL receptor regulation, J Biol Chem, 282(28):20502-20512, (2007).
Foks et al., Interruption of the OX40-OX40 ligand pathway in LDL receptor-deficient mice causes regression of atherosclerosis, J. Immunol. 191:4573-4580 (2013).
Folsom et al., Variation in PCSK9, low LDL cholesterol, and risk of peripheral arterial disease, Atherosclerosis, 202(1):211-215, (2009).
Fong et al., Nature, 376(6):66-70 (1995). Role of the Flt-1 receptor tyrosine kinase in regulating the assembly of vascular endothelium.
Fouchier et al., PCSK9 mutations found in patients diagnosed with autosomal dominant hypercholesterolemia in the Netherlands, Circulation, 110 (17 Suppl. S) Oct. 26, 2004.
Fouchier et al., Update of the molecular basis of familial hypercholesterolemia in the Netherlands, Human Mutation, 26(6), pp. 550-556, Dec. 2005.
Frampton, J.E., et al., Pregabalin: in the treatment of painful diabetic peripheral neuropathy, vol. 64, No. 24, pp. 2813-2820, 2004.
Francisco et al., PD-L1 regulates the development, maintenance, and function of induced regulatory T cells. J. Exp. Med. 206(13): 3015-3029 (2009).
Franco et al., Blood, 118(10): 2906-2917 (2011). Pericytes promote endothelial cell survival through induction of autocrine VEGF-A signaling and Bcl-w expression.
Frank-Kamenetsky et al., Therapeutic RNAi targeting PCSK9 acutely lowers plasma cholesterol in rodents and LDL cholesterol in non-human primates, Proc Natl Acad Sci., 105(33):11915-11920, (2008).
Freeman et al., Engagement of the PD-1 immunoinhibitory receptor by a novel B7 family member leads to negative regulation of lymphocyte activation, J Exp Med, 192(7):1027-34 (2000).
French et al., A thresfold sodiumchannell in pyramidal cells in rat hippocampus, Neuroscience Letters, 56:289-294, 1985.

(56) References Cited

OTHER PUBLICATIONS

French et al., What is conservative substitution? J. Mol. Evol. 1983; 19;171-5.
Fu et al. (2000). Folding pathway mediated by an intramolecular chaperone. The inhibitory and chaperone functions of the subtilisin propeptide are not obligatorily linked. J. Biol. Chem. 275, 16871-16878.
Fu et al., The ICOS/ICOSL pathway is required for optimal anti-tumor responses mediated by anti-CTLA-4 therapy. Cancer Res. Aug. 15, 2011;71(16):5445-54.
Gallego-Pinazo et al., Update on the principles and novel local and systemic therapies for the treatment of non-infectious uveitis, Inflamm Allergy Drug Targets, 12(1):38-45 (2013).
Galluzzi et al., Immunological mechanisms underneath the efficacy of cancer therapy. Canc. Imm. Res. 4:895-902 (2016).
Galon et al., Approaches to treat immune hot, altered and cold tumours with combination immunotherapies, Nature Reviews Drug Discovery, Published online Jan. 4, 2019 (22 pages).
Garnett et al., Treatment and management of graft-versus-host disease: improving response and survival, Ther Adv Hematol 4(6):366-78 (2013).
Gattinoni et al., A human memory T cell subset with stem cell-like properties, Nat Med, 17(10):1290-1297 (2011).
Gattinoni, L. & Restifo, N.P., Comment on Moving T memory stem cells to the clinic, Blood, 121(4):567-568 (2013).
Gauvreau et al., OX40L blockade and allergen-induced airway responses in subjects with mild asthma, Clinical Experimental Allergy, 44:29-37 (2013).
Ge et al., CDI34-Allodepletion allows selective elimination of alloreactive human T cells without loss of virus-specific and leukemia-specific effectors, Biology of Blood and Marrow Transplantation 14:518-530 (2008).
GenomeNet Database: UniProt, Entry: A0E922, Parte, Aury et al., 2006.
Gerritsen et al., A dose-escalation trial of GM-CSF-gene transduced allogeneic prostate cancer cellular immunotherapy in combination with a fully human anti-CTLA antibody (MDX-010, ipilimumab) in patients with metastatic hormone-refractory prostate cancer (mHRPC) Journal of Clinical Oncology, 24(18), Published online Dec. 12, 2016 at http://ascopubs.org/doi/abs/10.1200/jco.2006.24.18_suppl.2500 (5 pages).
Gillessen et al., A phase I dose-escalation study of the immunocytokine EMD 521873 (Selectikine) in patients with advanced solid tumours. Eur J Cancer (2012), 10 pages.
Gillies et al., A Low-Toxicity IL-2-Based Immunocytokine Retains Antitumor Activity Despite Its High Degree of IL-2 Receptor Selectivity. Clin Cancer Res, 2011; 17:3673-3682.
Gilly et al., Threshold channels—a novel type of sodium channel in squid giant axon, Nature. May 31-Jun. 6, 1984;309(5967):448-450.
Gilly, et al. (1989) Properties of appropriately and inappropriately expressed sodium channels in squid giant axon and its somata, J. Neurosci., 9(4): 1362-1374.
Goel et al. (2004) Plasticity within the Antigen-Combining Site May Manifest as Molecular Mimicry in the Humoral Immune Response, J Immunol, 173(12): 7358-7367.
Goldberg et al., Loss-of-function mutations in the Nav1.7 gene underlie congenital indifference to pain in multiple human populations, Clin Genet. Apr. 2007;71(4):311-9.
Goldstein et al. Familial hypercholesterolemia in The Metabolic & Molecular Bases of Inherited Disease (eds. Scriver, C.S. et al.) 2863-2913 (McGraw-Hill, New York, 2001).
Goldstein, J.L. & Brown, M.S. The cholesterol quartet. Science 292, 1310-1312 (2001).
Golub et al. Molecular classification of cancer: Class discovery and class prediction by gene expression monitoring. Science 286, 531-537 (1999).
Gong et al., PLoS One., 8(12):e84069 (2013). Association of VEGF gene polymorphisms with diabetic retinopathy: a meta-analysis.
Gonoi, T., et al., Voltage Clamp Analysis of Tetrodotoxin-sensitive and -insensitive Sodium Channels in Rat Muscle Cells Developing in Vitro1, J. Neurosci., vol. 5, No. 9, pp. 2559-2564, 1985.
Graadt Van Roggen et al., FH Afrikaner-3 LDL receptor mutation results in defective LDL receptors and causes a mild form of familial hypercholesterolemia, Arteriosclerosis, Thrombosis, and Vascular Biology, 15(6), pp. 765-772, Jun. 1995.
Graadt Van Roggen et al., Low density lipoprotein receptor founder mutations in Afrikaner familial hypercholesterolaemic patients: A comparison of two geographical areas, Human Genetics, 88(2), pp. 204-208, 1991.
Graham et al. Antisense inhibition of proprotein convertase subtilisin/kexin type 9 reduces serum LDL in hyperlipidemic mice. J Lipid Research 2007, 48:763-767.
Graham et al., Genetic screening protocol for familial hypercholesterolemia which includes splicing defects gives an improved mutation detection rate, Atherosclerosis, 182(2), pp. 331-340, Oct. 2005.
Grefhorst et al., Plasma PCSK9 preferentially reduces liver LDL receptors in mice, J Liped Res., 49(6):1303-1311, (2008).
Gross et al., Aryl sulfonamido tetralin inhibitors of the Kv1.5 ion channel, Bioorg Med Chem Lett. Jun. 1, 2009;19(11):3063-6.
Grozdanov et al. Expression and localization of PCSK9 in rat hepatic cells Biochemistry and Cell Biology, Feb. 2006, 84(1):80-92.
Grozdanov et al. Expression of Posk9 in rat hepatic cells, FASEB Journal, 19(4, Suppl. S, Part 1, Mar. 4, 2005.
Gul et al., Antibody-Dependent Phagocytosis of Tumor Cells by Macrophages: A Potent Effector Mechanism of Monoclonal Antibody Therapy of Cancer. Cancer Res., 75(23), Dec. 1, 2015.
Guo et al. The type I IFN induction pathway constrains Th17-mediated autoimmune inflammation in mice. J. Clin. Invest. 118, 1680-1690 (2008).
Hallman et al., Relation of PCSK9 mutations to serum low-density lipoprotein cholesterol in childhood and adulthood (from the Bogalusa Heart Study), Am J Cardiol., 100(1):69-72, (2007).
Hamada et al., Carrier Cell-mediated Delivery of a Replication-competent Adenovirus for Cancer Gene Therapy, Molecular Therapy 15(6): 1121-1128 (2007).
Hamanishi et al., PNAS 104(9):3360-3365 (2007). Programmed cell death 1 ligand 1 and tumor-inflitrating CD8+ T lymphocytes are prognostic factors of human ovarian cancer.
Hampton et al. The Crystal Structure of PCSK9 at 1.9 Angstroms Resolution Reveals Structure Homology to Resistin within the C-Terminal Domain (Released Sep. 18, 2007).
Hampton et al., The self-inhibited structure of full-length PCSK9 at 1.9 A reveals structural homology with resistin within the C-terminal domain, Proc Nat Acad Sci USA, Sep. 2007, 104(37): 14604-14609.
Han et al., J Diabetes Res. 2014:805801 (2014). The associations between VEGF gene polymorphisms and diabetic retinopathy susceptibility: a meta-analysis of 11 case-control studies.
Hanzelmann et al., GSVA: gene set variation analysis for microarray and RNA-Seq data. BMC Bioinformatics, vol. 14, No. 1, p. 7, 2013.
Harvey et al., Efficacy of Anti-ICOS Agonist Monoclonal Antibodies in Preclinical Models Provides a Rationale for Clinical Development for cancer immunotherapy. Journal for Immunotherapy of Cancer 3(Suppl 2):09 (2015).
Hasenhindl et al., Creating stable stem regions for loop elongation in Fcabs—Insights from combining yeast surface display, in silico loop reconstruction and molecular dynamics simulations. Biochimica et Biophysica Acta 1844: 1530-1540 (2014).
Hattori et al., Blockade of the OX40 ligand prolongs corneal allograft survival, Eur. J. Immunol. 37:3597-3604 (2007).
Hayashi et al., Eur J Endocrinol. 158(6):817-22 (2008). Association of an A/C single nucleotide polymorphism in programmed cell death-ligand 1 gene with Graves' disease in Japanese patients.
Heaton et al., Human Interleukin 2 Analogues That Preferentially Bind the Intermediate-Affinity Interleukin 2 Receptor Lead to Reduced Secondary Cytokine Secretion: Implications for the Use of These Interleuken 2 Analogues in Cancer Immunotherapy. Cancer Res, 53:2597-2602 (1993).
Helfand, AstraZeneca's Imfinzi fails key Mystic trial in lung cancer. What now? Published online Nov. 16, 2018 at https://www.

(56) References Cited

OTHER PUBLICATIONS fiercepharma.com/pharma/astrazeneca-s-imfinzi-fails-key-mystic-trial-lung-cancer-what-now (4 pages).
Henrich et al. (2003). The crystal structure of the proprotein processing proteinase furin explains its stringent specificity. Nat Struct. Biol. 10, 520-526.
Henrich et al. (2005). Proprotein convertase models based on the crystal structures of furin and kexin: Explanation of their Specificity Journal of Molecular Biology vol. 345, Issue 2, Jan. 14, 2005, pp. 211-227.
Herbst et al., Predictive correlates of response to the anti-PD-L1 antibody MPDL3280A in cancer patients, Nature, 515(7528):563-7 (2014).
Herley et al., Biochemical and Biophysical Research Communications. 262:731-738 (1999). Characterization of the VEGF binding site on the Flt-1 receptor.
Hermann et al., Ophthalmology. 121(4):905-10. (2014). Polymorphisms in vascular endothelial growth factor receptor 2 are associated with better response rates to ranibizumab treatment in age-related macular degeneration.
Hirano et al., Blockade of B7-H1 and PD-1 by monoclonal antibodies potentiates cancer therapeutic immunity, Cancer Res, 65(3): 1089-96 (2005).
Hirsch et al., Biomarker Driven Indication Selection in JTX-2011 Iconic Clinical Trial. Poster presented at the American Society of Clinical Oncology (ASCO) Annual Meeting, Jun. 2-6, 2017 in Chicago, Illinois.
Hirsch, A biomarker-driven approach for the development of the ICOS agonist antibody, JTX-2011, presentation for the Society for Immunotherapy of Cancer. Nov. 8, 2017 in National Harbor, Maryland, 11 pages.
Hitt E. (2011) FDA Approves Belatacept for Kidney Transplant Patients. Accessed at http://www.medscape.com/viewarticle/744723 on Jun. 17, 2017. 2 pages.
Hodge et al., Multiple Costimulatory Modalities Enhance CTL Avidity, J. Immunol. 174: 5994-6004 (2005).
Hodi et al., Immunologic and clinical effects of antibody blockade of cytotoxic T lymphocyte-associated antigen 4 in previously vaccinated cancer patients. PNAS Feb. 26, 2008;105(8):3005-10.
Holla et al., Degradation of the LDL receptors by PCSK9 is not mediated by a secreted protein acted upon by PCSK9 extracelluarly, BMC Cell Biol., 8:9, (2007).
Holla et al., Low-density lipoprotein receptor activity in Epstein-Barr virus-transformed lymphocytes from heterozygotes for the D374Y mutation in the PCSK9 gene, Scand J Clin Lab., 66(4):317-328, (2006).
Homer et al, (2008) Identification and characterization of two non-secreted PCSK9 mutants associated with familial hypercholesterolemia in cohorts from New Zealand and South Africa, Atherosclerosis, 196(2): 659-666.
Hooper et al., The C679X mutation in PCSK9 is present and lowers blood cholesterol in a Southern African population, Atherosclerosis, 193(2):445-448, (2007).
Hopkins et al., (2013) Abstract 17156: A Randomized Placebo-phase Clinical Trial With the Monoclonal Antibody Alirocumab Demonstrates Reductions in Low-density Lipoprotein Cholesterol in Patients With Proprotein Convertase Subtilisin/Kexin Type 9 Gain-of-Function Mutations, Circulation, 128(Suppl. 22): 17156, Abstract only.
Horkheimer et al. Induction of type I IFN is required for overcoming tumor-specific T-cell tolerance after stem cell transplantation. Blood 113, 5330-5339 (2009).
Horton et al., Molecular biology of PCSK9: its role in LDL metabolism, Trends in Biochemical Sciences, 2006, vol. 32, No. 2, pp. 71-77.
Hoshino et al., Critical role for OX40 ligand in the development of pathogenic Th2 cells in a murine model of asthma, EurJ Immunol, 33(4):861-9 (2003).
Houghten et al., Relative Importance of Position and Individual Amino Acid Residues in Peptide Antigen-Antibody Interactions: Implications in the Mechanism of Antigenic Drift and Antigenic Shift, New Approaches to Immunization, Vaccines 86, Cold Spring Harbor Laboratory, p. 21-25, 1986.
Houot et al., Therapeutic effect of CD137 immunomodulation in lymphoma and its enhancement by Treg depletion. Blood 114:3431-3438 (2009).
Hoyt et al., Benzazepinone Nav1.7 blockers: potential treatments for neuropathic pain, Bioorg Med Chem Lett. Nov. 15, 2007;17(22):6172-7.
Hsieh et al. Allogeneic hematopoietic stem-cell transplantation for sickle cell disease. N. Engl. J. Med. 361, 2309-2317 (2009).
Hu et al., Generation of low-toxicity interleukin-2 fusion proteins devoid of vasopermeability activity. Immunobiology, vol. 101, No. 12: 4853-4861 (2003).
Hua et al., Breast Cancer Res Treat. 129:195-201 (2011). PD-1 polymorphims are associated with sporadic breast cancer in Chinese Han population of northeastChina.
Huang et al. Bioinformatics enrichment tools: Paths toward the comprehensive functional analysis of large gene lists. Nucleic Acids Res. 37, 1-13 (2009).
Huang et al. Systematic and integrative analysis of large gene lists using David bioinformatics resources. Nat. Protoc. 4, 44-57 (2009).
Huang et al., Rheumatology (Oxford) 50(10):1809-13 (2011). Effects of genetic polymorphisms of programmed cell death 1 and its ligands on the development of ankylosing spondylitis.
Human Proprotein Convertase 9/PCSK9 Antibody, Antigen Affinity-purified Polyclonal Sheep IgG, Catalog No. AF3888. R & D Systems: Tools for Cell Biology ResearchTM Rev: Oct. 21, 2010 p. 1 of 1.
Human/Mouse Proprotein Convertase 9/PCSK9 Antibody, Monoclonal Rat IgG, Clone # 407119, Catalog No. MAB3888. R & D Systems: Tools for Cell Biology ResearchTM Rev. Oct. 12, 2010 p. 1 of 1. Available for sale since Jun. 2007.
Human/Mouse Proprotein Convertase 9/PCSK9 Antibody, Monoclonal Rat IgG, Clone # 407119, Catalog No. MAB38881. R & D Systems: Tools for Cell Biology ResearchTM Rev. Oct. 12, 2010 p. 1 of 1. Available for sale since Apr. 2008.
Human/Mouse Proprotein Convertase 9/PCSK9 Antibody, Monoclonal Rat IgG, Clone # 407119, Catalog No. MAB38882. R & D Systems: Tools for Cell Biology ResearchTM Rev. Oct. 12, 2010 p. 1 of 1. Available for sale since Feb. 2009.
Hutloff et al., ICOS is an inducible T-cell co-stimulator structurally and functionally related to CD28. Nature. 1999; 397(6716):263-6.
Idusogie et al., Engineered antibodies with increased activity to recruit complement. J. Immunol. 2001, 166:2571-2575.
Ikeda et al., Na+ and Ca2+ currents of acutely isolated adult rat nodose ganglion cells, J Neurophysiol. Mar. 1986;55(3):527-39.
Ikemura et al., (1987). Requirement of pro-sequence for the production of active subtilisin E in *Escherichia coli*. J. Biol. Chem. 262, 7859-7864.
Inman et al., Cancer 109:1499-505 (2007). PD-L1 (B7-H1) expression by urothelial carcinoma of the bladder and BCG-iinduced granulomata.
Inman, Costimulation, Coinhibition, and Cancer. Current Cancer Drug Targets, 7, 15-30 (2007).
International Search Report & Written Opinion dated Apr. 1, 2019, for PCT International Patent Application No. PCT/GB2018/053698.
International Search Report & Written Opinion dated Feb. 5, 2018, for PCT International Patent Application No. PCT/GB2017/052352.
International Search Report & Written Opinion dated May 27, 2019, for PCT International Patent Application No. PCT/GB2018/053701.
International Search Report & Written Opinion dated May 3, 2018, for PCT International Patent Application No. PCT/GB2017/053826.
International Search Report & Written Opinion dated May 7, 2019, for PCT International Patent Application No. PCT/GB2018/051714.
International Search Report & Written Opinion dated Oct. 4, 2017, for PCT International Patent Application No. PCT/GB2017/051796.
International Search Report & Written Opinion dated Sep. 22, 2017, for PCT International Patent Application No. PCT/GB2017/051794.
International Search Report & Written Opinion dated Sep. 25, 2017, for PCT International Patent Application No. PCT/GB2017/051795.

(56) References Cited

OTHER PUBLICATIONS

Irizarry et al. Exploration, normalization, and summaries of high density oligonucleotide array probe level data. Biostatistics 4, 249-264 (2003).
Ito et al. J. Biol. Chem. 273:23410-23418 (1998). Cell biology and metabolism: Identification of vascular endothelial growth factor factor receptor-1 tyrosine phosphorylation sites and binding of SH2 domain-containing molecules.
Iwai et al., Involvement of PD-L1 on tumor cells in the escape from host immune system and tumor immunotherapy by PD-L1 blockade, Proc Natl Acad Sci USA, 99(19):12293-7 (2002).
Jacquemin et al., OX40 ligand contributes to human lupus pathogenesis by promoting T follicular helper response, Immunity, 4:1-12 (2015).
Janke et al., Eminent role of ICOS costimulation for T cells interacting with plasmacytoid dendritic cells. Immunology, 11: 353-360 (2006).
Jeon, H. & Blacklow, S.C. Structure and physiologic function of the low-density lipoprotein receptor. Annu. Rev. Biochem. 74, 535-562 (2005).
Jian-Fei et al., Regulatory T cells, especially Icos+ FOXP3(+) regulatory T cells, are increased in the hepatocellular carcinoma microenvironment and predict reduced survival. Scientific Reports, vol. 6, www.nature.com/scientificreports Published Oct. 11, 2016 (8 pages).
Jiang et al., Role of IL-2 in cancer immunotherapy. OncoImmunology, 5:6, e1163462, DOI: 10.1080/2162402X.2016.1163462, 2016, 10 pages.
Jiang et al., The principle of gating charge movement in a voltage-dependent K+ channel, Nature. May 1, 2003;423(6935):42-8.
Jirholt et al., How does mutant proprotein convertase neural apoptosis-regulated convertase 1 induce autosomal dominant hypercholersterolemia, Arteriosclerosis, Thrombosis and Vascular Biology, 24 (8) pp. 1334-1336, 2004.
Jo et al. Am J Pathol. 168(6):2036-53 (2006). Inhibition of platelet-derived growth factor B signaling enhances the efficacy of anti-vascular endothelial growth factor therapy in multiple models of ocular neovascularisation.
Johansson et al., Arthritis Rheum., 52(6):1665-9 (2005). Association of a PDCD1 polymorphism with renal manifestations in systemic lupus erythematosus.
Johnson, W.E., Adjusting batch effects in microarray expression data using empirical Bayes methods. Biostatistics 8, 118-127 (2007).
Johnson, Z.P., et al. Immunogenetic management software: A new tool for visualization and analysis of complex immunogenetic datasets. Immunogenetics 64, 329-336 (2012).
Johnston et al. Sirolimus and mycophenolate mofetli as GVHD prophylaxis in myeloablative, matched-related donor hematopoietic cell transplantation. Bone Marrow Transplant. 47, 581-588 (2012).
Jones, S.W., Sodium Currents in Dissociated Bull-Frog Sympathetic Neurones, J. Physiol., vol. 389, pp. 605-627, 1987.
Jounce Therapeutics Press Release, Jounce Therapeutics Initiates Phase 1/2 Iconic Study of JTX-2011 in Patients with Advanced Solid Tumors, Sep. 7, 2016, 2 pages.
Jounce Therapeutics Press Release, Jounce Therapeutics Initiates Phase 2 Portion of Iconic Study of JTX-2011 in Patients with Advanced Solid Tumors, Apr. 20, 2017, 3 pages.
Jounce Therapeutics Press Release, Jounce Therapeutics Presents Data Highlighting Advances From Two Programs in its Immuno-Oncology Pipeline at the 2016 AACR Annual Meeting, Apr. 17, 2016, 2 pages.
Jounce Therapeutics Press Release, Jounce Therapeutics Presents Phase 1 Data from ICONIC Study of JTX-2011 in Patients with Advanced Solid Tumors at 2017 ASCO Annual Meeting, Jun. 5, 2017, 6 pages.
Jounce Therapeutics Press Release, Jounce Therapeutics to Present at AACR Annual Meeting on JTX-2011 Cancer Immunotherapy Program, Mar. 22, 2017, 5 pages.
Jounce Therapeutics Press Release, Jounce Therapeutics to Present Phase 1 Data from JTX-2011 Iconic Trial at 2017 American Society of Clinical Oncology Annual Meeting, May 17, 2017, 5 pages.
Jounce Therapeutics Press Release, Jounce Therapeutics to Present Program Updates at AACR Annual Meeting 2016, Mar. 16, 2016, 2 pages.
Jounce Therapeutics, Advancing Cancer Immunotherapy Worldwide. Presentation for SITC Conference, Nov. 8-12, 2017.
Kabelitz, Expression and function of Toll-like receptors in T lymphocytes. Curr. Opin. Immunol. 19, 39-45 (2007).
Kahn et al. 'Adjustable Locks and Flexible Keys: Plasticity of Epitope-Paratope Interactions in Germline Antibodies.' J. Immunol. 192:5398-5405, 2014.
Kaiser et al., Reduced tumor-antigen density leads to PD-1/PD-L1-mediated impairment of partially exhausted CD8+ T cells, Eur J Immunol, 42(3):662-71 (2012).
Kala et al., Phage Displayed Antibodies to Heat Stable Alkaline Phosphatase: Framework Region as a Determinant of Specificity, J. Biochem., 2002, pp. 535-541, vol. 132.
Kastelein et al., What promise does PCSK9 hold?, J Am Coll Cardiol., 45(10):1620-1621, (2005).
Kathiresan et al., A PCSK9 missense variant associated with a reduced risk of early-onset myocardial infarction, N Engl J Med., 358(21):2299-2300, (2008).
KEGG DRUG: D10354, Dupilumab, originally retrieved on Aug. 16, 2019, obtained from url: https://www.genome.jp/dbget-bin/www_bget?dr:D10354.
Keir et al., PD-1 and Its Ligands in Tolerance and Immunity, Annu. Rev. Immunol. 26:677-704 (2008).
Kilpatrick et al., Rapid development of affinity matured monoclonal antibodies using RIMMS. Hybridoma, 1997; 16(4):381-9.
Kim et al. Long-distance PCR-based screening for large rearrangements of the LDL receptor gene in Korean patients with familial hypercholesterolemia, Clinical Chemistry, 45(9), p. 1424-1430, 1999.
Kinnear et al. A diametric role for OX40 in the response of effector/memory CD4+ T cells and regulatory T cells to alloantigen. J. Immunol. 191, 1465-1475 (2013).
Kitchens et al., Interruption of OX40L signaling prevents costimulation blockade-resistant allograft rejection, JCI Insight 2(5):e90317 (2017) https://doi.org/10.1172/jci.insight.90317.
Klionsky, L., et al., A Polyclonal Antibody to the Prepare Loop of Transient Receptor Potential Vanilloid Type1 Blocks Channel Activation, The Journal of Pharmacology and Experimental Therapeutics, vol. 319, No. 1, pp. 192-198, 2006.
Knappik et al., Fully Synthetic Human Combinatorial Antibody Libraries (HuCAL) Based on Modular Consensus Frameworks and CDRs Randomized with Trinucleotides. J Mol. Bio1.296 (2000): 57-86.
Kole et al. Type I IFNs regulate effector and regulator T cell accumulation and anti-inflammatory cytokine production during T cell-mediated colitis. J. Immunol. 191, 2771-2779 (2013).
Kondo et al., Gene 208:297-305 (1998). Genomic organization of the flt-1 gene encoding for vascular endothelial growth factor (VEGF) receptor-1 suggest an intimate evolutionary relationship between the 7-Ig and the 5-Ig tyrosine kinase receptors.
Kong et al., Arthritis Rheum. 52(4):1058-62 (2005). A new haplotype of PDCD1 is associated with rheumatoid arthritis in Hong Kong Chinese.
Konishi et al., Clin. Cancer Res. 10:5094-100 (2004). B7-H1 expression on non-small cell lung cancer cells and its relationship with tumor-infiltrating lymphocytes and their PD-1 expression.
Kopf et al. OX40-deficient mice are defective in Th cell proliferation but are competent in generating B cell and CTL Responses after virus infection. Immunity 11, 699-708 (1999).
Kostyuk et al., Ionic currents in the somatic membrane of rat dorsal root ganglion neurons—I. Sodium currents, Neuroscience. 1981;6(12):2423-30.
Kotani et al., Correlation of peripheral blood OX40+(CD134+) T cells with chronic graft-versus-host disease in patients who underwent allogeneic hematopoietic stem cell transplantation: Presented in part at the 42nd Annual Meeting and Exposition of the America Society of Hematology, Blood, 98(10):3160-3164 (2001).

(56) References Cited

OTHER PUBLICATIONS

Kotowski et al., A spectrum of PCSK9 alleles contributes to plasma levels of low-density lipoprotein cholesterol., Am. J. Hum. Genet. 2006;78:410-422.
Kotowski et al., Multiple sequence variations in PCSK9 contribute to decreased plasma levels of LDL cholesterol, Circulation, 112 (17, Suppl. S), Oct. 25, 2005. Abstract No. 1766.
Kotze et al., Familial hypercholesterolemia: Potential diagnostic value of mutation screening in a pediatric population of South Africa, Clinical Genetics, 54(1), pp. 74-78, Jul. 1998.
Koura et al. In vivo T cel costimulation blockade with abatacept for acute graft-versus-host disease prevention: A first-in-disease trial. Biol. BloodMarrow Transplant. 19, 1638-1649 (2013).
Kourimate et al, Dual mechanisms for the fibrate-mediated repression of proprotein convertase subtilisin/kexin type 9, J Biol Chem., 283(15):9666-9673, (2008).
Kraman et al., A LAG-3/PD-L1 bispecific antibody inhibits tumour growth in two syngeneic colon carcinoma patients. Keystone Symposium, 2017, Poster 3005.
Kroemer et al. OX40 controls functionally different T cell subsets and their resistance to depletion therapy. J. Immunol. 179, 5584-5591 (2007).
Kroemer et al., Immunologic Cell Death in Cancer Therapy. Ann Rev Immunol. 2013; 31:51-72.
Kroner et al., Ann Neurol. 58(1):50-7 (2005). A PD-1 polymorphism is associated with disease progression in multiple sclerosis.
Kunis et al., IFN-y-Dependent Activation of the Brain's Choroid Plexus for CNS Immune Surveillance and Repair, Brain 136: 3427-3440 (2013).
Kunis et al., Immunization with a Myelin-Derived Antigen Activates the Brain's Choroid Plexus for Recruitment of Immunoregulatory Cells to the CNS and Attenuates Disease Progression in a Mouse Model of ALS, J. Neurosci. 35(16): 6381-6393 (2015).
Kuo et al., Expert Rev Ophthalmol., 8(2): 127-140 (2013). Genetic risk, ethnic variations and pharmacogenetic biomarkers in age-related macular degeneration and polypoidal choroidal vasculopathy.
Kussie et al. (1994) A single engineered amino acid substitution changes antibody fine specificity, J. Immunol., 152(1): 146-152.
Kwon et al. Molecular basis for LDL receptor recognition by PSK9. PNAS Feb. 12, 2008, 105(6):1820-1825.
Lagace et al. (2006) Secreted PCSK9 Decreases the Number of LDL Receptors in Hepatocytes and in Livers of Parabiotic Mice, J. Clin. Invest. 116(11):2995-3005.
Lalanne et al., Wild-type PCSK9 inhibits LDL clearance but does not affect apoB-containing lipoprotein production in mouse and cultured cells, J Lipid Res., 46(6):1312-1319, (2005).
Lambert et al. PCSK9: a promising therapeutic target for dyslipidemias? Trends Endocrinol. Metab. 17, 79-81 (2006).
Lambert et al., Fasting induces hyperlipidemia in mice overexpressing proprotein convertase subtilisin kexin type 9: lack of modulation of very-low density lipoprotein hepatic output by the low-density lipoprotein receptor, Endocrinology, 147(10):4985-4995, (2006).
Lambert et al., Molecular basis of PCSK9 function, Atherosclerosis, 203(1):1-7, (2009).
Lambert et al., Plasma PCSK9 concentrations correlate with LDL and total cholesterol in diabetic patients and are decreased by fenofibrate treatment, Clin Chem., 54(6):1038-1045, (2008).
Lambert et al., Unravelling the functional significance of PCSK9, Curr Opin Lipidol., 18(3):304-309, (2007).
Lamminmaki et al., Crystal Structure of a Recombinant Anti-estradiol Fab Fragment in Complex with 1713-Estradiol, The Journal of Biological Chemistry, vol. 276 (39), Sep. 28, 2001, pp. 36687 36694.
Langer, New methods of drug delivery. (1990) Science 249:1527-1533.
Langhi et al., Activation of the farnesoid X receptor represses PCSK9 expression in human hepatocytes, FEBS Lett., 582(6):949-955, (2008).
Lank et al. Ultra-high resolution HLA genotyping and allele discovery by highly multiplexed cDNA amplicon pyrosequencing. BMC Genomics 13, 378 (2012).
Larsen et al. An MHC-defined primate model reveals significant rejection of bone marrow after mixed chimerism induction despite full MHC matching. Am. J. Transplant. 10, 2396-2409 (2010).
Laustsen et al., Soluble OX40L is associated with presence of autoantibodies in early rheumatoid arthritis, Arthritis Research & Therapy 16:747 (2014).
Lazar et al., Engineered antibody Fc variants with enhanced effector function. 2006, Proc. Natl. Acad. Sci. U.S.A., Mar. 14; 103(11):4005-10.
Le et al., Follicular B Lymphomas Generate Regulatory T Cells via the ICOS/ICOSL Pathway and Are Susceptible to Treatment by Anti-ICOS/ICOSL Therapy. Cancer Res., 76(16):4648-4660 (2016).
Lederman et al. (1991) A single amino acid substitution in a common african allele of the CD4 molecule ablates binding of the monoclonal antibody, OKT4, Molecular Immunology 28(11): 1171-1181.
Lee et al. (2014) RETRACTED: A Monoclonal Antibody that Targets a NaV1.7 Channel Voltage Sensor for Pain and Itch Relief, Cell, 157(6): 1393-1404.
Lee et al., Complete humanization of the mouse immunoglobulin loci enables efficient therapeutic antibody discovery. Nature Biotechnology, 2014; 32: 356-363.
Lee, J.S. et al. Recruitment of Sprouty1 to immune synapse regulates T cell receptor signaling. J. Immunol. 183, 7178-7186 (2009).
Lefranc, IMGT unique numbering for immunoglobulin and T cell receptor variable domains and Ig superfamily V-like domains. Dev Comp Immunol. 2003; 27(1):55-77.
Leren et al., Mutations in the PCSK9 gene in Norwegian subjects with autosomal dominant hypercholesterolemia, Clin Genet., 65(5):419-422, (2004).
Levine et al., A prognostic score for acute graft-versus-host disease based on biomarkers: a multicentre study, Haematology, 2:e21-e29 (2015).
Li et al. (1980) beta-Endorphin omission analogs: dissociation of immunoreactivity from other biological activities, PNAS, 77(6): 3211-3214.
Li et al., Secreted PCSK9 promotes LDL receptor degradation independently of proteolytic activity, Biochem J. 406, 203-207 (2007).
Liakou et al., CTLA-4 blockade increases IFNgamma-producing CD4+ICOShi cells to shift the ratio of effector to regulatory T cells in cancer patients. Proc Natl Acad Sci USA. Sep. 30, 2008;105(39):14987-92.
Lin et al., The PD-1/PD-L1 complex resembles the antigen-binding Fv domains of antibodies and T cell receptors, Proc Natl Acad Sci USA, 105(8):3011-6 (2008).
Liston et al., Dicer-dependent microRNA pathway safeguards regulatory T cell function, J Exp Med 205(9): 1993-2004 (2008).
Liu et al., Blood 110:296-304 (2007). Plasma cells from multiple myeloma patients express B7-H1 (PD-L1) and increase expression after stimulation with IFN-y and TLR ligands via a MyD88-, TRAF6-, and Mek-dependent pathway.
Liu et al., Rheumatol Int., 31(2):209-13 (2011). Programmed cell death 1 gene polymorphisms is associated with ankylosing spondylitis in Chinese Han population.
Liu, J.L., et al., Isolation of anti-toxin single domain antibodies from a semi-synthetic spiny dogfish shark display library, BMC Biotechnology, vol. 7:78, 2007.
Llinas, et al., Electrophysiological properties of in vitro Purkinje cell dendrites in mammalian cerebellar slices, J. Physiol. (Land.), vol. 305, pp. 197-213, 1980.
Lloyd et al. Protein Engineering, Design & Selection 2009, 22:159-168 (Year: 2009).
Lode et al., Natural Killer Cell-Mediated Eradication of Neuroblastoma Metastases to Bone Marrow by Targeted Interleukin-2 Therapy. Blood, vol. 91, No. 5: 1706-1715 (1998).
Lohning et al., Expression of ICOS in Vivo Defines CD4+ Effector T Cells with High Inflammatory Potential and a Strong Bias for Secretion of Interleukin 10. J. Exp. Med., 197(2): 181-193 (2003).

(56) References Cited

OTHER PUBLICATIONS

Long et al., Crystal structure of a mammalian voltage-dependent Shaker family K+ channel, Science. Aug. 5, 2005;309(5736): 897-903.
Lopez et al., Inhibition of PCSK9 as a novel strategy for the treatment of hypercholesterolemia, Drug News Perspect., 21(6):323-330, (2008).
Lopez et al., PCSK9: an enigmatic process, Biochim Biophys Acta., 1781(4):184-191, (2008).
Lu et al., BMC Ophthalmol. 13:56 (2013). Two polymorphisms (rs699947, rs2010963) in the VEGF-A gene and diabetic retinopathy: an updated meta-analysis.
Ma et al., Functional Characterization of Novel Genes Regulated in a Cell Culture Model of Neuronal Apoptosis, Neuroscience 2002 Abstract, Nov. 5, 2002, p. 1.
Mabry et al., MAbs. 2(1): 20-34 (2010). A dual-targeting PDGFRbeta/VEGF-A molecule assembled from stable antibody fragments demonstrates anti-angiogenic activity in vitro and in vivo.
MacCallum, et al. (1996) Antibody-antigen interactions: contact analysis and binding site topography, Journal of Molecular Biology, 262(5): 732-745.
Mak et al., Costimulation through the inducible costimulator ligand is essential for both T helper and B cell functions in T cell-dependent B cell responses. Nat Immunol. 2003; 4(8):765-72.
Marais et al., The diagnosis and management of familial hypercholesterolaemia, European Review for Medical and Pharmacological Sciences, 9(3), pp. 141-149, May 2005.
Mariuzza et al., Annu Rev Biophys Chem., 1987, 16: 139-159.
Martin-Orozco et al., Melanoma Cells Express ICOS Ligand to Promote the Activation and Expansion of T-Regulatory Cells. Cancer Research 70(23):9581-9590 2010.
Martin-Orozco et al., Paradoxical dampening of anti-islet self-reactivity but promotion of diabetes by OX40 ligand, J Immunol. 171:6954-6960 (2003).
Maxwell et al. Adenoviral-mediated expression of PCSK9 in mice results in a low-desnity lipoprotein receptor knockout phenotype, Proc Natl Acad Sci USA, May 2004, 101(18): 7100-7105.
Maxwell et al. Novel putative SREBP and LXR target genes identified by microarray analysis in liver of cholesterol-fed mice Journal of Lipid Research, vol. 14, 2109-2119, 2003.
Maxwell et al. Overexpression of PCSK9 accelerates the degradation of the LDLR in a post-endoplasmic reticulum compartment Proc. Natl. Acad. Sci. USA (2005) 102, 2069-2074.
Maxwell et al., Overexpression of Pcsk9 leads to the formation of an LDLR-Pcsk9 complex and acceleration of LDLR degredation, Circulation, 110 (17 Suppl. S) Oct. 26, 2004. Abstract No. 1171.
Maxwell, K.N. & Breslow, J.L. Proprotein convertase subtilisin kexin 9: the third locus implicated in autosomal dominant hypercholesterolemia. Curr. Opin. Lipidol. 16, 167-172 (2005).
Mayne et al. (2013) Differential effects of PCSK9 loss of function variants on serum lipid and PCSK9 levels in Caucasian and African Canadian populations, Lipids in Health and Disease, 12(70): 1-11.
Mayne et al., Plasma PCSK9 levels are significantly modified by statins and fibrates in humans, Lipids Health Dis., 7:22, (2008).
Mayne et al., Plasma PCSK9 Levels Correlate with Cholesterol in Men but not in Women. Biochemical and Biophysical Research Communications (BBRC) 361 (2007): 451-456.
Mbikay et al., Of PCSK9, cholesterol homeostasis and parasitic infections: possible survival benefits of loss-of-function PCSK9 genetic polymorphisms, Med Hypotheses, 69(5):1010-1017, (2007).
McAdam et al., Mouse Inducible Costimulatory Molecule (ICOS) Expression is Enhanced by CD28 Costimulation and Regulates Differentiation of CD4+ T Cells. J. Immunology, 165:5035-5040 (2000).
McCourt et al., KY1055, a novel anti-ICOS/PD-L1 bispecific antibody, enhances T cell activation and delivers potent monotherapy anti-tumour responses in vivo. poster, 1 page, 2018.
McCourt et al., KY1055, a novel anti-ICOS/PD-L1 bispecific antibody, enhances T cell activation and delivers potent monotherapy anti-tumour responses in vivo. PowerPoint, 13 pages, 2018.
Mcgarrity et al. (2017) Hippocampal Neural Disinhibition Causes Attentional and Memory Deficits, Cerebral Cortex, 27(9): 4447-4462.
McGowan et al., A peripherally acting Na(v)1.7 sodium channel blocker reverses hyperalgesia and allodynia on rat models of inflammatory and neuropathic pain, Anesth Analg. Sep. 2009;109(3):951-8.
McNutt et al., Catalytic Activity Is Not Required for Secreted PCSK9 to Reduce Low Density Lipoprotein Receptors in HepG2 Cells, Journal of Biological Chemistry, vol. 282, No. 29, pp. 20799-20803 (Jul. 20, 2007).
McNutt, M.C. et al. Antagonism of secreted PCSK9 increases low density lipoprotein receptor expression in HepG2 cells—2009—Journal of Biological Chemistry, 284:10561-10570.
Meiri et al., Detection of cell surface sodium channels by monoclonal antibodies—could the channels become exposed to the external surface and 'down regulated' by binding to antibodies?, Brain Res. Mar. 12, 1986;368(1):188-92.
Meiri et al., Monoclonal antibodies associated with sodium channel block nerve impulse and stain nodes of Ranvier, Brain Res. Sep. 17, 1984; 310(1):168-73.
Mendez et al. (1997) Functional transplant of megabase human immunoglobulin loci recapitulates human antibody response in mice, Nature Genetics, 15(2): 146-156.
Metzger et al., ICOS Promotes the Function of CD4.sup.+ Effector T Cells during Anti-OX40-Mediated Tumor Rejection. Cancer Res, 76(13): 3684-3689 (2016).
Michaelson, Preclinical Assessment of JTX-2011, An Agonist Antibody Targeting ICOS, Supports Evaluation in Iconic Clinical Trial, Presentation 2017, 27 pages.
Miller et al. GVHD after haploidentical transplantation: A novel, MHC-defined rhesus macaque model identifies CD28-CD8+ T cells as a resevoir of breakthrough T-cell proliferation during costimulation blockade and sirolimus-based immunosuppression. Blood 116, 5403-5418 (2010).
Mitchell et al., J Clin Endocrinol Metab. 94(12):5139-45 (2009). Programmed death ligand 1 (PD-L1) gene variants contribute to autoimmune Addison's disease and Graves' disease susceptibility.
Miura et al., Molecular cloning and characterization of a novel glycoprotein, gp34, that is specifically induced by the human T-cell leukemia virus type 1 transactivator p40 tax, Molecular and Cellular Biology 11 (3): 1313-1325 (1991).
Miyake et al. (2008) Genetic variants in PCSK9 in the Japanese population: Rare genetic variants in PCSK9 might collectively contribute to plasma LDL cholesterol levels in the general population, Atherosclerosis, 196(1): 29-36.
Mojtahedi et al., Gene 508(2):229-32 (2012). Programmed death-1 gene polymorphism (PD-1.5 C/T) is associated with colon cancer.
Moore et al., Anti-PD1 x anti-ICOS bispecific antibody XmAb23104 brings together PD1 blockade and ICOS costimulation to promote human T cell activation and proliferation. SITC 2017 Poster P347.
Mootha et al. PGC-1a-responsive genes involved in oxidative phosphorylation are coordinately downregulated in human diabetes. Nat. Genet. 34, 267-273 (2003).
Moreno et al. (2016) Response to Programmed Cell Death-1 Blockade in a Murine Melanoma Syngeneic Model Requires Costimulation, CD4, and CD8 T Cells, Cancer Immunol Res, 4(10): 845-857.
Morishita et al., J Biol Chem 270:27948-27953 (1995). Nucleic Acids, Protein Synthesis, and Molecular Genetics: A novel promoter for vascular endothelial growth factor receptor (flt-1) that confers endothelial-speicific gene expression.
Moschen et al. Interferon-alpha controls IL-17 expression in vitro and in vivo. Immunobiology 213, 779-787 (2008).
Moynihan et al., Eradication of large established tumors in mice by combination immunotherapy that engages innate and adaptive immune responses. Nature Medicine, 12 pages (2016).
Munson, An improved technique for calculating relative response in cellular proliferation experiments. Cytometry A 77, 909-910 (2010).
Murata et al. Impairment of antigen-presenting cell function in mice lacking expression of OX40 ligand. J. Exp. Med. 191, 365-374 (2000).

(56) References Cited

OTHER PUBLICATIONS

Muto et al., Improving the Cross-Reactivity of an Antibody Using Site-Directed Mutagenesis, TOSOH Research and Technology Review, 2012, vol. 56: 3-9.
Naidoo et al. 'Toxicities of the anti-PD-1 and anti-PD-L1 immune checkpoint antibodies.' Ann Onc. 26:2375-2391, 2015.
Nair et al., A simple practice guide for dose conversion between animals and human. J Basic Clin Pharma 2016;7:27-31.
Nakanishi et al., Cancer Immunol. Immunother. 56:1173-82. (2007). Overexpression of B7-H1 (PD-L1) significantly associates with tumor grade and postoperative prognosis in human urothelial cancers.
Namaka et al., A treatment algorithm for neuropathic pain, Clin Ther. Jul. 2004;26(7):951-79.
Naoumova et al., Severe hypercholesterolemia in four British families with the D374Y mutation in the PCSK9 gene: Long-term follow-up and treatment response, Arteriosclerosis, Thrombosis, and Vascular Biology, 25(12), pp. 2654-2660, Dec. 2005.
Nassar et al. (2004) Nociceptor-specific gene deletion reveals a major role for Nav1.7 (PN1) in acute and inflammatory pain, PNAS, 101(34): 12706-12711.
Nassoury et al. The Cellular Trafficking of the Secretory Proprotein Convertase PCSK9 and Its Dependence on the LDLR, Traffic, 2007, 8: 718-732.
Natsume et al., Engineered Antibodies of IgG1/IgG3 Mixed Isotype with Enhanced Cytotoxic Activities. Cancer Res., 68: 3863-3872 (2008).
Natsume et al., Improving effector functions of antibodies for cancer treatment: Enhancing ADCC and CDC. Drug Des. Devel. Ther. 3:7-16 (2009).
Naureckiene et al. Functional Characterization of Narc1, a Novel Proteinase Related to Proteinase K, Arch Biochem Biophys. Dec. 1, 2003;420(1):55-67.
Nemunaitis, Vaccines in Cancer: GVAX®, a GM-CSF gene vaccine, Expert Rev. Vaccines 4(3): 259-274 (2005).
Neri et al., Immunocytokines for cancer treatment: past, present and future. Current Opinion in Immunology, GB vol. 40, Apr. 6, 2016, pp. 96-102.
Neufeld et al. FASEB Journal. 13:11-22 (1999). Vascular endothelial growth factor VEGF) and its receptors.
Newcomb et al. Human TH17 cells express a functional IL-13 receptor and IL-13 attenuates IL-17A production. J. Allergy Clin. Immunol. 127, 1006-1013 (2011).
Newman et al. Modification of the Fc region of a primatized IgG antibody to human CD4 retains its ability to modulate CD4 receptors but does not deplete CD4+ T cells in chimpanzees. Clin. Immunol. 98, 164-174 (2001).
Ngo et al. (1994) Computational Complexity, Protein Structure Prediction, and the Levinthal Paradox, The Protein Folding Problem and Tertiary Structure Prediction, pp. 433-506.
Ni Yan G et al. A PCSK9 C-terminal Domain Binding Fab Inhibits PCSK9 Internalization and Restores LDL-uptake: Circulation, vol. 120 No. 18 Suppl 2, Nov. 2009, p. S477. Abstract No. 1318.
Nielsen et al., Tissue Antigens., 62(6):492-7 (2003). Association of a putative regulatory polymorphism in the PD-1 gene with susceptibility to type 1 diabetes.
Nohara et al., Amelioration of experimental autoimmune encephalomyelitis with anti-OX40 ligand monoclonal antibody: a critical role for OX40 ligand in migration, but not development, of pathogenic T cells, J Immunol, 166 (3):2108-15 (2001).
Nomi et al., Clin. Cancer Res. 13:2151-57 (2007). Clinical Significance and therapeutic potential of the programmed Death-1 ligand/programmed Death-1 Pathway in Human Pancreatic Cancer.
Odegard et al., ICOS Controls Effector Function but Not Trafficking Receptor Expression of Kidney-Infiltrating Effector T Cells in Murine Lupus, J Immunology 182:4076-84 (2009).
Ohaegbulam et al., Human cancer immunotherapy with antibodies to the PD-1 and PD-L1 pathway. Trends Mol Med., 21(1): 24-33, 23 pages (2014).
Ong et al., J. Pers. Med. 3:40-69 (2013). Personalized Medicine in Ophthalmology: From Pharmacogenetic Biomarkers to Therapeutic and Dosage Optimization.
Orlandi, et al., Cloning immunoglobulin variable domains for expression by the polymerase chain reaction, PNAS USA, vol. 86, pp. 3833-3837, 1989.
Otwinowski et al., Multiparametric scaling of diffraction intensities, Acta Crystallogr A 59, 228-34 (2003).
Ouguerram et al., Apolipoprotein B100 metabolism in autosomal-dominant hypercholesterolemia related to mutations in PCSK9, Arterioscler thromb Vasc Biol. 24: 1448-1453, 2004.
Padlan et al. (1989) Structure of an antibody-antigen complex: Crystal structure of the HyHEL-10 Fab-lysozyme complex, PNAS, 86: 5938-5942.
Pakala et al., Prevention of diabetes in NOD mice at a late stage by targeting OX40/OX40 ligand interactions, Eur. J. Immunol. 34:3039-3046 (2004).
Pandit et al., Functional analysis of sites within PCSK9 responsible for hypercholesterolemia, J Lipid Res., 49(6):1333-1343, (2008).
Parhofer et al., What we have learned about VLDL and LDL metabolism from human kinetics studies, Journal of Lipid Research, 47(8), pp. 1620-1630, 2006.
Park et al., (2004). Post-transcriptional regulation of low density lipoprotein receptor protein by proprotein convertase subtilisin/kexin type 9a in mouse liver. J. Biol. Chem. 279, 50630-50638.
Parsa et al., Nat. Med. 13:84-88 (2007). Loss of tumor suppressor PTEN function increases B7-H1 expression and immunoresistance in glioma.
Paul, Fundamental Immunology, 3rd Edition, 1993, pp. 292-295, under the heading Fv Structure and Diversity in Three Dimensions.
Peccatori et al. Sirolimus-based graft-versus-host disease prophylaxis promotes the in vivo expansion of regulatory T cells and permits peripheral blood stem cell transplantation from haploidentical donors. Leukemia 29, 396-405 (2015).
Perkey et al. (2018) New Insights into Graft-Versus-Host Disease and Graft Rejection, Annual Rev. Pathol., 13: 219-245.
Peterson et al., PCSK9 function and physiology, J Lipid Res., 49(7):1595-1599, (2008).
Piatesi et al., Immunological Optimizatino of a Generic Hydrophobic Pocket for High Affinity Hapten Binding and Diels-Alder Activicy, ChemBio Chem, Apr. 2004, pp. 460-466, vol. 5(4).
Piche-Nicholas et al., (2018) Changes in complementarity-determining regions significantly alter IgG binding to the neonatal Fc receptor (FcRn) and pharmacokinetics, MAbs, 10(1): 81-94.
Piconese et al. A non-redundant role for OX40 in the competitive fitness of Treg in response to IL-2. Eur. J. Immunol. 40, 2902-2913 (2010).
Piconese et al. OX40 triggering blocks suppression by regulatory T cells and facilitates tumor rejection. J. Exp. Med. 205, 825-839 (2008).
Pidala et al. A randomized phase II study to evaluate tacrolimus in combination with sirolimus or methotrexate after allogeneic hematopoletic cell transplantation. Haematologica 97, 1882-1889 (2012).
Piper et al., The Crystal Structure of PCSK9: A Regulator of Plasma LDL-Cholesterol, Structure, 15, 1-8, pp. 545-552 (May 2007).
Pisciotta et al., Additive effect of mutations in LDLR and PCSK9 genes on the phenotype of familial hypercholesterolemia, Atherosclerosis 186(2), pp. 433-440, Jun. 2006.
Poirier et al., Implication of the proprotein convertase NARC-1/PCSK9 in the development of the nervous system, J Neurochem, 98(3):838-850, (2006).
Poirier et al., The proprotein convertase PCSK9 induces the degradation of the low density lipoprotein receptor (LDLR) and its closest family members VLDLR and ApoER2, J Biol Chem., 283(4):2363-2372, (2008).
Polisecki et al., Genetic variation a the PCSK9 locus moderately lowers low-density lipoprotein cholesterol levels, but does not significantly lower vascular disease risk in an elderly population, Atherosclerosis, 200(1): 95-101, (2008).
Polte et al., Different roles of C30 in the development of acute and chronic airways inflammation in a murine asthma model, Eur. J. 39:1736-1742 (2009).

(56) References Cited

OTHER PUBLICATIONS

Poosarla et al. 'Computational De Novo Design of Antibodies Binding to a Peptide With High Affinity.' Biotech. Bioeng. 114(6): 1331-1342, 2017.
Powell et al., Compendium of excipients for parenteral formulations. PDA J Pharm Sci Technol, 1998; 52:238-311.
Preston et al., The ratios of CD8+ T cells to CD4+CD25+ FOXP3+ and FOXP3− T cells correlate with poor clinical outcome in human serous ovarian cancer. PLoS One Nov. 14;8(11):e80063 (2013).
Proleukin (aldesleukin) FDA Fact Sheet, 2012 (19 pages).
Przepiorka et al., 1994 Consensus Conference on Acute GVHD Grading, Bone Marrow Transplant, 15(6):825-8 (1995).
Puhler et al., Generation of a recombinant oncolytic Newcastle disease virus and expression of a full IgG antibody from two transgenes, Gene Ther. 15: 371-383 (2008).
Qian et al., Advances in the treatment of acute graft-versus-host disease, J Cell Mol Med, 17(8):966-75 (2013).
Qian et al., Secreted PCSK9 downregulates low density lipoprotein receptor through receptor-mediated endocytosis, J Lipid Res., 48(7):1488-1498, (2007).
Qiang et al., Clinical cancer research : an official journal of the American Association for Cancer Research / 15 (3):971-9 (2009). Overexpression of PD-L1 significantly associates with tumor aggressiveness and postoperative recurrence in human hepatocellular carcinoma.
Quezada et al., CTLA4 blockade and GM-CSF combination immunotherapy alters the intratumor balance of effector and regulatory T cells, Journal of Clinical Investigation, 116(7): 1935-45 (2006).
Qui et al., Gene, 518(2):310-315 (2013). VEGF 634G>C polymorphism and diabetic retinopathy risk: A meta-analysis.
Rader et al. Monogenic hypercholesterolemia: New insights in pathogenesis and treatment, Journal of Clinical Investigation, 111 (12), pp. 1795-1803, 2003.
Rao et al. 'Anti-PD-1/PD-L1 therapy for infectious diseases: learning from the cancer paradigm.' J. Infect. Dis. 56:221-228, 2017.
Raouf et al. (2010) Pain as a channelopathy, J. Clin. Invest., 120(11): 3745-3752.
Rasband, M.N., et al., Distinct potassium channels on pain-sensing neurons, PNAS, vol. 98, No. 23, pp. 13373-13378, 2001.
Rashid et al. (2005) Decreased Plasma Cholesterol and Hypersensitivity to Statins in Mice Lacking PCSK9, Proc Natl Acad Sci USA 102(15):5374-5379.
Ratliff et al., Transgenic Expression of CYP7A1 in LDL Receptor-Deficient Mice Blocks Diet-Induced Hypercholesterolemia, Journal of Lipid Research, 47, 2006, ;; 1513-1520.
Rawlings et al. The JAK/STAT signaling pathway. J. Cell Sci. 117, 1281-1283 (2004).
Rawlings et al., (2006). MEROPS: the peptidase database. Nucleic Acids Res. 34, D270-D272.
RCSB Protein Data Bank: An Information Portal to Biological Macromolecular Structures. Search Results for keyword pcsk9, search conducted Jan. 10, 2008. Website accessed at http://www.rcsb.org/pdb/home/home.do.
Reardon et al. (2015) Glioblastoma Eradication Following Immune Checkpoint Blockade in an Orthotopic, Immunocompetent Model, Cancer Immunol Res, 4(2):124-135.
Redoglia et al., Characterization of H4: a mouse T Lymphocyte activation molecule functionally associated with the DC3/T cell receptor. Eur. J. Immunol., 11: 2781-9 (1996).
Reimann et al. (2010) Pain perception is altered by a nucleotide polymorphism in SCN9A, PNAS, 107(11): 5148-5153.
Renfrey et al., The painful reality, Nat Rev Drug Discov. Mar. 2003;2(3):175-6.
Riella et al. Deleterious effect of CTLA4-Ig on a Treg-dependent transplant model. Am. J. Transplant. 12, 846-855 (2012).
Robb et al. The interferon-dependent orchestration of innate and adaptive immunity after transplantation. Blood 119, 5351-5358 (2012).
Robb et al. Type I-IFNs control GVHD and GVL responses after transplantation. Blood 118, 3399-3409 (2011).
Roberto et al., Role of naive-derived T memory stem cells in T-cell reconstitution following allogeneic transplantation, Blood, 125(18):2855-2864 (2015).
Rosenberg et al., Atezolizumab in patients with locally advanced and metastatic urothelial carcinoma who have progressed following treatment with platinum-based chemotherapy: a single-arm, multicentre, phase 2 trial, Lancet, 387(10031):1909-20 (2016).
Rosenzweig et al. (2019) PD-1/PD-L1 checkpoint blockade harnesses monocyte-derived macrophages to combat cognitive impairment in a tauopathy mouse model, Nature Communications, vol. 10, Article 465.
Rossi et al., Optimization of multivalent bispecific antibodies and immunocytokines with improved in vivo properties, Bioconjug Chem, 24(1):63-71 (2013).
Rubio et al. Ex vivo identification, isolation and analysis of tumor-cytolytic T cells. Nat Med. 2003; 9(11):1377-82, plus 9 pages supplemental material.
Ruby et al. Cutting edge: OX40 agonists can drive regulatory T cell expansion if the cytokine milieu is right. J. Immunol. 183, 4853-4857 (2009).
Rudenko et al., Structure of the LDL Receptor Extracellular Domain at Endosomal pH, Science 298, 2353-8 (2002).
Rudikoff et al. Single Amino Acid Substitution Altering Antigen Binding Specificity Proc. Natl. Acad. Sci. 79: 1979-1983, 1982.
Ruutu et al., Prophylaxis and treatment of GVHD: EBMT-ELN working group recommendations for a standardized practice, Bone Marrow Transplant, 49(2):168-73 (2014).
Saerens, D., et al., Single Domain Antibodies Derived from Dromedary Lymph Node and Peripheral Blood Lymphocytes Sensing Conformational Variants of Prostate-specific Antigen, J. Bioi. Chem., vol. 279, No. 50, pp. 51965-51972, 2004.
Sainson et al., A novel antibody targeting ICOS increases intratumoural cytotoxic to regulatory T cell ratio and induces tumour regression, bioRxiv preprint first posted online Sep. 16, 2019, https://www.biorxiv.org/content/biorxiv/early/2019/09/16/771493.full.pdf—Retrieved Oct. 21, 2019 (80 pages).
Sainson et al., KY1044, a novel anti-ICOS antibody, elicits long term in vivo anti-tumour efficacy as monotherapy and in combination with immune checkpoint inhibitors. 1 page, 2017.
Sainson et al., KY1055, a novel ICOS/PD-L1 bispecific antibody, efficiently enhances T cell activation and delivers a potent anti-tumour response in vivo. 1 page, 2018.
Saint-Jore et al. Autosomal dominant type lla hypercholesterolemia: Evaluation of the respective contributions of LDLR and APOB gene defects as well as a third major group of defects, European Journal of Human Genetics, 8(8), pp. 621-630, 2000.
Saito, Y. et al., Sodium Channel Mutation in Irritable Bowel Syndrome: Evidence Ior an Ion C4 Channelopathy, Am. J. Physiol. Gatrointest. Liver Physiol., vol. 296, pp. G211-G218, 2009.
Sakai et al., (1998). Molecular identification of the sterol-regulated lumina! protease that cleaves SREBPs and controls lipid composition of animal cells. Mol. Cell 2, 505-514.
Salek-Ardakani et al., OX40 (CD134) controls memory T helper 2 cells that drive lung inflammation, J Exp Med, 198(2):315-24 (2003).
Salek-Ardakani, S., et al., OX40:OX40L Axis: Emerging Targets for Immunotherapy of Human Disease, Current Immunology Reviews 2: 37-53 (2006).
Sanchez et al. Kinetic of regulatory CD25high and activated CD134+ (OX40) T lymphocytes during acute and chronic graft-versus-host disease after allogeneic bone marrow transplantation. Br. J. Haematol. 126, 697-703 (2004).
Sanmamed et al., Agonists of Co-stimulation in Cancer Immunotherapy Directed Against CD137, OX40, GITR, CD27, CD28, and ICOS. Seminars in Oncology, 42(4):640-655 (2015).
Sanofi and Regeneron Report Positive Preliminary Phase 2 Program Results for Anti-PCSK9 Antibody in Hypercholesterolemia, http://www.prnewswire.com/news-releases/sanofi-and-regeneron-report-posit- ive-preliminary-phase-2-program-results-for-anti-pcsk9-antibody-in-hyperch- olesterolemia-133590188.html, PR Newswire, Nov. 10, 2011, pp. 1-3.

(56) References Cited

OTHER PUBLICATIONS

Saresella et al. (2012) A potential role for the PD1/PD-L1 pathway in the neuroinflammation of Alzheimer's disease, Neurobiology of Aging, 33(3): 624.e11-22.
Sato et al., Spatially selective depletion of tumor-associated regulatory T cells with near-infrared photoimmunotherapy. Science Translational Medicine, 2016; 8(352):1-12, plus 27 pages supplemental material.
Savabkar et al., Gastroenterol Hepatol Bed Bench., 6(4):178-82 (2013). Programmed death-1 gene polymorphism (PD-1.5 C/T) is associated with gastric cancer.
Schmalhofer, W.A., et al., ProTx-11, a Selective Inhibitor of Nav1.7 Sodium Channels, Blocks Action Potential Propagation in Nociceptors, Mol Pharmacal, vol. 74, pp. 1476-1484,2008.
Schmid et al., Basophil sensitivity reflects long-term clinical outcome of subcutaneous immunotherapy in grass pollen-allergic patients, Allergy, May 2021, 76(5): 1528-1538.
Schmidt et al. A Novel Splicing Variant of Proprotein Convertase Subtilisin/Kexin Type 9, DNA Cell Biol. Apr. 2008; 27(4):183-189.
Schmidt et al., A 15-ketosterol is a liver X receptor ligand that suppresses sterol-responsive element binding prSeidah et al., The proprotein convertases and their implication in sterol and/or lipid metabolism, Biological Chemistry, 387(7), 871-877 (2006)otein-2 activity, Journal of Lipid Research, 47(5), May 2006, 1037-1044.
Schmidt et al., Secreted proprotein convertase subtilisin/kexin type 9 reduces both hepatic and extrahepatic low-density lipoprotein receptors in vivo, Biochem Biophys Res Commun., 370(4):634-640, (2008).
Schneider et al., Clin Cancer Res 15(17):5297-5302 (2009). The Role of Vascular Endothelial Growth Factor Genetic Variability in Cancer.
Schoggins et al. Interferon-stimulated genes and their antiviral effector functions. Curr. Opin. Virol. 1, 519-525 (2011).
Schonrich et al., The PD-1/PD-L1 Axis and Virus Infections: A Delicate Balance, Front Cell Infect Microbiol, 2019, 9: 207.
Schwartz et al. (2019) Potential immunotherapy for Alzheimer disease and age-related dementia, Dialogues Clin Neurosci., 21(1): 21-25.
Schwartz et al., The Resolution of Neuroinflammation in Neurodegeneration: Leukocyte Recruitment via the Choroid Plexus, EMBO J. 33(1): 7-20 (2014).
Sears et al., ICONIC: Phase 1/2 Trial of ICOS Agonist JTX-2011 Alone and in Combination with Nivolumab (nivo). (2017).
Seidah et al., (1999). Mammalian subtilisin/kexin isozyme SKI-1: a widely expressed proprotein convertase with a unique cleavage specificity and cellular localization. Proc. Natl. Acad. Sci. USA 96, 1321-1326.
Seidah et al., The proprotein convertases and their implication in sterol and/or lipid metabolism, Biological Chemistry, 387(7), 871-877 (2006).
Seidah et al., The proprotein convertases in health and disease, Molecular & Cellular Proteomics, 2(9), Sep. 2003.
Seidah et al., The secretory proprotein convertase neural apoptosis-regulated convertase 1 (NARC-1): Liver regeneration and neuronal differentiation PNAS 100:928-933, 2003.
Seidah, N.G. and Pratt, A., The proprotein convertases are potential targets in the treatment of dyslipidemia, J. Mol. Med., 95:685-696, Mar. 10, 2007.
Selby et al., Anti-CTLA-4 antibodies of IgG2a isotype enhance antitumor activity through reduction of intratumoral regulatory T cells. Cancer Immunology Research, 1(1):32-42 (2013).
Seshasayee et al., In vivo blockade of OX40 ligand inhibits thymic stromal lymphopoietin driven atopic inflammation. J Clin Invest 117(12): 3868-3878 (2007).
Shan et al., PCSK9 binds to multiple receptors and can be functionally inhibited by an EGF-A peptide, Biochem. Biophys. Res. Commun., pp. 1-5 (2008).
Shanafelt et al., A T-cell-selective interleukin 2 mutein exhibits potent antitumor activity and is well tolerated in vivo. Nature Biotechnology, 18: 1197-1202 (2000).
Sharma et al., Immune Checkpoint Targeting in Cancer Therapy: Toward Combination Strategies with Curative Potential. Cell, 161: 205-214 (2015).
Sharma et al., J. Clin. Invest. 117:2570-82 (2007). Plasmacytoid dendritic cells from mouse tumor-draining lymph nodes directly activate mature tregs via indoleamine 2,3-dioxygenase.
Sharma et al., The future of immune checkpoint therapy. Science, 348(6230): 56-61 (2015).
Shen, et al., The molecular genetics of coronary artery disease and myocardial infarction, Acute Coronary Syndromes, 6 (4), pp. 129-141, 2004.
Shibata, et al, No genetic association between PCSK9 polymorphisms and Alzheimer's disease and plasma cholesterol level in Japanese patients, Psychiatric Genetics, 2005, vol. 15, pp. 239.
Shields et al., High resolution mapping of the binding site on human IgG1 for Fc gamma RI, Fc gamma RII, Fc gamma RIII, and FcRn and design of IgG1 variants with improved binding to the Fc gamma R. 2001, J. Biol. Chem., Mar. 2; 276(9):6591-604.
Shields et al., Lack of Fucose on Human IgG1 N-Linked Oligosaccharide Improves Binding to Human Fc.gamma.RIII and Antibody-dependent Cellular Toxicity. (2002) JBC 277:26733.
Shimauchi et al., Int. J. Cancer 121: 2585-90 (2007). Augmented expression of programmed death-1 in both neoplastic and non-neoplastic CD4+ T-cells in adult T-cell leukemia/lymphoma.
Shinohara et al. Engagement of the type I interferon receptor on dendritic cells inhibits T helper 17 cell development: Role of intracellular osteopontin. Immunity 29, 68-78 (2008).
Shioji et al., Genetic variants in PCSK9 affect the cholesterol level in Japanese, Journal of Human Genetics, 49 (2) pp. 109-114, 2004.
Shirakawa, The Current Status of Adenovirus-based Cancer Gene Therapy, Mol. Cells, 25(4): 462-466 (2008).
Sim et al., IL-2 therapy promotes suppressive ICOS+ Treg expansion in melanoma patients. J Clin Invest, 124(1): 99-110 (2014).
Sim et al., IL-2 variant circumvents ICOS+ regulatory T cell expansion and promotes NK cell activation. Cancer Immunol Res (2016).
Simpson et al., Fc-dependent depletion of tumor-infiltrating regulatory T cells co-defines the efficacy of anti-CTLA-4 therapy against melanoma. J. Exp. Med. 210(9):1695-1710 (2013).
Simpson et al., Regulation of CD4 T cell activation and effector function by inducible costimulatory (ICOS). Current Opinion in Immunology 22: 326-332 (2010).
Skobe et al., Nature Medicine 3:1222-1227 (1997). Halting angiogenesis suppress carcinoma cell invasion.
Skolnick et al. (2000) From genes to protein structure and function: novel applications of computational approaches in the genomic era, Trends in Biotech, 18(1): 34-39.
Slimani, et al. (Mar. 6, 2014) Effect of E670G Polymorphism in PCSK9 Gene on the Risk and Severity of Coronary Heart Disease and Ischemic Stroke in a Tunisian Cohort, J Mol Neurosci., 53(2): 150-157.
Soleimanifar et al. Inflammation, 34(6):707-12 (2011). Study of programmed cell death 1 (PDCD1) gene polymorphims in Iranian patients with ankylosing spondylitis.
Solomon et al., TIGIT: a novel immunotherapy target moving from bench to bedside. Cancer Immunol Immunother. 67(11):1659-1667 (2018).
Song et al., Overexpression of B7-H1 correlates with malignant cell proliferation in pancreatic cancer, Oncol Rep, 31(3)1191-8 (2014).
Song et al., Small-molecule modulators of the OX40-OX40 ligand co-stimulatory protein-protein interaction, British Journal of Pharmacology 171:4955-4969 (2014).
Soroosh et al., OX40-OX40 ligand interaction though T cell-T cell contact contributes to CD4 T Cell longevity, J. Immunol. 176:5975-5987 (2006).
Souza et al., Expression of lymphocyte-endothelial receptor-ligand pairs, 4beta7/MAdCAM-1 and OX40/OX40 ligand in the colon and jejunum of patients with inflammatory bowel disease, Gut 45:856-863 (1999).
Spoerl et al. Activity of therapeutic JAK 1/2 blockade in graft-versus-host disease. Blood 123, 3832-3242 (2014).
Stahl, Neil, Regeneron: Investor Day Early Clinical Development #1 REGN727: anti-PCSK9 Jul. 15, 2010: pp. 1-21.

(56) References Cited

OTHER PUBLICATIONS

Stallone et al., mTOR inhibitors effects on regulatory T cells and on dendritic cells, J Transl Med, 14(1):152 (2016).sub.—9pp.
Statement of Opposition filed at European Patent Office against European Patent No. EP2482849 on Mar. 6, 2019 (62 pages).
Stewart et al. Interferon-dependent IL-10 production by Tregs limits tumor Th17 inflammation. J. Clin. Invest. 123, 4859-4874 (2013).
Stewart et al., Identification and Characterization of MED14736 an Antagonistic Anti-PD-L1 Monoclonal Antibody, Cancer Immunol Res., 2015, 3(9): 1052-1062.
Strauss et al., Expression of ICOS on Human Melanoma-Infiltrating CD4.sup.+CD25.sup.highFoxp3.sup.+ T Regulatory Cells: Implications and Impact on Tumor-Mediated Immune Suppression. J. Immunol 180(5): 2967-2980 (2008).
Strohl, Fusion Proteins for Half-Life Extension of Biologics as a Strategy to Make Biobetters. BioDrugs (2015) 29:215-239.
Strom et al., Therapeutic approach to organ transplantation (Therapeutic Immunology, Austen et al. (Ed.) Blackwell Science, Cambridge MA, 1996, p. 451-456).
Strome et al., Cancer Res. 63:6501-6505 (2003). B7-H1 Blockade Augments adoptive T-Cells Immunotherapy for squamous cell carcinoma.
Stuber et al., Involvement of OX40-OX40L interactions in the intestinal manifestations of the murine acute graft-versus-host disease, Gastroenterology, 115(5):1205-15 (1998).
Subramanian et al. Gene set enrichment analysis: A knowledge-based approach for interpreting genome-wide expression profiles. Proc. Natl. Acad. Sci. U.S.A. 102, 15545-15550 (2005).
Sugamura et al., Therapeutic targeting of the effector T-cell co-stimulatory molecule OX40, Nat Rev Immunol, 4(6):420-31 (2004).
Summary of PubMed search results, Nov. 2016, 1 page.
Sun et al., PD-1/PD-L1 in cardiovascular disease, Clinica Chimica Acta, Jun. 2020, 505: 26-30.
Sun X-M et al, Evidence for effect of mutant PCSK9 on apoliprotein B secretion as the cause of unusually severe dominant hypercholesterolemia, Human Molecular Genetics 14: 1161-1169, 2005.
Sun, Hong et al., Prevention of Chronic Rejection in Mouse Aortic Allografts by Combined Treatment with CTLA4-Ig and Anti-CD40 Ligand Monoclonal Antibody, Transplantation, 1997, 64:1838-56.
Swallow et al., B7h, a novel costimulatory homolog of B7.1 and B7.2, is induced by TNFalpha. Immunity. Oct. 1999;11(4):423-32.
Tall, Protease variants, LDL, and coronary heart disease, New England Journal of Medicine, 354(12), pp. 1310-1312, Mar. 23, 2006.
Tanaka et al., Generation and characterization of monoclonal antibodies against multiple epitopes on the c-terminal half of envelope gp46 of human t-cell leukemia virus type-I (HTLV-I), Int. J. Cancer, 46:675-681 (1990).
Tanaka et al., Jpn J Cancer Res., 88:867-876 (1997). , Characterization of the extracellular domain in vascular endothelial growth factor receptor-1 (Fit-1 Tyrosine kinase).
Tangrea et al., (2002). Solution structure of the pro-hormone convertase 1 pro-domain from Mus musculus. J. Mol. Biol. 320, 801-812.
Tao, M., et al., Structural Features of Human Immunoglobulin G that Determine Isotype-specific Differences in Complement Activation, J. Exp. Med, vol. 178, pp. 661-667, 1993.
Tao, M., et al., The Differential Ability of Human IgG1 and lgG4 to Activate Complement Is Determined by the COOH-terminal Sequence of the CH2 Domain, J. Exp. Med, vol. 173, pp. 1 025-1028, 1991.
Tarwana et al., Blockers of voltage-gated sodium channels for the treatment of central nervous system diseases, Recent Pat CNS Drug Discov. Jan. 2007;2(1):57-78.
Taylor et al., The classification of amino acid conservation. J. Theor. Biol., 1986; 119;205-218.
Taylor, AstraZeneca tremelimumab fails another phase 3 cancer trial, Published online Dec. 7, 2018 at https://fiercebiotech.com/biotech/astrazeneca-s-tremelimumab-fails-another-phase-3-cancer-trial (4 pages).
Taylor, P., D-1 inhibitors shine at ASH conference. Published online by PMLive and retrieved from http://www.pmlive.com/pharma.sub.--news/pd-1.sub.--inhibitors.sub.--shine- .sub.--at.sub.--ash.sub.--conference.sub.--622370. Published Dec. 8, 2014.
Terman et al., Biochem Biophys Res Comm 187(3):1579-1586 (1992). , Identification of the KDR tyrosine kinase as a receptor for vascular endothelial cell growth factor.
Terman et al., Oncogene 6:1677-1683. (1991). Identification of a new endothelial cell growth factor receptor tyrosine kinase.
Thompson et al., Proc. Natl. Acad. Sci. USA 101:17174-79 (2004). Costimulatory B7-H1 in renal cell carcinoma patients: indicator of tumor aggressiveness and potential therapeutic target.
Thompson et al., Tumor B7-H1 is associated with poor prognosis in renal cell carcinoma patients with long-term follow-up, Cancer Res, 66(7):3381-5 (2006).
Tickle, S., et al., High-Throughput Screening for High Affinity Antibodies, Journal of the Association for Laboratory Automation, vol. 14, pp. 303-307, 2009.
Timms et al., A mutation in PCSK9 causing autosomal-dominant hypercholesterolemia in a Utah pedigree, Hum Genet., 114(4):349-353, (2004).
Toledo-Aral, et al. (1997) Identification of PN1, a predominant voltage-dependent sodium channel expressed principally in peripheral neurons, PNAS, 94(4): 1527-1532.
Tong et al. Molecular Vision 2010, 16:1958-1981 (2010). LOC387715/HTRA1 gene polymorphisms and susceptibility to age-related macular degeneration: A HuGE review and meta-analysis.
Topalian et al., Safety, activity, and immune correlates of anti-PD-1 antibody in cancer, N Engl J Med, 366 (26):2443-54 (2012).
Topol E.J., Cholesterol, racial variation and targeted medicines, Nature Medicine, 11(2), pp. 122-123, Feb. 2005.
Topol et al., Genetic susceptibility to myocardial infarction and coronary artery disease, Human Molecular Genetics, 15 (Rev. Issue 2), R117-R123, 2006.
Totsuka et al., Therapeutic effect of anti-OX40L and anti-TNF-beta MAbs in a murine model of chronic colitis, Am Physiol Gastrointest Liver Physiol. 284:G595-G603 (2003).
Tsukada et al., Blockade of CD134 (OX40)-CD143L interaction ameliorates lethal acute graft-versus-host in a murine model of allogeneic bone marrow transplantation, Blood, 95:2434-2439 (2000).
Tsutsumi et al., Thrombosis and Haemostasis 77(1):168-173 (1997). PEGylation of interleukin-6 effectively increases its thrombopoietic potency.
Tu et al., Regulatory T cells, especially Icos FOXP3+ regulatory T cells, are increased in the hepatocellular carcinoma microenvironment and predict reduced survival. Scientific Reports, 6:35056 (2016).
U.S. National Library of Medicine, Anti-ICOS Monoclonal Antibody MEDI-570 in Treating Patients with Relapsed or Refractory Peripheral T-cell Lymphoma Follicular Variant or Angioimmunoblastic T-cell Lymphoma, ClinicalTrials.gov Identifier No. NCT02520791. First posted Aug. 13, 2015. Retrieved at https://clinicaltrials.gov/ct2/show/NCT02520791.
Ueha et al., Robust Antitumor Effects of Combined Anti-CD4-Depleting Antibody and Anti-PD-1/PD-LI Immune Checkpoint Antibody Treatment in Mice. Cancer Immunology Research, 3(6); pp. 631-640 (2015).
Ueno et al., OX40/OX40L axis: not a friend in autoimmunity, Obcotgarget, 6(26):21779-21780 (2015).
Ukyo et al., Costimulation through OX40 is crucial for induction of an alloreactive human T-cell response, Immunology, 109:226-231 (2003).
Vajdos et al., Comprehensive Functional Maps of the Antigen Binding Site of an Anti ErbB2 Antibody Obtained with Shotgun Scanning Mutagenesis, J. Mol. Biol., 2002, vol. 320, pp. 415 428.
Van Berkel et al., CD28 and ICOS: Similar or separate costimulators of T cells? Immunology Letters 105: 115-122 (2006).
Van Elsas et al., Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation, J Exp Med 190(3): 355-66 (1999).

(56) References Cited

OTHER PUBLICATIONS

Van Regenmortel et al., Mapping Epitope Structure and Activity: From One-Dimensional Prediction to Four-Dimensional Description of Antigenic Specificity. Methods: A Companion to Methods in Enzymology 9 (1996): 465-472.
Varret et al. A Third Major Locus for Autosomal Dominant Hypercholesterolema Maps to 1p34.1-p32 Am. J. Hum. Genet, 64:1378-1387, 1999.
Varret et al., ARH and HCHOLA3: Two different genes at 1p both implicated in familial hypercholesterolemia, American Journal of Human Genetics, 71(4 Supplement), Oct. 2002 abstract 1597.
Varret et al., Familial autosomal dominant hypercholesterolemia: Highly skewed contribution of mutations in the LDLR, APOB, FH3 and FH4 genes, Circulation, 106 (19 Supplement) Nov. 5, 2002 abstract 1461.
Vazquez-Lombardi et al., Potent antititumour activity of interleukin-2-Fc fusion proteins requires Fc-mediated depletion of regulatory T-cells. Nature Communications, vol. 8, May 12, 2017, pp. 1-12.
Vetterman et al., A signalling-enhanced chimeric receptor to activate the ICOS pathway in T cells. Journal of Immunological Methods, 424: 14-19 (2015).
Villeger, et al., Familial hypercholesterolemia: 30 years after Brown and Goldstein, Recent Research Developments in Human Genetics, 1(pt. 1), pp. 35-51, 2002.
Vonderheide et al., Tremelimumab in combination with exemestane in patients with advanced breast cancer and treatment-associated modulation of inducible costimulator expression on patient T cells. Clin. Cancer Res. 16:3485-3494 (2010).
Vu et al. OX40 costimulation turns off Foxp3+ Tregs. Blood 110, 2501-2510 (2007).
Wang et al., Cancer Immunol Res. 2(9):846-856 (2014). In vitro characterization of the anti-PD-1 antibody nivolumab, BMS-936558, and in vivo toxicology in non-human primates.
Wang et al., Costimulation of T cells by B7-H2, a B7-like molecule that binds ICOS. Blood. Oct. 15, 2000, 96(8):2808-13.
Wang et al., Hum Genet 132(6):641-8 (2013). A miR-570 binding site polymorphism in the B7-H1 gene is associated with the risk of gastric adenocarcinoma.
Wang et al., In Vitro Characterization of the Anti-PD-1 Antibody Nivolumab, BMS-936558, and In Vivo Toxicology in Non-Human Primates. Cancer Immunology Research, vol. 2, No. 9, May 28, 2014 (May 28, 2014), pp. 846-856.
Wang et al., J Clin Immunol., 27(6):563-7 (2007). Polymorphisms of genes for programmed cell death 1 ligands in patients with rheumatoid arthritis.
Ward et al. (1989) Binding activities of a repertoire of single immunoglobulin variable domains secreted from *Escherichia coli*, Nature, 341: 544-546.
Ward et al., Targeting Costimulatory Pathways for Tumor Immunotherapy, International Reviews of Immunology, 26:161-196 (2007).
Webster, R.M., Nature Reviews Drug Discovery 13:883-884 (2014). From the Analyst's Couch: The Immune checkpoint inhibitors: where are we now?
Weigel et al., Mutant proteins of human interleukin 2. Eur. J. Biochem. 180: 295-300 (1989).
Weiss, R.E., et al., Functional differences between two classes of sodium channels in developing rat skeletal muscle, Science, vol. 233, pp. 361-364, 1986.
Wells (1990) Additivity of mutational effects in proteins, Biochemistry, 29(37): 8509-8517.
West et al., PD-L1 blockade synergizes with IL-2 therapy in reinvigorating exhausted T cells, J Clin Invest, 123 (6):2604-15 (2013).
Wing et al. CTLA-4 control over Foxp3+ regulator T cell function. Science 322, 271-275 (2008).
Wiseman et al. Major histocompatibility complex genotyping with massively parallel pyrosequencing. Nat. Med. 15, 1322-1326 (2009).
Wosornu et al., Genetic deficiency of proprotein convertase Subtilisin/Kexin 9: identification of a compound heterozygote with No. PCSK9, Circulation, 114 (18, Suppl. S). Oct. 31, 2006.
Wozniak-Knopp et al., Introducing antigen-binding sites in structural loops of immunoglobulin constant domains : Fc fragments with engineered HER2/neu-binding sites and antibody properties. Protein Engineering, Design & Selection, 23(4) ; 289-297 (2010).
Wu et al., Acta Histochemica 108:19-24 (2006). Immunohistochemical localization of programmed death-1 ligand-1 (PD-L1) in gastric carcinoma and its clinical significance.
Wu et al., Humanization of a Murine Monoclonal Antibody by Simultaneous Optimization of Framework and CDR Residues, J. Mol. Biol., 1999, vol. 294, pp. 151 162.
Wu et al., Leuk Lymphoma , 54(10):2251-4 (2013). Association between polymorphisms in PDCD1 gene and aplastic anemia in Chinese Han population.
Xu et al., Diversity in the CDR3 region of VH is sufficient for most antibody specificities. Immunity 13(1):37-45 (2000).
Xu et al., The roles of stem cell memory T cells in hematological malignancies, J Hematol Oncol, 8:113 (2015).
Yagi et al., Research and Reports in Neonatology ,1:5-11 (2011). ; VEGF 936C>T is predictive of threshold retinopathy of prematurity in Japanese infants with a 30-week gestational age or less.
Yang et al., Clin Exp Rheumatol. 29(1):13-8 (2011). Association of polymorphisms in the programmed cell death 1 (PD-1) and PD-1 ligand genes with ankylosing spondylitis in a Chinese population.
Yang et al., Programmed cell death-ligand 1 expression in surgically resected stage I pulmonary adenocarcinoma and its correlation with driver mutations and clinical outcomes, Eur J Cancer, 50(7):1361-9 (2014).
Yang, J., et al., 3-(4-Phenoxyphenyl)pyrazoles: A Novel Class of Sodium Channel Blockers, J. Med. Chem., vol. 47, No. 6, pp. 1547-1552, 2004.
Yap et al., ICONIC : Biologic and clinical activity of first in class ICOS against antibody JTX-2011 +/− nivolumab (nivo) in patients with advanced cancers. Presented at 2018 ASCO Annual Meeting (18 pages).
Yende et al., Genetic polymorphisms that predict outcome and need for treatment in cardiovascular disease, Current Opinion in Critical Care 12(5), pp. 420-425, Oct. 2006.
Yuan et al. The Role of the CD134-CD134 Ligand Costimulatory Pathway in Alloimmune Responses In Vivo, J. Immunol. 170, 2949-2955 (2003).
Yue et al., The c.43.sub.--44insCTG variation in PCSK9 is associated with low plasma LDL-cholesterol in a Caucasian population, Human Mutation, 27(5), pp. 460-466, May 2006.
Yusa et al., A hyperactive piggyBac transposase for mammalian applications. Proc Natl Acad Sci USA. Jan. 25, 2011: 108(4): 1531-1536.
Zachary et al. Experimental Nephrology. 6:480-487 (1998). Vascular Endothelial Growth Factor: How it transmits its signal.
Zaid et al., Proprotein convertase subtilisin/kexin type 9 (PCSK9): hepatocyte-specific low-density lipoprotein receptor degradation and critical role in mouse liver regeneration, Hepatology, 48(2):646-654, (2008).
Zang et al., The B7 family and cancer therapy: costimulation and coinhibition. Clinical Cancer Research, 13(18): 5271-5279 (2007).
Zhang et al. An obligate cell-intrinsic function for CD28 in Tregs. J. Clin. Invest. 123, 580-593 (2013).
Zhang et al. Binding of PCSK9 to EGF-A Repeat of LDL Receptor Decreases Receptor Recycling and Increases Degradation, Journal of Biological Chemistry Apr. 23, 2007.
Zhang et al. Structural requirements for PCSK9-mediated degradation of the low-density lipoprotein receptor. PNAS, Sep. 2, 2008, 105 (35): 13045-13050.
Zhang et al., Activation of OX40 augments Th17 cytokine expression and antigen-specific uveitis, The American Journal of Pathology, 177(6):2912-2920 (2010).
Zhang et al., Binding of Proprotein Convertase Subtilisin/Kexin Type 9 to Epidermal Growth Factor-like Repeat A of Low Density Lipoprotein Receptor Decreases Receptor Recycling and Increases Degradation, Journal of Biological Chemistry, vol. 282, No. 25, pp. 18602-18612, Jun. 22, 2007.

(56) References Cited

OTHER PUBLICATIONS

Zhao et al., (2006). Molecular characterization of loss-of-function mutations in PCSK9 and identification of a compound heterozygote. Am. J. Hum. Genet. 79, 514-523.
Zhao et al., Functional characterization of sequence variations in PCSK9, Circulation, 112 (17, Suppl. S.), Oct. 25, 2005.
Zucker, L.S., et al., Chimeric Human-Mouse IgG Antibodies with Shuffled Constant Region Exons Demonstrate that Multiple Domains Contribute to in Vivo Half-Life, Cancer Research, vol. 58, pp. 3905-3908, 1998.
Abuabara et al., The prevalence of atopic dermatitis beyond childhood: A systematic review and meta-analysis of longitudinal studies, Allergy, Mar. 2018, 73(3): 696-704.
Akiba et al., Critical contribution of OX40 ligand to T helper cell type 2 differentiation in experimental leishmaniasis, J. Exp. Med., 2000, 191(2): 375-380.
Aspeslagh et al., Rationale for anti-OX40 cancer immunotherapy, Eur. J. Cancer., 2016, 2: 50-66.
Aten et al., Strong and Selective Glomerular Localization of CD134 Ligand and TNF Receptor-1 in Proliferative Lupus Nephritis, JASN, 2000, 11(8): 1426-1438.
Bieber et al., Atopic dermatitis: an expanding therapeutic pipeline for a complex disease, Nat Rev Drug Discov., Jan. 2022, 21(1): 21-40.
Boettler et al., OX40 Facilitates Control of a Persistent Virus Infection, PLoS, Pathog., 2012, 8(9): 1-11.
Brunner et al., The immunology of atopic dermatitis and its reversibility with broad-spectrum and targeted therapies, J Allergy Clin Immunol., Apr. 2017, 139(4S): S65-S76.
Bugelski et al., Critical Review of Preclinical Approaches to Evaluate the Potential of Immunosuppressive Drugs to Influence Human Neoplasia, Int J Toxicol., 2010, 29(5): 435-466.
Burrows et al., Peer Review Correspondence: OX40 blockade inhibits house dust mite driven allergic lung inflammation in mice and in vitro allergic responses in humans, European Journal of Immunology, 2014.
Byun et al., Inherited human OX40 deficiency underlying classic Kaposi sarcoma of childhood, J Exp. Med., 2013, 210(9): 1743-1759.
Carboni et al., CD134 plays a crucial role in the pathogenesis of EAE and is upregulated in the CNS of patients with multiple sclerosis, J. Neuroimmunol., 2013, 145: 1-11.
Catley et al., Monoclonal antibodies for the treatment of asthma, Pharmacol Ther., Dec. 2011, 132(3): 333-351.
Cho et al., OX40 and 4-1 BB downregulate kaposi's sarcoma-associated herpes virus replication in lymphatic endothelial cells, but 4-1 BB and not OX40 inhibits viral replication in B-cells, J. Gen. Viral., 2015, 96(12): 3635-3645.
Clark et al., Determination of Absolute Counts of Circulating Regulatory T Cells in Cynomolgus Macaques Using an Optimised Flow Cytometric Method, Toxic. Pathol., 2012, 40: 107-112.
Compaan et al., The Crystal Structure of the Costimulatory OX40-OX40L Complex, Structure, 2006, 14(8): 1321-1330.
Croft et al., Clinical targeting of the TNF and TNER superfamilies, Nat Rev Drug Discov., 2013, 12(2): 147-168.
Croft et al., The significance of OX40 and OX40L to T-cell biology and immune disease, Immunol. Rev., 2009, 229(1): 173-191.
Deckers et al., Investigating International Time Trends in the Incidence and Prevalence of Atopic Eczema 1990-2010: A Systematic Review of Epidemiological Studies., PLoS ONE, Jul. 11, 2012, 7(7): e39803.
Declaration of Dr Nicholas William England under 37 C.F.R 1.132 and Exhibit B, declaration submitted in U.S. Appl. No. 15/661,658, 2018.
Dolff et al., Increased expression of costimulatory markers CD134 and COBO on interleukin-17 producing T cells in patients with systemic lupus erythematosus, Arthritis Research & Therapy, 2010, 12(4): R150.
Drucker et al., The Burden of Atopic Dermatitis: Summary of a Report for the National Eczema Association, J Invest Dermatol., Jan. 2017, 137(1): 26-30.
Ekkens et al., The Role of OX40 Ligand Interactions in the Development of the Th2 Response to the Gastrointestinal Nematode Parasite Heligmosomoides polygyrus, J. Immunol., 2003, 170(1): 384-393.
Elhai et al., OX40L blockade protects against inflammation-driven fibrosis, PNAS, 2016, E3901-E3910.
Elsner et al., The OX40 Axis is Associated with Both Systemic and Local Involvement in Atopic Dermatitis, Acta Derm Venereol., Mar. 31, 2020, 100(6): adv00099.
Florido et al., Contribution of CD30/CD153 but not of CD27/CD70, CD134/OX40L, or CD137/4-1BBL to the optimal induction of protective immunity to *Mycobacterium avium*, J Leukoc Biol., 2004, 76(5): 1039-1046.
Fu et al., Therapeutic strategies for the costimulatory molecule OX40 in T-cell-mediated immunity, Acta Pharmaceutica Sinica B, 2020, 10(3): 414-333.
Fujita et al., Lesional dendritic cells in patients with chronic atopic dermatitis and psoriasis exhibit parallel ability to activate T-cell subsets, J. Allergy Clin. Immunol., 2011, 128(3): 574-582.
Furue et al., OX40L-OX40 Signaling in Atopic Dermatitis, J Clin Med., 2021, 10(12): 2578.
Garmhausen et al., Characterization of different courses of atopic dermatitis in adolescent and adult patients, Allergy, Apr. 2013, 68(4): 498-506.
Glenmark Pharmaceuticals Ltd., Glenmark's Novel Monoclonal Antibody GBR 830 to Enter Phase 2 Clinical Studies in Atopic Dermatitis and Celiac Disease in US and Europe, Glenmark Pharmaceuticals, Inc.; 2015—online only e.g. at: https://www.prnewswire.com/news-releases/glenmarks-novel-monoclonalantibody-gbr-830-to-enter-phase-2-clinical-studies-in-atopic-dermatitis-and-celiac-disease-in-us-and-europe-524062301.html.
Gourh et al., Association of TNFSF4 (OX40L) polymorphisms with susceptibility to systemic sclerosis, Ann Rheum Dis., 2010, 69(3): 550-555.
Grogan et al., Activation and Expansion of CD81 T Effector Cells in Patients with Chronic Graft-versus-Host Disease, Biol Blood Marrow Transplant, 2011, 17: 1121-1132.
Guttman-Yassky et al., 453 GBR 830 induces progressive and sustained changes in atopic dermatitis biomarkers in patient skin lesions, J Invest Dermatol., May 1, 2018, 138(5): S77.
Guttman-Yassky et al., GBR 830, an anti-OX40, improves skin gene signatures and clinical scores in patients with atopic dermatitis, J Allergy Clin Immunol., Aug. 2019, 144(2): 482-493.e7.
Halim et al., Tissue-Restricted Adaptive Type 2 Immunity Is Orchestrated by Expression of the Costimulatory Molecule OX40L on Group 2 Innate Lymphoid Cells, Immunity, Jun. 2018, 48(6): 1195-1207.e6.
Hay et al., The Global Burden of Skin Disease in 2010: An Analysis of the Prevalence and Impact of Skin Conditions, J Invest Dermatol., Jun. 2014, 134(6): 1527-1534.
Hendriks et al., During viral infection of the respiratory tract, CD27, 4-1 BB, and OX40 collectively determine formation of CDS+ memory T cells and their capacity for secondary expansion, J. Immunol., 2005, 175(3): 1665-1676.
Hirano et al., OX40 ligand newly expressed on bronchiolar progenitors mediates influenza infection and further exacerbates pneumonia, EMBO Mol. Med., 2016, 8(4): 422-436.
Horwitz et al., Rebalancing Immune Homeostasis to Treat Autoimmune Diseases, Trends Immunol., Oct. 2019, 40(10): 888-908.
Hou, Glenmark, an Indian Pharmaceutical Company in Switzerland—Innovation with a touch of spice, Neuchatel, Switzerland: Systems Biology Verification, Mar. 2014.
Humphreys et al., A critical role for OX40 in T cell-mediated immunopathology during lung viral infection, J. Exp. Med., 2003, 198(8): 1237-1242.
Humphreys et al., OX40 Costimulation Promotes Persistence of Cytomegalovirus-Specific CDS T-Cells: A CD4-Dependent Mechanism, J. Immunol., 2007, 179(4): 2195-2202.
Hurley et al., Perspectives on immunoglobulins in colostrum and milk, Nutrients, 2011, 3(4): 442-474.

(56) References Cited

OTHER PUBLICATIONS

Ilves et al., OX40 ligand and OX40 are increased in atopic dermatitis lesions but do not correlate with clinical severity, Journal of the European Academy of Dermatology and Venereology, 2013, 27: e197-e205.
International Search Report and Written Opinion dated Apr. 17, 2018, for PCT International Application No. PCT/EP2017/078202.
Ishii et al., OX40-OX40 ligand interaction in T-cell-mediated immunity and immunopathology, Advances in Immunology, 1st Ed., 2010, 105: 63-98.
Jacobsohn et al., Novel pharmacotherapeutic approaches to prevention and treatment of GVDH, Drugs, 2002, 62(6): 879-889.
Kay et al., The prevalence of childhood atopic eczema in a general population, J Am Acad Dermatol., Jan. 1994, 30(1): 35-39.
Kitamura et al., OX40 costimulation can abrogate Foxp3+ regulatory T cell-mediated suppression of antitumor immunity, Int. J. Cancer, 2009, 125(3): 630-638.
Kymab News Release, Kymab Announces Positive Phase 2a Results for KY1005 in Moderate to Severe Atopic Dermatitis, Aug. 11, 2020.
Kymab, Kymab and Seattle Children's Research Institute publish impressive results using Kymab's KY1005 in a model of Acute Graft versus Host Disease (aGVHD) in Science Translational Medicine, press release issued on Sep. 21, 2017.
Kymab, Kymab announces clinical update on its promising new antibody KY1005 for treatment of autoimmune diseases, press released issued on Jul. 31, 2017.
Kymab, Kymab announces promising results from initial clinical study of new antibody KY1005 for treatment of autoimmune diseases, news release issued on Jul. 30, 2018.
Kymab, Kymab new therapeutic antibody for autoimmune diseases shows potential for improvement in post-transplant survival, press released issued on Dec. 5, 2016.
Lambert et al., Immunomodulatory effects of OX40 agonists in a defined antigen challenge in cynomolgus macaques, (May 20, 2015): 33, No. 15, Suppl. 1, Abstract No. 3086-3086.
Langer et al., Atopic Dermatitis, The Lancet, Aug. 2020, 396(10247): 345-360.
Linch et al., OX40 Agonists and Combination Immunotherapy: Putting the Pedal to the Metal, Front. Oneal., 2015, 5(34): 1-14.
Liu et al., The clinical implications of increased OX40 ligand expression in patients with acute coronary syndrome, Clin Chim Acta Int J Clin Chem., Nov. 2008, 397(1-2): 22-26.
Lu et al., Association of TNFSF4 polymorphisms with systemic lupus erythematosus: A meta-analysis, Mod Rheumatol., 2013, 23(4): 686-693.
Maeda, Current understanding of the pathophysiology and management of acute graft versus host disease, Journal of Japan Society for Hematopoietic Cell Transplantation, 2013, vol. 2, No. 1, pp. 12-23, English abstract included.
Manku et al., Association of the co-stimulator OX40L with systemic lupus erythematosus, J. Mol. Med., 2009, 87(3): 229-234.
Matsumura et al., Expression of CD134 and CD134 ligand in lesional and nonlesional psoriatic skin, Arch. Dermatol. Res., 2003, 294: 563-566.
Mayes et al., The promise and challenges of immune agonist antibody development in cancer, Nat Rev Drug Discov., Jun. 15, 2018, 17(7): 509-527.
Megna et al., Systemic Treatment of Adult Atopic Dermatitis: A Review, Dermatol Ther (Heidelb)., Mar. 2017, 7(1): 1-23.
Morimoto et al., CD134L engagement enhances human B cell Ig production: CD154/CD40, CD70/CD27, and CD134/CD134L interactions coordinately regulate T cell-dependent B cell responses, J Immunol, 2000, 164(8): 4097-4104.
Mousavi et al., OX40 costimulatory signals potentiate the memory commitment of effector CDS+ T cells, J. Immunol., 2008, 181(9): 5990-6001.
Nakagawa et al., Safety, tolerability and efficacy of repeated intravenous infusions of KHK4083, a fully human anti-OX40 monoclonal antibody, in Japanese patients with moderate to severe atopic dermatitis, J Dermatol Sci., Aug. 1, 2020, 99(2): 82-89.
Noda et al., The Asian atopic dermatitis phenotype combines features of atopic dermatitis and psoriasis with increased TH17 polarization, J Allergy Clin Immunol., Nov. 2015, 136(5): 1254-1264.
Ohshima et al., Expression and function of OX40 ligand on human dendritic cells, J Immunol, 1997, 159(8): 3838-3848.
Papp et al., Phase I randomized study of KHK4083, an anti-OX40 monoclonal antibody, in patients with mild to moderate plaque psoriasis, J Eur Acad Dermatol Venereol., Aug. 2017, 31(8): 1324-1332.
Perkin et al., the ALSPAC Study Team. Natural history of atopic dermatitis and its relationship to serum total immunoglobulin E in a population-based birth cohort study, Pediatr Allergy Immunol., Jun. 2004, 15(3): 221-229.
Perz et al., CD4+CD25highCD127low Regulatory T cells in peripheral blood are not an independent factor for chronic graft-versus-host disease after allogeneic stem cell transplantation, The Scientific World Journal, 2012, 2012: 606839.
Petersone et al., T Cell/B Cell Collaboration and Autoimmunity: An Intimate Relationship, Front Immunol, Mar. 6, 2019, ePublished Aug. 27, 2018, 9, Available from: https://www.frontiersin.org/article/10.3389/fimmu.2018.01941/full.
Pham et al., De novo proteomic sequencing of a monoclonal antibody raised against OX40 ligand, Anal Biochem, May 1, 2006, 352(1): 77-86.
Pippig et al., Robust B cell immunity but impaired T cell proliferation in the absence of CD134 (OX40), J. Immunol., 1999, 163(12): 6520-6529.
Pollmann et al., Hepatitis C virus-induced natural killer cell proliferation involves monocyte-derived cells and the OX40/OX40L axis, J Hepatol., Mar. 2018, 68(3): 421-430.
Publicover et al., An OX40/OX40L interaction directs successful immunity to hepatitis B virus, Sci Transl Med., Mar. 21, 2018, 10(433): eaah5766.
Saghari et al., KY1005 An Anti-OX40L MAB with Potential in Atopic Dermatitis (AD) Results of a Phase 1 Study Assessing the Safety, Pharmacokinetics, and T-Cell-Dependent Antibody Response (TDAR) in Healthy Volunteers, Abstract from 24th World Congress of Dermatology, Milan, Jun. 10-15, 2019.
Saghari et al., KY1005 An Anti-OX40L MAB with Potential in Atopic Dermatitis (AD) Results of a Phase 1 Study Assessing the Safety, Pharmacokinetics, and T-Cell- Dependent Antibody Response (TDAR) in Healthy Volunteers, Poster from 24th World Congress of Dermatology, Milan, Jun. 10-15, 2019.
Saghari et al., OX40L Blocking Monoclonal Antibody KY1005 Strongly Suppresses the Delayed-Type Hypersensitivity Skin Response to KLH in Healthy Volunteers, Abstract from 24th World Congress of Dermatology, Milan, Jun. 10-15, 2019.
Saghari et al., OX40L Blocking Monoclonal Antibody KY1005 Strongly Suppresses the Delayed-Type Hypersensitivity Skin Response to KLH in Healthy Volunteers, Poster from 24th World Congress of Dermatology, Milan, Jun. 10-15, 2019.
Sanyal et al., Atopic dermatitis in African American patients is TH2/TH22-skewed with TH1/TH17 attenuation, Ann Allergy Asthma Immunol Off Publ Am Coll Allergy Asthma Immunol., Jan. 2019, 122(1): 99-110.e6.
Silverberg et al., Adult eczema prevalence and associations with asthma and other health and demographic factors: A US population-based study, J Allergy Clin Immunol., Nov. 2013, 132(5): 1132-1138.
Simpson, Drug therapy for acute graft-versus-host disease prophylaxis, J Hematother Stem Cell Res., Jun. 2000, 9(3): 317-325.
So et al., OX40 complexes with phosphoinositide 3-kinase and protein kinase B (PKB) to augment TCR-dependent PKB signaling. J Immunol., 2011, 186(6): 3547-3555.
Sochat et al., Exhibit I—Immunosuppressant targets, First Aid for the USMLE Step 1, p. 216.
Stewart et al., The role of Fc gamma receptors in the activity of immunomodulatory antibodies for cancer, J Immunother Cancer, 2014, 2(1): 29.

(56) References Cited

OTHER PUBLICATIONS

Stuber et al., Cross-linking of OX40 ligand, a member of the TNF/NGF cytokine family, induces proliferation and differentiation in murine splenic B cells, Immunity, 1995, 2(5): 507-521.
Stüber et al., The expression of OX40 in immunologically mediated diseases of the gastrointestinal tract (celiac disease, Crohn's disease, ulcerative colitis), European Journal of Clinical Investigation, 2000, 30: 594-599.
Tkachev et al., AB3341- Striking Clinical, Molecular and Immunological Outcomes in Non-Human Primate Hematopoietic Stem Cell Transplantation Using a Novel OX40L Blockade Agent, KY1005, Combined with Rapamycin, ASH: 58th Annual Meeting and Exposition Experimental Transplantation: Basic Biology, Pre-Clinical Models, Dec. 3-6, 2016, San Diego, CA, USA.
Tkachev et al., Combined OX40L and mTOR blockade controls effector T cell activation while preserving Treg reconstitution after transplant, *Science Translational Medicine*, 2017, 9: eaan3085.
Tripathi et al., Prevention of acute graft-versus-host disease by anti-human OX40L monoclonal antibody, The Journal of Immunology [Internet], [cited Jul. 1, 20187]. Available from: http://www.jimmunol.org/content/198/1_Supplement/82.9.
Tuladhar et al., Ox40L-Ox40 pathway plays distinct roles in regulating Th2 responses but does not determine outcome of cutaneous leishmaniasis caused by Leishmania mexicana and Leishmania major, Exp. Parasitol., 2015, 148: 49-55.
Wang et al., A novel agonist anti-human OX40L monoclonal antibody that stimulates T cell proliferation and enhances cytokine secretion, Hybridoma, Aug. 2009, 28(4): 269-276.
Wang et al., An Immunotherapeutic strategy for prolonging graft survival in mice, Transplant Immunology, 2015, 33(2): 84-94.
Wang et al., Characterization and functional study of five novel monoclonal antibodies against human OX40L highlight reverse signalling: Enhancement of IgG production of B cells and promotion of maturation of DCs, Tissue Antigens, 2004, 64(5): 566-557.
Wang et al., Combination of antibodies inhibits accelerated rejection mediated by memory T cells in xenoantigen-primed mice, Xenotransplantation, 2010, 17(6): 640-468.
Watkins et al., CD28 blockade controls T cell activation to prevent graft-versus-host disease in primates, J Clin Invest., Aug. 31, 2018, 128(9): 3991-4007.
Webb et al., "OX40, OX40L and Autoimmunity: a Comprehensive Review," Clin. Rev Allergy Immunol. 50(3):312-32 (2016).
Weidinger et al., Atopic dermatitis, Nature Reviews Disease Primers, 2018, 4(1).
Weinberg et al., Science gone translational: the OX40 agonist story, Immunol. Rev., 2011, 244(1): 218-231.
Willoughby et al., OX40: Structure and function—What questions remain?, Molecular Immunology, 2017, 83: 13-22.
Wu et al., A novel polymorphism of FcgammaRIIIa (CD16) alters receptor function and predisposes to autoimmune disease, J Clin Invest., Sep. 1, 1997, 100(5):1059-1070.
Zuckier, L.S., et al., Chimeric Human-Mouse IgG Antibodies with Shuffled Constant Region Exons Demonstrate that Multiple Domains Contribute to in Vivo Half-Life, Cancer Research, vol. 58, pp. 3905-3908, 1998.
Jayazeri et al., "Fc-based cytokines: Prospects for engineering superior therapeutics", BioDrugs, 2008, 22(1): 11-26.
Lastovicka, "The Phenotypic Markers of CD4+CD25+ T Regulatory Lymphocytes", Res Immunol: Intl J. Article 119348, 2013, 14 pages.
Mirsky et al., "Antibody-Specific Model of Amino Acid Substitution for Immunological Inferences from Alignments of Antibody Sequences", Mol Biol Evol., 2014, 32(3): 806-819.
Velaga et al., "Reconstitution and phenotype of Tregs in CMV following patients receiving allogeneic hematopoietic stem cell transplantation", Immunol Invest., 2013, 42(1): 18-35.
Venken et al., "Memory CD4+CD127high T cells from patients with multiple sclerosis produce IL-17 in response to myelin antigens", J Neuroimmunol, 2010, 226: 185- 191.
Benes et al., "The role of regulatory T cells in the biology of graft versus host disease," Front Immunol., Jun. 24, 2013, 4: 163.
Cicchese et al., "Dynamic balance of pro- and anti-inflammatory signals controls disease and limits pathology", Immunol Rev., Sep. 2018, 285(1): 147-167.
Czarnowicki et al., "Evolution of pathologic T-cell subsets in patients with atopic dermatitis from infancy to adulthood", J Allergy Clin Immunol., Jan. 2020, 145(1): 215-228, Epublished Oct. 15, 2019.
Ellman et al. (1991) "[15] Biosynthetic method for introducing unnatural amino acids site-specifically into proteins," Meth. Enzymol., 202: 301-336.
EU Clinical Trials Register, "A Phase IIa, Randomised, Double Blind, Placebo Controlled, Parallel Group, Multicentre Study of an Anti OX40L Monoclonal Antibody (KY1005) in Moderate to Severe Atopic Dermatitis", Eudra CT No. 2018-002299-41, National Competent Authority—MHRA, Oct. 29, 2018.
EU Clinical Trials Register, "A Phase IIb, Randomised, Double Blind, Placebo Controlled, Parallel Group, Multicentre Dose Ranging Study of a Subcutaneous Anti-OX40L Monoclonal Antibody (KY1005) in Moderate to Severe Atopic Dermatitis", Eudra CT No. 2021-000725-28, National Competent Authority—Spain—AEMPS, Nov. 2, 2021.
EU Clinical Trials Register, "Clinical trial results: A Phase IIa, Randomised, Double Blind, Placebo Controlled, Parallel Group, Multicentre Study of an Anti OX40L Monoclonal Antibody (KY1005) in Moderate to Severe Atopic Dermatitis", Eudra CT No. 2018-002299-41, Oct. 8, 2021.
EU Clinical Trials Register, "Clinical trial results: A Phase IIb, Randomised, Double Blind, Placebo Controlled, Parallel Group, Multicentre Dose Ranging Study of a Subcutaneous Anti-OX40L Monoclonal Antibody (KY1005) in Moderate to Severe Atopic Dermatitis", Eudra CT No. 2021-000725-28, Mar. 30, 2025.
Fimmel et al., "Comorbidities of hidradenitis suppurativa (acne inversa)", Dermatoendocrinol., Jan. 2010, 2(1): 9-16.
Frew et al., "Hidradenitis suppurativa is an autoinflammatory keratinization disease: A review of the clinical, histologic, and molecular evidence", JAAD Int., Jun. 27, 2020, 1(1): 62-72.
Goronzy et al., "T-cell co-stimulatory pathways in autoimmunity", Arthritis Res Ther., 2008, 10(Suppl 1): S3, Epublished Oct. 15, 2008.
Gudjonsson et al., "Contribution of plasma cells and B cells to hidradenitis suppurativa pathogenesis", JCI Insight, Oct. 2, 2020, 5(19): e139930.
Guttman-Yassky et al., "Efficacy and Safety of Lebrikizumab, a High-Affinity Interleukin 13 Inhibitor, in Adults With Moderate to Severe Atopic Dermatitis. A Phase 2b Randomized Clinical Trial", JAMA Dermatol., Feb. 26, 2020, 156(4): 411-420.
Hambly et al., "B-cell and complement signature in severe hidradenitis suppurativa that does not respond to adalimumab", Br. J. Dermatol., Jan. 23, 2023, 188(1): 52-63.
Informed Consent Form, "A phase IIa, randomised, double blind, placebo-controlled, parallel group, multicentre study of an anti-OX40L monoclonal antibody (KY1005) in moderate to severe atopic dermatitis", Study code: KY1005-CT02, Jul. 4, 2019.
Informed Consent Form, "A phase IIb, randomised, double blind, placebo-controlled, parallel group, multicentre dose ranging study of a subcutaneous anti-OX40L monoclonal antibody (KY1005) in moderate to severe atopic dermatitis", Study code: KY1005-CT05, Jul. 14, 2021.
International Search Report & Written Opinion for PCT International Patent Application No. PCT/EP2024/060094, dated Aug. 28, 2024.
International Search Report & Written Opinion for PCT International Patent Application No. PCT/EP2024/067352, dated Oct. 1, 2024.
International Search Report & Written Opinion for PCT International Patent Application No. PCT/EP2024/067333, dated Sep. 25, 2024.
International Standard, "Needle-based injection systems for medical use—Requirements and test methods," Part 1: Needle-based injection systems, Reference No. ISO 11608-1, Third edition, Dec. 15, 2014.

(56) References Cited

OTHER PUBLICATIONS

Kang et al., "Rapid Formulation Development for Monoclonal Antibodies," BioProcess International, Apr. 12, 2016, 14(4).
Kohler et al., "Continuous cultures of fused cells secreting antibody of predefined specificity," Nature, Aug. 7, 1975, 256(5517): 495-497.
Krohn et al., "T-cell subsets in the skin and their role in inflammatory skin disorders", Allergy, Mar. 2022, 77(3): 827-842, Epublished Sep. 24, 2021.
Kurzen et al., "What causes hidradenitis suppurativa?", Expl. Dermatol., May 2008, 17(5): 455-472.
Langan et al., "Atopic dermatitis", Lancet, Aug. 1, 2020, 396(10247): 345-360.
Lé et al., "OX40-OX40L inhibition for the treatment of atopic dermatitis—focus on Rocatinlimab and Amlitelimab", Pharmaceutics, 2022, 14(12): 2753.
Lowe et al., "Immunopathogenesis of hidradenitis suppurativa and response to anti—TNF-α therapy", JCI Insight, Oct. 2, 2020, 5(19): e139932.
Luo et al., "Th17/Treg Imbalance Induced by Dietary Salt Variation Indicates Inflammation of Target Organs in Humans," Sci Rep. Jun. 2016., 29: 6: 26767.
Magenau et al., Frequency of CD4(+)CD25(hi)FOXP3(+) regulatory T cells has diagnostic and prognostic value as a biomarker for acute graft-versus-host-disease, Biol. Blood Marrow Transplant, Jul. 2010, 16(7): 907-914. Epub Mar. 17, 2010.
McCafferty et al. (Dec. 6, 1990) "Phage antibodies: filamentous phage displaying antibody variable domains," Nature, 348(6301): 552-554.
Meehan et al. (May 5, 1997) "A microinfusor device for the delivery of therapeutic levels of peptides and macromolecules," J. Controlled Release, 46(1-2): 107-116.
Mirniam et al., "Decrease of Tregs cells and increase of exhausted Treg cells as the predictors of COVID19 severity," Journal of Clinical Virology Plus, vol. 4, Issue 3, Aug. 2024: 100189.
Nie et al., "FOXP3+ Treg cells and gender bias in autoimmune diseases," Front Immunol., Sep. 28, 2015: 6: 493.
Noren et al., "A general method for site-specific incorporation of unnatural amino acids into proteins," Science, Apr. 14, 1989, 244(4901): 182-188.
Pluckthun et al., "Antibodies from Escherichia coli," The Pharmacology of Monoclonal Antibodies, Rosenberg and Moore Eds., 1994, Chapter 11, 269-315.
Robinson, "Protein deamidation," PNAS USA, Apr. 16, 2002, 99(8): 5283-5288.
Sabat et al., "Hidradenitis suppurativa", Nat. Rev. Dis. Primers, Mar. 12, 2020, 6(1): 18.
Saghari et al., "OX40L inhibition suppresses KLH-driven immune responses in healthy volunteers: a randomised controlled trial demonstrating proof-of-pharmcacoloty for KY1005", Clinical Pharmacology and Therapeutics, 2022, 111(5): 1121-1132, Epublished Mar. 1, 2022.
Simpson et al., "Two Phase 3 Trials of Dupilumab versus Placebo in Atopic Dermatitis", N. Engl. J. Med., Dec. 15, 2016, 375(24): 2335-2348. Epub Sep. 30, 2016.
Strickley et al., "A review of formulations of commercially available antibodies," J Pharm Sci., Jul. 2021, 110(7): 2590-2608.e56. Epub Mar. 2021. 28.
Tai et al., "Molecular Mechanisms of T Cells Activation by Dendritic Cells in Autoimmune Diseases", Front Pharmacol., Jun. 26, 2018, 9: 642.
Uchiyama et al., "Liquid formulation for antibody drugs," Biochim Biophys Acta, Nov. 2014, 1844(11): 2041-2052. Epub Aug. 13, 2014.
Viola et al., "Subcutaneous delivery of monoclonal antibodies: How do we get there?," J. Control Release, Sep. 28, 2018, 286: 301-314. Epub Aug. 2, 2018.
Whitaker et al., "A Formulation Development Approach to Identify and Select Stable Ultra-High-Concentration Monoclonal Antibody Formulations With Reduced Viscosities," J. Pharm. Sci., Nov. 2017, 106(11): 3230-3241. Epub Jun. 28, 2017.
Wollenberg et al., " Tralokinumab for moderate-to-severe atopic dermatitis: results from two 52-week, randomized, double-blind, multicentre, placebo-controlled phase III trials (ECZTRA 1 and ECZTRA 2)", Br. J. Dermatol., Dec. 30, 2020, 184(3): 437-449.
Zouboulis et al., "Alterations in innate immunity and epithelial cell differentiation are the molecular pillars of hidradenitis suppurativa", J. Eur. Acad. Dermatol. Venereol., Apr. 2020, 34(4): 846-861. Epub Jan. 30, 2020.
Zouboulis et al., "Hidradenitis Suppurativa and Comorbid Disorder Biomarkers, Druggable Genes, New Drugs and Drug Repurposing—A Molecular Meta-Analysis", Pharmaceutics, Dec. 26, 2021, 14(1): 44.
U.S. Appl. No. 14/700,896 U.S. Pat. No. 9,139,653, filed Apr. 30, 2015 Sep. 22, 2015, Jamie Campbell, Anti-Human Ox40L Antibodies and Methods of Treatment.
U.S. Appl. No. 14/811,163 U.S. Pat. No. 9,234,043, filed Jul. 28, 2015 Jan. 12, 2016, Jamies Campbell, Anti-Human OX40L Antibodies.
U.S. Appl. No. 14/955,843, filed Dec. 1, 2015, Jamie Campbell, Antibodies, Uses & Methods.
U.S. Appl. No. 15/122,298 2016/0368997 U.S. Pat. No. 10,669,342, filed Mar. 3, 2015 Dec. 22, 2016 Jun. 2, 2020, Jamie Campbell, Anti-Ox40l Antibodies and Methods of Treating Graft Versus Host Disease.
U.S. Appl. No. 15/259,553 2017/0002083 U.S. Pat. No. 9,587,030, filed Sep. 8, 2016 Jan. 5, 2017 Mar. 7, 2017, Jamie Campbell, Anti-OX40L Antibodies, Uses, & Methods.
U.S. Appl. No. 15/340,497 2017/0044250 U.S. Pat. No. 10,654,935, filed Nov. 1, 2016 Feb. 16, 2017 May 19, 2020, Jamie Campbell, Methods of Treating SLE With Anti-Ox40l Antibodies.
U.S. Appl. No. 15/661,658 2017/0327587 U.S. Pat. No. 11,396, filed Jul. 27, 2017 Nov. 16, 2017 Jul. 26, 2022, Jamie Campbell, Methods of Treating Comprising Administering Anti-OX40L Antibodies.
U.S. Appl. No. 16/188,541 2019/0276547, filed Nov. 13, 2018 Sep. 12, 2019, Jamie Campbell, Antibodies, Uses & Methods.
U.S. Appl. No. 17/115,021 2021/0087287 U.S. Pat. No. 11,753,479, filed Dec. 8, 2020 Mar. 25, 2021 Sep. 12, 2023, Jamie Campbell, Nucleic Acids Encoding Anti OX40L Antibodies.
U.S. Appl. No. 17/390,413 2021/0395378 U.S. Pat. No. 11,773,175, filed Jul. 30, 2021 Dec. 23, 2021 Oct. 3, 2023, Jamie Campbell, Antibodies, Uses & Methods.
U.S. Appl. No. 18/364,906 2024/0132605, filed Aug. 3, 2023 Apr. 25, 2024, Jamie Campbell, Antibodies, Uses & Methods.
U.S. Appl. No. 17/816,698, filed Aug. 1, 2022, Jamie Campbell, Anti-Human Ox40L Antibodies and Methods of Treatment.
U.S. Appl. No. 14/935,937 U.S. Pat. No. 9,434,785, filed Nov. 9, 2015 Sep. 6, 2016, Philip Bland-Ward, Anti-Human OX40L Antibodies and Methods of Treating Graft Versus Host Disease With The Same.
U.S. Appl. No. 15/142,538 2016/0264675 U.S. Pat. No. 9,512,229, filed Apr. 29, 2016 Sep. 15, 2016 Dec. 6, 2016, Philip Bland-Ward, Synergistic Combinations of OX40L Antibodies for The Treatment of GVHD.
U.S. Appl. No. 15/333,517 2017/0037137, filed Oct. 25, 2016 Feb. 9, 2017, Philip Bland-Ward, Synergistic Combinations of OX40L Antibodies for The Treatment of GVHD.
U.S. Appl. No. 15/604,495 2017/0260279 U.S. Pat. No. 9,868,789, filed May 24, 2017 Sep. 14, 2017 Jan. 16, 2018, Philip Bland-Ward, Synergistic Combinations of OX40L Antibodies for The Treatment of GVHD.
U.S. Appl. No. 15/661,584 2017/0327586 U.S. Pat. No. 9,868,790, filed Jul. 27, 2017 Nov. 16, 2017 Jan. 16, 2018, Philip Bland-Ward, Synergistic Combinations of OX40L Antibodies for The Treatment of GVHD.
U.S. Appl. No. 17/725,228 2022/0372153, filed Apr. 20, 2022 Nov. 24, 2022, Philip Bland-Ward, Synergistic Combinations of OX40L Antibodies for The Treatment of GVHD.

(56) References Cited

OTHER PUBLICATIONS

U.S. Appl. No. 16/346,675 2019/0275084 U.S. Pat. No. 11,779,604, filed May 1, 2019 Sep. 12, 2019 Oct. 10, 2023, Philip Bland-Ward, Antibodies, Combinations Comprising Antibodies, Biomarkers, Uses & Methods.
U.S. Appl. No. 18/459,995 2024/0122985, filed Sep. 1, 2023 Apr. 18, 2024, Philip Bland-Ward, Antibodies, Combinations Comprising Antibodies, Biomarkers, Uses & Methods.
U.S. Appl. No. 17/818,397 2023/0235069, filed Aug. 9, 2022 Jul. 27, 2023, Ben Porter-Brown, Treatment of Atopic Dermatitis.
U.S. Appl. No. 18/634,191 2024/0392021, filed Apr. 12, 2024 Nov. 28, 2024, Chen Zhu, Pharmaceutical Formuations Containing Anti-Ox40L Antibodies.
U.S. Appl. No. 18/748,458, filed Jun. 20, 2024, Charlotte Bernigaud, Dosing and Treatment of Immune-Mediated Diseases and Biomarkers Associated with Immune-Mediated Diseases.
Bertolini et al., "Abnormal interactions between perifollicular mast cells and CD8+ T-cells may contribute to the pathogenesis of alopecia areata", PLoS One, May 15, 2014, 9(5): e94260.
Lamb et al., "Expression of CD134 (OX40) on T-cells during the first 100 days following allogeneic bone marrow transplantation as a marker for lymphocyte activation and therapy-resistant graft-versus-host disease", Cytometry, Oct. 15, 1999, 38(5): 238-243.
ClinicalTrials,gov, "A Study of huMAb OX40L in the Prevention of Allergen-Induced Airway Obstruction in Adults With Mild Allergic Asthma", Sep. 2009, ClinicalTrials.gov ID NCT00983658, Retrieved from url: https://clinicaltrials.gov/study/NCT00983658?term=NCT00983658&rank=1.
Giacomelli et al., "T lymphocytes in the synovial fluid of patients with active rheumatoid arthritis display CD134-OX40 surface antigen," Clin. Exp. Rheumatol. 19(3):317-320 (2001).
Kamara et al., P01-46 "Roles of granzyme A in pathology of patients with atopic dermatitis", Journal of Dermatological Science, Oct. 1, 2016, 84(1): E17.
Liu et al., "CD127 expression inversely correlates with FoxP3 and suppressive function of human CD4+ T reg cells", The Journal of Experimental Medicine, Jul. 10, 2006, 203(7): 1701-1711.
Nedoszytko, "The role of regulatory T cells and genes involved in their differentiation in pathogenesis of selected inflammatory and neoplastic skin diseases. Part II: The Treg role in skin diseases pathogenesis", Adv Dermatol Allergol., 2017, XXXIV(5): 405-417.
Ou et al., "T regulatory cells in atopic dermatitis and subversion of their activity by superantigens", Dermatologic and ocular diseases, J Allergy Clin Immunol., 113(4): 756-763. 2004.
Wang et al., Application of OX40 in Immunotherapy, Foreign Medical Sciences (Section of Immunology Foreign Medical Sciences), vol. 26 (5) (2003).
Wikipedia, "NOD mice", Retrieved from url: https://en.wikipedia.org/wiki/NOD_mice, last updated Sep. 16, 2023.
Rose, "Prediction and Prevention of Autoimmune Disease in the 21st Century: A Review and Preview", American Journal of Epidemiology, Mar. 1, 2016, 183(5): 403-406, Epublished Feb. 17, 2016.
Blauvelt et al., "Improvements on Patient-Reported Outcome (PRO) Measures With 24 Weeks of Amlitelimab Treatment in Adults With Moderate-to-Severe Atopic Dermatitis: Results From a Phase 2b Trial (STREAM-AD)", Mar. 8, 2024, pp. 1-1.
ClinicalTrials.gov, "Study Testing Response Effect of KY1005 Against Moderate-to-Severe Atopic Dermatitis, The STREAM-AD Study (STREAM-AD)", Clinical Trials.gov ID: NCT05131477, Dec. 13, 2021.
Gori et al., "Head and Neck Atopic Dermatitis: Still a Challenging Manifestation in the Biologic Era", Expert Opinion on Biological Therapy, Jun. 14, 2023, 23(7): 575-577.
Reich et al., "Impact of Amlitelimab (an Anti-OX40 Ligand Antibody) on Atopic Dermatitis of the Head and Neck: Post Hoc Results From the Stream Ad Phase 2b Study of Moderate to Severe Atopic Dermatitis", Sep. 25, 2024, pp. 1-1.
ClinicalTrials.gov, Record for Study for "A Study of Subcutaneous KY1005 in Healthy Volunteers" ClinicalTrials.gov ID: NCT04449939, Dec. 17, 2020.
ClinicalTrials.gov, "A Study of KY1005 in Healthy Volunteers", Clinical Trials.gov ID: NCT03161288, May 29, 2017.

* cited by examiner

DTH = delayed type hypersensitivity; PK = pharmacokinetics

Percentage change in anti-TT IgG and IgM titre versus placebo at Day 85, Cohorts 4 to 8 (95% CI; PP analysis population) adjusted for baseline variability Bar Chart of vIGA 0/1 Responders Over Time (FAS)

~5.5 months without treatment

KY1005 Low Dose

| Subject | Screening | Baseline | Day 15 | Day 29 | Day 57 | Last IMP dose<br>Day 85 | Primary endpoint<br>Day 113 | Day 169 | Day 253 |
|---|---|---|---|---|---|---|---|---|---|
| 202-1001 | 32.7 | 36.9 | 29.6 | 21.4 | 8.9 | 7.6 | 3.5 | 2.9 | WD |
| 213-1001 | 31.1 | 32.3 | 18.6 | 11.4 | 18 | 9.6 | 2.8 | 0.8 | 19.8 |
| 304-1002 | 32.4 | 44.4 | 6.8 | 9.9 | 28.8 | 4.2 | 1.5 | 11.1 | 17.2 |
| 113-1002 | 40.6 | 48 | 16.3 | 14 | 6.6 | 1.4 | 2.1 | 4.1 | 16.5 |
| 203-1008 | 24.6 | 27.2 | 24.2 | 23.6 | 3.6 | 3.6 | 3.6 | 1.9 | 2.8 |
| 204-1004 | 22.3 | 34 | 16 | 13.3 | 7.8 | 2.8 | 2.8 | 0.7 | 1.8 |
| 303-1002 | 42.7 | 47.2 | 57.6 | 26.8 | 25.6 | 17.8 | 4.8 | 0 | 1.6 |
| 206-1009 | 16.8 | 19.9 | 12 | 19.3 | 7.8 | 1.1 | 1 | 0.4 | 0.6 |
| 206-1002 | 13.3 | 26.5 | 17.6 | 20.8 | 13.4 | 11.3 | 1.3 | 0.5 | 0.3 |
| 203-1003 | 16.9 | 39.2 | 36.6 | 4.3 | 5.2 | 0.5 | 0 | 0 | 0 |
| 213-1005 | 30.9 | 27.5 | 21.5 | 14.3 | 2.1 | 2.9 | 3 | 2.7 | 5.2 |
| 212-1001 | 34 | 29.8 | 22.2 | 10.5 | 7 | 0 | 0 | 0 | 0 |

FIG. 7

| Group | Subject | Screening | Baseline | Day 15 | Day 29 | Day 57 | Day 85 | Day 113 | Day 169 | Day 253 |
|---|---|---|---|---|---|---|---|---|---|---|
| KY1005 High Dose | 207-1006 | 55 | 61 | 44.2 | 22 | 3.2 | 0 | 0 | 0.2 | WD |
| | 207-1002 | 54.9 | 45.6 | 3.4 | 26.7 | 3.2 | 0 | 3.7 | 0 | WD |
| | 213-1007 | 19.4 | 24.5 | 17 | 12 | 11.6 | 8.5 | 5.2 | 6.6 | 6.8 |
| | 206-1006 | 15.7 | 24.1 | 17 | 16.6 | 13.5 | 3.6 | 2.8 | 1.2 | 1.6 |
| | 206-1003 | 23.5 | 23.6 | 13.6 | 18.1 | 11.7 | 5.2 | 0.7 | 0.4 | 0.3 |
| | 206-1010 | 12.2 | 21.8 | 13.8 | 20.6 | 11.1 | 0.3 | 0.4 | 0.2 | 0.2 |
| | 303-1001 | 13.7 | 17.1 | 21.4 | 2.2 | 7 | 0.5 | 0.6 | 0 | 0 |
| | 210-1005 | 26 | 26.7 | 16 | 1.9 | 0.9 | 0.8 | 0.8 | 0.4 | 0 |
| | 303-1005 | 25.5 | 33.2 | 20 | 9.6 | 2.1 | 1.9 | 0.4 | 0.4 | 1.4 |
| | 212-1002 | 27.6 | 38.8 | 9.4 | 2.8 | 3.9 | 0 | 0 | 0 | 2 |

| Group | Subject | Screening | Baseline | Day 15 | Day 29 | Day 57 | Day 85 | Day 113 | Day 169 | Day 253 |
|---|---|---|---|---|---|---|---|---|---|---|
| Placebo | 212-1006 | 18.2 | 23.8 | 14.4 | 9.8 | 4.2 | 20 | 0 | 1.2 | 2.6 |
| | 113-1005 | 16.8 | 34.4 | 21.6 | 21.2 | 18.6 | 5 | 2.4 | 8.5 | 3 |

Non QC'd output | WD = withdrawn | Cut off: 9 Oct 2020

FIG. 7 (Continued)

Mean serum concentration-time plots (linear and semi-logarithmic) of KY1005 up to 92 days after single intravenous and subcutaneous doses: PK concentration population (n=8 per group)

Mean serum concentration-time plots (linear and semi-logarithmic) of KY1005 up to 24 h after single intravenous and subcutaneous doses (n=8 per group)

Predicted Cmin at Week 24 for Induction Senarios I-III (varying doses) and IV - XII (varying regimes)

Weight: 50 kg, 75 kg, 100 kg, 120 kg

Cmin, SS of Reference: 0.15 mg/kg Q4W IV, 0.45 mg/kg Q4W IV

IV MODEL: ../Output/71_Select_Final_Models_IV_SC/02_FINALMODEL_SC_IV_cov
SC assumptions: Fabs1 = 0.779, ka = 0.222, CV(Fabs1) = 0.05, CV(ka) = 0.477

Predicted Cmin at Week 24 for Induction Senarios I-III (varying doses) and IV - XII (varying regimes)

Weight
50 kg 75 kg 100 kg 120 kg

Cmin, SS of Reference
0.15 mg/kg Q4W IV 0.45 mg/kg Q4W IV

IV MODEL: ../Output/71_Select_Final_Models_IV_SC/02_FINALMODEL_SC_IV_cov
SC assumptions: Fabs1 = 0.779, ka = 0.222, CV(Fabs1) = 0.05, CV(ka) = 0.477

Predicted Cmin after 24 weeks of Induction Period

Weight 50 kg — 75 kg — 100 kg — 120 kg

Cmin reference 0.15 mg/kg Q4W IV — 0.45 mg/kg Q4W IV

Circulating IL-13 over time†

TREATMENT OF ATOPIC DERMATITIS

RELATED APPLICATIONS

This application claims the benefit of Great Britain Priority Application Nos. GB 2111492.1, filed on Aug. 10, 2021, GB 2115152.7, filed on Oct. 21, 2021, GB 2204211.3, filed on Mar. 24, 2022, and GB 2204291.5, filed on Mar. 25, 2022, the contents of which are incorporated herein by reference in their entireties for all purposes.

Sequence Listing

The instant application contains a Sequence Listing which has been submitted electronically in XML format and is hereby incorporated by reference in its entirety. Said XML copy, created on Aug. 8, 2022, is named 732195_SA9-641_ST26.xml and is 236,697 bytes in size.

BACKGROUND

Atopic dermatitis (AD) is the most common type of eczema, affecting more than 9.6 million children and about 16.5 million adults in the United States. It is a chronic condition that can come and go for years or throughout life, and can overlap with other types of eczema.

In people with AD, the immune system becomes disordered and overactive. This triggers inflammation that damages the skin barrier, leaving it dry and prone to itching and rashes that may appear purple, brown or grayish hue in darker skin tones and red in lighter skin tones.

Research shows that some people with eczema, especially atopic dermatitis, have a mutation of the gene responsible for creating filaggrin. Filaggrin is a protein that helps our bodies maintain a healthy, protective barrier on the very top layer of the skin. Without enough filaggrin to build a strong skin barrier, moisture can escape and bacteria, viruses and more can enter. This is why many people with AD have very dry and infection-prone skin.

Itching is the hallmark of AD, with some data showing that more than 85% of people with the condition experience this distressing symptom every day. Sore or painful skin and poor sleep caused by itching are also common.

People with AD can get rashes anywhere on the body that can ooze, weep fluid and bleed when scratched, making skin vulnerable to infection. Skin can become dry and discoloured, and repeated scratching can cause thickening and hardening—a process called lichenification. Although AD can affect any part of the body, it most often affects the hands, insides of the elbows, backs of the knees and the face and scalp in children.

Atopic dermatitis typically begins in childhood, usually in the first six months of a baby's life. Even though it's a common form of eczema, it's also severe and long-lasting. When you or your child have atopic dermatitis, it may improve at times; but at other times, it may get worse. In some children, symptoms may taper off as they grow up, while other children will have atopic dermatitis flares into adulthood.

Atopic dermatitis exists with two other allergic conditions: asthma and hay fever (allergic rhinitis). People who have asthma and/or hay fever or who have family members who do, are more likely to develop AD.

There is currently no cure for AD, but depending on the severity of AD, treatments include lifestyle changes, over-the-counter (OTC) remedies or prescription medication.

The main treatments for AD are:

- emollients (moisturisers)—used every day to stop the skin becoming dry, and
- topical corticosteroids—creams and ointments used to reduce swelling and redness during flare-ups Other treatments include:

- topical pimecrolimus or tacrolimus for eczema in sensitive sites not responding to simpler treatment
- antihistamines for severe itching
- bandages or special body suits to allow the body to heal underneath
- DUPIXENT (dupilumab) is indicated for the treatment of adult patients with moderate-to-severe AD whose disease is not adequately controlled with topical prescription therapies or when those therapies are not advisable. DUPIXENT can be used with or without topical corticosteroids. As described for example by Tubau et al., Immunotherapy 13:327-344, 2021, dupilumab, which is currently the only approved mAb for AD treatment, blocks IL-13 but also IL-4 by inhibiting the IL-4Rα1 subunit of their common receptor. It is highly effective, with an excellent safety profile, even though a significant proportion of patients develop dry eyes and/or blepharoconjunctivitis that complicate their management.
- Pipeline products include JAK inhibitors, IL-13 inhibitors and IL-31 inhibitors. However, JAK inhibitors are associated with safety concerns (e.g., black-box warning) and Anti-IL-31 shows poorer efficacy.

OX40 ligand (OX40L) is a TNF family member; a 34 kDa type II transmembrane protein. The crystallized complex of human OX40 and OX40L is a trimeric configuration of one OX40L (trimer) and three OX40 monomers. The human extracellular domain is 42% homologous to mouse OX40L.

OX40L is not constitutively expressed but can be induced on professional APCs such as B-cells, dendritic cells (DCs) and macrophages. Other cell types such as Langerhans cells, endothelial cells, smooth muscle cells, mast cells and natural killer (NK) cells can be induced to express OX40L. T-cells can also express OX40L. The OX40L receptor, OX40, is expressed on activated T-cells ($CD4^+$ and $CD8^+$ T-cells, Th2, Th1 and Th17 cells) and $CD4^+$ $Foxp3^+$ cells, even in the absence of activation.

The interaction between OX40 and OX40L occurs during the T-cell-DC interaction 2 or 3 days after antigen recognition. After leaving DCs, the OX40-expressing T-cell may interact with an OX40L-expressing cell other than a DC and receive an OX40 signal from this cell, which may provide essential signals for the generation of memory T-cells, the enhancement of Th2 response and the prolongation of the inflammatory responses. OX40 signals into responder T-cells render them resistant to Treg mediated suppression.

WO2015/132580, WO2016/139482 and WO2018/083248 describe anti-human OX40L (hOX40L) antibodies and fragments and medical applications for treating or preventing hOX40L-mediated diseases or conditions in humans.

SUMMARY

In some embodiments is provided a treatment targeting an upstream OX40L dependent pathway, to be effective in treating inflammatory diseases or disorders, immune-mediated diseases or disorders, inflammatory skin diseases or disorders. Some embodiments provide a treatment targeting an upstream OX40L dependent pathway, to be effective in treating both acute and chronic AD. The treatment is associated with an attractive dosing frequency, a low-volume induction and maintenance regime and strong efficacy and safety profiles. Advantages of formulations for subcutaneous administration include being more patient-friendly, as it may be administered by the patient at home, and an inconvenient physician visit can thus be avoided. Also, administration times may shortened, which is beneficial for patients and healthcare providers. Some embodiments also provide reduced needle burden, i.e., a reduced number of injections per year, which will result in potentially improved compliance and thus patient outcomes. Some embodiments also provide treatments with surprisingly consistent pharmacokinetic (PK) parameter estimates in IV and subcutaneous population PK models, which are not meaningfully impacted by anti-drug antibodies, which is especially surprising for subcutaneous administration. To this end, some embodiments provide:

In a first configuration, there is provided a method of treating Atopic Dermatitis in a human subject comprising administering a therapeutically effective amount of an anti-OX40L antibody, or antigen-binding fragment thereof, wherein the antibody or fragment thereof is administered via injection.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is administered via injection and the method comprises administering at least one injection at a dose of at least about 20 mg of the antibody or fragment thereof.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is a disease modifying drug.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is administered at least twice with at least one interval of 2 to 6 months.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is administered at least twice with at least one interval of 6 months.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration EASI score is reduced at least 10% relative to a baseline EASI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration vIGA-AD score is reduced at least 10% relative to a baseline vIGA-AD score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration IGA-AD score is reduced at least 10% relative to a baseline IGA-AD score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration BSA score is reduced at least 10% relative to a baseline BSA score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration SCORAD index is reduced at least 10% relative to a baseline SCORAD index.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration PO-SCORAD index is reduced at least 10% relative to a baseline PO-SCORAD index.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration DQLI score is reduced at least 10% relative to a baseline DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein the subject is a chronic Atopic Dermatitis patient.

In a second configuration, there is provided a glass vial containing an anti-OX40L antibody, or antigen-binding fragment thereof.

In a third configuration, there is provided a prefilled syringe containing an anti-OX40L antibody, or antigen-binding fragment thereof.

In a fourth configuration, there is provided a microinfusor containing an anti-OX40L antibody, or antigen-binding fragment thereof.

In a fifth configuration, there is provided a pen delivery device containing an anti-OX40L antibody, or antigen-binding fragment thereof.

In a sixth configuration, there is provided an autoinjector delivery device containing an anti-OX40L antibody, or antigen-binding fragment thereof.

In an seventh configuration, there is provided a kit comprising a glass vial, drug delivery device, prefilled syringe, microinfusor, pen delivery device or autoinjector according to any of the third to sixth configurations; and a label and/or instructions specifying administration in accordance with a method of the first configuration.

In a further configuration, there is provided an anti-OX40L antibody, or antigen-binding fragment thereof, for use in a method of treating Atopic Dermatitis in accordance with a method of the first configuration.

In a further configuration, there is provided a glass vial, drug delivery device, prefilled syringe, microinfusor, pen delivery device, autoinjector or kit according to any one of the second to seventh configurations, for use in a method of treating Atopic Dermatitis in accordance with a method of the first configuration.

In a further configuration, there is provided the use of an anti-OX40L antibody, or antigen-binding fragment thereof, for the manufacture of a medicament for the treatment of Atopic Dermatitis in accordance with a method of the first configuration.

In a further configuration, there is provided the use of a glass vial, drug delivery device, prefilled syringe, microinfusor, pen delivery device, autoinjector or kit according to any one of third to eighth configurations, for the manufacture of a medicament for the treatment of Atopic Dermatitis in accordance with a method of the first configuration.

In a further configuration, there is provided a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered via injection.

In a further configuration, there is provided a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered via subcutaneous injection.

In a further configuration, there is provided an anti-OX40L antibody, or antigen-binding fragment thereof, for use in a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered via injection.

In a further configuration, there is provided an anti-OX40L antibody, or antigen-binding fragment thereof, for use in a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered via subcutaneous injection.

In another configuration, there is provided a method of treating atopic dermatitis in a subject, the method comprising selecting a subject having atopic dermatitis, and administering to the subject a pharmaceutical composition comprising a therapeutically effective amount of an anti-OX40L antibody or antigen-binding fragment thereof, wherein the anti-OX40L antibody or antigen-binding fragment thereof comprises heavy chain complementarity regions (HCDRs) of SEQ ID NOs: 42, 44 and 46, and light chain complementarity determining regions (LCDRs) of SEQ ID NOs: 56, 58 and 60.

References to the first configuration as used herein include the "first configuration" and any "alternative statement of the first configuration". The features of any statement of the first configuration may read in combination with any of the second and subsequent configurations of the invention.

BRIEF DESCRIPTION OF FIGURES

FIG. 7 depicts EASI scores in a table for patients receiving high or low dose KY1005 or placebo during the study and through the safety follow up period. This figure represents all patients who achieved a vIGA0/1 at Week 16 and were assessed for efficacy during the safety follow up period. This figure shows that in those subjects who achieved vIGA0/1 at day 113, there was evidence of long and sustained response up to 5.5 months following last dose (~70% of those receiving KY1005).

FIG. 20A depicts Induction Scenario I (200 mg once 10 every four weeks (Q4W) SC, 100 mg Q4W SC, 50 mg Q4W SC, and 25 mg Q4W SC). FIG. 20B depicts Induction Scenario II (300 mg Q4W SC, 250 mg Q4W SC, 200 mg Q4W SC, and 150 mg Q4W SC). FIG. 20C depicts Induction Scenario III (500 mg Q4W SC, 450 mg Q4W SC, 400 mg Q4W SC, and 350 mg Q4W SC). FIG. 20D depicts Induction Scenario IV (125 mg once every 2 weeks (Q2W) SC, 125 mg Q4W SC, 125 mg once every six weeks (Q6W) SC, and 125 mg once every 8 weeks (Q8W) SC). FIG. 20E depicts Induction Scenario V (150 mg Q2W SC, 150 mg Q4W SC, 150 mg Q6W SC, and 150 mg Q8W SC). FIG. 20F depicts Induction Scenario VI (200 mg Q2W SC, 200 mg Q4W SC, 200 mg Q6W SC, and 200 mg Q8W SC).

FIG. 21A depicts Induction Scenario VII (250 mg Q2W SC, 250 mg Q4W SC, 250 mg Q6W SC, and 250 mg Q8W SC). FIG. 21B depicts Induction Scenario VIII (300 mg Q2W SC, 300 mg Q4W SC, 300 mg Q6W SC, and 300 mg Q8W SC). FIG. 21C depicts Induction Scenario IX (350 mg Q2W SC, 350 mg Q4W SC, 350 mg Q6W SC, and 350 mg Q8W SC). FIG. 21D depicts Induction Scenario X (400 mg Q2W SC, 400 mg Q4W SC, 400 mg Q6W SC, and 400 mg Q8W SC). FIG. 21E depicts Induction Scenario XI (450 mg Q2W SC, 450 mg Q4W SC, 450 mg Q6W SC, and 450 mg Q8W SC). FIG. 21F depicts Induction Scenario XII (500 mg Q2W SC, 500 mg Q4W SC, 500 mg Q6W SC, and 500 mg Q8W SC).

FIG. 22A depicts maintenance Q8W after week 52, FIG. 22B depicts maintenance Q12W after week 52, and FIG. 22C depicts maintenance Q16W after week 52.

FIG. 23A depicts four doses of 62.5 mg KY1005 administered every 4 weeks (Q4W). FIG. 23B depicts four doses of 125 mg KY1005 administered Q4W. FIG. 23C depicts four doses of 250 mg KY1005 administered Q4W. FIG. 23D depicts one dose of 500 mg KY1005 followed by three doses of 250 mg administered Q4W.

FIG. 29A-B illustrate that KY1005 is associated with reduction in Th2-related serum cytokine. FIG. 29**C-F illustrate that KY1005 is associated with reduction in cytokines typically linked to Th22 & Th17 responses.

DETAILED DESCRIPTION

Figure 1:
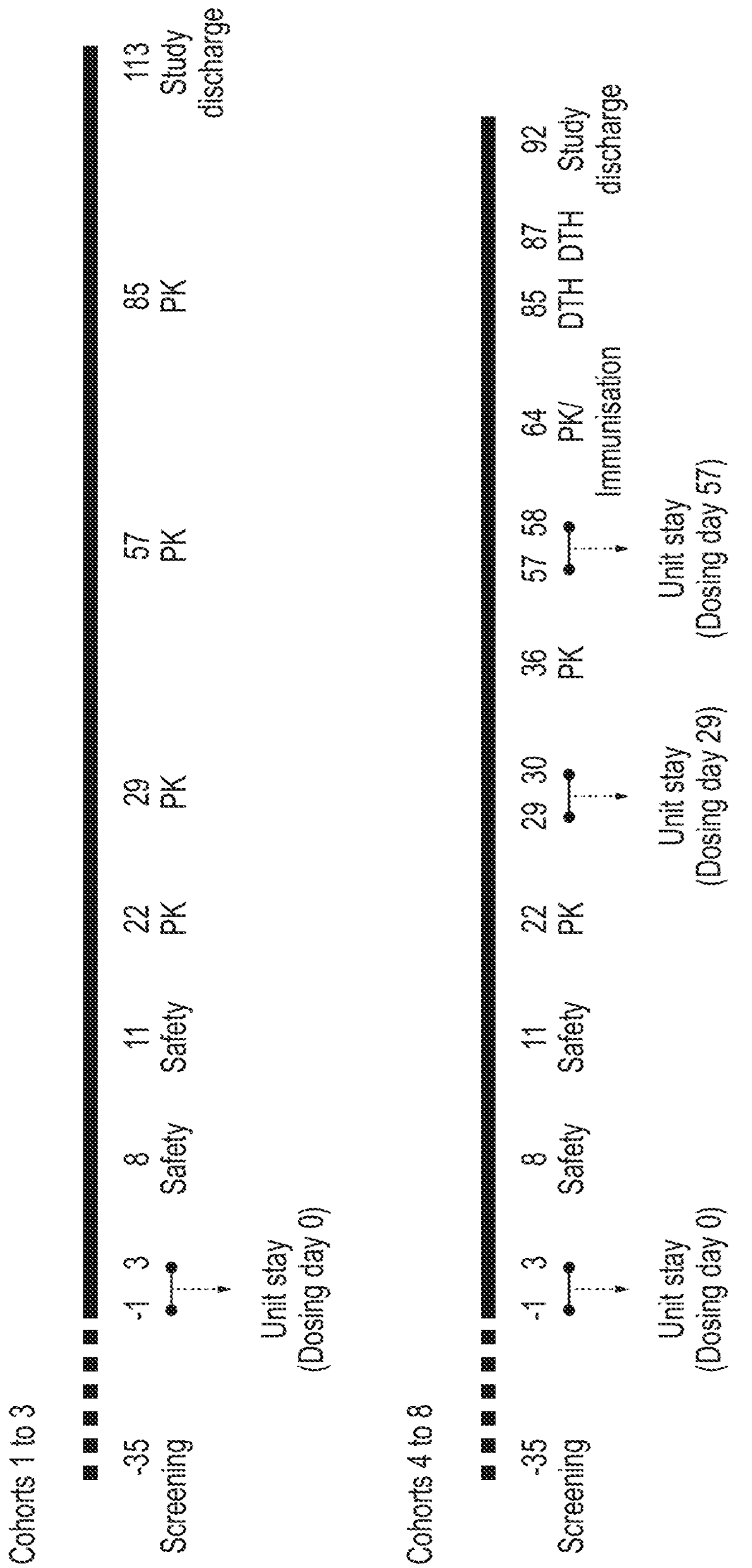
FIG. 1 graphically depicts the overview of study design of Example 1. Healthy volunteers in Cohorts 1 to 3 received a single I.V. infusion of KY1005 (0.006, 0.018 or 0.05 mg/kg) or placebo, with blood samples taken up to Day 113. Cohorts 4 to 8 received an initial loading dose on Day 1 (0.15, 0.45, 1.35, 4.0 or 12 mg/kg), and two maintenance doses (50% of the loading dose), administered on Days 29 and 57.

In a first configuration, there is provided a method of treating Atopic Dermatitis in a human subject comprising administering a therapeutically effective amount of an anti-OX40L antibody, or antigen-binding fragment thereof, wherein the antibody or fragment thereof is administered via injection. The antibody or fragment thereof may be administered via subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is a disease modifying drug. After administering the disease modifying drug, the subject may achieve an IGA-AD score of 0 or 1 for at least six months. Any other suitable disease severity measure described herein, such as EASI75 or EASI90, which may indicate disease modification, may be substituted for an IGA-AD score of 0 or 1. The at least six months may be at least seven months, at least eight months or at least nine months. After treatment with the disease modifying drug is stopped, the subject may maintain an IGA-AD score of 0 or 1 for at least six months. The at least six months may be at least seven months, at least eight months or at least nine months. A therapeutic effect may persist after the last administration of the antibody or fragment thereof by at least around six half lives of the antibody or fragment thereof. The at least six half lives may be at least around seven half lives, at least around eight half lives or at least around nine half lives of the antibody or fragment thereof. The antibody or fragment thereof may be administered via injection, optionally subcutaneous injection. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, BSA score, SCORAD index, PO-SCORAD index and/or DQLI score may be reduced at least 10% relative to a corresponding baseline EASI score, vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is administered via injection and the method comprises administering at least one injection at a dose of at least about 20 mg of the antibody or fragment thereof. The antibody or fragment thereof may be administered via subcutaneous injection. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, BSA score, SCORAD index, PO-SCORAD index and/or DQLI score may be reduced at least 10% relative to a corresponding baseline EASI score, vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is a disease modifying drug. The antibody or fragment thereof may be administered via injection, optionally subcutaneous injection. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, BSA score, SCORAD index, PO-SCORAD index and/or DQLI score may be reduced at least 10% relative to a corresponding baseline EASI score, vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is administered at least twice with at least one interval of 2 to 6 months. The antibody or fragment thereof may be administered at least twice with at least one interval of 2 to 5.5 months, at least one interval of 2 to 5 months, at least one interval of 2 to 4.5 months, or at least one interval of 2 to 4 months. The antibody or fragment thereof may be administered at least twice with at least one interval of around 3 months. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The subject may be a chronic Atopic Dermatitis patient. A post-administration EASI score, vIGA-AD score, IGA-AD score, BSA score, SCORAD index, PO-SCORAD index and/or DQLI score may be reduced at least 10% relative to a corresponding baseline EASI score, vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein the antibody or fragment thereof is administered at least twice with at least one interval of 6 months. The antibody or fragment thereof may be administered at least twice with at least one interval of 5.5 months, at least one interval of 5 months, at least one interval of 4.5 months, or at least one interval of 4 months. The antibody or fragment thereof may be administered at least twice with at least one interval of around 3 months. Any period expressed in months may alternatively be expressed in weeks, for example in one embodiment one month is equal to four weeks. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The subject may be a chronic Atopic Dermatitis patient. A post-administration EASI score, vIGA-AD score, IGA-AD score, BSA score, SCORAD index, PO-SCORAD index and/or DQLI score may be reduced at least 10% relative to a corresponding baseline EASI score, vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein the subject is a chronic Atopic Dermatitis patient. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. A post-administration EASI score, vIGA-AD score, IGA-AD score, BSA score, SCORAD index, PO-SCORAD index and/or DQLI score may be reduced at least 10% relative to a corresponding baseline EASI score, vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration EASI score is reduced at least 10% relative to a baseline EASI score. The post-administration EASI score may be reduced at least 10% relative to the baseline EASI score on day 15 through at least day 113 (optionally on day 7 through at least day 113 or on day 29 through at least day 113) after administration of the anti-OX40L antibody, or antigen-binding fragment thereof. The post-administration EASI score may be reduced at least 10% relative to the baseline EASI score on day 15 through at least day 169 or at least day 253 after administration of the anti-OX40L antibody, or antigen-binding fragment thereof. The post-administration EASI score may be reduced at least 20% relative to the baseline EASI score on around day 113 after administration of the anti-OX40L antibody, or antigen-binding fragment thereof. The post-administration EASI score may be reduced at least 15%, at least 20%, at least 30%, at least 40% or at least 45% relative to the baseline EASI score on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration vIGA-AD score, IGA-AD score, BSA score, SCORAD index, PO-SCORAD index and/or DQLI score may be reduced at least 10% relative to a corresponding baseline vIGA-AD score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration vIGA-AD score is reduced at least 10% relative to a baseline vIGA-AD score. The post-administration vIGA-AD score may be reduced at least 10% relative to the baseline vIGA-AD score on day 15 through at least day 113 (optionally on day 7 through at least day 113 or on day 29 through at least day 113) after administration of the anti-OX40L antibody, or antigen-binding fragment thereof. The post-administration vIGA-AD score may be reduced at least 10% relative to the baseline vIGA-AD score on day 15 through at least day 169 or at least day 253 after administration of the anti-OX40L antibody, or antigen-binding fragment thereof. The post-administration vIGA-AD score may be reduced at least 20% relative to the baseline vIGA-AD score on around day 113 after administration of the anti-OX40L antibody, or antigen-binding fragment thereof. The post-administration vIGA-AD score may be reduced at least 15%, at least 20%, at least 30%, at least 40% or at least 45% relative to the baseline vIGA-AD score on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, IGA-AD score, BSA score, SCORAD index, PO-SCORAD index and/or DQLI score may be reduced at least 10% relative to a corresponding baseline EASI score, IGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration IGA-AD score is reduced at least 10% relative to a baseline IGA-AD score. The post-administration IGA-AD score may be reduced at least 10% relative to the baseline IGA-AD score on day 15 through at least day 113 (optionally on day 7 through at least day 113 or on day 29 through at least day 113) after administration of the anti-OX40L antibody, or antigen-binding fragment thereof. The post-administration IGA-AD score may be reduced at least 10% relative to the baseline IGA-AD score on day 15 through at least day 169 or at least day 253 after administration of the anti-OX40L antibody, or antigen-binding fragment thereof. The post-administration IGA-AD score may be reduced at least 20% relative to the baseline IGA-AD score on around day 113 after administration of the anti-OX40L antibody, or antigen-binding fragment thereof. The post-administration IGA-AD score may be reduced at least 15%, at least 20%, at least 30%, at least 40% or at least 45% relative to the baseline IGA-AD score on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, BSA score, SCORAD index, PO-SCORAD index and/or DQLI score may be reduced at least 10% relative to a corresponding baseline EASI score, vIGA-AD score, BSA score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration BSA score is reduced at least 10% relative to a baseline BSA score. The post-administration BSA score may be reduced at least 10% relative to the baseline BSA score on day 29 through at least day 113 (optionally on day 7 through at least day 113 or on day 15 through at least day 113) after administration of the anti-OX40L antibody, or antigen-binding fragment thereof. The post-administration BSA score may be reduced at least 20% relative to the baseline BSA score on around day 113 after administration of the anti-OX40L antibody, or antigen-binding fragment thereof. The post-administration BSA score may be reduced at least 30% or at least 35% relative to the baseline BSA score on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, SCORAD index, PO-SCORAD index and/or DQLI score may be reduced at least 10% relative to a corresponding baseline EASI score, vIGA-AD score, IGA-AD score, SCORAD index, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration SCORAD index is reduced at least 10% relative to a baseline SCORAD index. The post-administration SCORAD index may be reduced at least 10% relative to the baseline SCORAD index on day 29 through at least day 113 (optionally on day 7 through at least day 113 or on day 15 through at least day 113) after administration of the anti-OX40L antibody, or antigen-binding fragment thereof. The post-administration SCORAD index may be reduced at least 20% relative to the baseline SCORAD index on around day 113 after administration of the anti-OX40L antibody, or antigen-binding fragment thereof. The post-administration SCORAD index may be reduced at least 30% or at least 35% relative to the baseline SCORAD index on around day 113 after administration of the anti-OX40L antibody, or antigen-binding fragment thereof. The post-administration SCORAD index may be reduced at least 45% or at least 60% relative to the baseline SCORAD index on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, BSA score, PO-SCORAD index and/or DQLI score may be reduced at least 10% relative to a corresponding baseline EASI score, vIGA-AD score, IGA-AD score, BSA score, PO-SCORAD index and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration PO-SCORAD index is reduced at least 10% relative to a baseline PO-SCORAD index. The post-administration PO-SCORAD index may be reduced at least 10% relative to the baseline PO-SCORAD index on day 29 through at least day 113 (optionally on day 7 through at least day 113 or on day 15 through at least day 113) after administration of the anti-OX40L antibody, or antigen-binding fragment thereof. The post-administration PO-SCORAD index may be reduced at least 15% relative to the baseline PO-SCORAD index on around day 113 after administration of the anti-OX40L antibody, or antigen-binding fragment thereof. The post-administration PO-SCORAD index may be reduced at least 20% or at least 30% relative to the baseline PO-SCORAD index on around day 113 after administration of the anti-OX40L antibody, or antigen-binding fragment thereof. The post-administration PO-SCORAD index may be reduced at least 40% or at least 50% relative to the baseline PO-SCORAD index on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, BSA score, SCORAD index, and/or DQLI score may be reduced at least 10% relative to a corresponding baseline EASI score, vIGA-AD score, IGA-AD score, BSA score, SCORAD index, and/or DQLI score.

In an alternative statement of the first configuration, there is provided a method of treating Atopic Dermatitis in a human subject comprising administering a therapeutically effective amount of an anti-OX40L antibody, or antigen-binding fragment thereof, wherein a post-administration DQLI score is reduced at least 10% relative to a baseline DQLI score. The post-administration DQLI score may be reduced at least 10% relative to the baseline DQLI score on day 85 through at least day 113 (optionally on day 7 through at least day 113 or on day 15 through at least day 113 or on day 29 through at least day 113) after administration of the anti-OX40L antibody, or antigen-binding fragment thereof. The post-administration DQLI score may be reduced at least 20% relative to the baseline DQLI score on around day 113 after administration of the anti-OX40L antibody, or antigen-binding fragment thereof. The post-administration DQLI score may be reduced at least 30% or at least 35% relative to the baseline DQLI score on around day 113 after administration of the anti-OX40L antibody, or antigen-binding fragment thereof. The antibody or fragment thereof may be administered via injection, optionally subcutaneous injection. The antibody or fragment thereof may be a disease modifying drug. Optionally, the method comprises administering at least one injection at a dose of at least about 20 mg of the antibody or fragment thereof. The antibody or fragment thereof may be administered at least twice with at least one interval of 2 to 6 months. The antibody or fragment thereof may be administered at least twice with at least one interval of 6 months. The subject may be a chronic Atopic Dermatitis patient. A post-administration EASI score, vIGA-AD score, IGA-AD score, BSA score, SCORAD index and/or PO-SCORAD index may be reduced at least 10% relative to a corresponding baseline EASI score, vIGA-AD score, IGA-AD score, BSA score, SCORAD index and/or PO-SCORAD index.

Any feature described in connection with one statement of the first configuration is explicitly contemplated in combination with the features of any other statement of the first configuration. Any one statement of the first configuration may be read in combination with any other part of the disclosure, unless otherwise apparent from the context. Any optional features described in any part of this disclosure, in connection with any one statement of the first configuration or any alternative statement of the first configuration, may be read in combination with any other part of the disclosure, unless otherwise apparent from the context.

In a further configuration, there is provided a method of treating inflammatory diseases or inflammatory disorders in a human subject comprising administering a therapeutically effective amount of an anti-OX40L antibody, or antigen-binding fragment thereof, wherein the antibody or fragment thereof is administered via injection.

In a further configuration, there is provided a method of treating immune-mediated diseases or immune-mediated disorders in a human subject comprising administering a therapeutically effective amount of an anti-OX40L antibody, or antigen-binding fragment thereof, wherein the antibody or fragment thereof is administered via injection.

In a further configuration, there is provided a method of treating inflammatory skin diseases or inflammatory skin disorders in a human subject comprising administering a therapeutically effective amount of an anti-OX40L antibody, or antigen-binding fragment thereof, wherein the antibody or fragment thereof is administered via injection.

In a further configuration, there is provided an anti-OX40L antibody, or antigen-binding fragment thereof, for use in a method of treating inflammatory diseases or inflammatory disorders in a human subject comprising administering a therapeutically effective amount of an anti-OX40L antibody, or antigen-binding fragment thereof, wherein the antibody or fragment thereof is administered via injection.

In a further configuration, there is provided an anti-OX40L antibody, or antigen-binding fragment thereof, for use in a method of treating immune-mediated diseases or immune-mediated disorders in a human subject comprising administering a therapeutically effective amount of an anti- OX40L antibody, or antigen-binding fragment thereof, wherein the antibody or fragment thereof is administered via injection.

In a further configuration, there is provided an anti-OX40L antibody, or antigen-binding fragment thereof, for use in a method of treating inflammatory skin diseases or inflammatory skin disorders in a human subject comprising administering a therapeutically effective amount of an anti-OX40L antibody, or antigen-binding fragment thereof, wherein the antibody or fragment thereof is administered via injection.

In a further configuration, there is provided a method treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered once every 4 weeks during induction phase and once every 12 weeks during maintenance phase.

In a further configuration, there is provided a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, via subcutaneous injection.

In a further configuration, there is provided a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered once every 4 weeks during induction phase and once every 12 weeks during maintenance phase, via subcutaneous injection.

In a further configuration, there is provided an anti-OX40L antibody, or antigen-binding fragment thereof, for use in a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered via subcutaneous injection.

In a further configuration, there is provided an anti-OX40L antibody, or antigen-binding fragment thereof, for use in a method of treating an inflammatory disease, an inflammatory disorder, an immune-mediated disease, an immune-mediated disorder, an inflammatory skin disease or an inflammatory skin disorder in a human subject comprising administering a therapeutically effective amount of an anti-OX40L antibody, or antigen-binding fragment thereof, wherein the antibody or fragment thereof is administered once every 4 weeks during induction phase and once every 12 weeks during maintenance phase, via subcutaneous injection.

In further configurations, there are provided the above-mentioned embodiments comprising administering a therapeutically effective amount of an OX40L antagonist antibody or antigen-binding fragment thereof.

Doses and Blood Serum Concentrations

The dose may be from 20 mg to 1000 mg. The dose may be from 20 mg to 600 mg. The dose may be up to 550 mg, up to 500 mg, up to 450 mg, up to 400 mg, up to 350 mg, up to 300 mg, up to 250 mg, up to 200 mg, up to 150 mg, up to 120 mg, up to 100 mg, or up to 50 mg. The dose may be up to 500 mg, up to 250 mg, or up to 150 mg. The dose may be at least 50 mg, at least 100 mg, at least 120 mg, at least 150 mg, at least 200 mg, at least 250 mg, at least 300 mg, at least 350 mg, at least 400 mg, at least 450 mg, at least 500 mg or at least 550 mg. The dose may be at least 50 mg, at least 120 mg or at least 150 mg. The dose may be selected from the group consisting of from 25 mg to 500 mg; from 50 mg to 450 mg; from 100 mg to 350 mg; from 120 mg to 300 mg; from 150 mg to 250 mg; and from 200 mg to 250 mg. The dose may be selected from the group consisting of from 60 mg to 500 mg; from 100 mg to 300 mg or from 125 mg to 150 mg.

The dose may be 62.5 mg, 125 mg, 150 mg, 250 mg or 500 mg. The dose may be 125 mg or 150 mg. The dose may be 125 mg. The dose may be 150 mg. The dose may be 62.5 mg. The dose may be 250 mg. The dose may be 500 mg.

The dose may be of up to 0.6 mg/kg, up to 0.7 mg/kg, up to 0.8 mg/kg, up to 0.9 mg/kg, up to 1 mg/kg, up to 1.1 mg/kg, up to 1.2 mg/kg, up to 1.3 mg/kg, up to 1.4 mg/kg, up to 1.5 mg/kg, up to 1.6 mg/kg, up to 1.7 mg/kg, up to 1.8 mg/kg, up to 1.9 mg/kg, up to 2 mg/kg, up to 2.1 mg/kg, up to 2.2 mg/kg, up to 2.3 mg/kg, up to 2.4 mg/kg, up to 2.5 mg/kg, up to 2.6 mg/kg, up to 2.7 mg/kg, up to 2.8 mg/kg, up to 2.9 mg/kg, up to 3 mg/kg, up to 4 mg/kg, up to 5 mg/kg, up to 6 mg/kg, up to 7 mg/kg, up to 8 mg/kg, up to 9 mg/kg, up to 10 mg/kg, up to 11 mg/kg or up to 12 mg/kg. The dose may be of up to 6 mg/kg or up to 3 mg/kg.

The dose may be of at least 0.45 mg/kg, at least 0.5 mg/kg, at least 0.6 mg/kg, at least 0.7 mg/kg, at least 0.8 mg/kg, at least 0.9 mg/kg, at least 1 mg/kg, at least 1.1 mg/kg, at least 1.2 mg/kg, at least 1.3 mg/kg, at least 1.4 mg/kg, at least 1.5 mg/kg, at least 1.6 mg/kg, at least 1.7 mg/kg, at least 1.8 mg/kg, at least 1.9 mg/kg, at least 2 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 11 mg/kg, or at least 12 mg/kg. The dose may be of at least 0.45 mg/kg. The dose may be of at least 0.7 mg/kg or at least 1.4 mg/kg.

The dose may be selected from the group consisting of from 0.1 mg/kg to 12 mg/kg; from 0.4 mg/kg to 11 mg/kg; from 0.7 mg/kg to 10 mg/kg; from 1 mg/kg to 9 mg/kg; from 1.3 mg/kg to 8 mg/kg; from 1.6 mg/kg to 7 mg/kg; from 1.9 mg/kg to 6 mg/kg; from 2.2 mg/kg to 5 mg/kg; from 2.5 mg/kg to 4 mg/kg; from 2.6 mg/kg to 3.8 mg/kg; from 2.7 mg/kg to 3.6 mg/kg; from 2.6 mg/kg to 3.4 mg/kg; from 2.7 mg/mg to 3.3 mg/kg; from 2.8 mg/kg to 3.2 mg/kg; and from 2.9 mg/kg to 3.1 mg/kg.

The dose may be selected from the group consisting of from 0.6 mg/kg to 11 mg/kg; from 0.7 mg/kg to 10 mg/kg; from 0.8 mg/kg to 9 mg/kg; from 0.9 mg/kg to 8 mg/kg; from 1 mg/kg to 7 mg/kg; from 1.1 mg/kg to 6 mg/kg; from 1.2 mg/kg to 5 mg/kg; from 1.3 mg/kg to 4 mg/kg; from 1.4 mg/kg to 3 mg/kg; from 1.5 mg/kg to 2.9 mg/kg; from 1.6 mg/kg to 2.8 mg/kg; from 1.7 mg/mg to 2.7 mg/kg; from 1.8 mg/kg to 2.6 mg/kg; from 1.9 mg/kg to 2.5 mg/kg; from 2 mg/kg to 2.4 mg/kg; and from 2.1 mg/kg to 2.3 mg/kg.

The dose may be from 0.7 mg/kg to 6 mg/kg. The dose may be from 1.4 mg/kg to 3 mg/kg.

Preclinical data noted that 0.405 μg/mL IC90 is required for inhibition of OX40L—OX40 interactions, that 1.09 μg/mL IC90 concentration is needed for inhibition of soluble OX40L-induced IL-2 release from primary human T cells and that 1.5 μg/mL IC90 concentration is needed to assess IL-2 decrease in the T cell allogeneic mixed lymphocyte reaction assay. Therefore, preclinical data suggests that minimum concentration needed at the site of action (skin) could to range from 0.405 to 1.5 μg/mL. The dose may be any suitable dose to deliver at least around 0.4 to 1.5 μg/mL to the skin.

The method may comprise administering at least two injections of the antibody or fragment thereof. The minimum blood serum concentration reached by the antibody or fragment thereof after administration of a first injection and prior to administration of a second injection ($C_{min}$) may be at least about 2.5 μg/ml.

The method may comprise administering at least three injections of the antibody or fragment thereof. The minimum blood serum concentration reached by the antibody or fragment thereof after administration of a second injection and prior to administration of a third injection ($C_{min}$) may be at least about 2.5 μg/ml. The minimum blood serum concentration reached by the antibody or fragment thereof after administration of a first injection and prior to administration of a third injection ($C_{min}$) may be at least about 2.5 μg/ml.

The method may comprise administering at least four injections of the antibody or fragment thereof. The minimum blood serum concentration reached by the antibody or fragment thereof after administration of a third injection and prior to administration of a fourth injection ($C_{min}$) may be at least about 2.5 μg/ml. The minimum blood serum concentration reached by the antibody or fragment thereof after administration of a first injection and prior to administration of a fourth injection ($C_{min}$) may be at least about 2.5 μg/ml. The minimum blood serum concentration reached by the antibody or fragment thereof after administration of a second injection and prior to administration of a fourth injection ($C_{min}$) may be at least about 2.5 μg/ml.

The $C_{min}$ in serum between any two injections may be between 2.5 μg/ml and 600 μg/ml. The $C_{min}$ in serum between any two injections may be between 2.5 μg/ml and 375 μg/ml. The $C_{min}$ in serum between any two injections may be between 4 μg/ml and 600 μg/ml. The $C_{min}$ in serum between any two injections may be at least 2.5 μg/ml, 2.6 μg/ml, at least 2.7 μg/ml, at least 2.8 μg/ml, at least 2.9 μg/ml, at least 3 μg/ml, at least 3.1 μg/ml, at least 3.2 μg/ml, at least 3.3 μg/ml, at least 3.4 μg/ml, at least 3.5 μg/ml, at least 3.6 μg/ml, at least 3.7 μg/ml, at least 3.8 μg/ml, at least 3.9 μg/ml, at least 4 μg/ml, at least 4.1 μg/ml, at least 4.2 μg/ml, at least 4.3 μg/ml, at least 4.4 μg/ml, at least 4.5 μg/ml, at least 4.6 μg/ml, at least 4.7 μg/ml, at least 4.8 μg/ml, at least 4.9 μg/ml, at least 5 μg/ml, at least 5.1 μg/ml, at least 5.2 μg/ml, at least 5.3 μg/ml, at least 5.4 μg/ml, at least 5.5 μg/ml, at least 5.6 μg/ml, at least 5.7 μg/ml, at least 5.8 μg/ml, at least 5.9 μg/ml, at least 6 μg/ml, at least 6.5 μg/ml, at least 7 μg/ml, at least 7.5 μg/ml, at least 8 μg/ml, at least 8.5 μg/ml, at least 9 μg/ml, at least 9.5 μg/ml, at least 10 μg/ml, at least 11 μg/ml, at least 12 μg/ml, at least 13 μg/ml, at least 14 μg/ml, at least 15 μg/ml, at least 16 μg/ml, at least 17 μg/ml, at least 18 μg/ml, at least 19 μg/ml, at least 20 μg/ml, at least 25 μg/ml, at least 30 μg/ml, at least 35 μg/ml, at least 40 μg/ml, at least 50 μg/ml, at least 60 μg/ml, at least 70 μg/ml, at least 80 μg/ml, at least 90 μg/ml, or at least 100 μg/ml. The $C_{min}$ in serum between any two injections may be at least about 4 μg/ml, at least about 5 μg/ml, or at least about 20 μg/ml. The $C_{min}$ in serum between any two injections may be at least about 4 μg/ml. The $C_{min}$ in serum between any two injections may be at least about 5 μg/ml. The $C_{min}$ in serum between any two injections may be at least about 20 μg/ml. The $C_{min}$ in serum between any two injections may be up to 600 μg/ml, up to 500 μg/ml, up to 450 μg/ml, up to 400 μg/ml, up to 350 μg/ml, up to 300 μg/ml, up to 275 μg/ml, up to 250 μg/ml, up to 225 μg/ml, up to 200 μg/ml, up to 175 μg/ml, up to 150 μg/ml, up to 125 μg/ml, up to 100 μg/ml, up to 90 μg/ml, up to 80 μg/ml, up to 70 μg/ml, up to 60 μg/ml, up to 50 μg/ml, up to 45 μg/ml, up to 40 μg/ml, up to 35 μg/ml, up to 30 μg/ml, up to 25 μg/ml, up to 23 μg/ml, up to 20 μg/ml, up to 15 μg/ml, up to 10 μg/ml, up to 9 μg/ml, up to 8 μg/ml, up to 7 μg/ml, up to 6 μg/ml, up to 5 μg/ml, up to 4 μg/ml, up to 3 μg/ml, or up to 2.5 μg/ml. The $C_{min}$ in serum may be up to about 50 μg/ml, up to about 25 μg/ml, up to about 15 μg/ml, or up to about 7 μg/ml. The $C_{min}$ in serum may be up to about 50 μg/ml. The $C_{min}$ in serum may be up to about 25 μg/ml. The $C_{min}$ in serum may be up to about 15 μg/ml. The $C_{min}$ in serum may be up to about 7 μg/ml. The $C_{min}$ in serum between any two injections may be selected from the group consisting of: at least 3 μg/ml and up to 350 μg/ml; at least 10 μg/ml and up to 300 μg/ml; at least 12.5 μg/ml and up to 250 μg/ml; at least 15 μg/ml and up to 250 μg/ml; at least 18 μg/ml and up to 240 μg/ml; at least 20 μg/ml and up to 220 μg/ml; at least 25 μg/ml and up to 190 μg/ml; at least 30 μg/ml and up to 150 μg/ml; at least 35 μg/ml and up to 125 μg/ml; at least 40 μg/ml and up to 90 μg/ml; and at least 50 μg/ml and up to 65 μg/ml.

The above values for $C_{min}$ are given as measured in blood serum. Serum $C_{min}$ values may be converted into tissue $C_{min}$ values. Shah & Betts (2013) mAbs 5:2, 297-305 calculated for mAbs that the distribution in the skin is around 16% of the systemic concentration. Accordingly, a serum $C_{min}$ value of 2.5 μg/ml would lead to a skin $C_{min}$ value of 0.4 μg/ml and a serum $C_{min}$ value of 375 μg/ml would lead to a skin $C_{min}$ value of 60 μg/ml. Alternative conversions are possible based on other distribution values assumed in the field, which may frequently range from around 10% to 15% of the systemic concentration distributing to the skin. Therefore, as a further example, assuming that distribution in skin is 10% the systemic concentration, a serum concentration level of 4 μg/mL would lead to a skin $C_{min}$ value of 0.4 μg/ml and a serum $C_{min}$ value of 600 μg/ml would lead to a skin $C_{min}$ value of 60 μg/ml.

The maximum blood serum concentration reached by the antibody or fragment thereof after administration of an injection and prior to administration of a subsequent injection ($C_{max}$) may be at least about 1.5 μg/ml, at least about 2 μg/ml, at least about 5 μg/ml, at least about 10 μg/ml, at least about 15 μg/ml, at least about 20 μg/ml, at least about 23 μg/ml, at least about 30 μg/ml, at least about 40 μg/ml, at least about 45 μg/ml, at least about 50 μg/ml, at least about 60 μg/ml, at least about 70 μg/ml, at least about 80 μg/ml, at least about 90 μg/ml, at least about 100 μg/ml, at least about 150 μg/ml, at least about 200 μg/ml, at least about 300 μg/ml or at least about 550 μg/ml. The maximum blood serum concentration reached by the antibody or fragment thereof after administration of an injection and prior to administration of a subsequent injection ($C_{max}$) is up to about 550 μg/ml, up to about 400 μg/ml, up to about 300 μg/ml, up to about 200 μg/ml, up to about 150 μg/ml, up to about 100 μg/ml, up to about 90 μg/ml, up to about 80 μg/ml, up to about 70 μg/ml, up to about 60 μg/ml, up to about 50 μg/ml, up to about 45 μg/ml, up to about 40 μg/ml, up to about 35

μg/ml, up to about 30 μg/ml, up to about 25 μg/ml, up to about 23 μg/ml, up to about 20 μg/ml, up to about 15 μg/ml, or up to about 10 μg/ml.

In some embodiments, the injection may be intravenous or subcutaneous. In some embodiments, the injection is subcutaneous, and the dose may be 62.5 mg, 125 mg, 150 mg, 250 mg or 500 mg. In some embodiments, the dose may be 125 mg or 150 mg. In other embodiments, the dose may be 125 mg. In still other embodiments, the dose may be 150 mg. In some embodiments, dose may be 62.5 mg. In some embodiments, the dose may be 250 mg. The dose may be 500 mg.

In some embodiments, the injection is subcutaneous and the maximum blood serum concentration reached by the antibody or fragment thereof after administration of an injection and prior to administration of a subsequent injection ($C_{max}$) may be 1.5 μg/ml to 275 μg/ml; 2 μg/ml to 200 μg/ml; 5 μg/ml to 150 μg/ml; 5 μg/ml to 100 μg/ml; 10 μg/ml to 80 μg/ml; 10 μg/ml to 25 μg/ml; 25 μg/ml to 50 μg/ml; or 35 μg/ml to 75 μg/ml. The $C_{max}$ maybe 10 μg/ml to 80 μg/ml. The $C_{max}$ may be 10 μg/ml to 25 μg/ml. The $C_{max}$ may be 25 μg/ml to 50 μg/ml The $C_{max}$ may be 35 μg/ml to 75 μg/ml.

In some embodiments, the injection is intravenous and the maximum blood serum concentration reached by the antibody or fragment thereof after administration of an injection and prior to administration of a subsequent injection ($C_{max}$) may be 6 μg/ml to 550 μg/ml; 15 μg/ml to 400 μg/ml; 20 μg/ml to 300 μg/ml; 30 μg/ml to 200 μg/ml; 30 μg/ml to 90 μg/ml; 40 μg/ml to 105 μg/ml; 95 μg/ml to 150 μg/ml; or 95 μg/ml to 200 μg/ml. The $C_{max}$ may be 30 μg/ml to 200 μg/ml. The $C_{max}$ may be 30 μg/ml to 90 μg/ml. The $C_{max}$ may be 40 μg/ml to 105 μg/ml. The $C_{max}$ may be 95 μg/ml to 150 μg/ml. The $C_{max}$ may be 95 μg/ml to 200 μg/ml.

The method may maintain the blood serum concentration of the antibody or fragment thereof above any $C_{min}$ value disclosed herein and below any $C_{max}$ value disclosed herein, wherein the $C_{min}$ value is below the $C_{max}$ value. For instance, the method may:

- maintain concentrations blood serum range between about 4 to about 15 μg/mL (tissue concentration of 0.4 to 1.5 μg/mL and above, assuming 10 to 15% tissue/skin penetration),
- maintain concentrations blood serum ranging between about 20 to about 45 μg/mL (tissue concentration of 2 to 6.7 μg/mL and above, assuming 10 to 15% tissue/skin penetration),
- maintain concentrations blood serum range between about 5 to about 23 μg/mL (tissue concentration of 0.5 to 3.5 μg/mL and above, assuming 10 to 15% tissue/skin penetration),
- maintain concentrations blood serum around or below 10 μg/mL.

The method may maintain a therapeutically effective concentration of the antibody or fragment thereof after the last administration. For example, a therapeutically effective concentration may be maintained for at least one month, at least two months or at least three months after the last administration. The therapeutically effective concentration may be at or above any $C_{min}$ value disclosed herein and/or at or below any $C_{max}$ value disclosed herein, wherein the $C_{min}$ value is below the $C_{max}$ value. The method may for instance maintain a serum concentration of about 3 to about 12 μg/mL; about 5 to about 12 μg/mL; or about 3 to about 5 μg/mL, optionally at least three months after the last administration.

The area under the serum concentration-time curve (AUC) following the first (AUC extrapolated to infinity [$AUC_{0-inf}$]) injection may be at least around 100,000 ng/ml*day, 500,000 ng/ml*day, at least around 600,000 ng/ml*day, at least around 700,000 ng/ml*day, at least around 800,000 ng/ml*day, at least around 900,000 ng/ml*day, at least around 1,000,000 ng/ml*day, at least around 1,100,000 ng/ml*day, at least around 1,300,000 ng/ml*day, at least around 1,500,000 ng/ml*day, at least around 1,700,000 ng/ml*day, at least around 2,000,000 ng/ml*day, at least around 2,500,000 ng/ml*day, at least around 3,000,000 ng/ml*day, at least around 3,300,000 ng/ml*day or at least around 3,500,000 ng/ml*day, eg at least around 1,000,000 ng/ml*day or at least around 3,000,000 ng/ml*day.

The area under the serum concentration-time curve (AUC) following the first (AUC extrapolated to infinity [$AUC_{0-inf}$]) injection may be up to around 4,500,000 ng/ml*day, up to around 4,200,000 ng/ml*day, up to around 4,000,000 ng/ml*day, up to around 3,800,000 ng/ml*day, up to around 3,600,000 ng/ml*day, up to around 3,400,000 ng/ml*day, up to around 3,200,000 ng/ml*day, up to around 3,000,000 ng/ml*day, up to around 2,800,000 ng/ml*day, up to around 2,500,000 ng/ml*day, up to around 2,000,000 ng/ml*day, up to around 1,800,000 ng/ml*day, up to around 1,500,000 ng/ml*day, up to around 1,200,000 ng/ml*day or up to around 1,000,000 ng/ml*day, eg up to around 1,500,000 ng/ml*day or up to around 3,800,000 ng/ml*day.

The area under the serum concentration-time curve (AUC) following the first (AUC extrapolated to infinity [$AUC_{0-inf}$]) injection may be from around 100,000 ng/ml*day to around 4,500,000 ng/ml*day or around 1,000,000 ng/ml*day to around 3,800,000 ng/ml*day. The area under the serum concentration-time curve (AUC) following the first (AUC extrapolated to infinity [$AUC_{0-inf}$]) injection may be from around 900,000 ng/ml*day to around 1,400,000 ng/ml*day or around 2,900,000 ng/ml*day to around 3,800,000 ng/ml*day.

Induction and Maintenance

The method may comprise an induction phase and a maintenance phase.

The induction phase may comprise administering one or more induction phase injections of the antibody or fragment thereof, at an induction dose of between 20 and 500 mg; 20 mg and 300 mg; between 50 mg and 300 mg; between 100 mg and 300 mg; or between 150 mg and 300 mg. The induction dose may be between 200 mg and 300 mg; or between 225 mg and 275 mg. The induction dose may be about 500 mg, 250 mg, about 125 mg or about 62.5 mg. The induction dose may be about 250 mg.

The induction phase may be at least 2 weeks, at least 4 weeks, at least 8 weeks, at least 16 weeks or at least 24 weeks in duration. The induction phase may comprise administering two or more induction phase injections of the antibody or fragment thereof.

Each induction phase injection may be administered at least 2 weeks, at least 4 weeks, at least 8 weeks, at least 16 weeks or at least 24 weeks apart. Each induction phase injection may be administered 4 weeks apart.

Each induction phase injection may comprise the same mass of the antibody or fragment thereof as each other induction phase injection. The dose of each induction phase injection may be the same.

Alternatively, one or more induction phase injection may have a different mass of the antibody or fragment thereof as one or more or all of the other induction phase injections. The dose of each induction phase injection may not be the same. A first induction phase injection may be at a loading dose.

The loading dose may comprise up to three times the mass of the antibody or fragment thereof as each subsequent induction phase injection. The loading dose may comprise greater than 2 times and up to three times the mass of the antibody or fragment thereof as each subsequent induction phase injection. The loading dose may comprise up to twice the mass of the antibody or fragment thereof as each subsequent induction dose. The loading dose may comprise up to 1.5 times the mass of the antibody or fragment thereof as each subsequent induction dose.

The loading dose may be between 100 and 600 mg; between 150 and 550 mg; or between 200 and 500 mg. The loading dose may be about 500 mg, about 250 mg or about 125 mg. The loading dose may be about 500 mg.

The induction phase may comprise administering two or more induction phase injections of the antibody or fragment thereof. The second induction phase injection may be administered 2 to 16 weeks after a first induction phase injection; administered 3 to 14 weeks after a first induction phase injection; or administered 4 to 12 weeks after a first induction phase injection. A second induction phase injection may be administered 2 to 14 weeks after a first induction phase injection; administered 2 to 12 weeks after a first induction phase injection; administered 2 to 10 weeks after a first induction phase injection; administered 2 to 8 weeks after a first induction phase injection; administered 2 to 7 weeks after a first induction phase injection; or administered 2 to 6 weeks after a first induction phase injection. A second induction phase injection may be administered 3 to 13 weeks after a first induction phase injection; administered 5 to 11 weeks after a first induction phase injection; or administered 6 to 10 weeks after a first induction phase injection; or administered 7 to 9 weeks after a first induction phase injection. A second induction phase injection may be administered 4 to 8 weeks after a first induction phase injection. A second induction phase injection may be administered about 4 weeks or about 8 weeks after a first induction phase injection. A second induction phase injection may be administered 4 weeks after a first induction phase injection.

The induction phase may comprise administering three or more induction phase injections of the antibody or fragment thereof. The third induction phase injection may be administered 2 to 16 weeks after the second induction phase injection; administered 3 to 14 weeks after the second induction phase injection; or administered 4 to 12 weeks after the second induction phase injection. The third induction phase injection may be administered 2 to 14 weeks after the second induction phase injection; administered 2 to 12 weeks after the second induction phase injection; administered 2 to 10 weeks after the second induction phase injection; administered 2 to 8 weeks after the second induction phase injection; administered 2 to 7 weeks after the second induction phase injection; or administered 2 to 6 weeks after the second induction phase injection. The third induction phase injection may be administered 3 to 13 weeks after the second induction phase injection; administered 5 to 11 weeks after the second induction phase injection; or administered 6 to 10 weeks after the second induction phase injection; or administered 7 to 9 weeks after the second induction phase injection. The third induction phase injection may be administered 4 to 8 weeks after the second induction dose. The third induction phase injection may be administered about 4 weeks or about 8 weeks after the second induction phase injection. The third induction phase injection may be administered 4 weeks after the second induction phase injection. The interval between the first induction phase injection and the second induction phase injection may have the same duration as the interval between the second induction phase injection and the third induction phase injection.

Each induction phase injection may comprise the same mass of the antibody or fragment thereof as each other induction phase injection and/or each interval between induction phase injections may have the same duration as each other interval between induction phase injections.

Each induction phase injection may therefore have the same dose. For example, a dose of 250 mg may be administered with every injection of the induction phase. The entire induction phase may have a dosing interval of for example 4 weeks. The induction phase may therefore involve giving a 250 mg dose every four weeks. Alternatively, the induction phase may involve giving a 125 mg dose every four weeks. Alternatively, the induction phase may involve giving a 62.5 mg dose every four weeks. A fixed dosing interval may be used without a fixed dose for every induction phase injection, for example because a loading dose may be administered. The induction phase may therefore involve giving a 500 mg loading dose, followed four weeks later by a 250 mg dose, with further 250 mg doses given every four weeks through the induction phase. Any and all combinations of doses and dose intervals and injection types (e.g., subcutaneous) described herein are explicitly contemplated.

The maintenance phase may comprise administering one or more maintenance phase injections of the antibody or fragment thereof, at a maintenance dose between 20 mg and 300 mg; between 50 mg and 300 mg; between 100 mg and 300 mg; or between 150 mg and 300 mg. The maintenance dose may be between 200 mg and 300 mg; or between 225 mg and 275 mg. The maintenance dose may be about 500 mg, 250 mg, about 125 mg or about 62.5 mg. The maintenance dose may be about 250 mg.

The maintenance phase may be at least 2 weeks, at least 4 weeks, at least 8 weeks, at least 16 weeks, at least 24 weeks, at least 32 weeks, at least 40 weeks, at least 52 weeks, or at least 100 weeks in duration. The duration of the maintenance phase may be of any suitable length to achieve a clinical objective and may therefore involve any suitable number of maintenance phase injections. The duration of the maintenance phase may therefore be determined by a clinician. The maintenance period may last as long as, in the patient and clinician's opinion, the patient benefits from such maintenance treatment or doesn't experience an adverse event that requires the treatment to be discontinued. For some subjects, the maintenance phase may be indefinite.

The maintenance phase may comprise administering two or more maintenance phase injections of the antibody or fragment thereof. Each maintenance phase injection may be administered at least 2 weeks, at least 4 weeks, at least 8 weeks, at least 16 weeks, at least 24 weeks, at least 32 weeks, at least 40 weeks or at least 52 weeks apart.

Each maintenance phase injection may comprise the same mass of the antibody or fragment thereof as each other maintenance phase injection. The dose of the antibody or fragment thereof used in the induction phase may be maintained for the maintenance phase, i.e. the induction phase dose (other than any loading dose) may be the same as the maintenance phase dose. The dosing interval for the maintenance phase may however be longer than the dosing interval for the induction phase. This may be because once a therapeutic effect has been initiated, the maintenance of the therapeutic effect may be possible at a lower tissue concentration of the antibody or fragment thereof. While a similar end may be obtained by maintaining the induction phase dosing interval while reducing the induction phase dose in the maintenance phase, it may be clinically preferable to reduce the number of injections rather than the dose per injection during the maintenance phase.

A second maintenance phase injection may be administered 2 to 16 weeks after a first maintenance phase injection; administered 3 to 14 weeks after a first maintenance phase injection; or administered 4 to 12 weeks after a first maintenance phase injection. A second maintenance phase injection may be administered 2 to 14 weeks after a first maintenance phase injection; administered 2 to 12 weeks after a first maintenance phase injection; administered 2 to 10 weeks after a first maintenance phase injection; administered 2 to 8 weeks after a first maintenance phase injection; administered 2 to 7 weeks after a first maintenance phase injection; or administered 2 to 6 weeks after a first maintenance phase injection. A second maintenance phase injection may be administered 3 to 13 weeks after a first maintenance phase injection; administered 5 to 11 weeks after a first maintenance phase injection; or administered 6 to 10 weeks after a first maintenance phase injection; or administered 7 to 9 weeks after a first maintenance phase injection. A second maintenance phase injection may be administered 4 to 8 weeks after a first maintenance phase injection. A second maintenance phase injection may be administered about 4 weeks or about 8 weeks after a first maintenance phase injection.

The maintenance phase may comprise administering three or more maintenance phase injections of the antibody or fragment thereof. A third maintenance phase injection may be administered 2 to 16 weeks after the second maintenance phase injection; administered 3 to 14 weeks after the second maintenance phase injection; or administered 4 to 12 weeks after the second maintenance phase injection. A third maintenance phase injection may be administered 2 to 14 weeks after the second maintenance phase injection; administered 2 to 12 weeks after the second maintenance phase injection; administered 2 to 10 weeks after the second maintenance phase injection; administered 2 to 8 weeks after the second maintenance phase injection; administered 2 to 7 weeks after the second maintenance phase injection; or administered 2 to 6 weeks after the second maintenance phase injection. A third maintenance phase injection may be administered 3 to 13 weeks after the second maintenance phase injection; administered 5 to 11 weeks after the second maintenance phase injection; or administered 6 to 10 weeks after the second maintenance phase injection; or administered 7 to 9 weeks after the second maintenance phase injection. A third maintenance phase injection may be administered 4 to 8 weeks after the second maintenance phase injection. A third maintenance phase injection may be administered about 4 weeks or about 8 weeks after the second maintenance phase injection.

The interval between the first maintenance phase injection and the second maintenance phase injection may have the same duration as the interval between the second maintenance phase injection and the third maintenance phase injection.

Each maintenance phase injection may comprise the same mass of the antibody or fragment thereof as each other maintenance phase injection and/or each interval between maintenance phase injections may have the same duration as each other interval between maintenance phase injections.

Each maintenance phase injection may therefore have the same dose. For example, a dose of 250 mg may be administered with every injection of the maintenance phase. The entire maintenance phase may have a dosing interval of for example 16 weeks. The maintenance phase may therefore involve giving a 250 mg dose every 16 weeks. Alternatively, the induction phase may involve giving a 125 mg dose every 16 weeks. Alternatively, the induction phase may involve giving a 62.5 mg dose every 16 weeks. For a further example, a dose of 250 mg may be administered with every injection of the maintenance phase. The entire maintenance phase may have a dosing interval of for example 1 weeks. The maintenance phase may therefore involve giving a 250 mg dose every 12 weeks. Alternatively, the induction phase may involve giving a 125 mg dose every 12 weeks. Alternatively, the induction phase may involve giving a 62.5 mg dose every 12 weeks. Any and all combinations of doses and dose intervals and injection types (e.g., subcutaneous) described herein are explicitly contemplated.

The interval between two or more maintenance phase injections may have an equal duration than or a longer duration than the interval between two or more induction phase injections. As described above, the dosing interval for the maintenance phase may however be longer than the dosing interval for the induction phase. Where a constant dosing interval is used for the induction phase and a consistent dosing interval is used for the maintenance phase then this may be a straightforward comparison of intervals, for example when the induction phase dosing interval is four weeks (Q4W) and the maintenance phase dosing interval is four weeks (Q4W) the interval between induction phase injections has an equal duration to the interval between maintenance phase injections. When the induction phase dosing interval is four weeks (Q4W) and the maintenance phase dosing interval is 12 weeks (Q12W) the interval between maintenance phase injections is longer than the interval between maintenance phase injections. The comparison between the dosing interval for the maintenance phase and the dosing interval for the induction phase may alternatively be calculated as the average (mean, median or mode) of all intervals within the induction and maintenance phase respectively. Alternatively, the comparison between the dosing interval for the maintenance phase and the dosing interval for the induction phase may be calculated by comparing specific examples of dosing intervals as further described below.

The interval between the first maintenance phase injection and the second maintenance phase injection may have an equal duration than or a longer duration than the interval between two or more induction phase injections. The interval between two or more induction phase injections may be about 2 weeks, about 4 weeks or about 8 weeks and the interval between two or more maintenance phase injections may be about 12 weeks or about 16 weeks. The interval between two or more induction phase injections may be about 4 weeks or about 8 weeks and the interval between two or more maintenance phase injections may be about 12 weeks. The interval between two or more induction phase injections may be about 4 weeks or about 8 weeks and the interval between two or more maintenance phase injections may be about 16 weeks. The interval between two or more induction phase injections may be about 4 weeks and the interval between two or more maintenance phase injections may be about 16 weeks. The interval between two or more induction phase injections may be about 4 weeks and the interval between two or more maintenance phase injections may be about 12 weeks. The interval between two or more induction phase injections may be about 4 weeks and the interval between two or more maintenance phase injections may be about 4 weeks. The interval between two or more induction phase injections may be about 8 weeks and the interval between two or more maintenance phase injections may be about 8 weeks. The interval between two or more induction phase injections may be about 2 weeks and the interval between two or more maintenance phase injections may be about 8 weeks.

The interval between three or more induction phase injections may be constant. Alternatively, the interval between three or more maintenance phase injections may vary.

The combined duration of the induction phase and the maintenance phase may be at least 52 weeks. The combined duration of the induction phase and the maintenance phase may be any duration achieved by totaling any duration of the induction phase described herein with any duration of the maintenance phase described herein. The combined duration of the induction phase and the maintenance phase may be indefinite, since the maintenance phase may be indefinite.

The subject may be transitioned from the induction phase to the maintenance phase based on:

(a) clinical response; and/or (b) the time since the administration of the first induction phase injection.

The clinical response may be defined by any post-administration score or index described herein. The clinical response may be achieving EASI50, EASI75, EASI90 or EASI100. The clinical response may be achieving IGA-AD0/1 and/or a reduction of at least 2 IGA-AD points. The clinical response is achieving a reduction of at least 3 NRS points or at least 4 NRS points. The clinical response may be determined at any clinically suitable time point, such as 16 weeks, 20 weeks or 24 weeks after the administration of the first induction phase injection.

The transition from the induction phase to the maintenance phase may take place 16 or more weeks after the administration of the first induction phase injection. The transition from the induction phase to the maintenance phase may take place 24 or more weeks after the administration of the first induction phase injection. The transition from the induction phase to the maintenance phase may take place up to one year after the administration of the first induction phase injection. The transition from the induction phase to the maintenance phase may take place 16 to 24 weeks after the administration of the first induction phase injection.

In some instances, the transition from the induction phase to the maintenance phase may take place based on a clinical response determined during the induction phase. This may occur for example when some time is needed to analyse data on disease severity. There may therefore be a lag between gathering the data on which a clinical response can be determined and transitioning the subject from the induction phase to the maintenance phase. The clinical response may for example be assessed at week 16 by collecting data on disease severity leading to a later transition from the induction phase to the maintenance phase if the clinical response is positive, for example at week 24 after the administration of the first induction phase injection. The decision to transition from the induction phase to the maintenance phase may further account for additional information available since the data on which a clinical response was determined were gathered, for example a subsequent clinical assessment at the time of transitioning from the induction phase to the maintenance phase.

The transition from the induction phase to the maintenance phase may take place at 24 weeks if the subject has achieved a clinical response of at least EASI75 at 16 weeks.

The induction phase may be a variable induction phase. By "variable" is meant the duration of the induction phase will vary between subjects and transition from induction phase to maintenance phase will depend on patient specific factors. The patient specific factors may include clinical response. For example the transition may occur when a patient has achieved IGA0/1, has clear/almost clear skin, has achieved EASI 50, has achieved EASI75 or has achieved EASI90.

The administration may be subcutaneous. The subcutaneous injection may be to any suitable side of injection, such as the abdomen or the outside of the thigh. In some embodiments, subcutaneous administration is used for treatment of Atopic Dermatitis because this is more convenient for patients and less resource intensive than intravenous injection. Any of the methods described herein may involve subcutaneous administration. The methods involves an induction and a maintenance period are primarily intended for use when administration is subcutaneous.

The method may comprise any one of the following four configurations of the induction and/or maintenance phase, administration for each of which may be subcutaneous:

1. The induction phase may comprise administering at least five induction phase injections, wherein the first induction phase injection is a loading dose of 500 mg of the antibody or fragment thereof, followed by at least four subsequent induction phase injections, wherein each subsequent induction phase injection is a dose of 250 mg of the antibody or fragment thereof and wherein each subsequent induction phase injection is administered 4 weeks after the preceding induction phase injection. The maintenance phase may comprise administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

2. The induction phase may comprise administering at least five induction phase injections, wherein each induction phase injection is a dose of 250 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

3. The induction phase may comprise administering at least five induction phase injections, wherein each induction phase injection is a dose of 125 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 125 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

4. The induction phase may comprise administering at least five induction phase injections, wherein each induction phase injection is a dose of 62.5 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 62.5 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

As used in the configurations set out herein "at least 4 weeks" may for instance be 4 weeks, 5 weeks, 6 weeks, 7 weeks, 8 weeks, 9 weeks, 10 weeks, 12 weeks, 13 weeks, 14 weeks, 15 weeks, 16 weeks, 17 weeks, 18 weeks, 19 weeks, 20 weeks, 21 weeks, 22 weeks, 23 weeks or 24 weeks. As used in the four configurations above "at least 4 weeks" may for instance be 4 weeks, 12 weeks or 16 weeks. This applies to the periods between induction phase injections, between final induction phase injection and first maintenance phase injection and between maintenance phase injections.

The method may comprise administering at least six induction phase injections or at least seven induction phase injections. The first maintenance phase injection may be administered from 4 weeks to 24 weeks or 4 weeks to 16 weeks after the final induction phase injection. The first maintenance phase injection may be administered 12 weeks after the final induction phase injection. The first maintenance phase injection may be administered 16 weeks after the final induction phase injection. The first maintenance phase injection may be administered 24 weeks after the final induction phase injection. The second maintenance phase injection and each subsequent maintenance phase injection may be administered from 4 weeks to 24 weeks or 4 weeks to 16 weeks after the preceding maintenance phase injection. The second maintenance phase injection and each subsequent maintenance phase injection may be administered 12 weeks after the preceding maintenance phase injection. The second maintenance phase injection and each subsequent maintenance phase injection may be administered 16 weeks after the preceding maintenance phase injection. The second maintenance phase injection may be administered 24 weeks after the preceding maintenance phase injection.

The method may:

(a) comprise administering at least seven induction phase injections;

(b) wherein the first maintenance phase injection is administered at least 12 weeks after the final induction phase injection; and (c) wherein the second maintenance phase injection and each subsequent maintenance phase injection is administered at least 4 weeks after the preceding maintenance phase injection.

The method may comprise any one of the following four further configurations of the induction and/or maintenance phase, administration for each of which may be subcutaneous:

1'. The induction phase may comprise administering at least five induction phase injections, wherein the first induction phase injection is a loading dose of 500 mg of the antibody or fragment thereof, followed by at least four subsequent induction phase injections, wherein each subsequent induction phase injection is a dose of 250 mg of the antibody or fragment thereof and wherein each subsequent induction phase injection is administered 4 weeks after the preceding induction phase injection. The maintenance phase may comprise administering at least 3 maintenance phase injections, wherein each maintenance phase injection is a dose of 250 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection.

2'. The induction phase may comprise administering at least five induction phase injections, wherein each induction phase injection is a dose of 250 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 250 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection.

3'. The induction phase may comprise administering at least five induction phase injections, wherein each induction phase injection is a dose of 125 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 125 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection.

4'. The induction phase may comprise administering at least five induction phase injections, wherein each induction phase injection is a dose of 62.5 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 62.5 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection.

The method may comprise any one of the following four further configurations of the induction and/or maintenance phase, administration for each of which may be subcutaneous:

1". The induction phase may comprise administering at least five induction phase injections, wherein the first induction phase injection is a loading dose of 500 mg of the antibody or fragment thereof, followed by at least four subsequent induction phase injections, wherein each subsequent induction phase injection is a dose of 250 mg of the antibody or fragment thereof and wherein each subsequent induction phase injection is administered 4 weeks after the preceding induction phase injection. The maintenance phase may comprise administering at least 3 maintenance phase injections, wherein each maintenance phase injection is a dose of 250 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection, wherein the subject has achieved a clinical response of at least EASI75 at 16 weeks after the first induction phase injection.

2''. The induction phase may comprise administering at least five induction phase injections, wherein each induction phase injection is a dose of 250 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 250 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection, wherein the subject has achieved a clinical response of at least EASI75 at 16 weeks after the first induction phase injection.

3''. The induction phase may comprise administering at least five induction phase injections, wherein each induction phase injection is a dose of 125 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 125 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection, wherein the subject has achieved a clinical response of at least EASI75 at 16 weeks after the first induction phase injection.

4''. The induction phase may comprise administering at least five induction phase injections, wherein each induction phase injection is a dose of 62.5 mg of the antibody or fragment thereof and wherein a second induction phase injection and each subsequent induction phase injection is administered 4 weeks after the preceding induction phase injection. The maintenance phase may comprise administering at least 3 maintenance phase injections, wherein each maintenance phase injection is a dose of 62.5 mg of the antibody or fragment thereof, wherein a first maintenance phase injection is administered at least 16 weeks after the final induction phase injection and wherein a second maintenance phase injection and each subsequent maintenance phase injection is administered at least 16 weeks after the preceding maintenance phase injection, wherein the subject has achieved a clinical response of at least EASI75 at 16 weeks after the first induction phase injection.

The method may comprise any one of the following four further configurations of the induction and/or maintenance phase, administration for each of which may be subcutaneous:

1'''. The induction phase may comprise administering at least five induction phase injections, wherein the first induction phase injection is a loading dose of 500 mg of the antibody or fragment thereof, followed by at least four subsequent induction phase injections, wherein each subsequent induction phase injection is a dose of 250 mg of the antibody or fragment thereof and wherein each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection, or
  (ii) the subject is withdrawn from the antibody or fragment thereof;
(b) wherein the subject has not achieved a clinical response of EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

2'''. The induction phase may comprise administering at least five induction phase injections, wherein each induction phase injection is a dose of 250 mg of the antibody or fragment thereof and wherein a second induction phase injection and each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection, or
  (ii) the subject is withdrawn from the antibody or fragment thereof;
(b) wherein the subject has not achieved a clinical response of EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

3'''. The induction phase may comprise administering at least five induction phase injections, wherein each induction phase injection is a dose of 125 mg of the antibody or fragment thereof and wherein a second induction phase injection and each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection, or
  (ii) the subject is withdrawn from the antibody or fragment thereof;
(b) wherein the subject has not achieved a clinical response of EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

4'''. The induction phase may comprise administering at least five induction phase injections, wherein each induction phase injection is a dose of 62.5 mg of the antibody or fragment thereof and wherein a second induction phase injection and each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection, or
  (ii) the subject is withdrawn from the antibody or fragment thereof;
(b) wherein the subject has not achieved a clinical response of EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

The method may comprise any one of the following four further configurations of the induction and/or maintenance phase, administration for each of which may be subcutaneous:

1''''. The induction phase may comprise administering at least five induction phase injections, wherein the first induction phase injection is a loading dose of 500 mg of the antibody or fragment thereof, followed by at least four subsequent induction phase injections, wherein each subsequent induction phase injection is a dose of 250 mg of the antibody or fragment thereof and wherein each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection, or
  (ii) the subject is withdrawn from the antibody or fragment thereof;
(b) wherein the subject has not achieved a clinical response of EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection.

2'''. The induction phase may comprise administering at least five induction phase injections, wherein each induction phase injection is a dose of 250 mg of the antibody or fragment thereof and wherein a second induction phase injection and each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:
  (i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection, or
  (ii) the subject is withdrawn from the antibody or fragment thereof;

(b) wherein the subject has not achieved a clinical response of EASI75 and/or IGA-AD 0/1 at 16 weeks after the first induction phase injection:

(i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection.

3'''. The induction phase may comprise administering at least five induction phase injections, wherein each induction phase injection is a dose of 125 mg of the antibody or fragment thereof and wherein a second induction phase injection and each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:

(i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection, or (ii) the subject is withdrawn from the antibody or fragment thereof;

(b) wherein the subject has not achieved a clinical response of EASI75 and/or IGA-AD 0/1 at 16 weeks after the first induction phase injection:

(i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection.

4'''. The induction phase may comprise administering at least five induction phase injections, wherein each induction phase injection is a dose of 62.5 mg of the antibody or fragment thereof and wherein a second induction phase injection and each subsequent induction phase injection is administered 4 weeks after the preceding induction phase injection. The maintenance phase may comprise:

(a) wherein the subject has achieved a clinical response of at least EASI75 and/or IGA-AD 0/1 at 16 weeks after the first induction phase injection:

(i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection, or (ii) the subject is withdrawn from the antibody or fragment thereof;

(b) wherein the subject has not achieved a clinical response of EASI75 and/or IGA-AD 0/1 at 16 weeks after the first induction phase injection:

(i) administering at least 3 maintenance phase injections, wherein each maintenance phase injection is a dose of 250 mg of the antibody or fragment thereof, wherein a first maintenance phase injection is administered at least 12 weeks after the final induction phase injection and wherein a second maintenance phase injection and each subsequent maintenance phase injection is administered at least 12 weeks after the preceding maintenance phase injection.

The method may:

(a) comprise administering at least seven induction phase injections;

(b) wherein the first maintenance phase injection is administered 4 weeks after the final induction phase injection; and (c) wherein the second maintenance phase injection and each subsequent maintenance phase injection is administered 4 weeks after the preceding maintenance phase injection.

The method may:

(a) comprise administering at least seven induction phase injections;

(b) wherein the first maintenance phase injection is administered 12 weeks after the final induction phase injection; and (c) wherein the second maintenance phase injection and each subsequent maintenance phase injection is administered 12 weeks after the preceding maintenance phase injection.

The method may:

(a) comprise administering at least seven induction phase injections;

(b) wherein the first maintenance phase injection is administered 16 weeks after the final induction phase injection; and (c) wherein the second maintenance phase injection and each subsequent maintenance phase injection is administered 16 weeks after the preceding maintenance phase injection.

The method may:

(a) comprise administering at least seven induction phase injections;

(b) wherein the first maintenance phase injection is administered 24 weeks after the final induction phase injection; and (c) wherein the second maintenance phase injection and each subsequent maintenance phase injection is administered 24 weeks after the preceding maintenance phase injection.

According to one embodiment, the method is a method of treating an inflammatory disease, an inflammatory disorder, an immune-mediated disease, an immune-mediated disorder, or an inflammatory skin disorder in a human subject comprising administering a therapeutically effective amount of an anti-OX40L antibody, or antigen-binding fragment thereof, wherein the antibody or fragment thereof is administered once every 4 weeks or once every 12 weeks or once every 6 months.

According to another embodiment, the method is a method of treating an inflammatory disease, an inflammatory disorder, an immune-mediated disease, an immune-mediated disorder, or an inflammatory skin disorder in a human subject comprising administering a therapeutically effective amount of an anti-OX40L antibody, or antigen-binding fragment thereof, wherein the antibody or fragment thereof is administered once every 4 weeks or once every 12 weeks or once every 6 months via subcutaneous injection.

According to another embodiment, the method is a method of treating an inflammatory disease, an inflammatory disorder, an immune-mediated disease, an immune-mediated disorder, or an inflammatory skin disorder in a human subject comprising administering a therapeutically effective amount of an anti-OX40L antibody, or antigen-binding fragment thereof, wherein the antibody or fragment thereof is administered once every 4 weeks or once every 12 weeks or once every 6 months.

In further configurations, there are provided the above-mentioned embodiments comprising administering a therapeutically effective amount of an OX40L antagonist antibody or antigen-binding fragment thereof.

Loading and Treatment Doses

The method may comprise:

(a) administering a first injection as a loading dose of the antibody or fragment thereof, followed by (b) administering at least a second injection as a first treatment dose of the antibody or fragment thereof.

The second injection may be administered 3 to 5 weeks after the first injection.

The method may further comprise administering at least a third injection as a treatment dose of the antibody or fragment thereof. The third injection may be administered 3 to 5 weeks after the second injection.

The method may further comprise administering at least a fourth injection as a treatment dose of the antibody or fragment thereof. The fourth injection may be administered 3 to 5 weeks after the third injection.

The method may comprise administering a fifth injection as a treatment dose. The fifth injection may be administered 3 to 5 weeks after the fourth injection.

The method may further comprise administering a sixth injection as a treatment dose. The sixth treatment dose may be administered 3 to 5 weeks after the fifth injection.

Each injection as a treatment dose may be administered 4 weeks after the preceding treatment dose.

The number of injections as treatment doses may be of any suitable number to achieve a clinical objective and may therefore involve any suitable number of injections as treatment doses. The number of injections as treatment doses may therefore be determined by a clinician. For example, the number of treatment does may be at least 6, at least 7, at least 8, at least 9 or at least 10. For some subjects, an indefinite number of injections as treatment doses may be administered.

The loading dose may comprise up to three times the mass of the antibody or fragment thereof as each subsequent injection as a treatment dose. The loading dose may comprise greater than 2 times and up to three times the mass of the antibody or fragment thereof as each subsequent injection as a treatment dose. The loading dose may comprise up to twice the mass of the antibody or fragment thereof as each subsequent injection as a treatment dose. The loading dose may comprise up to 1.5 times the mass of the antibody or fragment thereof as each subsequent injection as a treatment dose.

Each treatment dose may comprise the same mass of the antibody or fragment thereof as each other treatment dose.

The loading dose may be between 100 and 600 mg; between 150 and 550 mg; or between 200 and 500 mg. The loading dose may be 200 mg or 500 mg.

Each treatment dose may be between 50 and 300 mg; or between 100 and 250 mg. Each treatment dose may be 100 mg or 250 mg.

An advantage of some embodiments is derived from the good safety profile of the antibody or fragment thereof. This allows a wide range of treatment doses to be used with a loading dose, which may not be advisable for other antibodies where higher doses could, for example, lead to toxicity or unacceptable side-effects. Any dose described herein may be used as a loading dose. Any dose described herein may be used as a treatment dose. Any dose described herein may be used as a treatment dose, with double the treatment dose being used as a loading dose. For example: a loading dose of 500 mg may be combined with a treatment dose of 250 mg; a loading dose of 250 mg may be combined with a treatment dose of 125 mg; or a loading dose of 125 mg may be combined with a treatment dose of 62.5 mg. KY1005 has a particularly advantageous safety profile and may be used with a loading dose when the treatment dose is any dose described herein.

A first maintenance injection as a maintenance dose may be administered between 4 and 8 months after the last injection as a treatment dose. One or more further maintenance injections as a maintenance dose is administered at intervals of between 4 and 8 months.

The administration may be intravenous. The injection may be a subcutaneous injection for embodiments comprising a loading dose and a treatment dose in particular. Disclosed herein are data from a randomized, double-blind, placebo-controlled Phase 2a clinical trial in moderate to severe AD, wherein administration was by intravenous injection.

Pharmacokinetic Properties

In some embodiments, the antibody or fragment thereof administered have been found to exhibit surprisingly consistent pharmacokinetic (PK) parameter estimates in IV and subcutaneous population PK models. One advantage observed is a linear PK (with the exception of some non-linearity seen in low doses, such as around 0.45 mg/kg, in healthy subjects), allowing the PK model to be described as a "linear two compartment distribution model", for both IV and subcutaneous administration. Here, the term "linear" refers to the clearance—encompassing the rate of clearance (CL) and the rate of clearance from the central compartment to the second compartment (Q1)—both of which are shown to be linear in the data disclosed herein. The same finding applies in both AD and healthy patients. Without being bound by theory, this may be related to a low expression of OX40L, such that the rate of clearance doesn't change based on concentration of drug (or therefore time).

In some embodiments, the antibody or fragment thereof administered have been found to exhibit surprisingly low immunogenicity. One component of a harmful immune response to a therapeutic protein is the formation of anti-drug antibodies (ADA). The consequences of an immune reaction to a therapeutic protein range from transient appearance of ADAs without any clinical significance to severe life-threatening conditions. Potential clinical consequences of an unwanted immune response include loss of efficacy of the therapeutic protein and serious acute immune effects such as anaphylaxis. ADAs can affect efficacy of a therapeutic protein either by interfering with the pharmacodynamic interaction between the therapeutic protein and its target or by altering its pharmacokinetic profile.

As described in the European Medicines Agency (EMA) Guideline on Immunogenicity assessment of therapeutic proteins (18 May 2017, EMEA/CHMP/BMWP/42832/2005

Rev1, Committee for Medicinal Products for Human Use (CHMP)), products given intravenously may be less immunogenic than drugs given subcutaneously. It is therefore surprising that the population PK profile for treatments of some embodiments are so similar between IV and subcutaneous administration scenarios (based on a single subcutaneous dose). No meaningful effect of ADA is apparent from the data disclosed herein.

Important factors influencing the immunogenicity of therapeutic proteins in general include the origin (e.g., foreign or human) and nature of the active substance (endogenous proteins, post-translational modifications), significant modifications of the therapeutic protein (e.g., pegylation and fusion proteins), product-related (e.g., degradation products, impurities, aggregates) and process-related impurities (host cell proteins, lipids or DNA, microbial contaminants), formulation (excipients) and the interactions between the drug and/or formulation with the primary product packaging (e.g., containers, closures).

Without being bound by theory, the antibody or fragment thereof administered according to some embodiments may advantageously maintain the native conformation of the antibody or fragment thereof. Denaturation and aggregation of a therapeutic protein may potentially trigger an immune response. Aggregation and adduct formation of proteins may reveal new epitopes or lead to the formation of multivalent epitopes, which may stimulate the immune system. In addition, aggregation can enhance a protein-specific immune response and lead to the formation of ADAs. Higher-molecular weight (MW) aggregates are more prone to elicit immune responses than lower-MW aggregates. The antibody or fragment thereof may exhibit advantageously low aggregation and adduct formation, especially of higher MW aggregates as administered according to some embodiments.

Additional factors influencing the immunogenicity of therapeutic proteins include properties of the active ingredient. Therapeutic protein analogues to human endogenous proteins may trigger an immune response due to variations in the amino acid sequence or changes to the protein structure compared to the endogenous protein as a result of post-translational modifications, or other changes during all steps of the drug substance and/or drug product manufacturing process, storage and administration. T cell epitopes are small linear peptides and may thus be modified by a difference in the amino acid sequence between an endogenous and a therapeutic protein. Accordingly, analyses to identify potential T cell epitopes may be helpful for selection of novel proteins or peptides for development. Glycosylation can influence both the physico-chemical and biological properties of a protein. The presence or absence, as well as the structure of carbohydrate moieties may have both a direct or indirect impact on the immunogenicity of therapeutic proteins; the glycan can induce an immune response itself (e.g., glycans of non-human origin), or its presence may affect the conformation of the protein in such a way that the protein becomes immunogenic. In some embodiments, the antibody or fragment thereof administered may advantageously minimise such properties and therefore minimise immunogenicity.

The antibody or fragment thereof may be capable of exhibiting one or more pharmacokinetic properties selected from the group consisting of:

(a) a rate of clearance (CL) of about 0.05 to about 0.18 L/day;
(b) an absorption constant (ka) of about 0.11 to about 0.33 L/day;
(c) a volume of central compartment volume (Vc) of about 1.6 to about 5.0 L;
(d) a second (peripheral compartment) volume (Vp1) of about 1.2 to about 3.6 L;
(e) a rate of clearance from the central compartment to the second compartment (Q) of about 0.31 to about 0.93 L/day; and
(f) a bioavailability (Fabs1) of about 0.6 to about 1.0.

The antibody or fragment thereof may have 1, 2, 3, 4, 5, or 6 of the pharmacokinetic properties (a) to (f).

The antibody or fragment thereof may exhibit a rate of clearance (CL) of about 0.05 to about 0.18 L/day; about 0.06 to about 0.17 L/day; about 0.07 to about 0.16 L/day; about 0.08 to about 0.15 L/day; about 0.09 to about 0.14 L/day; or about 0.10 to about 0.13 L/day. The antibody or fragment thereof may exhibit a rate of clearance (CL) of about 0.115 L/day.

The antibody or fragment thereof may exhibit an absorption constant (ka) of about 0.11 to about 0.33 L/day; about 0.12 to about 0.32 L/day; about 0.13 to about 0.31 L/day; about 0.14 to about 0.30 L/day; about 0.15 to about 0.29 L/day; about 0.16 to about 0.28 L/day; about 0.17 to about 0.27 L/day; about 0.18 to about 0.26 L/day; about 0.19 to about 0.25 L/day; about 0.20 to about 0.24 L/day; or about 0.21 to about 0.23 L/day. The antibody or fragment thereof may exhibit an absorption constant (ka) of about 0.22 L/day.

The antibody or fragment thereof may exhibit a volume of central compartment volume (Vc) of about 1.6 to about 5.0 L; about 1.8 to about 4.8 L; about 2.0 to about 4.6 L; about 2.2 to about 4.4 L; about 2.4 to about 4.2 L; about 2.6 to about 4.0 L; about 2.8 to about 3.8 L; about 3.0 to about 3.6 L; or about 3.2 to about 3.4 L. The antibody or fragment thereof may exhibit a volume of central compartment volume (Vc) of about 3.3 L.

The antibody or fragment thereof may exhibit a second (peripheral compartment) volume (Vp1) of about 1.2 to about 3.6 L; about 1.4 to about 3.4 L; about 1.6 to about 3.2 L; about 1.8 to about 3.0 L; about 2.0 to about 2.8 L; about 2.2 to about 2.6 L; or about 2.3 to about 2.5 L. The antibody or fragment thereof may exhibit a second (peripheral compartment) volume (Vp1) of about 2.4 L.

The antibody or fragment thereof may exhibit a rate of clearance from the central compartment to the second compartment (Q1) of about 0.31 to about 0.93 L/day; about 0.36 to about 0.88 L/day; about 0.41 to about 0.83 L/day; about 0.46 to about 0.78 L/day; about 0.51 to about 0.73 L/day; about 0.56 to about 0.68 L/day; about 0.60 to about 0.64 L/day; or about 0.61 to about 0.63 L/day. The antibody or fragment thereof may exhibit a rate of clearance from the central compartment to the second compartment (Q1) of about 0.62 L/day.

The antibody or fragment thereof may exhibit a bioavailability (Fabs1) of about 0.6 to about 1.0; about 0.65 to about 0.95; about 0.70 to about 0.90; or about 0.75 to about 0.85. The antibody or fragment thereof may exhibit a bioavailability (Fabs1) of about 0.8.

The pharmacokinetic properties may result from administration of a single dose of the antibody, or fragment thereof. The pharmacokinetic properties may alternatively result from administration of more than one dose (e.g., 2, 3, 4, 5, 6, 7, 8, 9, 10 or more) of the antibody, or fragment thereof. The subject may be dosed with the antibody or fragment thereof such that the antibody or fragment thereof is present in the subject at a steady state level.

The pharmacokinetic properties may be determined based on samples from a single subject. The pharmacokinetic properties may alternatively be determined based on samples of a population, e.g., a mixed population (e.g., healthy and not healthy), a population with AD, or a population with moderate to severe AD.

Said pharmacokinetic properties may be determined using a two-compartment model. The two-compartment model may be a linear two-compartment model. In a linear two-compartment model, CL and Q1 may be linear with respect to the concentration of the antibody or fragment thereof.

The antibody or fragment thereof may have at least any two of the pharmacokinetic properties above as determined using a two-compartment model. The antibody or fragment thereof may have at least any three of the pharmacokinetic properties above as determined using a two-compartment model. The antibody or fragment thereof may have at least any four of the pharmacokinetic properties above as determined using a two-compartment model. The antibody or fragment thereof may have at least any five of the pharmacokinetic properties above as determined using a two-compartment model. The antibody or fragment thereof may have six of the pharmacokinetic properties above as determined using a two-compartment model.

The pharmacokinetic properties may result from administration of the antibody of fragment thereof by intravenous injection or by subcutaneous injection. The pharmacokinetic properties may result from administration of any dose or combination of doses described herein.

The method may further comprise obtaining one or more blood samples from the subject and optionally measuring the blood serum concentration reached by the antibody or fragment thereof.

Patient Populations

The subject is a human subject. The subject may be a male subject. The subject may be a female subject. The subject may be between about 6 and about 100 years of age; about 15 and about 100 years of age; about 18 and about 93 years of age; about 20 and about 80 years of age; about 30 and about 70 years of age; or about 40 and about 60 years of age. The subject may be about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years of age. The subject may be 44 years of age. The subject may weigh about 92 kg. The subject may weigh between about 40 and about 210 kg. The subject may weigh between about 50 and 200 kg, about 60 and about 150 kg; or about 75 and about 100 kg. The subject may weigh about 40, 43, 45, 50, 55, 60, 65, 70, 75, 80, 85, 90, 92, 95, 100, 105, 110, 115, 120, 125, 130, 135, 140, 145, 150, 155, 160, 165, 170, 175, 180, 185, 190, 195, 200, 205 or 210 kg.

The subject may have an age selected from the group consisting of up to 6 years of age; from 6 years of age to 12 years of age; from 12 years of age to 18 years of age; at least 18 years of age; and less than 75 years of age. The subject may be at least 18 years of age and/or less than 75 years of age. The subject may have an age of 6 months to 11 years. The subject may have an age of 12 years to 17 years.

The subject may be an inflammatory diseases or inflammatory disorders patient. The subject may be an immune-mediated diseases or immune-mediated disorders. The subject may be an inflammatory skin diseases or inflammatory skin disorders patient.

The subject may be a Type 2 patient. The subject may be a high Type 2 patient. The subject may be a low Type 2 patient. The subject may be a non-Type 2 patient. The subject may be a patient with mixed inflammatory responses.

The subject may have been diagnosed with Atopic Dermatitis at least one year before administration of the antibody or fragment thereof. The subject may be a chronic Atopic Dermatitis patient. The antibody or fragment thereof may be a first line treatment. The antibody or fragment thereof may be a second line treatment. The Atopic Dermatitis may be moderate-to-severe Atopic Dermatitis. The Atopic Dermatitis may be not adequately controlled with topical prescription and/or systemic therapies or when those therapies are not advisable.

The subject may be a moderate-to-severe Atopic Dermatitis patient who is candidate for systemic therapy. The subject may be a moderate-to-severe Atopic Dermatitis patient whose disease is not adequately controlled with topical prescription therapies or when those therapies are not advisable.

The subject may be defined by biomarker levels. The biomarker levels may be any suitable biomarker levels known in the art or described elsewhere herein.

Topical Corticosteroids

Topical corticosteroids are a type of steroid medicine applied directly to the skin to reduce inflammation and irritation. Topical corticosteroids may be used for treatment of AD, for example to reduce swelling, redness and itching during flare-ups. When used correctly, topical corticosteroids serious side effects tend to be rare, although are reported. However, they may not be sufficiently effective as the sole treatment for many subject's AD, especially when the AD is moderate to severe AD. An approach described herein is benefitting from the use of topical corticosteroids by also treating with an anti-OX40L antibody, or antigen-binding fragment thereof, in accordance with embodiments of the method.

The Atopic Dermatitis may be resistant, non-responsive or inadequately responsive to treatment by either topical corticosteroids and/or systemic therapies or when those therapies are not advisable or wherein the subject has had an inadequate response to, was intolerant to, or is refractory to one or more topical corticosteroids. The Atopic Dermatitis may not be adequately controlled or inadequately responsive to treatment by topical corticosteroids. The subject may have had an inadequate response to, was intolerant to, or is refractory to one or more topical corticosteroids. The subject may also be being treated with one or more topical corticosteroids. The antibody or fragment thereof may be used with topical corticosteroids. The subject may have been previously treated with one or more topical corticosteroid.

The method may further comprise administering a therapeutically effective amount of one or more topical corticosteroid. The one or more topical corticosteroid may be administered prior to the anti-OX40L antibody, or antigen-binding fragment thereof. A first injection of the anti-OX40L antibody, or antigen-binding fragment thereof may be administered on the day that the subject discontinues treatment with the one or more topical corticosteroid. A first injection of the anti-OX40L antibody, or antigen-binding fragment thereof may be administered on the day that a clinical decision is taken to discontinue treatment with the one or more topical corticosteroid.

A clinical decision to discontinue treatment with the one or more topical corticosteroid may be taken or the subject may discontinue treatment for a number of reasons. For example, the subject may have an inadequate response to the one or more topical corticosteroid, be intolerant to the one or more topical corticosteroid or be refractory to the one or more topical corticosteroid. The likely time course for discontinuing treatment may depend on the reason for discontinuing treatment. For example, it may be rapidly evident to a clinician that a patient is intolerant to the one or more topical corticosteroid so that the decision to discontinue treatment can be taken relatively quickly. It may take longer to determine that a patient is refractory to, or has an inadequate response to the one or more topical corticosteroid, so the decision to discontinue treatment for these reasons may be taken less quickly accordingly. The reasons may be a primary efficacy failure, a secondary efficacy failure or intolerance. A primary efficacy failure may be where no response to the start of treatment is seen. In this case, the treatment may be discontinued quickly. A secondary efficacy failure may be when a patient loses responsiveness and doesn't respond to further treatment, which may occur at any time after an initial response has been observed, for example after six months, after one year, after 18 months or after two years. Intolerance can be at any time after start of treatment, for some it may be evident early on, for others it may be after a period of time that adverse events start to show.

A clinical decision may be taken to discontinue treatment or the subject may discontinue treatment with the one or more topical corticosteroid at least 2 months, at least 3 months, at least four months, at least 5 months, at least 6 months or 4 to 6 months after administering a first administration of the one or more topical corticosteroid.

The one or more topical corticosteroid may be administered after the anti-OX40L antibody, or antigen-binding fragment thereof. A first administration of the one or more topical corticosteroid may be administered on the day that the subject discontinues treatment with the anti-OX40L antibody, or antigen-binding fragment thereof. A first administration of the one or more topical corticosteroid may be administered on the day that a clinical decision is taken to discontinue treatment with the anti-OX40L antibody, or antigen-binding fragment thereof.

A clinical decision may be taken to discontinue treatment or the subject may discontinue treatment with the anti-OX40L antibody, or antigen-binding fragment thereof, at least 2 months, at least 3 months, at least four months, at least 5 months, at least 6 months or 4 to 6 months after administering a first injection of the anti-OX40L antibody, or antigen-binding fragment thereof.

In many instances, the subject may undergo combined treatment with both a topical corticosteroid and the anti-OX40L antibody, or antigen-binding fragment thereof. However, in some instances, The one or more topical corticosteroid and the anti-OX40L antibody, or antigen-binding fragment thereof may be administered sequentially and a period between administering an administration of the one or more topical corticosteroid and an injection of the anti-OX40L antibody, or antigen-binding fragment thereof is at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, at least 8 weeks, at least 10 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks or at least 52 weeks.

The one or more topical corticosteroid may be administered concurrently with the anti-OX40L antibody, or antigen-binding fragment thereof. Concurrent administration may include overlapping dosage regimes and/or coadministration.

The topical corticosteroid may be any suitable topical corticosteroid. The topical corticosteroid may be selected from the group consisting of betamethasone dipropionate, clobetasol propionate, dexamethasone, methylprednisolone, methylprednisolone aceponate, mometasone furoate, diflorasone diacetate, halobetasol propionate, amcinonide, augmented betamethasone dipropionate, fluocinonide, halcinonide, triamcinolone acetonide, betamethasone valerate, clocortolone pivalate, desoximetasone, fluocinolone acetonide, flurandrenolide, fluticasone propionate, hydrocortisone butyrate, hydrocortisone probutate, hydrocortisone valerate, prednicarbate, alclometasone dipropionate, desonide, hydrocortisone and hydrocortisone acetate. The topical corticosteroid may be selected from the group consisting of betamethasone dipropionate, betamethasone dipropionate;gentamicin sulphate, clobetasol propionate, dexamethasone, methylprednisolone, methylprednisolone aceponate and mometasone furoate. The topical corticosteroid may be betamethasone dipropionate, optionally wherein the betamethasone dipropionate is combined with gentamicin sulphate.

The topical corticosteroid may be formulated as a cream, ointment, gel, foam, solution, lotion or gel. The topical corticosteroid may be applied twice daily or once daily. The topical corticosteroid may be applied once weekly or twice weekly.

The duration of topical corticosteroid administration may be of any suitable length to achieve a clinical objective and may therefore involve any suitable number of administrations. The duration of topical corticosteroid administration may therefore be determined by a clinician. For some subjects, topical corticosteroid administration may be indefinite.

In further configurations, there are provided the above-mentioned embodiments comprising administering a therapeutically effective amount of an OX40L antagonist antibody or antigen-binding fragment thereof.

Calcineurin Inhibitors

Topical calcineurin inhibitors (TCIs) work by altering the immune system and have been developed for treating atopic dermatitis. There are two types available: tacrolimus ointment (Protopic) for moderate to severe atopic dermatitis and pimecrolimus cream (Elidel) for mild to moderate atopic dermatitis. 'Topical' means applied to the skin. 'Calcineurin inhibitor' means that they block Calcineurin that can contribute to the flaring of atopic dermatitis. TCIs are used to treat atopic dermatitis in adults and children over 2 years of age who are not responding adequately to or who cannot tolerate conventional therapies such as topical steroids. They can be used for both treating and preventing flares. An approach described herein is benefitting from the use of topical calcineurin inhibitor by also treating with an anti-OX40L antibody, or antigen-binding fragment thereof, in accordance with the embodiments of the method.

The Atopic Dermatitis may be resistant, non responsive or inadequately responsive to treatment by either topical calcineurin inhibitor and/or systemic therapies or when those therapies are not advisable or wherein the subject has had an inadequate response to, was intolerant to, or is refractory to one or more topical calcineurin inhibitor. The Atopic Dermatitis may not be adequately controlled or inadequately responsive to treatment by topical calcineurin inhibitor. The subject may have had an inadequate response to, was intolerant to, or is refractory to one or more topical calcineurin inhibitor. The subject may also be being treated with one or more topical calcineurin inhibitor. The antibody or fragment thereof may be used with topical calcineurin inhibitor. The subject may have been previously treated with one or more topical calcineurin inhibitor.

The method may further comprise administering a therapeutically effective amount of one or more topical calcineurin inhibitor. The one or more topical calcineurin inhibitor may be administered prior to the anti-OX40L antibody, or antigen-binding fragment thereof. A first injection of the anti-OX40L antibody, or antigen-binding fragment thereof may be administered on the day that the subject discontinues treatment with the one or more topical calcineurin inhibitor. A first injection of the anti-OX40L antibody, or antigen-binding fragment thereof may be administered on the day that a clinical decision is taken to discontinue treatment with the one or more topical calcineurin inhibitor.

A clinical decision to discontinue treatment with the one or more topical calcineurin inhibitor may be taken or the subject may discontinue treatment for a number of reasons. For example, the subject may have an inadequate response to the one or more topical calcineurin inhibitor, be intolerant to the one or more topical calcineurin inhibitor or be refractory to the one or more topical calcineurin inhibitor. The likely time course for discontinuing treatment may depend on the reason for discontinuing treatment. For example, it may be rapidly evident to a clinician that a patient is intolerant to the one or more topical calcineurin inhibitor so that the decision to discontinue treatment can be taken relatively quickly. It may take longer to determine that a patient is refractory to, or has an inadequate response to the one or more topical calcineurin inhibitor, so the decision to discontinue treatment for these reasons may be taken less quickly accordingly. The reasons may be a primary efficacy failure, a secondary efficacy failure or intolerance. A primary efficacy failure may be where no response to the start of treatment is seen. In this case, the treatment may be discontinued quickly. A secondary efficacy failure may be when a patient loses responsiveness and doesn't respond to further treatment, which may occur at any time after an initial response has been observed, for example after six months, after one year, after 18 months or after two years. Intolerance can be at any time after start of treatment, for some it may be evident early on, for others it may be after a period of time that adverse events start to show.

A clinical decision may be taken to discontinue treatment with the one or more topical calcineurin inhibitor at least 2 months, at least 3 months, at least four months, at least 5 months, at least 6 months or 4 to 6 months after administering a first administration of the one or more topical calcineurin inhibitor.

The one or more topical calcineurin inhibitor may be administered after the anti-OX40L antibody, or antigen-binding fragment thereof. A first administration of the one or more topical calcineurin inhibitor may be administered on the day that the subject discontinues treatment with the anti-OX40L antibody, or antigen-binding fragment thereof. A first administration of the one or more topical calcineurin inhibitor may be administered on the day that a clinical decision is taken to discontinue treatment with the anti-OX40L antibody, or antigen-binding fragment thereof.

A clinical decision may be taken to discontinue treatment or the subject may discontinue treatment with the anti-OX40L antibody, or antigen-binding fragment thereof, at least 2 months, at least 3 months, at least four months, at least 5 months, at least 6 months or 4 to 6 months after administering a first injection of the anti-OX40L antibody, or antigen-binding fragment thereof.

In many instances, the subject may undergo combined treatment with both a topical calcineurin inhibitor and the anti-OX40L antibody, or antigen-binding fragment thereof. However, in some instances, the one or more topical calcineurin inhibitor and the anti-OX40L antibody, or antigen-binding fragment thereof may be administered sequentially and a period between administering an administration of the one or more topical calcineurin inhibitor and an injection of the anti-OX40L antibody, or antigen-binding fragment thereof is at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, at least 8 weeks, at least 10 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks or at least 52 weeks.

The one or more topical calcineurin inhibitor may be administered concurrently with the anti-OX40L antibody, or antigen-binding fragment thereof. Concurrent administration may include overlapping dosage regimes and/or coadministration.

The topical calcineurin inhibitor may be any suitable topical calcineurin inhibitor. The topical calcineurin inhibitor may be tacrolimus ointment or pimecrolimus cream, e.g., tacrolimus ointment.

The topical calcineurin inhibitor may be formulated as a cream, ointment, gel, foam, solution, lotion or gel. The topical calcineurin inhibitor may be applied twice daily or once daily. The topical calcineurin inhibitor may be applied two to three times weekly.

The duration of topical calcineurin inhibitor administration may be of any suitable length to achieve a clinical objective and may therefore involve any suitable number of administrations. The duration of topical calcineurin inhibitor administration may therefore be determined by a clinician. For some subjects, topical calcineurin inhibitor administration may be indefinite.

In further configurations, there are provided the above-mentioned embodiments comprising administering a therapeutically effective amount of an OX40L antagonist antibody or antigen-binding fragment thereof.

Other Co-Treatments

Any other suitable treatment for Atopic Dermatitis may characterise the subject to be treated and/or be used in combination with the antibody or fragment thereof according to the methods described herein.

The subject may also be being treated with one or more topical antihistamine. The antibody or fragment thereof may be used with one or more topical antihistamine.

The subject may also be being treated with one or more oral steroid. The antibody or fragment thereof may be used with one or more oral steroid.

Disease Severity

There are several different methods which can be used to assign the severity of disease when assessing atopic dermatitis patients. Each method of assigning disease severity may therefore inform patient selection for embodiments of the methods. Each method of assigning disease severity may be used to monitor subject treatment for the embodiments of the methods. Each method of assigning disease severity may be used to transition a patient from the induction phase to the maintenance phase. Each method of assigning disease severity may be used to identify a treatment as disease modifying. Each method of assigning disease severity may be performed as described below and/or in the Examples, as applicable. The methods of assigning disease severity include:

EASI (including E4SI75 and EASI90)

The EASI is a continuous scale (0 (no disease)-72 (most severe disease)) used to assess the severity and extent of atopic dermatitis. It is described for example in Schram M E, Spuls P I, Leeflang M M, Lindeboom R, Bos J D, Schmitt J. EASI, (objective) SCORAD and POEM for atopic eczema: responsiveness and minimal clinically important difference. Allergy. 2012 January;67(1):99-106 and Hanifin J M, Thurston M, Omoto M, Cherill R, Tofte S J, Graeber M. The eczema area and severity index (EASI): assessment of reliability in atopic dermatitis. EASI Evaluator Group. Exp Dermatol. 2001 Feb;10(1):11-8. Methods for determining an EASI score are known and may be as described below and/or in the Examples, as applicable.

In EASI, four disease characteristics of AD (erythema, infiltration/papulation, excoriations, and lichenification) are assessed for severity by the investigator on a scale of 0 (absent) to 3 (severe). The scores are added up for each of the four body regions (head, arms, trunk, and legs). The assigned percentages of body surface area (BSA) for each section of the body are 10% for head, 20% for arms, 30% for trunk, and 40% for legs, respectively. Each subtotal score is multiplied by the BSA represented by that region. In addition, an area score of 0 to 6 is assigned for each body region, depending on the percentage of AD-affected skin in that area: 0 (none), 1 (1% to 9%), 2 (10% to 29%), 3 (30% to 49%), 4 (50% to 69%), 5 (70% to 89%), or 6 (90% to 100%). Each of the body area scores are multiplied by the area affected. The resulting EASI score ranges from 0 to 72 points, with the highest score indicating worse severity of AD.

It has been suggested that the severity of AD based on EASI score should be categorized as follows: 0=clear; 0.1 to 1.0=almost clear; 1.1 to 7.0=mild; 7.1 to 21.0=moderate; 21.1 to 50.0=severe; 50.1 to 72.0=very severe. EASI50 indicates 50% improvement from baseline. EASI75 indicates >75% improvement from baseline. EASI90 indicates 90% improvement from baseline. EASI100 indicates 100% improvement from baseline.

It is thought that the overall minimal clinically important difference (MCID) is 6.6 points.

Baseline Scores—EA51

The atopic dermatitis may have been assessed by determining a baseline EASI score. Determining a baseline EASI score may comprise:

(a) Selecting a body region from the group consisting of head and neck; trunk including the genital area; upper extremities; and lower extremities including the buttocks;

(b) Assessing the extent of atopic dermatitis in the selected body region and assigning a region score based on the extent of atopic dermatitis in the selected body region;

(c) Assessing the severity of each of the following signs in the selected body region:

1. Erythema,
2. Edema and/or papulation,
3. Excoriation, and
4. Licenification, and assigning a severity score to each sign in the selected body region;

(d) Determining a total score for the selected body region based on the region score and the severity score for each sign in the selected body region;

(e) Repeating steps (b) to (d) for each of the remaining body regions; and (f) Determining a baseline EASI score based on the total score for each body region.

The baseline EASI score may be any score indicating moderate to severe AD. The baseline EASI score may be at least 12.1, at least 16.1, or at least 21.1. The baseline EASI score may be at least 16.1.

A first injection of the anti-OX40L antibody or fragment thereof may be administered on the same day as the baseline EASI score is determined.

Some embodiments of the method may further comprise determining the baseline EASI score.

Clinical Outcomes—EASI

Some embodiments of the method may further comprise assessing the atopic dermatitis by determining a post-administration EASI score at least 7 days or at least 15 days after administering a first injection of the antibody or fragment thereof. Obtaining a post-administration EASI score at least 7 days or at least 15 days after administering a first injection of the antibody or fragment thereof is expected to be the earliest a change in EASI score could reliably be observed due to the action of the antibody or fragment thereof, however any clinically suitable delay from administration to assessing may be employed. The post-administration EASI score may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration EASI score may be determined at around 7 days, at around 15 days, around 29 days, around 57 days, around 85 days, around 113 days, around 169 days and/or around 253 days after administering a first injection of the antibody or fragment thereof. The post-administration EASI score may be determined at the end of the induction phase.

The post-administration EASI score may be less than or equal to 21.0. The post-administration EASI score may indicate the AD is no longer severe AD. The post-administration EASI score may be less than or equal to 16.0. The post-administration EASI score may be less than or equal to 16.0, less than or equal to 15.0, less than or equal to 14.0, less than or equal to 13.0, less than or equal to 12.0, less than or equal to 11.0, less than or equal to 10.0, less than or equal to 9.0, less than or equal to 8.0, less than or equal to 7.0, less than or equal to 6.0, less than or equal to 5.0, less than or equal to 4.0, less than or equal to 3.0, less than or equal to 2.0, less than or equal to 1.0 or around 0. The post-administration EASI score may indicate the AD is no longer moderate AD. The post-administration EASI score may be less than or equal to 7.0 or less than or equal to 1.0. The post-administration EASI score may indicate the AD is mild AD. The post-administration EASI score may indicate the AD is almost clear. The post-administration EASI score may be reduced at least 10 percent, at least 25 percent or at least 50 percent relative to the baseline EASI score. The post-administration EASI score may be reduced at least 6 points, at least 6.6 points, at least 7 points, at least 8 points, at least 9 points or at least 10 points relative to the baseline EASI score.

Some embodiments of the method may further comprise assessing the atopic dermatitis by determining one or more further post-administration EASI score. The one or more further post-administration EASI score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration EASI score may be determined at around 29 days, around 57 days, around 85 days, around 113 days, around 169 days and/or around 253 days after administering a first injection of the antibody or fragment thereof. The one or more further post-administration EASI score may be determined at the end of the induction phase.

The one or more further post-administration EASI score may be less than or equal to 21.0. The one or more further post-administration EASI score may indicate the AD is no longer severe AD. The one or more further post-administration EASI score may be less than or equal to 16.0, less than or equal to 15.0, less than or equal to 14.0, less than or equal to 13.0, less than or equal to 12.0, less than or equal to 11.0, less than or equal to 10.0, less than or equal to 9.0, less than or equal to 8.0, less than or equal to 7.0, less than or equal to 6.0, less than or equal to 5.0, less than or equal to 4.0, less than or equal to 3.0, less than or equal to 2.0, less than or equal to 1.0 or around 0. The one or more further post-administration EASI score may indicate the AD is no longer moderate AD.

The one or more further post-administration EASI score may be less than or equal to 7.0 or less than or equal to 1.0. The one or more further post-administration EASI score may indicate the AD is mild AD. The one or more further post-administration EASI score may indicate the AD is almost clear. The one or more further post-administration EASI score may be reduced at least 10 percent, at least 25 percent or at least 50 percent relative to the baseline EASI score. The one or more further post-administration EASI score is reduced at least 6 points, at least 6.6 points, at least 7 points, at least 8 points, at least 9 points or at least 10 points relative to the baseline EASI score. The one or more further post-administration EASI score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline EASI score. The post-administration EASI score may be maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

Determining the post-administration EASI score and/or the one or more further post-administration EASI score may comprise:

(a) Selecting a body region from the group consisting of head and neck; trunk including the genital area; upper extremities; and lower extremities including the buttocks;

(b) Assessing the extent of atopic dermatitis in the selected body region and assigning a region score based on the extent of atopic dermatitis in the selected body region;

(c) Assessing the severity of each of the following signs in the selected body region:

1. Erythema,
2. Edema and/or papulation,
3. Excoriation, and
4. Licenification, and assigning a severity score to each sign in the selected body region;

(d) Determining a total score for the selected body region based on the region score and the severity score for each sign in the selected body region;

(e) Repeating steps (b) to (d) for each of the remaining body regions; and (f) Determining a baseline EASI score based on the total score for each body region.

The post-administration EASI and/or further post-administration EASI may be determined at least around 113 days after administering a first injection of the antibody or fragment thereof and the post-administration EASI and/or further post-administration EASI may be EASI50, EASI75, EASI90 or EASI100. The post-administration EASI and/or further post-administration EASI may be determined at least around 169 days after administering a first injection of the antibody or fragment thereof and wherein the post-administration EASI and/or further post-administration EASI may be EASI50, EASI75, EASI90 or EASI100. The post-administration EASI and/or further post-administration EASI may be determined at least around 253 days after administering a first injection of the antibody or fragment thereof and wherein the post-administration EASI and/or further post-administration EASI may be EASI50, EASI75, EASI90 or EASI100. The Atopic Dermatitis may be treated as evidenced by a reduction in the EASI score by at least 40% after the third injection as a treatment dose and wherein the reduction in EASI score is persistent for at least 2 months, at least 3 months, at least 4 months, at least 5 months or at least 6 months after administration of the last injection as a treatment dose.

According to certain embodiments, administration of a therapeutically effective amount of an anti-OX40L antibody, or antigen-binding fragment thereof to a patient results in a decrease in EASI score. Some embodiments include therapeutic methods which result in a decrease from baseline in EASI score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration EASI score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline EASI score. The reduction of the post-administration EASI score relative to the baseline EASI score may be derived from any baseline EASI score and any post-administration EASI score, at any time point or between any time points, disclosed herein. In certain exemplary embodiments, administration of an anti-OX40L antibody, or antigen-binding fragment thereof to a subject results in a decrease from baseline in EASI score of at least 15%, at least 20% or at least 30%, optionally at around day 113 after the first administration of the anti-OX40L antibody, or antigen-binding fragment thereof. In certain exemplary embodiments, administration of an anti-OX40L antibody, or antigen-binding fragment thereof to a subject results in a decrease from baseline in EASI score of at least 40% or at least 45%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in EASI score equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

Investigator Global Assessment—Atopic Dermatitis (IGA-AD)

The IGA-AD scale, which ranges from 0-4, and is assigned by physicians, was developed by Eli Lilly in collaboration with a number of clinical experts in Atopic Dermatitis and was reviewed by the FDA and agreed upon. Methods for determining an IGA-AD score are known and may be as described below and/or in the Examples, as applicable.

A summary of the assignment of the different scores is in Table 1a below.

TABLE 1a

| IGA-AD scores | |
|---|---|
| Score | Morphological Description |
| 0—Clear | No inflammatory signs of atopic dermatitis (no erythema, no induration/papulation, no oozing/crusting). Post-inflammatory hyperpigmentation and/or hypopigmentation may be present. |
| 1—Almost clear | Barely perceptible erythema, and/or barely perceptible induration/papulation. No oozing or crusting. |
| 2—Mild | Slight but definite erythema (pink), and/or slight but definite induration/papulation. No oozing or crusting. |
| 3—Moderate | Clearly perceptible erythema (dull red), and/or clearly perceptible induration/papulation. Oozing and crusting may be present. |
| 4—Severe | Marked erythema (deep or bright red), and/or marked induration/papulation. Disease is widespread in extent. Oozing or crusting may be present. |

A decrease in IGA-AD score therefore relates to an improvement in signs and/or symptoms.

Baseline Scores—IGA-AD

The atopic dermatitis may have been assessed by determining a baseline IGA-AD score. Determining a baseline IGA-AD score may comprise describing the overall appearance of AD lesions at a given time point by:

(a) Assigning a score of 0—clear—when the most applicable morphological description is:
  No inflammatory signs of atopic dermatitis (no erythema, no induration/papulation, no lichenification, no oozing/crusting); post-inflammatory hyperpigmentation and/or hypopigmentation may be present;
(b) Assigning a score of 1—almost clear—when the most applicable morphological description is:
  Barely perceptible erythema, and/or barely perceptible induration/papulation; no oozing or crusting;
(c) Assigning a score of 2—mild—when the most applicable morphological description is:
  Slight but definite erythema (pink), and/or slight but definite induration/papulation; no oozing or crusting;
(d) Assigning a score of 3—moderate—when the most applicable morphological description is:
  Clearly perceptible erythema (dull red), and/or clearly perceptible induration/papulation; oozing and crusting may be present;
(e) Assigning a score of 4—severe—when the most applicable morphological description is:
  Marked erythema (deep or bright red), and/or marked induration/papulation; disease is widespread in extent; oozing or crusting may be present.

The baseline IGA-AD score may be any score indicating moderate to severe AD. The baseline IGA-AD score may be 3 or 4.

A first injection of the anti-OX40L antibody or fragment thereof may be administered on the same day as the baseline IGA-AD score is determined.

Some embodiments of the method may further comprise determining the baseline IGA-AD score.

Clinical Outcomes—IGA-AD

Some embodiments of the method may further comprise assessing the atopic dermatitis by determining a post-administration IGA-AD score at least 15 days after administering a first injection of the antibody or fragment thereof. Obtaining a post-administration IGA-AD score at least 7 days or at least 15 days after administering a first injection of the antibody or fragment thereof is expected to be the earliest a change in IGA-AD score could reliably be observed due to the action of the antibody or fragment thereof, however any clinically suitable delay from administration to assessing may be employed. The post-administration IGA-AD score may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration IGA-AD score may be determined at around 7 days, at around 15 days, around 29 days, around 57 days, around 85 days, around 113 days, around 169 days and/or around 253 days after administering a first injection of the antibody or fragment thereof. The post-administration IGA-AD score may be determined at the end of the induction phase.

The post-administration IGA-AD score may be 0 or 1. The post-administration IGA-AD score may indicate the AD is no longer severe AD. The post-administration IGA-AD score may indicate the AD is no longer moderate AD. The post-administration IGA-AD score may indicate the AD is almost clear. The post-administration IGA-AD score may be reduced at least 1 point, at least 2 points, at least 3 points or up to 4 points relative to the baseline IGA-AD score. The post-administration IGA-AD score may be reduced at least 2 points relative to the baseline IGA-AD score. The post-administration IGA-AD score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline IGA-AD score. The the post-administration IGA-AD score may be maintained, without additional administration of an anti-OX40L antibody, or antigen-binding fragment thereof, for:

(a) at least 2 months, at least 3 months, at least 4 months, at least 5 months or at least 6 months after administration of the last injection; or
(b) at least about 4, 8, 15, 22, 25, 29, 36, 43, 50, 57, 64, 71, 85, 113, 169 or 253 days.

Some embodiments of the method may further comprise assessing the atopic dermatitis by determining one or more further post-administration IGA-AD score. The one or more further post-administration IGA-AD score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration IGA-AD score is determined at around 29 days, around 57 days, around 85 days, around 113 days, around 169 days and/or around 253 days after administering a first injection of the antibody or fragment thereof. The one or more further post-administration IGA-AD score may be determined at the end of the induction phase.

The one or more further post-administration IGA-AD score may be 0 or 1. The one or more further post-administration IGA-AD score may indicate the AD is no longer severe AD. The one or more further post-administration IGA-AD score may indicate the AD is no longer moderate AD. The one or more further post-administration IGA-AD score may indicate the AD is almost clear. The one or more further post-administration IGA-AD score may be reduced at least 1 point, at least 2 points, at least 3 points or up to 4 points relative to the baseline IGA-AD score. The one or more further post-administration IGA-AD score may be reduced at least 2 points relative to the baseline IGA-AD score.

Determining the post-administration IGA-AD score and/or the one or more further post-administration IGA-AD score may comprise describing the overall appearance of AD lesions at a given time point by:

(a) Assigning a score of 0—clear—when the most applicable morphological description is:
    No inflammatory signs of atopic dermatitis (no erythema, no induration/papulation, no oozing/crusting); post-inflammatory hyperpigmentation and/or hypopigmentation may be present;
(b) Assigning a score of 1—almost clear—when the most applicable morphological description is:
    Barely perceptible erythema, and/or barely perceptible induration/papulation; no oozing or crusting;
(c) Assigning a score of 2—mild—when the most applicable morphological description is:
    Slight but definite erythema (pink), and/or slight but definite induration/papulation; no oozing or crusting;
(d) Assigning a score of 3—moderate—when the most applicable morphological description is:
    Clearly perceptible erythema (dull red), and/or clearly perceptible induration/papulation; oozing and crusting may be present;
(e) Assigning a score of 4—severe—when the most applicable morphological description is:
    Marked erythema (deep or bright red), and/or marked induration/papulation; disease is widespread in extent; oozing or crusting may be present.

The post-administration IGA-AD and/or further post-administration IGA-AD may be determined at least around 113 days after administering a first injection of the antibody or fragment thereof and the post-administration IGA-AD and/or further post-administration IGA-AD may be:

(a) A IGA-AD score of 0 or 1, and/or
(b) reduced at least 2 points relative to the baseline IGA-AD score.

The post-administration IGA-AD and/or further post-administration IGA-AD may be determined at least around 169 days after administering a first injection of the antibody or fragment thereof and wherein the post-administration IGA-AD and/or further post-administration IGA-AD may be:

(a) A IGA-AD score of 0 or 1, and/or
(b) reduced at least 2 points relative to the baseline IGA-AD score.

The post-administration IGA-AD and/or further post-administration IGA-AD may be determined at least around 253 days after administering a first injection of the antibody or fragment thereof and wherein the post-administration IGA-AD and/or further post-administration IGA-AD may be:

(a) A IGA-AD score of 0 or 1, and/or
(b) reduced at least 2 points relative to the baseline IGA-AD score.

The Atopic Dermatitis may be treated as evidenced by a reduction in the IGA-AD score by at least 2 points after the third injection as a treatment dose and wherein the reduction in IGA-AD score is persistent for at least 2 months, at least 3 months, at least 4 months, at least 5 months or at least 6 months after administration of the last injection as a treatment dose.

According to certain embodiments of, administration of a therapeutically effective amount of an anti-OX40L antibody, or antigen-binding fragment thereof to a patient results in a decrease in IGA-AD score. Some embodiments include therapeutic methods which result in a decrease from baseline in IGA-AD score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration IGA-AD score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline IGA-AD score. The reduction of the post-administration IGA-AD score relative to the baseline IGA-AD score may be derived from any baseline IGA-AD score and any post-administration IGA-AD score, at any time point or between any time points, disclosed herein. In certain exemplary embodiments, administration of an anti-OX40L antibody, or antigen-binding fragment thereof to a subject results in a decrease from baseline in IGA-AD score of at least 15%, at least 20% or at least 30%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in IGA-AD score equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

Validated Investigator Global Assessment—Atopic Dermatitis (vIGA-AD)

The vIGA-AD scale, which ranges from 0-4, and is assigned by physicians, was developed by Eli Lilly in collaboration with a number of clinical experts in Atopic Dermatitis and was reviewed by the FDA and agreed upon. Further information can be found in Simpson et al., "The Validated Investigator Global Assessment for Atopic Dermatitis (vIGA-AD): The development and reliability testing of a novel clinical outcome measurement instrument for the severity of atopic dermatitis", J. Am. Acad. Dermatol., 2020 Sep;83(3):839-846. doi: 10.1016/j.jaad.2020.04.104. Epub 2020 Apr 25. The vIGA-AD scale corresponds to the IGA-AD scale but further takes into account lichenification. Methods for determining a vIGA-AD score are known and may be as described below and/or in the Examples, as applicable.

A summary of the assignment of the different scores is in Table 1b below.

(d) Assigning a score of 3—moderate—when the most applicable morphological description is:

Clearly perceptible erythema (dull red), clearly perceptible induration/papulation, and/or clearly perceptible lichenification; oozing and crusting may be present;

(e) Assigning a score of 4—severe—when the most applicable morphological description is:

Marked erythema (deep or bright red), marked induration/papulation, and/or marked lichenification; disease is widespread in extent; oozing or crusting may be present.

The baseline vIGA-AD score may be any score indicating moderate to severe AD. The baseline vIGA-AD score may be 3 or 4.

A first injection of the anti-OX40L antibody or fragment thereof may be administered on the same day as the baseline vIGA-AD score is determined.

Some embodiments of the method may further comprise determining the baseline vIGA-AD score.

Clinical Outcomes—vIGA-AD

Some embodiments of the method may further comprise assessing the atopic dermatitis by determining a post-administration vIGA-AD score at least 15 days after admin- TABLE 1b vIGA-AD scores

| Score | Morphological Description |
|---|---|
| 0—Clear | No inflammatory signs of atopic dermatitis (no erythema, no induration/papulation, no lichenification, no oozing/crusting). Post-inflammatory hyperpigmentation and/or hypopigmentation may be present. |
| 1—Almost clear | Barely perceptible erythema, barely perceptible induration/papulation, and/or minimal lichenification. No oozing or crusting. |
| 2—Mild | Slight but definite erythema (pink), slight but definite induration/papulation, and/or slight but definite lichenification. No oozing or crusting. |
| 3—Moderate | Clearly perceptible erythema (dull red), clearly perceptible induration/papulation, and/or clearly perceptible lichenification. Oozing and crusting may be present. |
| 4—Severe | Marked erythema (deep or bright red), marked induration/papulation, and/or marked lichenification. Disease is widespread in extent. Oozing or crusting may be present. |

A decrease in vIGA-AD score therefore relates to an improvement in signs and/or symptoms.

Baseline Scores—vIGA-AD

The atopic dermatitis may have been assessed by determining a baseline vIGA-AD score.

Determining a baseline vIGA-AD score may comprise describing the overall appearance of AD lesions at a given time point by:

(a) Assigning a score of 0—clear—when the most applicable morphological description is:

No inflammatory signs of atopic dermatitis (no erythema, no induration/papulation, no lichenification, no oozing/crusting); post-inflammatory hyperpigmentation and/or hypopigmentation may be present;

(b) Assigning a score of 1—almost clear—when the most applicable morphological description is:

Barely perceptible erythema, barely perceptible induration/papulation, and/or minimal lichenification; no oozing or crusting;

(c) Assigning a score of 2—mild—when the most applicable morphological description is:

Slight but definite erythema (pink), slight but definite induration/papulation, and/or slight but definite lichenification; no oozing or crusting;

istering a first injection of the antibody or fragment thereof. Obtaining a post-administration vIGA-AD score at least 7 days or at least 15 days after administering a first injection of the antibody or fragment thereof is expected to be the earliest a change in vIGA-AD score could reliably be observed due to the action of the antibody or fragment thereof, however any clinically suitable delay from administration to assessing may be employed. The post-administration vIGA-AD score may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration vIGA-AD score may be determined at around 7 days, at around 15 days, around 29 days, around 57 days, around 85 days, around 113 days, around 169 days and/or around 253 days after administering a first injection of the antibody or fragment thereof. The post-administration vIGA-AD score may be determined at the end of the induction phase.

The post-administration vIGA-AD score may be 0 or 1. The post-administration vIGA-AD score may indicate the AD is no longer severe AD. The post-administration vIGA-AD score may indicate the AD is no longer moderate AD. The post-administration vIGA-AD score may indicate the AD is almost clear. The post-administration vIGA-AD score may be reduced at least 1 point, at least 2 points, at least 3 points or up to 4 points relative to the baseline vIGA-AD score. The post-administration vIGA-AD score may be reduced at least 2 points relative to the baseline vIGA-AD score. The post-administration vIGA-AD score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline vIGA-AD score. The post-administration vIGA-AD score may be maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

Some embodiments of the method may further comprise assessing the atopic dermatitis by determining one or more further post-administration vIGA-AD score. The one or more further post-administration vIGA-AD score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration vIGA-AD score is determined at around 29 days, around 57 days, around 85 days, around 113 days, around 169 days and/or around 253 days after administering a first injection of the antibody or fragment thereof. The one or more further post-administration vIGA-AD score may be determined at the end of the induction phase.

The one or more further post-administration vIGA-AD score may be 0 or 1. The one or more further post-administration vIGA-AD score may indicate the AD is no longer severe AD. The one or more further post-administration vIGA-AD score may indicate the AD is no longer moderate AD. The one or more further post-administration vIGA-AD score may indicate the AD is almost clear. The one or more further post-administration vIGA-AD score may be reduced at least 1 point, at least 2 points, at least 3 points or up to 4 points relative to the baseline vIGA-AD score. The one or more further post-administration vIGA-AD score may be reduced at least 2 points relative to the baseline vIGA-AD score.

Determining the post-administration vIGA-AD score and/or the one or more further post-administration vIGA-AD score may comprise describing the overall appearance of AD lesions at a given time point by:

(a) Assigning a score of 0—clear—when the most applicable morphological description is:

No inflammatory signs of atopic dermatitis (no erythema, no induration/papulation, no lichenification, no oozing/crusting); post-inflammatory hyperpigmentation and/or hypopigmentation may be present;

(b) Assigning a score of 1—almost clear—when the most applicable morphological description is:

Barely perceptible erythema, barely perceptible induration/papulation, and/or minimal lichenification; no oozing or crusting;

(c) Assigning a score of 2—mild—when the most applicable morphological description is:

Slight but definite erythema (pink), slight but definite induration/papulation, and/or slight but definite lichenification; no oozing or crusting;

(d) Assigning a score of 3—moderate—when the most applicable morphological description is:

Clearly perceptible erythema (dull red), clearly perceptible induration/papulation, and/or clearly perceptible lichenification; oozing and crusting may be present;

(e) Assigning a score of 4—severe—when the most applicable morphological description is:

Marked erythema (deep or bright red), marked induration/papulation, and/or marked lichenification; disease is widespread in extent; oozing or crusting may be present.

The post-administration vIGA-AD and/or further post-administration vIGA-AD may be determined at least around 113 days after administering a first injection of the antibody or fragment thereof and the post-administration vIGA-AD and/or further post-administration vIGA-AD may be:

(a) A vIGA-AD score of 0 or 1, and/or (b) reduced at least 2 points relative to the baseline vIGA-AD score.

The post-administration vIGA-AD and/or further post-administration vIGA-AD may be determined at least around 169 days after administering a first injection of the antibody or fragment thereof and wherein the post-administration vIGA-AD and/or further post-administration vIGA-AD may be:

(a) A vIGA-AD score of 0 or 1, and/or (b) reduced at least 2 points relative to the baseline vIGA-AD score.

The post-administration vIGA-AD and/or further post-administration vIGA-AD may be determined at least around 253 days after administering a first injection of the antibody or fragment thereof and wherein the post-administration vIGA-AD and/or further post-administration vIGA-AD may be:

(a) A vIGA-AD score of 0 or 1, and/or (b) reduced at least 2 points relative to the baseline vIGA-AD score.

The Atopic Dermatitis may be treated as evidenced by a reduction in the vIGA-AD score by at least 2 points after the third injection as a treatment dose and wherein the reduction in vIGA-AD score is persistent for at least 2 months, at least 3 months, at least 4 months, at least 5 months or at least 6 months after administration of the last injection as a treatment dose.

According to certain embodiments, administration of a therapeutically effective amount of an anti-OX40L antibody, or antigen-binding fragment thereof to a patient results in a decrease in vIGA-AD score. Some embodiments include therapeutic methods which result in a decrease from baseline in vIGA-AD score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration vIGA-AD score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline vIGA-AD score. The reduction of the post-administration vIGA-AD score relative to the baseline vIGA-AD score may be derived from any baseline vIGA-AD score and any post-administration vIGA-AD score, at any time point or between any time points, disclosed herein. In certain exemplary embodiments, administration of an anti-OX40L antibody, or antigen-binding fragment thereof to a subject results in a decrease from baseline in vIGA-AD score of at least 15%, at least 20% or at least 30%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in vIGA-AD score equal to or greater than the minimal clinically important difference (MCID), at day 4, 8, 15, 22, 25, 29, 36, 43, 50, 57, 64, 71, 85, 113, 169, 253 or later following administration of the anti-OX 40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin for at least 113 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin for at least 169 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin for at least 253 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in an almost clear skin for at least 113 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in an almost clear skin for at least 169 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in an almost clear skin for at least 253 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin or an almost clear skin for at least 113 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin or an almost clear skin for at least 169 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin or an almost clear skin for at least 253 days following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

According to certain embodiments, administration of a therapeutically effective amount of an anti-OX40L antibody, or antigen-binding fragment thereof to a patient results in a clear skin or an almost clear skin at least 2 months after administration of the last injection.

According to certain embodiments, administration of a therapeutically effective amount of an anti-OX40L antibody, or antigen-binding fragment thereof to a patient results in a clear skin or an almost clear skin at least 3 months after administration of the last injection.

According to certain embodiments, administration of a therapeutically effective amount of an anti-OX40L antibody, or antigen-binding fragment thereof to a patient results in a clear skin or an almost clear skin at least 4 months after administration of the last injection.

According to certain embodiments, administration of a therapeutically effective amount of an anti-OX40L antibody, or antigen-binding fragment thereof to a patient results in a clear skin or an almost clear skin at least 5 months after administration of the last injection.

According to certain embodiments, administration of a therapeutically effective amount of an anti-OX40L antibody, or antigen-binding fragment thereof to a patient results in a clear skin or an almost clear skin at least 6 months after administration of the last injection.

Numerical Rating Scale (NRS) for Pruritus

The Numerical Rating Scale for Pruritus (NRS) is described in Reich et al, Acta Derm Venereol 2016 Nov. 2;96(7):978-980. As used herein the terms “pruritus” and “itch” are interchangeable. Methods for determining an NRS score are known and may be as described below and/or in the Examples, as applicable. Determining an NRS score comprises the subject providing a numerical rating of their worst itch in the past 24 hours on a scale of "0" being no itch to "10" being the worst imaginable itch. In English, the question posed to the subject is "On a scale of "0" (no itch) to "10" (worst imaginable itch), how was your worst itch in the past 24 hours?". The subject is asked to mark only one number on a scale of 0 to 10.

The mean values of absolute NRS values are calculated per week, i.e. for the corresponding day and the previous 6 days, if at least 4 values are available. For these mean values the absolute change from baseline is calculated. The Baseline value is the value assessed on Day 1. The values from early termination visits are used for the actual day on which the early termination visit was performed.

It is thought that the most appropriate definition of a responder on the Pruritus NRS is in the range of 2 to 4 points.

Baseline Scores—NRS: Pruritus/Itch

The atopic dermatitis may have been assessed by determining a baseline NRS score. Determining a baseline NRS score may comprise the subject providing a numerical rating of their worst itch in the past 24 hours on a scale of 0 to 10, wherein "0" is no itch and "10" is the worst imaginable itch. Determining a baseline NRS score may comprise the patient providing a numerical rating of their worst itch in the past 24 hours once per day for 7 days and taking the average numerical rating as the baseline NRS score.

The baseline NRS score may be any score associated with a moderate to severe case of AD. While AD is often associated with itch, NRS does not measure the severity of AD per se. It is possible to have severe AD with no itch. However, itch may contribute to the severity of AD, for example, excoriation is a sign assessed when determining an EASI score. NRS may therefore be a relevant descriptor for AD. The baseline NRS score may be selected from the group consisting of at least 3, at least 4, at least 5, at least 6, at least 7, at least 8, 6 to 9, and 7 to 8.

A first injection of the anti-OX40L antibody or fragment thereof may be administered on the same day as the baseline NRS score is determined.

Some embodiments may further comprise determining the baseline NRS score.

Clinical Outcomes—NRS: Pruritus/Itch

Some embodiments may further comprise assessing the atopic dermatitis by determining a post-administration NRS (numerical rating scale) score after administering a first injection of the antibody or fragment thereof. Any clinically suitable delay from administration to assessing may be employed. Changes in NRS score have been observed rapidly with, for example, JAKi, and some topical creams may provide instantaneous improvement. The post-administration NRS score may be determined within 2 hours, within 6 hours, within 12 hours, within 24 hours, within 24 hours, or within 7 days of administering a first injection of the antibody or fragment thereof. Although the onset of effect may be measurable more quickly with NRS than with other disease severity measures, the post-administration NRS score may be determined on a similar time scale as one or more other disease severity measure, where this is clinically expedient. The post-administration NRS score may be determined at least around 15 days, at least around 29 days, at least around 57 days, at least around 85 days, at least around 113 days, at least around 169 days and/or at least around 253 days after administering a first injection of the antibody or fragment thereof. The post-administration NRS score may be determined at around 15 days, around 29 days, around 57 days, around 85 days, around 113 days, around 169 days and/or around 253 days after administering a first injection of the antibody or fragment thereof. The post-administration NRS score is determined at the end of the induction phase.

The post-administration NRS score may be 0 to 7. The post-administration NRS score may be reduced at least 1 point, at least 2 points, at least 3 points, at least 4 points, at least 5 points, at least 6 points, at least 7 points, at least 8 points, at least 9 points or 10 points relative to the baseline NRS score. The post-administration NRS score may be reduced at least 3 points or at least 4 points relative to the baseline NRS score. The post-administration NRS score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline NRS score. The post-administration NRS score may be maintained, without additional administration of an anti-OX40L antibody, or antigen-binding fragment thereof, for:

(a) at least 2 months, at least 3 months, at least 4 months, at least 5 months or at least 6 months after administration of the last injection; or
(b) at least about 4, 8, 15, 22, 25, 29, 36, 43, 50, 57, 64, 71, 85, 113, 169 or 253 days.

Some embodiments may further comprise assessing the atopic dermatitis by determining one or more further post-administration NRS score. The one or more further post-administration NRS score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration NRS score may be determined at around 29 days, around 57 days, around 85 days, around 113 days, around 169 days and/or around 253 days after administering a first injection of the antibody or fragment thereof. The one or more further post-administration NRS score may be determined at the end of the induction phase.

The one or more further post-administration NRS score may be 0 to 7. The one or more further post-administration NRS score may be reduced at least 1 point, at least 2 points, at least 3 points, at least 4 points, at least 5 points, at least 6 points, at least 7 points, at least 8 points, at least 9 points or 10 points relative to the baseline NRS score. The one or more further post-administration NRS score may be:

(a) reduced at least 3 points relative to the baseline NRS score wherein the baseline NRS score is selected from the group consisting of at least 3, at least 4, at least 5, at least 6, at least 7, at least 8, 6 to 9, and 7 to 8; or
(b) reduced at least 4 points relative to the baseline NRS score wherein the baseline NRS score is selected from the group consisting of at least 4, at least 5, at least 6, at least 7, at least 8, 6 to 9, and 7 to 8.

Determining the post-administration NRS score and/or the one or more further post-administration NRS score may comprise the subject providing a numerical rating of their worst itch in the past 24 hours on a scale of 0 to 10, wherein "0" is no itch and "10" is the worst imaginable itch.

The post-administration NRS and/or further post-administration NRS may be determined at least around 113 days after administering a first injection of the antibody or fragment thereof and wherein the post-administration NRS and/or further post-administration NRS may be:

(a) reduced at least 3 points relative to the baseline NRS score wherein the baseline NRS score is selected from the group consisting of at least 3, at least 4, at least 5, at least 6, at least 7, at least 8, 6 to 9, and 7 to 8; or (b) reduced at least 4 points relative to the baseline NRS score wherein the baseline NRS score is selected from the group consisting of at least 4, at least 5, at least 6, at least 7, at least 8, 6 to 9, and 7 to 8.

The post-administration NRS and/or further post-administration NRS may be determined at least around 169 days after administering a first injection of the antibody or fragment thereof and wherein the post-administration NRS and/or further post-administration NRS may be:

(a) reduced at least 3 points relative to the baseline NRS score wherein the baseline NRS score is selected from the group consisting of at least 3, at least 4, at least 5, at least 6, at least 7, at least 8, 6 to 9, and 7 to 8; or (b) reduced at least 4 points relative to the baseline NRS score wherein the baseline NRS score is selected from the group consisting of at least 4, at least 5, at least 6, at least 7, at least 8, 6 to 9, and 7 to 8.

The post-administration NRS and/or further post-administration NRS may be determined at least around 253 days after administering a first injection of the antibody or fragment thereof and wherein the post-administration NRS and/or further post-administration NRS may be:

(a) reduced at least 3 points relative to the baseline NRS score wherein the baseline NRS score is selected from the group consisting of at least 3, at least 4, at least 5, at least 6, at least 7, at least 8, 6 to 9, and 7 to 8; or (b) reduced at least 4 points relative to the baseline NRS score wherein the baseline NRS score is selected from the group consisting of at least 4, at least 5, at least 6, at least 7, at least 8, 6 to 9, and 7 to 8.

The Atopic Dermatitis may be treated as evidenced by a reduction in the NRS score by at least 4 points after the third injection as a treatment dose. The reduction in NRS score may be persistent for at least 2 months, at least 3 months, at least 4 months, at least 5 months or at least 6 months after administration of the last injection as a treatment dose.

According to certain embodiments, administration of a therapeutically effective amount of an anti-OX40L antibody, or antigen-binding fragment thereof to a patient results in a decrease in NRS score. Some embodiments include therapeutic methods which result in a decrease from baseline in NRS score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration NRS score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline NRS score. The reduction of the post-administration NRS score relative to the baseline NRS score may be derived from any baseline NRS score and any post-administration NRS score, at any time point or between any time points, disclosed herein. In certain exemplary embodiments, administration of an anti-OX40L antibody, or antigen-binding fragment thereof to a subject results in a decrease from baseline in NRS score of at least 15%, at least 20% or at least 30%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in NRS score equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

Patient Oriented (PO) Eczema Measure (POEM)

The POEM is a seven-item, questionnaire used to assess disease symptoms in children and adults. It is described in Charman C R, Venn A J, Williams H C. The patient-oriented eczema measure: development and initial validation of a new tool for measuring atopic eczema severity from the patients' perspective. Arch Dermatol. 2004 December; 140 (12):1513-9. Methods for determining a POEM score are known and may be as described below and/or in the Examples, as applicable.

Based on frequency of occurrence during the past week, the seven events (dryness, itching, flaking, cracking, sleep loss, bleeding, and weeping) are assessed using a five-point scale. Each of the seven questions carries equal weight and is scored from 0 to 4. The possible scores for each question are: 0 (no days), 1 (1 to 2 days), 2 (3 to 4 days), 3 (5 to 6 days), and 4 (every day). The maximum total score is 28. If one question is left unanswered this is scored 0 and the scores are summed and expressed as usual out of a maximum of 28. If two or more questions are left unanswered the questionnaire is not scored. If two or more response options are selected, the response option with the highest score should be recorded.

A high score is indicative of poor quality of life. 0 to 2 indicates clear or almost clear skin, 3 to 7 indicates mild eczema, 8 to 16 indicates moderate eczema, 17 to 24 indicates severe eczema, and 25 to 28 indicates very severe eczema. It is thought that the overall mean MCID of the POEM is 3.4 points.

Baseline Scores—POEM

The atopic dermatitis may have been assessed by determining a baseline POEM (Patient-Orientated Eczema Measure) score. Determining a baseline POEM score may comprise the subject providing a frequency rating for how often the following events have been caused by their eczema over the last week:

i. Itchy skin,
ii. Disturbed sleep,.
iii. Bleeding skin,
iv. Skin weeping or oozing clear fluid,
v. Cracked skin,
vi. Skin flaking off, and
vii. Skin felt dry or rough.

The frequency rating may be selected from the group consisting of:

i. "no days",
ii. "1-2 days",
iii. "3-4 days",
iv. "5-6 days", and
v. "every day".

The method may further comprise:

assigning a frequency rating score to each frequency rating, wherein "every day" is assigned a score of 4, "5-6 days" is assigned a score of 3, "3-4 days" is assigned a score of 2, "1-2 days" is assigned a score of 1 and "no days" is assigned a score of 0, and adding together the frequency rating scores to calculate the POEM score.

A baseline POEM score of 0 to 2 may indicate clear or almost clear eczema; a baseline POEM score of 3 to 7 may indicate mild eczema; a baseline POEM score of 8 to 16 may indicate moderate eczema; a baseline POEM score of 17 to 24 may indicate severe eczema and a baseline POEM score of 25 to 28 may indicate very severe eczema.

The baseline POEM score may be any score indicating moderate to severe or very severe AD. The baseline POEM score may be selected from the group consisting of at least 8, at least 9, at least 10, at least 11, at least 12, at least 13, at least 14, at least 15, at least 16, at least 17, at least 18, at least 19, at least 20, at least 21, at least 22, at least 23, at least 24, 8 to 28, 8 to 24, 8 to 16, 17 to 24 and 25 to 28.

A first injection of the anti-OX40L antibody or fragment thereof may be administered on the same day as the baseline POEM score is determined.

Some embodiments may further comprise determining the baseline POEM score.

Clinical Outcomes—POEM

Some embodiments may further comprise assessing the atopic dermatitis by determining a post-administration POEM score at least 15 days after administering a first injection of the antibody or fragment thereof. Obtaining a post-administration POEM score at least 7 days or at least 15 days after administering a first injection of the antibody or fragment thereof is expected to be the earliest a change in POEM score could reliably be observed due to the action of the antibody or fragment thereof, however any clinically suitable delay from administration to assessing may be employed. The post-administration POEM score may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration POEM score may be determined at around 7 days, at around 15 days, around 29 days, around 57 days, around 85 days, around 113 days, around 169 days and/or around 253 days after administering a first injection of the antibody or fragment thereof. The post-administration POEM score may be determined at the end of the induction phase.

The post-administration POEM score may be selected from the group consisting of 0 to 2; 3 to 7; 8 to 16; 17 to 24 and 25 to 28. The post-administration POEM score may indicate the AD is no longer very severe AD. The post-administration POEM score may indicate the AD is no longer severe AD. The post-administration POEM score may indicate the AD is no longer moderate AD. The post-administration POEM score may indicate the AD is mild AD. The post-administration POEM score may indicate the AD is almost clear. The post-administration POEM score may be reduced at least 2 points, at least 3 points, at least 3.4 points, at least 4 points, at least 5 points, at least 6 points, at least 7 points, at least 8 points, at least 9 points or 10 points relative to the baseline POEM score. The post-administration POEM score may be reduced at least 2 points or at least 3 points relative to the baseline POEM score. The post-administration POEM score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline POEM score. The post-administration POEM score may be maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

Some embodiments may further comprise assessing the atopic dermatitis by determining one or more further post-administration POEM score. The one or more further post-administration POEM score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration POEM score may be determined at around 29 days, around 57 days, around 85 days, around 113 days, around 169 days and/or around 253 days after administering a first injection of the antibody or fragment thereof. The one or more further post-administration POEM score may be determined at the end of the induction phase.

The one or more further post-administration POEM score may be selected from the group consisting of 0 to 2; 3 to 7; 8 to 16; 17 to 24 and 25 to 28. The one or more further post-administration POEM score may indicate the AD is no longer very severe AD. The one or more further post-administration POEM score may indicate the AD is no longer severe AD. The one or more further post-administration POEM score may indicate the AD is no longer moderate AD. The one or more further post-administration POEM score may indicate the AD is mild AD. The one or more further post-administration POEM score may indicate the AD is almost clear. The one or more further post-administration POEM score may be reduced at least 2 points, at least 3 points, at least 4 points, at least 5 points, at least 6 points, at least 7 points, at least 8 points, at least 9 points or 10 points relative to the baseline POEM score. The one or more further post-administration POEM score may be reduced at least 2 points or at least 3 points relative to the baseline POEM score.

Determining the post-administration POEM score and/or the one or more further post-administration POEM score may comprise the subject providing a frequency rating for how often the following events have been caused by their eczema over the last week:

i. Itchy skin,
ii. Disturbed sleep,.
iii. Bleeding skin,
iv. Skin weeping or oozing clear fluid,
V. Cracked skin,
vi. Skin flaking off, and
vii. Skin felt dry or rough.

The frequency rating may be selected from the group consisting of:

i. "no days",
ii. "1-2 days",
iii. "3-4 days",
iv. "5-6 days", and
v. "every day".

The method may further comprise:

assigning a frequency rating score to each frequency rating, wherein "every day" is assigned a score of 4, "5-6 days" is assigned a score of 3, "3-4 days" is assigned a score of 2, "1-2 days" is assigned a score of 1 and "no days" is assigned a score of 0, and adding together the frequency rating scores to calculate the POEM score.

The post-administration POEM and/or further post-administration POEM may be determined at least around 113 days after administering a first injection of the antibody or fragment thereof and wherein the post-administration POEM and/or further post-administration POEM is reduced at least 2 points or at least 3 points relative to the baseline POEM score.

The post-administration POEM and/or further post-administration POEM may be determined at least around 169 days after administering a first injection of the antibody or fragment thereof and wherein the post-administration POEM and/or further post-administration POEM is reduced at least 2 points or at least 3 points relative to the baseline POEM score.

The post-administration POEM and/or further post-administration POEM may be determined at least around 253 days after administering a first injection of the antibody or fragment thereof and wherein the post-administration POEM and/or further post-administration POEM is reduced at least 2 points or at least 3 points relative to the baseline POEM score.

The Atopic Dermatitis may be treated as evidenced by a reduction in the POEM score by at least 2 points after the third injection as a treatment dose. The reduction in POEM score may be persistent for at least 2 months, at least 3 months, at least 4 months, at least 5 months or at least 6 months after administration of the last injection as a treatment dose.

According to certain embodiments of, administration of a therapeutically effective amount of an anti-OX40L antibody, or antigen-binding fragment thereof to a patient results in a decrease in POEM score. Some embodiments include therapeutic methods which result in a decrease from baseline in POEM score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration POEM score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline POEM score. The reduction of the post-administration POEM score relative to the baseline POEM score may be derived from any baseline POEM score and any post-administration POEM score, at any time point or between any time points, disclosed herein. In certain exemplary embodiments, administration of an anti-OX40L antibody, or antigen-binding fragment thereof to a subject results in a decrease from baseline in POEM score of at least 15%, at least 20% or at least 30%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in POEM score equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

Affected Body Surface Area (BSA)

The extent of AD can also be described using BSA. Methods for determining a BSA score are known and may be as described below and/or in the Examples, as applicable. BSA typically uses the "rule of 9's" where body areas are divided into 9% (or fractions thereof)—see Table 2 below. Alternative calculations may be made for children and adults related to different body proportions as indicated in Table 2. Extent by each individual area is calculated and then totalled.

TABLE 2

BSA Rule of 9s

| Body Part | Estimated BSA Adults | Estimated BSA Children |
|---|---|---|
| Entire left arm | 9% | 9% |
| Entire right arm | 9% | 9% |
| Entire head | 9% | 18% |
| Entire chest | 9% | 9% |
| Entire abdomen | 9% | 9% |
| Entire back | 18% | 18% |
| Entire left leg | 18% | 13.5% |
| Entire right leg | 18% | 13.5% |
| Groin | 1% | 1% |

BSA or a variant thereof is part of EASI, SCORAD and POSCORAD. BSA in itself can be said not to characterise disease severity per se, as a patient can have lots of coverage with low grade disease or have limited coverage with highly severe disease which would be more clinically problematic. Nonetheless, following treatment, a reduction in BSA from baseline may indicate a clinical improvement when AD severity is not increased (optionally measured by an alternative method described herein) in the areas still exhibiting AD involvement.

Baseline Scores—BSA

The atopic dermatitis may have been assessed by determining a baseline BSA (Body Surface Area) score. Determining a baseline BSA score may comprise:

(a) Assigning a BSA value to each of the following body parts:
 (a) Entire left arm,
 (b) Entire right arm,
 (c) Entire head,
 (d) Entire chest,
 (e) Entire abdomen,
 (f) Entire back,
 (g) Entire left leg,
 (h) Entire right leg, and
 (i) Groin,
(b) Estimating the proportion of each body part affected by atopic dermatitis,
(c) Multiplying the proportion of each body part affected by dermatitis by the BSA value for the body part to provide an affected BSA value for each body part, and
(d) Adding together the affected BSA values for the body parts to provide a BSA score.

The baseline BSA score may be any score associated with a moderate to severe case of AD. BSA may not measure the severity of AD per se. It is possible to have high extent of coverage at low severity levels meaning the overall AD severity may not be very high. However, BSA may contribute to the severity of AD, for example, assigning percentages of body surface area is part of determining an EASI score. BSA may therefore be a relevant descriptor for AD. The baseline BSA score is at least 10%, at least 15, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

A first injection of the anti-OX40L antibody or fragment thereof may be administered on the same day as the baseline BSA score is determined.

Some embodiments may further comprise determining the baseline BSA score.

Clinical Outcomes—BSA

Some embodiments may further comprise assessing the atopic dermatitis by determining a post-administration BSA score at least 15 days after administering a first injection of the antibody or fragment thereof. Obtaining a post-administration BSA score at least 7 days or at least 15 days after administering a first injection of the antibody or fragment thereof is expected to be the earliest a change in BSA score could reliably be observed due to the action of the antibody or fragment thereof, however any clinically suitable delay from administration to assessing may be employed. The post-administration BSA score may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration BSA score may be determined at around 7 days, around 15 days, around 29 days, around 57 days, around 85 days, around 113 days, around 169 days and/or around 253 days after administering a first injection of the antibody or fragment thereof. The post-administration BSA score may be determined at the end of the induction phase.

The post-administration BSA score may be selected from the group consisting of less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90% and less than 95%. The post-administration BSA score may indicate the AD is no longer severe AD. The post-administration BSA score may indicate the AD is no longer moderate AD. The post-administration BSA score may indicate the AD is mild AD. The post-administration BSA score may indicate the AD is almost clear. The post-administration BSA score may be reduced at least 2 percentage points, at least 3 percentage points, at least 4 percentage points, at least 5 percentage points, at least 6 percentage points, at least 7 percentage points, at least 8 percentage points, at least 9 percentage points, 10 percentage points, at least 11 percentage points, at least 12 percentage points, at least 13 percentage points, at least 14 percentage points, at least 15 percentage points, at least 20 percentage points, at least 25 percentage points, at least 30 percentage points, at least 40 percentage points, at least 50 percentage points, at least 60 percentage points, at least 70 percentage points, at least 80 percentage points or at least 90 percentage points relative to the baseline BSA score. The post-administration BSA score may be reduced at least 5 percentage points relative to the baseline BSA score. The post-administration BSA score may be reduced at least 10 percentage points relative to the baseline BSA score, wherein the baseline BSA score is at least 10%. The post-administration BSA score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline BSA score. The post-administration BSA score may be maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

Some embodiments may further comprise assessing the atopic dermatitis by determining one or more further post-administration BSA score. The one or more further post-administration BSA score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration BSA score may be determined at around 29 days, around 57 days, around 85 days, around 113 days, around 169 days and/or around 253 days after administering a first injection of the antibody or fragment thereof. The one or more further post-administration BSA score may be determined at the end of the induction phase.

The one or more further post-administration BSA score may be selected from the group consisting of less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90% and less than 95%. The one or more further post-administration BSA score may indicate the AD is no longer severe AD. The one or more further post-administration BSA score may indicate the AD is no longer moderate AD. The one or more further post-administration BSA score may indicate the AD is mild AD. The one or more further post-administration BSA score may indicate the AD is almost clear. The one or more further post-administration BSA score may be reduced at least 2 percentage points, at least 3 percentage points, at least 4 percentage points, at least 5 percentage points, at least 6 percentage points, at least 7 percentage points, at least 8 percentage points, at least 9 percentage points, 10 percentage points, at least 11 percentage points, at least 12 percentage points, at least 13 percentage points, at least 14 percentage points, at least 15 percentage points, at least 20 percentage points, at least 25 percentage points, at least 30 percentage points, at least 40 percentage points, at least 50 percentage points, at least 60 percentage points, at least 70 percentage points, at least 80 percentage points or at least 90 percentage points relative to the baseline BSA score. The one or more further post-administration BSA score may be reduced at least 10 percentage points relative to the baseline BSA score.

Determining the post-administration BSA score and/or the one or more further post-administration BSA score may comprise:

(a) Assigning a BSA value to each of the following body parts:
  (a) Entire left arm,
  (b) Entire right arm,
  (c) Entire head,
  (d) Entire chest,
  (e) Entire abdomen, (f) Entire back,
(g) Entire left leg,
(h) Entire right leg, and
(i) Groin, (b) Estimating the proportion of each body part affected by atopic dermatitis, (c) Multiplying the proportion of each body part affected by dermatitis by the BSA value for the body part to provide an affected BSA value for each body part, and (d) Adding together the affected BSA values for the body parts to provide a BSA score.

The post-administration BSA and/or further post-administration BSA may be determined at least around 113 days after administering a first injection of the antibody or fragment thereof and the post-administration BSA and/or further post-administration BSA may be reduced at least 10 percentage points relative to the baseline BSA score. The post-administration BSA and/or further post-administration BSA may be determined at least around 169 days after administering a first injection of the antibody or fragment thereof and the post-administration BSA and/or further post-administration BSA may be reduced at least 10 percentage points relative to the baseline BSA score. The post-administration BSA and/or further post-administration BSA may be determined at least around 253 days after administering a first injection of the antibody or fragment thereof and wherein the post-administration BSA and/or further post-administration BSA may be reduced at least 10 percentage points relative to the baseline BSA score.

The Atopic Dermatitis may be treated as evidenced by a reduction in the BSA score by at least 10 percentage points after the third injection as a treatment dose. The reduction in BSA score may be persistent for at least 2 months, at least 3 months, at least 4 months, at least 5 months or at least 6 months after administration of the last injection as a treatment dose.

According to certain embodiments of, administration of a therapeutically effective amount of an anti-OX40L antibody, or antigen-binding fragment thereof to a patient results in a decrease in BSA score. Some embodiments include therapeutic methods which result in a decrease from baseline in BSA score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration BSA score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline BSA score. The reduction of the post-administration BSA score relative to the baseline BSA score may be derived from any baseline BSA score and any post-administration BSA score, at any time point or between any time points, disclosed herein. In certain exemplary embodiments, administration of an anti-OX40L antibody, or antigen-binding fragment thereof to a subject results in a decrease from baseline in BSA score of at least 20%, at least 30% or at least 35%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in BSA score equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

SCORinq of Atopic Dermatitis (SCORAD) Index

The SCORAD was developed to standardize the evaluation of the extent and severity of Atopic Dermatitis. See Severity scoring of atopic dermatitis: the SCORAD index. Consensus Report of the European Task Force on Atopic Dermatitis. Dermatology. 1993; 186(1):23-31. It assesses three components of AD: the affected BSA, severity of clinical signs, and symptoms.

Methods for determining a SCORAD index are known and may be as described below and/or in the Examples, as applicable.

The extent of AD is assessed as a percentage of each defined body area and reported as the sum of all areas. The maximum score is 100%. The severity of six specific symptoms of AD (redness, swelling, oozing/crusting, excoriation, skin thickening/lichenification, dryness) is assessed using a four-point scale (i.e., none=0, mild=1, moderate=2, severe=3) with a maximum possible total of 18 points. The symptoms (itch and sleeplessness) are recorded by the patient or caregiver on a visual analogue scale, where 0 is no symptoms and 10 is the worst imaginable symptom, with a maximum possible score of 20. The maximum possible SCORAD score is 103; higher scores indicate poorer or more severe condition.

A difference of 8.7 points in SCORAD has been estimated as the minimal clinically important difference (MCID) for patients with atopic dermatitis (Schram M E, Spuls P I, Leeflang M M, Lindeboom R, Bos J D, Schmitt J. EASI, (objective) SCORAD and POEM for atopic eczema: responsiveness and minimal clinically important difference. Allergy. 2012 January;67(1):99-106).

Baseline Scores—SCORAD Index

The atopic dermatitis may have been assessed by determining a baseline SCORAD (SCORing Atopic Dermatitis) index. Determining a baseline SCORAD index may comprise:

(a) Estimating the extent of the atopic dermatitis as a percentage of body area involvement to provide an extent score "A", (b) Assessing the intensity of the following clinical signs to provide an intensity score "B":
(i) erythema,
(ii) edema/papulation,
(iii) oozing/crust,
(iv) excoriation,
(v) lichenification, and
(vi) dryness;

(c) Assessing the severity of the following symptoms to provide a severity score "C":
(i) pruritus, and
(ii) sleep loss;

and (d) Calculating the baseline SCORAD index using the extent score "A", the intensity score
B" and the severity score "C".

Determining a baseline SCORAD index may further comprise assigning to each clinical sign a sign intensity level selected from the group consisting of:

i. "absent"

ii. "mild"

iii. "moderate", and iv. "severe".

Determining a baseline SCORAD index may further comprise:

assigning a sign intensity score to each sign intensity level, wherein "severe" is assigned a score of 3, "moderate" is assigned a score of 2, "mild" is assigned a score of 1 and "absent" is assigned a score of 0, and adding together the sign intensity scores to calculate the intensity score "B".

Determining the baseline SCORAD index may comprise the subject or a caregiver providing a numerical rating of symptom severity for pruritus and sleep loss in the past 3 days and/or nights on a scale of 0 to 10, wherein "0" is no symptom and "10" is the worst imaginable symptom. Determining a baseline SCORAD index may further comprise adding together the numerical ratings of symptom severity for pruritus and sleep loss to calculate the severity score "C".

Determining the baseline SCORAD index may comprise calculating the baseline SCORAD index using the formula: SCORAD index=A/5+7B/2+C.

The baseline SCORAD index may be any index indicating moderate to severe AD. A baseline SCORAD index of 0 to 24 may indicate mild disease; a baseline SCORAD index of 25 to 50 may indicate moderate disease; and a baseline SCORAD index of 51 to 103 may indicate severe disease. The baseline SCORAD index may be at least 25, at least 30, at least 35, at least 40, at least 45, at least 50, at least 55, at least 60, at least 65, at least 70, at least 75, at least 80, at least 85, at least 90 or at least 95.

A first injection of the anti-OX40L antibody or fragment thereof may be administered on the same day as the baseline SCORAD index is determined.

Some embodiments may further comprise determining the baseline SCORAD index.

Based Around Clinical Outcomes—SCORAD

Some embodiments may further comprise assessing the atopic dermatitis by determining a post-administration SCORAD index at least 15 days after administering a first injection of the antibody or fragment thereof. Obtaining a post-administration SCORAD index at least 7 days or at least 15 days after administering a first injection of the antibody or fragment thereof is expected to be the earliest a change in SCORAD index could reliably be observed due to the action of the antibody or fragment thereof, however any clinically suitable delay from administration to assessing may be employed. The post-administration SCORAD index may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration SCORAD index may be determined at around 7 days, around 15 days, around 29 days, around 57 days, around 85 days, around 113 days, around 169 days and/or around 253 days after administering a first injection of the antibody or fragment thereof. The post-administration SCORAD index may be determined at the end of the induction phase.

The post-administration SCORAD index may be selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95. The post-administration SCORAD index may be reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline SCORAD index. The post-administration SCORAD index may be reduced at least 20 points relative to the baseline SCORAD index. The post-administration SCORAD index may indicate the AD is no longer very severe AD. The post-administration SCORAD index may indicate the AD is no longer severe AD. The post-administration SCORAD index may indicate the AD is no longer moderate AD. The post-administration SCORAD index may indicate the AD is mild AD. The post-administration SCORAD index may indicate the AD is almost clear. The post-administration SCORAD index may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline SCORAD index. The post-administration SCORAD index may be maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

Some embodiments may further comprise assessing the atopic dermatitis by determining one or more further post-administration SCORAD index. The one or more further post-administration SCORAD index may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration SCORAD index may be determined at around 29 days, around 57 days, around 85 days, around 113 days, around 169 days and/or around 253 days after administering a first injection of the antibody or fragment thereof. The one or more further post-administration SCORAD index may be determined at the end of the induction phase.

The one or more further post-administration SCORAD index may be selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95. The one or more further post-administration SCORAD index may be reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points elative to the baseline SCORAD index. The one or more further post-administration SCORAD index may be reduced at least 20 points relative to the baseline SCORAD index. The one or more further post-administration SCORAD index may indicate the AD is no longer very severe AD. The one or more further post-administration SCORAD index may indicate the AD is no longer severe AD. The one or more further post-administration SCORAD index may indicate the AD is no longer moderate AD. The one or more further post-administration SCORAD index may indicate the AD is mild AD. The one or more further post-administration SCORAD index may indicate the AD is almost clear.

Determining the post-administration SCORAD index and/or the one or more further post-administration SCORAD index may comprise:

(a) Estimating the extent of the atopic dermatitis as a percentage of body area involvement to provide an extent score “A”, (b) Assessing the intensity of the following clinical signs to provide an intensity score “B”:
  (i) erythema,
  (ii) edema/papulation,
  (iii) oozing/crust,
  (iv) excoriation,
  (v) lichenification, and
  (vi) dryness;

(c) Assessing the severity of the following symptoms to provide a severity score “C”:
  (i) pruritus, and
  (ii) sleep loss;

and (d) Calculating the SCORAD index using the extent score “A”, the intensity score “B” and the severity score “C”.

Determining the post-administration SCORAD index and/or the one or more further post-administration SCORAD index may further comprise assigning to each clinical sign a sign intensity level selected from the group consisting of:

i.“absent”
ii.“mild”
iii.“moderate”, and
iv.“severe”.

Determining the post-administration SCORAD index and/or the one or more further post-administration SCORAD index may further comprise:

assigning a sign intensity score to each sign intensity level, wherein “severe” is assigned a score of 3, “moderate” is assigned a score of 2, “mild” is assigned a score of 1 and “absent” is assigned a score of 0, and adding together the sign intensity scores to calculate the intensity score “B”.

Determining the post-administration SCORAD index and/or the one or more further post-administration SCORAD index may comprise the subject or a caregiver providing a numerical rating of symptom severity for pruritus and sleep loss in the past 3 days and/or nights on a scale of 0 to 10, wherein “0” is no symptom and “10” is the worst imaginable symptom. The method may further comprise adding together the numerical ratings of symptom severity for pruritus and sleep loss to calculate the severity score “C”.

Determining the post-administration SCORAD index and/or the one or more further post-administration SCORAD index comprises calculating the SCORAD index using the formula: SCORAD index=A/5+7B/2+C.

The post-administration SCORAD and/or further post-administration SCORAD may be determined at least around 113 days after administering a first injection of the antibody or fragment thereof and wherein the post-administration SCORAD and/or further post-administration SCORAD may be reduced at least 20 points relative to the baseline SCORAD index. The post-administration SCORAD and/or further post-administration SCORAD may be determined at least around 169 days after administering a first injection of the antibody or fragment thereof and wherein the post-administration SCORAD and/or further post-administration SCORAD may be reduced at least 20 points relative to the baseline SCORAD index. The post-administration SCORAD and/or further post-administration SCORAD may be determined at least around 253 days after administering a first injection of the antibody or fragment thereof and wherein the post-administration SCORAD and/or further post-administration SCORAD may be reduced at least 20 points relative to the baseline SCORAD index. The Atopic Dermatitis may be treated as evidenced by a reduction in the SCORAD index by at least 20 points after the third injection as a treatment dose. The reduction in SCORAD index may be persistent for at least 2 months, at least 3 months, at least 4 months, at least 5 months or at least 6 monthsafter administration of the last injection as a treatment dose.

According to certain embodiments, administration of a therapeutically effective amount of an anti-OX40L antibody, or antigen-binding fragment thereof to a patient results in a decrease in SCORAD index. Some embodiments include therapeutic methods which result in a decrease from baseline in SCORAD index of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration SCORAD index may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline SCORAD index. The reduction of the post-administration SCORAD index relative to the baseline SCORAD index may be derived from any baseline SCORAD index and any post-administration SCORAD index, at any time point or between any time points, disclosed herein. In certain exemplary embodiments, administration of an anti-OX40L antibody, or antigen-binding fragment thereof to a subject results in a decrease from baseline in SCORAD index of at least 20%, at least 30% or at least 35%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in SCORAD index equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

Patient Oriented SCORing of Atopic Dermatitis (POSCORAD)

POSCORAD is derived from the SCORAD, and can be easily used by a patient without any particular experience. POSCORAD was created for the patient in order to help patients or caregivers to follow the course of the disease and the effect of the treatment. POSCORAD has been validated in several studies including Vourc’h-Jourdain M, Barbarot S, Taieb A et al. Patient-oriented SCORAD: a self-assessment score in atopic dermatitis. A preliminary feasibility study.

Dermatology. 2009; 218:246-251 and Stalder J F, Barbarot S, Wollenberg A et al. Patient-Oriented SCORAD (PO-SCORAD): a new self-assessment scale in atopic dermatitis validated in Europe. Allergy. 2011; 66:1114-1121.

POSCORAD is available as software for mobile devices and computers. A regular (weekly) use of the POSCORAD software allows the patient to create a curve representing the fluctuations of their disease between consultations.

Methods for determining a PO-SCORAD index are known and may be as described below and/or in the Examples, as applicable.

Baseline Scores—PO-SCORAD

The atopic dermatitis may have been assessed by determining a baseline PO-SCORAD (Patient-Oriented SCORing Atopic Dermatitis) index. Determining a baseline PO-SCORAD index may comprise:

(a) Estimating the extent of the atopic dermatitis as a percentage of body area involvement to provide an extent score "A", (b) Assessing the intensity of the following clinical signs to provide an intensity score "B":

(i) redness, (ii) swelling, (iii) oozing/scabs, (iv) scratch marks, (v) thickening of skin, and (vi) dryness;

(c) Assessing the severity of the following symptoms to provide a severity score "C":

(i) itching, and (ii) trouble sleeping and (d) Calculating the baseline PO-SCORAD index using the extent score "A", the intensity score "B" and the severity score "C".

Inputs for steps (a), (b) and (c) may be provided by the subject or a caregiver. Inputs for steps (a), (b) and (c) may be inputted into a computer program via a graphical user interface by the subject or a caregiver. Estimating the extent of the atopic dermatitis as a percentage of body area involvement to provide an extent score "A" may be performed by a computer program.

Determining the baseline PO-SCORAD index may comprise the subject or a caregiver providing a sign intensity score for each clinical sign selected from the group consisting of:

i. "0"

ii. "1"

iii. "2", and iv. "3";

wherein "0" is the lowest intensity and "3" is the highest intensity;

and wherein the sign intensity scores are added together to calculate the intensity score "B". Adding together of the sign intensity scores to calculate the intensity score "B" may be performed by a computer program.

Determining the baseline PO-SCORAD index may comprise the subject or a caregiver providing a numerical rating of symptom severity for itching and trouble sleeping in the past 2 days and/or nights on a scale of 0 to 10, wherein "0" is no symptom and "10" is the worst imaginable symptom. The method may further comprise adding together the numerical ratings of symptom severity for itching and trouble sleeping to calculate the severity score "C". Adding together the numerical ratings of symptom severity for itching and trouble sleeping to calculate the severity score "C" may be performed by a computer program.

Determining the baseline PO-SCORAD index may comprise calculating the baseline PO-SCORAD index using the formula: PO-SCORAD index=A/5+7B/2+C.

The baseline PO-SCORAD index may be any index indicating moderate to severe AD. The baseline PO-SCORAD index may be at least 25, at least 30, at least 35, at least 40, at least 45, at least 50, at least 55, at least 60, at least 65, at least 70, at least 75, at least 80, at least 85, at least 90 or at least 95.

A first injection of the anti-OX40L antibody or fragment thereof may be administered on the same day as the baseline PO-SCORAD index is determined.

Some embodiments may further comprise determining the baseline PO-SCORAD index.

Based Around Clinical Outcomes—PO-SCORAD

Some embodiments may further comprise assessing the atopic dermatitis by determining a post-administration PO-SCORAD index at least 15 days after administering a first injection of the antibody or fragment thereof. Obtaining a post-administration PO-SCORAD index at least 7 days or at least 15 days after administering a first injection of the antibody or fragment thereof is expected to be the earliest a change in PO-SCORAD score could reliably be observed due to the action of the antibody or fragment thereof, however any clinically suitable delay from administration to assessing may be employed. The post-administration PO-SCORAD index may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration PO-SCORAD index may be determined at around 7 days, at around 15 days, around 29 days, around 57 days, around 85 days, around 113 days, around 169 days and/or around 253 days after administering a first injection of the antibody or fragment thereof. The post-administration PO-SCORAD index may be determined at the end of the induction phase.

The post-administration PO-SCORAD index may be selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95. The post-administration PO-SCORAD index may be reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline PO-SCORAD index. The post-administration PO-SCORAD index may be reduced at least 20 points relative to the baseline PO-SCORAD index. The post-administration PO-SCORAD index may indicate the AD is no longer very severe AD. The post-administration PO-SCORAD index may indicate the AD is no longer severe AD. The post-administration PO-SCORAD index may indicate the AD is no longer moderate AD. The post-administration PO-SCORAD index may indicate the AD is mild AD. The post-administration PO-SCORAD index may indicate the AD is almost clear. The post-administration PO-SCORAD index may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline PO-SCORAD index.

The post-administration PO-SCORAD index may be maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

Some embodiments may further comprise assessing the atopic dermatitis by determining one or more further post-administration PO-SCORAD index. The one or more further post-administration PO-SCORAD index may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration PO-SCORAD index may be determined at around 29 days, around 57 days, around 85 days, around 113 days, around 169 days and/or around 253 days after administering a first injection of the antibody or fragment thereof. The one or more further post-administration PO-SCORAD index may be determined at the end of the induction phase.

The one or more further post-administration PO-SCORAD index is selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95. The one or more further post-administration PO-SCORAD index may be reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline PO-SCORAD index. The one or more further post-administration PO-SCORAD index may be reduced at least 20 points relative to the baseline PO-SCORAD index.

Determining the post-administration PO-SCORAD index and/or the one or more further post-administration PO-SCORAD index may comprise:

(a) Estimating the extent of the atopic dermatitis as a percentage of body area involvement to provide an extent score "A", (b) Assessing the intensity of the following clinical signs to provide an intensity score "B":
   (i) redness,
   (ii) swelling,
   (iii) oozing/scabs,
   (iv) scratch marks,
   (v) thickening of skin, and
   (vi) dryness;

(c) Assessing the severity of the following symptoms to provide a severity score "C":
   (i) itching, and
   (ii) trouble sleeping;

and (d) Calculating the PO-SCORAD index using the extent score "A", the intensity score "B" and the severity score "C".

Inputs for steps (a), (b) and (c) may be provided by the subject or a caregiver. Inputs for steps (a), (b) and (c) may be inputted into a computer program via a graphical user interface by the subject or a caregiver. Estimating the extent of the atopic dermatitis as a percentage of body area involvement to provide an extent score "A" may be performed by a computer program.

Determining the post-administration PO-SCORAD index may comprise the subject or a caregiver providing a sign intensity score for each clinical sign selected from the group consisting of:

i. "0"
ii. "1"
iii. "2", and
iv. "3";

wherein "0" is the lowest intensity and "3" is the highest intensity;

and wherein the sign intensity scores are added together to calculate the intensity score "B". The adding together of the sign intensity scores to calculate the intensity score "B" may be performed by a computer program.

Determining the post-administration PO-SCORAD index may comprise the subject or a caregiver providing a numerical rating of symptom severity for itching and trouble sleeping in the past 2 days and/or nights on a scale of 0 to 10, wherein "0" is no symptom and "10" is the worst imaginable symptom. The method may further comprise adding together the numerical ratings of symptom severity for itching and trouble sleeping to calculate the severity score "C". Adding together the numerical ratings of symptom severity for itching and trouble sleeping to calculate the severity score "C" may be performed by a computer program.

Determining the post-administration PO-SCORAD index and/or the one or more further post-administration PO-SCORAD index may comprise calculating the PO-SCORAD index using the formula: PO-SCORAD index=A/5+7B/2+C.

The post-administration PO-SCORAD and/or further post-administration PO-SCORAD may be determined at least around 113 days after administering a first injection of the antibody or fragment thereof and wherein the post-administration PO-SCORAD and/or further post-administration PO-SCORAD may be reduced at least 20 points relative to the baseline PO-SCORAD index. The post-administration PO-SCORAD and/or further post-administration PO-SCORAD may be determined at least around 169 days after administering a first injection of the antibody or fragment thereof and wherein the post-administration PO-SCORAD and/or further post-administration PO-SCORAD may be reduced at least 20 points relative to the baseline PO-SCORAD index. The post-administration PO-SCORAD and/or further post-administration PO-SCORAD may be determined at least around 253 days after administering a first injection of the antibody or fragment thereof and wherein the post-administration PO-SCORAD and/or further post-administration PO-SCORAD may be reduced at least 20 points relative to the baseline PO-SCORAD index. The Atopic Dermatitis may be treated as evidenced by a reduction in the PO-SCORAD index by at least 20 points after the third injection as a treatment dose. The reduction in PO-SCORAD index may be persistent for at least 2 months, at least 3 months, at least 4 months, at least 5 months or at least 6 months after administration of the last injection as a treatment dose. According to certain embodiments, administration of a therapeutically effective amount of an anti-OX40L antibody, or antigen-binding fragment thereof to a patient results in a decrease in PO-SCORAD index. In some embodiments, the therapeutic methods which result in a decrease from baseline in PO-SCORAD index of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration PO-SCORAD index may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline PO-SCORAD index. The reduction of the post-administration PO-SCORAD index relative to the baseline PO-SCORAD index may be derived from any baseline PO-SCORAD index and any post-administration PO-SCORAD index, at any time point or between any time points, disclosed herein. In certain exemplary embodiments, administration of an anti-OX40L antibody, or antigen-binding fragment thereof to a subject results in a decrease from baseline in PO-SCORAD index of at least 15%, at least 20% or at least 30%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in PO-SCORAD index equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

Dermatology Life Quality Index (DLQI)

The DLQI is designed to measure the health-related quality of life of patients suffering from a skin disease, including Atopic Dermatitis. The DLQI was published in 1994 and was the first dermatology-specific quality of life questionnaire. See Finlay A Y, Khan G K. Dermatology Life Quality Index (DLQI)-a simple practical measure for routine clinical use. Clin Exp Dermatol. 1994 May; 19(3):210-6. Methods for determining a DQLI score are known and may be as described below and/or in the Examples, as applicable.

The DLQI consists of 10 questions concerning patients' perception of the impact of skin diseases on different aspects of their health-related quality of life over the last week. The DLQI is designed for use in adults, i.e. patients aged 16 years and over.

Each question is scored on a four-point Likert scale:

Very much=3

A lot=2

A little=1

Not at all=0

Not relevant=0

Question unanswered=0

The DLQI is calculated by adding the score of each question, resulting in a maximum of 30 and a minimum of 0. The higher the score, the more quality of life is impaired. A score higher than 10 indicates that the patient's life is being severely affected by their skin disease.

Meaning of Scores:

0-1=no effect at all on patient's life 2-5=small effect on patient's life 6-10=moderate effect on patient's life 11-20=very large effect on patient's life 21-30=extremely large effect on patient's life For general inflammatory skin conditions, a change in DLQI score of at least four points is considered clinically important. In alternative embodiments, a change in DLQI score of from 2.2 to 6.9 points is considered clinically important.

Baseline Scores—DQLI

The atopic dermatitis may have been assessed by determining a baseline DQLI (Dermatology Quality of Life Index) score. Determining a baseline DQLI score may comprise the subject providing an answer for how much their skin problem has affected their life over the past week in the following areas:

i. how itchy, sore, painful or stinging their skin has been,
ii. how embarrassed or self conscious they have been because of their skin,
iii. how much their skin has interfered with them going shopping or looking after their home or garden,
iv. how much their skin has influenced the clothes they wear,
v. how much their skin has affected any social or leisure activities,
vi. how much their skin has made it difficult to do any sport
vii. whether their skin has prevented them from working or studying or if not how much their skin has been a problem at work or studying,
viii. how much their skin has created problems with their partner of any of their close friends or relatives,
ix. how much their skin has caused any sexual difficulties
x. how much of a problem has the treatment for their skin been.

Each answer may be selected from the group consisting of:

i. "Very much"
ii. "A lot"
iii. "A little"
iv. "Not at all"
v. "Not relevant"

The method may further comprise:

assigning an answer score to each answer, wherein "very much" is assigned a score of 3, "a lot" is assigned a score of 2, "a little" is assigned a score of 1 and "not at all", "not relevant" or question unanswered are assigned a score of 0, and adding together the answer scores to calculate a DQLI score.

The baseline DQLI index may be any index indicating AD is having a moderate effect, a large effect or an extremely large effect on the subject's life. The baseline DQLI score may be selected from the group consisting of at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, 6 to 30, 6 to 10, 11 to 20, and 21 to 30.

A first injection of the anti-OX40L antibody or fragment thereof may be administered on the same day as the baseline DQLI score is determined.

Some embodiments may further comprise determining the baseline DQLI score.

Based Around Clinical Outcomes—DQLI

Some embodiments may further comprise assessing the atopic dermatitis by determining a post-administration DQLI score at least 15 days after administering a first injection of the antibody or fragment thereof. Obtaining a post-administration DQLI score at least 7 days or at least 15 days after administering a first injection of the antibody or fragment thereof is expected to be the earliest a change in DQLI score could reliably be observed due to the action of the antibody or fragment thereof, however any clinically suitable delay from administration to assessing may be employed. The post-administration DQLI score may be determined at least around 7 days, at least around 15 days, at least around 29 days, at least around 57 days, at least around 85 days, at least around 113 days, at least around 169 days and/or at least around 253 days after administering a first injection of the antibody or fragment thereof. The post-administration DQLI score may be determined at around 7 days, at around 15 days, around 29 days, around 57 days, around 85 days, around 113 days, around 169 days and/or around 253 days after administering a first injection of the antibody or fragment thereof. The post-administration DQLI score may be determined at the end of the induction phase.

The post-administration DQLI score may be selected from the group consisting of 0 to 1; 2 to 5; 6 to 10; 11 to 20; and 21 to 30. The post-administration DQLI score may be reduced at least 4 points, at least 5 points, at least 6 points, at least 7 points, at least 8 points, at least 9 points, at least 10 points, at least 15 points or at least 20 points relative to the baseline DQLI score. The post-administration DQLI score may be reduced at least 2.2 points or at least 6.9 points relative to the baseline DQLI score. The post-administration DQLI score may be reduced at least 4 points relative to the baseline DQLI score. The post-administration DQLI score may be reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline DQLI score. The post-administration DQLI score may be maintained, without additional administration of an anti-OX40L antibody, or antigen-binding fragment thereof, for:

(a) at least 2 months, at least 3 months, at least 4 months, at least 5 months or at least 6 months after administration of the last injection; or
(b) at least about 4, 8, 15, 22, 25, 29, 36, 43, 50, 57, 64, 71, 85, 113, 169 or 253 days.

Some embodiments may further comprise assessing the atopic dermatitis by determining one or more further post-administration DQLI score. The one or more further post-administration DQLI score may be determined at least around 15 days, at least around 29 days, at least around 57 days, at least around 85 days, at least around 113 days, at least around 169 days and/or at least around 253 days after administering a first injection of the antibody or fragment thereof. The one or more further post-administration DQLI score may be determined at around 29 days, around 57 days, around 85 days, around 113 days, around 169 days and/or around 253 days after administering a first injection of the antibody or fragment thereof. The one or more further post-administration DQLI score may be determined at the end of the induction phase.

The one or more further post-administration DQLI score may be selected from the group consisting of 0 to 1; 2 to 5; 6 to 10; 11 to 20; and 21 to 30. The one or more further post-administration DQLI score may be reduced at least 4 points, at least 5 points, at least 6 points, at least 7 points, at least 8 points, at least 9 points, at least 10 points, at least 15 points or at least 20 points relative to the baseline DQLI score. The one or more further post-administration DQLI score may be reduced at least 2.2 points or at least 6.9 points relative to the baseline DQLI score. The one or more further post-administration DQLI score may be reduced at least 4 points relative to the baseline DQLI score.

Determining the post-administration DQLI score and/or the one or more further post-administration DQLI score may comprise the subject providing an answer for how much their skin problem has affected their life over the past week in the following areas:

i. how itchy, sore, painful or stinging their skin has been,
ii. how embarrassed or self conscious they have been because of their skin,
iii. how much their skin has interfered with them going shopping or looking after their home or garden,
iv. how much their skin has influenced the clothes they wear,
v. how much their skin has affected any social or leisure activities,
vi. how much their skin has made it difficult to do any sport
vii. whether their skin has prevented them from working or studying or if not how much their skin has been a problem at work or studying,
viii. how much their skin has created problems with their partner of any of their close friends or relatives,
ix. how much their skin has caused any sexual difficulties
x. how much of a problem has the treatment for their skin been.

Each answer may be selected from the group consisting of:

i. "Very much"
ii. "A lot"
iii. "A little"
iv. "Not at all"
v. "Not relevant"

The method may further comprise:

assigning an answer score to each answer, wherein "very much" is assigned a score of 3, "a lot" is assigned a score of 2, "a little" is assigned a score of 1 and "not at all", "not relevant" or question unanswered are assigned a score of 0, and adding together the answer scores to calculate a DQLI score.

The post-administration DQLI score and/or further post-administration DQLI score may be determined at least around 113 days after administering a first injection of the antibody or fragment thereof and wherein the post-administration DQLI score and/or further post-administration DQLI score may be reduced at least 4 points relative to the baseline DQLI score. The post-administration DQLI score and/or further post-administration DQLI score may be determined at least around 169 days after administering a first injection of the antibody or fragment thereof and wherein the post-administration DQLI score and/or further post-administration DQLI score may be reduced at least 4 points relative to the baseline DQLI score. The post-administration DQLI score and/or further post-administration DQLI score may be determined at least around 253 days after administering a first injection of the antibody or fragment thereof and wherein the post-administration DQLI score and/or further post-administration DQLI score may be reduced at least 4 points relative to the baseline DQLI score. The Atopic Dermatitis may be treated as evidenced by a reduction in the DQLI score by at least 4 points after the third injection as a treatment dose. The reduction in DQLI score may be persistent for at least 2 months, at least 3 months, at least 4 months, at least 5 months or at least 6 months after administration of the last injection as a treatment dose.

According to certain embodiments of, administration of a therapeutically effective amount of an anti-OX40L antibody, or antigen-binding fragment thereof to a patient results in a decrease in DQLI score. Some embodiments include therapeutic methods which result in a decrease from baseline in DQLI score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof). The post-administration DQLI score may be reduced at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline DQLI score. The reduction of the post-administration DQLI score relative to the baseline DQLI score may be derived from any baseline DQLI score and any post-administration DQLI score, at any time point or between any time points, disclosed herein. In certain exemplary embodiments, administration of an anti-OX40L antibody, or antigen-binding fragment thereof to a subject results in a decrease from baseline in DQLI score of at least 20%, at least 30% or at least 35%, optionally at around day 113 after the first administration of the anti-OX40L antibody, or antigen-binding fragment thereof.

According to certain embodiments, administration of a therapeutically effective amount of an anti-OX40L antibody, or antigen-binding fragment thereof to a patient results in a decrease in DQLI score equal to or greater than the minimal clinically important difference (MCID), at day 4, 8, 15, 22, 25, 29, 36, 43, 50, 57, 64, 71, 85, 113, 169, 253 or later following administration of the anti-OX40L antibody, or antigen-binding fragment thereof (e.g., following subcutaneous administration of about 62.5 mg, 125 mg, 250 mg or a 500 mg loading dose followed by 250 mg of an anti-OX40L antibody, or antigen-binding fragment thereof).

In further configurations, there are provided the above-mentioned embodiments comprising administering a therapeutically effective amount of an OX40L antagonist antibody or antigen-binding fragment thereof.

Population Level Clinical Effects

The advantageous effects of some embodiments may be described on a population level, that is considering the effects across multiple subjects, such as average effects. The effects on a population level may be relative to a control. The control may be placebo. The control may be untreated patients. The control may be a baseline, such as an average of subject baselines obtained before treatment. Effects of some embodiments may include:

- At least a 35% improvement in the proportion of patients achieving IGA-AD 0/1 at assessment. The improvement may be seen at an assessment conducted around 16 weeks after administering the first dose.
- A further around 5% improvement in the proportion of patients achieving IGA-AD 0/1 at a further assessment. The improvement may be seen at an assessment conducted around 16 weeks to 24 weeks after administering the first dose.
- At least a 40% improvement in the proportion of patients achieving EASI75 at assessment. The improvement may be seen at an assessment conducted around 16 weeks after administering the first dose.
- A further around 10% improvement in the proportion of patients achieving EASI75 at a further assessment. The improvement may be seen at an assessment conducted around 16 weeks to 24 weeks after administering the first dose.
- At least a 35% improvement in the proportion of patients achieving EASI90 at assessment. The improvement may be seen at an assessment conducted around 16 weeks after administering the first dose.
- A further around 5% improvement in the proportion of patients achieving EASI90 at a further assessment. The improvement may be seen at an assessment conducted around 24 weeks after administering the first dose.
- At least a≤25% improvement in the proportion of patients achieving at least a 4-point improvement in Pruritus NRS score at assessment. The improvement may be seen at an assessment conducted around 16 weeks after administering the first dose.
- A further around 5% improvement in the proportion of patients achieving at least a 4-point improvement in Pruritus NRS at assessment. The improvement may be seen at an assessment conducted around 24 weeks after administering the first dose.
- A reduction in the EASI score by at least 40% after a third treatment dose and wherein the reduction in EASI score is persistent for at least 2 months after administration of the last dose.

Any one or more of the above effects may be taken as evidence that the Atopic Dermatitis has been treated.

Another embodiment is related to a method of treating atopic dermatitis in a patient, the method comprising administering a pharmaceutical composition comprising a therapeutically effective amount of an anti-OX40L antibody, or antigen-binding fragment thereof to the patient, wherein the administration of the anti-OX40L antibody, or antigen-binding fragment thereof results in at least one improvement selected from the group consisting of:

a. a decrease from baseline in vIGA score of at least 2 points, or
b. achieving clear or almost clear skin (vIGA0/1) from baseline.

Another embodiment is related to a method of treating atopic dermatitis in a patient, the method comprising administering a pharmaceutical composition comprising a therapeutically effective amount of an anti-OX40L antibody, or antigen-binding fragment thereof to the patient, wherein the administration of the anti-OX40L antibody, or antigen-binding fragment thereof results in at least one improvement selected from the group consisting of:

a. a decrease from baseline in EASI score of at least 50%, or
b. a decrease from baseline in EASI score of at least 75%, or
c. achieving EASI-75, or
d. achieving EASI-90, or
e. achieve at least 3 points a pruritus NRS, or
f. achieve at least 4 points a pruritus NRS, or
g. a decrease from baseline in SCORAD Index of at least 50%, or
h. a decrease from baseline in SCORAD Index of at least 55%, or
i. a decrease from baseline in affected BSA of at least 60%
j. a decrease from baseline in affected BSA of at least 70%

Another embodiment is related to a method of treating an inflammatory disease, an inflammatory disorder, an immune-mediated disease, an immune-mediated disorder, an inflammatory skin disorder, atopic dermatitis or moderate-to-severe atopic dermatitis in a patient, the method comprising administering a pharmaceutical composition comprising a therapeutically effective amount of an anti-OX40L antibody, or antigen-binding fragment thereof to the patient, wherein the administration of the anti-OX40L antibody, or antigen-binding fragment thereof results in the decrease in serum levels of at least one biomarker selected from the group consisting of: IL-13, IL-22, IL-17A, IL-31 and IgE.

According to certain embodiment of the above-mentioned methods, at least one of the improvements is achieved at week 16. According to certain embodiment of the above-mentioned methods, at least one of the improvements is maintained for at least 12 weeks or at least 24 weeks following the final dose.

In further configurations, there are provided the above-mentioned embodiments comprising administering a therapeutically effective amount of an OX40L antagonist antibody or antigen-binding fragment thereof.

Administration to Children

Atopic Dermatitis may develop in early childhood. Children therefore represent an important group for treatment. Patient bodyweight may be accounted for in dosing, so doses administered to children may be lower than those administered to adults. The subject may be aged from 12 to 18 years old. The subject may have an age of 6 months to 11 years. The subject may have an age of 12 years to 17 years.

Depending on the dose used, the antibody or fragment thereof may be administered either intravenously or subcutaneously based on the judgment of a clinician who will determine which route of administration is best for their patient accounting for their bodyweight.

Formulations

IV and SC formulations of anti-OX40L antibodies, such as KY1005 have been found to exhibit surprisingly consistent pharmacokinetic (PK) parameter estimates in IV and subcutaneous population PK models. One advantage observed is a linear PK (with the exception of some non-linearity seen in low doses, such as around 0.45 mg/kg, in healthy subjects), allowing the PK model to be described as a "linear two compartment distribution model", for both IV and subcutaneous administration. Here, the term "linear" refers to the clearance—encompassing the rate of clearance (CL) and the rate of clearance from the central compartment to the second compartment (Q1)—both of which are shown to be linear in the data disclosed herein. The same finding applies in both AD and healthy patients. Without being bound by theory, this may be related to a low expression of OX40L, such that the rate of clearance does not change based on concentration of drug (or therefore time).

IV and SC formulations of anti-OX40L antibodies, such as KY1005 have been found to exhibit surprisingly low immunogenicity. One component of a harmful immune response to a therapeutic protein is the formation of anti-drug antibodies (ADA). The consequences of an immune reaction to a therapeutic protein range from transient appearance of ADAs without any clinical significance to severe life-threatening conditions. Potential clinical consequences of an unwanted immune response include loss of efficacy of the therapeutic protein and serious acute immune effects such as anaphylaxis. ADAs can affect efficacy of a therapeutic protein either by interfering with the pharmacodynamic interaction between the therapeutic protein and its target or by altering its pharmacokinetic profile.

As described in the European Medicines Agency (EMA) Guideline on Immunogenicity assessment of therapeutic proteins (18 May 2017, EMEA/CHMP/BMWP/42832/2005 Rev1, Committee for Medicinal Products for Human Use (CHMP)), products given intravenously may be less immunogenic than drugs given subcutaneously. It is therefore surprising that the population PK profile formulations of anti-OX40L antibodies, such as KY1005 are so similar between IV and subcutaneous administration scenarios (based on a single subcutaneous dose). No meaningful effect of ADA is apparent from the data disclosed herein.

In some embodiments, the IV and SC formulations of anti-OX40L antibodies, such as KY1005 are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA. See also Powell et al. "Compendium of excipients for parenteral formulations" PDA (1998) J Pharm Sci Technol. 52:238-311.

In further configurations, there are provided the above-mentioned embodiments comprising administering a therapeutically effective amount of an OX40L antagonist antibody or antigen-binding fragment thereof.

Products

A liquid formulation comprising an anti-OX40L antibody, or antigen-binding fragment thereof may be contained in a medical container, e.g., a vial, syringe, IV container or an injection device (e.g., a subcutaneous injection device). In an example, the liquid formulation comprising the anti-OX40L antibody, or antigen-binding fragment thereof is in vitro,.e.g., in a sterile container.

Some embodiments therefore also provides:

A glass vial containing a liquid formulation comprising an anti-OX40L antibody, or antigen-binding fragment thereof.

A drug delivery device containing a liquid formulation comprising an anti-OX40L antibody, or antigen-binding fragment thereof.

A prefilled syringe containing a liquid formulation comprising an anti-OX40L antibody, or antigen-binding fragment thereof.

A microinfusor containing a liquid formulation comprising an anti-OX40L antibody, or antigen-binding fragment thereof.

A pen delivery device containing a liquid formulation comprising an anti-OX40L antibody, or antigen-binding fragment thereof. The pen delivery device may be a reusable pen delivery device. The pen delivery device may be a disposable pen delivery device.

An autoinjector delivery device containing a liquid formulation comprising an anti-OX40L antibody, or antigen-binding fragment thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

In some embodiments, he glass vial, drug delivery device, prefilled syringe, microinfusor, pen delivery device or auto-injector may contain a volume of a liquid formulation comprising an anti-OX40L antibody, or antigen-binding fragment thereof is up to 1 mL, up to 2 mL or up to 2.25 mL.

In some embodiments, a kit comprising a glass vial, drug delivery device, prefilled syringe, microinfusor, pen delivery device or autoinjector; and a label and/or instructions specifying administration in accordance with some embodiments, optionally wherein the label or instructions comprise a marketing authorisation number (e.g., an FDA or EMA authorisation number). In an example, is provided a kit comprising a liquid formulation comprising the anti-OX40L antibody, or antigen-binding fragment thereof, packaging and instructions for use in treating Atopic Dermatitis. In an example, the human is of Chinese (e.g., Han or CHS) ethnicity and the instructions are in Chinese (e.g., Mandarin).

In further configurations, there are provided the above-mentioned embodiments comprising administering a therapeutically effective amount of an OX40L antagonist antibody or antigen-binding fragment thereof.

Formulations & Products in Method

In some embodiments, he products may be used in embodiments of the described methods.

In some embodiments is provided a method, wherein the antibody or fragment thereof is administered from a prefilled syringe, a microinfusor, a pen delivery device or an auto-injector delivery device.

In some embodiments is provided a method, wherein the antibody or fragment thereof is administered from a prefilled syringe.

In further configurations, there are provided the above-mentioned embodiments comprising administering a therapeutically effective amount of an OX40L antagonist antibody or antigen-binding fragment thereof.

Medical Uses

Embodiments of the invention also provides the following medical uses:

- An anti-OX40L antibody, or antigen-binding fragment thereof, for use in a method of treating Atopic Dermatitis in accordance with some embodiments of the method.
- A glass vial, drug delivery device, prefilled syringe, microinfusor, pen delivery device, autoinjector or kit, for use in a method of treating Atopic Dermatitis in accordance with some embodiments of the method.
- The use of an anti-OX40L antibody, or antigen-binding fragment thereof, for the manufacture of a medicament for the treatment of Atopic Dermatitis in accordance with some embodiments of the method.
- The use of a glass vial, drug delivery device, prefilled syringe, microinfusor, pen delivery device, autoinjector or kit, for the manufacture of a medicament for the treatment of Atopic Dermatitis in accordance with some embodiments of the method.
- In any of the above medical uses, the Atopic Dermatitis may be Chronic Atopic Dermatitis.

Some embodiments also provides the following medical uses: inflammatory diseases, inflammatory disorders, immune-mediated diseases, immune-mediated disorders, inflammatory skin diseases or inflammatory skin disorders.

Some embodiments also provides the following medical uses: inflammatory diseases, inflammatory disorders, immune-mediated diseases, immune-mediated disorders, inflammatory skin diseases or inflammatory skin disorders in both Th2 and non-Th2 patient populations or patient populations having mixed phenotype or patient with mixed inflammatory responses. The invention also provides the following medical uses: inflammatory diseases, inflammatory disorders, immune-mediated diseases, immune-mediated disorders, inflammatory skin diseases or inflammatory skin disorders in Th2 patient populations, non-Th2 patient populations, high Th2 patient populations, low Th2 patient populations or non Th2 patient populations.

Some embodiments also provides the following medical uses: inflammatory diseases, inflammatory disorders, immune-mediated diseases, immune-mediated disorders, inflammatory skin diseases or inflammatory skin disorders in both Type 2 and non-Type 2 patient populations or patient populations having mixed phenotype or patient with mixed inflammatory responses. The invention also provides the following medical uses: inflammatory diseases, inflammatory disorders, immune-mediated diseases, immune-mediated disorders, inflammatory skin diseases or inflammatory skin disorders in Type 2 patient populations, non-Type 2 patient populations, high Type 2 patient populations, low Type 2 patient populations or non-Type 2 patient populations.

In Further Configurations, there are Provided the Above-Mentioned Embodiments Comprising Administering a Therapeutically Effective Amount of an OX40L Antagonist Antibody or Antigen-Binding Fragment Thereof.Antibodies In some embodiments, antibodies include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, antibodies provided herein include immunoglobulin molecules and immunologically active portions of immunoglobulin molecules, i.e., molecules that contain an antigen binding site that specifically binds to a hOX40L antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, preferably an IgG1 or IgG4. In certain embodiments, the antibodies comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE.

Variants and derivatives of antibodies include antibody fragments that retain the ability to specifically bind to an epitope. In some embodiments the fragments include Fab fragments; Fab' (an antibody fragment containing a single anti-binding domain comprising an Fab and an additional portion of the heavy chain through the hinge region); $F(ab')_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv; a disulfide-linked Fv, or dsFv; a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

In some embodiments, the antibodies may be from any animal origin including birds and mammals (e.g., human, murine, donkey, sheep, rabbit, goat, guinea pig, camel, horse, or chicken). In certain embodiments, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In some embodiments, the antibodies are fully human antibodies, such as fully human antibodies that specifically bind a hOX40L polypeptide, a hOX40L polypeptide fragment, or a hOX40L epitope. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies (e.g., anti-hOX40L antibodies derived from other species) when administered to the subject.

In some embodiments, the antibodies may be monospecific, bispecific, trispecific or of greater multispecificity. Multispecific antibodies may be specific for different epitopes of a hOX40L polypeptide or may be specific for both a hOX40L polypeptide as well as for a heterologous epitope, such as a heterologous polypeptide or solid support material. In some embodiments, the antibodies provided herein are monospecific for a given epitope of a hOX40L polypeptide and do not specifically bind to other epitopes.

Also provided herein is a B-cell (e.g., an immortalised B-cell) or a hybridoma that produces an anti-hOX40L antibody or fragment described herein.

In certain embodiments, an isolated antibody is provided herein that specifically binds to a hOX40L epitope wherein the binding to the hOX40L epitope by the antibody is competitively blocked („ in a dose-dependent manner) by an antibody or fragment. The antibody may or may not be a fully human antibody. In some embodiments, the antibody is a fully human monoclonal anti-hOX40L antibody, and even more preferably a fully human, monoclonal, antagonist anti-hOX40L antibody. Exemplary competitive blocking tests that can be used are provided in the Examples herein.

In some embodiments, the antibody or fragment competes (e.g., in a dose-dependent manner) with OX40 Receptor (or a fusion protein thereof) for binding to cell surface-expressed hOX40L. In other embodiments, the antibody or fragment competes (e.g., in a dose-dependent manner) with OX40 Receptor (or a fusion protein thereof) for binding to soluble hOX40L. Exemplary competitive binding assays that can be used are provided in the Examples herein. In one embodiment, the antibody or fragment partially or completely inhibits binding of hOX40 to cell surface-expressed OX40L, such as hOX40L. In another embodiment, the antibody partially or completely inhibits binding of hOX40 to soluble hOX40L. In some embodiments, the antibody or fragment partially or completely inhibits the secretion of CCL20, IL-8, and/or RANTES, or INF-$\gamma$, TNF-$\alpha$ or IL-2, in particular INF-$\gamma$ from a cell having cell surface-expressed OX40. In certain embodiments, the cell expressing the OX40 is a colonic epithelial cell.

In some embodiments, the antibodies are fully human, monoclonal antibodies, such as fully human, monoclonal antagonist antibodies, that specifically bind to hOX40L. In some embodiments, the antibodies are OX40L antagonist antibodies. In some embodiments, the antibodies are fully human, monoclonal antibodies, such as fully human, monoclonal OX40L antagonist antibodies.

In some embodiments, the antibody or fragment provided herein binds to a hOX40L epitope that is a three-dimensional surface feature of a hOX40L polypeptide (e.g., in a trimeric form of a hOX40L polypeptide). A region of a hOX40L polypeptide contributing to an epitope may be contiguous amino acids of the polypeptide or the epitope may come together from two or more non-contiguous regions of the polypeptide A hOX40L epitope may be present in (a) the trimeric form ("a trimeric hOX40L epitope") of hOX40L, (b) the monomeric form ("a monomeric hOX40L epitope") of hOX40L, (c) both the trimeric and monomeric form of hOX40L, (d) the trimeric form, but not the monomeric form of hOX40L, or (e) the monomeric form, but not the trimeric form of hOX40L.

For example, in some embodiments, the epitope is only present or available for binding in the trimeric (native) form, but is not present or available for binding in the monomeric (denatured) form by an anti-hOX40L antibody. In other embodiments, the hOX40L epitope is linear feature of the hOX40L polypeptide (e.g., in a trimeric form or monomeric form of the hOX40L polypeptide). Antibodies provided herein may specifically bind to (a) an epitope of the monomeric form of hOX40L, (b) an epitope of the trimeric form of hOX40L, (c) an epitope of the monomeric but not the trimeric form of hOX40L, (d) an epitope of the trimeric but not the monomeric form of hOX40L, or (e) both the monomeric form and the trimeric form of hOX40L. In some embodiments, the antibodies provided herein specifically bind to an epitope of the trimeric form of hOX40L but do not specifically bind to an epitope the monomeric form of hOX40L.

Some embodiments also provide antibodies that specifically bind to a hOX40L epitope, the antibodies comprising derivatives of the VH domains, VH CDRs, VL domains, and VL CDRs described herein that specifically bind to a hOX40L antigen. Some embodiments also provide antibodies comprising derivatives of antibodies disclosed in the Examples, wherein said antibodies specifically bind to a hOX40L epitope. Standard techniques known to those of skill in the art can be used to introduce mutations in the nucleotide sequence encoding a molecule, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In another embodiment, the derivatives have conservative amino acid substitutions. In a some embodiments, the derivatives have conservative amino acid substitutions are made at one or more predicted non-essential amino acid residues. Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In another embodiment, an antibody that specifically binds to a hOX40L epitope comprises a variable domain amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a variable domain amino acid sequence of the sequence listing.

In specific embodiments, the antibody is a fully human anti-human antibody, such as a fully human monoclonal antibody. Fully human antibodies may be produced by any method known in the art. Exemplary methods include immunization with a hOX40L antigen (any hOX40L polypeptide capable of eliciting an immune response, and optionally conjugated to a carrier) of transgenic animals (e.g., mice) that are capable of producing a repertoire of human antibodies in the absence of endogenous immunoglobulin production; see, e.g., Jakobovits et al., (1993) Proc. Nati. Acad. Sci., 90:2551; Jakobovits et al, (1993) Nature, 362:255 258 (1993); Bruggermann et al, (1993) Year in Immunol., 7:33. Other methods of producing fully human anti-hOX40L antibodies can be found in the Examples provided herein.

Alternatively, fully human antibodies may be generated through the in vitro screening of phage display antibody libraries; see e.g., Hoogenboom et al., J. Mol. Biol., 227:381 (1991); Marks et al., J. Mol. Biol., 222:581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target.

In some embodiments, the antibodies and fragments include antibodies and fragments that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

Some embodiments also provide antibodies that specifically bind to a hOX40L antigen which comprise a framework region known to those of skill in the art (e.g., a human or non-human fragment). The framework region may, for example, be naturally occurring or consensus framework regions. In some embodiments, the framework region of an antibody is human (see, e.g., Chothia et al., 1998, J. Mol. Biol. 278:457-479 for a listing of human framework regions, which is incorporated by reference herein in its entirety). See also Kabat et al. (1991) Sequences of Proteins of Immunological Interest (U.S. Department of Health and Human Services, Washington, D.C.) 5th ed.

Some embodiments, provide for antibodies that specifically bind to a hOX40L antigen, said antibodies comprising the amino acid sequence of one or more of the CDRs in the sequence listing (i.e. Seq ID No:4, Seq ID No:10, Seq ID No:36, Seq ID No:42, Seq ID No:68, Seq ID No:74, Seq ID No:96 or Seq ID No:102, in particular, Seq ID No:36 or Seq ID No:42 for HCDR1; Seq ID No:6, Seq ID No:12, Seq ID No:38, Seq ID No:44, Seq ID No:70, Seq ID No:76, Seq ID No:98 or Seq ID No:104, in particular Seq ID No:38 or Seq ID No:44 for HCDR2; Seq ID No:8, Seq ID No:14, Seq ID No:40, Seq ID No:46, Seq ID No:72, Seq ID No:78, Seq ID No:100 or Seq ID No:106, in particular Seq ID No:40 or Seq ID No:46 for HCDR3; Seq ID No:18, Seq ID No:24, Seq ID No:50, Seq ID No:56, Seq ID No:82, Seq ID No:88, Seq ID No:110 or Seq ID No:116, in particular Seq ID No:50 or Seq ID No:56 for LCDR1; Seq ID No:20, Seq ID No:26, Seq ID No:52, Seq ID No:58, Seq ID No:84, Seq ID No:90, Seq ID No:112 or Seq ID No:118, in particular Seq ID No:52 or Seq ID No:58 for LCDR2; and Seq ID No:22, Seq ID No:28, Seq ID No:54, Seq ID No:60, Seq ID No:86, Seq ID No:92, Seq ID No:114 or Seq ID No:120, in particular Seq ID No:54 or Seq ID No:60 for LCDR3) and human framework regions with one or more amino acid substitutions at one, two, three or more of the following residues: (a) rare framework residues that differ between the murine antibody framework (i.e., donor antibody framework) and the human antibody framework (i.e., acceptor antibody framework); (b) Vernier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that specifically bind to a hOX40L antigen comprising the human framework regions with one or more amino acid substitutions at one, two, three or more of the above-identified residues are antagonistic hOX40L antibodies.

Some embodiments encompass antibodies that specifically bind to a hOX40L antigen, said antibodies comprising the amino acid sequence of the VH domain and/or VL domain in the sequence listing (i.e. Seq ID No:2, Seq ID No:34, Seq ID No:66 or Seq ID No:94, in particular Seq ID No:34 for VH domains; Seq ID No:16, Seq ID No:48, Seq ID No:80, or Seq ID No:108, in particular Seq ID No:48 for VL domains) but having mutations (e.g., one or more amino acid substitutions) in the framework regions. In certain embodiments, antibodies that specifically bind to a hOX40L antigen comprise the amino acid sequence of the VH domain and/or VL domain or an antigen-binding fragment thereof of an antibody disclosed in the Examples with one or more amino acid residue substitutions in the framework regions of the VH and/or VL domains.

In some embodiments, antibodies provided herein decrease or inhibit binding of hOX40L hOX40, and/or decrease or inhibit a hOX40L biological activity, such as secretion of CCL20, IL8 and/or RANTES, or INF-γ, TNF-α or IL-2, in particular INF-γ, in subject (e.g., a human subject). In certain embodiments, antibodies provided herein, such as a human monoclonal anti-hOX40L antibody, decreases or inhibits binding of a soluble or cell-surface expressed hOX40L to hOX40, and/or decreases or inhibits secretion of CCL20 and/or RANTES, or INF-γ, TNF-α or IL-2, in particular INF-γ after contact with a soluble or cell-surface expressed hOX40L, in a subject. Blocking activity of an antibody provided herein of hOX40L binding to hOX40 can be detected using an assay as described in the Examples. Inhibition of biological activity of cells expressing OX40 by a hOX40L antibody provided herein can be detected using an assay as described in the Examples.

Some embodiments also provide for fusion proteins comprising an antibody provided herein that specifically binds to a hOX40L antigen and a heterologous polypeptide. In some embodiments, the heterologous polypeptide to which the antibody is fused is useful for targeting the antibody to cells having cell surface-expressed hOX40L.

Optionally, the antibody or fragment specifically binds hOX40L with an affinity (apparent affinity, Kd) of less than 1 mM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, e.g., in the range of 1 mM to 1 pM (e.g., 1 mM to 100 pM; 10 nM to 100 pM; 1 nM to 10 pM; or 100 pM to 1 pM) as determined by SPR, e.g., under SPR conditions disclosed herein). Additionally or alternatively, the antibody or fragment specifically binds rhesus monkey OX40L with an affinity (apparent affinity, Kd) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, e.g., in the range of 1 mM to 1 pM (e.g., 1 mM to 100 pM; 10 nM to 100 pM; 1 nM to 10 pM; or 100 pM to 1 pM) as determined by SPR, e.g., under SPR conditions disclosed herein). Such binding measurements can be made using a variety of binding assays known in the art, e.g., using surface plasmon resonance (SPR), such as by Biacore™ or using the ProteOn XPR36™ (Bio-Rad®), using KinExA® (Sapidyne Instruments, Inc), or using ForteBio Octet (Pall ForteBio Corp.).

OX40L binding ability, specificity and affinity ($K_D$, $k_{off}$ and/or $k_{on}$) can be determined by any routine method in the art, e.g., by surface plasmon resonance (SPR). The term "$k_{on}$" or "$k_a$" as used herein refers to the association constant. The term "$k_d$" or "$k_{off}$" as used herein refers to the dissociation constant. The term "$K_D$", as used herein, is intended to refer to the equilibrium dissociation constant of a particular antibody-antigen interaction. Such binding measurements can be made using a variety of binding assays known in the art, e.g., using surface plasmon resonance (SPR), such as by Biacore™ or using the ProteOn XPR36™ (Bio-Rad®), using KinExA® (Sapidyne Instruments, Inc), or using ForteBio Octet (Pall ForteBio Corp.).

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (e.g., using Hepes buffered saline at pH7.6 (also referred to as HBS-EP)).

In one embodiment, the SPR is carried out at a physiological salt level, e.g., 150 mM NaCl.

In one embodiment, the SPR is carried out at a detergent level of no greater than 0.05% by volume, e.g., in the presence of P20 (polysorbate 20; e.g., Tween-20™) at 0.05% and EDTA at 3 mM.

In one example, the SPR is carried out at 25° C. or 37° C. in a buffer at pH7.6, 150 mM NaCl, 0.05% detergent (e.g., P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody or fragment is determined using SPR by 1. Coupling anti-mouse (or other relevant human, rat or non-human vertebrate antibody constant region species-matched) IgG (e.g., Biacore™ BR-1008-38) to a biosensor chip (e.g., GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a OnM (i.e. buffer alone); and
4. And determining the affinity of binding of test antibody to test antigen using surface plasmon resonance, e.g., under an SPR condition discussed above (e.g., at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, e.g., using a model inherent to the ProteOn XPR36™ analysis software.

In another embodiment, the anti-OX40L antibodies described herein have a $k_{ON}$ or "$k_a$" rate (e.g., as measured by SPR, e.g., at 37° C.) of approximately 400,000 to 3,000,000 $M^{-1}$ $s^{-1}$, for example approximately 1,500,000 to 3,000,000 $M^{-1}$ $s^{-1}$ or approximately 2,000,000 to 3,000,000 $M^{-1}$ $s^{-1}$. In another embodiment, optionally wherein the OX40L is human OX40L and/or optionally wherein the antibody is KY1005 the $k_{ON}$ rate is approximately 1,900,000

$M^{-1}$ $s^{-1}$, approximately 2,100,000 $M^{-1}$ $s^{-1}$, approximately 2,200,000 $M^{-1}$ s–$^1$, approximately 2,300,000 $M^{-1}$ $s^{-1}$ or approximately 2,500,000 $M^{-1}$ $s^{-1}$. The $k_{ON}$ rate may be approximately 2,200,000 $M^{-1}$ $s^{-1}$. In another embodiment, optionally wherein the OX40L is rhesus OX40L and/or optionally wherein the antibody is KY1005, the $k_{ON}$ rate is approximately 2,300,000 $M^1$ $s^{-1}$, approximately 2,500,000 $M^{-1}$ $s^{-1}$, approximately 2,570,000 $M^{-1}$ $s^{-1}$, approximately 2,600,000 $M^1$ $s^1$ or approximately 2,800,000 $M^{-1}$ $s^{-1}$. The $k_{ON}$ rate may be approximately 2,570,000 $M^{-1}$ $s^{-1}$.

In another embodiment, the anti-OX40L antibodies described herein have a $k_{OFF}$ or "$k_d$" rate (e.g., as measured by SPR, e.g., at 37° C.) of approximately 0.00100 to 0.00220 $s^{-1}$, for example approximately 0.00130 to 0.00210 $s^{-1}$, or approximately 0.00150 to 0.00200 $s^{-1}$. In another embodiment, optionally wherein the OX40L is human OX40L and/or optionally wherein the antibody is KY1005, the $k_{OFF}$ rate is approximately 0.00150 to 0.00210 $s^1$, or approximately 0.00160 to 0.00200 $s^1$, e.g., approximately 0.00170 $s^1$, approximately 0.00175 $s^{-1}$, approximately 0.00177 $s^{-1}$, approximately 0.00180 $s^1$ or approximately 0.00185 $s^{-1}$. The $k_{OFF}$ rate may be approximately 0.00177 $s^1$. In another embodiment, optionally wherein the OX40L is rhesus OX40L and/or optionally wherein the antibody is KY1005, the $k_{OFF}$ rate is approximately 0.00180 to 0.00210 $s^{-1}$, is approximately 0.00185 $s^{-1}$, approximately 0.00192 $s^{-1}$, or approximately 0.00200 $s^{-1}$. The $k_{OFF}$ rate may be approximately 0.00192 $s^{-1}$.

In another embodiment, the anti-OX40L antibodies described herein have a $K_D$ (e.g., as measured by SPR, e.g., at 37° C.) of approximately 0.01 to 2.0 nM, for example approximately 0.3 to 1.5 nM, or approximately 0.5 to 1.1 nM. In another embodiment, optionally wherein the OX40L is human OX40L and/or optionally wherein the antibody is KY1005, the $K_D$ is approximately 0.60 to 1.0 nM, or approximately 0.70 to 0.90 nM, e.g., approximately 0.75 nM, approximately 0.80 nM, approximately 0.81 nM, approximately 0.82 nM or approximately 0.87 nM. The $K_D$ may be approximately 0.81 nM. In another embodiment, optionally wherein the OX40L is rhesus OX40L and/or optionally wherein the antibody is KY1005, the $K_D$ is approximately 0.60 to 0.90 nM, is approximately 0.70 nM, approximately 0.75 nM, or approximately 0.80 nM. The $K_D$ may be approximately 0.75 nM.

Sequences of antibodies 2D10 (also known as KY1005), 10A7 (also known as KY1007), 09H04 and 19H01 are disclosed herein. Sequences belonging to each antibody 2D10, 10A7, 09H04 and 19H01 are as identified in the sequence listing below. In some embodiments the sequences of antibodies are 2D10 and 10A7. Any list containing sequences from antibodies 2D10, 10A7, 09H04 and 19H01 may therefore be presented as a list of sequences from antibodies 2D10 and 10A7. In some embodiments, the sequences of antibody is 2D10. Any list containing sequences from antibodies 2D10, 10A7, 09H04 and 19H01 (or from antibodies 2D10 and 10A7) may therefore be presented as a list of sequences from antibody 2D10.

The antibody or fragment thereof may be a biosimilar of any antibody disclosed herein. The antibody or fragment thereof may be a biosimilar of 2D10. As used herein a "biosimilar" is a biological product that is highly similar to and has no clinically meaningful differences from a reference product. The reference product may be any antibody disclosed herein, such as 2D10. As used herein, whether a biological product is "highly similar" to a reference product may be determined using known techniques comparing product characteristics such as purity, chemical identity and bioactivity. The results from these comparative tests, along with other information, may be used to demonstrate that the biosimilar is highly similar to the reference product. Minor differences between the reference product and the proposed biosimilar product in clinically inactive components are acceptable. For example, these could include minor differences in the stabilizer or buffer compared to what is used in the reference product. In some instances, different glycosylation levels may be considered minor differences. Any differences between the proposed biosimilar product and the reference product are carefully evaluated by a regulator, such as the FDA to ensure the biosimilar meets the regulator's high approval standards. As mentioned above, slight differences (i.e., acceptable within-product variations) are expected during the manufacturing process for biological products, regardless of whether the product is a biosimilar or a reference product. For both reference products and biosimilars, lot-to-lot differences (i.e., acceptable within-product differences) are carefully controlled and monitored. As used herein, whether a biological product has "no clinically meaningful differences" to a reference product means there are no clinically meaningful differences from the reference product in terms of safety, purity, and potency (safety and effectiveness). This is generally demonstrated through human pharmacokinetic (exposure) and pharmacodynamic (response) studies, an assessment of clinical immunogenicity, and, if needed, additional clinical studies.

The antibody or fragment thereof may specifically bind to human OX40L (hOX40L). The antibody may block or neutralise the interaction between hOX40L and hOX40 receptor. Methods for determining antagonism, neutralising or blocking functionality may be as described herein, or as well-known by those skilled in the art. For example, in vitro techniques include SPR and/or ELISA, which are described elsewhere herein.

The antibody or fragment thereof may specifically bind to hOX40L with a $K_D$ of from 1 nM to 0.01 nM, optionally wherein the specific binding is measured by surface plasmon resonance (SPR).

The antibody or fragment thereof may compete for binding to hOX40L with 02D10. The antibody or fragment thereof may compete for binding to hOX40L with the antibody 02D10, wherein the antibody or fragment comprises a VH domain which comprises a HCDR3 comprising the motif VRGXYYY (SEQ ID NO: 235), wherein X is any amino acid. Optionally X is P or G.

In an embodiment, X is P or G. In an embodiment, X is selected from P, N, A or G. In another embodiment, X is selected from P, G or N. In another embodiment, X is selected from P, G or A.

In one embodiment, the antibody or fragment competes with the variable regions of 02D10 (e.g., competes with an antibody comprising the heavy chain variable region of SEQ ID No: 34 and the light chain variable region of SEQ ID No:48). In another embodiment, the antibody or fragment competes with 02D10 IgG4-PE having a heavy chain amino acid sequence of SEQ ID No:62 and a light chain amino acid sequence of SEQ ID No:64.

In one embodiment, the amino acid is any naturally-occurring amino acid.

The antibody or fragment thereof may antagonise specific binding of hOX40L to OX40, optionally as determined using SPR or ELISA. The antibody or fragment thereof may be referred to as an anti-OX40L antibody that antagonises OX40L accordingly.

The antibody or fragment thereof may decrease IL-2 secretion by at least 50% (e.g., 55%, 60%, 65% or 70%) as compared to IL-2 secretion in the absence of the anti-OX40L antibody or fragment, optionally wherein IL-2 secretion is measured in an allogenic mixed lymphocyte reaction (MLR) assay.

The antibody or fragment thereof may decrease IL-13 secretion by at least 50% (e.g., 55%, 60%, 65% or 70%) as compared to IL-2 secretion in the absence of the anti-OX40L antibody or fragment, optionally wherein IL-13 secretion is measured in an allogenic mixed lymphocyte reaction (MLR) assay.

The antibody may be a humanized, human or fully human antibody.

The fragment may be selected from the group consisting of multispecific antibodies (eg. bi-specific antibodies), intrabodies, single-chain Fv antibodies (scFv), camelized antibodies, Fab fragments, F(ab') fragments, disulfide-linked Fvs (sdFv), anti-idiotypic (anti-Id) antibodies single-chain antibodies, single domain antibodies, domain antibodies, Fv fragments, F(ab')2 fragments, dimeric variable regions (diabodies), linear antibodies, and epitope-binding fragments thereof.

The antibody or fragment thereof may comprise a HCDR3 of from 16 to 27 amino acids and derived from the recombination of a human VH gene segment, a human D gene segment and a human JH gene segment, wherein the human JH gene segment is IGHJ6 (e.g., IGHJ6*02).

The antibody or fragment thereof may comprise a CDR selected from:

a. the HCDR3 of antibody 2D10 (SEQ ID No:40 or SEQ ID No:46);
b. a CDR3 of any of the nanobodies having the variable region amino acid sequence of SEQ ID Nos: 177 to 213;
c. an HCDR3 of any of the antibodies having the variable region amino acid sequence of SEQ ID Nos: 215, 217, 219, 221, 223, 225, 227, 229 or 230; or
d. an HCDR3 of any of the antibodies having the variable region amino acid sequence of SEQ ID Nos: 232 or 234.

The antibody or fragment thereof may comprise the HCDR3 of antibody 2D10 (SEQ ID No:40 or SEQ ID No:46).

The antibody or fragment thereof may comprise the HCDR2 of antibody 2D10 (SEQ ID No:38 or SEQ ID No:44).

The antibody or fragment thereof may comprise the HCDR1 of antibody 2D10 (SEQ ID No:36 or SEQ ID No:42).

The antibody or fragment thereof may comprise the LCDR3 of antibody 2D10 (SEQ ID No:54 or SEQ ID No:60).

The antibody or fragment thereof may comprise the LCDR2 of antibody 2D10 (SEQ ID No:52 or SEQ ID No:58).

The antibody or fragment thereof may comprise the LCDR1 of antibody 2D10 (SEQ ID No:50 or SEQ ID No:56).

The antibody or fragment thereof may comprise any one, two, three, four, five or six of the CDRs selected from the group consisting of:

the HCDR3 of antibody 2D10 (SEQ ID No:40 or SEQ ID No:46),
the HCDR2 of antibody 2D10 (SEQ ID No:38 or SEQ ID No:44),
the HCDR1 of antibody 2D10 (SEQ ID No:36 or SEQ ID No:42), the LCDR3 of antibody 2D10 (SEQ ID No:54 or SEQ ID No:60),
the LCDR2 of antibody 2D10 (SEQ ID No:52 or SEQ ID No:58) and
the LCDR1 of antibody 2D10 (SEQ ID No:50 or SEQ ID No:56).

The antibody or fragment thereof may comprise:

a. the CDRs of antibody 2D10 (SEQ ID No:40 or SEQ ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2 and SEQ ID No:54 or SEQ ID No:60 for CDRL3);
b. the CDRs of any of the nanobodies having the variable region amino acid sequence of SEQ ID Nos: 177 to 213;
c. the heavy chain CDRs of any of the antibodies having the heavy chain variable region amino acid sequence of SEQ ID Nos: 215, 217, 219, 221, 223, 225, 227, 229 or 230, and the light chain CDRs of any of the antibodies having the light chain variable region amino acid sequence of SEQ ID Nos: 216, 218, 220, 222, 224, 226 or 228; or
d. the heavy chain CDRs of any of the antibodies having the heavy chain variable region amino acid sequence of SEQ ID Nos: 232 or 234, and the light chain CDRs of any of the antibodies having the light chain variable region amino acid sequence of SEQ ID Nos:231 or 233.

The antibody or fragment thereof may comprise the CDRs of antibody 2D10 (SEQ ID No:40 or SEQ ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2 and SEQ ID No:54 or SEQ ID No:60 for CDRL3).

The antibody or fragment thereof may comprise the CDRH1 sequence of the VH region of 2D10 as in SEQ ID No: 34.

The antibody or fragment thereof may comprise the CDRH2 sequence of the VH region of 2D10 as in SEQ ID No: 34.

The antibody or fragment thereof may comprise the CDRH3 sequence of the VH region of 2D10 as in SEQ ID No: 34.

The antibody or fragment thereof may comprise the CDRL1 sequence of the VL region of 2D10 as in SEQ ID No: 48.

The antibody or fragment thereof may comprise the CDRL2 sequence of the VL region of 2D10 as in SEQ ID No: 48.

The antibody or fragment thereof may comprise the CDRL3 sequence of the VL region of 2D10 as in SEQ ID No: 48.

The antibody or fragment thereof may comprise any one, two, three, four, five or six of the CDRs selected from the group consisting of:

the CDRH1 sequence of the VH region of 2D10 as in SEQ ID No: 34,
the CDRH2 sequence of the VH region of 2D10 as in SEQ ID No: 34,
the CDRH3 sequence of the VH region of 2D10 as in SEQ ID No: 34,
the CDRL1 sequence of the VL region of 2D10 as in SEQ ID No: 48,
the CDRL2 sequence of the VL region of 2D10 as in SEQ ID No: 48 and the CDRL3 sequence of the VL region of 2D10 as in SEQ ID No: 48.

The antibody or fragment thereof may comprise an IgG4 constant region. The IgG4 constant region may be IgG4*1, IgG4*2, IgG4*3 or IgG4-PE. The IgG4 may have an amino acid sequence according to any one of SEQ ID Nos: 121, 123, 125, 127, 129 or 131.

The antibody or fragment thereof may comprise an IgG4 constant region comprising a Leu235Glu mutation and/or a Ser228Pro mutation. Ser228Pro/Leu235Glu mutations are according to the EU index numbering system.

The antibody or fragment thereof may comprise an IgG4-PE constant region having an amino acid sequence according to SEQ ID No:128.

The antibody or fragment thereof may comprise an IgG4-PE constant region having an amino acid sequence according to SEQ ID No:128; a VH domain having an amino acid sequence according to SEQ ID No:34 and a VL domain having an amino acid sequence according to SEQ ID No:48.

The antibody or fragment thereof may comprise an IgG4-PE constant region having an amino acid sequence according to SEQ ID No:128 and a VH and/or VL domain of an anti-OX40L antibody disclosed herein.

The antibody or fragment thereof may comprise an IgG4-PE constant region having an amino acid sequence according to SEQ ID No:128 and a VH and/or VL domain comprising CDR sequences of an anti-OX40L antibody disclosed herein. The antibody or fragment thereof may comprise an IgG4-PE constant region having an amino acid sequence according to SEQ ID No:128 and a. the CDRs of antibody 2D10 (SEQ ID No:40 or SEQ ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2 and SEQ ID No:54 or SEQ ID No:60 for CDRL3);
b. the CDRs of any of the nanobodies having the variable region amino acid sequence of SEQ ID Nos: 177 to 213;
c. the heavy chain CDRs of any of the antibodies having the heavy chain variable region amino acid sequence of SEQ ID Nos: 215, 217, 219, 221, 223, 225, 227, 229 or 230, and the light chain CDRs of any of the antibodies having the light chain variable region amino acid sequence of SEQ ID Nos: 216, 218, 220, 222, 224, 226 or 228; or
d. the heavy chain CDRs of any of the antibodies having the heavy chain variable region amino acid sequence of SEQ ID Nos: 232 or 234, and the light chain CDRs of any of the antibodies having the light chain variable region amino acid sequence of SEQ ID Nos:231 or 233.

The antibody or fragment thereof may comprise an IgG4-PE constant region having a heavy chain having an amino acid sequence according to SEQ ID No:62 and a light chain having an amino acid sequence according to SEQ ID No:64.

The antibody may be oxelumab.

Embodiments

In the following embodiments, the antibody may be 02D10.

The antibody or fragment thereof may be administered at most once every 12 weeks. The antibody or fragment thereof may be administered every 12 weeks to 24 weeks. The antibody or fragment thereof may be administered every 12 weeks or every 24 weeks. The administration may be by subcutaneous injection.

The dose may be 125 mg. The dose may be an initial dose of 250 mg followed by 125 mg. The administration may be by subcutaneous injection.

The dose may be 125 mg administered every 12 weeks. The administration may be by subcutaneous injection.

The dose may be an initial dose of 250 mg followed by 125 mg administered every 12 weeks. The administration may be by subcutaneous injection.

Advantages include 02D10 (also referred to as KY1005 or Amlitelimab) as a potential first-in-class anti-OX40-L. Subcutaneous administration is advantageously convenient. Furthermore, as shown herein ~70% of IGA 0/1 patients with sustained response off drug for 24 weeks. 02D10 also provides an attractive target product profile due to infrequent dosing regimen and durability of response, addressing mixed-phenotype AD populations.

In some embodiments, the method defined herein may further comprise the use of a biomarker described herein. The use of a biomarker may for instance be any use defined herein. The biomarker may be any one or more biomarker described herein. The biomarker may be selected from the group consisting of IL-13, IL-22, and IL-17A. IL-13 may be considered a Th2 biomarker. IL-22 and IL-17A may be considered non-Th2 biomarkers. The effect of 02D10 (also referred to as KY1005 or Amlitelimab) on IL-13, IL-22, and IL-17A disclosed herein indicates that in some embodiments, the methods may be effective in both Th2 and non-Th2 AD patient populations.

In further configurations, there are provided the above-mentioned embodiments comprising administering a therapeutically effective amount of an OX40L antagonist antibody or antigen-binding fragment thereof.

Diagnostic Biomarkers

The method may comprise use of a diagnostic biomarker. The diagnostic biomarker may be selected from the group consisting of IL-13, IL-22, IL-17A, IL-31 and IgE. Any mention of a "biomarker" in the following paragraphs under the heading of "Diagnostic biomarkers" may refer to a diagnostic biomarker.

Some embodiments include a pharmaceutical composition comprising an anti-OX40L antibody, or antigen-binding fragment thereof, for use in treating AD in a patient with a biomarker selected from the group consisting of IL-13, IL-22, IL-17A, IL-31 and IgE.

Some embodiments include a pharmaceutical composition comprising an anti-OX40L antibody, or antigen-binding fragment thereof, for use in the treatment of AD in a patient population classified as Th2 high. Some embodiments include a pharmaceutical composition comprising an anti-OX40L antibody, or antigen-binding fragment thereof, for use in the treatment of AD in a patient population classified as Th2 low.

Some embodiments include a pharmaceutical composition comprising an anti-OX40L antibody, or antigen-binding fragment thereof, for use in treating Th2 high AD.

Some embodiments include a pharmaceutical composition comprising an anti-OX40L antibody, or antigen-binding fragment thereof, for use in treating Th2 low AD.

Some embodiments include a pharmaceutical composition comprising an anti-OX40L antibody, or antigen-binding fragment thereof, for use in treating Th2 high and Th2 low AD.

Some embodiments include a pharmaceutical composition comprising an anti-OX40L antibody, or antigen-binding fragment thereof, for use in treating AD patients with mixed inflammatory responses.

Some embodiments include a pharmaceutical composition comprising an anti-OX40L antibody, or antigen-binding fragment thereof, for use in the treatment of AD in a patient having an elevated level of a biomarker selected from the group consisting of IL-13, IL-22, IL-17A, IL-31 and IgE.

Some embodiments include a pharmaceutical composition comprising an anti-OX40L antibody, or antigen-binding fragment thereof, for therapeutic use in inflammatory diseases with AD-associated biomarkers.

Some embodiments include a pharmaceutical composition comprising an OX40L blocking agent for the uses as described herein.

The biomarker may be selected from the group consisting of IL-13, IL-22, IL-17A, IL-31 and IgE. IL-13 may be considered a Th2 biomarker. Patients with an elevated IL-13 level may be classified as a Th2 AD patient or Th2 high AD patient. The method may comprise detecting an elevated IL-13 level and classifying the patient as a Th2 AD patient or Th2 high AD patient. IL-22 and IL-17A may be considered non-Th2 biomarkers. Patients with an elevated IL-22 and/or IL-17A level may be classified as a non-Th2 AD patient or Th2 low AD patient. The method may comprise detecting an elevated IL-22 and/or IL-17A level and classifying the patient as a non-Th2 AD patient or Th2 low AD patient. In some embodiments, the effect of 02D10 (also referred to as KY1005 or Amlitelimab) on IL-13, IL-22, and IL-17A disclosed herein indicates that the methods may be effective in both Th2 and non-Th2 AD patient populations. The subject may be classified as a Th2 AD patient and/or a non-Th2 AD patient. The subject may be classified as a Th2 high AD patient and/or a Th2 low AD patient. The subject may be a Th2 AD patient. The subject may be a non-Th2 AD patient. The subject may be a Th2 high AD. The patient may be a Th2 low AD patient.

According to certain aspects, methods for treating AD are provided which comprise: (a) selecting a subject who exhibits a level of at least one AD-associated biomarker prior to or at the time of treatment which signifies the disease state; and (b) administering to the subject a pharmaceutical composition comprising a therapeutically effective amount of an anti-OX40L antibody, or antigen-binding fragment thereof. In certain embodiments, the patient is selected by determining if the level of an AD-associated biomarker is elevated. The level of an AD-associated biomarker is determined or quantified by acquiring a sample from the patient for a biomarker assay known in the art. In certain other embodiments, a patient is selected by determining the patient has an elevated level of an AD-associated biomarker from the patient. In certain embodiments of this aspect, the subject is selected on the basis of an elevated level of IL-13, IL-22 and/or IL-17A.

The patient sample may be a blood, serum, tissue biopsy or other sample. The patient sample may be acquired at any point before, after, or during a course of treatment.

Some embodiments also include methods for determining whether a subject is a suitable subject for whom administration of a pharmaceutical composition comprising an anti-OX40L antibody, or antigen-binding fragment thereof, would be beneficial. For example, if an individual, prior to receiving a pharmaceutical composition comprising an anti-OX40L antibody, or antigen-binding fragment thereof, exhibits a level of an AD-associated biomarker which signifies the disease state, the individual is therefore identified as a suitable patient for whom administration of a pharmaceutical composition of (e.g., a composition comprising an anti-OX40L antibody, or antigen-binding fragment thereof) would be beneficial. In a related embodiment, includes methods for treating suitable subjects, wherein a suitable subject may be more susceptible to AD, for example, due to race or ethnicity. Some embodiments include methods comprising administering an anti-OX40L antibody, or antigen-binding fragment thereof, to African-American subjects who may be more susceptible to AD. Such a subject population may have an elevated level of an AD-associated biomarker.

According to certain exemplary embodiments, an individual may be identified as a suitable subject for anti-OX40L antibody, or antigen-binding fragment thereof therapy, if the individual exhibits an elevated level of a biomarker selected from the group consisting of IL-13, IL-22, IL-17A, IL-31 and IgE.

According to other exemplary embodiments, the present invention provides methods for treating AD in a subject, the methods comprising: (a) selecting a subject who exhibits an elevated level of at least one AD-associated biomarker; and (b) administering to the subject a pharmaceutical composition comprising a therapeutically effective amount of an anti-OX40L antibody, or antigen-binding fragment thereof. Exemplary AD-associated biomarkers that can be evaluated and/or measured in the context of the present invention include IL-13, IL-22, IL-17A, IL-31 and IgE. In some embodiments, the methods comprise determining the level of an AD-associated biomarker in a patient in need thereof, selecting a patient with an elevated level of the AD-associated biomarker, and administering a therapeutically effective amount anti-OX40L antibody, or antigen-binding fragment thereof. In some embodiments, the patient is selected by determining the patient has level of an AD-associated biomarker in a patient. In some embodiments, the level of an AD-associated biomarker is determined by an assay or test known in the art or as disclosed elsewhere herein. In one embodiment, the patient is selected on the basis of exhibiting an elevated level of a biomarker selected from the group consisting of IL-13, IL-22, IL-17A, IL-31 and IgE, prior to or at the time of treatment. In one embodiment, the patient is selected on the basis of exhibiting an elevated level of one or more biomarkers selected from the group consisting of IL-13, IL-22, IL-17A, IL-31 and IgE prior to or at the time of treatment.

In certain embodiments, the methods may be used to treat patients that show elevated levels of one or more AD-associated biomarkers (described elsewhere herein). For example, the methods of the present invention comprise administering an anti-OX40L antibody, or antigen-binding fragment thereof, to patients with elevated levels of biomarkers selected from the group consisting of IL-13, IL-22, IL-17A, IL-31 and IgE. In some embodiments, the methods herein may be used to treat AD in children who are <1 year old.

According to certain aspects, methods for treating AD are provided which comprise: (a) selecting a subject who exhibits a level of at least one AD-associated biomarker prior to or at the time of treatment which signifies the disease state; and (b) administering to the subject a pharmaceutical composition comprising a therapeutically effective amount of an anti-OX40L antibody, or antigen-binding fragment thereof. In certain embodiments of this aspect, the subject is selected on the basis of an elevated level of biomarkers selected from the group consisting of IL-13, IL-22, IL-17A, IL-31 and IgE.

Some embodiments also include methods for determining whether a subject is a suitable subject for whom administration of a pharmaceutical composition comprising an anti-OX40L antibody, or antigen-binding fragment thereof, would be beneficial. For example, if an individual, prior to receiving a pharmaceutical composition comprising an anti- OX40L antibody, or antigen-binding fragment thereof, exhibits a level of an AD-associated biomarker which signifies the disease state, the individual is therefore identified as a suitable patient for whom administration of a pharmaceutical composition (e.g., a composition comprising an anti-OX40L antibody, or antigen-binding fragment thereof) would be beneficial.

As used herein, the expression "a suitable subject" means a human or non-human mammal that exhibits one or more symptoms or indications of AD, and/or who has been diagnosed with AD. A suitable subject may have been assigned a disease severity by any suitable method disclosed herein. In certain embodiments, the methods may be used to treat patients that show elevated levels of one or more AD-associated biomarkers (described elsewhere herein). Some embodiments comprise administering an anti-OX40L antibody, or antigen-binding fragment thereof, to patients with elevated levels of biomarkers selected from the group consisting of IL-13, IL-22, IL-17A, IL-31 and IgE. The term "a suitable subject" may also include, e.g., subjects who, prior to treatment, exhibit (or have exhibited) one or more indications of AD.

In some embodiments,, "a suitable subject" may include a subset of population which is more susceptible to AD or may show an elevated level of an AD-associated biomarker such as IL-13, IL-22, IL-17A, IL-31 and IgE.

According to certain exemplary embodiments, an individual may be identified as a suitable subject for treatment with an anti-OX40L antibody, or antigen-binding fragment thereof, if the individual exhibits an elevated level of one or more biomarkers selected from the group consisting of IL-13, IL-22, IL-17A, IL-31 and IgE.

Some embodiments also include methods for determining whether a subject is a suitable subject for whom administration of a pharmaceutical composition comprising an anti-OX40L antibody, or antigen-binding fragment thereof would be beneficial. For example, if an individual, prior to receiving a pharmaceutical composition comprising an anti-OX40L antibody, or antigen-binding fragment thereof, exhibits a level of an AD-associated biomarker which signifies the disease state, the individual is therefore identified as a suitable patient for whom administration of a pharmaceutical composition (e.g., a composition comprising an anti-OX40L antibody, or antigen-binding fragment thereof) would be beneficial. According to certain exemplary embodiments, an individual may be identified as a good candidate for therapy comprising administration of an anti-OX40L antibody, or antigen-binding fragment thereof, if the individual exhibits an elevated level of one or more biomarkers selected from the group consisting of IL-13, IL-22, IL-17A, IL-31 and IgE.

According to certain exemplary embodiments, are methods for treating AD in a subject, the methods comprising: (a) selecting a subject who exhibits an elevated level of at least one AD-associated biomarker; and (b) administering to the subject a pharmaceutical composition comprising a therapeutically effective amount of an anti-OX40L antibody, or antigen-binding fragment thereof. According to a related aspect, methods for treating AD are provided which comprise administering to a subject a pharmaceutical composition comprising a therapeutically effective amount of an anti-OX40L antibody, or antigen-binding fragment thereof, wherein administration of the pharmaceutical composition to the subject results in a decrease in at least one AD-associated biomarker in the subject. Exemplary AD-associated biomarkers that can be evaluated and/or measured include: IL-13, IL-22, IL-17A, IL-31 and IgE.

In some embodiments, an anti-OX40L antibody, or antigen-binding fragment thereof, for use in a method for treating AD in a subject, wherein the subject exhibits an elevated level of at least one AD-associated biomarker prior to or at the time of treatment.

According to certain embodiments, is provided methods for treating AD in a subject comprising administering to the subject a pharmaceutical composition comprising a therapeutically effective amount of an anti-OX40L antibody, or antigen-binding fragment thereof, wherein the subject has been diagnosed with AD and has also been selected for treatment on the basis of the subject exhibiting an increased level of an AD-associated biomarker before treatment. The increased level may be increased as compared to a reference level of the biomarker. The reference level of the biomarker may be the normal level in a healthy subject. The reference level may be a normal level for the subject, which may be determined for example by comparison to a level of the biomarker when the subject was healthy, for example using samples obtained from the subject before the onset of AD. The reference level may be expression of the biomarker in a subset of subjects diagnosed with AD and/or expression of the biomarker in healthy subjects.

According to certain aspects, methods for treating AD are provided which comprise: (a) selecting a subject who exhibits a level of at least one AD-associated biomarker prior to or at the time of treatment which signifies the disease state, and (b) administering to the subject a pharmaceutical composition comprising a therapeutically effective amount of an anti-OX40L antibody, or antigen-binding fragment thereof. In certain embodiments of this aspect, the subject is selected on the basis of an elevated level of biomarker selected from the group consisting of IL-13, IL-22, IL-17A, IL-31 and IgE.

In some embodiments, an anti-OX40L antibody, or antigen-binding fragment thereof for use in treating AD in a patient, wherein the treatment comprises assaying a sample from a patient to determine if a patient has a biomarker selected from the group consisting of IL-13, IL-22, IL-17A, IL-31 and IgE; and administering a therapeutically effective amount of the anti-OX40L antibody, or antigen-binding fragment thereof if IL-13, IL-22, IL-17A, IL-31 and IgE is present.

In one aspect, is provided a method of determining whether a patient suspected to suffer from AD is a candidate for therapy comprising administration of an anti-OX40L antibody, or antigen-binding fragment thereof, for the said AD comprising the step of subjecting a patient's biological sample to at least one assay to measure at baseline the level of a biomarker selected from the group consisting of IL-13, IL-22, IL-17A, IL-31 and IgE, wherein when the biological sample of the biomarker level is high relative to a reference level of expression of the biomarker, the patient is identified as a candidate for therapy comprising administration of an anti-OX40L antibody, or antigen-binding fragment thereof, for AD. In some embodiments the at least one assay is an Olink assay. In some embodiments the at least one assay is a Simoa assay.

In some embodiments is a method for treating AD in a patient in need thereof, wherein the method comprises (a) measuring the level of a biomarker selected from the group consisting of IL-13, IL-22, IL-17A, IL-31 and IgE in the biologic fluid of the patient; (b) comparing the measured level with a reference level or threshold level; and (c) if the level of said biomarker is above the reference level or threshold level, administering to the patient an anti-OX40L antibody, or antigen-binding fragment thereof.

In some embodiments is a method for treating a patient with AD with an anti-OX40L antibody, or antigen-binding fragment thereof, comprising administering a therapeutically effective amount of an anti-OX40L antibody, or antigen-binding fragment thereof, to the patient, wherein the level of a biomarker selected from the group consisting of IL-13, IL-22, IL-17A, IL-31 and IgE, in the patient's biological sample is high relative to a reference level of expression of the biomarker.

In further configurations, there are provided the above-mentioned embodiments comprising administering a therapeutically effective amount of an OX40L antagonist antibody or antigen-binding fragment thereof.

Monitoring Biomarkers

The method may comprise use of a monitoring biomarker. The monitoring biomarker may be selected from the group consisting of IL-13, IL-22, IL-17A, IL-31 and IgE. Any mention of a "biomarker" in the following paragraphs under the heading of "Monitoring biomarkers" may refer to a monitoring biomarker. Uses of monitoring biomarkers described in the following paragraphs under the heading of "Monitoring biomarkers" may alternatively be described as uses of pharmacodynamic or response biomarkers as appropriate.

Some embodiments also provide methods for decreasing the level of one or more AD-associated biomarker(s) in a subject, or improving one or more AD-associated parameter(s) in a subject, wherein the methods comprise sequentially administering to a subject in need thereof a single initial dose of a pharmaceutical composition comprising an anti-OX40L antibody, or antigen-binding fragment thereof, followed by one or more secondary doses of the pharmaceutical composition comprising the anti-OX40L antibody, or antigen-binding fragment thereof. The single initial dose may be any dose defined herein. The single initial dose may be a loading dose defined herein. The one or more secondary doses may be any doses defined herein. The one or more secondary doses may be a maintenance dose defined herein. Any reference to the term "dose" under the heading of "Monitoring biomarkers" may refer instead to an "injection".

According to certain embodiments, isprovided methods for decreasing the level of one or more AD-associated biomarker(s) in a subject, or improving one or more AD-associated parameter(s) in a subject, wherein the methods comprise administering to the subject a dose of a pharmaceutical composition comprising an anti-OX40L antibody, or antigen-binding fragment thereof.

According to a related aspect, methods for treating AD are provided which comprise administering to a subject a pharmaceutical composition comprising a therapeutically effective amount of an anti-OX40L antibody, or antigen-binding fragment thereof, wherein administration of the pharmaceutical composition to the subject results in a decrease in at least one AD-associated biomarker (for example IL-13, IL-22, IL-17A, IL-31 and IgE). The decrease may be by day 1, 29, 113, 169, 253 or later in the subject following administration. The decrease may be measured in a sample obtained from the subject on day 1, 29, 113, 169, 253 or later in the subject following administration. In certain embodiments, the patient exhibits between a $-0.01 \log_{10}$ to a $-0.50 \log_{10}$ decrease in IL-13, IL-22, IL-17A, IL-31 and IgE level from the baseline at day 29 or later following administration. In certain embodiments, the patient exhibits between a $-0.01 \log_{10}$ to a $-0.50 \log_{10}$ decrease, such as a $-0.05 \log_{10}$ to a $-0.30 \log_{10}$ decrease, such as about a $-0.1 \log_{10}$ decrease or about a $-0.15 \log_{10}$ decrease in IL-13 level from the baseline at day 29 or later following administration. In certain embodiments, the patient exhibits between a $-0.01 \log_{10}$ to a $-0.50 \log_{10}$ decrease, such as a $-0.05 \log_{10}$ to a $-0.30 \log_{10}$ decrease, such as about a $-0.1 \log_{10}$ decrease or about a $-0.15 \log_{10}$ decrease in IL-22 level from the baseline at day 29 or later following administration. In certain embodiments, the patient exhibits between a $-0.01 \log_{10}$ to a $-0.50 \log_{10}$ decrease, such as a $-0.01 \log_{10}$ to a $-0.20 \log_{10}$ decrease, such as about a $-0.02 \log_{10}$ decrease or about a $-0.025 \log_{10}$ decrease in IL-17A level from the baseline at day 29 or later following administration. In certain embodiments, the patient exhibits between a $-0.01 \log_{10}$ to a $-1.0 \log_{10}$ decrease in IL-13, IL-22, and/or IL-17A level from the baseline at day 113 or later following administration. In certain embodiments, the patient exhibits between a $-0.01 \log_{10}$ to a $-1.0 \log_{10}$ decrease, such as a $-0.3 \log_{10}$ to a $-0.6 \log_{10}$ decrease, such as about a $-0.4 \log_{10}$ decrease or about a $-0.45 \log_{10}$ decrease in IL-13 level from the baseline at day 113 or later following administration. In certain embodiments, the patient exhibits between a $-0.01 \log_{10}$ to a $-1.0 \log_{10}$ decrease, such as a $-0.40 \log_{10}$ to a $-0.70 \log_{10}$ decrease, such as about a $-0.5 \log_{10}$ decrease or about a $-0.55 \log_{10}$ decrease in IL-22 level from the baseline at day 113 or later following administration. In certain embodiments, the patient exhibits between a $-0.01 \log_{10}$ to a $-1.0 \log_{10}$ decrease, such as a $-0.01 \log_{10}$ to a $-0.10 \log_{10}$ decrease, such as about a $-0.05 \log_{10}$ decrease or about a $-0.055 \log_{10}$ decrease in IL-17A level from the baseline at day 113 or later following administration. Alternatively, administration of the pharmaceutical composition to the subject results in a decrease in at least one AD-associated biomarker by day 4, 8, 15, 22, 25, 29, 36 or later in the subject following administration. In certain embodiments, the patient exhibits between 5% and 20% decrease in IL-13, IL-22, IL-17A, IL-31 and IgE level from the baseline at day 36 or later following administration.

In another aspect, is provided monitoring the effectiveness of treatment of moderate-to-severe AD in a subject with an anti-OX40L antibody, or antigen-binding fragment thereof, the method comprising: (a) determining the expression level of an AD-associated biomarker, such as IL-13, IL-22, IL-17A, IL-31 and IgE in a biological sample acquired from the subject before treatment with the anti-OX40L antibody, or antigen-binding fragment thereof; (b) determining the expression level of at least one of IL-13, IL-22, IL-17A, IL-31 and IgE in a biological sample acquired from the subject after treatment with the anti-OX40L antibody, or antigen-binding fragment thereof; (c) comparing the level determined in step (a) with the level in step (b); and (d) concluding that the treatment is effective when the level determined in step (b) is lower than the level determined in step (a), or concluding that the treatment is not effective when the level determined in step (b) is the same or higher than the level determined in step (a). In one embodiment, the level in step (b) is determined after determining the level in step (a). In one embodiment, the biomarker is one or more of the biomarkers selected from the group consisting of IL-13, IL-22, IL-17A, IL-31 and IgE and if IL-13, IL-22, IL-17A, IL-31 and IgE levels decrease following administration of the anti-OX40L antibody, or antigen-binding fragment thereof, then treatment with the anti-OX40L antibody, or antigen-binding fragment thereof is determined to be effective.

The expression level of the biomarker can be determined after administration of the anti-OX40L antibody, or antigen-binding fragment thereof, and compared to the expression level prior to administration of the anti-OX40L antibody, or antigen-binding fragment thereof. The dose or the dosing regimen of the anti-OX40L antibody, or antigen-binding fragment thereof can be adjusted following the determination. For example, if the expression of the biomarker fails to decrease following administration of the anti-OX40L antibody, or antigen-binding fragment thereof, then treatment with the anti-OX40L antibody, or antigen-binding fragment thereof can be stopped, or the dose of the anti-OX40L antibody, or antigen-binding fragment thereof can be increased. If expression of the biomarker decreases following administration of the antagonist, the dosage of the antagonist can be maintained or decreased, such as to identify a minimal effective dose. In some embodiments, treatment is maintained at the minimal effective dose.

In another aspect, is provided methods for monitoring a subject's response to treatment with an anti-OX40L antibody, or antigen-binding fragment thereof, wherein the subject has moderate-to-severe AD, the method comprising: (a) determining the expression level of at least one of IL-13, IL-22, IL-17A, IL-31 and IgE in a biological sample from the subject following administration of the anti-OX40L antibody, or antigen-binding fragment thereof, to the subject; and (b) providing an indication that the treatment should be continued if the expression level of IL-13, IL-22, IL-17A, IL-31 and IgE has decreased as compared to the level before treatment with the anti-OX40L antibody. In one embodiment, the biomarker is one or more of the biomarkers selected from the group consisting of IL-13, IL-22, IL-17A, IL-31 and IgE and if IL-13, IL-22, IL-17A, IL-31 and IgE levels are determined to decrease following administration of the anti-OX40L antibody, or antigen-binding fragment thereof, then an indication is provided to continue treatment with the anti-OX40L antibody, or antigen-binding fragment thereof.

As will be appreciated by a person of ordinary skill in the art, an increase or decrease in an AD-associated biomarker can be determined by comparing (i) the level of the biomarker measured in a subject at a defined time point after administration of the pharmaceutical composition comprising an anti-OX40L antibody, or antigen-binding fragment thereof to (ii) the level of the biomarker measured in the patient prior to the administration of the pharmaceutical composition comprising an anti-OX40L antibody, or antigen-binding fragment thereof (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more after administration of the of the pharmaceutical composition comprising an anti-OX40L antibody, or antigen-binding fragment thereof. The defined time point at which the biomarker is measured can be, e.g., day 1, 29, 113, 169, 253 or later after administration of the of the pharmaceutical composition comprising an anti-OX40L antibody, or antigen-binding fragment thereof.

According to certain embodiments, a subject may exhibit a decrease in the level of one or more of IL-13, IL-22, IL-17A, IL-31 and IgE following administration of a pharmaceutical composition comprising an anti-OX40L antibody, or antigen-binding fragment thereof. For example, at about day 1, 29, 113, 169, 253 or later, following administration of a dose of a pharmaceutical composition comprising an anti-OX40L antibody, or antigen-binding fragment thereof, the subject,, may exhibit a decrease in one or more of IL-13, IL-22, IL-17A, IL-31 and IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IL-13, IL-22, and/or IL-17A in the subject just prior to the first administration). For example, at about day 1, day 4, day 8, day 15, day 22, day 25, day 29, day 36, day 43, day 50, day 57, day 64, day 71 or day 85, following administration of a dose of a pharmaceutical composition comprising an anti-OX40L antibody, or antigen-binding fragment thereof, the subject, according to the present invention, may exhibit a decrease in one or more of IL-13, IL-22, IL-17A, IL-31 and IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IL-13, IL-22, IL-17A, IL-31 and IgE in the subject just prior to the first administration).

Some embodiments also provide methods for treating AD by administering to the subject a pharmaceutical composition comprising a therapeutically effective amount of an anti-OX40L antibody, or antigen-binding fragment thereof, wherein the subject has been diagnosed with AD, has already been treated with the anti-OX40L antibody, or antigen-binding fragment thereof for a defined period of time, and has been selected for further treatment with the anti-OX40L antibody, or antigen-binding fragment thereof on the basis of exhibiting reduced expression of a biomarker (e.g., IL-13, IL-22, IL-17A, IL-31 and IgE) after treatment for the defined period of time (e.g., 1 day, 29 days, 113 days, 169 days, 253 days), wherein the reduced expression of the biomarker is determined based on a comparison to the level of expression of the respective biomarker in the subject prior to treatment with the anti-OX40L antibody, or antigen-binding fragment thereof.

Some embodiments also include an anti-OX40L antibody, or antigen-binding fragment thereof for use in a method for treating AD in a subject, wherein the subject exhibits a higher level of at least one AD-associated biomarker prior to or at the time of treatment (e.g., as compared to a population of AD patients or a subset of the AD patient population), as compared to a reference level of the biomarker. Some embodiments also include an anti-OX40L antibody, or antigen-binding fragment thereof for use in a method for treating AD in a subject, wherein the subject exhibits a lower level of at least one AD-associated biomarker after treatment with the anti-OX40L antibody, or antigen-binding fragment thereof for a defined period of time (e.g., 1 day, 29 days, 113 days, 169 days, 253 days) as compared to the level of the one or more biomarkers prior to treatment.

In further configurations, there are provided the above-mentioned embodiments comprising administering a therapeutically effective amount of an OX40L antagonist antibody or antigen-binding fragment thereof.

Pharmacodynamic/Response Biomarkers

The method may comprise use of a pharmacodynamic biomarker or response biomarker. The pharmacodynamic biomarker or response biomarker may be selected from the group consisting of IL-13, IL-22, IL-17A, IL-31 and IgE. Any mention of a "biomarker" in the following paragraphs under the heading of "Pharmacodynamic/response biomarkers" may refer to either a pharmacodynamic biomarker or a response biomarker. Uses of monitoring biomarkers described in the following paragraphs under the heading of "Pharmacodynamic/response biomarkers" may alternatively be described as uses of monitoring biomarkers as appropriate.

Some embodiments provide an in vitro method for determining efficacy of a treatment of a subject having AD by administration of an anti-OX40L antibody, or antigen-binding fragment thereof, comprising determining in vitro a level of one or more biomarker selected from the group consisting of IL-13, IL-22, IL-17A, IL-31 and IgE in a sample of said subject having AD, wherein said treatment is considered efficient if the level of IL-13, IL-22 and/or IL-17A is decreased. The decrease may be a decrease in the level of IL-13, IL-22, IL-17A, IL-31 and IgE by day 1, 29, 113, 169, 253 or later in the subject following administration. In certain embodiments, the patient exhibits between a −0.01 $\log_{10}$ to a −0.50 $\log_{10}$ decrease in IL-13, IL-22, IL-17A, IL-31 and IgE level from the baseline at day 29 or later following administration. In certain embodiments, the patient exhibits between a −0.01 $\log_{10}$ to a −0.50 $\log_{10}$ decrease, such as a −0.05 $\log_{10}$ to a −0.30 $\log_{10}$ decrease, such as about a −0.1 $\log_{10}$ decrease or about a −0.15 $\log_{10}$ decrease in IL-13 level from the baseline at day 29 or later following administration. In certain embodiments, the patient exhibits between a −0.01 $\log_{10}$ to a −0.50 $\log_{10}$ decrease, such as a −0.05 $\log_{10}$ to a −0.30 $\log_{10}$ decrease, such as about a −0.1 $\log_{10}$ decrease or about a −0.15 $\log_{10}$ decrease in IL-22 level from the baseline at day 29 or later following administration. In certain embodiments, the patient exhibits between a −0.01 $\log_{10}$ to a −0.50 $\log_{10}$ decrease, such as a −0.01 $\log_{10}$ to a −0.20 $\log_{10}$ decrease, such as about a −0.02 $\log_{10}$ decrease or about a −0.025 $\log_{10}$ decrease in IL-17A level from the baseline at day 29 or later following administration. In certain embodiments, the patient exhibits between a −0.01 $\log_{10}$ to a −1.0 $\log_{10}$ decrease in IL-13, IL-22, and/or IL-17A level from the baseline at day 113 or later following administration. In certain embodiments, the patient exhibits between a −0.01 $\log_{10}$ to a −1.0 $\log_{10}$ decrease, such as a −0.3 $\log_{10}$ to a −0.6 $\log_{10}$ decrease, such as about a −0.4 $\log_{10}$ decrease or about a −0.45 $\log_{10}$ decrease in IL-13 level from the baseline at day 113 or later following administration. In certain embodiments, the patient exhibits between a −0.01 $\log_{10}$ to a −1.0 $\log_{10}$ decrease, such as a −0.40 $\log_{10}$ to a −0.70 $\log_{10}$ decrease, such as about a −0.5 $\log_{10}$ decrease or about a −0.55 $\log_{10}$ decrease in IL-22 level from the baseline at day 113 or later following administration. In certain embodiments, the patient exhibits between a −0.01 $\log_{10}$ to a −1.0 $\log_{10}$ decrease, such as a −0.01 $\log_{10}$ to a −0.10 $\log_{10}$ decrease, such as about a −0.05 $\log_{10}$ decrease or about a −0.055 $\log_{10}$ decrease in IL-17A level from the baseline at day 113 or later following administration. Alternatively, administration of the pharmaceutical composition to the subject results in a decrease in at least one AD-associated biomarker by day 4, 8, 15, 22, 25, 29, 36 or later in the subject following administration. In certain embodiments, the patient exhibits between 5% and 20% decrease in IL-13, IL-22, IL-17A, IL-31 and IgE level from the baseline at day 36 or later following administration.

Some embodiments include a pharmaceutical composition comprising an anti-OX40L antibody, or antigen-binding fragment thereof for use in improving an AD-associated parameter, or for reducing the level of one or more AD-associated biomarkers in a subject in need thereof, wherein the pharmaceutical composition is sequentially administered to the subject as a single initial dose followed by one or more secondary doses. The one or more AD-associated biomarkers may be selected from the group consisting of IL-13, IL-22, IL-17A, IL-31 and IgE. The single initial dose may be any dose defined herein. The single initial dose may be a loading dose defined herein. The one or more secondary doses may be any doses defined herein. The one or more secondary doses may be a maintenance dose defined herein.

Any reference to the term "dose" under the heading of "Pharmacodynamic/response biomarkers" may refer instead to an "injection".

In addition, some embodiments include a pharmaceutical composition comprising an anti-OX40L antibody, or antigen-binding fragment thereof, for use in reducing the level of one or more AD-associated biomarkers in a subject in need thereof. The one or more AD-associated biomarkers may be selected from the group consisting of IL-13, IL-22, IL-17A, IL-31 and IgE.

Some embodiments include a pharmaceutical composition comprising an anti-OX40L antibody, or antigen-binding fragment thereof, for use in the treatment of AD in a subject wherein the treatment results in a decrease in one or more AD-associated biomarkers in the subject (for example, by day 1, 29, 113, 169, or 253) following treatment as compared to the level of biomarker in the subject prior to treatment. In certain embodiments, the AD-associated biomarker is at least one of IL-13, IL-22, IL-17A, IL-31 and IgE.

According to other aspects of, methods for treating AD are provided which comprise administering to a subject a pharmaceutical composition comprising a therapeutically effective amount of an anti-OX40L antibody, or antigen-binding fragment thereof, wherein administration of the pharmaceutical composition to the subject results in a decrease in at least one AD-associated biomarker (e.g., IL-13, IL-22, IL-17A, IL-31 and IgE) at a time after administration of the pharmaceutical composition, as compared to the level of the biomarker in the subject prior to the administration.

As will be appreciated by a person of ordinary skill in the art, an increase or decrease in an AD-associated biomarker can be determined by comparing (i) the level of the biomarker measured in a subject at a defined time point after administration of the pharmaceutical composition comprising an anti-OX40L antibody, or antigen-binding fragment thereof to (ii) the level of the biomarker measured in the patient prior to the administration of the pharmaceutical composition comprising an anti-OX40L antibody, or antigen-binding fragment thereof (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more after administration of the of the pharmaceutical composition comprising an anti-OX40L antibody, or antigen-binding fragment thereof. The defined time point at which the biomarker is measured can be, e.g., day 1, 29, 113, 169, 253 or later after administration of the of the pharmaceutical composition comprising an anti-OX40L antibody, or antigen-binding fragment thereof. According to certain particular embodiments, a subject may exhibit a decrease in the level of one or more of IL-13, IL-22, IL-17A, IL-31 and IgE following administration of a pharmaceutical composition comprising an anti-OX40L antibody, or antigen-binding fragment thereof. For example, following administration of a dose of a pharmaceutical composition comprising an anti-OX40L antibody, or antigen-binding fragment thereof, the subject, may exhibit a decrease in IL-13, IL-22, IL-17A, IL-31 and IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IL-13, IL-22, IL-17A, IL-31 and IgE in the subject just prior to the first administration).

According to other aspects, methods for treating AD are provided which comprise administering to a subject a pharmaceutical composition comprising a therapeutically effective amount of an anti-OX40L antibody, or antigen-binding fragment thereof, wherein administration of the pharmaceutical composition to the subject results in a decrease in at least one AD-associated biomarker (e.g., IL-13, IL-22, IL-17A, IL-31 and IgE) at a time after administration of the pharmaceutical composition, as compared to the level of the biomarker in the subject prior to the administration.

In other aspects provide methods for decreasing the level of one or more AD-associated biomarker(s) in a subject, or improving one or more AD-associated parameter(s) in a subject, wherein the methods comprise sequentially administering to a subject in need thereof a single initial dose of a pharmaceutical composition comprising an anti-OX40L antibody, or antigen-binding fragment thereof, followed by one or more secondary doses of the pharmaceutical composition comprising the anti-OX40L antibody, or antigen-binding fragment thereof.

According to certain embodiments, is provided methods for decreasing the level of one or more AD-associated biomarker(s) in a subject, or improving one or more AD-associated parameter(s) in a subject, wherein the methods comprise administering to the subject a pharmaceutical composition comprising an anti-OX40L antibody, or antigen-binding fragment thereof.

In further configurations, there are provided the above-mentioned embodiments comprising administering a therapeutically effective amount of an OX40L antagonist antibody or antigen-binding fragment thereof.Listed below are further embodiments.

Embodiments

1. A method of treating Atopic Dermatitis in a human subject comprising administering a therapeutically effective amount of an anti-OX40L antibody, or antigen-binding fragment thereof, wherein the antibody or fragment thereof is administered via injection.

2. A method according to embodiment 1, wherein the antibody or fragment thereof is administered via subcutaneous injection.

3. A method of treating Atopic Dermatitis in a human subject comprising administering a therapeutically effective amount of an anti-OX40L antibody, or antigen-binding fragment thereof, wherein the antibody or fragment thereof is administered via injection and the method comprises administering at least one injection at a dose of at least about 20 mg of the antibody or fragment thereof.

4. A method of treating Atopic Dermatitis in a human subject comprising administering a therapeutically effective amount of an anti-OX40L antibody, or antigen-binding fragment thereof, wherein the antibody or fragment thereof is a disease modifying drug.

5. The method of embodiment 4 wherein after administering the disease modifying drug, the subject achieves an IGA-AD score of 0 or 1 for at least six months.

6. The method of any one of embodiments 4 or 5 wherein after treatment with the disease modifying drug is stopped, the subject maintains an IGA-AD score of 0 or 1 for at least six months.

7. The method of any one of embodiments 5 or 6 wherein the at least six months is at least seven months, at least eight months or at least nine months.

8. The method of any one of embodiments 4 to 7 wherein a therapeutic effect persists after the last administration of the antibody or fragment thereof by at least around six half lives of the antibody or fragment thereof.

9. The method of embodiment 8 wherein the at least six half lives is at least around seven half lives, at least around eight half lives or at least around nine half lives of the antibody or fragment thereof.

10. A method of treating Atopic Dermatitis in a human subject comprising administering a therapeutically effective amount of an anti-OX40L antibody, or antigen-binding fragment thereof, optionally according to any one of embodiments 1 to 9, wherein the antibody or fragment thereof is administered at least twice with at least one interval of 2 to 6 months.

11. The method of embodiment 10 wherein the antibody or fragment thereof is administered at least twice with at least one interval of 2 to 5.5 months, at least one interval of 2 to 5 months, at least one interval of 2 to 4.5 months, or at least one interval of 2 to 4 months.

12. The method of any one of embodiments 10 or 11 wherein the antibody or fragment thereof is administered at least twice with at least one interval of around 3 months.

13. A method of treating Atopic Dermatitis in a human subject comprising administering a therapeutically effective amount of an anti-OX40L antibody, or antigen-binding fragment thereof, optionally according to any one of embodiments 1 to 12, wherein the antibody or fragment thereof is administered at least twice with at least one interval of 6 months.

14. The method of embodiment 13 wherein the antibody or fragment thereof is administered at least twice with at least one interval of 5.5 months, at least one interval of 5 months, at least one interval of 4.5 months, or at least one interval of 4 months.

15. The method of any one of embodiments 13 or 14 wherein the antibody or fragment thereof is administered at least twice with at least one interval of around 3 months.

16. A method of treating Atopic Dermatitis in a human subject comprising administering a therapeutically effective amount of an anti-OX40L antibody, or antigen-binding fragment thereof, optionally according to any one of embodiments 1 to 15, wherein a post-administration EASI score is reduced at least 10% relative to a baseline EASI score.

17. The method of embodiment 16 wherein the post-administration EASI score is reduced at least 10% relative to the baseline EASI score on day 15 through at least day 113 after administration of the anti-OX40L antibody, or antigen-binding fragment thereof.

18. The method of any one of embodiments 16 to 17 wherein the post-administration EASI score is reduced at least 15% relative to the baseline EASI score on around day 113 after administration of the anti-OX40L antibody, or antigen-binding fragment thereof.

19. The method of any one of embodiments 16 to 18 wherein the post-administration EASI score is reduced at least 20% or at least 30% relative to the baseline EASI score on around day 113 after administration of the anti-OX40L antibody, or antigen-binding fragment thereof.

20. The method of any one of embodiments 16 to 19 wherein the post-administration EASI score is reduced at least 40% or at least 45% relative to the baseline EASI score on around day 113 after administration of the anti-OX40L antibody, or antigen-binding fragment thereof.

21. A method of treating Atopic Dermatitis in a human subject comprising administering a therapeutically effective amount of an anti-OX40L antibody, or antigen-binding fragment thereof, optionally according to any one of embodiments 1 to 20, wherein a post-administration vIGA-AD score is reduced at least 10% relative to a baseline vIGA-AD score.

22. The method of embodiment 21 wherein the post-administration vIGA-AD score is reduced at least 10% relative to the baseline vIGA-AD score on day 15 through at least day 113 after administration of the anti-OX40L antibody, or antigen-binding fragment thereof.

23. The method of any one of embodiments 21 or 22 wherein the post-administration vIGA-AD score is reduced at least 15% relative to the baseline vIGA-AD score on around day 113 after administration of the anti-OX40L antibody, or antigen-binding fragment thereof.

24. The method of any one of embodiments 21 to 23 wherein the post-administration vIGA-AD score is reduced at least 20% or at least 30% relative to the baseline vIGA-AD score on around day 113 after administration of the anti-OX40L antibody, or antigen-binding fragment thereof.

25. The method of any one of embodiments 21 to 24 wherein the post-administration vIGA-AD score is reduced at least 40% or at least 45% relative to the baseline vIGA-AD score on around day 113 after administration of the anti-OX40L antibody, or antigen-binding fragment thereof.

26. A method of treating Atopic Dermatitis in a human subject comprising administering a therapeutically effective amount of an anti-OX40L antibody, or antigen-binding fragment thereof, optionally according to any one of embodiments 1 to 25, wherein a post-administration IGA-AD score is reduced at least 10% relative to a baseline IGA-AD score.

27. The method of embodiment 26 wherein the post-administration IGA-AD score is reduced at least 10% relative to the baseline IGA-AD score on day 15 through at least day 113 after administration of the anti-OX40L antibody, or antigen-binding fragment thereof.

28. The method of any one of embodiments 26 to 27 wherein the post-administration IGA-AD score is reduced at least 15% relative to the baseline IGA-AD score on around day 113 after administration of the anti-OX40L antibody, or antigen-binding fragment thereof.

29. The method of any one of embodiments 26 to 28 wherein the post-administration IGA-AD score is reduced at least 20% or at least 30% relative to the baseline IGA-AD score on around day 113 after administration of the anti-OX40L antibody, or antigen-binding fragment thereof.

30. The method of any one of embodiments 26 to 29 wherein the post-administration IGA-AD score is reduced at least 40% or at least 45% relative to the baseline IGA-AD score on around day 113 after administration of the anti-OX40L antibody, or antigen-binding fragment thereof.

31. A method of treating Atopic Dermatitis in a human subject comprising administering a therapeutically effective amount of an anti-OX40L antibody, or antigen-binding fragment thereof, optionally according to any one of embodiments 1 to 30, wherein a post-administration BSA score is reduced at least 10% relative to a baseline BSA score.

32. The method of embodiment 31 wherein the post-administration BSA score is reduced at least 10% relative to the baseline BSA score on day 29 through at least day 113 after administration of the anti-OX40L antibody, or antigen-binding fragment thereof.

33. The method of any one of embodiments 31 to 32 wherein the post-administration BSA score is reduced at least 20% relative to the baseline BSA score on around day 113 after administration of the anti-OX40L antibody, or antigen-binding fragment thereof.

34. The method of any one of embodiments 31 to 33 wherein the post-administration BSA score is reduced at least 30% or at least 35% relative to the baseline BSA score on around day 113 after administration of the anti-OX40L antibody, or antigen-binding fragment thereof.

35. A method of treating Atopic Dermatitis in a human subject comprising administering a therapeutically effective amount of an anti-OX40L antibody, or antigen-binding fragment thereof, optionally according to any one of embodiments 1 to 34, wherein a post-administration SCORAD index is reduced at least 10% relative to a baseline SCORAD index.

36. The method of embodiment 35 wherein the post-administration SCORAD index is reduced at least 10% relative to the baseline SCORAD index on day 29 through at least day 113 after administration of the anti-OX40L antibody, or antigen-binding fragment thereof.

37. The method of any one of embodiments 35 to 36 wherein the post-administration SCORAD index is reduced at least 20% relative to the baseline SCORAD index on around day 113 after administration of the anti-OX40L antibody, or antigen-binding fragment thereof.

38. The method of any one of embodiments 35 to 37 wherein the post-administration SCORAD index is reduced at least 30% or at least 35% relative to the baseline SCORAD index on around day 113 after administration of the anti-OX40L antibody, or antigen-binding fragment thereof.

39. The method of any one of embodiments 35 to 38 wherein the post-administration SCORAD index is reduced at least 45% or at least 60% relative to the baseline SCORAD index on around day 113 after administration of the anti-OX40L antibody, or antigen-binding fragment thereof.

40. A method of treating Atopic Dermatitis in a human subject comprising administering a therapeutically effective amount of an anti-OX40L antibody, or antigen-binding fragment thereof, optionally according to any one of embodiments 1 to 39, wherein a post-administration PO-SCORAD index is reduced at least 10% relative to a baseline PO-SCORAD index.

41. The method of embodiment 40 wherein the post-administration PO-SCORAD index is reduced at least 10% relative to the baseline PO-SCORAD index on day 29 through at least day 113 after administration of the anti-OX40L antibody, or antigen-binding fragment thereof.

42. The method of any one of embodiments 40 to 41 wherein the post-administration PO-SCORAD index is reduced at least 15% relative to the baseline PO-SCORAD index on around day 113 after administration of the anti-OX40L antibody, or antigen-binding fragment thereof.

43. The method of any one of embodiments 40 to 42 wherein the post-administration PO-SCORAD index is reduced at least 20% or at least 30% relative to the baseline PO-SCORAD index on around day 113 after administration of the anti-OX40L antibody, or antigen-binding fragment thereof.

44. The method of any one of embodiments 40 to 43 wherein the post-administration PO-SCORAD index is reduced at least 40% or at least 50% relative to the baseline PO-SCORAD index on around day 113 after administration of the anti-OX40L antibody, or antigen-binding fragment thereof.

45. A method of treating Atopic Dermatitis in a human subject comprising administering a therapeutically effective amount of an anti-OX40L antibody, or antigen-binding fragment thereof, optionally according to any one of embodiments 1 to 44, wherein a post-administration DQLI score is reduced at least 10% relative to a baseline DQLI score.

46. The method of embodiment 45 wherein the post-administration DQLI score is reduced at least 10% relative to the baseline DQLI score on day 85 through at least day 113 after administration of the anti-OX40L antibody, or antigen-binding fragment thereof.

47. The method of any one of embodiments 45 to 46 wherein the post-administration DQLI score is reduced at least 20% relative to the baseline DQLI score on around day 113 after administration of the anti-OX40L antibody, or antigen-binding fragment thereof.

48. The method of any one of embodiments 45 to 47 wherein the post-administration DQLI score is reduced at least 30% or at least 35% relative to the baseline DQLI score on around day 113 after administration of the anti-OX40L antibody, or antigen-binding fragment thereof.

49. A method of treating Atopic Dermatitis in a human subject comprising administering a therapeutically effective amount of an anti-OX40L antibody, or antigen-binding fragment thereof, optionally according to any one of embodiments 1 to 48, wherein the subject is a chronic Atopic Dermatitis patient.

50. A method according to any preceding embodiment wherein the dose is of from 20 mg to 1000 mg.

51. A method according to any preceding embodiment wherein the dose is of from 20 mg to 600 mg.

52. A method according to any preceding embodiment wherein the dose is up to 550 mg, up to 500 mg, up to 450 mg, up to 400 mg, up to 350 mg, up to 300 mg, up to 250 mg, up to 200 mg, up to 150 mg, up to 120 mg, up to 100 mg, or up to 50 mg.

53. A method according to any preceding embodiment wherein the dose is up to 500 mg, up to 250 mg, or up to 150 mg.

54. A method according to any preceding embodiment wherein the dose is at least 50 mg, at least 100 mg, at least 120 mg, at least 150 mg, at least 200 mg, at least 250 mg, at least 300 mg, at least 350 mg, at least 400 mg, at least 450 mg, at least 500 mg or at least 550 mg.

55. A method according to any preceding embodiment wherein the dose is at least 50 mg, at least 120 mg or at least 150 mg.

56. A method according to any preceding embodiment wherein the dose is selected from the group consisting of from 25 mg to 500 mg; from 50 mg to 450 mg; from 100 mg to 350 mg; from 120 mg to 300 mg; from 150 mg to 250 mg; and from 200 mg to 250 mg.

57. A method according to any preceding embodiment wherein the dose is selected from the group consisting of from 60 mg to 500 mg; from 100 mg to 300 mg or from 125 mg to 150 mg.

58. A method according to any preceding embodiment wherein the dose is 62.5 mg, 125 mg, 150 mg, 250 mg or 500 mg.

59. A method according to any preceding embodiment wherein the dose is 125 mg or 150 mg.

60. A method according to any preceding embodiment wherein the dose is 125 mg.

61. A method according to any one of embodiments 1 to 59, wherein the dose is 150 mg.

62. A method according to any one of embodiments 1 to 58 wherein the dose is 62.5 mg.

63. A method according to any one of embodiments 1 to 58 wherein the dose is 250 mg.

64. A method according to any preceding embodiment wherein the dose is of up to 0.6 mg/kg, up to 0.7 mg/kg, up to 0.8 mg/kg, up to 0.9 mg/kg, up to 1 mg/kg, up to 1.1 mg/kg, up to 1.2 mg/kg, up to 1.3 mg/kg, up to 1.4 mg/kg, up to 1.5 mg/kg, up to 1.6 mg/kg, up to 1.7 mg/kg, up to 1.8 mg/kg, up to 1.9 mg/kg, up to 2 mg/kg, up to 2.1 mg/kg, up to 2.2 mg/kg, up to 2.3 mg/kg, up to 2.4 mg/kg, up to 2.5 mg/kg, up to 2.6 mg/kg, up to 2.7 mg/kg, up to 2.8 mg/kg, up to 2.9 mg/kg, up to 3 mg/kg, up to 4 mg/kg, up to 5 mg/kg, up to 6 mg/kg, up to 7 mg/kg, up to 8 mg/kg, up to 9 mg/kg, up to 10 mg/kg, up to 11 mg/kg or up to 12 mg/kg.

65. A method according to any preceding embodiment wherein the dose is of up to 6 mg/kg or up to 3 mg/kg.

66. A method according to any preceding embodiment wherein the dose is of at least 0.45 mg/kg, at least 0.5 mg/kg, at least 0.6 mg/kg, at least 0.7 mg/kg, at least 0.8 mg/kg, at least 0.9 mg/kg, at least 1 mg/kg, at least 1.1 mg/kg, at least 1.2 mg/kg, at least 1.3 mg/kg, at least 1.4 mg/kg, at least 1.5 mg/kg, at least 1.6 mg/kg, at least 1.7 mg/kg, at least 1.8 mg/kg, at least 1.9 mg/kg, at least 2 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 11 mg/kg, or at least 12 mg/kg.

67. A method according to any preceding embodiment wherein the dose is of at least 0.7 mg/kg or at least 1.4 mg/kg.

68. A method according to any preceding embodiment wherein the dose is selected from the group consisting of from 0.1 mg/kg to 12 mg/kg; from 0.4 mg/kg to 11 mg/kg; from 0.7 mg/kg to 10 mg/kg; from 1 mg/kg to 9 mg/kg; from 1.3 mg/kg to 8 mg/kg; from 1.6 mg/kg to 7 mg/kg; from 1.9 mg/kg to 6 mg/kg; from 2.2 mg/kg to 5 mg/kg; from 2.5 mg/kg to 4 mg/kg; from 2.6 mg/kg to 3.8 mg/kg; from 2.7 mg/kg to 3.6 mg/kg; from 2.6 mg/kg to 3.4 mg/kg; from 2.7 mg/mg to 3.3 mg/kg; from 2.8 mg/kg to 3.2 mg/kg; and from 2.9 mg/kg to 3.1 mg/kg.

69. A method according to any preceding embodiment wherein the dose is selected from the group consisting of from 0.6 mg/kg to 11 mg/kg; from 0.7 mg/kg to 10 mg/kg; from 0.8 mg/kg to 9 mg/kg; from 0.9 mg/kg to 8 mg/kg; from 1 mg/kg to 7 mg/kg; from 1.1 mg/kg to 6 mg/kg; from 1.2 mg/kg to 5 mg/kg; from 1.3 mg/kg to 4 mg/kg; from 1.4 mg/kg to 3 mg/kg; from 1.5 mg/kg to 2.9 mg/kg; from 1.6 mg/kg to 2.8 mg/kg; from 1.7 mg/mg to 2.7 mg/kg; from 1.8 mg/kg to 2.6 mg/kg; from 1.9 mg/kg to 2.5 mg/kg; from 2 mg/kg to 2.4 mg/kg; and from 2.1 mg/kg to 2.3 mg/kg.

70. A method according to any preceding embodiment wherein the dose is from 0.7 mg/kg to 6 mg/kg.

71. A method according to any preceding embodiment wherein the dose is from 1.4 mg/kg to 3 mg/kg.

72. A method according to any preceding embodiment comprising administering at least two injections of the antibody or fragment thereof.

73. The method of embodiment 72 wherein the minimum blood serum concentration reached by the antibody or fragment thereof after administration of a first injection and prior to administration of a second injection ($C_{min}$) is at least about 2.5 μg/ml.

74. A method according to any preceding embodiment comprising administering at least three injections of the antibody or fragment thereof.

75. The method of embodiment 74 wherein the minimum blood serum concentration reached by the antibody or fragment thereof after administration of a second injection and prior to administration of a third injection ($C_{min}$) is at least about 0.5 μg/ml.

76. The method of any one of embodiments 74 to 75 wherein the minimum blood serum concentration reached by the antibody or fragment thereof after administration of a first injection and prior to administration of a third injection ($C_{min}$) is at least about 0.5 μg/ml.

77. A method according to any preceding embodiment comprising administering at least four injections of the antibody or fragment thereof.

78. The method of embodiment 77 wherein the minimum blood serum concentration reached by the antibody or fragment thereof after administration of a third injection and prior to administration of a fourth injection ($C_{min}$) is at least about 0.5 μg/ml.

79. The method of any one of embodiments 77 to 78 wherein the minimum blood serum concentration reached by the antibody or fragment thereof after administration of a first injection and prior to administration of a fourth injection ($C_{min}$) is at least about 0.5 μg/ml.

80. The method of any one of embodiments 77 to 79 wherein the minimum blood serum concentration reached by the antibody or fragment thereof after administration of a second injection and prior to administration of a fourth injection ($C_{min}$) is at least about 0.5 μg/ml.

81. The method of any preceding embodiment wherein the minimum blood serum concentration reached by the antibody or fragment thereof between any two injections ($C_{min}$) is between 2.5 μg/ml and 600 μg/ml.

82. The method of any preceding embodiment wherein the minimum blood serum concentration reached by the antibody or fragment thereof between any two injections ($C_{min}$) is at least 2.5 μg/ml, 2.6 μg/ml, at least 2.7 μg/ml, at least 2.8 μg/ml, at least 2.9 μg/ml, at least 3 μg/ml, at least 3.1 μg/ml, at least 3.2 μg/ml, at least 3.3 μg/ml, at least 3.4 μg/ml, at least 3.5 μg/ml, at least 3.6 μg/ml, at least 3.7 μg/ml, at least 3.8 μg/ml, at least 3.9 μg/ml, at least 4 μg/ml, at least 4.1 μg/ml, at least 4.2 μg/ml, at least 4.3 μg/ml, at least 4.4 μg/ml, at least 4.5 μg/ml, at least 4.6 μg/ml, at least 4.7 μg/ml, at least 4.8 μg/ml, at least 4.9 μg/ml, at least 5 μg/ml, at least 5.1 μg/ml, at least 5.2 μg/ml, at least 5.3 μg/ml, at least 5.4 μg/ml, at least 5.5 μg/ml, at least 5.6 μg/ml, at least 5.7 μg/ml, at least 5.8 μg/ml, at least 5.9 μg/ml, at least 6 μg/ml, at least 6.5 μg/ml, at least 7 μg/ml, at least 7.5 μg/ml, at least 8 μg/ml, at least 8.5 μg/ml, at least 9 μg/ml, at least 9.5 μg/ml, at least 10 μg/ml, at least 11 μg/ml, at least 12 μg/ml, at least 13 μg/ml, at least 14 μg/ml, at least 15 μg/ml, at least 16 μg/ml, at least 17 μg/ml, at least 18 μg/ml, at least 19 μg/ml, at least 20 μg/ml, at least 25 μg/ml, at least 30 μg/ml, at least 35 μg/ml, at least 40 μg/ml, at least 50 μg/ml, at least 60 μg/ml, at least 70 μg/ml, at least 80 μg/ml, at least 90 μg/ml, or at least 100 μg/ml.

83. The method of any preceding embodiment wherein the minimum blood serum concentration reached by the antibody or fragment thereof between any two injections ($C_{min}$) is at least about 4 μg/ml, at least about 5 μg/ml, or at least about 20 μg/ml.

84. The method of any preceding embodiment wherein the minimum blood serum concentration reached by the antibody or fragment thereof between any two injections ($C_{min}$) is up to 600 μg/ml, up to 500 μg/ml, up to 450 μg/ml, up to 400 μg/ml, up to 350 μg/ml, up to 300 μg/ml, up to 275 μg/ml, up to 250 μg/ml, up to 225 μg/ml, up to 200 μg/ml, up to 175 μg/ml, up to 150 μg/ml, up to 125 μg/ml, up to 100 μg/ml, up to 90 μg/ml, up to 80 μg/ml, up to 70 μg/ml, up to 60 μg/ml, up to 50 μg/ml, up to 45 μg/ml, up to 40 μg/ml, up to 35 μg/ml, up to 30 μg/ml, up to 25 μg/ml, up to 23 μg/ml, up to 20 μg/ml, up to 15 μg/ml, up to 10 μg/ml, up to 9 μg/ml, up to 8 μg/ml, up to 7 μg/ml, up to 6 μg/ml, up to 5 μg/ml, up to 4 μg/ml, up to 3 μg/ml, or up to 2.5 μg/ml.

85. The method of any preceding embodiment wherein the minimum blood serum concentration reached by the antibody or fragment thereof between any two injections ($C_{min}$) is up to about 50 μg/ml, up to about 25 μg/ml, up to about 15 μg/ml, or up to about 7 μg/ml.

86. The method of any preceding embodiment wherein the minimum blood serum concentration reached by the antibody or fragment thereof between any two injections ($C_{min}$) is selected from the group consisting of at least 3 μg/ml and up to 350 μg/ml; at least 10 μg/ml and up to 300 μg/ml; at least 12.5 μg/ml and up to 250 μg/ml; at least 15 μg/ml and up to 250 μg/ml; at least 18 μg/ml and up to 240 μg/ml; at least 20 μg/ml and up to 220 μg/ml; at least 25 μg/ml and up to 190 μg/ml; at least 30 μg/ml and up to 150 μg/ml; at least 35 μg/ml and up to 125 μg/ml; at least 40 μg/ml and up to 90 μg/ml; and at least 50 μg/ml and up to 65 μg/ml.

87. The method of any preceding embodiment wherein the maximum blood serum concentration reached by the antibody or fragment thereof after administration of an injection and prior to administration of a subsequent injection ($C_{max}$) is at least about 1.5 μg/ml, at least about 2 μg/ml, at least about 5 μg/ml, at least about 10 μg/ml, at least about 20 μg/ml, at least about 30 μg/ml, at least about 40 μg/ml, at least about 50 μg/ml, at least about 60 μg/ml, at least about 70 μg/ml, at least about 80 μg/ml, at least about 90 μg/ml, at least about 100 μg/ml, at least about 150 μg/ml, at least about 200 μg/ml, at least about 300 μg/ml or at least about 550 μg/ml.

88. The method of any preceding embodiment wherein the maximum blood serum concentration reached by the antibody or fragment thereof after administration of an injection and prior to administration of a subsequent injection ($C_{max}$) is up to about 550 μg/ml, up to about 400 μg/ml, up to about 300 μg/ml, up to about 200 μg/ml, up to about 150 μg/ml, up to about 100 μg/ml, up to about 90 μg/ml, up to about 80 μg/ml, up to about 70 μg/ml, up to about 60 μg/ml, up to about 50 μg/ml, up to about 45 μg/ml, up to about 40 μg/ml, up to about 35 μg/ml, up to about 30 μg/ml, up to about 25 μg/ml, up to about 23 μg/ml, up to about 20 μg/ml, up to about 15 μg/ml, or up to about 10 μg/ml.

89. The method of any preceding embodiment wherein the injection is subcutaneous and the maximum blood serum concentration reached by the antibody or fragment thereof after administration of an injection and prior to administration of a subsequent injection ($C_{max}$) is 1.5 μg/ml to 275 μg/ml; 2 μg/ml to 200 μg/ml; 5 μg/ml to 150 μg/ml; 5 μg/ml to 100 μg/ml; 10 μg/ml to 80 μg/ml; 10 μg/ml to 25 μg/ml; 25 μg/ml to 50 μg/ml; or 35 μg/ml to 75 μg/ml.

90. The method of any preceding embodiment wherein the injection is intravenous and the maximum blood serum concentration reached by the antibody or fragment thereof after administration of an injection and prior to administration of a subsequent injection ($C_{max}$) is 6 μg/ml to 550 μg/ml; 15 μg/ml to 400 μg/ml; 20 μg/ml to 300 μg/ml; 30 μg/ml to 200 μg/ml; 30 μg/ml to 90 μg/ml; 40 μg/ml to 105 μg/ml; 95 μg/ml to 150 μg/ml; or 95 μg/ml to 200 μg/ml.

91. The method of any preceding embodiment wherein blood serum concentrations of the antibody or fragment thereof during treatment range between about 4 μg/mL to about 15 μg/mL.

92. The method of any preceding embodiment wherein blood serum concentrations of the antibody or fragment thereof during treatment range between about 20 μg/mL to about 45 μg/mL.

93. The method of any preceding embodiment wherein blood serum concentrations of the antibody or fragment thereof during treatment range between about 5 μg/mL to about 23 μg/mL.

94. The method of any preceding embodiment wherein blood serum concentrations of the antibody or fragment thereof during treatment are around or below 10 μg/mL.

95. The method of any preceding embodiment wherein the area under the serum concentration-time curve (AUC) following the first (AUC extrapolated to infinity [$AUC_{0-inf}$]) injection may be at least around 100,000 ng/ml*day, 500,000 ng/ml*day, at least around 600,000 ng/ml*day, at least around 700,000 ng/ml*day, at least around 800,000 ng/ml*day, at least around 900,000 ng/ml*day, at least around 1,000,000 ng/ml*day, at least around 1,100,000 ng/ml*day, at least around 1,300,000 ng/ml*day, at least around 1,500,000 ng/ml*day, at least around 1,700,000 ng/ml*day, at least around 2,000,000 ng/ml*day, at least around 2,500,000 ng/ml*day, at least around 3,000,000 ng/ml*day, at least around 3,300,000 ng/ml*day or at least around 3,500,000 ng/ml*day, eg at least around 1,000,000 ng/ml*day or at least around 3,000,000 ng/ml*day.

96. The method of any preceding embodiment wherein the area under the serum concentration-time curve (AUC) following the first (AUC extrapolated to infinity [$AUC_{0-inf}$]) injection may be up to around 4,500,000 ng/ml*day, up to around 4,200,000 ng/ml*day, up to around 4,000,000 ng/ml*day, up to around 3,800,000 ng/ml*day, up to around 3,600,000 ng/ml*day, up to around 3,400,000 ng/ml*day, up to around 3,200,000 ng/ml*day, up to around 3,000,000 ng/ml*day, up to around 2,800,000 ng/ml*day, up to around 2,500,000 ng/ml*day, up to around 2,000,000 ng/ml*day, up to around 1,800,000 ng/ml*day, up to around 1,500,000 ng/ml*day, up to around 1,200,000 ng/ml*day or up to around 1,000,000 ng/ml*day, eg up to around 1,500,000 ng/ml*day or up to around 3,800,000 ng/ml*day.

97. The method of any preceding embodiment wherein the area under the serum concentration-time curve (AUC) following the first (AUC extrapolated to infinity [$AUC_{0-inf}$]) injection may be from around 100,000 ng/ml*day to around 4,500,000 ng/ml*day or around 1,000,000 ng/ml*day to around 3,800,000 ng/ml*day.

98. The method of any preceding embodiment wherein the antibody or fragment thereof is administered at most once every 12 weeks.

99. The method of any preceding embodiment wherein the antibody or fragment thereof is administered every 12 weeks or every 24 weeks.

100. The method of any preceding embodiment wherein the dose is 125 mg.

101. The method of any preceding embodiment wherein the dose is an initial dose of 250 mg followed by 125 mg.

102. The method of any preceding embodiment wherein the dose is 125 mg administered every 12 weeks.

103. The method of any preceding embodiment wherein the dose is an initial dose of 250 mg followed by 125 mg administered every 12 weeks.

104. The method of any preceding embodiment, comprising an induction phase and a maintenance phase.

105. The method of embodiment 104, wherein the induction phase comprises administering one or more induction phase injections of the antibody or fragment thereof, at an induction dose of between 20 and 500 mg; 20 mg and 300 mg; between 50 mg and 300 mg; between 100 mg and 300 mg; or between 150 mg and 300 mg.

106. The method of embodiment 104 wherein the induction dose is between 200 mg and 300 mg; or between 225 mg and 275 mg.

107. The method of embodiment 104 wherein the induction dose is about 500 mg, 250 mg, about 125 mg or about 62.5 mg.

108. The method of embodiment 104 wherein the induction dose is about 250 mg.

109. The method of any one of embodiments 104 to 108 wherein the induction phase is at least 2 weeks, at least 4 weeks, at least 8 weeks, at least 16 weeks or at least 24 weeks in duration.

110. The method of any one of embodiments 104 to 109 wherein the induction phase comprises administering two or more induction phase injections of the antibody or fragment thereof.

111. The method of embodiment 110 wherein each induction phase injection is administered at least 2 weeks, at least 4 weeks, at least 8 weeks, at least 16 weeks or at least 24 weeks apart.

112. The method of any one of embodiments 110 to 111 wherein each induction phase injection comprises the same mass of the antibody or fragment thereof as each other induction phase injection.

113. The method of any one of embodiments 110 to 111, wherein the first induction phase injection is at a loading dose and wherein the loading dose comprises up to three times the mass of the antibody or fragment thereof as each subsequent induction phase injection.

114. The method of any one of embodiments 110 to 111, wherein the first induction phase injection is at a loading dose and wherein the loading dose comprises up to twice the mass of the antibody or fragment thereof as each subsequent induction phase injection.

115. The method of any one of embodiments 110 to 111, wherein the first induction phase injection is at a loading dose and wherein the loading dose comprises up to 1.5 times the mass of the antibody or fragment thereof as each subsequent induction phase injection.

116. The method of embodiment any one of embodiments 113 to 115, wherein the loading dose is between 100 and 600 mg; between 150 and 550 mg; or between 200 and 500 mg.

117. The method of embodiment 116 wherein the loading dose is about 500 mg, about 250 mg or about 125 mg.

118. The method of embodiment 117 wherein the loading dose is about 500 mg.

119. The method of any one of embodiments 110 to 118 wherein the second induction phase injection is administered 2 to 16 weeks after the first induction phase injection; administered 3 to 14 weeks after the first induction phase injection; or administered 4 to 12 weeks after the first induction phase injection.

120. The method of any one of embodiments 110 to 119 wherein the second induction phase injection is administered 2 to 14 weeks after the first induction phase injection; administered 2 to 12 weeks after the first induction phase injection; administered 2 to 10 weeks after the first induction phase injection; administered 2 to 8 weeks after the first induction phase injection; administered 2 to 7 weeks after the first induction phase injection; or administered 2 to 6 weeks after the first induction phase injection.

121. The method of any one of embodiments 110 to 120 wherein the second induction phase injection is administered 3 to 13 weeks after the first induction phase injection; administered 5 to 11 weeks after the first induction phase injection; or administered 6 to 10 weeks after the first induction phase injection; or administered 7 to 9 weeks after the first induction phase injection.

122. The method of any one of embodiments 110 to 121 wherein the second induction phase injection is administered 4 to 8 weeks after the first induction phase injection.

123. The method of any one of embodiments 110 to 122 wherein the second induction phase injection is administered about 4 weeks or about 8 weeks after the first induction phase injection.

124. The method of any one of embodiments 110 to 123 wherein the second induction phase injection is administered 4 weeks after the first induction phase injection.

125. The method of any one of embodiments 110 to 124 wherein the induction phase comprises administering three or more induction phase injections of the antibody or fragment thereof.

126. The method of embodiment 125 wherein the third induction phase injection is administered 2 to 16 weeks after the second induction phase injection; administered 3 to 14 weeks after the second induction phase injection; or administered 4 to 12 weeks after the second induction phase injection.

127. The method of any one of embodiments 125 to 126 wherein the third induction phase injection is administered 2 to 14 weeks after the second induction phase injection; administered 2 to 12 weeks after the second induction phase injection; administered 2 to 10 weeks after the second induction phase injection; administered 2 to 8 weeks after the second induction phase injection; administered 2 to 7 weeks after the second induction phase injection; or administered 2 to 6 weeks after the second induction phase injection.

128. The method of any one of embodiments 125 to 127 wherein the third induction phase injection is administered 3 to 13 weeks after the second induction phase injection; administered 5 to 11 weeks after the second induction phase injection; or administered 6 to 10 weeks after the second induction phase injection; or administered 7 to 9 weeks after the second induction phase injection.

129. The method of any one of embodiments 125 to 128 wherein the third induction phase injection is administered 4 to 8 weeks after the second induction phase injection.

130. The method of any one of embodiments 125 to 129 wherein the third induction phase injection is administered about 4 weeks or about 8 weeks after the second induction phase injection.

131. The method of any one of embodiments 125 to 130 wherein the third induction phase injection is administered 4 weeks after the second induction phase injection.

132. The method of any one of embodiments 125 to 131 wherein the interval between the first induction phase injection and the second induction phase injection has the same duration as the interval between the second induction phase injection and the third induction phase injection.

133. The method of any one of embodiments 125 to 132 wherein each induction phase injection comprises the same mass of the antibody or fragment thereof as each other induction phase injection and/or wherein each interval between induction phase injections has the same duration as each other interval between induction phase injections.

134. The method of any one of embodiments 104 to 133, wherein the maintenance phase comprises administering one or more maintenance phase injections of the antibody or fragment thereof, at a maintenance dose between 20 mg and 300 mg; between 50 mg and 300 mg; between 100 mg and 300 mg; or between 150 mg and 300 mg.

135. The method of any one of embodiments 104 to 134 wherein the maintenance dose is between 200 mg and 300 mg; or between 225 mg and 275 mg.

136. The method of any one of embodiments 104 to 134 wherein the maintenance dose is about 500 mg, 250 mg, about 125 mg or about 62.5 mg.

137. The method of any one of embodiments 104 to 136 wherein the maintenance dose is about 250 mg.

138. The method of any one of embodiments 104 to 137 wherein the maintenance phase is at least 2 weeks, at least 4 weeks, at least 8 weeks, at least 16 weeks, at least 24 weeks, at least 32 weeks, at least 40 weeks, at least 52 weeks, or at least 100 weeks in duration.

139. The method of any one of embodiments 104 to 138 wherein the maintenance phase comprises administering two or more maintenance phase injections of the antibody or fragment thereof.

140. The method of embodiment 139 wherein each maintenance phase injection is administered at least 2 weeks, at least 4 weeks, at least 8 weeks, at least 16 weeks, at least 24 weeks, at least 32 weeks, at least 40 weeks or at least 52 weeks apart.

141. The method of any one of embodiments 139 to 140 wherein each maintenance phase injection comprises the same mass of the antibody or fragment thereof as each other maintenance phase injection.

142. The method of any one of embodiments 139 to 141 wherein a second maintenance phase injection is administered 2 to 16 weeks after a first maintenance phase injection; administered 3 to 14 weeks after a first maintenance phase injection; or administered 4 to 12 weeks after a first maintenance phase injection.

143. The method of any one of embodiments 139 to 142 wherein a second maintenance phase injection is administered 2 to 14 weeks after a first maintenance phase injection; administered 2 to 12 weeks after a first maintenance phase injection; administered 2 to 10 weeks after a first maintenance phase injection; administered 2 to 8 weeks after a first maintenance phase injection; administered 2 to 7 weeks after a first maintenance phase injection; or administered 2 to 6 weeks after a first maintenance phase injection.

144. The method of any one of embodiments 139 to 143 wherein a second maintenance phase injection is administered 3 to 13 weeks after a first maintenance phase injection; administered 5 to 11 weeks after a first maintenance phase injection; or administered 6 to 10 weeks after a first maintenance phase injection; or administered 7 to 9 weeks after a first maintenance phase injection.

145. The method of any one of embodiments 139 to 144 wherein a second maintenance phase injection is administered 4 to 8 weeks after a first maintenance phase injection.

146. The method of any one of embodiments 139 to 145 wherein a second maintenance phase injection is administered about 4 weeks or about 8 weeks after a first maintenance phase injection.

147. The method of any one of embodiments 139 to 146 wherein a second maintenance phase injection is administered about 4 weeks after a first maintenance phase injection.

148. The method of embodiment any one of embodiments 139 to 147 wherein the maintenance phase comprises administering three or more maintenance phase injections of the antibody or fragment thereof.

149. The method of embodiment 148 wherein the third maintenance phase injection is administered 2 to 16 weeks after the second maintenance phase injection; administered 3 to 14 weeks after the second maintenance phase injection; or administered 4 to 12 weeks after the second maintenance phase injection.

150. The method of any one of embodiments 148 to 149 wherein the third maintenance phase injection is administered 2 to 14 weeks after the second maintenance phase injection; administered 2 to 12 weeks after the second maintenance phase injection; administered 2 to 10 weeks after the second maintenance phase injection; administered 2 to 8 weeks after the second maintenance phase injection; administered 2 to 7 weeks after the second maintenance phase injection; or administered 2 to 6 weeks after the second maintenance phase injection.

151. The method of any one of embodiments 148 to 150 wherein the third maintenance phase injection is administered 3 to 13 weeks after the second maintenance phase injection; administered 5 to 11 weeks after the second maintenance phase injection; or administered 6 to 10 weeks after the second maintenance phase injection; or administered 7 to 9 weeks after the second maintenance phase injection.

152. The method of any one of embodiments 148 to 151 wherein the third maintenance phase injection is administered 4 to 8 weeks after the second maintenance phase injection.

153. The method of any one of embodiments 148 to 152 wherein the third maintenance phase injection is administered about 4 weeks or about 8 weeks after the second maintenance phase injection.

154. The method of any one of embodiments 148 to 153 wherein the interval between the first maintenance phase injection and the second maintenance phase injection has the same duration as the interval between the second maintenance phase injection and the third maintenance phase injection.

155. The method of any one of embodiments 148 to 154 wherein each maintenance phase injection comprises the same mass of the antibody or fragment thereof as each other maintenance phase injection and/or wherein each interval between maintenance phase injections has the same duration as each other interval between maintenance phase injections.

156. The method of any one of embodiments 104 to 155, wherein the interval between two or more maintenance phase injections has an equal duration than or a longer duration than the interval between two or more induction phase injections.

157. The method of any one of embodiments 104 to 156, wherein the interval between the first maintenance phase injection and the second maintenance phase injection has an equal duration than or a longer duration than the interval between two or more induction phase injections.

158. The method of any one of embodiments 104 to 157, wherein the interval between two or more induction phase injections is about 2 weeks, about 4 weeks or about 8 weeks and the interval between two or more maintenance phase injections is about 12 weeks or about 16 weeks.

159. The method of any one of embodiments 104 to 158, wherein the interval between two or more induction phase injections is about 4 weeks or about 8 weeks and the interval between two or more maintenance phase injections is about 12 weeks.

160. The method of any one of embodiments 104 to 158, wherein the interval between two or more induction phase injections is about 4 weeks and the interval between two or more maintenance phase injections is about 16 weeks.

161. The method of any one of embodiments 104 to 159, wherein the interval between two or more induction phase injections is about 4 weeks and the interval between two or more maintenance phase injections is about 12 weeks.

162. The method of any one of embodiments 104 to 157, wherein the interval between two or more induction phase injections is about 4 weeks and the interval between two or more maintenance phase injections is about 4 weeks.

163. The method of any one of embodiments 104 to 157, wherein the interval between two or more induction phase injections is about 8 weeks and the interval between two or more maintenance phase injections is about 8 weeks.

164. The method of any one of embodiments 104 to 157, wherein the interval between two or more induction phase injections is about 2 weeks and the interval between two or more maintenance phase injections is about 8 weeks.

165. The method of any one of embodiments 104 to 164, wherein the interval between three or more induction phase injections is constant.

166. The method of any one of embodiments 104 to 165, wherein the interval between three or more maintenance phase injections varies.

167. The method of any one of embodiments 104 to 166, wherein the combined duration of the induction phase and the mantenance phase is at least 52 weeks.

168. The method of any one of embodiments 104 to 167, wherein the subject is transitioned from the induction phase to the maintenance phase based on:

(a) clinical response; and/or (b) the time since the administration of the first induction phase injection.

169. The method of embodiment 168, wherein the clinical response is assessed at 16 weeks after the administration of the first induction phase injection.

170. The method of any one of embodiments 168 to 169, wherein the clinical response is achieving EASI50, EASI75, EASI90 or EASI100.

171. The method of any one of embodiments 168 to 170, wherein the clinical response is achieving IGA-AD0/1 and/or a reduction of at least 2 IGA-AD points.

172. The method of any one of embodiments 168 to 171, wherein the clinical response is achieving a reduction of at least 3 NRS points or at least 4 NRS points.

173. The method of any one of embodiments 168 to 172, wherein the transition from the induction phase to the maintenance phase takes place 16 or more weeks after the administration of the first induction phase injection.

174. The method of any one of embodiments 168 to 173, wherein the transition from the induction phase to the maintenance phase takes place 24 or more weeks after the administration of the first induction phase injection.

175. The method of any one of embodiments 168 to 174, wherein the transition from the induction phase to the maintenance phase takes place up to one year after the administration of the first induction phase injection.

176. The method of any one of embodiments 168 to 174, wherein the transition from the induction phase to the maintenance phase takes place 16 to 24 weeks after the administration of the first induction phase injection.

177. The method of any one of embodiments 168 to 176, wherein the transition from the induction phase to the maintenance phase takes place 24 weeks after the administration of the first induction phase injection, if the subject has achieved a clinical response of at least EASI75 at 16 weeks.

178. The method of any preceding embodiment wherein the administration is subcutaneous.

179. The method of embodiment 178 wherein the induction phase comprises administering at least five induction phase injections, wherein the first induction phase injection is a loading dose of 500 mg of the antibody or fragment thereof, followed by at least four subsequent induction phase injections, wherein each subsequent induction phase injection is a dose of 250 mg of the antibody or fragment thereof and wherein each subsequent induction phase injection is administered 4 weeks after the preceding induction phase injection.

180. The method of any one of embodiments 178 or 179 wherein the maintenance phase comprises administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

181. The method of embodiment 178 wherein the induction phase comprises administering at least five induction phase injections, wherein each induction phase injection is a dose of 250 mg of the antibody or fragment thereof and wherein a second induction phase injection and each subsequent induction phase injection is administered 4 weeks after the preceding induction phase injection.

182. The method of any one of embodiments 178 or 181 wherein the maintenance phase comprises administering at least 3 maintenance phase injections, wherein each maintenance phase injection is a dose of 250 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

183. The method of embodiment 178 wherein the induction phase comprises administering at least five induction phase injections, wherein each induction phase injection is a dose of 125 mg of the antibody or fragment thereof and wherein a second induction phase injection and each subsequent induction phase injection is administered 4 weeks after the preceding induction phase injection.

184. The method of any one of embodiments 178 or 183 wherein the maintenance phase comprises administering at least 3 maintenance phase injections, wherein each maintenance phase injection is a dose of 125 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

185. The method of embodiment 178 wherein the induction phase comprises administering at least five induction phase injections, wherein each induction phase injection is a dose of 62.5 mg of the antibody or fragment thereof and wherein a second induction phase injection and each subsequent induction phase injection is administered 4 weeks after the preceding induction phase injection.

186. The method of any one of embodiments 178 or 185 wherein the maintenance phase comprises administering at least 3 maintenance phase injections, wherein each maintenance phase injection is a dose of 62.5 mg of the antibody or fragment thereof, wherein a first maintenance phase injection is administered at least 4 weeks after the final induction phase injection and wherein a second maintenance phase injection and each subsequent maintenance phase injection is administered at least 4 weeks after the preceding maintenance phase injection.

187. The method of any one of embodiments 179 to 186 comprising administering at least six induction phase injections or at least seven induction phase injections.

188. The method of any one of embodiments 179 to 187 wherein the first maintenance phase injection is administered from 4 weeks to 24 weeks or 4 weeks to 16 weeks after the final induction phase injection.

189. The method of any one of embodiments 179 to 188 wherein the first maintenance phase injection is administered 12 weeks after the final induction phase injection.

190. The method of any one of embodiments 179 to 189 wherein the second maintenance phase injection and each subsequent maintenance phase injection is administered from 4 weeks to 24 weeks or 4 weeks to 16 weeks after the preceding maintenance phase injection.

191. The method of any one of embodiments 179 to 190 wherein the second maintenance phase injection and each subsequent maintenance phase injection is administered 12 weeks after the preceding maintenance phase injection.

192. The method of any one of embodiments 179 to 191
- (a) comprising administering at least seven induction phase injections;
- (b) wherein the first maintenance phase injection is administered at least 4 weeks after the final induction phase injection; and
- (c) wherein the second maintenance phase injection and each subsequent maintenance phase injection is administered at least 4 weeks after the preceding maintenance phase injection.

193. The method of any one of embodiments 179 to 191
- (a) comprising administering at least seven induction phase injections;
- (b) wherein the first maintenance phase injection is administered 12 weeks after the final induction phase injection; and
- (c) wherein the second maintenance phase injection and each subsequent maintenance phase injection is administered 12 weeks after the preceding maintenance phase injection.

194. The method of any one of embodiments 179 to 191
- (a) comprising administering at least seven induction phase injections;
- (b) wherein the first maintenance phase injection is administered 16 weeks after the final induction phase injection; and
- (c) wherein the second maintenance phase injection and each subsequent maintenance phase injection is administered 16 weeks after the preceding maintenance phase injection.

195. The method of any one of embodiments 179 to 191
- (a) comprising administering at least seven induction phase injections;
- (b) wherein the first maintenance phase injection is administered 24 weeks after the final induction phase injection; and
- (c) wherein the second maintenance phase injection and each subsequent maintenance phase injection is administered 24 weeks after the preceding maintenance phase injection.

196. The method of any preceding embodiment wherein the antibody or fragment thereof is capable of exhibiting one or more pharmacokinetic properties selected from the group consisting of:

(a) a rate of clearance (CL) of about 0.05 to about 0.18 L/day;
(b) an absorption constant ($k_a$) of about 0.11 to about 0.33 L/day;
(c) a volume of central compartment volume (Vc) of about 1.6 to about 5.0 L;
(d) a second (peripheral compartment) volume (Vp1) of about 1.2 to about 3.6 L;
(e) a rate of clearance from the central compartment to the second compartment (Q) of about 0.31 to about 0.93 L/day; and
(f) a bioavailability (Fabs1) of about 0.6 to about 1.0.

197. The method of embodiment 196, wherein the antibody or fragment thereof has 1, 2, 3, 4, 5, or 6 of the pharmacokinetic properties listed in (a) to (f).

198. The method of any one of embodiments 196 to 197, wherein the antibody or fragment thereof exhibits a rate of clearance (CL) of about 0.05 to about 0.18 L/day; about 0.06 to about 0.17 L/day; about 0.07 to about 0.16 L/day; about 0.08 to about 0.15 L/day; about 0.09 to about 0.14 L/day; or about 0.10 to about 0.13 L/day.

199. The method of any one of embodiments 196 to 198, wherein the antibody or fragment thereof exhibits a rate of clearance (CL) of about 0.115 L/day.

200. The method of any one of embodiments 196 to 199, wherein the antibody or fragment thereof exhibits an absorption constant ($k_a$) of about 0.11 to about 0.33 L/day; about 0.12 to about 0.32 L/day; about 0.13 to about 0.31 L/day; about 0.14 to about 0.30 L/day; about 0.15 to about 0.29 L/day; about 0.16 to about 0.28 L/day; about 0.17 to about 0.27 L/day; about 0.18 to about 0.26 L/day; about 0.19 to about 0.25 L/day; about 0.20 to about 0.24 L/day; or about 0.21 to about 0.23 L/day.

201. The method of any one of embodiments 196 to 200, wherein the antibody or fragment thereof exhibits an absorption constant ($k_a$) of about 0.22 L/day.

202. The method of any one of embodiments 196 to 201, wherein the antibody or fragment thereof exhibits a volume of central compartment volume (Vc) of about 1.6 to about 5.0 L; about 1.8 to about 4.8 L; about 2.0 to about 4.6 L; about 2.2 to about 4.4 L; about 2.4 to about 4.2 L; about 2.6 to about 4.0 L; about 2.8 to about 3.8 L; about 3.0 to about 3.6 L; or about 3.2 to about 3.4 L.

203. The method of any one of embodiments 196 to 202, wherein the antibody or fragment thereof exhibits a volume of central compartment volume (Vc) of about 3.3 L.

204. The method of any one of embodiments 196 to 203, wherein the antibody or fragment thereof exhibits a second (peripheral compartment) volume (Vp1) of about 1.2 to about 3.6 L; about 1.4 to about 3.4 L; about 1.6 to about 3.2 L; about 1.8 to about 3.0 L; about 2.0 to about 2.8 L; about 2.2 to about 2.6 L; or about 2.3 to about 2.5 L.

205. The method of any one of embodiments 196 to 204, wherein the antibody or fragment thereof exhibits a second (peripheral compartment) volume (Vp1) of about 2.4 L.

206. The method of any one of embodiments 196 to 205, wherein the antibody or fragment thereof exhibits a rate of clearance from the central compartment to the second compartment (Q1) of about 0.31 to about 0.93 L/day; about 0.36 to about 0.88 L/day; about 0.41 to about 0.83 L/day; about 0.46 to about 0.78 L/day; about 0.51 to about 0.73 L/day; about 0.56 to about 0.68 L/day; about 0.60 to about 0.64 L/day; or about 0.61 to about 0.63 L/day.

207. The method of any one of embodiments 196 to 206, wherein the antibody or fragment thereof exhibits a rate of clearance from the central compartment to the second compartment (Q1) of about 0.62 L/day.

208. The method of any one of embodiments 196 to 207, wherein the antibody or fragment thereof exhibits a bioavailability (Fabs1) of about 0.6 to about 1.0; about 0.65 to about 0.95; about 0.70 to about 0.90; or about 0.75 to about 0.85.

209. The method of any one of embodiments 196 to 208, wherein the antibody or fragment thereof exhibits a bioavailability (Fabs1) of about 0.8.

210. The method of any one of embodiments 196 to 209, wherein said pharmacokinetic properties are determined using a two-compartment model.

211. The method of embodiment 210 wherein the two-compartment model is a linear two-compartment model.

212. The method of any preceding embodiment further comprising obtaining one or more blood samples from the subject and optionally measuring the blood serum concentration reached by the antibody or fragment thereof.

213. The method of any preceding embodiment, wherein the subject has an age selected from the group consisting of up to 6 years of age; from 6 years of age to 12 years of age; from 12 years of age to 18 years of age; at least 18 years of age; and less than 75 years of age.

214. The method of any preceding embodiment, wherein the subject is at least 18 years of age and/or less than 75 years of age.

215. The method of any preceding embodiment, wherein the Atopic Dermatitis is moderate-to-severe Atopic Dermatitis.

216. The method of any preceding embodiment, wherein the subject was diagnosed with Atopic Dermatitis at least one year before administration of the antibody or fragment thereof.

217. The method of any preceding embodiment, wherein the subject is a chronic Atopic Dermatitis patient.

218. The method of any preceding embodiment, wherein the antibody or fragment thereof is a second line treatment.

219. The method of any preceding embodiment, wherein the Atopic Dermatitis is not adequately controlled with topical prescription and/or systemic therapies or when those therapies are not advisable.

220. The method of any preceding embodiment, wherein the Atopic Dermatitis is resistant, non responsive or inadequately responsive to treatment by either topical corticosteroids and/or systemic therapies or when those therapies are not advisable or wherein the subject has had an inadequate response to, was intolerant to, or is refractory to one or more topical corticosteroids.

221. The method of any preceding embodiment, wherein the Atopic Dermatitis is not adequately controlled or inadequately responsive to treatment by topical corticosteroids.

222. The method of any preceding embodiment, wherein the subject is also being treated with one or more topical corticosteroids and/or wherein the antibody or fragment thereof is used with topical corticosteroids.

223. The method of any preceding embodiment, wherein the subject was previously treated with one or more topical corticosteroid.

224. A method according to any preceding embodiment further comprising administering a therapeutically effective amount of one or more topical corticosteroid.

225. A method according to embodiment 224 wherein the one or more topical corticosteroid is administered prior to the anti-OX40L antibody, or antigen-binding fragment thereof.

226. A method according to embodiment 225 wherein a first injection of the anti-OX40L antibody, or antigen-binding fragment thereof is administered on the day that the subject discontinues treatment with the one or more topical corticosteroid.

227. A method according to embodiment 226 wherein the subject discontinues treatment with the one or more topical corticosteroid at least 2 months, at least 3 months, at least four months, at least 5 months, at least 6 months or 4 to 6 months after administering a first administration of the one or more topical corticosteroid.

228. A method according to embodiment 224 wherein the one or more topical corticosteroid is administered after the anti-OX40L antibody, or antigen-binding fragment thereof.

229. A method according to embodiment 228 wherein a first administration of the one or more topical corticosteroid is administered on the day that the subject discontinues treatment with the anti-OX40L antibody, or antigen-binding fragment thereof.

230. A method according to embodiment 229 wherein the subject discontinues treatment with the anti-OX40L antibody, or antigen-binding fragment thereof, at least 2 months, at least 3 months, at least four months, at least 5 months, at least 6 months or 4 to 6 months after administering a first injection of the anti-OX40L antibody, or antigen-binding fragment thereof.

231. A method according to any one of embodiments 226 and 229 wherein the one or more topical corticosteroid and the anti-OX40L antibody, or antigen-binding fragment thereof are administered sequentially and a period between administering an administration of the one or more topical corticosteroid and an injection of the anti-OX40L antibody, or antigen-binding fragment thereof is at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, at least 8 weeks, at least 10 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks or at least 52 weeks.

232. A method according to embodiment 224 wherein the one or more topical corticosteroid is administered concurrently with the anti-OX40L antibody, or antigen-binding fragment thereof.

233. The method of any one of embodiments 220 to 232 wherein the topical corticosteroid is selected from the group consisting of betamethasone dipropionate, clobetasol propionate, dexamethasone, methylprednisolone, methylprednisolone aceponate, mometasone furoate, diflorasone diacetate, halobetasol propionate, amcinonide, augmented betamethasone dipropionate, fluocinonide, halcinonide, triamcinolone acetonide, betamethasone valerate, clocortolone pivalate, desoximetasone, fluocinolone acetonide, flurandrenolide, fluticasone propionate, hydrocortisone butyrate, hydrocortisone probutate, hydrocortisone valerate, prednicarbate, alclometasone dipropionate, desonide, hydrocortisone and hydrocortisone acetate.

234. The method of any one of embodiments 220 to 233 wherein the topical corticosteroid is selected from the group consisting of betamethasone dipropionate, betamethasone dipropionate;gentamicin sulphate, clobetasol propionate, dexamethasone, methylprednisolone, methylprednisolone aceponate and mometasone furoate.

235. The method of any one of embodiments 220 to 234 wherein the topical corticosteroid is betamethasone dipropionate, optionally wherein the betamethasone dipropionate is combined with gentamicin sulphate.

236. The method of any one of embodiments 220 to 235 wherein the topical corticosteroid is formulated as a cream, ointment, gel, foam, solution, lotion or gel.

237. The method of any one of embodiments 220 to 236 wherein the topical corticosteroid is applied twice daily or once daily.

238. The method of any one of embodiments 220 to 236 wherein the topical corticosteroid is applied once weekly or twice weekly.

239. The method of any preceding embodiment, wherein the Atopic Dermatitis is resistant, non responsive or inadequately responsive to treatment by either topical calcineurin inhibitors and/or systemic therapies or when those therapies are not advisable or wherein the subject has had an inadequate response to, was intolerant to, or is refractory to one or more topical calcineurin inhibitors 240. The method of any preceding embodiment, wherein the Atopic Dermatitis is not adequately controlled or inadequately responsive to treatment by topical calcineurin inhibitors.

241. The method of any preceding embodiment, wherein the subject is also being treated with one or more topical calcineurin inhibitor and/or wherein the antibody or fragment thereof is used with one or more topical calcineurin inhibitor.

242. The method of any preceding embodiment, wherein the subject was previously treated with one or more topical calcineurin inhibitor.

243. A method according to any preceding embodiment further comprising administering a therapeutically effective amount of one or more topical calcineurin inhibitor.

244. A method according to embodiment 243 wherein the one or more topical calcineurin inhibitor is administered prior to the anti-OX40L antibody, or antigen-binding fragment thereof.

245. A method according to embodiment 244 wherein a first injection of the anti-OX40L antibody, or antigen-binding fragment thereof is administered on the day that the subject discontinues treatment with the one or more topical calcineurin inhibitor.

246. A method according to embodiment 245 wherein the subject discontinues treatment with the one or more topical calcineurin inhibitor at least 2 months, at least 3 months, at least four months, at least 5 months, at least 6 months or 4 to 6 months after administering a first administration of the one or more topical calcineurin inhibitor.

247. A method according to embodiment 243 wherein the one or more topical calcineurin inhibitor is administered after the anti-OX40L antibody, or antigen-binding fragment thereof.

248. A method according to embodiment 247 wherein a first administration of the one or more topical calcineurin inhibitor is administered on the day that the subject discontinues treatment with the anti-OX40L antibody, or antigen-binding fragment thereof.

249. A method according to embodiment 248 wherein the subject discontinues treatment with the anti-OX40L antibody, or antigen-binding fragment thereof, at least 2 months, at least 3 months, at least four months, at least 5 months, at least 6 months or 4 to 6 months after administering a first injection of the anti-OX40L antibody, or antigen-binding fragment thereof.

250. A method according to any one of embodiments 244 and 247 wherein the one or more topical calcineurin inhibitor and the anti-OX40L antibody, or antigen-binding fragment thereof are administered sequentially and a period between administering an administration of the one or more topical calcineurin inhibitor and an injection of the anti-OX40L antibody, or antigen-binding fragment thereof is at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, at least 8 weeks, at least 10 weeks, at least 12 weeks, at least 16 weeks, at least 20 weeks, at least 24 weeks, at least 28 weeks, at least 32 weeks, at least 36 weeks, at least 40 weeks, at least 44 weeks, at least 48 weeks or at least 52 weeks.

251. A method according to embodiment 243 wherein the one or more topical calcineurin inhibitor is administered concurrently with the anti-OX40L antibody, or antigen-binding fragment thereof.

252. The method of any one of embodiments 239 to 251 wherein the topical calcineurin inhibitor is tacrolimus ointment or pimecrolimus cream, e.g., tacrolimus ointment.

253. The method of any one of embodiments 239 to 252 wherein the topical calcineurin inhibitor is applied twice daily or once daily.

254. The method of any one of embodiments 239 to 253 wherein the topical calcineurin inhibitor is applied two to three times weekly.

255. The method of any preceding embodiment, wherein the subject is also being treated with one or more topical antihistamine and/or wherein the antibody or fragment thereof is used with one or more topical antihistamine.

256. The method of any preceding embodiment, wherein the subject is also being treated with one or more oral steroid and/or wherein the antibody or fragment thereof is used with one or more oral steroid.

257. The method of any preceding embodiment, wherein the atopic dermatitis has been assessed by determining a baseline EASI score.

258. The method of embodiment 257 wherein the determining a baseline EASI score comprises:

(a) Selecting a body region from the group consisting of head and neck; trunk including the genital area; upper extremities; and lower extremities including the buttocks;
(b) Assessing the extent of atopic dermatitis in the selected body region and assigning a region score based on the extent of atopic dermatitis in the selected body region;
(c) Assessing the severity of each of the following signs in the selected body region:
   1. Erythema,
   2. Edema and/or papulation,
   3. Excoriation, and
   4. Licenification, and assigning a severity score to each sign in the selected body region;
(d) Determining a total score for the selected body region based on the region score and the severity score for each sign in the selected body region;
(e) Repeating steps (b) to (d) for each of the remaining body regions; and
(f) Determining a baseline EASI score based on the total score for each body region.

259. The method of any one of embodiments 257 to 258, wherein the baseline EASI score is at least 12.1, at least 16.1, or at least 21.1.

260. The method of any one of embodiments 257 to 259, wherein the baseline EASI score is at least 16.1.

261. The method of any one of embodiments 257 to 260, wherein a first injection of the anti-OX40L antibody or fragment thereof is administered on the same day as the baseline EASI score is determined.

262. The method of any one of embodiments 257 to 261, further comprising determining the baseline EASI score.

263. The method of any preceding embodiment, further comprising assessing the atopic dermatitis by determining a post-administration EASI score at least 7 days or at least 15 days after administering a first injection of the antibody or fragment thereof.

264. The method of any preceding embodiment wherein the post-administration EASI score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

265. The method of any preceding embodiment wherein the post-administration EASI score is determined at around 7 days, at around 15 days, around 29 days, around 57 days, around 85 days, around 113 days, around 169 days and/or around 253 days after administering a first injection of the antibody or fragment thereof.

266. The method of any preceding embodiment wherein the post-administration EASI score is determined at the end of the induction phase.

267. The method of any preceding embodiment wherein the post-administration EASI score is less than or equal to 21.0.

268. The method of any preceding embodiment wherein the post-administration EASI score is less than or equal to 16.0.

269. The method of any preceding embodiment wherein the post-administration EASI score is less than or equal to 16.0, less than or equal to 15.0, less than or equal to 14.0, less than or equal to 13.0, less than or equal to 12.0, less than or equal to 11.0, less than or equal to 10.0, less than or equal to 9.0, less than or equal to 8.0, less than or equal to 7.0, less than or equal to 6.0, less than or equal to 5.0, less than or equal to 4.0, less than or equal to 3.0, less than or equal to 2.0, less than or equal to 1.0 or around 0.

270. The method of any preceding embodiment wherein the post-administration EASI score is less than or equal to 7.0 or less than or equal to 1.0.

271. The method of any preceding embodiment wherein the post-administration EASI score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline EASI score.

272. The method of any preceding embodiment wherein the post-administration EASI score is maintained, without additional administration of an anti-OX40L antibody, or antigen-binding fragment thereof, for:

(a) at least 2 months, at least 3 months, at least 4 months, at least 5 months or at least 6 months after administration of the last injection; or
(b) at least about 4, 8, 15, 22, 25, 29, 36, 43, 50, 57, 64, 71, 85, 113, 169 or 253 days.

273. The method of any preceding embodiment wherein the post-administration EASI score is reduced at least 6 points, at least 6.6 points, at least 7 points, at least 8 points, at least 9 points or at least 10 points relative to the baseline EASI score.

274. The method of any preceding embodiment, further comprising assessing the atopic dermatitis by determining one or more further post-administration EASI score.

275. The method of any preceding embodiment wherein the one or more further post-administration EASI score is determined at least around 15 days, at least around 29 days, at least around 57 days, at least around 85 days, at least around 113 days, at least around 169 days and/or at least around 253 days after administering a first injection of the antibody or fragment thereof.

276. The method of any preceding embodiment wherein the one or more further post-administration EASI score is determined at around 29 days, around 57 days, around 85 days, around 113 days, around 169 days and/or around 253 days after administering a first injection of the antibody or fragment thereof.

277. The method of any preceding embodiment wherein the one or more further post-administration EASI score is determined at the end of the induction phase.

278. The method of any preceding embodiment wherein the one or more further post-administration EASI score is less than or equal to 21.0.

279. The method of any preceding embodiment wherein the one or more further post-administration EASI score is less than or equal to 16.0, less than or equal to 15.0, less than or equal to 14.0, less than or equal to 13.0, less than or equal to 12.0, less than or equal to 11.0, less than or equal to 10.0, less than or equal to 9.0, less than or equal to 8.0, less than or equal to 7.0, less than or equal to 6.0, less than or equal to 5.0, less than or equal to 4.0, less than or equal to 3.0, less than or equal to 2.0, less than or equal to 1.0 or around 0.

280. The method of any preceding embodiment wherein the one or more further post-administration EASI score is less than or equal to 7.0 or less than or equal to 1.0.

281. The method of any preceding embodiment wherein the one or more further post-administration EASI score is reduced at least 10 percent, at least 25 percent or at least 50 percent relative to the baseline EASI score.

282. The method of any preceding embodiment wherein the one or more further post-administration EASI score is reduced at least 6 points, at least 6.6 points, at least 7 points, at least 8 points, at least 9 points or at least 10 points relative to the baseline EASI score.

283. The method of an any preceding embodiment wherein determining the post-administration EASI score and/or the one or more further post-administration EASI score comprises:

(a) Selecting a body region from the group consisting of head and neck; trunk including the genital area; upper extremities; and lower extremities including the buttocks;
(b) Assessing the extent of atopic dermatitis in the selected body region and assigning a region score based on the extent of atopic dermatitis in the selected body region;
(c) Assessing the severity of each of the following signs in the selected body region:
    1. Erythema,
    2. Edema and/or papulation,
    3. Excoriation, and
    4. Licenification, and assigning a severity score to each sign in the selected body region;
(d) Determining a total score for the selected body region based on the region score and the severity score for each sign in the selected body region;
(e) Repeating steps (b) to (d) for each of the remaining body regions; and
(f) Determining a baseline EASI score based on the total score for each body region.

284. The method of any preceding embodiment wherein the post-administration EASI and/or further post-administration EASI is determined at least around 113 days after administering a first injection of the antibody or fragment thereof and wherein the post-administration EASI and/or further post-administration EASI is EASI50, EASI75, EASI90 or EASI100.

285. The method of any preceding embodiment wherein the post-administration EASI and/or further post-administration EASI is determined at least around 169 days after administering a first injection of the antibody or fragment thereof and wherein the post-administration EASI and/or further post-administration EASI is EASI50, EASI75, EASI90 or EASI100.

286. The method of any preceding embodiment wherein the post-administration EASI and/or further post-administration EASI is determined at least around 253 days after administering a first injection of the antibody or fragment thereof and wherein the post-administration EASI and/or further post-administration EASI is EASI50, EASI75, EASI90 or EASI100.

287. The method of any preceding embodiment wherein the Atopic Dermatitis is treated as evidenced by a reduction in the EASI score by at least 40% after the third injection as a treatment dose and wherein the reduction in EASI score is persistent for at least 2 months, at least 3 months, at least 4 months, at least 5 months or at least 6 months after administration of the last injection as a treatment dose.

288. The method of any preceding embodiment, wherein the atopic dermatitis has been assessed by determining a baseline IGA-AD score.

289. The method of embodiment 288 wherein the determining a baseline IGA-AD score comprises describing the overall appearance of AD lesions at a given time point by:

(f) Assigning a score of 0—clear—when the most applicable morphological description is:
    No inflammatory signs of atopic dermatitis (no erythema, no induration/papulation, no oozing/crusting); post-inflammatory hyperpigmentation and/or hypopigmentation may be present;
(g) Assigning a score of 1—almost clear—when the most applicable morphological description is:
    Barely perceptible erythema, and/or barely perceptible induration/papulation, no oozing or crusting;
(h) Assigning a score of 2—mild—when the most applicable morphological description is:
    Slight but definite erythema (pink), and/or slight but definite induration/papulation; no oozing or crusting;
(i) Assigning a score of 3—moderate—when the most applicable morphological description is:
    Clearly perceptible erythema (dull red), and/or clearly perceptible induration/papulation; oozing and crusting may be present;
(j) Assigning a score of 4—severe—when the most applicable morphological description is:
    Marked erythema (deep or bright red), and/or marked induration/papulation; disease is widespread in extent; oozing or crusting may be present.

290. The method of any one of embodiments 288 to 289, wherein the baseline IGA-AD score is 3 or 4.

291. The method of any one of embodiments 288 to 290, wherein a first injection of the anti-OX40L antibody or fragment thereof is administered on the same day as the baseline IGA-AD score is determined.

292. The method of any one of embodiments 288 to 291, further comprising determining the baseline IGA-AD score.

293. The method of any preceding embodiment, further comprising assessing the atopic dermatitis by determining a post-administration IGA-AD score at least 7 days or at least 15 days after administering a first injection of the antibody or fragment thereof.

294. The method of any preceding embodiment wherein the post-administration IGA-AD score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

295. The method of any preceding embodiment wherein the post-administration IGA-AD score is determined at around 7 days, at around 15 days, around 29 days, around 57 days, around 85 days, around 113 days, around 169 days and/or around 253 days after administering a first injection of the antibody or fragment thereof.

296. The method of any preceding embodiment wherein the post-administration IGA-AD score is determined at the end of the induction phase.

297. The method of any preceding embodiment wherein the post-administration IGA-AD score is 0 or 1.

298. The method of any preceding embodiment wherein the post-administration IGA-AD score is reduced at least 1 point, at least 2 points, at least 3 points or up to 4 points relative to the baseline IGA-AD score.

299. The method of any preceding embodiment wherein the post-administration IGA-AD score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline IGA-AD score.

300. The method of any preceding embodiment wherein the post-administration IGA-AD score is maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

301. The method any preceding embodiment, further comprising assessing the atopic dermatitis by determining one or more further post-administration IGA-AD score.

302. The method of any preceding embodiment wherein the one or more further post-administration IGA-AD score is determined at least around 15 days, at least around 29 days, at least around 57 days, at least around 85 days, at least around 113 days, at least around 169 days and/or at least around 253 days after administering a first injection of the antibody or fragment thereof.

303. The method of any preceding embodiment wherein the one or more further post-administration IGA-AD score is determined at around 29 days, around 57 days, around 85 days, around 113 days, around 169 days and/or around 253 days after administering a first injection of the antibody or fragment thereof.

304. The method of any preceding embodiment wherein the one or more further post-administration IGA-AD score is determined at the end of the induction phase.

305. The method of any preceding embodiment wherein the one or more further post-administration IGA-AD score is 0 or 1.

306. The method of any preceding embodiment wherein the one or more further post-administration IGA-AD score is reduced at least 1 point, at least 2 points, at least 3 points or up to 4 points relative to the baseline IGA-AD score.

307. The method of any preceding embodiment wherein determining the post-administration IGA-AD score and/or the one or more further post-administration IGA-AD score comprises describing the overall appearance of AD lesions at a given time point by:

(f) Assigning a score of 0—clear—when the most applicable morphological description is:

No inflammatory signs of atopic dermatitis (no erythema, no induration/papulation, no lichenification, no oozing/crusting); post-inflammatory hyperpigmentation and/or hypopigmentation may be present;

(g) Assigning a score of 1—almost clear—when the most applicable morphological description is:

Barely perceptible erythema, barely perceptible induration/papulation, and/or minimal lichenification; no oozing or crusting;

(h) Assigning a score of 2—mild—when the most applicable morphological description is:

Slight but definite erythema (pink), slight but definite induration/papulation, and/or slight but definite lichenification; no oozing or crusting;

(i) Assigning a score of 3—moderate—when the most applicable morphological description is:

Clearly perceptible erythema (dull red), clearly perceptible induration/papulation, and/or clearly perceptible lichenification; oozing and crusting may be present;

(j) Assigning a score of 4—severe—when the most applicable morphological description is:

Marked erythema (deep or bright red), marked induration/papulation, and/or marked lichenification; disease is widespread in extent; oozing or crusting may be present.

308. The method of any preceding embodiment wherein the post-administration IGA-AD and/or further post-administration IGA-AD is determined at least around 113 days after administering a first injection of the antibody or fragment thereof and wherein the post-administration IGA-AD and/or further post-administration IGA-AD is:

(c) A IGA-AD score of 0 or 1, and/or (d) reduced at least 2 points relative to the baseline IGA-AD score.

309. The method of any preceding embodiment wherein the post-administration IGA-AD and/or further post-administration IGA-AD is determined at least around 169 days after administering a first injection of the antibody or fragment thereof and wherein the post-administration IGA-AD and/or further post-administration IGA-AD is:

(c) A IGA-AD score of 0 or 1, and/or (d) reduced at least 2 points relative to the baseline IGA-AD score.

310. The method of any preceding embodiment wherein the post-administration IGA-AD and/or further post-administration IGA-AD is determined at least around 253 days after administering a first injection of the antibody or fragment thereof and wherein the post-administration IGA-AD and/or further post-administration IGA-AD is:

(c) A IGA-AD score of 0 or 1, and/or (d) reduced at least 2 points relative to the baseline IGA-AD score.

311. The method of any preceding embodiment wherein the Atopic Dermatitis is treated as evidenced by a reduction in the IGA-AD score by at least 2 points after the third injection as a treatment dose and wherein the reduction in IGA-AD score is persistent for at least 2 months, at least 3 months, at least 4 months, at least 5 months or at least 6 months after administration of the last injection as a treatment dose.

312. The method of any preceding embodiment, wherein the atopic dermatitis has been assessed by determining a baseline vIGA-AD score.

313. The method of embodiment 312 wherein the determining a baseline vIGA-AD score comprises describing the overall appearance of AD lesions at a given time point by:

(a) Assigning a score of 0—clear—when the most applicable morphological description is:
No inflammatory signs of atopic dermatitis (no erythema, no induration/papulation, no lichenification, no oozing/crusting); post-inflammatory hyperpigmentation and/or hypopigmentation may be present;

(b) Assigning a score of 1—almost clear—when the most applicable morphological description is:
Barely perceptible erythema, barely perceptible induration/papulation, and/or minimal lichenification; no oozing or crusting;

(c) Assigning a score of 2—mild—when the most applicable morphological description is:
Slight but definite erythema (pink), slight but definite induration/papulation, and/or slight but definite lichenification; no oozing or crusting;

(d) Assigning a score of 3—moderate—when the most applicable morphological description is:
Clearly perceptible erythema (dull red), clearly perceptible induration/papulation, and/or clearly perceptible lichenification; oozing and crusting may be present;

(e) Assigning a score of 4—severe—when the most applicable morphological description is:
Marked erythema (deep or bright red), marked induration/papulation, and/or marked lichenification; disease is widespread in extent; oozing or crusting may be present.

314. The method of any one of embodiments 312 to 313, wherein the baseline vIGA-AD score is 3 or 4.

315. The method of any one of embodiments 312 to 314, wherein a first injection of the anti-OX40L antibody or fragment thereof is administered on the same day as the baseline vIGA-AD score is determined.

316. The method of any one of embodiments 312 to 315, further comprising determining the baseline vIGA-AD score.

317. The method of any preceding embodiment, further comprising assessing the atopic dermatitis by determining a post-administration vIGA-AD score at least 7 days or at least 15 days after administering a first injection of the antibody or fragment thereof.

318. The method of any preceding embodiment wherein the post-administration vIGA-AD score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

319. The method of any preceding embodiment wherein the post-administration vIGA-AD score is determined at around 7 days, at around 15 days, around 29 days, around 57 days, around 85 days, around 113 days, around 169 days and/or around 253 days after administering a first injection of the antibody or fragment thereof.

320. The method of any preceding embodiment wherein the post-administration vIGA-AD score is determined at the end of the induction phase.

321. The method of any preceding embodiment wherein the post-administration vIGA-AD score is 0 or 1.

322. The method of any preceding embodiment wherein the post-administration vIGA-AD score is reduced at least 1 point, at least 2 points, at least 3 points or up to 4 points relative to the baseline vIGA-AD score.

323. The method of any preceding embodiment wherein the post-administration vIGA-AD score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline vIGA-AD score.

324. The method of any preceding embodiment wherein the post-administration vIGA-AD score is maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

325. The method of any preceding embodiment, further comprising assessing the atopic dermatitis by determining one or more further post-administration vIGA-AD score.

326. The method of any preceding embodiment wherein the one or more further post-administration vIGA-AD score is determined at least around 15 days, at least around 29 days, at least around 57 days, at least around 85 days, at least around 113 days, at least around 169 days and/or at least around 253 days after administering a first injection of the antibody or fragment thereof.

327. The method of any preceding embodiment wherein the one or more further post-administration vIGA-AD score is determined at around 29 days, around 57 days, around 85 days, around 113 days, around 169 days and/or around 253 days after administering a first injection of the antibody or fragment thereof.

328. The method of any preceding embodiment wherein the one or more further post-administration vIGA-AD score is determined at the end of the induction phase.

329. The method of any preceding embodiment wherein the one or more further post-administration vIGA-AD score is 0 or 1.

330. The method of any preceding embodiment wherein the one or more further post-administration vIGA-AD score is reduced at least 1 point, at least 2 points, at least 3 points or up to 4 points relative to the baseline vIGA-AD score.

331. The method of any preceding embodiment wherein determining the post-administration vIGA-AD score and/or the one or more further post-administration vIGA-AD score comprises describing the overall appearance of AD lesions at a given time point by:

(a) Assigning a score of 0—clear—when the most applicable morphological description is:
No inflammatory signs of atopic dermatitis (no erythema, no induration/papulation, no lichenification, no oozing/crusting); post-inflammatory hyperpigmentation and/or hypopigmentation may be present;

(b) Assigning a score of 1—almost clear—when the most applicable morphological description is:
Barely perceptible erythema, barely perceptible induration/papulation, and/or minimal lichenification; no oozing or crusting;

(c) Assigning a score of 2—mild—when the most applicable morphological description is:
Slight but definite erythema (pink), slight but definite induration/papulation, and/or slight but definite lichenification; no oozing or crusting;
(d) Assigning a score of 3—moderate—when the most applicable morphological description is:
Clearly perceptible erythema (dull red), clearly perceptible induration/papulation, and/or clearly perceptible lichenification; oozing and crusting may be present;
(e) Assigning a score of 4—severe—when the most applicable morphological description is:
Marked erythema (deep or bright red), marked induration/papulation, and/or marked lichenification; disease is widespread in extent; oozing or crusting may be present.

332. The method of any preceding embodiment wherein the post-administration vIGA-AD and/or further post-administration vIGA-AD is determined at least around 113 days after administering a first injection of the antibody or fragment thereof and wherein the post-administration vIGA-AD and/or further post-administration vIGA-AD is:
(a) A vIGA-AD score of 0 or 1, and/or
(b) reduced at least 2 points relative to the baseline vIGA-AD score.

333. The method of any preceding embodiment wherein the post-administration vIGA-AD and/or further post-administration vIGA-AD is determined at least around 169 days after administering a first injection of the antibody or fragment thereof and wherein the post-administration vIGA-AD and/or further post-administration vIGA-AD is:
(a) A vIGA-AD score of 0 or 1, and/or
(b) reduced at least 2 points relative to the baseline vIGA-AD score.

334. The method of any preceding embodiment wherein the post-administration vIGA-AD and/or further post-administration vIGA-AD is determined at least around 253 days after administering a first injection of the antibody or fragment thereof and wherein the post-administration vIGA-AD and/or further post-administration vIGA-AD is:
(a) A vIGA-AD score of 0 or 1, and/or
(b) reduced at least 2 points relative to the baseline vIGA-AD score.

335. The method of any preceding embodiment wherein the Atopic Dermatitis is treated as evidenced by a reduction in the vIGA-AD score by at least 2 points after the third injection as a treatment dose and wherein the reduction in vIGA-AD score is persistent for at least 2 months, at least 3 months, at least 4 months, at least 5 months or at least 6 months after administration of the last injection as a treatment dose.

336. The method of any preceding embodiment, wherein the atopic dermatitis has been assessed by determining a baseline NRS score.

337. The method of embodiment 336 wherein the determining a baseline NRS score comprises the subject providing a numerical rating of their worst itch in the past 24 hours on a scale of 0 to 10, wherein "0" is no itch and "10" is the worst imaginable itch.

338. The method of embodiment 337 wherein the determining a baseline NRS score comprises the patient providing a numerical rating of their worst itch in the past 24 hours according to embodiment 337 once per day for 7 days and taking the average numerical rating as the baseline NRS score.

339. The method of any one of embodiments 336 to 338, wherein the baseline NRS score is selected from the group consisting of at least 3, at least 4, at least 5, at least 6, at least 7, at least 8, 6 to 9, and 7 to 8.

340. The method of any one of embodiments 336 to 339, wherein a first injection of the anti-OX40L antibody or fragment thereof is administered on the same day as the baseline NRS score is determined.

341. The method of any one of embodiments 336 to 340, further comprising determining the baseline NRS score.

342. The method of any preceding embodiment, further comprising assessing the atopic dermatitis by determining a post-administration NRS (numerical rating scale) score after administering a first injection of the antibody or fragment thereof.

343. The method of any preceding embodiment wherein the post-administration NRS score is determined within 2 hours, within 6 hours, within 12 hours, within 24 hours, within 24 hours, or within 7 days of administering a first injection of the antibody or fragment thereof.

344. The method of any preceding embodiment wherein the post-administration NRS score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

345. The method of any preceding embodiment wherein the post-administration NRS score is determined at around 7 days, at around 15 days, around 29 days, around 57 days, around 85 days, around 113 days, around 169 days and/or around 253 days after administering a first injection of the antibody or fragment thereof.

346. The method of any preceding embodiment wherein the post-administration NRS score is determined at the end of the induction phase.

347. The method of any preceding embodiment wherein the post-administration NRS score is 0 to 7.

348. The method of any preceding embodiment wherein the post-administration NRS score is reduced at least 1 point, at least 2 points, at least 3 points, at least 4 points, at least 5 points, at least 6 points, at least 7 points, at least 8 points, at least 9 points or 10 points relative to the baseline NRS score.

349. The method of any preceding embodiment wherein the post-administration NRS score is reduced at least 2 points, at least 3 points or at least 4 points relative to the baseline NRS score.

350. The method of any preceding embodiment wherein the post-administration NRS score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline NRS score.

351. The method of any preceding embodiment wherein the post-administration NRS score is maintained, without additional administration of an anti-OX40L antibody, or antigen-binding fragment thereof, for:
(a) at least 2 months, at least 3 months, at least 4 months, at least 5 months or at least 6 months after administration of the last injection; or
(b) at least about 4, 8, 15, 22, 25, 29, 36, 43, 50, 57, 64, 71, 85, 113, 169 or 253 days.

352. The method of any preceding embodiment, further comprising assessing the atopic dermatitis by determining one or more further post-administration NRS score.

353. The method of any preceding embodiment wherein the one or more further post-administration NRS score is determined at least around 15 days, at least around 29 days, at least around 57 days, at least around 85 days, at least around 113 days, at least around 169 days and/or at least around 253 days after administering a first injection of the antibody or fragment thereof.

354. The method of any preceding embodiment wherein the one or more further post-administration NRS score is determined at around 29 days, around 57 days, around 85 days, around 113 days, around 169 days and/or around 253 days after administering a first injection of the antibody or fragment thereof.

355. The method of any preceding embodiment wherein the one or more further post-administration NRS score is determined at the end of the induction phase.

356. The method of any preceding embodiment wherein the one or more further post-administration NRS score is 0 to 7.

357. The method of any preceding embodiment wherein the one or more further post-administration NRS score is reduced at least 1 point, at least 2 points, at least 3 points, at least 4 points, at least 5 points, at least 6 points, at least 7 points, at least 8 points, at least 9 points or 10 points relative to the baseline NRS score.

358. The method of any preceding embodiment wherein the one or more further post-administration NRS score is:

(c) reduced at least 3 points relative to the baseline NRS score wherein the baseline NRS score is selected from the group consisting of at least 3, at least 4, at least 5, at least 6, at least 7, at least 8, 6 to 9, and 7 to 8; or (d) reduced at least 4 points relative to the baseline NRS score wherein the baseline NRS score is selected from the group consisting of at least 4, at least 5, at least 6, at least 7, at least 8, 6 to 9, and 7 to 8.

359. The method of any preceding embodiment wherein determining the post-administration NRS score and/or the one or more further post-administration NRS score comprises the subject providing a numerical rating of their worst itch in the past 24 hours on a scale of 0 to 10, wherein “0” is no itch and “10” is the worst imaginable itch.

360. The method of any preceding embodiment wherein the post-administration NRS and/or further post-administration NRS is determined at least around 113 days after administering a first injection of the antibody or fragment thereof and wherein the post-administration NRS and/or further post-administration NRS is:

(c) reduced at least 3 points relative to the baseline NRS score wherein the baseline NRS score is selected from the group consisting of at least 3, at least 4, at least 5, at least 6, at least 7, at least 8, 6 to 9, and 7 to 8; or (d) reduced at least 4 points relative to the baseline NRS score wherein the baseline NRS score is selected from the group consisting of at least 4, at least 5, at least 6, at least 7, at least 8, 6 to 9, and 7 to 8.

361. The method of any preceding embodiment wherein the post-administration NRS and/or further post-administration NRS is determined at least around 169 days after administering a first injection of the antibody or fragment thereof and wherein the post-administration NRS and/or further post-administration NRS is:

(c) reduced at least 3 points relative to the baseline NRS score wherein the baseline NRS score is selected from the group consisting of at least 3, at least 4, at least 5, at least 6, at least 7, at least 8, 6 to 9, and 7 to 8; or (d) reduced at least 4 points relative to the baseline NRS score wherein the baseline NRS score is selected from the group consisting of at least 4, at least 5, at least 6, at least 7, at least 8, 6 to 9, and 7 to 8.

362. The method of any preceding embodiment wherein the post-administration NRS and/or further post-administration NRS is determined at least around 253 days after administering a first injection of the antibody or fragment thereof and wherein the post-administration NRS and/or further post-administration NRS is:

(c) reduced at least 3 points relative to the baseline NRS score wherein the baseline NRS score is selected from the group consisting of at least 3, at least 4, at least 5, at least 6, at least 7, at least 8, 6 to 9, and 7 to 8; or (d) reduced at least 4 points relative to the baseline NRS score wherein the baseline NRS score is selected from the group consisting of at least 4, at least 5, at least 6, at least 7, at least 8, 6 to 9, and 7 to 8.

363. The method of any preceding embodiment wherein the Atopic Dermatitis is treated as evidenced by a reduction in the NRS score by at least 4 points after the third injection as a treatment dose.

364. The method of any preceding embodiment wherein the reduction in NRS score is persistent for at least 2 months, at least 3 months, at least 4 months, at least 5 months or at least 6 months after administration of the last injection as a treatment dose.

365. The method of any preceding embodiment, wherein the atopic dermatitis has been assessed by determining a baseline POEM (Patient-Orientated Eczema Measure) score.

366. The method of embodiment 365 wherein the determining a baseline POEM score comprises the subject providing a frequency rating for how often the following events have been caused by their eczema over the last week:

viii. Itchy skin,
ix. Disturbed sleep,.
x. Bleeding skin,
xi. Skin weeping or oozing clear fluid,
xii. Cracked skin,
xiii. Skin flaking off, and
xiv. Skin felt dry or rough.

367. The method of embodiment 366 wherein the frequency rating is selected from the group consisting of:

vi. “no days”,
vii. “1-2 days”,
viii. “3-4 days”,
ix. “5-6 days”, and
x. “every day”.

368. The method of embodiment 367 comprising assigning a frequency rating score to each frequency rating, wherein “every day” is assigned a score of 4, “5-6 days” is assigned a score of 3, “3-4 days” is assigned a score of 2, “1-2 days” is assigned a score of 1 and “no days” is assigned a score of 0, and adding together the frequency rating scores to calculate the POEM score.

369. The method of any one of embodiments 365 to 368, wherein a baseline POEM score of 0 to 2 indicates clear or almost clear eczema; a baseline POEM score of 3 to 7 indicates mild eczema; a baseline POEM score of 8 to 16 indicates moderate eczema; a baseline POEM score of 17 to 24 indicates severe eczema and a baseline POEM score of 25 to 28 indicates very severe eczema.

370. The method of any one of embodiments 365 to 369, wherein the baseline POEM score is selected from the group consisting of at least 8, at least 9, at least 10, at least 11, at least 12, at least 13, at least 14, at least 15, at least 16, at least 17, at least 18, at least 19, at least 20, at least 21, at least 22, at least 23, at least 24, 8 to 28, 8 to 24, 8 to 16, 17 to 24 and 25 to 28.

371. The method of any one of embodiments 365 to 370, wherein a first injection of the anti-OX40L antibody or fragment thereof is administered on the same day as the baseline POEM score is determined.

372. The method of any one of embodiments 365 to 371, further comprising determining the baseline POEM score.

373. The method of any preceding embodiment, further comprising assessing the atopic dermatitis by determining a post-administration POEM score at least 7 days or at least 15 days after administering a first injection of the antibody or fragment thereof.

374. The method of any preceding embodiment wherein the post-administration POEM score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

375. The method of any preceding embodiment wherein the post-administration POEM score is determined at around 7 days, at around 15 days, around 29 days, around 57 days, around 85 days, around 113 days, around 169 days and/or around 253 days after administering a first injection of the antibody or fragment thereof.

376. The method of any preceding embodiment wherein the post-administration POEM score is determined at the end of the induction phase.

377. The method of any preceding embodiment wherein the post-administration POEM score is selected from the group consisting of 0 to 2; 3 to 7; 8 to 16; 17 to 24 and 25 to 28.

378. The method of any preceding embodiment wherein the post-administration POEM score is reduced at least 2 points, at least 3 points, at least 3.4 points, at least 4 points, at least 5 points, at least 6 points, at least 7 points, at least 8 points, at least 9 points or 10 points relative to the baseline POEM score.

379. The method of any preceding embodiment wherein the post-administration POEM score is reduced at least 2 points or at least 3 points relative to the baseline POEM score.

380. The method of any preceding embodiment wherein the post-administration POEM score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline POEM score.

381. The method of any preceding embodiment wherein the post-administration POEM score is maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

382. The method of any preceding embodiment, further comprising assessing the atopic dermatitis by determining one or more further post-administration POEM score.

383. The method of any preceding embodiment wherein the one or more further post-administration POEM score is determined at least around 15 days, at least around 29 days, at least around 57 days, at least around 85 days, at least around 113 days, at least around 169 days and/or at least around 253 days after administering a first injection of the antibody or fragment thereof.

384. The method of any preceding embodiment wherein the one or more further post-administration POEM score is determined at around 29 days, around 57 days, around 85 days, around 113 days, around 169 days and/or around 253 days after administering a first injection of the antibody or fragment thereof.

385. The method of any preceding embodiment wherein the one or more further post-administration POEM score is determined at the end of the induction phase.

386. The method of any preceding embodiment wherein the one or more further post-administration POEM score is selected from the group consisting of 0 to 2; 3 to 7; 8 to 16; 17 to 24 and 25 to 28.

387. The method of any preceding embodiment wherein the one or more further post-administration POEM score is reduced at least 2 points, at least 3 points, at least 4 points, at least 5 points, at least 6 points, at least 7 points, at least 8 points, at least 9 points or 10 points relative to the baseline POEM score.

388. The method of any preceding embodiment wherein the one or more further post-administration POEM score is reduced at least 2 points or at least 3 points relative to the baseline POEM score.

389. The method of any preceding embodiment wherein determining the post-administration POEM score and/or the one or more further post-administration POEM score comprises the subject providing a frequency rating for how often the following events have been caused by their eczema over the last week:

viii. Itchy skin, ix. Disturbed sleep, x. Bleeding skin, xi. Skin weeping or oozing clear fluid, xii. Cracked skin, xiii. Skin flaking off, and xiv. Skin felt dry or rough.

390. The method of embodiment 389 wherein the frequency rating is selected from the group consisting of:

vi. "no days", vii. "1-2 days", viii. "3-4 days", ix. "5-6 days", and x. "every day".

391. The method of embodiment 390 comprising assigning a frequency rating score to each frequency rating, wherein "every day" is assigned a score of 4, "5-6 days" is assigned a score of 3, "3-4 days" is assigned a score of 2, "1-2 days" is assigned a score of 1 and "no days" is assigned a score of 0, and adding together the frequency rating scores to calculate the POEM score.

392. The method of any preceding embodiment wherein the post-administration POEM and/or further post-administration POEM is determined at least around 113 days after administering a first injection of the antibody or fragment thereof and wherein the post-administration POEM and/or further post-administration POEM is reduced at least 2 points or at least 3 points relative to the baseline POEM score.

393. The method of any preceding embodiment wherein the post-administration POEM and/or further post-administration POEM is determined at least around 169 days after administering a first injection of the antibody or fragment thereof and wherein the post-administration POEM and/or further post-administration POEM is reduced at least 2 points or at least 3 points relative to the baseline POEM score.

394. The method of any preceding embodiment wherein the post-administration POEM and/or further post-administration POEM is determined at least around 253 days after administering a first injection of the antibody or fragment thereof and wherein the post-administration POEM and/or further post-administration POEM is reduced at least 2 points or at least 3 points relative to the baseline POEM score.

395. The method of any preceding embodiment wherein the Atopic Dermatitis is treated as evidenced by a reduction in the POEM score by at least 2 points after the third injection as a treatment dose.

396. The method of any preceding embodiment wherein the reduction in POEM score is persistent for at least 2 months, at least 3 months, at least 4 months, at least 5 months or at least 6 months after administration of the last injection as a dose.

397. The method of any preceding embodiment, wherein the atopic dermatitis has been assessed by determining a baseline BSA (Body Surface Area) score.

398. The method of embodiment 397 wherein the determining a baseline BSA score comprises:

(a) Assigning a BSA value to each of the following body parts:
  (j) Entire left arm,
  (k) Entire right arm,
  (I) Entire head,
  (m) Entire chest,
  (n) Entire abdomen,
  (o) Entire back,
  (p) Entire left leg,
  (q) Entire right leg, and
  (r) Groin,
(b) Estimating the proportion of each body part affected by atopic dermatitis,
(c) Multiplying the proportion of each body part affected by dermatitis by the BSA value for the body part to provide an affected BSA value for each body part, and
(d) Adding together the affected BSA values for the body parts to provide a BSA score.

399. The method of any one of embodiments 397 to 398, wherein the baseline BSA score is at least 10%, at least 15, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

400. The method of any one of embodiments 397 to 399, wherein a first injection of the anti-OX40L antibody or fragment thereof is administered on the same day as the baseline BSA score is determined.

401. The method of any one of embodiments 397 to 400, further comprising determining the baseline BSA score.

402. The method of any preceding embodiment, further comprising assessing the atopic dermatitis by determining a post-administration BSA score at least 7 days or at least 15 days after administering a first injection of the antibody or fragment thereof.

403. The method of any preceding embodiment wherein the post-administration BSA score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

404. The method of any preceding embodiment wherein the post-administration BSA score is determined at around 7 days, at around 15 days, around 29 days, around 57 days, around 85 days, around 113 days, around 169 days and/or around 253 days after administering a first injection of the antibody or fragment thereof.

405. The method of any preceding embodiment wherein the post-administration BSA score is determined at the end of the induction phase.

406. The method of any preceding embodiment wherein the post-administration BSA score is selected from the group consisting of less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90% and less than 95%, 407. The method of any preceding embodiment wherein the post-administration BSA score is reduced at least 2 percentage points, at least 3 percentage points, at least 4 percentage points, at least 5 percentage points, at least 6 percentage points, at least 7 percentage points, at least 8 percentage points, at least 9 percentage points, 10 percentage points, at least 11 percentage points, at least 12 percentage points, at least 13 percentage points, at least 14 percentage points, at least 15 percentage points, at least 20 percentage points, at least 25 percentage points, at least 30 percentage points, at least 40 percentage points, at least 50 percentage points, at least 60 percentage points, at least 70 percentage points, at least 80 percentage points or at least 90 percentage points relative to the baseline BSA score.

408. The method of any preceding embodiment wherein the post-administration BSA score is reduced at least 5 percentage points relative to the baseline BSA score.

409. The method of any preceding embodiment wherein the post-administration BSA score is reduced at least 10 percentage points relative to the baseline BSA score, wherein the baseline BSA score is at least 10%, 410. The method of any preceding embodiment wherein the post-administration BSA score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline BSA score.

411. The method of any preceding embodiment wherein the post-administration BSA score is maintained, without additional administration of an anti-OX40L antibody, or antigen-binding fragment thereof, for:

(a) at least 2 months, at least 3 months, at least 4 months, at least 5 months or at least 6 months after administration of the last injection; or
(b) at least about 4, 8, 15, 22, 25, 29, 36, 43, 50, 57, 64, 71, 85, 113, 169 or 253 days.

412. The method of any preceding embodiment, further comprising assessing the atopic dermatitis by determining one or more further post-administration BSA score.

413. The method of any preceding embodiment wherein the one or more further post-administration BSA score is determined at least around 15 days, at least around 29 days, at least around 57 days, at least around 85 days, at least around 113 days, at least around 169 days and/or at least around 253 days after administering a first injection of the antibody or fragment thereof.

414. The method of any preceding embodiment wherein the one or more further post-administration BSA score is determined at around 29 days, around 57 days, around 85 days, around 113 days, around 169 days and/or around 253 days after administering a first injection of the antibody or fragment thereof.

415. The method of any preceding embodiment wherein the one or more further post-administration BSA score is determined at the end of the induction phase.

416. The method of any preceding embodiment wherein the one or more further post-administration BSA score is selected from the group consisting of less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90% and less than 95%.

417. The method of any preceding embodiment wherein the one or more further post-administration BSA score is reduced at least 2 percentage points, at least 3 percentage points, at least 4 percentage points, at least 5 percentage points, at least 6 percentage points, at least 7 percentage points, at least 8 percentage points, at least 9 percentage points, 10 percentage points, at least 11 percentage points, at least 12 percentage points, at least 13 percentage points, at least 14 percentage points, at least 15 percentage points, at least 20 percentage points, at least 25 percentage points, at least 30 percentage points, at least 40 percentage points, at least 50 percentage points, at least 60 percentage points, at least 70 percentage points, at least 80 percentage points or at least 90 percentage points relative to the baseline BSA score.

418. The method of any preceding embodiment wherein the one or more further post-administration BSA score is reduced at least 10 percentage points relative to the baseline BSA score.

419. The method of any preceding embodiment wherein determining the post-administration BSA score and/or the one or more further post-administration BSA score comprises:

(a) Assigning a BSA value to each of the following body parts:
  (j) Entire left arm,
  (k) Entire right arm,
  (l) Entire head,
  (m) Entire chest,
  (n) Entire abdomen,
  (o) Entire back,
  (p) Entire left leg,
  (q) Entire right leg, and
  (r) Groin,
(b) Estimating the proportion of each body part affected by atopic dermatitis,
(c) Multiplying the proportion of each body part affected by dermatitis by the BSA value for the body part to provide an affected BSA value for each body part, and
(d) Adding together the affected BSA values for the body parts to provide a BSA score.

420. The method of any preceding embodiment wherein the post-administration BSA and/or further post-administration BSA is determined at least around 113 days after administering a first injection of the antibody or fragment thereof and wherein the post-administration BSA and/or further post-administration BSA is reduced at least 10 percentage points relative to the baseline BSA score.

421. The method of any preceding embodiment wherein the post-administration BSA and/or further post-administration BSA is determined at least around 169 days after administering a first injection of the antibody or fragment thereof and wherein the post-administration BSA and/or further post-administration BSA is reduced at least 10 percentage points relative to the baseline BSA score.

422. The method of any preceding embodiment wherein the post-administration BSA and/or further post-administration BSA is determined at least around 253 days after administering a first injection of the antibody or fragment thereof and wherein the post-administration BSA and/or further post-administration BSA is reduced at least 10 percentage points relative to the baseline BSA score.

423. The method of any preceding embodiment wherein the Atopic Dermatitis is treated as evidenced by a reduction in the BSA score by at least 10 percentage points after the third injection as a treatment dose.

424. The method of any preceding embodiment wherein the reduction in BSA score is persistent for at least 2 months, at least 3 months, at least 4 months, at least 5 months or at least 6 months after administration of the last injection as a treatment dose.

425. The method of any preceding embodiment, wherein the atopic dermatitis has been assessed by determining a baseline SCORAD (SCORing Atopic Dermatitis) index.

426. The method of embodiment 425 wherein the determining a baseline SCORAD index comprises:

(a) Estimating the extent of the atopic dermatitis as a percentage of body area involvement to provide an extent score "A",
(b) Assessing the intensity of the following clinical signs to provide an intensity score "B":
  (i) erythema,
  (ii) edema/papulation,
  (iii) oozing/crust,
  (iv) excoriation,
  (v) lichenification, and
  (vi) dryness;
(c) Assessing the severity of the following symptoms to provide a severity score "C":
  (i) puritis, and
  (ii) sleep loss;
and
(d) Calculating the baseline SCORAD index using the extent score "A", the intensity score "B" and the severity score "C".

427. The method of embodiment 426 wherein determining the baseline SCORAD index comprises assigning to each clinical sign a sign intensity level selected from the group consisting of:

v. "absent"
vi. "mild"
vii. "moderate", and
viii. "severe".

428. The method of embodiment 427 comprising assigning a sign intensity score to each sign intensity level, wherein "severe" is assigned a score of 3, "moderate" is assigned a score of 2, "mild" is assigned a score of 1 and "absent" is assigned a score of 0, and adding together the sign intensity scores to calculate the intensity score "B".

429. The method of any one of embodiments 425 to 428 wherein determining the baseline SCORAD index comprises the subject or a caregiver providing a numerical rating of symptom severity for puritis and sleep loss in the past 3 days and/or nights on a scale of 0 to 10, wherein "0" is no symptom and "10" is the worst imaginable symptom.

430. The method of embodiment 429 comprising adding together the numerical ratings of symptom severity for puritis and sleep loss to calculate the severity score "C".

431. The method of any one of embodiments 425 to 430 wherein determining the baseline SCORAD index comprises calculating the baseline SCORAD index using the formula: SCORAD index=A/5+7B/2+C.

432. The method of embodiment 425 to 431, wherein a baseline SCORAD index of 0 to 24 indicates mild disease; a baseline SCORAD index of 25 to 50 indicates moderate disease; and a baseline SCORAD index of 51 to 103 indicates severe disease.

433. The method of any one of embodiments 425 to 432, wherein the baseline SCORAD index is at least 25, at least 30, at least 35, at least 40, at least 45, at least 50, at least 55, at least 60, at least 65, at least 70, at least 75, at least 80, at least 85, at least 90 or at least 95.

434. The method of any one of embodiments 425 to 433, wherein a first injection of the anti-OX40L antibody or fragment thereof is administered on the same day as the baseline SCORAD index is determined.

435. The method of any one of embodiments 425 to 434, further comprising determining the baseline SCORAD index.

436. The method of any preceding embodiment, further comprising assessing the atopic dermatitis by determining a post-administration SCORAD index at least 7 days or at least 15 days after administering a first injection of the antibody or fragment thereof.

437. The method of any preceding embodiment wherein the post-administration SCORAD index is determined at least around 7 days, at least around 15 days, at least around 29 days, at least around 57 days, at least around 85 days, at least around 113 days, at least around 169 days and/or at least around 253 days after administering a first injection of the antibody or fragment thereof.

438. The method of any preceding embodiment wherein the post-administration SCORAD index is determined at least around 7 days, at around 15 days, around 29 days, around 57 days, around 85 days, around 113 days, around 169 days and/or around 253 days after administering a first injection of the antibody or fragment thereof.

439. The method of any preceding embodiment wherein the post-administration SCORAD index is determined at the end of the induction phase.

440. The method of any preceding embodiment wherein the post-administration SCORAD index is selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95.

441. The method of any preceding embodiment wherein the post-administration SCORAD index is reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline SCORAD index.

442. The method of any preceding embodiment wherein the post-administration SCORAD index is reduced at least 20 points relative to the baseline SCORAD index.

443. The method of any preceding embodiment wherein the post-administration SCORAD index is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline SCORAD index.

444. The method of any preceding embodiment wherein the post-administration SCORAD index is maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

445. The method of any preceding embodiment, further comprising assessing the atopic dermatitis by determining one or more further post-administration SCORAD index.

446. The method of any preceding embodiment wherein the one or more further post-administration SCORAD index is determined at least around 15 days, at least around 29 days, at least around 57 days, at least around 85 days, at least around 113 days, at least around 169 days and/or at least around 253 days after administering a first injection of the antibody or fragment thereof.

447. The method of any preceding embodiment wherein the one or more further post-administration SCORAD index is determined at around 29 days, around 57 days, around 85 days, around 113 days, around 169 days and/or around 253 days after administering a first injection of the antibody or fragment thereof.

448. The method of any preceding embodiment wherein the one or more further post-administration SCORAD index is determined at the end of the induction phase.

449. The method of any preceding embodiment wherein the one or more further post-administration SCORAD index is selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95.

450. The method of any preceding embodiment wherein the one or more further post-administration SCORAD index is reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline SCORAD index.

451. The method of any preceding embodiment wherein the one or more further post-administration SCORAD index is reduced at least 20 points relative to the baseline SCORAD index.

452. The method of any preceding embodiment wherein determining the post-administration SCORAD index and/or the one or more further post-administration SCORAD index comprises:

(a) Estimating the extent of the atopic dermatitis as a percentage of body area involvement to provide an extent score "A", (b) Assessing the intensity of the following clinical signs to provide an intensity score "B":

(i) erythema, (ii) edema/papulation, (iii) oozing/crust, (iv) excoriation, (v) lichenification, and (vi) dryness;

(c) Assessing the severity of the following symptoms to provide a severity score "C":

(i) puritis, and (ii) sleep loss;

and (d) Calculating the SCORAD index using the extent score "A", the intensity score "B" and the severity score "C".

453. The method of any preceding embodiment wherein determining the post-administration SCORAD index and/or the one or more further post-administration SCORAD index comprises assigning to each clinical sign a sign intensity level selected from the group consisting of:

v. "absent"

vi. "mild"

vii. "moderate", and viii. "severe".

454. The method of embodiment 453 comprising assigning a sign intensity score to each sign intensity level, wherein "severe" is assigned a score of 3, "moderate" is assigned a score of 2, "mild" is assigned a score of 1 and "absent" is assigned a score of 0, and adding together the sign intensity scores to calculate the intensity score "B".

455. The method of any preceding embodiment wherein determining the post-administration SCORAD index and/or the one or more further post-administration SCORAD index comprises the subject or a caregiver providing a numerical rating of symptom severity for puritis and sleep loss in the past 3 days and/or nights on a scale of 0 to 10, wherein "0" is no symptom and "10" is the worst imaginable symptom.

456. The method of embodiment 455 comprising adding together the numerical ratings of symptom severity for puritis and sleep loss to calculate the severity score "C".

457. The method of any preceding embodiment wherein determining the post-administration SCORAD index and/or the one or more further post-administration SCORAD index comprises calculating the SCORAD index using the formula: SCORAD index=A/5+7B/2+C.

458. The method of any preceding embodiment wherein the post-administration SCORAD and/or further post-administration SCORAD is determined at least around 113 days after administering a first injection of the antibody or fragment thereof and wherein the post-administration SCORAD and/or further post-administration SCORAD is reduced at least 20 points relative to the baseline SCORAD index.

459. The method of any preceding embodiment wherein the post-administration SCORAD and/or further post-administration SCORAD is determined at least around 169 days after administering a first injection of the antibody or fragment thereof and wherein the post-administration SCORAD and/or further post-administration SCORAD is reduced at least 20 points relative to the baseline SCORAD index.

460. The method of any preceding embodiment wherein the post-administration SCORAD and/or further post-administration SCORAD is determined at least around 253 days after administering a first injection of the antibody or fragment thereof and wherein the post-administration SCORAD and/or further post-administration SCORAD is reduced at least 20 points relative to the baseline SCORAD index.

461. The method of any preceding embodiment wherein the Atopic Dermatitis is treated as evidenced by a reduction in the SCORAD index by at least 20 points after the third injection as a treatment dose.

462. The method of any preceding embodiment wherein the reduction in SCORAD index is persistent for at least 2 months, at least 3 months, at least 4 months, at least 5 months or at least 6 months after administration of the last injection as a treatment dose.

463. The method of any preceding embodiment, wherein the atopic dermatitis has been assessed by determining a baseline PO-SCORAD (Patient-Oriented SCORing Atopic Dermatitis) index.

464. The method of embodiment 463 wherein the determining a baseline PO-SCORAD index comprises:

(a) Estimating the extent of the atopic dermatitis as a percentage of body area involvement to provide an extent score "A", (b) Assessing the intensity of the following clinical signs to provide an intensity score "B":

(i) redness, (ii) swelling, (iii) oozing/scabs, (iv) scratch marks, (v) thickening of skin, and (vi) dryness;

(c) Assessing the severity of the following symptoms to provide a severity score "C":

(i) itching, and (ii) trouble sleeping and (d) Calculating the baseline PO-SCORAD index using the extent score "A", the intensity score "B" and the severity score "C".

465. The method of embodiment 464 wherein inputs for steps (a), (b) and (c) are provided by the subject or a caregiver.

466. The method of embodiment 465 wherein inputs for steps (a), (b) and (c) are inputted into a computer program via a graphical user interface by the subject or a caregiver.

467. The method of embodiment 466 wherein the estimating the extent of the atopic dermatitis as a percentage of body area involvement to provide an extent score "A" is performed by a computer program.

468. The method of any one of embodiments 464 to 467 wherein determining the baseline PO-SCORAD index comprises the subject or a caregiver providing a sign intensity score for each clinical sign selected from the group consisting of:

i. "0"

ii. "1"

iii. "2", and iv. "3";

wherein "0" is the lowest intensity and "3" is the highest intensity;

and wherein the sign intensity scores are added together to calculate the intensity score "B".

469. The method of embodiment 468 wherein the adding together of the sign intensity scores to calculate the intensity score "B" is performed by a computer program.

470. The method of any one of embodiments 463 to 469 wherein determining the baseline PO-SCORAD index comprises the subject or a caregiver providing a numerical rating of symptom severity for itching and trouble sleeping in the past 2 days and/or nights on a scale of 0 to 10, wherein "0" is no symptom and "10" is the worst imaginable symptom.

471. The method of embodiment 470 comprising adding together the numerical ratings of symptom severity for itching and trouble sleeping to calculate the severity score "C".

472. The method of embodiment 471 wherein the adding together the numerical ratings of symptom severity for itching and trouble sleeping to calculate the severity score "C" is performed by a computer program.

473. The method of any one of embodiments 463 to 472 wherein determining the baseline PO-SCORAD index comprises calculating the baseline PO-SCORAD index using the the formula: PO-SCORAD index=A/5+7B/2+C.

474. The method of any one of embodiments 463 to 473, wherein the baseline PO-SCORAD index is at least 25, at least 30, at least 35, at least 40, at least 45, at least 50, at least 55, at least 60, at least 65, at least 70, at least 75, at least 80, at least 85, at least 90 or at least 95.

475. The method of any one of embodiments 463 to 474, wherein a first injection of the anti-OX40L antibody or fragment thereof is administered on the same day as the baseline PO-SCORAD index is determined.

476. The method of any one of embodiments 463 to 475, further comprising determining the baseline PO-SCORAD index.

477. The method of any preceding embodiment, further comprising assessing the atopic dermatitis by determining a post-administration PO-SCORAD index at least 7 days or at least 15 days after administering a first injection of the antibody or fragment thereof.

478. The method of any preceding embodiment wherein the post-administration PO-SCORAD index is determined at least around 7 days, at least around 15 days, at least around 29 days, at least around 57 days, at least around 85 days, at least around 113 days, at least around 169 days and/or at least around 253 days after administering a first injection of the antibody or fragment thereof.

479. The method of any preceding embodiment wherein the post-administration PO-SCORAD index is determined at around 7 days, at around 15 days, around 29 days, around 57 days, around 85 days, around 113 days, around 169 days and/or around 253 days after administering a first injection of the antibody or fragment thereof.

480. The method of any preceding embodiment wherein the post-administration PO-SCORAD index is determined at the end of the induction phase.

481. The method of any preceding embodiment wherein the post-administration PO-SCORAD index is selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95.

482. The method of any preceding embodiment wherein the post-administration PO-SCORAD index is reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline PO-SCORAD index.

483. The method of any preceding embodiment wherein the post-administration PO-SCORAD index is reduced at least 20 points relative to the baseline PO-SCORAD index.

484. The method of any preceding embodiment wherein the post-administration PO-SCORAD index is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline PO-SCORAD index.

485. The method of any preceding embodiment wherein the post-administration PO-SCORAD index is maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

486. The method of any preceding embodiment, further comprising assessing the atopic dermatitis by determining one or more further post-administration PO-SCORAD index.

487. The method of any preceding embodiment wherein the one or more further post-administration PO-SCORAD index is determined at least around 15 days, at least around 29 days, at least around 57 days, at least around 85 days, at least around 113 days, at least around 169 days and/or at least around 253 days after administering a first injection of the antibody or fragment thereof.

488. The method of any preceding embodiment wherein the one or more further post-administration PO-SCORAD index is determined at around 29 days, around 57 days, around 85 days, around 113 days, around 169 days and/or around 253 days after administering a first injection of the antibody or fragment thereof.

489. The method of any preceding embodiment wherein the one or more further post-administration PO-SCORAD index is determined at the end of the induction phase.

490. The method of any preceding embodiment wherein the one or more further post-administration PO-SCORAD index is selected from the group consisting of less than 10, less than 15, less than 20, less than 25, less than 30, less than 35, less than 40, less than 45, less than 50, less than 55, less than 60, less than 65, less than 70, less than 75, less than 80, less than 85, less than 90 and less than 95.

491. The method of any preceding embodiment wherein the one or more further post-administration PO-SCORAD index is reduced at least 8 points, at least 8.7 points, at least 9 points, 10 points, at least 11 points, at least 12 points, at least 13 points, at least 14 points, at least 15 points, at least 20 points, at least 25 points, at least 30 points, at least 40 points, at least 50 points, at least 55 points, at least 60 points, at least 65 points, at least 70 points, at least 80 points or at least 90 points relative to the baseline PO-SCORAD index.

492. The method of any preceding embodiment wherein the one or more further post-administration PO-SCORAD index is reduced at least 20 points relative to the baseline PO-SCORAD index.

493. The method of any preceding embodiment wherein determining the post-administration PO-SCORAD index and/or the one or more further post-administration PO-SCORAD index comprises:

(a) Estimating the extent of the atopic dermatitis as a percentage of body area involvement to provide an extent score "A", (b) Assessing the intensity of the following clinical signs to provide an intensity score "B":

(i) redness, (ii) swelling, (iii) oozing/scabs, (iv) scratch marks, (v) thickening of skin, and (vi) dryness;

(c) Assessing the severity of the following symptoms to provide a severity score (i) itching, and (ii) trouble sleeping;

and (d) Calculating the PO-SCORAD index using the extent score "A", the intensity score "B" and the severity score "C".

494. The method of embodiment 493 wherein inputs for steps (a), (b) and (c) are provided by the subject or a caregiver.

495. The method of embodiment 494 wherein inputs for steps (a), (b) and (c) are inputted into a computer program via a graphical user interface by the subject or a caregiver.

496. The method of embodiment 495 wherein the estimating the extent of the atopic dermatitis as a percentage of body area involvement to provide an extent score "A" is performed by a computer program.

497. The method of any one of embodiments 493 to 496 wherein determining the post-administration PO-SCORAD index comprises the subject or a caregiver providing a sign intensity score for each clinical sign selected from the group consisting of:

v. "0"

vi. "1"

vii. "2", and viii. "3";

wherein "0" is the lowest intensity and "3" is the highest intensity;

and wherein the sign intensity scores are added together to calculate the intensity score "B".

498. The method of embodiment 497 wherein the adding together of the sign intensity scores to calculate the intensity score "B" is performed by a computer program.

499. The method of any preceding embodiment wherein determining the post-administration PO-SCORAD index comprises the subject or a caregiver providing a numerical rating of symptom severity for itching and trouble sleeping in the past 2 days and/or nights on a scale of 0 to 10, wherein "0" is no symptom and "10" is the worst imaginable symptom.

500. The method of embodiment 499 comprising adding together the numerical ratings of symptom severity for itching and trouble sleeping to calculate the severity score "C".

501. The method of embodiment 500 wherein the adding together the numerical ratings of symptom severity for itching and trouble sleeping to calculate the severity score "C" is performed by a computer program.

502. The method of any preceding embodiment wherein determining the post-administration PO-SCORAD index and/or the one or more further post-administration PO-SCORAD index comprises calculating the PO-SCORAD index using the formula: PO-SCORAD index=A/5+7B/2+C.

503. The method of any preceding embodiment wherein the post-administration PO-SCORAD and/or further post-administration PO-SCORAD is determined at least around 113 days after administering a first injection of the antibody or fragment thereof and wherein the post-administration PO-SCORAD and/or further post-administration PO-SCORAD is reduced at least 20 points relative to the baseline PO-SCORAD index.

504. The method of any preceding embodiment wherein the post-administration PO-SCORAD and/or further post-administration PO-SCORAD is determined at least around 169 days after administering a first injection of the antibody or fragment thereof and wherein the post-administration PO-SCORAD and/or further post-administration PO-SCORAD is reduced at least 20 points relative to the baseline PO-SCORAD index.

505. The method of any preceding embodiment wherein the post-administration PO-SCORAD and/or further post-administration PO-SCORAD is determined at least around 253 days after administering a first injection of the antibody or fragment thereof and wherein the post-administration PO-SCORAD and/or further post-administration PO-SCORAD is reduced at least 20 points relative to the baseline PO-SCORAD index.

506. The method of any preceding embodiment wherein the Atopic Dermatitis is treated as evidenced by a reduction in the PO-SCORAD index by at least 20 points after the third injection as a treatment dose.

507. The method of any preceding embodiment wherein the reduction in PO-SCORAD index is persistent for at least 2 months, at least 3 months, at least 4 months, at least 5 months or at least 6 months after administration of the last injection as a treatment dose.

508. The method of any preceding embodiment, wherein the atopic dermatitis has been assessed by determining a baseline DQLI (Dermatology Quality of Life Index) score.

509. The method of embodiment 508 wherein the determining a baseline DQLI score comprises the subject providing an answer for how much their skin problem has affected their life over the past week in the following areas:

xi. how itchy, sore, painful or stinging their skin has been, xii. how embarrassed or self conscious they have been because of their skin, xiii. how much their skin has interfered with them going shopping or looking after their home or garden, xiv. how much their skin has influenced the clothes they wear, xv. how much their skin has affected any social or leisure activities, xvi. how much their skin has made it difficult to do any sport xvii. whether their skin has prevented them from working or studying or if not how much their skin has been a problem at work or studying, xviii. how much their skin has created problems with their partner of any of their close friends or relatives, xix. how much their skin has caused any sexual difficulties xx. how much of a problem has the treatment for their skin been.

510. The method of embodiment 509 wherein each answer is selected from the group consisting of:

vi. "Very much"

vii. "A lot"

viii. "A little"

ix. "Not at all"

x. "Not relevant"

511. The method of embodiment 510 comprising assigning an answer score to each answer, wherein "very much" is assigned a score of 3, "a lot" is assigned a score of 2, "a little" is assigned a score of 1 and "not at all", "not relevant" or question unanswered are assigned a score of 0, and adding together the answer scores to calculate a DQLI score.

512. The method of any one of embodiments 509 to 511, wherein the baseline DQLI score is selected from the group consisting of at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, 6 to 30, 6 to 10, 11 to 20, and 21 to 30.

513. The method of any one of embodiments 508 to 512, wherein a first injection of the anti-OX40L antibody or fragment thereof is administered on the same day as the baseline DQLI score is determined.

514. The method of any one of embodiments 508 to 513, further comprising determining the baseline DQLI score.

515. The method of any preceding embodiment, further comprising assessing the atopic dermatitis by determining a post-administration DQLI score at least 7 days or at least 15 days after administering a first injection of the antibody or fragment thereof.

516. The method of any preceding embodiment wherein the post-administration DQLI score is determined at least around 7 days, at least around 15 days, at least around 29 days, at least around 57 days, at least around 85 days, at least around 113 days, at least around 169 days and/or at least around 253 days after administering a first injection of the antibody or fragment thereof.

517. The method of any preceding embodiment wherein the post-administration DQLI score is determined at around 7 days, at around 15 days, around 29 days, around 57 days, around 85 days, around 113 days, around 169 days and/or around 253 days after administering a first injection of the antibody or fragment thereof.

518. The method of any preceding embodiment wherein the post-administration DQLI score is determined at the end of the induction phase.

519. The method of any preceding embodiment wherein the post-administration DQLI score is selected from the group consisting of 0 to 1; 2 to 5; 6 to 10; 11 to 20; and 21 to 30.

520. The method of any preceding embodiment wherein the post-administration DQLI score is reduced at least 4 points, at least 5 points, at least 6 points, at least 7 points, at least 8 points, at least 9 points, at least 10 points, at least 15 points or at least 20 points relative to the baseline DQLI score.

521. The method of any preceding embodiment wherein the post-administration DQLI score is reduced at least 2.2 points or at least 6.9 points relative to the baseline DQLI score.

522. The method of any preceding embodiment wherein the post-administration DQLI score is reduced at least 4 points relative to the baseline DQLI score.

523. The method of any preceding embodiment wherein the post-administration DQLI score is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or at least 90% relative to the baseline DQLI score.

524. The method of any preceding embodiment wherein the post-administration DQLI score is maintained, without additional administration of an anti-OX40L antibody, or antigen-binding fragment thereof, for:

(a) at least 2 months, at least 3 months, at least 4 months, at least 5 months or at least 6 months after administration of the last injection; or (b) at least about 4, 8, 15, 22, 25, 29, 36, 43, 50, 57, 64, 71, 85, 113, 169 or 253 days.

525. The method of any preceding embodiment, further comprising assessing the atopic dermatitis by determining one or more further post-administration DQLI score.

526. The method of any preceding embodiment wherein the one or more further post-administration DQLI score is determined at least around 15 days, at least around 29 days, at least around 57 days, at least around 85 days, at least around 113 days, at least around 169 days and/or at least around 253 days after administering a first injection of the antibody or fragment thereof.

527. The method of any preceding embodiment wherein the one or more further post-administration DQLI score is determined at around 29 days, around 57 days, around 85 days, around 113 days, around 169 days and/or around 253 days after administering a first injection of the antibody or fragment thereof.

528. The method of any preceding embodiment wherein the one or more further post-administration DQLI score is determined at the end of the induction phase.

529. The method of any preceding embodiment wherein the one or more further post-administration DQLI score is selected from the group consisting of 0 to 1; 2 to 5; 6 to 10; 11 to 20; and 21 to 30.

530. The method of any preceding embodiment wherein the one or more further post-administration DQLI score is reduced at least 4 points, at least 5 points, at least 6 points, at least 7 points, at least 8 points, at least 9 points, at least 10 points, at least 15 points or at least 20 points relative to the baseline DQLI score.

531. The method of any preceding embodiment wherein the one or more further post-administration DQLI score is reduced at least 2.2 points or at least 6.9 points relative to the baseline DQLI score.

532. The method of any preceding embodiment wherein the one or more further post-administration DQLI score is reduced at least 4 points relative to the baseline DQLI score.

533. The method of any preceding embodiment wherein determining the post-administration DQLI score and/or the one or more further post-administration DQLI score comprises the subject providing an answer for how much their skin problem has affected their life over the past week in the following areas:

xi. how itchy, sore, painful or stinging their skin has been, xii. how embarrassed or self conscious they have been because of their skin, xiii. how much their skin has interfered with them going shopping or looking after their home or garden, xiv. how much their skin has influenced the clothes they wear, xv. how much their skin has affected any social or leisure activities, xvi. how much their skin has made it difficult to do any sport xvii. whether their skin has prevented them from working or studying or if not how much their skin has been a problem at work or studying, xviii. how much their skin has created problems with their partner of any of their close friends or relatives, xix. how much their skin has caused any sexual difficulties xx. how much of a problem has the treatment for their skin been.

534. The method of embodiment 533 wherein each answer is selected from the group consisting of:

vi. “Very much”

vii. “A lot”

viii. “A little”

ix. “Not at all”

x. “Not relevant”

535. The method of embodiment 534 comprising assigning an answer score to each answer, wherein “very much” is assigned a score of 3, “a lot” is assigned a score of 2, “a little” is assigned a score of 1 and “not at all”, “not relevant”

or question unanswered are assigned a score of 0, and adding together the answer scores to calculate a DQLI score.

536. The method of any preceding embodiment wherein the post-administration DQLI score and/or further post-administration DQLI score is determined at least around 113 days after administering a first injection of the antibody or fragment thereof and wherein the post-administration DQLI score and/or further post-administration DQLI score is reduced at least 4 points relative to the baseline DQLI score.

537. The method of any preceding embodiment wherein the post-administration DQLI score and/or further post-administration DQLI score is determined at least around 169 days after administering a first injection of the antibody or fragment thereof and wherein the post-administration DQLI score and/or further post-administration DQLI score is reduced at least 4 points relative to the baseline DQLI score.

538. The method of any preceding embodiment wherein the post-administration DQLI score and/or further post-administration DQLI score is determined at least around 253 days after administering a first injection of the antibody or fragment thereof and wherein the post-administration DQLI score and/or further post-administration DQLI score is reduced at least 4 points relative to the baseline DQLI score.

539. The method of any preceding embodiment wherein the Atopic Dermatitis is treated as evidenced by a reduction in the DQLI score by at least 4 points after the third injection as a treatment dose.

540. The method of any preceding embodiment wherein the reduction in DQLI score is persistent for at least 2 months, at least 3 months, at least 4 months, at least 5 months or at least 6 months after administration of the last injection as a treatment dose.

541. A glass vial containing a liquid formulation comprising an anti-OX40L antibody, or antigen-binding fragment thereof.

542. A drug delivery device containing a liquid formulation comprising an anti-OX40L antibody, or antigen-binding fragment thereof.

543. A prefilled syringe containing a liquid formulation comprising an anti-OX40L antibody, or antigen-binding fragment.

544. A microinfusor containing a liquid formulation comprising an anti-OX40L antibody, or antigen-binding fragment thereof.

545. A pen delivery device containing a liquid formulation comprising an anti-OX40L antibody, or antigen-binding fragment thereof.

546. The pen delivery device of embodiment 545 wherein the pen delivery device is a reusable pen delivery device.

547. The pen delivery device of embodiment 545 wherein the pen delivery device is a disposable pen delivery device.

548. An autoinjector delivery device containing a liquid formulation comprising an anti-OX40L antibody, or antigen-binding fragment thereof.

549. The glass vial, drug delivery device, prefilled syringe, microinfusor, pen delivery device or autoinjector according to any one of embodiments 541 to 548 wherein the volume of the liquid formulation is up to 1 mL, up to 2 mL or up to 2.25 mL.

550. A kit comprising a glass vial, drug delivery device, prefilled syringe, microinfusor, pen delivery device or autoinjector according to any one of embodiments 541 to 548; and a label and/or instructions specifying administration in accordance with any one of embodiments 1 to 540.

551. A method according to any one of embodiments 1 to 540, wherein the antibody or fragment thereof is administered from a drug delivery device according to embodiment 542 or embodiment 549, a prefilled syringe according to embodiments 543 or embodiment 549, a microinfusor according to embodiment 544 or embodiment 549, a pen delivery device according to embodiment 546, embodiment 547 or embodiment 549 or an autoinjector delivery device according to embodiment 548 or embodiment 549.

552. A method according to any one of embodiments 1 to 540, wherein the antibody or fragment thereof is administered from a prefilled syringe according to embodiments 543 or embodiment 549.

553. An anti-OX40L antibody, or antigen-binding fragment thereof, for use in a method of treating Atopic Dermatitis in accordance with any one of embodiments 1 to 540.

554. A glass vial, drug delivery device, prefilled syringe, microinfusor, pen delivery device, autoinjector or kit according to any one of embodiments 541 to 550, for use in a method of treating Atopic Dermatitis in accordance with any one of embodiments 1 to 540.

555. An anti-OX40L antibody, or antigen-binding fragment thereof, glass vial, drug delivery device, prefilled syringe, microinfusor, pen delivery device, autoinjector or kit for use according to any one of embodiments 551 to 554 wherein the Atopic Dermatitis is Chronic Atopic Dermatitis.

556. The use of an anti-OX40L antibody, or antigen-binding fragment thereof, for the manufacture of a medicament for the treatment of Atopic Dermatitis in accordance with any one of embodiments 1 to 540.

557. The use of a glass vial, drug delivery device, prefilled syringe, microinfusor, pen delivery device, autoinjector or kit according to any one of embodiments 541 to 550, for the manufacture of a medicament for the treatment of Atopic Dermatitis in accordance with any one of embodiments 1 to 540.

558. The use of an anti-OX40L antibody, or antigen-binding fragment thereof, glass vial, drug delivery device, prefilled syringe, microinfusor, pen delivery device, autoinjector or kit according to any one of embodiments 556 to 557 wherein the Atopic Dermatitis is Chronic Atopic Dermatitis.

559. A method, glass vial, drug delivery device, prefilled syringe, microinfusor, pen delivery device, autoinjector, kit, or use according to any preceding embodiment, wherein the antibody or fragment thereof specifically binds to human OX40L (hOX40L), optionally wherein the antibody blocks or neutralises the interaction between hOX40L and hOX40 receptor.

560. A method, glass vial, drug delivery device, prefilled syringe, microinfusor, pen delivery device, autoinjector, kit, or use according to any preceding embodiment, wherein the antibody or fragment thereof specifically binds to hOX40L with a $K_D$ of from 1 nM to 0.01 nM, optionally wherein the specific binding is measured by surface plasmon resonance (SPR).

561. A method, glass vial, drug delivery device, prefilled syringe, microinfusor, pen delivery device, autoinjector, kit, or use according to any preceding embodiment, wherein the antibody or fragment thereof competes for binding to hOX40L with 02D10.

562. A method, glass vial, prefilled syringe, microinfusor, pen delivery device, autoinjector, kit, or use according to any preceding embodiment, wherein the antibody or fragment thereof antagonises specific binding of hOX40L to OX40, optionally as determined using SPR or ELISA.

563. A method, glass vial, drug delivery device, prefilled syringe, microinfusor, pen delivery device, autoinjector, kit, or use according to any preceding embodiment, wherein the antibody or fragment thereof decreases IL-2 secretion by at least 50% (e.g., 55%, 60%, 65% or 70%) as compared to IL-2 secretion in the absence of the anti-OX40L antibody or fragment, optionally wherein IL-2 secretion is measured in an allogenic mixed lymphocyte reaction (MLR) assay.

564. A method, glass vial, drug delivery device, prefilled syringe, microinfusor, pen delivery device, autoinjector, kit, or use according to any preceding embodiment, wherein the antibody or fragment thereof decreases IL-13 secretion by at least 50% (e.g., 55%, 60%, 65% or 70%) as compared to IL-2 secretion in the absence of the anti-OX40L antibody or fragment, optionally wherein IL-13 secretion is measured in an allogenic mixed lymphocyte reaction (MLR) assay.

565. A method, glass vial, drug delivery device, prefilled syringe, microinfusor, pen delivery device, autoinjector, kit, or use according to any preceding embodiment, wherein the antibody is a humanized, human or fully human antibody.

566. A method, glass vial, drug delivery device, prefilled syringe, microinfusor, pen delivery device, autoinjector, kit, or use according to any preceding embodiment, wherein the fragment is selected from the group consisting of multispecific antibodies (eg., bi-specific antibodies), intrabodies, single-chain Fv antibodies (scFv), camelized antibodies, Fab fragments, F(ab') fragments, disulfide-linked Fvs (sdFv), anti-idiotypic (anti-Id) antibodies single-chain antibodies, single domain antibodies, domain antibodies, Fv fragments, F(ab')2 fragments, dimeric variable regions (diabodies), linear antibodies, and epitope-binding fragments thereof.

567. A method, glass vial, drug delivery device, prefilled syringe, microinfusor, pen delivery device, autoinjector, kit, or use according to any preceding embodiment, wherein the antibody or fragment thereof comprises a HCDR3 of from 16 to 27 amino acids and derived from the recombination of a human VH gene segment, a human D gene segment and a human JH gene segment, wherein the human JH gene segment is IGHJ6 (e.g., IGHJ6*02).

568. A method, glass vial, drug delivery device, prefilled syringe, microinfusor, pen delivery device, autoinjector, kit, or use according to any preceding embodiment, wherein the antibody or fragment thereof comprises the HCDR3 of antibody 2D10 (SEQ ID No:40 or SEQ ID No:46).

569. A method, glass vial, drug delivery device, prefilled syringe, microinfusor, pen delivery device, autoinjector, kit, or use according to any preceding embodiment, wherein the antibody or fragment thereof comprises the HCDR2 of antibody 2D10 (SEQ ID No:38 or SEQ ID No:44).

570. A method, glass vial, drug delivery device, prefilled syringe, microinfusor, pen delivery device, autoinjector, kit, or use according to any preceding embodiment, wherein the antibody or fragment thereof comprises the HCDR1 of antibody 2D10 (SEQ ID No:36 or SEQ ID No:42).

571. A method, glass vial, drug delivery device, prefilled syringe, microinfusor, pen delivery device, autoinjector, kit, or use according to any preceding embodiment, wherein the antibody or fragment thereof comprises the LCDR3 of antibody 2D10 (SEQ ID No:54 or SEQ ID No:60).

572. A method, glass vial, drug delivery device, prefilled syringe, microinfusor, pen delivery device, autoinjector, kit, or use according to any preceding embodiment, wherein the antibody or fragment thereof comprises the LCDR2 of antibody 2D10 (SEQ ID No:52 or SEQ ID No:58).

573. A method, glass vial, drug delivery device, prefilled syringe, microinfusor, pen delivery device, autoinjector, kit, or use according to any preceding embodiment, wherein the antibody or fragment thereof comprises the LCDR1 of antibody 2D10 (SEQ ID No:50 or SEQ ID No:56).

574. A method, glass vial, drug delivery device, prefilled syringe, microinfusor, pen delivery device, autoinjector, kit, or use according to any preceding embodiment, wherein the antibody or fragment thereof comprises:

the CDRs of antibody 2D10 (SEQ ID No:40 or SEQ ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2 and SEQ ID No:54 or SEQ ID No:60 for CDRL3).

575. A method, glass vial, drug delivery device, prefilled syringe, microinfusor, pen delivery device, autoinjector, kit, or use according to any preceding embodiment, wherein the antibody or fragment thereof comprises the CDRH1 sequence of the VH region of 2D10 as in SEQ ID No: 34.

576. A method, glass vial, drug delivery device, prefilled syringe, microinfusor, pen delivery device, autoinjector, kit, or use according to any preceding embodiment, wherein the antibody or fragment thereof comprises the CDRH2 sequence of the VH region of 2D10 as in SEQ ID No: 34.

577. A method, glass vial, drug delivery device, prefilled syringe, microinfusor, pen delivery device, autoinjector, kit, or use according to any preceding embodiment, wherein the antibody or fragment thereof comprises the CDRH3 sequence of the VH region of 2D10 as in SEQ ID No: 34.

578. A method, glass vial, drug delivery device, prefilled syringe, microinfusor, pen delivery device, autoinjector, kit, or use according to any preceding embodiment, wherein the antibody or fragment thereof comprises the CDRL1 sequence of the VL region of 2D10 as in SEQ ID No: 48.

579. A method, glass vial, drug delivery device, prefilled syringe, microinfusor, pen delivery device, autoinjector, kit, or use according to any preceding embodiment, wherein the antibody or fragment thereof comprises the CDRL2 sequence of the VL region of 2D10 as in SEQ ID No: 48.

580. A method, glass vial, drug delivery device, prefilled syringe, microinfusor, pen delivery device, autoinjector, kit, or use according to any preceding embodiment, wherein the antibody or fragment thereof comprises the CDRL3 sequence of the VL region of 2D10 as in SEQ ID No: 48.

581. A method, glass vial, drug delivery device, prefilled syringe, microinfusor, pen delivery device, autoinjector, kit, or use according to any preceding embodiment, wherein the antibody or fragment thereof comprises the VH and/or VL domains selected from the following:

the VH and/or VL domains of antibody 2D10 (SEQ ID No:34 for VH and/or SEQ ID No:48 for VL).

582. A method, glass vial, drug delivery device, prefilled syringe, microinfusor, pen delivery device, autoinjector, kit, or use according to any preceding embodiment, wherein the antibody or fragment thereof comprises an IgG4 constant region.

583. A method, glass vial, drug delivery device, prefilled syringe, microinfusor, pen delivery device, autoinjector, kit, or use according to any preceding embodiment, wherein the antibody or fragment thereof comprises an IgG4 constant region comprising a Leu235Glu mutation and/or a Ser228Pro mutation according to the EU numbering system.

584. A method, glass vial, drug delivery device, prefilled syringe, microinfusor, pen delivery device, autoinjector, kit, or use according to any preceding embodiment, wherein the antibody comprises an IgG4-PE constant region having an amino acid sequence according to SEQ ID No:128.

585. A method, glass vial, drug delivery device, prefilled syringe, microinfusor, pen delivery device, autoinjector, kit, or use according to any preceding embodiment, wherein the antibody or fragment thereof comprises an IgG4-PE constant region having an amino acid sequence according to SEQ ID No:128; a VH domain having an amino acid sequence according to SEQ ID No:34 and a VL domain having an amino acid sequence according to SEQ ID No:48.

586. A method, glass vial, drug delivery device, prefilled syringe, microinfusor, pen delivery device, autoinjector, kit, or use according to any preceding embodiment, wherein the antibody or fragment thereof comprises a heavy chain having an amino acid sequence according to SEQ ID No:62 and a light chain having an amino acid sequence according to SEQ ID No:64.

587. A method, glass vial, drug delivery device, prefilled syringe, microinfusor, pen delivery device, autoinjector, kit, or use according to any preceding embodiment, for use in treating AD in a patient with a biomarker selected from the group consisting of IL-13, IL-22, and IL17A.

588. A method, glass vial, drug delivery device, prefilled syringe, microinfusor, pen delivery device, autoinjector, kit, or use according to any preceding embodiment, for use in treating AD in a patient having an elevated level of a biomarker selected from the group consisting of IL-13, IL-22, and IL17A.

589. A method, glass vial, drug delivery device, prefilled syringe, microinfusor, pen delivery device, autoinjector, kit, or use according to any preceding embodiment, wherein the subject is classified as a Th2 AD patient and/or a non-Th2 AD patient.

590. A method, glass vial, drug delivery device, prefilled syringe, microinfusor, pen delivery device, autoinjector, kit, or use according to embodiment 589, wherein the subject classified as a non-Th2 AD patient has an elevated IL-22 and/or IL17A level.

591. A method, glass vial, drug delivery device, prefilled syringe, microinfusor, pen delivery device, autoinjector, kit, or use according to embodiment 589 or 590, wherein the subject classified as a Th2 AD patient has an elevated IL-13 level.

592. A method, glass vial, drug delivery device, prefilled syringe, microinfusor, pen delivery device, autoinjector, kit, or use according to any preceding embodiment, wherein the method is a method for treating AD in a patient in need thereof, wherein the method comprises (a) measuring the level of a biomarker selected from the group consisting of IL-13, IL-22, and IL-17A in the biologic fluid of the patient; (b) comparing the measured level with a reference level or threshold level; and (c) if the level of said biomarker is above the reference level or threshold level, administering to the patient the anti-OX40L antibody, or antigen-binding fragment thereof.

593. A method, glass vial, drug delivery device, prefilled syringe, microinfusor, pen delivery device, autoinjector, kit, or use according to any preceding embodiment, wherein the method comprises administering to a subject a pharmaceutical composition comprising a therapeutically effective amount of the anti-OX40L antibody, or antigen-binding fragment thereof, wherein administration of the pharmaceutical composition to the subject results in a decrease in at least one biomarker selected from the group consisting of IL-13, IL-22, and IL-17A.

594. A method, glass vial, drug delivery device, prefilled syringe, microinfusor, pen delivery device, autoinjector, kit, or use according to any preceding embodiment, wherein the method comprises an in vitro method for determining efficacy of a treatment of a subject having AD by administration of the anti-OX40L antibody, or antigen-binding fragment thereof, comprising determining in vitro a level of one or more biomarker selected from the group consisting of IL-13, IL-22 and IL-17A in a sample of said subject having AD, wherein said treatment is considered efficient if the level of IL-13, IL-22 and/or IL-17A is decreased.

595. A method, glass vial, drug delivery device, prefilled syringe, microinfusor, pen delivery device, autoinjector, kit, or use according to embodiment 593 or 594, wherein the decrease is by day 1, 29, 113, 169, 253 or later in the subject following administration.

Definitions

The term "about" or "approximately" means within 20%, preferably within 10%, and more preferably within 5% (or 4%, or 3% or 2%, or, in an example, 1% or less) of a given value or range.

"Dose" refers to a quantity or amount of a medicine or drug taken or recommended to be taken at a particular time. As used herein, it is typically expressed in mg of the antibody or fragment thereof. It may alternatively be expressed in terms of mg/kg, accounting for patient bodyweight.

"Injection" refers to a means of administration and encompasses for example IV and subcutaneous injections. An IV injection may be referred to as an infusion. It is also used herein to refer to an instance of administration wherein that administration is by injection, for example in the phrase "one or more induction phase injections". Each injection will involve administration of a dose of antibody or fragment thereof.

"Disease modifying" refers to a long and sustained response or therapeutic effect. A skilled person knows how to recognize a long and sustained response or therapeutic effect. The response or therapeutic effect may last longer than the presence of a therapeutically effective concentration of the antibody or fragment thereof in the body, such as in the skin. A long and sustained response or therapeutic effect may for instance be a response or therapeutic effect which persists after the last administration of the antibody or fragment thereof at least around seven half-lives, at least around eight half-lives, or at least around nine half-lives of the antibody or fragment thereof. A long and sustained response or therapeutic effect may for instance be a response or therapeutic effect which persists at least around six months, at least around seven months, at least around eight months or at least around nine months or longer after the last injection of the antibody or fragment thereof. A long and sustained response or therapeutic effect may be determined using any one of the methods of assigning disease severity disclosed herein, such as EASI (including EASI75 and EASI90) and IGA-AD. Disease modification may be apparent in an individual who has received drug and has achieved an IGA-AD of 0 or 1 for at least six months, optionally at least seven months, at least eight months or at least nine months. The disease modification (for example of at least six months) may begin at any suitable time after administration of the disease modifying drug. For example, the disease modification may begin at least 7 days or at least 15 days after administering the antibody or fragment thereof. The disease modification (for example of at least six months) may be during a period in which the subject is being treated, such as during an induction and/or maintenance phase as defined herein. The subject may receive a plurality (such as two, three, four, five, six, seven, eight, nine, ten etc) administrations of the antibody or fragment thereof during the at least six months during which an IGA-AD of 0 or 1 is maintained. When the drug treatment is stopped, the IGA-AD of 0 or 1 is maintained (i.e. is persistent) for at least a further 6 months, optionally at least a further seven months, at least a further eight months or at least a further nine months.

Cmin refers to the lowest concentration of the antibody or fragment thereof following administration and may also be termed the "trough concentration". Cmin may be measured between any two injections. Cmin (trough) values are typically the serum concentration in a sample obtained prior to drug administration on a day on which the subject is dosed. Cmin is therefore typically measured in a sample obtained on the day of a second (or a subsequent) injection of the antibody or fragment thereof, prior to injection of the antibody or fragment thereof. The sample may have been obtained within four hours before the injection of the antibody or fragment thereof. "Within four hours" may preferably refer to within three hours, within two hours, within one hour or within 45 minutes. The method may comprise measuring the serum concentration of the antibody or fragment thereof in one or more patient sample and determining Cmin, optionally further comprising obtaining the one or more patient sample.

Cmax refers to the peak concentration of the antibody or fragment thereof following administration. Cmax may be measured after a single injection or between any two injections. The calculated Cmax values are typically the highest drug serum concentration following each administration. This concentration may be measured in either an end-of-infusion blood sample (for example at 45 mins, or other infusion period) or in some cases in the next nominal sampling point, for example at 4 hrs after infusion. Typically, for an i.v. infusion the Cmax would usually occur at the end of infusion. Surprisingly, antibodies disclosed herein, in particular KY1005 may exhibit a Cmax which is delayed after the end of infusion (or delayed after injection). For example, Cmax may be at around 1 hour, 2 hours, 3 hours or 4 hours after the end of infusion (or after the injection). Cmin (trough) values are typically the serum concentration in a sample obtained prior to drug administration on a day on which the subject is dosed. Cmax is therefore typically measured in a sample obtained on the day of a first, a second (or a subsequent) injection of the antibody or fragment thereof, within four hours after injection or the start of the infusion of the antibody or fragment thereof. "Within four hours" may preferably refer to within three hours, within two hours, within one hour or within 45 minutes. The method may comprise measuring the serum concentration of the antibody or fragment thereof in one or more patient sample and determining Cmin, optionally further comprising obtaining the one or more patient sample.

Cmin and Cmax may be determined by measuring serum concentrations of an antibody or fragment thereof by any suitable known technique. As an example of a technique appropriate for measuring serum concentrations of an antibody or fragment thereof, concentrations of KY1005 in human serum were obtained using a validated chromogenic enzyme linked immunosorbent assay (ELISA) ligand binding assay that comprised a format of human OX40 ligand as capture antigen and a peroxidase labelled mouse anti-human IgG4 antibody as detector. The chosen format was considered to enable the measurement of free or active unbound KY1005 serum concentrations. The matrix KY1005 assay calibration curve ranged between 46.9 ng/mL (low limit of quantitation, LLOQ) and 1500 ng/mL. In pre-study validation, inter-assay imprecision (CV %) was <10.9% and inter-assay accuracy (% relative error) was 11.9%. Cmin and Cmax may be derived from modelling, using methods such as those described elsewhere herein.

The area under the serum concentration-time curve (AUC) following the first (AUC extrapolated to infinity [$AUC_{0-inf}$]) injection may be determined by any suitable known technique. $AUC_{0-inf}$ represents the total drug exposure across time and may for example be used to indicate whether two formulations of the same dose result in equal amounts of tissue or serum exposure.

As used herein "induction phase" refers to a phase or period of treatment during which a therapeutic effect may be established. The induction phase can be of any suitable length and comprise one or more induction phase injections. Where a maintenance phase is also present, the induction phase precedes the maintenance phase.

As used herein, "induction phase injection" refers to an injection administered during the induction phase, including at the start of the induction phase and at the end of the induction phase.

As used herein, "induction dose" refers to the quantity or amount of the antibody or fragment thereof administered in an induction phase injection.

Das used herein, "maintenance phase" refers to a phase or period of treatment during which a previously established therapeutic effect may be maintained. The maintenance phase can be of any suitable length and comprise one or more maintenance phase injections. Where an induction phase is also present, the induction phase precedes the maintenance phase.

As used herein, "maintenance phase injection" refers to an injection administered during the maintenance phase, including at the start of the maintenance phase and at the end of the maintenance phase.

As used herein, "maintenance dose" refers to the quantity or amount of the antibody or fragment thereof administered in an maintenance phase injection.

As used herein, a "loading dose" refers to a higher dose administered prior to a subsequent lower dose.

As used herein "clinical response" refers to the outcome of a process to measure disease severity changes in response to a method of treatment. The clinical response may therefore be the outcome of any method which can be used to assign the severity of disease when assessing atopic dermatitis patients, including any of the methods of assigning disease severity described herein. The clinical response may be a post-administration score or index as described herein, such as a post-administration EASI score, post-administration IGA-AD score, post-administration NRS score or post-administration SCORAD index. The clinical response may be determined based on the experience of a clinician. The clinical response may be positive meaning there has been an improvement in the patient's AD following treatment. The clinical response may be negative meaning there has been no improvement, or a worsening of the patient's AD following treatment. A clinician may use a positive clinical response to transition a patient from an induction phase to a maintenance phase or to end treatment, for example. Alternatively, a negative clinical response may suggest the treatment has not yet been effective and should be continued, for example by prolonging the induction phase or the maintenance phase. A negative clinical response may also be used by a clinician to determine that treatment with the antibody or fragment thereof should cease.

As used herein a "treatment dose" refers to any administration of antibody or fragment thereof which comprises a therapeutically effective amount of antibody or fragment thereof. The term "treatment dose" is primarily used in the context of methods involving a loading dose, where the treatment dose is the dose or doses following the loading dose. The amount of antibody or fragment thereof in the loading dose may be defined relative to the treatment dose, for example the loading dose may have twice the amount of antibody or fragment thereof as the treatment dose. In some instances, the method may involve one or more treatment dose and one or more maintenance dose. The maintenance dose is defined as above. The maintenance dose may comprise the same amount of antibody or fragment thereof as the treatment dose. Alternatively, the maintenance dose may comprise a different amount of antibody or fragment thereof as the treatment dose. The dose interval between maintenance doses may be the same as the dose interval between treatment doses. Alternatively, the dose interval between maintenance doses may be different to the dose interval between treatment doses. However, where the method comprises both a maintenance dose and a treatment dose, the maintenance dose is administered after the treatment dose. The term "treatment dose" may be used interchangeably with the term "induction dose" accordingly. Likewise, the time period during which treatment doses and a loading dose are being administered may be referred to as a "treatment phase" which is distinguishable from the "maintenance phase" and corresponds to the "induction phase" used elsewhere herein.

The amount of anti-OX40L antibody, or antigen-binding fragment thereof, administered to a subject according to the methods is, generally, a therapeutically effective amount. As used herein, the phrase "therapeutically effective amount" may mean an amount of anti-OX40L antibody, or antigen-binding fragment thereof, that results in one or more of: (a) an improvement in one or more AD-associated parameters (as defined elsewhere herein); (b) an improvement and/or reduction in one or more AD-associated biomarkers; and/or (c) a detectable improvement in one or more symptoms or indicia of atopic dermatitis. A "therapeutically effective amount" also may include an amount of anti-OX40L antibody, or antigen-binding fragment thereof, that inhibits, prevents, lessens, or delays the progression of AD in a subject.

The term "$C_{max}$" refers to the maximum or peak concentration of an agent observed in a subject after its administration. "$T_{max}$" refers to the time it takes from dosing to reach $C_{max}$. With bolus intravenous administration, $C_{max}$ is defined as occurring at the time of injection; therefore, $T_{max}$ may be defined as zero.

The term "serum" is used herein in the context of pharmacokinetic measurements and derived parameters, however the term "plasma" (which further contains clotting factors) may be used interchangeably with the term "serum".

The term "absorption constant" or "ka" is the rate of absorption of a drug from its site of application through the body, and is typically only considered if the drug is administered by a route other than intravenous administration (e.g., subcutaneous administration). If a drug is administered intravenously by single rapid injection, absorption is bypassed. The time for such injections is usually so short compared to other pharmacokinetic processes that it is customary, in one-compartment systems, to consider the peak serum (or plasma) concentration and the equilibrium distribution to occur simultaneously (see, e.g., Remington's Pharmaceutical Sciences, 16th Edition, Chapter 37. c. 1980 Mack Publishing Company).

The term "volume of distribution" or "Vd" is used to quantify the distribution of an administered drug. In a one compartment model, the body is assumed to behave as though it were a single compartment, that is, as if there were no barriers to the movement of drug within the total body space and the final equilibrium distribution is attained instantaneously. Vd is not necessarily the volume of the body or the total body water. The volume Vd is a fictive one considered to be equal to $lD/C_p$, where f is the fraction absorbed, D is the dose, and Cp is the serum (or plasma) concentration, in which it is hypothetically assumed that the concentration is the same throughout the volume and is equal to the serum (or plasma) concentration. In reality, concentration is not homogenous throughout, but this cannot be determined from Cp alone (which simply averages all inputs and outputs); as long as distribution equilibrium is rapidly achieved, the kinetics as perceived through blood or urine concentrations are the same whether distribution is homogeneous or heterogeneous (see, e.g., Remington's Pharmaceutical Sciences, 16th 25 Edition, Chapter 37. c. 1980 Mack Publishing Company).

The "central compartment" or "Vc", is used to describe the first volume of distribution of a drug using a two-compartment model. In the two-compartment model, the body is considered to have two compartments in dynamic equilibrium. The compartment, into which the drug is directly absorbed and from which the drug eliminated, is called compartment 1 or the central compartment. The blood is a part of this compartment, is the transporting and distributing medium, and is the medium actually sampled for chemical and pharmacokinetic analysis (see, e.g., Remington's Pharmaceutical Sciences, 16th Edition, Chapter 37. c. 1980 Mack Publishing Company).

The term "Vp1", "Vp", "$V_2$", or "peripheral compartment" in a simple two-compartment model is closed and communicates with the environment only through the central compartment, being, as it were, peripheral to the events of absorption and elimination (see, e.g., Remington's Pharmaceutical Sciences, 16th Edition, Chapter 37. c. 1980 Mack Publishing Company).

The term "$V_z$" is the volume of distribution is used with single compartment models. Apparent $V_z$ can be defined as $V_z/F$ for subcutaneous administration.

The terms "Ve", "Vp", and "$V_z$" are fictive and defined by kinetic behaviour of the drug within the body and not necessarily by identifiable anatomical entities. The movement of drugs within and between compartments is defined e.g., by characteristic first-order rate constants, and the rate of movement of the drug from the first compartment to the second compartment, or in the reverse direction can be calculated in a manner similar to the rate of absorption (see, e.g., Remington's Pharmaceutical Sciences, 16th Edition, Chapter 37. c. 1980 Mack Publishing Company).

The term "Q" describes the rate in which a drug moves from or is cleared from the first compartment to the second compartment in a two-compartment model (intercompartmental clearance).

The term "CL", "rate of clearance" or "clearance" is the rate that a drug is eliminated from the serum (or plasma), typically substantially through the kidney and liver, however, other paths of elimination are also possible depending on the specific characteristics of the drug. CL may increase with increasing bodyweight, e.g., increases by approximately 10% per 10 kg change from greater than 75 kg to about 105 kg, and then increases approximately 7.5% when weight is greater than about 105 kg. CL may increase in the presence of ADA and neutralizing ADA, e.g., increases by about 30% in the presence of ADA and increases by about 66% in the presence of neutralizing ADA.

"Apparent clearance" can be defined as CL/F for subcutaneous administration.

The term "bioavailability" or "Fabs1" or "F %" or "F1" refers to a fraction or percent of a dose which is absorbed and enters the systemic circulation after administration of a given dosage form.

The dose of the agent may be administered through any route, preferably, via intravenous or subcutaneous injection.

"Half life" or "t/2" is the amount of time after administration of the drug for half of the dose to clear the subject.

"Area under the curve" or "AUC" is used to describe the serum concentration curve in single compartment pharmacokinetic calculations.

"Dupilumab" is a recombinant human monoclonal antibody that inhibits interleukin-4 and interleukin-13 signalling. Dupilumab is licensed for the treatment of adults and children aged 12-17 with moderate-to-severe atopic dermatitis (atopic eczema) who are possible candidates for systemic therapy. Dupilumab is described in WO2010053751 and EP2356151, both of which are hereby incorporated by reference in their entireties.

As used herein, "inadequate response" refers to a response that is not clinically sufficient.

As used herein, "intolerant to" refers to a treatment causing an undesirable clinical reaction in a patient, such as anaphylaxis.

As used herein, "refractory to" refers to an inadequate response in a patient who previously responded to treatment.

"Topical corticosteroid" refers to a type of steroid medicine applied directly to the skin to reduce inflammation and irritation. Steroids are a man-made version of hormones normally produced by the adrenal glands which are 2 small glands found above the kidneys. When taken in doses higher than the amount your body normally produces, steroids reduce redness and swelling (inflammation). This can help with inflammatory conditions such as asthma and eczema. Steroids also reduce the activity of the immune system, which is the body's natural defence against illness and infection.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al., J. Theor. Biol. 119(1986);205-218 and S. French and B. Robson, J. Mol. Evol., 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

As used herein an "antibody" refers to IgG, IgM, IgA, IgD or IgE molecules or antigen-specific antibody fragments thereof (including, but not limited to, a Fab, $F(ab')_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanized using routine technology.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody fragment" refers to a polypeptide that includes at least one immunoglobulin variable domain or immunoglobulin variable domain sequence and which specifically binds a given antigen. An antibody fragment can comprise an antibody or a polypeptide comprising an antigen-binding domain of an antibody. In some embodiments, an antibody fragment can comprise a monoclonal antibody or a polypeptide comprising an antigen-binding domain of a monoclonal antibody. For example, an antibody can include a heavy (H) chain variable region (abbreviated herein as VH), and an OX40L (L) chain variable region (abbreviated herein as VL). In another example, an antibody includes two heavy (H) chain variable regions and two OX40L (L) chain variable regions. The term "antibody fragment" encompasses antigen-binding fragments of antibodies (e.g., single chain antibodies, Fab and sFab fragments, F(ab')2, Fd fragments, Fv fragments, scFv, and domain antibodies (dAb) fragments (see, e.g., de Wildt et al., Eur J. Immunol., 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

As used herein, "antibody variable domain" refers to the portions of the OX40L and heavy chains of antibody molecules that include amino acid sequences of Complementarity Determining Regions (CDRs; i.e., CDR1, CDR2, and CDR3), and Framework Regions (FRs). VH refers to the variable domain of the heavy chain. VL refers to the variable domain of the Light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature.

As used herein, the term "antibody binding site" refers to a polypeptide or domain that comprises one or more CDRs of an antibody and is capable of binding an antigen. For example, the polypeptide comprises a CDR3 (e.g., HCDR3). For example the polypeptide comprises CDRs 1 and 2 (e.g., HCDR1 and 2) or CDRs 1-3 of a variable domain of an antibody (e.g., HCDRs1-3). In an example, the antibody binding site is provided by a single variable domain (e.g., a VH or VL domain). In another example, the binding site comprises a VH/VL pair or two or more of such pairs.

As used herein, "OX40L antagonistic antibody" or "OX40L antagonist antibody" refers to an antibody or antigen-binding fragment thereof that is capable of inhibiting and/or neutralizing the biological signaling activity of OX40L, for example by blocking binding or substantially reducing binding of OX40 to OX40L.

As used herein, "genotyping" refers to a process of determining the specific allelic composition of a cell and/or subject at one or more position within the genome, e.g., by determining the nucleic acid sequence at that position. Genotyping refers to a nucleic acid analysis and/or analysis at the nucleic acid level. As used herein, "phenotyping" refers a process of determining the identity and/or composition of an expression product of a cell and/or subject, e.g., by determining the polypeptide sequence of an expression product. Phenotyping refers to a protein analysis and/or analysis at the protein level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well.

As used herein, the term "pharmaceutical composition" refers to the active agent in combination with a pharmaceutically acceptable carrier e.g., a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Multiple compositions can be administered separately or simultaneously. Separate administration refers to the two compositions being administered at different times, e.g., at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g., less than 10 or less than 5 minutes apart. Compositions administered simultaneously can, in some aspects, be administered as a mixture, with or without similar or different time release mechanism for each of the components.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g., the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, a "buffer" refers to a chemical agent that is able to absorb a certain quantity of acid or base without undergoing a strong variation in pH.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labeling, etc.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

As used herein the term "comprising" or "comprises" is used in reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example"

Moderate-to-severe AD may also be considered to be present in patients who require frequent treatment with topical corticosteroids. A patient may also be said to have moderate-to-severe AD when the patient is resistant or refractory to treatment by either a topical corticosteroid or a calcineurin inhibitor or any other commonly used therapeutic agent known in the art. AD is a chronic inflammatory disease with recurrent symptoms often appearing as a rash on the skin. Signs and symptoms can include intense, persistent itching and skin dryness, cracking, redness, crusting and oozing.

As used herein a "diagnostic biomarker" is a biomarker used to detect or confirm presence of a disease or condition of interest or to identify individuals with a subtype of the disease.

As used herein a "monitoring biomarker" is a biomarker measured repeatedly for assessing status of a disease or medical condition or for evidence of exposure to (or effect of) a medical product or an environmental agent.

As used herein a "pharmacodynamic biomarker" is a biomarker used to show that a biological response has occurred in an individual who has been exposed to a medical product or an environmental agent. The terms "pharmacodynamic biomarker" and "response biomarker" may be used interchangeably.

"IL-13" is expressed by Th2 cells, but also other cells (e.g., mast cells or ILC2s), and has been reported as one of the main drivers of Th2 responses in AD patients. IL-13 may be produced by Th2 cells. IL-13 may be described as a Th2 biomarker. As used herein "IL-13" may refer to a protein comprising IL-13, a fragment, sub-unit, or polypeptide sequence thereof.

"IL-22" is mainly produced by Th22 and Th17 cells, but also Th1 and other cell types, and signals through the IL22 receptor, which is expressed on tissue cells such as keratinocytes, but not on immune cells. IL-22 may be described as a non-Th2 biomarker. As used herein "IL-22" may refer to a protein comprising IL-22, a fragment, sub-unit, or polypeptide sequence thereof.

"IL-17A" is a cytokine produced by T-helper 17 cells. IL-17A plays important roles in allergic responses. IL-17A promotes inflammation by inducing various proinflammatory cytokines and chemokines, recruiting neutrophils, enhancing antibody production, and activating T cells. IL-17A is thought not to be produced by Th2 cells. IL-17A may be described as a non-Th2 biomarker. As used herein "IL-17A" may refer to a protein comprising IL-17A, a fragment, sub-unit, or polypeptide sequence thereof.

"IL-31" as a pruritogen is an important mediator of AD-associated itch. It is a Th2 cell-associated cytokine.

"IgE" is produced in response to parasitic infection but are also a hallmark of allergic reactions. High local and blood IgE levels are associated with allergic diseases such as asthma, allergic rhinitis and AD.

Some embodiments also include methods involving the use, quantification, and analysis of AD-associated biomarkers. As used herein, the term "AD-associated biomarker" means any biological response, cell type, parameter, protein, polypeptide, enzyme, enzyme activity, metabolite, nucleic acid, carbohydrate, or other biomolecule which is present or detectable in an AD patient at a level or amount that is different from (e.g., greater than or less than) the level or amount of the marker present or detectable in a non-AD patient. In some embodiments, the term "AD-associated biomarker" includes a biomarker associated with Type 2 helper T-cell (Th2)-driven inflammation. Exemplary AD-associated biomarkers include: IL-13, IL-22 and IL-17A. Certain embodiments of pertain to use of these biomarkers for monitoring disease reversal with the administration of an anti-OX40L antibody, or antigen-binding fragment thereof. Methods for detecting and/or quantifying such AD-associated biomarkers are known in the art; kits for measuring such AD-associated biomarkers are available from various commercial sources; and various commercial diagnostic laboratories offer services which provide measurements of such biomarkers as well.

As used herein, the terms "level" and "levels" can be used interchangeably with the terms "concentration" and "concentrations".

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, standard procedures were used, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in OX40L of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, concepts, aspects, examples, clauses and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word “a” or “an” when used in conjunction with the term “comprising” in the claims and/or the specification may mean “one,” but it is also consistent with the meaning of “one or more,” “at least one,” and “one or more than one.” The use of the term “or” in the claims is used to mean “and/or” unless explicitly indicated to refer to alternatives only or the alternatives are mutually exclusive, although the disclosure supports a definition that refers to only alternatives and “and/or.” Throughout this application, the term “about” is used to indicate that a value includes the inherent variation of error for the device, the method being employed to determine the value, or the variation that exists among the study subjects.

As used in this specification and claim(s), the words “comprising” (and any form of comprising, such as “comprise” and “comprises”), “having” (and any form of having, such as “have” and “has”), “including” (and any form of including, such as “includes” and “include”) or “containing” (and any form of containing, such as “contains” and “contain”) are inclusive or open-ended and do not exclude additional, unrecited elements or method steps.

Any part of this disclosure may be read in combination with any other part of the disclosure, unless otherwise apparent from the context.

All of the compositions and/or methods disclosed and claimed herein can be made and executed without undue experimentation in OX40L of the present disclosure. While the compositions and methods have been described in terms of embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

Example 1. A Single and Multiple Ascending Dose, Placebo-controlled, Double-blind, Phase 1 Study to Evaluate the Safety and Tolerability of KY1005 in Healthy Volunteers, ClinicalTrials.gov Identifier: NCT03161288 (KY1005-CT01)

Study Design and Objectives

Male volunteers aged 18 to 45 years were recruited to a total of eight cohorts. In each cohort, KY1005 was administered by intravenous (IV) infusion over a period of 30 minutes to six volunteers, with two volunteers receiving placebo to match.

The primary objective of the study was to evaluate the safety and tolerability of KY1005. The secondary objective of the study was to evaluate the pharmacokinetics (PK) of KY1005 following single and repeat doses. Exploratory objectives were to evaluate the effect of KY1005 on dermal delayed type hyper sensitivity (DTH) and humoral responses to immune challenges, immunophenotype and also to assess the immunogenicity of KY1005.

The overall study design is presented in FIG. 1. Healthy volunteers in Cohorts 1 to 3 received a single I.V. infusion of KY1005 (0.006, 0.018 or 0.05 mg/kg) or placebo, with blood samples taken up to Day 113. Cohorts 4 to 8 received an initial loading dose on Day 1 (0.15, 0.45, 1.35, 4.0 or 12 mg/kg), and two maintenance doses (50% of the loading dose), administered on Days 29 and 57.

Subjects were followed up to Day 113 (Cohorts 1 to 3) and Day 92 (Cohorts 4 to 8) and then discharged from the study.

Safety and Tolerability

The primary objective of this study was to evaluate the safety and tolerability of KY1005. The following variables were assessed:

- Occurrence of AEs, SAEs and subject partner pregnancy up to Day 113 (Cohorts 1 to 3) and Day 92 (Cohorts 4 to 8).
- Changes in vital signs, laboratory safety data, anti-viral antibody levels and viral DNA, acute cytokines and ECGs.
- Changes in physical examination findings.

There were no SAEs and no pregnancies were reported in the partners of participating subjects.

Eight subjects were recruited to each of the eight cohorts. There were five withdrawals.

No AEs were judged to be severe. There were no reactions at the infusion site.

Physical examinations, vital signs, ECGs and laboratory safety data, including acute cytokines (evaluated in all cohorts) and markers of viral reactivation yielded no findings of concern. The hematology tests showed no evidence of an effect of treatment on the platelet count.

Pharmacokinetics

Serum concentrations of KY1005 were assessed using a validated enzyme-linked immunosorbent assay (ELISA) bioanalytical method. For Cohorts 1 to 3, serum concentrations of KY1005 were assessed at the following time points: Days 1 to 3: pre- and at end of infusion, 4, 12, 24 and 48 hours after the end of infusion; Days 8, 11, 22, 29, 57, 85 and 113: single sample on each day. For Cohorts 4 to 8, serum concentrations of KY1005 were assessed at the following time points: Days 1 to 3: pre- and at end of infusion, 4, 12, 24 and 48 hours after the end of infusion; Days 8, 11, 22, 36, 64, 85 and 92: single sample on each day; Days 29 and 57: pre- and at end of infusion, 4, 12, 24 hours after the end of infusion.

The following PK measures were derived:

- $C_{max}$ following the first, and, for Cohorts 4 to 8, second and third infusions.
- $T_{max}$ following the first and, for Cohorts 4 to 8, second and third infusions.
- Trough concentrations ($C_{min}$) in Cohorts 4 to 8 following the first and second infusions and concentrations 28 days after the third infusion.
- Area under the serum concentration time curve (AUC) calculated using the linear trapezoidal method, including AUC from time zero to infinity ($AUC_{inf}$), AUC from time zero to time of last measurable concentration ($AUC_{tlast}$), AUC extrapolated from time (t) to infinity as a percentage of total AUC ($AUC_{\%\ extrapolated}$) and AUC during a dosage interval ($AUC_{I}$) following the first, and where relevant, second and third infusions.
- Apparent total body clearance of the drug from serum (CL).
- Apparent volume of distribution during terminal phase (Vz) and apparent volume of distribution at steady state (Vss).
- Apparent terminal half-life ($t_{1/2}$).

The profiles following single doses provided estimates of the PK measures following low (single) doses of KY1005 in Cohorts 1 to 3 as shown below (Table 3). These measures showed an increase in $C_{max}$ that was proportional to dose. However, the CL was higher and the $t_{1/2}$ correspondingly shorter, particularly following the lowest dose (0.0177 L/h and 169.67 hours, respectively, for the dose of 0.006 mg/kg).

TABLE 3

Pharmacokinetics following a single dose (Cohorts 1 to 3)

| | $C_{max}$ (ng/mL) (geomean) | $T_{max}$ (h) (median) | CL (L/h) (geomean) | Vz (L) (geomean) | $t_{1/2}$ (h) (average) |
|---|---|---|---|---|---|
| 0.006 mg/kg, N = 6 | 133.14 | 0.53 | 0.0177 | 4.1579 | 169.67 |
| 0.018 mg/kg, N = 6 | 331.47 | 4.02 | 0.0146 | 6.4348 | 322.67 |
| 0.05 mg/kg, N | 1260.27 | 2.25 | 0.0091 | 3.7463 | 289.83 |

CL = apparent total body clearance of the drug from serum; $C_{max}$ = maximum observed serum concentration; CSR = clinical study report; geomean = geometric mean; NCA = non-compartmental analysis; $t_{1/2}$ = apparent terminal half-life; $T_{max}$ = time to maximum observed serum concentration; $V_z$ = apparent volume of distribution.

The dosing strategy of a loading/maintenance dose approximated steady state concentrations as shown by the $C_{max}$ and $C_{min}$ below (Table 4).

TABLE 4

Serum concentrations following loading and maintenance doses

| Loading/ Maintenance dose (mg/kg) | $C_{max}$ (ng/mL)/ trough 1 (ng/mL) (geomean) | $C_{max}$ (ng/mL)/ trough 2 (ng/mL) (geomean) | $C_{max}$ (ng/mL)/ trough 3 (ng/mL) (geomean) |
|---|---|---|---|
| 0.15/0.075 N = 6/6 | 3966.79/884.34 | 2803.32/995.72 | 2989.75/1149.80 |
| 0.45/0.225 N = 6/6 | 11762.33/2970.72 | 8079.09/2862.25 | 8595.40/3058.23 |
| 1.35/0.675 N = 6/6 | 33865.41/9611.21 | 25745.70/8828.21 | 28362.12/12802.80 |

TABLE 4-continued

| Serum concentrations following loading and maintenance doses | | | |
|---|---|---|---|
| Loading/ Maintenance dose (mg/kg) | $C_{max}$ (ng/mL)/ trough 1 (ng/mL) (geomean) | $C_{max}$ (ng/mL)/ trough 2 (ng/mL) (geomean) | $C_{max}$ (ng/mL)/ trough 3 (ng/mL) (geomean) |
| 4.0/2.0 N = 6/6 | 106503.19/25802.81 | 85508.52/30095.07 | 62765.34/31679.62 |
| 12/6.0 N = 6/5 | 286401.27/80667.81 | 228632.25/88400.59 | 247496.61/89074.93 |

$C_{max}$ = maximum observed serum concentration; CSR = clinical study report; geomean = geometric mean; NCA = non-compartmental analysis.

Despite poor characterization of the terminal phase in the loading/maintenance dose cohorts (an inherent issue with repeat dosing), the PK measures following loading doses between 0.15 and 12 mg/kg (Cohorts 4 to 8) provided a useful insight. The elimination characteristics following the first dose in Cohorts 4 to 8 are shown below (Table 5).

TABLE 5

| Pharmacokinetics following loading doses | | | |
|---|---|---|---|
| Loading/ Maintenance dose (mg/kg) | CL (L/h) (geomean) | Vz (L) (geomean) | $t_{1/2}$ (h) (average) |
| 0.15/0.075 N = 6 | 0.00666 | 4.65 | 498.2 |
| 0.45/0.225 N = 6 | 0.00596 | 4.64 | 554.5 |
| 1.35/0.675 N = 6 | 0.00561 | 4.16 | 557.1 |
| 4.0/2.0 N = 6 | 0.0067 | 4.63 | 486.4 |
| 12/6.0 N = 6 | 0.00701 | 5.4 | 545.4 |

CL = apparent total body clearance of the drug from serum; CSR = clinical study report; geomean = geometric mean; NCA = non-compartmental analysis; $t_{1/2}$ = apparent terminal half-life; $V_z$ = apparent volume of distribution.

The $t_{1/2}$ estimates following these loading doses ranged between 486.4 and 557.1 hours (20 and 23 days), with no dose-related trend. A population PK analysis of the full data set provided a terminal half-life estimate of 38 days.

Immunogenicity and Pharmacodynamic (PD) Assessments

For evaluation of anti-KY1005 antibody response, serum titers of anti-KY1005 antibodies were assessed using a sensitive solid-phase extraction with acid dissociation (SPEAD) assay in blood samples pre-infusion and Days 11, 29, 57, 85 and 113 (or withdrawal) (Cohorts 1 to 3) or pre-first infusion and Days 11, 29 (pre-infusion), 57 (pre-infusion) and 92 (or withdrawal) (Cohorts 4 to 8).

Anti-KY1005 antibodies developed in some subjects who received KY1005 in Cohorts 1, 2, 3, 4, 5, 6 and 7 (Table 6), however, where ADAs were observed, no impact on PK was noted, suggesting weak or non-neutralizing antibody generation.

TABLE 6

| Presence of anti-drug antibodies (FAS population) | | | | |
|---|---|---|---|---|
| Treatment | Protocol day | Negative | Positive | Missing |
| Cohorts 1 to 3, n (%) | | | | |
| KY1005 0.006 mg/kg | 0 | 5 (83) | 1 (17) | 0 |
| | 11 | 5 (83) | 1 (17) | 0 |
| | 29 | 5 (83) | 1 (17) | 0 |
| | 57 | 5 (83) | 1 (17) | 0 |
| | 85 | 5 (83) | 1 (17) | 0 |
| | 113 | 4 (67) | 2 (33) | 0 |
| KY1005 0.018 mg/kg | 0 | 6 (100) | 0 | 0 |
| | 11 | 6 (100) | 0 | 0 |
| | 29 | 5 (83) | 1 (17) | 0 |
| | 57 | 4 (67) | 2 (33) | 0 |
| | 85 | 4 (67) | 2 (33) | 0 |
| | 113 | 4 (67) | 2 (33) | 0 |
| KY1005 0.05 mg/kg | 0 | 6 (100) | 0 | 0 |
| | 11 | 6 (100) | 0 | 0 |
| | 29 | 5 (83) | 1 (17) | 0 |
| | 57 | 4 (67) | 2 (33) | 0 |
| | 85 | 3 (50) | 3 (50) | 0 |
| | 113 | 1 (17) | 5 (83) | 0 |
| Placebo | 0 | 6 (100) | 0 | 0 |
| | 11 | 6 (100) | 0 | 0 |
| | 29 | 6 (100) | 0 | 0 |
| | 57 | 6 (100) | 0 | 0 |
| | 85 | 5 (83) | 0 | 1 (17) |
| | 113 | 6 (100) | 0 | 0 |
| Cohorts 4 to 8 | | | | |
| KY1005 0.15 mg/kg | 0 | 6 (100) | 0 | 0 |
| | 11 | 5 (83) | 1 (17) | 0 |
| | 29 | 5 (83) | 1 (17) | 0 |
| | 57 | 5 (83) | 1 (17) | 0 |
| | 92 | 2 (33) | 4 (67) | 0 |
| KY1005 0.45 mg/kg | 0 | 6 (100) | 0 | 0 |
| | 11 | 6 (100) | 0 | 0 |
| | 29 | 6 (100) | 0 | 0 |
| | 57 | 4 (67) | 2 (33) | 0 |
| | 92 | 4 (67) | 2 (33) | 0 |
| KY1005 1.35 mg/kg | 0 | 6 (100) | 0 | 0 |
| | 11 | 6 (100) | 0 | 0 |
| | 29 | 6 (100) | 0 | 0 |
| | 57 | 6 (100) | 0 | 0 |
| | 92 | 5 (83) | 1 (17) | 0 |
| KY1005 4 mg/kg | 0 | 6 (100) | 0 | 0 |
| | 11 | 6 (100) | 0 | 0 |
| | 29 | 5 (83) | 1 (17) | 0 |
| | 57 | 5 (83) | 1 (17) | 0 |
| | 92 | 6 (100) | 0 | 0 |
| KY1005 12 mg/kg | 0 | 6 (100) | 0 | 0 |
| | 11 | 6 (100) | 0 | 0 |
| | 29 | 6 (100) | 0 | 0 |
| | 57 | 6 (100) | 0 | 0 |
| | 92 | 6 (100) | 0 | 0 |
| Placebo | 0 | 10 (100) | 0 | 0 |
| | 1 | 1 (100) | 0 | 0 |
| | 11 | 10 (100) | 0 | 0 |
| | 29 | 10 (100) | 0 | 0 |
| | 57 | 9 (90) | 0 | 1 (10) |
| | 92 | 9 (100) | 0 | 0 |

FAS = Full Analysis Set

PD assessments demonstrated that KY1005 is a pharmacologically active compound in inhibiting the neo-antigen response and blunting the DTH skin changes. (see "KY1005 a novel anti-OX40L mAb with potential in atopic dermatitis (AD): Results of a Phase 1 study assessing the safety, pharmacokinetics, and T-cell-dependent antibody response (TDAR) in healthy volunteers", M. Saghari, et al, 24th World Congress of Dermatology, Milan, Jun. 10-15, 2019 and "OX40L blocking monoclonal antibody KY1005 strongly suppresses the delayed-type hyper sensitivity skin response to KLH in healthy volunteers", M. Saghari, et al, 24th World Congress of Dermatology, Milan, Jun. 10-15, 2019)

Figure 2A:
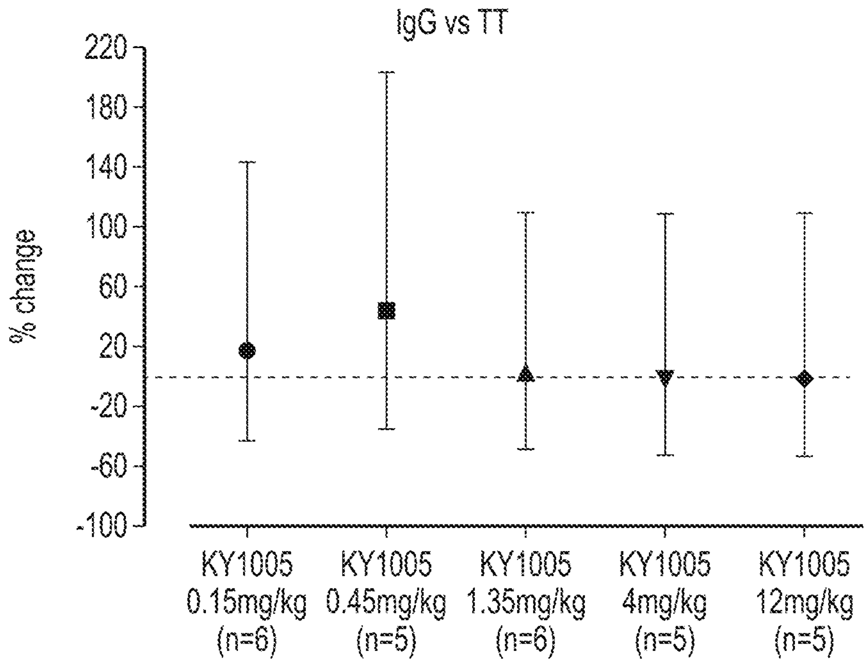
FIG. 2A-2B graphically depict percentage change in anti-tetanus toxoid (TT) IgG and IgM titer versus placebo at Day 85, Cohorts 4 to 8 (95% CI) adjusted for baseline variability. Immunization with recall antigen, tetanus toxoid (TT), resulted in a humoral (IgM and IgG) response in all who were immunized. No observable effect of KY1005 on mean anti-TT IgG levels (FIG. 2A) were observed although anti-TT IgM (FIG. 2B) suppression was numerically greater than placebo in all treatment arms but not dose dependent.
Figure 2B:
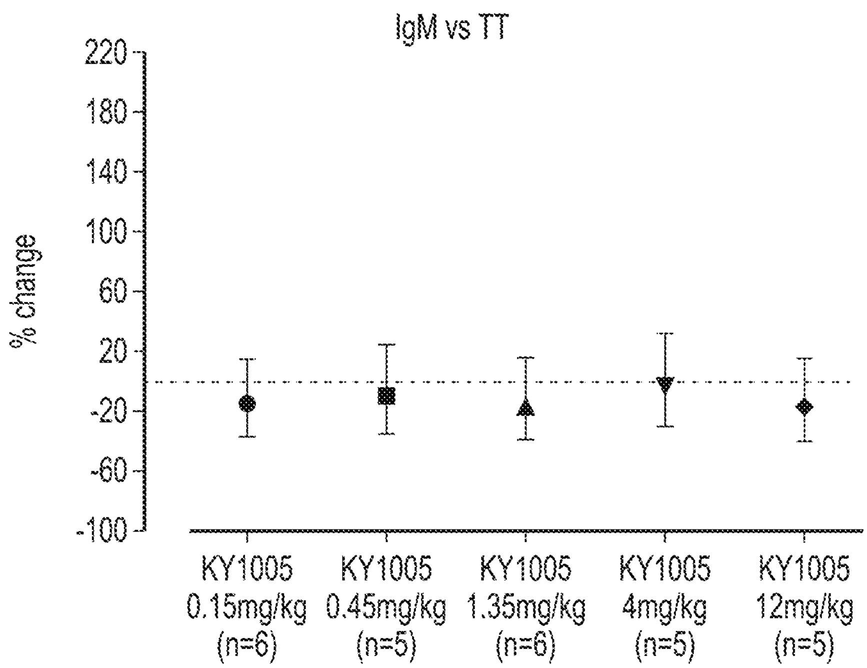

As shown FIG. 2A-B, immunization with recall antigen, tetanus toxoid (TT), resulted in a humoral (IgM and IgG) response in all who were immunized. No observable effect of KY1005 on mean anti-TT IgG levels (FIG. 2A) were observed although anti-TT IgM (FIG. 2B) suppression was numerically greater than placebo in all treatment arms but not dose dependent.

Conclusions

KY1005 was studied in healthy volunteers in eight cohorts across a dose range. There was no evidence for cytokine release, reduction in platelet counts or predisposition to infection.

PK evaluation revealed a consistent dose-proportional $C_{max}$ and $C_{min}$. KY1005 was cleared slowly and the serum concentrations at 4 and 12 hours were very similar to those at the end-of-infusion. The elimination characteristics suggested a more rapid clearance at lower doses. This may have been caused by OX40L-mediated clearance dominating at lower doses. At higher doses, clearance appeared to be independent of dose and unaffected on repeat dosing. The $t_{1/2}$ based on the loading doses ranged between 20 and 23 days, while a population PK analysis of the full data set provided a terminal half-life estimate of 38 days (99), so the first $C_{max}$ was greater than the maintenance dose $C_{max}$. However, $C_{max}$ and $C_{min}$ on this dosing strategy provided acceptable exposure throughout the dosing interval.

Anti-drug antibodies were detected in a minority of subjects. The PK of KY1005 did not appear to be affected in those subjects who reacted, suggesting weak or non-neutralizing antibody generation.

The PD assessments showed an immunomodulatory effect in response to neo-antigen exposure, statistically significant at some dose regimes, for the DTH skin assessment. The results of downregulation of antibody responses to neo-antigen challenge were less clear than for DTH but provided additional evidence of relevant pharmacological activity. Suppression of the T-cell dependent antibody response (TDAR) against a neo-antigen (KLH subunit) was observed above the lowest dose of KY1005 (0.15 mg/kg). The suppression in the IgG response was more marked than the IgM response. TDAR against recall antigen (TT) highlighted no observable effect of KY1005 on anti-TT IgG although anti-TT IgM suppression was numerically greater than placebo in all treatment arms but not dose dependent.

As is usual in these kinds of assessments, there was no clear dose-response relationship, although there is some indication that KY1005 was more effective in cohorts dosed at 0.45 mg/kg and above, with the most pronounced response being observed in the 12 mg/kg cohort. Based on these PD assessments, it can be concluded that KY1005 is a pharmacologically active compound in inhibiting the neo-antigen response and blunting the DTH skin changes.

Example 2. A Phase Ha, Randomized, Double Blind, Placebo Controlled, Parallel Group, Multicenter Study of An Anti-0x40L Monoclonal Antibody (KY1005) In Moderate To Severe Atopic Dermatitis, ClinicalTrials.qov Identifier: NCT03754309 (KY1005-CT02)

Primary Objective

The primary objective of the study was to explore the efficacy and safety of two regimes of KY1005 on the signs of AD using the Eczema Area and Severity Index (EASI) and the incidence of treatment-emergent adverse events (TEAEs).

Secondary Objectives

- To explore the effect of two regimes of KY1005 on changes in EASI over time.
- To characterize the pharmacodynamic (PD) response to KY1005

Additional Objectives

- To explore the effect of two regimes of KY1005 on additional physician assessments of AD activity/severity (EASI 50, EASI 75, EASI 90, validated Investigator Global Assessment (vIGA), SCORing of Atopic Dermatitis (SCORAD) Index and affected body surface area (BSA))
- To explore the effect of two regimes of KY1005 on patient-reported AD activity/severity (Patient Oriented Eczema Measure (POEM), Patient Oriented (PO) SCORAD, Dermatology Quality of Life Index (DLQI) and Numerical Rating Scale (NRS) for pruritus)
- To characterize the PK of KY1005
- To characterize the PD response of KY1005 including the anti-KY1005 antibody response
- To explore the durability of clinical response and safety up to 253 days from Baseline in patients who were defined as responders at Day 113;
- To characterize the PD response to KY1005

Primary Endpoints

- Percentage change in EASI from Baseline to Day 113
- Incidence of TEAEs

Additional Endpoints

- Percentage and absolute change from Baseline in EASI over time (Also analyzed for the responder group)
- Percentage of patients with at least a 50% reduction from Baseline in EASI (EASI 50) at Days 15, 29, 57, 85 and 113 (Also analyzed for the responder group)
- Percentage of patients with at least a 75% reduction from Baseline in EASI (EASI 75) at Days 15, 29, 57, 85 and 113 (Also analyzed for the responder group)
- Percentage of patients with at least a 90% reduction from Baseline in EASI (EASI 90) at Days 15, 29, 57, 85 and 113 (Also analyzed for the responder group)
- Percentage of patients with a response of vIGA 0 or 1 at Day 113 and over time (Also analyzed for the responder group)
- Change in affected BSA from Baseline to Day 113 and over time (Also analyzed for the responder group)
- Change in vIGA, SCORAD Index, POEM, PO-SCORAD, DLQI and NRS from Baseline to Day 113 and over time (Also analyzed for the responder group)
- For each patient (receiving KY1005) and for both KY1005 regimes:
  - Maximum observed serum concentration ($C_{max}$) following the first and fourth (third maintenance) infusions. Peak concentrations (end of infusion) following all infusions Time to maximum observed serum concentration ($t_{max}$) following the first and fourth infusions Trough concentration ($C_{min}$) following the first, second and third infusions and the concentration 28 days after the fourth infusion Area under the serum concentration-time curve (AUC) following the first (AUC extrapolated to infinity [$AUC_{0-inf}$]) and fourth (AUC in the dosing interval [$AUC_{0-28}$]) infusions Estimates of clearance (CL), apparent volume of distribution (Vd) and $t_{1/2}$ Anti-KY1005 antibody titer and number of patients with positive response (Also analyzed for the responder group)

Study Design

Figure 3:
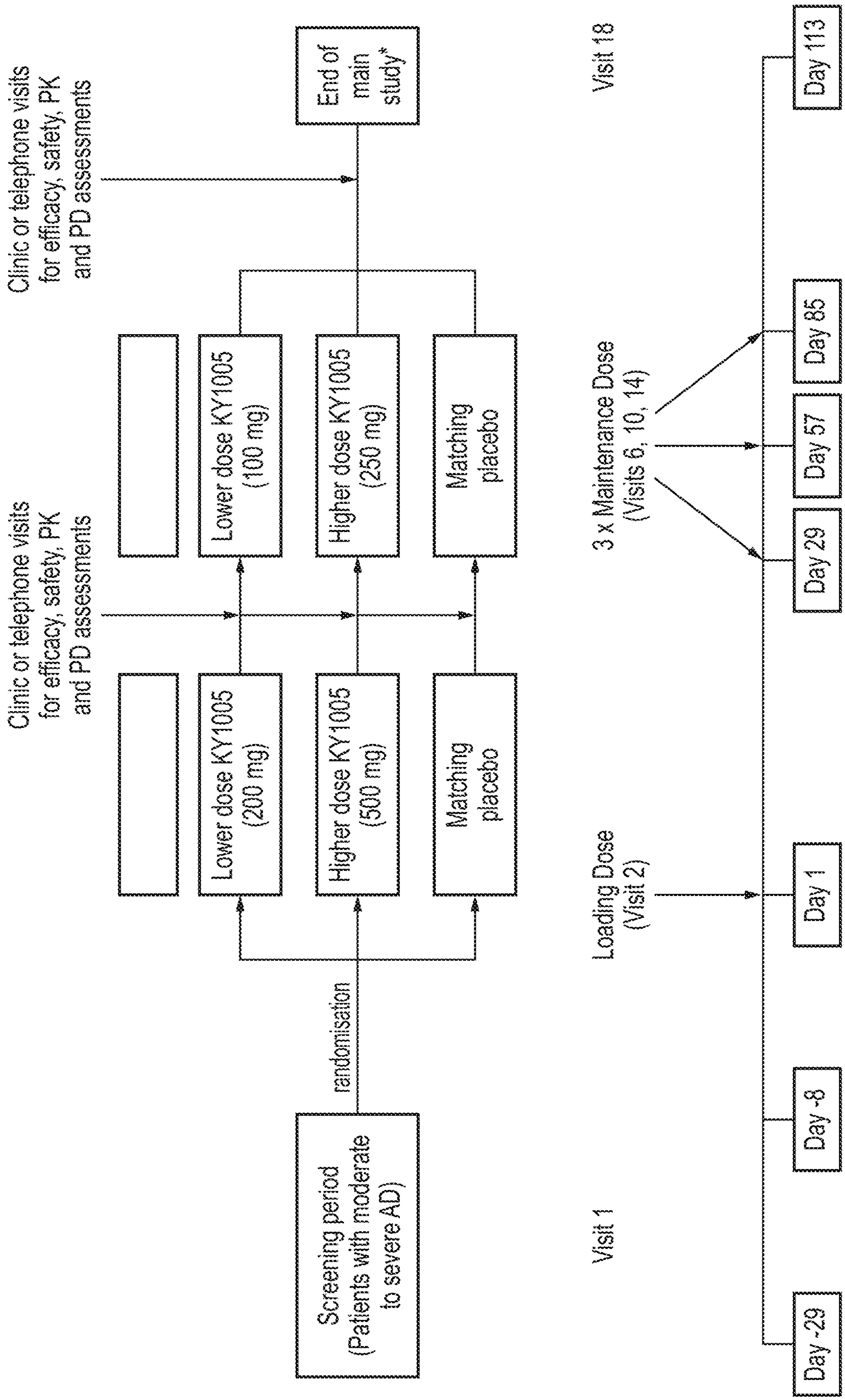
FIG. 3 graphically depicts the overview of study design of Example 2. Patients underwent Day 1/baseline assessments and were randomized in a 1:1:1 ratio to receive an intravenous (I.V.) injection of KY1005 at a low (200 mg) or high (500 mg) dose, followed by three maintenance doses at 50% of the loading dose at 28-day intervals on Days 29, 57 and 85, or matching placebo.

This was a phase Ha, randomized, double-blind, placebo-controlled, parallel group, multicenter study to explore the efficacy and safety of KY1005 in adult patients with moderate to severe AD who had a documented history, within 6 months prior to baseline, of either inadequate response to topical treatments or inadvisability of topical treatments. Approximately 84 patients aged 18 to 75 years were to be enrolled in the study with a study duration of up to 28 days for screening and then up to Day 113 for all patients in the main study. The overall study design is depicted in FIG. 3.

After providing informed consent, patients were assessed for study eligibility at the screening visit, which was completed within 28 days prior to randomization. During the Screening period, treatments for AD were washed out for at least 14 days prior to baseline (except bland moisturizers). Patients were required to apply bland moisturizers (emollients) with no additives (e.g., urea) at least twice daily for at least the 7 consecutive days before baseline and continued throughout the study.

Patients who continued to meet eligibility criteria at Baseline underwent Day 1/Baseline assessments and were randomized in a 1:1:1 ratio to receive an I.V. injection of KY1005 at a low (200 mg) or high (500 mg) dose, followed by three maintenance doses at 50% of the loading dose at 28-day intervals on Days 29, 57 and 85, or matching placebo.

Efficacy, safety, PK and PD assessments were performed at clinic or telephone visits at 7-day intervals from Day 1 through Day 113 (main study). To explore the safety and durability of effect for up to 253 days from baseline, all patients continued in the study extension (to Day 253 (Visit 23)), with assessments up to the time that they relapsed or commenced drugs that have significant impact on AD. Patients who had responded (vIGA 0/1) at Day 113 (Visit 18) assessment were required to continue with all assessments. Patients who did not respond (vIGA 2-4) were assessed for safety only.

The primary analysis occurred once all patients had completed Day 113 (or earlier/withdrawal). It was planned that patients would be discharged from this study no later than 253 days after administration of the loading dose.

Inclusion Criteria

1. Adults (>18 years but <75 years of age) with AD for 1 year or longer at Baseline (Day 1; prior to first administration of treatment).
2. EASI of 12 or higher at the Screening Visit and 16 or higher at Baseline.
3. vIGA of 3 or 4 at Baseline.
4. AD involvement of 10% or more of BSA at Baseline.
5. Documented history, within 6 months prior to Baseline, of either inadequate response to topical treatments or inadvisability of topical treatments.
6. Must have applied a stable dose of topical bland emollient (simple moisturiser, no additives [e.g., urea]) at least twice daily for at least 7 consecutive days before Baseline.

Exclusion Criteria

1. Treatment with any of the following prior to first KY1005 administration (Baseline):
   - Systemic corticosteroids and tacrolimus within 4 weeks
   - Systemic cyclosporin A within 3 weeks
   - Other systemic immunosuppressive or immunomodulatory drugs (including leukotriene inhibitors) within 3 months
   - Topical corticosteroids, tacrolimus or pimecrolimus, within 2 weeks
   - Prescription or non-prescription moisturisers with additives (e.g., urea, filaggrin) within 2 weeks
   - Phototherapy or allergen immunotherapy within 4 weeks
   - Dupilumab within 3 months
   - Investigational therapy for the treatment of other conditions within 5 half-lives or the limit of PD effects or 3 months where the apparent terminal half-life ($t_{1/2}$) is not known
2. Weight <40 kg or >120 kg at baseline (Other Inclusion and Exclusion Criteria available online at ClinicalTrials.gov, Identifier: NCT03754309)

Treatments Administered

All patients received a total of four I.V. infusions. For patients randomized to KY1005, patients in the high and low dose groups received a loading dose of 500 mg and 200 mg KY1005, respectively, on Day 1, followed by three maintenance doses at 50% of the loading dose at 28-day intervals on Days 29, 57 and 85. Patients randomized to the placebo group received four infusions of matching placebo on Days 1, 29, 57 and 85.

Identity of Investiaational Product(s)

KY1005 and matching placebo were presented as colourless or slightly yellow, clear to slightly opalescent sterile solutions filled to a nominal 10 mL volume in a 10 mL clear glass vial for I.V. administration from an infusion bag.

KY1005 was formulated at a concentration of 10 mg/mL.

The matching placebo contained identical components but without KY1005 and was also used to dilute KY1005 to the correct dose concentration in a fixed volume to maintain blinding.

The bulk supplies of drug and prepared doses were stored at 2° C. to 8° C. Prepared doses were to be used within 28 hours of preparation. The maximum period of storage at 2° C. to 8° C. was the first 24 hours; doses were then to be brought to room temperature for no more than four hours, prior to administration Selection of Doses in the Study A healthy volunteer study (as described in Example 1 above, KY1005-CT01) was conducted in which the repeat dose part involved a dosing strategy (loading/maintenance) comparable to the regime proposed for this study. The volunteers received an initial loading dose (0.15, 0.45, 1.35, 4.0 or 12 mg/kg) and two maintenance doses at 50% of the loading dose (0.075, 0.225, 0.675, 2.0 or 6.0 mg/kg, respectively), administered at 28-day intervals.

The PK evaluation revealed a consistent dose-proportional $C_{max}$ and $C_{min}$, with $t_{max}$ most often occurring at the end-of-infusion. At doses that encompassed the proposed 100 to 500 mg flat dose, CL was independent of dose and unaffected on repeat dosing. The healthy volunteer study involved dosing once every 28 days. Peak and trough concentrations on this strategy provided acceptable exposure throughout the dosing interval.

The PD assessments showed an immunomodulatory effect of KY1005 although there was no clear dose-response relationship. However, there was some indication that 0.15 mg/kg followed by two doses of 0.075 mg/kg was placebo-like in terms of the immunomodulatory effect. A pharmacological effect (as assessed by KLH TDAR and DTH) was seen at the higher dose regimes 0.45/0.225, 1.35/0.675, 4.0/2.0 and 12/6.0 mg/kg.

The two active treatment regimes in this study represent a more than two-fold difference in exposure in a range that has been shown to have PD effects on delayed type hyper sensitivity immune challenge to the skin in healthy volunteers. The I.V. route facilitated the administration of the proposed doses in a blinded design.

(Area Score) and then converted to a score of zero (none in that region) to 6 (>90% to 100% of the entire region affected.)

For each major section of the body (head, upper extremities, trunk and lower extremities), EASI score=(E+I+X+L)×Area Score. The total EASI score was the weighted total of the section EASI using the weights 10% (head), 20% (upper extremities), 30% (trunk) and 40% (lower extremities). The minimum possible EASI score was zero and the maximum possible EASI score was 72, where a higher score indicates increased extent and severity of AD.

Validated Investigator Global Assessment

The vIGA is a validated Investigator-lead assessment scale used to determine severity of AD and clinical response to treatment. As shown in Table 7, it is based on a 5-point scale, ranging from 0 (clear) to 4 (severe).

TABLE 7

Validated Investigator Global Assessment

| Score | Morphological description |
|---|---|
| 0—Clear | No inflammatory signs of atopic dermatitis (no erythema, no induration/papulation, no lichenification, no oozing/crusting). Post-inflammatory hyperpigmentation and/or hypopigmentation may be present. |
| 1—Almost clear | Barely perceptible erythema, barely perceptible induration/papulation, and/or minimal lichenification. No oozing or crusting. |
| 2—Mild | Slight but definite erythema (pink), slight but definite induration/papulation, and/or slight but definite lichenification. No oozing or crusting. |
| 3—Moderate | Clearly perceptible erythema (dull red), clearly perceptible induration/papulation, and/or clearly perceptible lichenification. Oozing and crusting may be present. |
| 4—Severe | Marked erythema (deep or bright red), marked induration/papulation, and/or marked lichenification. Disease is widespread in extent. Oozing or crusting may be present. |

Selection and Timing of Dose for Each Patient

Patients received KY1005 low dose (flat dose of 200 mg [loading dose]/100 mg [maintenance dose]), KY1005 high dose (flat dose of 500 mg [loading dose]/250 mg [maintenance dose]) or matching placebo (FIG. 3). The loading dose of KY1005 was followed 28 days later by three maintenance doses each given at further 28-day intervals. A loading dose followed by maintenance doses was expected to achieve steady state more rapidly in the target tissues, potentially allowing an earlier onset of effect.

Efficacy Assessments

The efficacy of KY1005 in the treatment of AD was assessed using change in EASI, vIGA, SCORAD Index and affected BSA. Investigator-performed assessments were carried out by the same assessor on each occasion for an individual patient. Patient-reported outcomes were assessed using the POEM, DLQI, PO-SCORAD Index and the NRS for pruritus. The POEM, PO-SCORAD, DLQI and NRS for pruritus were recorded by the patient using an internet-enabled device in their local language.

Eczema Area Severity Index

The EASI is an Investigator-assessed validated tool used to measure the extent (area) and severity of AD (Hanifin J M, et al. The eczema area and severity index (EASI): assessment of reliability in atopic dermatitis: EASI: assessment of reliability in AD. Exp Dermatol., 2001 Feb;10(1):11-8.)

The Investigator assessed the severity of four disease characteristics (erythema (E), induration/papulation (I), excoriation (X) and lichenification (L)) on a scale of zero (absent) to 3 (severe). In addition, the extent of involvement of four body sites (head/neck, trunk, upper extremities and lower extremities) was assessed as a percentage of BSA SCORing of Atopic Dermatitis (SCORAD) Index The SCORAD Index is a validated clinical tool that was developed to standardize the evaluation of the extent and severity of AD (Severity Scoring of Atopic Dermatitis: The SCORAD Index. Dermatology. 1993; 186(1):23-31.)

To determine the extent of AD, the affected area (A) as a percentage of the whole body was determined, with a maximum score of 100% (head and neck (9%), upper limbs (9% each), lower limbs (18% each), anterior trunk (18%), back (18%), genitals (1%). The severity (B) of six specific symptoms of AD (redness, swelling, oozing/crusting, scratch marks, skin thickening [lichenification], dryness [area where there was no inflammation]) was assessed on a 4-point scale, with a maximum score of 18: none (0), mild (1), moderate (2) or severe (3). Subjective symptoms (i.e., itch and sleeplessness; C) were recorded as scored by the patient or relative on a visual analogue scale, where 0 was no itch (or sleeplessness) and 10 was the worst imaginable itch (or sleeplessness), with a maximum possible score of 20. The SCORAD score for each patient was calculated as: A/5+7B/2+C.

Body Surface Area (BSA) Involvement of Atopic Dermatitis

The BSA affected by AD was assessed for each major section of the body (head, trunk, upper extremities and lower extremities) and was reported as a percentage of the total from each body section. The total BSA involvement was derived from the sum of each body section.

Patient Oriented Eczema Measure (POEM)

The POEM is a tool used for monitoring atopic eczema severity. It focuses on the illness as experienced by the patient and was completed using an internet-enabled device. The questionnaire consisted of seven questions pertaining to the symptoms of AD and their frequency. Scores were based on a scale of zero (no days) to 4 (every day in the last week) for each question, with a maximum score of 28 possible for all questions. A POEM total score was correlated to eczema severity (0-2 [clear or almost clear], 3-7 [mild], 8-16 [moderate], 17-24 [severe], 25-28 [very severe].)

Patient Oriented—SCORing of Atopic Dermatitis Index (PO-SCORAD)

The PO-SCORAD Index is a validated self-assessment score that allows the patient to comprehensively evaluate the actual course of AD, using subjective and objective criteria derived mainly from the SCORAD Index (Stalder J-F, et al., Patient-Oriented SCORAD (PO-SCORAD): a new self-assessment scale in atopic dermatitis validated in Europe: PO-SCORAD self-assessment scale validation, Allergy, 2011 Aug;66(8):1114-21.) An internet-enabled device was used to complete the PO-SCORAD Index. The total PO-SCORAD score was calculated as the sum of the surface area score, intensity score and subjective symptom score, and was interpreted as mild (<20), moderate (>20 to 540) and severe (>40).

Dermatology Quality of Life (QoL) Index (DLQ1)

The DLQI is a dermatology-specific QoL instrument and is a simple, validated questionnaire. The instrument consists of ten questions pertaining to the effect of AD on QoL. Scores were based on a scale of zero (not at all/not relevant/question unanswered) to 3 (very much/prevented work or studying), with a maximum score of 30 possible for all questions. The total score was correlated to the detrimental effect of AD on QoL (0-1 [no effect at all on patient's life], 2-5 [small effect], 6-10 [moderate effect], 11-20 [very large effect] and 21-30 [extremely large effect].)

Numerical Rating Scale (NRS) for Pruritus

The NRS for pruritus is an assessment tool that was used to assess the patient's worst itch as a result of their AD in the previous 24 hours. This was recorded daily, ideally in the morning, using an internet-enabled device with patients asked, "On a scale of "0" (no itch) to "10" (worst imaginable itch), how was your worst itch in the past 24 hours?"

Pharmacokinetic Assessments

Serum concentrations of KY1005 were assessed in blood samples taken during the study using a validated ELISA bioanalytical method.

At least two samples for serum concentration of KY1005 were withdrawn on infusion days. Samples for serum concentration of KY1005 were also withdrawn on non-infusion days.

Samples were analyzed, unblinded

Pharmacokinetic Parameter Derivation

In the main study, the following PK values were derived for each patient (receiving KY1005) and for both KY1005 regimes. In the study extension, the following PK values were determined from individual concentration-time data of KY1005 in serum for both KY1005 treatment groups by non-compartmental analysis using the actual, exact blood sampling times based on the PK Population:

$C_{max}$ following the first and fourth (third maintenance) infusions.

$t_{max}$ following the first and fourth infusions.

$C_{min}$ following the first, second, third and fourth infusions.

Concentration of KY1005 45 minutes after the start of all infusions ('peak concentrations').

$AUC_{0-28}$ following the first and fourth infusions.

$AUC_{0-inf}$ following the first and fourth infusions.

AUC percentage extrapolated area ($AUC_{extrap[\%]}$) following the first and fourth infusion.

Terminal rate constant (λz) following the first infusion $t_{1/2}$ following the first and fourth infusions CL (mL/day) for the fourth infusion.

Vd (L) for the fourth infusion.

λz for the fourth infusion.

Average concentration after the fourth infusion.

Fluctuation (%) after the fourth infusion.

Expected accumulation index after the fourth infusion.

Blood Samples for Assessment of Serum Anti-Drug Antibodies

Serum titers of anti-KY1005 antibodies were assessed in blood samples taken during the study using a validated semi-quantitative ECLIA bioanalytical method. Samples were analyzed, unblinded.

Disposition of Patients

A total of 89 patients were randomized in the study, comprising 29, 30 and 30 patients in the KY1005 low dose, KY1005 high dose and placebo groups, respectively. One patient in the placebo group terminated the study early due to a protocol deviation and did not receive study treatment. Of the 88 treated patients, 20 (69.0%), 22 (73.3%) and 17 (58.6%), respectively, completed the main study (up to Day 113). Three patients terminated the study early due to AEs, all of whom were in the placebo group. The remaining reasons for early termination were withdrawal of consent (six, five and three patients in the KY1005 low dose, KY1005 high dose and placebo groups, respectively), 'Other' reasons (two, three and five patients, respectively) pertaining to issues with data from Site 216 and failure to meet randomization criteria (one patient in the KY1005 low dose group). Overall, 17 (58.6%), 19 (63.3%) and 14 (48.3%) patients in the KY1005 low dose, KY1005 high dose and placebo groups, respectively, completed the study extension (up to Day 253).

Baseline Disease Characteristics

Disease characteristics at Baseline are summarized for the FAS in Table 8. Baseline disease characteristics were as expected for a population of patients with moderate to severe AD and were generally well matched across the treatment groups. The number of patients in the FAS with a vIGA score of 4 (severe) was higher in the placebo group (15 [62.5%] patients) compared to the KY1005 groups (10 [37.0%] and 9 [33.3%] in the low and high dose groups, respectively). There were no other notable differences between treatment groups in baseline disease characteristics, including affected BSA, EASI, SCORAD, NRS for pruritus and prior exposure to dupilumab.

TABLE 8

Baseline Disease Characteristics (FAS)

| Characteristic | Parameter | KY1005 Low Dose (N = 27) | KY1005 High Dose (N = 27) | Placebo (N = 24) |
|---|---|---|---|---|
| Affected BSA (%) | Mean (SD) | 55.6 (20.82) | 47.6 (19.17) | 52.5 (20.62) |
| | Median | 51.5 | 40.5 | 55.3 |

TABLE 8-continued

| Baseline Disease Characteristics (FAS) | | | | |
|---|---|---|---|---|
| Characteristic | Parameter | KY1005 Low Dose (N = 27) | KY1005 High Dose (N = 27) | Placebo (N = 24) |
| EASI | Mean (SD) | 32.9 (12.82) | 28.4 (11.54) | 32.8 (14.46) |
| | Median | 29.8 | 24.1 | 28.9 |
| EASI >21 at Baseline | n (%) | 21 (77.8%) | 20 (74.1%) | 18 (75.0%) |
| SCORAD | Mean (SD) | 69.0 (12.36) | 66.2 (11.62) | 67.6 (15.51) |
| | Median | 68.7 | 63.8 | 64.2 |
| vIGA score of 4 | n (%) | 10 (37.0%) | 9 (33.3%) | 15 (62.5%) |
| NRS for pruritus (itch) | Mean (SD) | 6.9 (2.32) | 6.7 (2.19) | 7.4 (1.60) |
| | Median | 7.5 | 7.0 | 8.0 |
| Dupilumab prior exposure | n (%) | 0 | 0 | 1 (4.2%) |

SD = standard deviation

Primary Efficacy Endpoint

Figure 4:
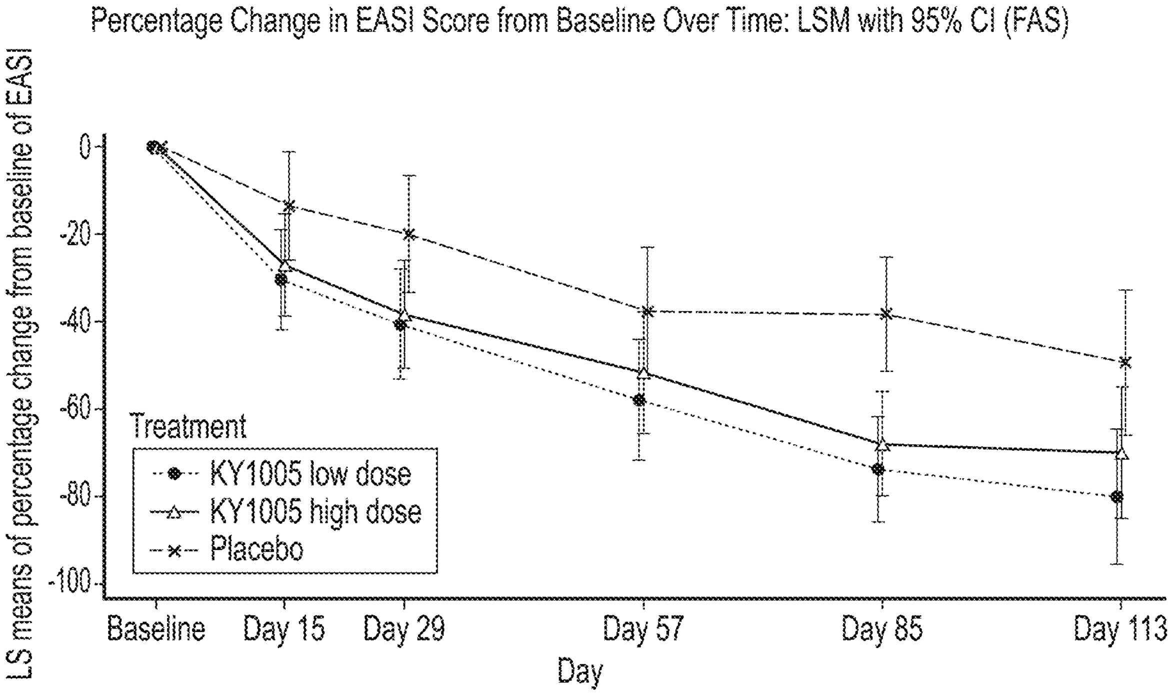
FIG. 4 graphically depicts percentage change in EASI score from baseline over time illustrated using LSM with 95% confidence interval (CI). Reductions in EASI score from baseline to Day 113 in the FAS were observed across all treatment groups, including placebo. Greater reductions were observed in the KY1005 groups.

The primary efficacy endpoint was the percentage change in EASI from baseline to Day 113. An overall summary of the percentage change in EASI score from Baseline to Day 113 is provided in Table 9 (FAS and Per Protocol Set (PPS)), and percentage change in EASI score from Baseline over time is illustrated using least square mean (LSM) with 95% CI in FIG. 4. Reductions in EASI score from Baseline to Day 113 in the FAS were observed across all treatment groups, including placebo. However, greater reductions were observed in the KY1005 groups (LSM percentage change [95% CI] from Baseline, −80.12 [−95.55, −64.68] and −69.97 [−85.04,−54.60] for the low and high dose groups, respectively) compared to placebo (−49.37 [−66.02, −32.72]). This difference versus placebo was nominally statistically significant for the KY1005 low dose group (difference in LSM [95% CI], −30.75 [−53.43, −8.06]; p=0.009) but not for the high dose group (difference in LSM [95% CI], −20.60 [−43.08, 1.88]; p=0.072). Thus, an effect in the KY1005 treatment groups versus placebo was observed from Day 15 and was maintained until Day 113.

For the PPS, the change from Baseline to Day 113 in EASI score across all treatment groups was similar to that observed for the FAS (Table 9). As was observed for the FAS, greater reductions were observed in the KY1005 groups compared to placebo, and this difference versus placebo was nominally statistically significant for the KY1005 low dose group (difference in LSM [95% CI], −28.03 [−51.36, −4.70]; p=0.019) but not for the high dose group (difference in LSM [95% CI], −17.58 [−40.76, 5.60]; p=0.135).

The mixed model for repeated measures (MMRM) was performed on the PPS with the exclusion of one patient in the KY1005 high dose group to assess the impact of the exclusion of this patient in the PPS due to a protocol deviation. As observed for the FAS, greater reductions were observed in the KY1005 groups compared to placebo, and this difference versus placebo was nominally statistically significant for the KY1005 low dose group (difference in LSM [95% CI], −28.01 [−51.33, −4.69]; p=0.019) but not for the high dose group (difference in LSM [95% CI],−17.01 [−40.20, 6.19]; p=0.148). No clinically relevant differences were observed when the sensitivity analysis was compared with the original PPS data.

When Baseline EASI stratum (EASI:21, EASI>21) was considered as a covariate, the change from Baseline to Day 113 in EASI score across all treatment groups was similar to that observed in the FAS for the primary analysis. Of note, three patients were randomized to the wrong EASI stratification due to their Baseline EASI values being changed after randomization. These patients were analyzed in the EASI subgroup analysis according to their planned stratification. As was observed for the primary analysis, greater reductions were observed in the KY1005 groups compared to placebo, and this difference versus placebo was nominally statistically significant for the KY1005 low dose group (difference in LSM [95% CI], −30.55 [−53.33, −7.77]; p=0.009) but not for the high dose group (difference in LSM [95% CI], −21.23 [−43.76, 1.31]; p=0.064). As documented in the

TABLE 9

| Percentage Change in EASI Score from Baseline to Day 113 MMRM (FAS and PPS) | | | | | | | |
|---|---|---|---|---|---|---|---|
| | | FAS | | | PPS | | |
| | Parameter | KY1005 Low Dose (N = 27) | KY1005 High Dose (N = 27) | Placebo (N = 24) | KY1005 Low Dose (N = 27) | KY1005 High Dose (N = 27) | Placebo (N = 21) |
| Day 113 | N | 118 | 120 | 101 | 118 | 120 | 88 |
| | LSM (95% CI) | −80.12 (−95.55, −64.68) | −69.97 (−85.04, −54.90) | −49.37 (−66.02, −32.72) | −80.41 (−95.73, −65.08) | −69.95 (−85.00, −54.90) | −52.37 (−69.96, −34.76) |
| | Differences in LSM, estimate (SE) [95% CI] | −30.75 (11.38) [−53.43, −8.06] | −20.60 (11−27) [−43.08, 1.88] | | −28.03 (11.69) [−51.36, −4.70] | −17.58 (11.62) [−40.76, 5.60] | |
| | P-value | 0.009 | 0.072 | | 0.019 | 0.135 | |

CI = confidence interval;
N = number of observations used;
SE = standard error.

Statistical Analysis Plan (SAP), the MMRM with country effect was not performed due to an insufficient number of patients per country.

The MMRM analysis of percentage change in EASI score was performed with the addition of rescue medication within the first month (yes/no) and rescue medication-by-treatment as fixed effects in the FAS to understand any impact of protocol permitted rescue use in the first 30 days. This analysis showed similar change from baseline to Day 113 in EASI score across all treatment groups to that observed for the primary analysis. As was observed for the primary analysis, greater reductions were observed in the KY1005 groups compared to placebo. This difference versus placebo was nominally statistically significant for both the KY1005 low dose group (difference in LSM [95% CI], −37.53 [−65.43, −9.63]; p=0.009) and high dose group (difference in LSM [95% CI], −28.43 [−56.35, −0.50]; p=0.046).

Secondary Efficacy Endpoints

The main secondary efficacy endpoint was the percentage and absolute change from baseline in EASI over time. A summary of the change in EASI score from baseline to Days 15, 29, 57, 85, 113 and the early termination visit in EASI score is summarized by treatment group in Table 10 for the FAS.

Progressive reductions in EASI score from Baseline to Days 15, 29, 57 and 85 (and Day 113) were observed across all treatment groups, including placebo. However, greater reductions were observed in the KY1005 groups compared to placebo at all time points.

TABLE 10

Change in EASI Score from Baseline to Days 15, 29, 57, 85, 113, and Early Termination Visit (FAS)

| | Parameter | KY1005 Low Dose | KY1005 High Dose | Placebo |
|---|---|---|---|---|
| Baseline | n | 27 | 27 | 24 |
| EASI Score | Mean (SD) | 32.87 (12.819) | 28.44 (11.536) | 32.77 (14.463) |
| | 95% CI | 27.80, 37.95 | 23.87, 33.00 | 26.66, 38.88 |
| | Median | 29.80 | 24.10 | 28.90 |
| | Min, max | 16.4, 63.6 | 16.1, 61.0 | 16.3, 65.7 |
| Day 15 | n | 26 | 25 | 21 |
| EASI score absolute | Mean (SD) | −10.67 | −9.55 (11.655) | −3.27 (8.834) |
| change from Baseline | 95% CI | −15.34, −6.00 | −14.36, −4.74 | −7.29, 0.75 |
| | Median | −7.50 | −8.90 | −3.60 |
| | Min, max | −37.6, 10.4 | −42.2, 12.3 | −22.2, 18.8 |
| EASI score percentage | Mean (SD) | −30.58 | −28.94 (33.753) | −15.16 (26.895) |
| change from Baseline | 95% CI | −40.46, −20.71 | −42.87, −15.00 | −27.40, −2.91 |
| | Median | −30.35 | −34.20 | −13.50 |
| | Min, max | −84.7, 22.0 | −92.5, 55.7 | −60.1, 48.2 |
| Day 29 | n | 25 | 26 | 22 |
| EASI score absolute | Mean (SD) | −15.64 | −11.32 (11.549) | −6.33 (8.356) |
| change from Baseline | 95% CI | −21.37, −9.92 | −15.98, −6.65 | −10.03, −2.62 |
| | Median | −13.20 | −10.40 | −6.90 |
| | Min, max | −45.9, 8.1 | −39.0, 13.9 | −23.7, 10.2 |
| EASI score percentage | Mean (SD) | −42.07 (28.495) | −37.29 (36.978) | −20.76 (28.318) |
| change from Baseline | 95% CI | −53.83, −30.31 | −52.22, −22.35 | −33.32, −8.21 |
| | Median | −43.20 | −40.10 | −22.85 |
| | Min, max | −89.0, 33.8 | −92.9, 72.0 | −68.2, 41.5 |
| Day 57 | n | 24 | 23 | 19 |
| EASI score absolute | Mean (SD) | −19.13 (14.343) | −17.45 (13.330) | −12.18 (10.436) |
| change from Baseline | 95% CI | −25.19, −13.08 | −23.21, −11.68 | −17.21, −7.15 |
| | Median | −17.20 | −11.90 | −11.70 |
| | Min, max | −51.7, 18.4 | −57.8, −0.1 | −39.4, 4.3 |
| EASI score percentage | Mean (SD) | −58.07 (32.798) | −56.77 (26.880) | −38.43 (26.516) |
| change from Baseline | 95% CI | −71.92, −44.22 | −68.40, −45.15 | −51.21, −25.65 |
| | Median | −68.45 | −52.70 | −32.40 |
| | Min, max | −98.6, 42.1 | −96.6, −0.6 | −82.4, 13.5 |
| Day 85 | n | 22 | 23 | 18 |
| EASI score absolute | Mean (SD) | −24.90 (12.588) | −21.43 (13.533) | −10.98 (9.768) |
| change from Baseline | 95% CI | −30.49, −19.32 | −27.28, −15.58 | −15.84, −6.12 |
| | Median | −24.10 | −18.40 | −10.30 |
| | Min, max | −46.6, 3.5 | −61.0, −5.3 | −29.4, 4.3 |
| EASI score percentage | Mean (SD) | −74.45 (23.790) | −71.06 (26.425) | −38.94 (30.860) |
| change from Baseline | 95% CI | −85.00, −63.90 | −82.49, −59.63 | −54.29, −23.60 |
| | Median | −76.85 | −75.80 | −36.45 |
| | Min, max | −100.0, 8.0 | −100.0, −21.5 | −92.6, 13.5 |
| Day 113 | n | 20 | 22 | 16 |
| EASI score absolute | Mean (SD) | −25.97 (14.803) | −21.95 (14.132) | −15.50 (11.719) |
| change from Baseline | 95% CI | −32.89, −19.04 | −28.21, −15.68 | −21.74, −9.26 |
| | Median | −24.85 | −21.30 | −15.40 |
| | Min, max | −48.9, 14.2 | −61.0, 12.1 | −32.0, 8.4 |
| EASI score percentage | Mean (SD) | −79.66 (29.755) | −74.11 (32.875) | −55.21 (38.820) |
| change from Baseline | 95% CI | −93.56, −65.73 | −88.69, −59.54 | −75.90, −34.53 |
| | Median | −89.45 | −79.20 | −63.35 |
| | Min, max | −100.0, 32.5 | −100.0, 50.4 | −100.0, 43.9 |
| Early Termination Main Study | n | 1 | 1 | 5 |
| EASI score absolute | Mean (SD) | −12.90 (—) | 19.90 (—) | −8.30 (9.443) |
| change from Baseline | 95% CI | — | — | −20.02, 3.42 |
| | Median | −12.90 | 19.90 | −13.40 |
| | Min, max | −12.9, −12.9 | 19.9, 19.9 | −18.0, 3.1 |

TABLE 10-continued

| Change in EASI Score from Baseline to Days 15, 29, 57, 85, 113, and Early Termination Visit (FAS) | | | | |
|---|---|---|---|---|
| | Parameter | KY1005 Low Dose | KY1005 High Dose | Placebo |
| EASI score percentage change from Baseline | Mean (SD) | −72.50 (—) | 103.10 (—) | −24.58 (32.572) |
| | 95% CI | — | — | −65.02, 15.86 |
| | Median | −72.50 | 103.10 | −22.10 |
| | Min, max | −72.5, −72.5 | 103.1, 103.1 | −71.0, 9.7 |

CI = confidence interval; Max = maximum; Min = Minimum; SD = standard deviation.

Percentage of Patients with at least 50%, 75% and 90% Reduction from Baseline in EASI (EASI50, EASI75 and E45190) at Days 15, 29, 57, 85 and 113

Figure 5A:
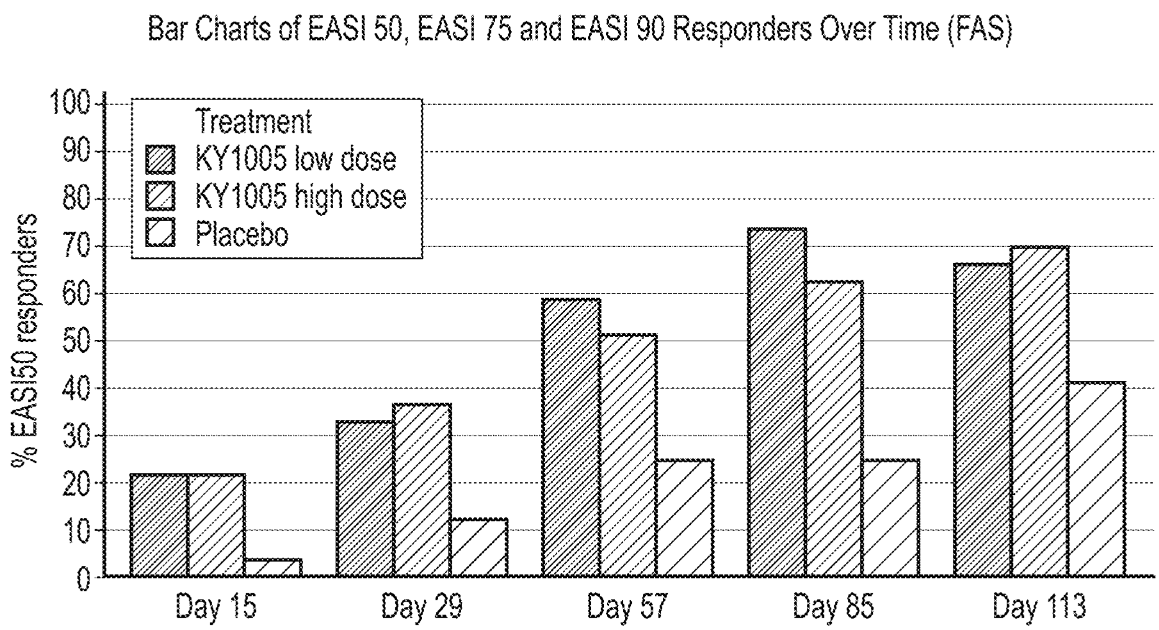
FIG. 5A-5C graphically depict EASI 50 (FIG. 5A), EASI 75 (FIG. 5B) and EASI 90 (FIG. 5C) responders over time. Progressive increases in the percentages of patients with at least a 50%, 75% and 90% reduction from baseline in EASI were generally observed across all treatment groups, including placebo. The percentages were greater in the KY1005 groups compared to placebo at all time points (with the exception of EASI 90 at Days 15 and 29, where percentages were zero for both the KY1005 low dose and placebo groups). Black represents KY1005 dose of 200 mg/100 mg; grey represents KY1005 dose of 500 mg/250 mg; and white represents placebo.
Figure 5B:
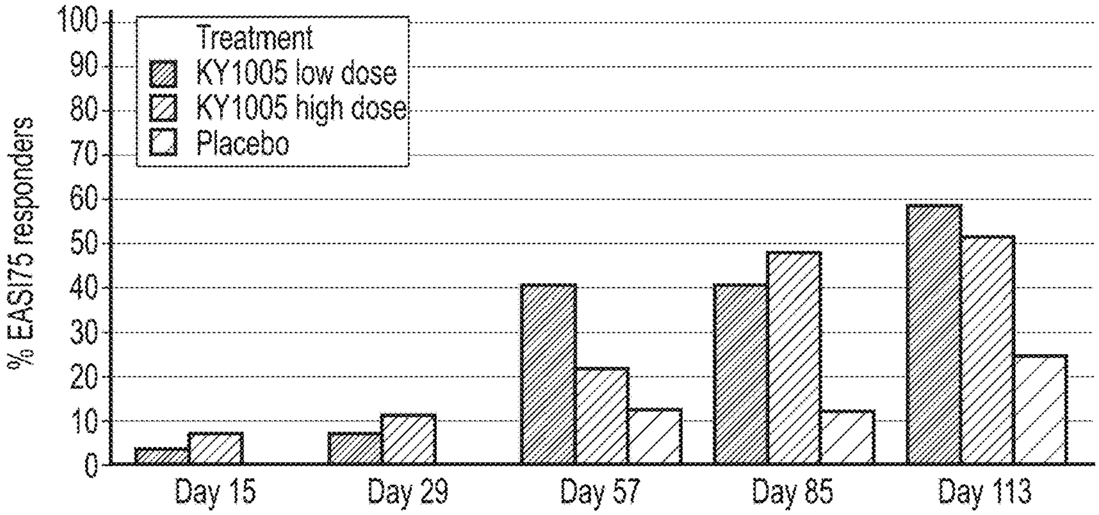
Figure 5C:
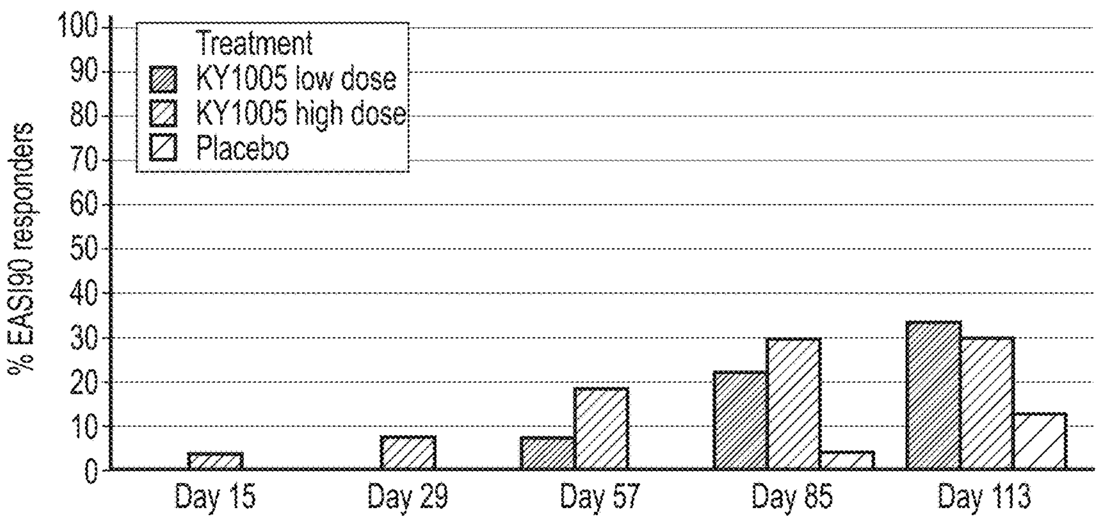

Bar charts illustrating EASI 50, EASI 75 and EASI 90 responders over time are presented in FIG. 5A-C. For this analysis, the values from early termination visits were assigned to the closest visit using the actual day on which the early termination visit was performed. If the closest visit was a visit that was performed, the value of the early termination was assigned to the next following visit.

Progressive increases in the percentages of patients with at least a 50%, 75% and 90% reduction from baseline in EASI were generally observed across all treatment groups, including placebo. However, the percentages were greater in the KY1005 groups compared to placebo at all time points (with the exception of EASI 90 at Days 15 and 29, where percentages were zero for both the KY1005 low dose and placebo groups).

For EASI 50, percentages were approximately 22% and 22% in the KY1005 low and high dose groups, respectively, versus 4% in the placebo group at Day 15; 33% and 37% (KY1005 groups) versus 13% (placebo) at Day 29; 59% and 52% (KY1005 groups) versus 25% (placebo) at Day 57; 74% and 63% (KY1005 groups) versus 25% (placebo) at Day 85; and 67% and 70% (KY1005 groups) versus 42% (placebo) at Day 113.

For EASI 75, percentages were approximately 4% and 7% in the KY1005 low and high dose groups, respectively, versus 0% in the placebo group at Day 15; 7% and 11% (KY1005 groups) versus 0% (placebo) at Day 29; 41% and 22% (KY1005 groups) versus 13% (placebo) at Day 57; 41% and 48% (KY1005 groups) versus 13% (placebo) at Day 85; and 59% and 52% (KY1005 groups) versus 25% (placebo) at Day 113.

For EASI 90, percentages were approximately 0% and 4% in the KY1005 low and high dose groups, respectively, versus 0% in the placebo group at Day 15; 0% and 7% (KY1005 groups) versus 0% (placebo) at Day 29; 7% and 19% (KY1005 groups) versus 0% (placebo) at Day 57; 22% and 30% (KY1005 groups) versus 4% (placebo) at Day 85; and 33% and 30% (KY1005 groups) versus 13% (placebo) at Day 113.

Figure 6A:
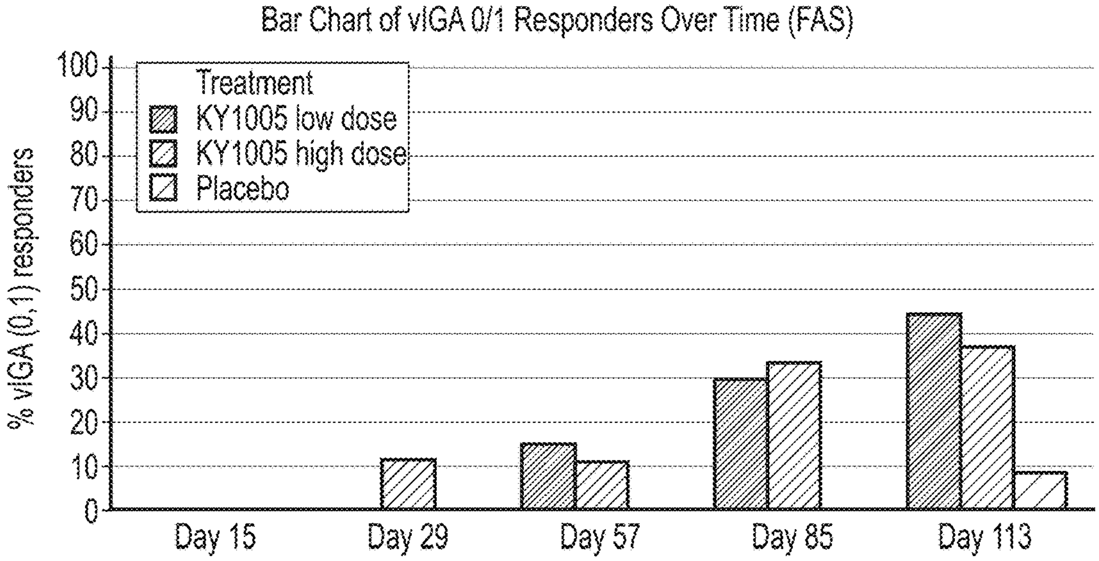
FIG. 6A graphically depicts vIGA 0 (clear) and 1 (almost clear) responders over time. Progressive increases in the percentages of vIGA 0/1 responders over time were generally observed in the KY1005 treatment groups, but not in the placebo group. By Day 113, the percentage of vIGA 0/1 responders was 44.4% (12/27) and 37.0% (10/27) in the KY1005 low and high dose groups, respectively, compared with 8.3% (2/24) in the placebo group. Grey represents KY1005 dose of 200 mg/100 mg; black represents KY1005 dose of 500 mg/250 mg; and white represents placebo.
Figure 6B:
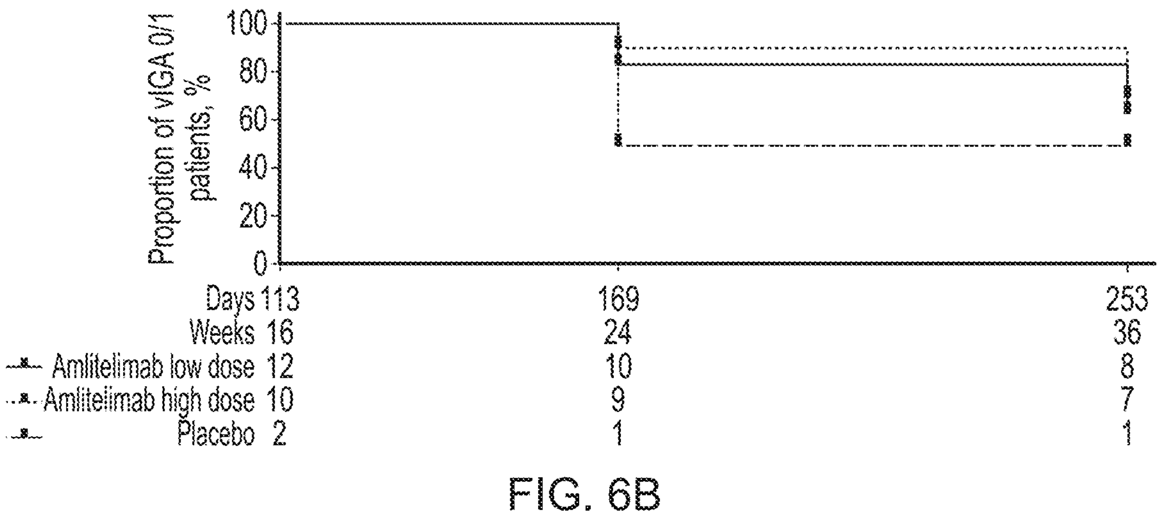
FIG. 6B graphically depicts the proportion of responders maintaining vIGA 0/1 over the study extension. vIGA, validated Investigator Global Assessment.
Figure 6C:
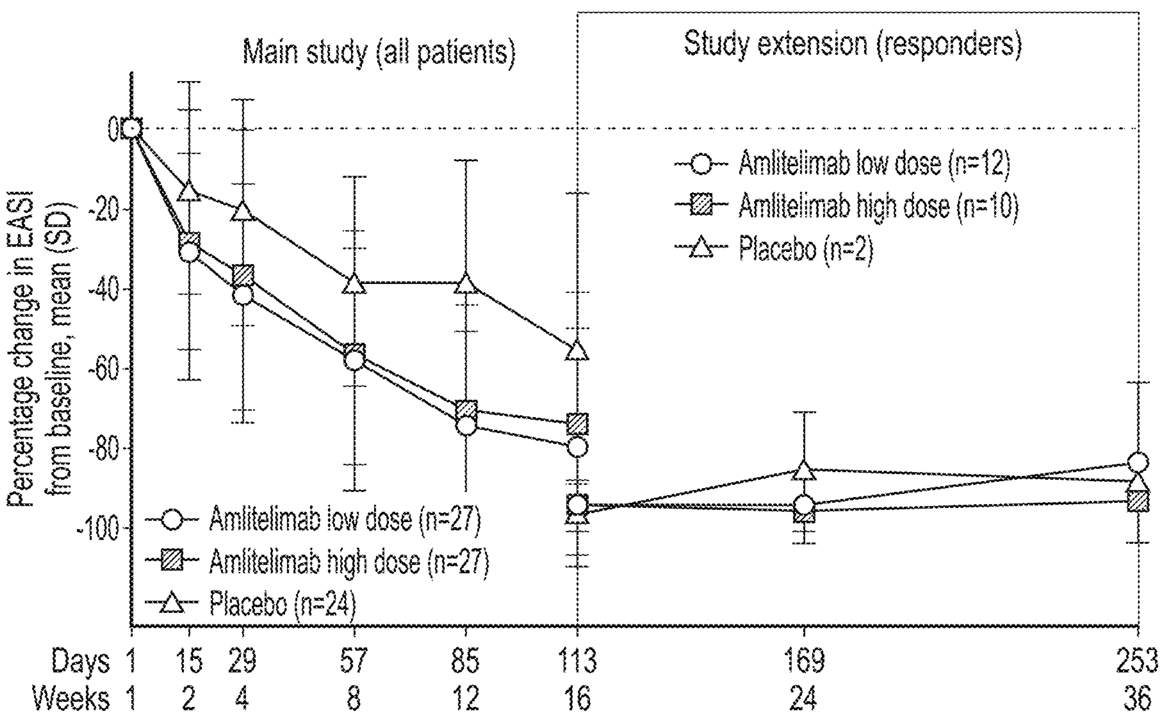
FIG. 6C graphically depicts percentage change in EASI over time. *Final dose administered at Week 12. EASI, Eczema Area and Severity Index; SD, standard deviation.

Percentage of Patients with a Response of 0 ('Clear') or 1 ('Almost Clear') at Day 113 and Over Time in vIGA Between Treatment Regimens The percentage of patients with a response of 0 (clear) or 1 (almost clear) in vIGA at Days 15, 29, 57, 85 and 113, with corresponding analysis using a Cochran-Mantel-Haenszel test, is summarized for the FAS in Table 11. A bar chart of vIGA 0/1 responders over time is presented in FIG. 6. For this analysis, the values from early termination visits were assigned to the closest visit using the actual day on which the early termination visit was performed. If the closest visit was a visit that was performed, the value of the early termination was assigned to the next following visit.

Progressive increases in the percentages of vIGA 0/1 responders over time were generally observed in the KY1005 treatment groups, but not in the placebo group. By Day 113, the percentage of vIGA 0/1 responders was 44.4% (12/27) and 37.0% (10/27) in the KY1005 low and high dose groups, respectively, compared with 8.3% (2/24) in the placebo group. Thus, treatment with KY1005 was associated with nominally statistically significant increased numbers of vIGA 0/1 responders compared to placebo (Cochran-Mantel-Haenszel $p<0.001$ for both the low and high dose groups).

FIG. 7 represents all patients who achieved a vIGA0/1 at Week 16 and were assessed for efficacy during the safety follow up period. The scores within the table are the EASI scores at each visit. This figure shows that in those subjects who achieved vIGA0/1 at day 113, there was evidence of long and sustained response up to 5.5 months following last dose (~70% of those receiving KY1005).

TABLE 11

| Percentage of Patients with a Response of 0 (Clear) or 1 (Almost Clear) in vIGA at Days 15, 29, 57, 85 and 113 (FAS) | | | | | | | |
|---|---|---|---|---|---|---|---|
| | Time | KY1005 Low Dose (N = 27) | | KY1005 High Dose (N = 27) | | Placebo (N = 24) | |
| Parameter | Point | n (%) | 95% CI | n (%) | 95% CI | n (%) | 95% CI |
| vIGA of 0 (Clear) or 1 (Almost clear) | Day 15 | 0 (0.0%) | 0.00, 0.00 | 0 (0.0%) | 0.00, 0.00 | 0 (0.0%) | 0.00, 0.00 |
| | Day 29 | 0 (0.0%) | 0.00, 0.00 | 3 (11.1%) | 0.00, 22.97 | 0 (0.0%) | 0.00, 0.00 |
| | Day 57 | 4 (14.8%) | 1.42, 28.21 | 3 (11.1%) | 0.00, 22.97 | 0 (0.0%) | 0.00, 0.00 |
| | Day 85 | 8 (29.6%) | 12.41, 46.85 | 9 (33.3%) | 15.55, 51.11 | 0 (0.0%) | 0.00, 0.00 |
| | Day 113 | 12 (44.4%) | 25.70, 63.19 | 10 (37.0%) | 18.82, 55.25 | 2 (8.3%) | 0.00,19.39 |
| Cochran-Mantel-Haenszel test versus placebo | | <0.001 | | <0.001 | | | |

CI = confidence interval

Change in vIGA from Baseline to Day 113 and Over Time

All patients had a vIGA of 3 (moderate) or 4 (severe) at Baseline, in line with the study inclusion criteria. Of note, the number of patients with a vIGA score of 4 (severe) at baseline was higher in the placebo group (15 [62.5%] patients) compared to the KY1005 groups (10 [37.0%] and 9 [33.3%] in the low and high dose groups, respectively).

Progressive improvements in vIGA from Baseline to Days 15, 29, 57, 85 and 113 were observed across all treatment groups, including placebo. However, the improvements were generally more pronounced in the KY1005 groups compared to placebo. For example, at Day 15, shifts in vIGA from 4 (severe) to 3 (moderate) were reported for 70.0% and 66.7% of the patients in the KY1005 low and high dose groups, respectively, compared with 25.0% of the patients in the placebo group. At Day 113, shifts in vIGA from 4 (severe) to 3 (moderate), 2 (mild), 1 (almost clear) and 0 (clear), respectively, were reported for 12.5%, 12.5%, 50.0% and 12.5% of the patients in the KY1005 low dose group and 12.5%, 12.5%, 37.5% and 12.5% of the patients in the KY1005 high dose group, compared with 37.5%, 37.5%, 0% and 0% of the patients in the placebo group. Greater improvements in vIGA in the KY1005 groups compared to placebo were similarly seen for patients with a vIGA of 3 (moderate) at baseline.

Change in SCORAD Index from Baseline to Day 113 and Over Time

Figure 8:
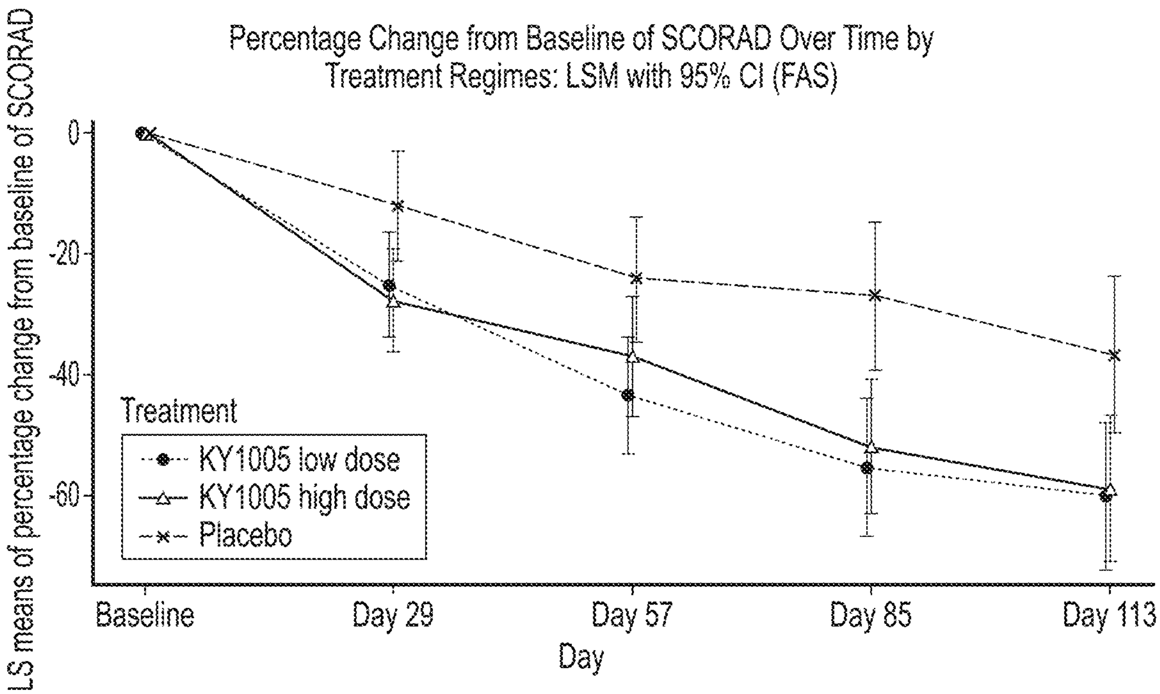
FIG. 8 graphically depicts the percentage change from Baseline in SCORAD Index between treatment regimens (MMRM analysis). Progressive reductions in SCORAD Index from Baseline to Days 29, 57, 85 and 113 were observed across all treatment groups, including placebo. However, greater reductions were observed in the KY1005 groups compared to placebo at all time points: LSM percentage change (95% CI) in SCORAD Index at Day 113 was −60.30 (−72.57, −48.04) and −58.96 (−71.04, −46.87) for the KY1005 low and high dose groups, respectively, compared to placebo (−36.79 [−49.94, −23.65]).

Analysis of the percentage change from baseline in SCORAD Index between treatment regimens (MMRM analysis) is presented in Table 12 and FIG. 8. Progressive reductions in SCORAD Index from Baseline to Days 29, 57, 85 and 113 were observed across all treatment groups, including placebo. However, greater reductions were observed in the KY1005 groups compared to placebo at all time points: LSM percentage change (95% CI) in SCORAD Index at Day 113 was −60.30 (−72.57, −48.04) and −58.96 (−71.04, −46.87) for the KY1005 low and high dose groups, respectively, compared to placebo (−36.79 [−49.94, −23.65]). These differences versus placebo were nominally statistically significant for both the KY1005 low dose group (difference in LSM [95% CI], −23.51 [−41.50, −5.52]; p=0.011) and the KY1005 high dose group (difference in LSM [95% CI], −22.16 [−40.00, −4.32]; p=0.016). Thus, an effect in the KY1005 treatment groups versus placebo was observed from Day 29 and maintained until Day 113.

Change in Affected BSA from Baseline to Day 113 and Over Time

Figure 9:
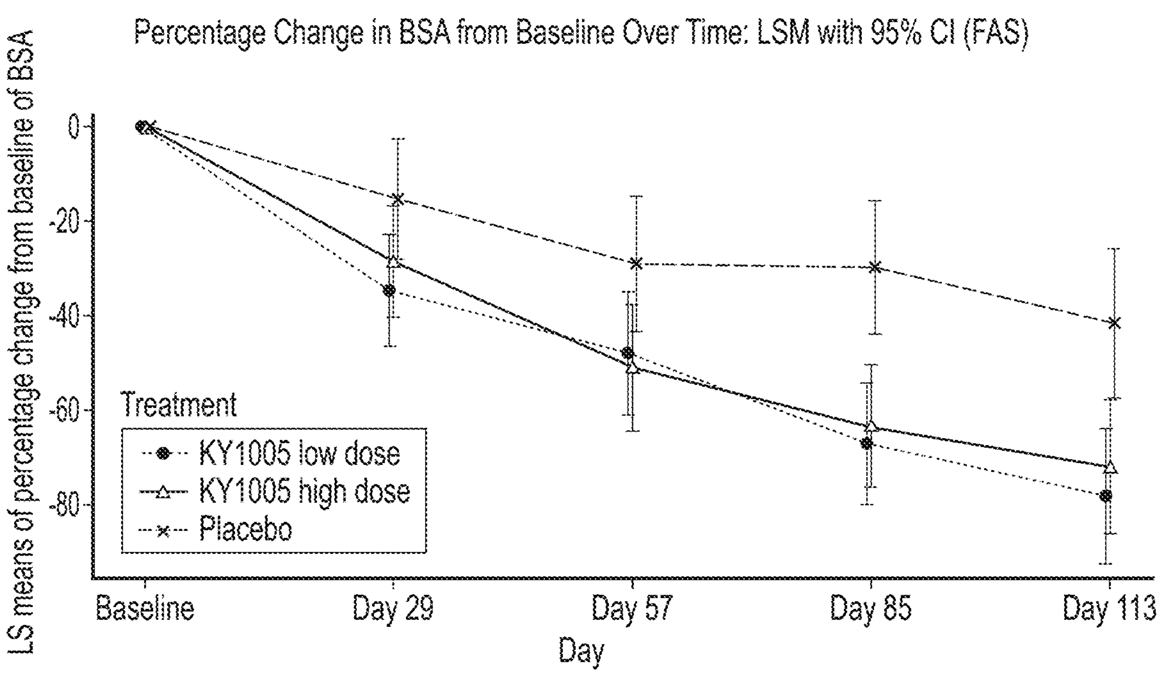
FIG. 9 graphically depicts percentage change in affected BSA from Baseline over time using LSM with 95% CI. Progressive reductions in affected BSA from Baseline to Days 29, 57, 85 and 113 were observed across all treatment groups, including placebo. However, greater reductions were observed in the KY1005 groups compared to placebo at all time points: Least square means percentage change (95% CI) in affected BSA at Day 113 was −78.07 (−92.35, −63.79) and −71.97 (−86.10, −57.84) for the KY1005 low and high dose groups, respectively, compared to placebo (−41.58 [−57.35, −25.80]).

Percentage change in affected BSA from Baseline over time is illustrated using LSM with 95% CI in FIG. 9. Progressive reductions in affected BSA from Baseline to Days 29, 57, 85 and 113 were observed across all treatment groups, including placebo. However, greater reductions were observed in the KY1005 groups compared to placebo at all time points: least square means percentage change (95% CI) in affected BSA at Day 113 was −78.07 (−92.35, −63.79) and −71.97 (−86.10, −57.84) for the KY1005 low and high dose groups, respectively, compared to placebo (−41.58 [−57.35, −25.80]). These differences versus placebo were nominally statistically significant for both the KY1005 low dose group (difference in LSM [95% CI], −36.49 [−57.84, −15.14]; p=0.001) and the KY1005 high dose group (difference in LSM [95% CI], −30.39 [−51.50, −9.29]; p=0.005) in the FAS. Thus, an effect in the KY1005 treatment groups versus placebo was observed from Day 29 and maintained until Day 113.

Change in PO-SCORAD Index from Baseline to Day 113 and Over Time

Figure 10:
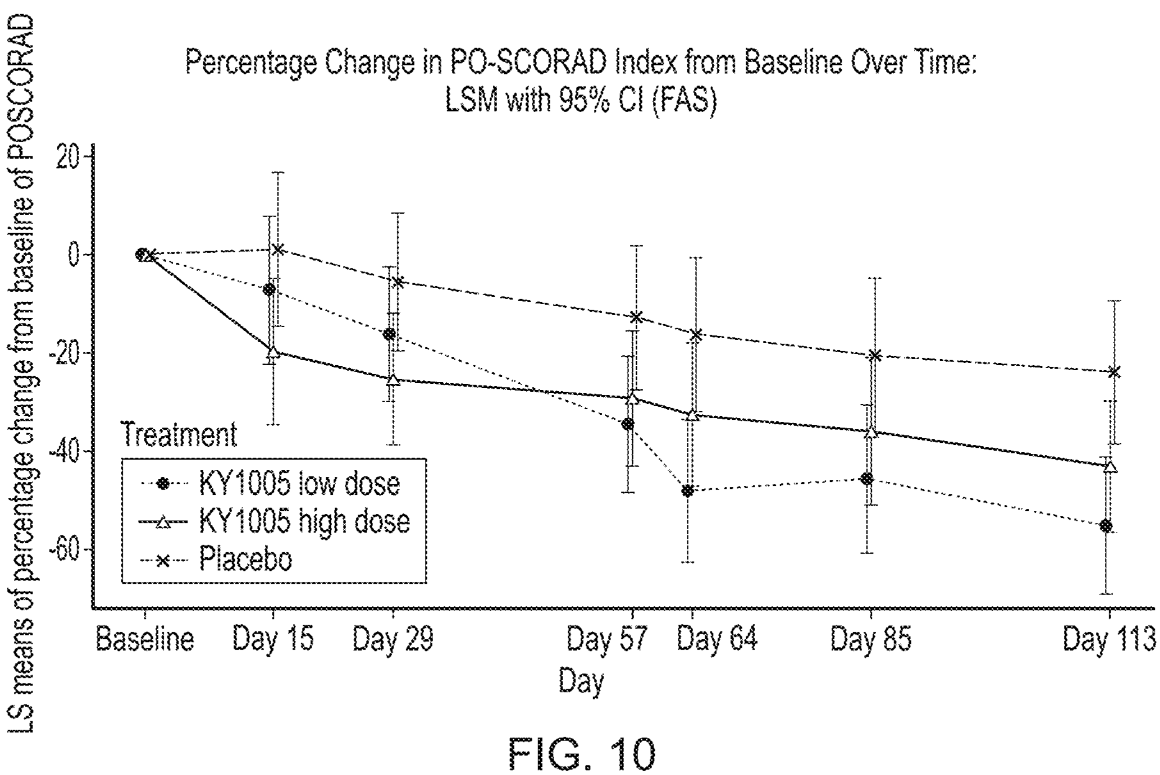
FIG. 10 graphically depicts percentage change in PO-SCORAD Index from Baseline over time, illustrated using LSM with 95% CI. Progressive reductions in PO-SCORAD Index from Baseline to Days 15, 29, 57, 64, 85 and 113 were generally observed across all treatment groups, including placebo. Greater reductions were observed in the KY1005 groups compared to placebo at nearly all time points: by Day 113, LSM percentage change (95% CI) in PO-SCORAD Index was −55.16 (−69.11, −41.21) and −43.04 (−56.41, −29.67) in the KY1005 low and high dose groups, respectively, versus −23.96 (−38.36, −9.46) in the placebo group.

Percentage change in PO-SCORAD Index from Baseline over time is illustrated using LSM with 95% CI in FIG. 10. Progressive reductions in PO-SCORAD Index from Baseline to Days 15, 29, 57, 64, 85 and 113 were generally observed across all treatment groups, including placebo. However, greater reductions were observed in the KY1005 groups compared to placebo at nearly all time points: by Day 113, LSM percentage change (95% CI) in PO-SCORAD Index was −55.16 (−69.11, −41.21) and −43.04 (−56.41, −29.67) in the KY1005 low and high dose groups, respectively, versus −23.96 (−38.36, −9.46) in the placebo group. These differences versus placebo were nominally statistically significant for the KY1005 low dose group (difference in LSM [95% CI], −31.20 [−51.29, −11.10]; p=0.003) and not for the KY1005 high dose group (difference in LSM [95% CI], −19.07 [−38.86, 0.71]; p=0.059).

TABLE 12

Percentage Change from Baseline in SCORAD Index Between Treatment Regimes MMRM (FAS)

| Time Point | Parameter | KY1005 Low Dose (N = 27) | KY1005 High Dose (N = 27) | Placebo (N = 24) |
|---|---|---|---|---|
| Day 29 | LSM (95% CI) | −25.14 (−33.84, −16.43) | −27.65 (−36.18, −19.13) | −12.16 (−21.23, −3.10) |
| | Differences in LSM, estimate (SE) [95% CI] | −12.97 (6.30) [−25.54, −0.40] | −15.49 (6.24) [−27.93, −3.05] | |
| | P-value | 0.043 | 0.015 | |
| Day 57 | LSM (95% CI) | −43.51 (−53.31, −33.72) | −37.05 (−47.07, −27.03) | −24.22 (−34.59, −13.84) |
| | Differences in LSM, estimate (SE) [95% CI] | −19.30 (7.16) [−33.57, −5.02] | −12.83 (7.23) [−27.26, 1.59] | |
| | P-value | 0.009 | 0.080 | |
| Day 85 | LSM (95% CI) | −55.48 (−66.94, −44.03) | −52.02 (−63.28, −40.75) | −26.95 (−39.24, −14.65) |
| | Differences in LSM, estimate (SE) [95% CI] | −28.54 (8.43) [−45.35, −11.73] | −25.07 (8.36) [−41.74, −8.40] | |
| | P-value | 0.001 | 0.004 | |
| Day 113 | LSM (95% CI) | −60.30 (−72.57, −48.04) | −58.96 (−71.04, −46.87) | −36.79 (−49.94, −23.65) |
| | Differences in LSM, estimate (SE) [95% CI] | −23.51 (9.02) [−41.50, −5.52] | −22.16 (8.95) [−40.00, −4.32] | |
| | P-value | 0.011 | 0.016 | |

CI = confidence interval; SE = standard error.

Change in DLQI from Baseline to Day 113 and Over Time

Figure 11:
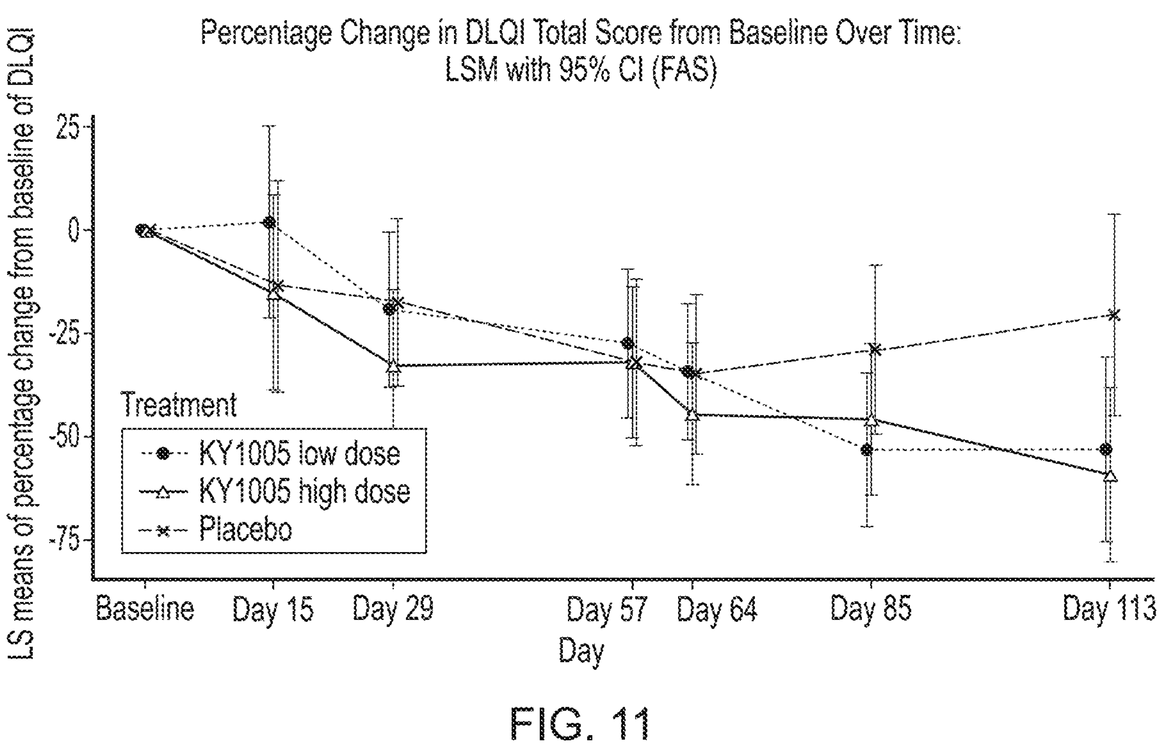
FIG. 11 graphically depicts percentage change in DLQI total score from baseline over time, illustrated using LSM with 95% CI. Progressive reductions in DLQI total score from baseline to Days 15, 29, 57, 64, 85 and 113 were generally observed across all treatment groups, including placebo. There were generally no clear differences between the treatment groups in the magnitude of the reductions, although there was a trend for greater reductions in the KY1005 treatment groups compared to placebo at Days 85 and 113: by Day 113, LSM percentage change (95% CI) in DLQI total score was −52.99 (−75.31, −30.67) and −59.15 (−80.32, −37.99) in the KY1005 low and high dose groups, respectively, versus −20.51 (−44.95, 3.93) in the placebo group.

Percentage change in DLQI total score from baseline over time is illustrated using LSM with 95% CI in FIG. 11. Progressive reductions in DLQI total score from baseline to Days 15, 29, 57, 64, 85 and 113 were generally observed across all treatment groups, including placebo. There were generally no clear differences between the treatment groups in the magnitude of the reductions, although there was a trend for greater reductions in the KY1005 treatment groups compared to placebo at Days 85 and 113: by Day 113, LSM percentage change (95% CI) in DLQI total score was −52.99 (−75.31, −30.67) and −59.15 (−80.32, −37.99) in the KY1005 low and high dose groups, respectively, versus −20.51 (−44.95, 3.93) in the placebo group. These differences versus placebo were not significant for the KY1005 low dose group (difference in LSM [95% CI], −32.48 [−65.82, 0.86]; p=0.056) and nominally statistically significant for the KY1005 high dose group (difference in LSM [95% CI], −38.65 [−71.05, −6.24]; p=0.020).

Improvements in DLQI total score, by category, were generally observed post-baseline across the treatment groups, including placebo. However, greater improvements were generally observed in the KY1005 groups compared to placebo. For example, by Day 113, the percentage of patients in the category "no effect at all on patient's life" was approximately 33% (6/18) and 38% (8/21) for the KY1005 low and high dose groups, respectively, compared with 6% (1/16) for the placebo group; conversely, the percentage of patients in the category "extremely large effect" was 0% for both KY1005 groups compared with 19% (3/16) for the placebo group.

Change in NRS for Pruritus from Baseline to Day 113 and Over Time

Analyses of the change in NRS for pruritus from Baseline to Day 113 and over time were performed using the mean values of absolute NRS values calculated per week, i.e., for the corresponding day and the previous 6 days, if at least four values were available. Using the average per week approach, post-hoc analyses of the percentage of patients with a best improvement in NRS for pruritus of at least 3 and 4 units with a baseline NRS for pruritus of at least 3 and at least 4, respectively, were performed. For all analyses, the baseline value was considered as the value taken on the date of the baseline visit.

Figure 12:
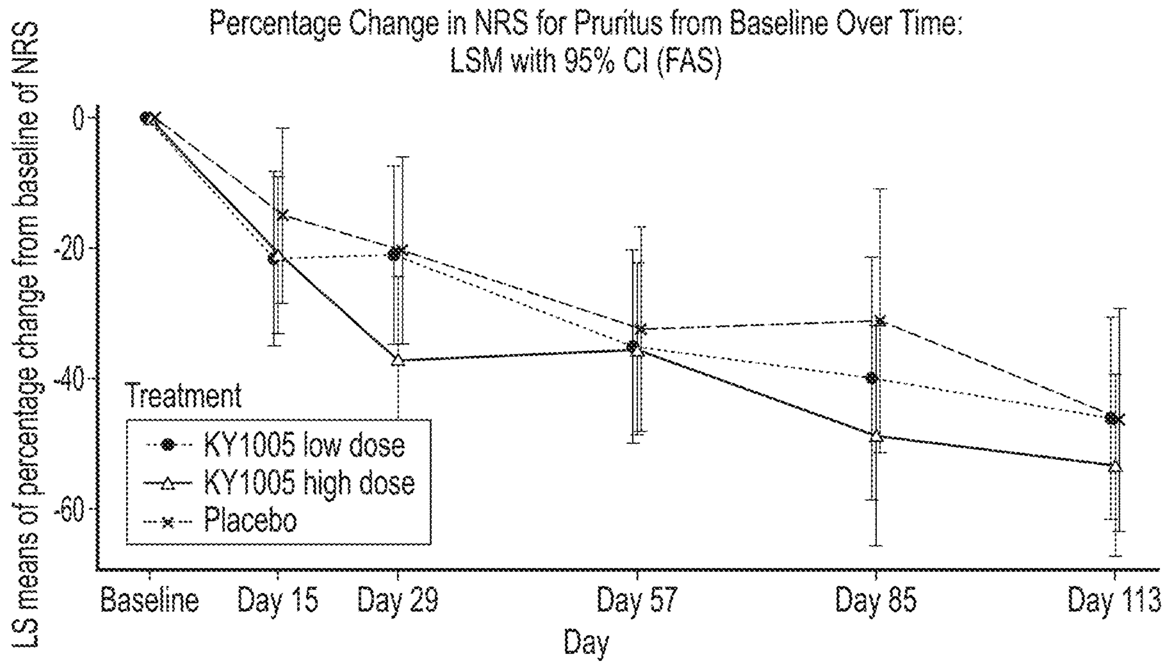
FIG. 12 graphically depicts percentage change in mean weekly NRS for pruritus from baseline over time using LSM with 95% CI. Progressive reductions in weekly mean values for NRS for pruritus from Baseline to Days 15, 29, 57, 85 and 113 were generally observed across all treatment groups, including placebo. There were no clear differences between the treatment groups in the magnitude of the reductions at any time point, and none of the comparisons of percentage change in NRS for pruritus between KY1005 groups and placebo revealed a nominally statistically significant difference.

Percentage change in mean weekly NRS for pruritus from Baseline over time is illustrated using LSM with 95% CI in FIG. 12. Progressive reductions in weekly mean values for NRS for pruritus from Baseline to Days 15, 29, 57, 85 and 113 were generally observed across all treatment groups, including placebo. There were no clear differences between the treatment groups in the magnitude of the reductions at any time point, and none of the comparisons of percentage change in NRS for pruritus between KY1005 groups and placebo revealed a nominally statistically significant difference.

In a post-hoc analysis for patients with a Baseline NRS of at least 3, the percentage of patients with a best improvement in NRS for pruritus by average per week of at least 3 units at week of Day

TABLE 13

Percentage of Patients with a Best Improvement in NRS for Pruritus of at Least 3 Units Based on Patients with a Baseline NRS of at Least 3 (FAS)

| | KY1005 Low Dose (N = 20) | | KY1005 High Dose (N = 25) | | Placebo (N = 21) | |
|---|---|---|---|---|---|---|
| | n (%) | 95% CI | n (%) | 95% CI | n (%) | 95% CI |
| Patients with a best improvement in NRS of at least 3 | | | | | | |
| Week of Day 113 | 11 (55.0%) | 33.20, 76.80 | 13 (52.0%) | 32.42, 71.58 | 7 (33.3%) | 13.17, 53.50 |
| Overall | 13 (65.0%) | 44.10, 85.90 | 18 (72.0%) | 54.40, 89.60 | 14 (66.7%) | 46.50, 86.83 |

CI = confidence interval

Overall, the percentage of patients with a best improvement in NRS for pruritus by average per week of at least 3 units was greater in the KY1005 high dose group (72.0% [18/25; 95% CI, 54.40, 89.60]) compared to the KY1005 low dose group (65.0% [13/20; 95% CI, 44.10, 85.90]) and the placebo group (66.7% [14/21; 95% CI, 46.50, 86.83]). Similar results to the week of Day 113 data were observed for the EASI>21 stratum, but the low numbers of patients included in the EASI 521 stratum makes it difficult to draw meaningful conclusions from this subgroup.

In another post-hoc analysis for patients with a baseline NRS of at least 4, the percentage of patients with a best improvement in NRS for pruritus by average per week of at least 4 units by week and overall is summarized in Table 14. Progressive improvements in NRS for pruritus were observed across all treatment groups, including placebo. However, greater improvements were observed in the KY1005 groups compared to placebo.

TABLE 14

Percentage of Patients with a Best Improvement in NRS for Pruritus by Average per Week of at Least 4 Units by Week and Overall Based on Patients with a Baseline NRS of at Least 4 (FAS)

| | KY1005 Low Dose (N = 19) | | KY1005 High Dose (N = 24) | | Placebo (N = 21) | |
|---|---|---|---|---|---|---|
| | n (%) | 95% CI | n (%) | 95% CI | n (%) | 95% CI |
| Patients with a best improvement in NRS of at least 4 | | | | | | |
| Week of Day 113 | 9 (47.4%) | 24.92, 69.82 | 9 (37.5%) | 18.13, 56.87 | 4(19.0%) | 2.25, 35.84 |
| Overall | 11 (57.9%) | 35.69, 80.10 | 15 (62.5%0 | 43.13, 81.87 | 8(38.1%) | 17.33, 58.87 |

CI = confidence interval

Overall, results were observed were 57.9% (11/19; 95% CI, 35.69, 80.10) and 62.5% (15/24; 95% CI, 43.13, 81.87) for the KY1005 low and high dose groups, respectively, compared to placebo (38.1% [8/21; 95% CI, 17.33, 58.87]). Similar results were observed for the EASI >21 and EASI 521 strata to those observed in the FAS, but the low numbers of patients included in the EASI 521 stratum makes it difficult to draw meaningful conclusions from this subgroup.

The overall conclusions from the post-hoc NRS analyses for pruritus were similar to those from the pre-specified analysis, with no clear differences between the treatment groups when considering the FAS population as a whole. However, in patients with severe disease at baseline (EASI >21), a difference of approximately 20 percentage points was observed between both KY1005 high and low dose groups (58.8% each) compared to placebo (35.7%) when considering the high hurdle response of at least 4 units in patients with a Baseline NRS of at least 4 (Table 15).

TABLE 15

Percentage of Patients with a Best Improvement in NRS for Pruritus by Average per Week of at Least 4 Units by Week and Overall Based on Patients with a Baseline NRS of at Least 4 (EASI >21)

| | KY1005 Low Dose (N = 17) | | KY1005 High Dose (N = 17) | | Placebo (N = 14) | |
|---|---|---|---|---|---|---|
| | n (%) | 95% CI | n (%) | 95% CI | n (%) | 95% CI |
| Patients with a best improvement in NRS of at least 4 | | | | | | |
| Week of Day 113 | 8 (47.1%) | 23.33, 70.79 | 5(29.4) | 7.75, 51.07 | 2(14.3%) | 0.00, 32.62 |
| Overall | 10 (58.8%) | 35.43, 82.22 | 10(58.8%) | 35.43, 82.22 | 5(35.7%) | 10.61, 60.81 |

CI = confidence interval

Exploratory Efficacy Analysis

Exploratory efficacy analyses were completed in the subset of patients in the FAS who were defined as responders at Day 113 (i.e., vIGA of 0 or 1), which comprised 12, 10 and 2 patients in the KY1005 low dose, KY1005 high dose and placebo groups, respectively (See section "Change in vIGA from Baseline to Day 113 and over time" above). Of note, if the vIGA score at Day 113 was missing, the next available vIGA score was used to determine whether the patient was a responder (vIGA 0/1).

Percentage and Absolute EASI Chanae from Day 113 Over Time (i.e., Day 169 and Day 253)

A summary of change in EASI score from Baseline to Days 113, 169 and 253 for patients who were defined as responders (vIGA 0/1) at Day 113 is provided in Table 15a.

TABLE 15a

| Change in EASI Score from Baseline to Days 113, 169 and 253 (Responders) | | | | |
|---|---|---|---|---|
| | Parameter | KY1005 Low Dose (N = 12) | KY1005 High Dose (N = 10) | Placebo (N = 2) |
| Day 113 | n | 12 | 10 | 2 |
| EASI score absolute | Mean (SD) | −32.21 (8.686) | −30.18 (13.748) | −27.90 (5.798) |
| change from Baseline | 95% CI | −37.73, −26.69 | −40.02, −20.34 | −80.00, 24.20 |
| | Median | −30.50 | −24.40 | −27.90 |
| | Min, max | −45.9, −18.9 | −61.0, −16.5 | −32.0, −23.8 |
| EASI score percentage | Mean (SD) | −93.47 (4.242) | −94.66 (6.662) | −96.50 (4.950) |
| change from Baseline | 95% CI | −96.16, −90.77 | −99.43, −89.89 | −140.97, −52.03 |
| | Median | −93.40 | −97.00 | −96.50 |
| | Min, max | −100.0, −86.8 | −100.0, −78.8 | −100.0, −93.0 |
| Day 169 | n | 12 | 10 | 2 |
| EASI score absolute | Mean (SD) | −32.28 (8.121) | −30.57 (14.093) | −24.25 (2.333) |
| change from Baseline | 95% CI | −37.44, −27.12 | −40.65, −20.49 | −45.22, −3.28 |
| | Median | −32.25 | −24.70 | −24.25 |
| | Min, max | −47.2, −19.5 | −60.8, −17.1 | −25.9, −22.6 |
| EASI score percentage | Mean (SD) | −94.34 (7.035) | −95.71 (8.489) | −85.15 (13.930) |
| change from Baseline | 95% CI | −98.81, −89.87 | −101.78, −89.64 | −210.31, 40.01 |
| | Median | −97.30 | −98.95 | −85.15 |
| | Min, max | −100.0, −75.0 | −100.0; −73.1 | −95.0; −75.3 |
| Day 253 | n | 11 | 8 | 2 |
| EASI score absolute | Mean (SD) | −28.17 (9.135) | −24.65 (6.813) | −25.70 (8.061) |
| change from Baseline | 95% CI | −34.31, −22.04 | −30.35, −18.95 | −98.13, 46.73 |
| | Median | −27.20 | −22.75 | −25.70 |
| | Min, max | −45.6, −12.5 | −36.8, −17.1 | −31.4, −20.0 |
| EASI score percentage | Mean (SD) | −83.85 (20.220) | −94.10 (9.178) | −87.65 (5.162) |
| change from Baseline | 95% CI | −97.44, −70.27 | −101.77, −86.43 | −134.03, −41.27 |
| | Median | −94.70 | −96.65 | −87.65 |
| | Min, max | −100.0, −38.7 | −100.0, −72.2 | −91.3, −84.0 |

AD = atopic dermatitis; CI = confidence interval; EASI = Eczema Area and Severity Index; max = maximum; min = minimum; SD = standard deviation.
Note:
The total EASI score is the weighted total of the section EASI using the weights 10% (head), 20% (upper extremities), 30% (trunk) and 40% (lower extremities). The minimum possible EASI score is zero and the maximum possible EASI score is 72, where a higher score indicates increased extent and severity of AD.

For responders, reductions in EASI score from Baseline to Days 113, 169 and 253 were observed in all treatment groups, including placebo.

Mean percentage change (95% CI) in EASI score at Day 169 was −94.34 (−98.81, −89.87), −95.71 (−101.78, −89.64) and −85.15 (−210.31, −40.01) for the KY1005 low dose (n=12), KY1005 high dose (n=10) and placebo (n=2) groups, respectively, and at Day 253 was −83.85 (−97.44, −70.27), −94.10 (−101.77, −86.43) and −87.65 (−134.03, −41.27) for the KY1005 low dose (n=11), KY1005 high dose (n=8) and placebo (n=2) groups, respectively.

EASI 50, 75 and 90 from Day 113 Over Time

The percentages of patients with at least a 50%, 75% and 90% reduction from Baseline in EASI at Days 113, 169 and 253 are summarised by treatment group for patients who were defined as responders (vIGA 0/1) at Day 113 in an overall summary provided in Table 15b.

All responders in all treatment groups had an EASI 50 response at Days 113 and 169. At Day 253, percentages were approximately 83%, 80% and 100% in the KY1005 low dose, KY1005 high dose and placebo groups, respectively.

All responders in all treatment groups had an EASI 75 response at Days 113 and 169, with the exception of the KY1005 high dose group at Day 169 (9/10). At Day 253, percentages were approximately 67% (8/12), 70% (7/10) and 100% (2/2) in the KY1005 low dose, KY1005 high dose and placebo groups, respectively.

For EASI 90, percentages were approximately 75% (9/12), 80% (8/10) and 100% (2/2) in the KY1005 low dose, KY1005 high dose and placebo groups, respectively, at Day 113; 92% (11/12), 90% (9/10) and 50% (1/2) in the KY1005 low dose, KY1005 high dose and placebo groups, respectively, at Day 169; and 50% (6/12), 70% (7/10) and 50% (1/2) in the KY1005 low dose, KY1005 high dose and placebo groups, respectively, at Day 253.

TABLE 15b

| Percentage of Patients with a 50%, 75% and 90% Reduction from Baseline at Days 113, 169 and 253 in EASI Score (Responders) | | | | | | | |
|---|---|---|---|---|---|---|---|
| | Time | KY1005 Low Dose (N = 12) | | KY1005 High Dose (N = 10) | | Placebo (N = 2) | |
| Parameter | Point | n (%) | 95% CI | n (%) | 95% CI | n (%) | 95% CI |
| 50% reduction from Baseline in EASI score | Day 113 | 12(100.0%) | 100.00, 100.00 | 10 (100.0%) | 100.00, 100.00 | 2 (100.0%) | 100.00, 100.00 |
| | Day 169 | 12(100.0%) | 100.00, 100.00 | 10 (100.0%) | 100.00, 100.00 | 2 (100.0%) | 100.00, 100.00 |
| | Day 253 | 10(83.3%) | 62.25, 100.00 | 8 (80.0%) | 55.21, 100.00 | 2 (100.0%) | 100.00, 100.00 |

TABLE 15b-continued

Percentage of Patients with a 50%, 75% and 90% Reduction from Baseline at Days 113, 169 and 253 in EASI Score (Responders)

| Parameter | Time Point | KY1005 Low Dose (N = 12) n (%) | 95% CI | KY1005 High Dose (N = 10) n (%) | 95% CI | Placebo (N = 2) n (%) | 95% CI |
|---|---|---|---|---|---|---|---|
| 75% reduction from Baseline in EASI score | Day 113 | 12(100.0%) | 100.00, 100.00 | 10 (100.0%) | 100.00, 100.00 | 2 (100.0%) | 100.00, 100.00 |
| | Day 169 | 12(100.0%) | 100.00, 100.00 | 9 (90.0%) | 71.41, 100.00 | 2 (100.0%) | 100.00, 100.00 |
| | Day 253 | 8 (66.7%) | 39.99, 93.34 | 7 (70.0%) | 41.60, 98.40 | 2 (100.0%) | 100.00, 100.00 |
| 90% reduction from Baseline in EASI score | Day 113 | 9 (75.0%) | 50.50, 99.50 | 8 (80.0%) | 55.21, 100.00 | 2 (100.0%) | 100.00, 100.00 |
| | Day 169 | 11(91.7%) | 76.03, 100.00 | 9 (90.0%) | 71.41, 100.00 | 1 (50.0%) | 0.00, 100.00 |
| | Day 253 | 6 (50.0%) | 21.71, 78.29 | 7 (70.0%) | 41.60, 98.40 | 1 (50.0%) | 0.00, 100.00 |

CI = confidence interval;
EASI = Eczema Area and Severity Index.
Note:
When lower CI is negative, it has been bound to 0.0.
Note:
When upper CI is greater than 100, it has been bound to 100.0.

vIGA from Day 113 Over Time

For patients who were defined as responders (vIGA 0/1) at Day 113, the percentages of patients in each vIGA category at Days 113, 169 and 253 are summarised in Table 15c.

At Day 169, one (8.3%) patient each in the KY1005 low dose group had a vIGA of 2 (mild) and 3 (moderate); one (10.0%) patient in the KY1005 high dose group had a vIGA of 2 (mild); and one (50.0%) patient in the placebo group had a vIGA of 2 (mild); the remaining patients (10, 9 and 1, respectively) still had a vIGA of 0 (clear) or 1 (almost clear).

At Day 253, three (27.3%) patients in the KY1005 low dose group had a vIGA of 3 (moderate); one (12.5%) patient in the KY1005 high dose group had a vIGA of 2 (mild); and one (50.0%) patient in the placebo group had a vIGA of 2 (mild); the remaining patients (8, 7 and 1, respectively) still had a vIGA of 0 (clear) or 1 (almost clear).

TABLE 15c

Percentage of Patients in vIGA Categories Between Treatment Regimens at Days 113, 169 and 253 (Responders)

| Time Point | | KY1005 Low Dose (N = 12) n (%) | 95% CI | KY1005 High Dose (N = 10) n (%) | 95% CI | Placebo (N = 2) n (%) | 95% CI |
|---|---|---|---|---|---|---|---|
| Day 113 | n | 12 | | 10 | | 2 | |
| | 0-Clear | 2 (16.7%) | 0.00, 37.75 | 3(30.0%) | 1.60, 58.40 | 1 (50.0%) | 0.00, 100.00 |
| | 1-Almost clear | 10(83.3%) | 62.25, 100.00 | 7(70.0%) | 41.60, 98.40 | 1 (50.0%) | 0.00, 100.00 |
| | 2-Mild | 0 (0.0%) | 0.00, 0.00 | 0 (0.0%) | 0.00, 0.00 | 0 (0.0%) | 0.00, 0.00 |
| | 3-Moderate | 0 (0.0%) | 0.00, 0.00 | 0 (0.0%) | 0.00, 0.00 | 0 (0.0%) | 0.00, 0.00 |
| | 4-Severe | 0 (0.0%) | 0.00, 0.00 | 0 (0.0%) | 0.00, 0.00 | 0 (0.0%) | 0.00, 0.00 |
| Day 169 | n | 12 | | 10 | | 2 | |
| | 0-Clear | 3 (25.0%) | 0.50, 49.50 | 4(40.0%) | 9.64, 70.36 | 0 (0.0%) | 0.00, 0.00 |
| | 1-Almost clear | 7 (58.3%) | 30.44, 86.23 | 5(50.0%) | 19.01, 80.99 | 1 (50.0%) | 0.00, 100.00 |
| | 2-Mild | 1 (8.3%) | 0.00, 23.97 | 1 (10.0%) | 0.00, 28.59 | 1 (50.0%) | 0.00, 100.00 |
| | 3-Moderate | 1 (8.3%) | 0.00, 23.97 | 0 (0.0%) | 0.00, 0.00 | 0 (0.0%) | 0.00, 0.00 |
| | 4-Severe | 0 (0.0%) | 0.00, 0.00 | 0 (0.0%) | 0.00, 0.00 | 0 (0.0%) | 0.00, 0.00 |
| Day 253 | n | 11 | | 8 | | 2 | |
| | 0-Clear | 2 (18.2%) | 0.00, 40.97 | 2(25.0%) | 0.00, 55.01 | 0 (0.0%) | 0.00, 0.00 |
| | 1-Almost clear | 6 (54.5%) | 25.12, 83.97 | 5(62.5%) | 28.95, 96.05 | 1 (50.0%) | 0.00, 100.00 |

TABLE 15c-continued

Percentage of Patients in vIGA Categories Between Treatment Regimens at Days 113, 169 and 253 (Responders)

| | KY1005 Low Dose (N = 12) | | KY1005 High Dose (N = 10) | | Placebo (N = 2) | |
|---|---|---|---|---|---|---|
| Time Point | n (%) | 95% CI | n (%) | 95% CI | n (%) | 95% CI |
| 2-Mild | 0 (0.0%) | 0.00, 0.00 | 1(12.5%) | 0.00, 35.42 | 1 (50.0%) | 0.00, 100.00 |
| 3-Moderate | 3 (27.3%) | 0.95, 53.59 | 0 (0.0%) | 0.00, 0.00 | 0 (0.0%) | 0.00, 0.00 |
| 4-Severe | 0 (0.0%) | 0.00, 0.00 | 0 (0.0%) | 0.00, 0.00 | 0 (0.0%) | 0.00, 0.00 |

CI = confidence interval;
vIGA = validated Investigator Global Assessment.
Note:
When lower CI is negative, it has been bound to 0.0.
Note:
When upper CI is greater than 100, it has been bound to 100.0.

Percentage of Patients with a Response of v1GA of 0 or 1 from Day 113 Over Time

The percentage of patients with a response of 0 (clear) or 1 (almost clear) in vIGA at Days 113, 169 and 253 is summarised for patients who were defined as responders (vIGA 0/1) at Day 113 in Table 15d.

TABLE 15d

Percentage of Patients with a Response of 0 (Clear) or 1 (Almost Clear) in vIGA at Days 113, 169 and 253 (Responders)

| | Time | KY1005 Low Dose (N = 12) | | KY1005 High Dose (N = 10) | | Placebo (N = 2) | |
|---|---|---|---|---|---|---|---|
| Parameter | Point | n (%) | 95% CI | n (%) | 95% CI | n (%) | 95% CI |
| vIGA of 0 (Clear) or 1 (Almost clear) | Day 113 | 12 (100.0%) | 100.00, 100.00 | 10 (100.0%) | 100.00, 100.00 | 2 (100.0%) | 100.00, 100.00 |
| | Day 169 | 10 (83.3%) | 62.25, 100.00 | 9 (90.0%) | 71.41, 100.00 | 1 (50.0%) | 0.00, 100.00 |
| | Day 253 | 8 (66.7%) | 39.99, 93.34 | 7 (70.0%) | 41.60, 98.40 | 1 (50.0%) | 0.00, 100.00 |

CI = confidence interval;
vIGA = validated Investigator Global Assessment.
Note:
Numbers on columns represent number of patients with a positive response (vIGA of '0' or '1' at Day 'xxx' = Yes).
Note:
When lower CI is negative, it has been bound to 0.0.
Note:
When upper CI is greater than 100, it has been bound to 100.0.

At Day 169, the percentage of vIGA 0/1 responders was 83.3% (10/12), 90.0% (9/10) and 50.0% (1/2) in the KY1005 low dose, KY1005 high dose and placebo groups, respectively. At Day 253, the percentage of vIGA 0/1 responders was 66.7% (8/12), 70.0% (7/10) and 50.0% (1/2) in the KY1005 low dose, KY1005 high dose and placebo groups, respectively.

Drug Serum Concentration Analysis

Figure 13:
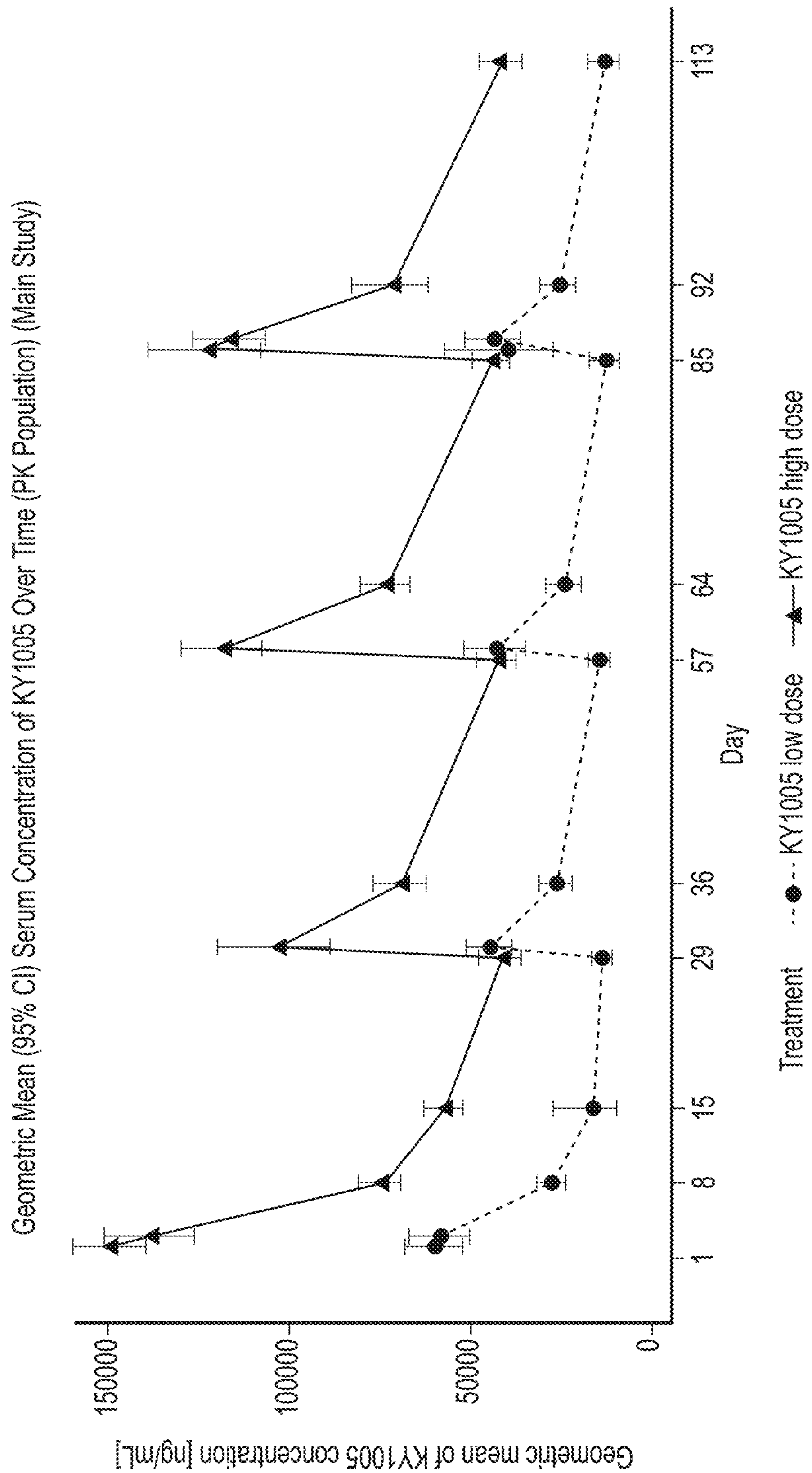
FIG. 13 graphically depicts serum KY1005 concentration versus time data presented using the geometric mean for the main study. Serum concentration profiles for KY1005 were similar between the KY1005 groups, with higher concentrations recorded for the KY1005 high dose group compared to the low dose group. With repeated I.V. administration, serum concentrations peaked rapidly and subsequently decreased after each dose.
Figure 14:
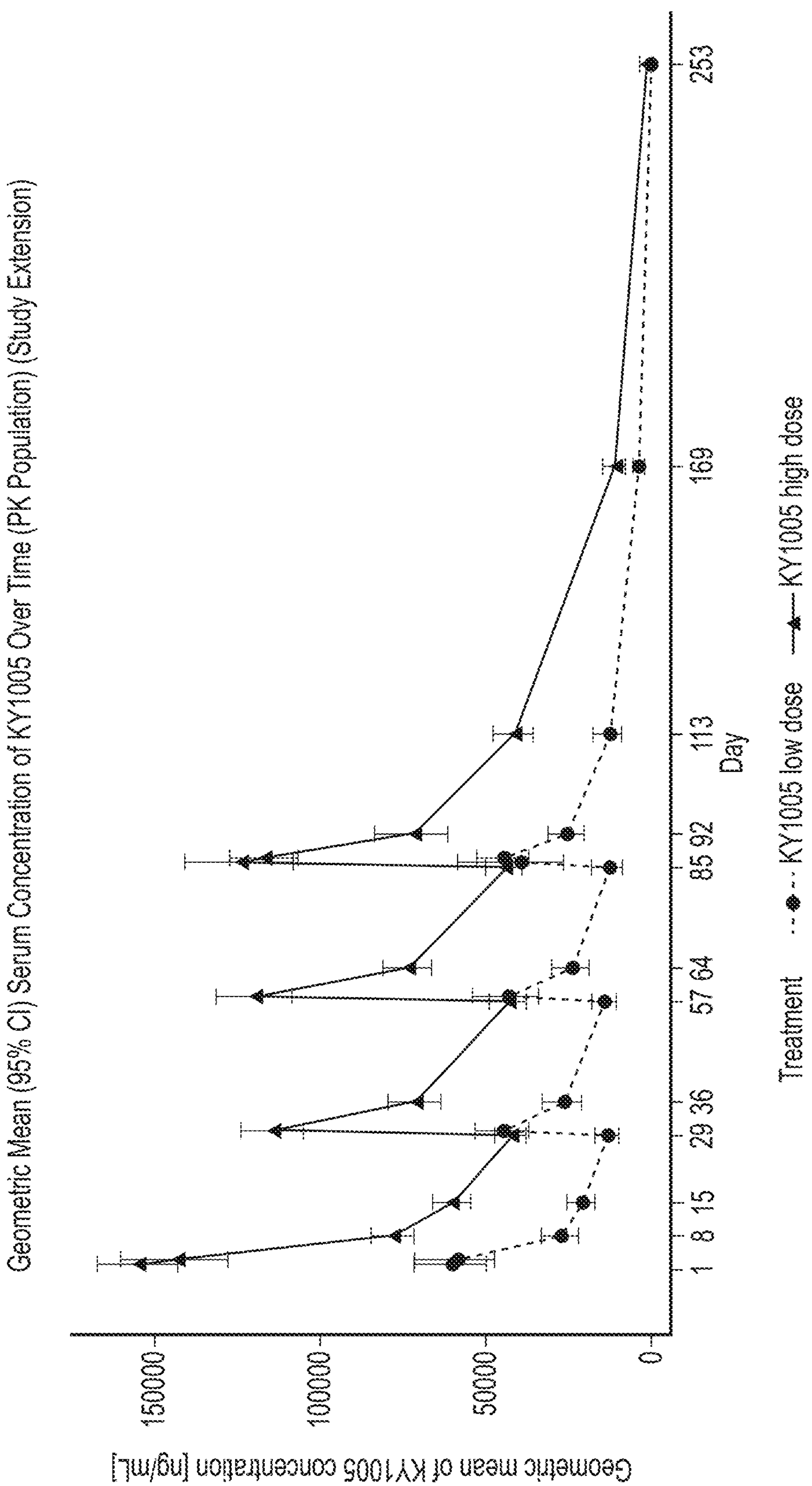
FIG. 14 graphically depicts serum KY1005 concentration versus time data presented using the geometric mean for the extension study. Serum concentration profiles for patients who entered the study extension were similar between the KY1005 groups, with higher KY1005 concentrations recorded for the KY1005 high dose group compared to the low dose group. Following the fourth infusion on Day 85, serum concentrations steadily decreased up to Day 253.

Serum KY1005 concentration versus time data are presented using the geometric mean in FIG. 13 and FIG. 14 (study extension).

For the main study, serum concentration profiles for KY1005 were similar between the KY1005 groups, with higher concentrations recorded for the KY1005 high dose group compared to the low dose group. With repeated I.V. administration, serum concentrations peaked rapidly and subsequently decreased after each dose.

As observed in the main study, serum concentration profiles for patients who entered the study extension were similar between the KY1005 groups, with higher KY1005 concentrations recorded for the KY1005 high dose group compared to the low dose group. Following the fourth infusion on Day 85, serum concentrations steadily decreased up to Day 253.

Serum Pharmacokinetic Analysis

Main Study (to Day 113):

Derived serum PK parameters for KY1005 in the main study are summarized in Table 16. Serum concentrations of KY1005 increased rapidly following dosing (see FIG. 13), with a median $t_{max}$ of 0.03 days for both the KY1005 low and high doses, after both the first and fourth (third maintenance) infusions, and an approximately dose proportional relationship for $C_{max}$, $AUC_{0\text{-}28}$ and $AUC_{0\text{-}inf}$ was observed. Following each dose, serum concentrations steadily decreased in a biphasic manner, with geometric mean $t_{1/2}$ values after the first infusion that were similar for the low (21.25 days) and high (24.46 days) doses. The $AUC_{extrap}$(%) was large (geometric mean, 35.84% and 39.23% for the low and high dose, respectively), which suggests that the reported $AUC_{0\text{-}inf}$ and $t_{1/2}$ may not be reliable.

TABLE 16

Serum PK Parameters of KY1005 (PK Population) (Main Study)

| Parameter | | | KY1005 Low Dose (N = 29) | KY1005 High Dose (N = 30) |
|---|---|---|---|---|
| $C_{max}$ (ng/mL) | After first infusion | n | 29 | 30 |
| | | Geometric mean (95% CI) | 62,456.97 (54,385.916, 71,725.801) | 153,299.41 (143,441.855, 163,834.383) |
| | | Min, max | 15,231.5, 106,325.7 | 104,366.1, 209,120.7 |
| | After fourth infusion | n | 21 | 22 |
| | | Geometric mean (95% CI) | 46,251.21 (38,892.865, 55,001.726) | 126,248.15 (111,684.117, 142,711.398) |
| | | Min, max | 22,259.2, 90,752.0 | 81,638.8, 304,976.5 |
| $t_{max}$ (day) | After first infusion | n | 29 | 30 |
| | | Median | 0.03 | 0.03 |
| | | Min, max | 0.0, 0.2 | 0.0, 0.2 |
| | After fourth infusion | n | 21 | 22 |
| | | Median | 0.03 | 0.03 |
| | | Min, max | 0.0; 0.2 | 0.0; 0.2 |
| $t_{1/2}$ | After first infusion (day) | n | 25 | 27 |
| | | Geometric mean (95% CI) | 21.25 (18.931, 23.858) | 24.46 (22.014, 27.170) |
| | | Min, max | 10.7, 34.9 | 10.8, 35.4 |
| $C_{min}$ (ng/mL) | After first infusion | n | 26 | 27 |
| | | Geometric mean (95% CI) | 13,470.53 (10,906.620, 16,637.156) | 41,394.53 (36,123.340, 47,434.904) |
| | | Min, max | 3,396.6, 36,213.5 | 21,620.3, 109,140.0 |
| | After second infusion | n | 24 | 23 |
| | | Geometric mean (95% CI) | 14,061.17 (11,408.279, 17,330.970) | 42,465.62 (37,407.532, 48,207.635) |
| | | Min, max | 3,176.2, 30,221.4 | 22,100.0, 70,221.4 |
| | After third infusion | n | 22 | 22 |
| | | Geometric mean (95% CI) | 12,320.94 (8,881.177, 17,092.959) | 44,016.54 (39,125.273, 49,519.290) |
| | | Min, max | 1,261.9, 29,377.1 | 23,811.2, 71,979.2 |
| | After fourth infusion | n | 20 | 21 |
| | | Geometric mean (95% CI) | 12,653.30 (9,054.512, 17,682.467) | 43,078.75 (38,269.947, 48,491.809) |
| | | Min, max | 1,301.2, 29,857.7 | 26,047.3, 65,983.9 |
| $C_{45}$ (ng/mL) | After first infusion | n | 29 | 30 |
| | | Geometric mean (95% CI) | 59,624.35 (52,239.076, 68,053.707) | 149,304.53 (139,527.726, 159,766.410) |
| | | Min, max | 15,231.5, 93,711.4 | 99,425.1, 209,120.7 |
| | After second infusion | n | 26 | 27 |
| | | Geometric mean (95% CI) | 44,449.66 (38,630.121, 51,145.900) | 103,004.25 (88,670.241, 119,655.422) |
| | | Min, max | 14,655.4, 71,812.5 | 26,957.0, 149,235.7 |
| | After third infusion | n | 24 | 23 |
| | | Geometric mean (95% CI) | 42,253.84 (34,556.654, 51,665.517) | 118,017.27 (107,339.641, 129,757.062) |
| | | Min, max | 12,282.9, 103,391.1 | 75,930.9, 166,144.2 |
| | After fourth infusion | n | 21 | 22 |
| | | Geometric mean (95% CI) | 39,327.14 (27,077.623, 57,118.173) | 122,207.32 (107,528.541, 138,889.897) |
| | | Min, max | 1,484.6, 90,752.0 | 77,203.9, 304,976.5 |
| $AUC_{0-28}$ (ng/mL*day) | After first infusion | n | 26 | 28 |
| | | Geometric mean (95% CI) | 686,940.88 (590,166.320, 799,584.390) | 1,883,507.76 (1,727,579.712, 2,053,509.580) |
| | | Min, max | 182,592.7, 1,250,598.2 | 1,239,102.4, 2,804,778.9 |
| | After fourth infusion | n | 20 | 21 |
| | | Geometric mean (95% CI) | 644,224.34 (528,261.893, 785,642.513) | 1,898,152.07 (1,724,488.487, 2,089,304.346) |
| | | Min, max | 268,463.7, 1,094,156.8 | 1,307,220.3, 2,603,856.9 |
| $AUC_{0-inf}$ (ng/mL*day) | After first infusion | n | 25 | 27 |
| | | Geometric mean (95% CI) | 1,117,227.16 (943,484.260, 1,322,964.871) | 3,313,855.91 (2,917,920.239, 3,763,516.513) |
| | | Min, max | 308,344.7, 1,725,098.3 | 1,600,199.5, 5,682,149.8 |
| $AUC_{extrap}$(%) | After first infusion | n | 25 | 27 |
| | | Geometric mean (95% CI) | 35.84 (31.273, 41.084) | 39.23 (32.565, 47.264) |
| | | Min, max | 12.4, 52.2 | 4.6, 56.2 |
| λz | After first infusion (1/day) | n | 25 | 27 |
| | | Geometric mean (95% CI) | 0.03 (0.029, 0.037) | 0.03 (0.024, 0.031) |
| | | Min, max | 0.0, 0.1 | 0.0, 0.1 |

λz = terminal rate constant; $AUC_{0-28}$ = area under the serum concentration-time curve in dosing interval; $AUC_{0-inf}$ = area under the serum concentration-time curve extrapolated to infinity; $AUC_{extrap(\%)}$ = area under the serum concentration-time curve percentage extrapolated area; CI = confidence interval; $C_{max}$ = maximum observed serum concentration; $C_{min}$ = trough concentration; max = maximum; min = minimum; PK = pharmacokinetic(s); $t_{1/2}$ = apparent terminal half-life; SD = standard deviation; $t_{max}$ = time to maximum observed serum concentration.

Geometric mean $C_{max}$ after the first infusion of KY1005 was 62,456.97 and 153,299.41 ng/mL for the low and high doses, respectively, and after the fourth (third maintenance) infusion was 46,251.21 and 126,248.15 ng/mL, respectively. Peak concentrations (45 minutes after the start of all infusions, using scheduled time points) following each maintenance dose (Days 29, 57 and 85) were slightly lower than those obtained following the loading dose. Minimum geometric mean serum concentrations remained above 10,000 ng/mL in both dose cohorts.

$C_{max}$ was greater following the KY1005 high dose compared to the low dose. However, $AUC_{0-28}$ and $C_{min}$ (trough) levels were similar when first (loading) and fourth (third maintenance) dose exposures were compared. Minimal accumulation was observed across the total four doses administered every 28 days.

In general, the mean serum concentration profile for KY1005 was dose proportional, where the 2.5-fold increase in dose attained an approximately 2.5-fold increase in exposure as measured by $C_{max}$ and $AUC_{0-28}$. No target mediated drug disposition was apparent in the two dose cohorts across the total four doses administered.

Study Extension (from Day 113):

Derived serum PK parameters for KY1005 in the study extension are summarized in Table 17. Following the fourth infusion, serum concentrations of KY1005 steadily decreased, and an approximately dose proportional relationship for $AUC_{0-inf}$ was observed. Geometric mean $t_1/2$ values were similar for the low (23.04 days) and high (28.02 days) doses. The $t_{1/2}$ values are more accurate than those derived from the main study after the first infusion, calculated using $AUC_{0-inf}$ values based on data up to 28 days after dosing only, since $AUC_{extrap}$(%) was <5%. Similar accumulation index, calculated after the fourth dose (about 2-fold), and Vd (about 5 L) was observed for the two KY1005 dose groups.

Geometric mean concentrations (95% CI) on Day 253 ($C_{min}$) were 365.63 ng/mL (163.823, 816.020) in the KY1005 low dose group and 1,739.90 ng/mL (884.622; 3,422.103) in the KY1005 high dose group (FIG. 14). No target mediated drug disposition was apparent from the PK profiles up to 168 days after the last dose for either of the two KY1005 dose groups.

TABLE 17

Serum PK Parameters of KY1005 (PK Population) (Study Extension)

| Parameter | | KY1005 Low Dose | KY1005 High Dose |
|---|---|---|---|
| AI (expected) after fourth infusion | n | 15 | 12 |
| | Geometric mean (95% CI) | 1.78 (1.619, 1.946) | 2.01 (1.834, 2.211) |
| | Min, max | 1.3, 2.3 | 1.5, 2.5 |
| $AUC_{0-inf}$ (ng/mL*day) after fourth infusion | n | 15 | 12 |
| | Geometric mean (95% CI) | 1,272,912.22 (975,475.562, 1,661,041.621) | 3,884,561.93 (3,236,022.502, 4,663,076.769) |
| | Min, max | 371,333.5, 2,334,167.2 | 2,405,791.7, 5,989,019.3 |
| $AUC_{extrap(\%)}$ after fourth infusion | n | 15 | 12 |
| | Geometric mean (95% CI) | 2.00 (0.751, 5.327) | 4.14 (1.711, 10.007) |
| | Min, max | 0.1, 40.5 | 0.7, 47.5 |
| $C_L$ (mL/day) after fourth infusion | n | 20 | 21 |
| | Geometric mean (95% CI) | 155.22 (127.283, 189.299) | 131.71 (119.658, 144.972) |
| | Min, max | 91.4, 372.5 | 96.0, 191.3 |
| $C_{avg}$ (ng/mL) after fourth infusion | n | 20 | 21 |
| | Geometric mean (95% CI) | 23,008.01 (18,866.497, 28,058.662) | 67,791.14 (61,588.874, 74,618.012) |
| | Min, max | 9,588.0, 39,077.0 | 46,686.4, 92,994.9 |
| Fluctuation (%) after fourth infusion | n | 20 | 21 |
| | Geometric mean (95% CI) | 140.49 (123.597, 159.690) | 117.89 (99.569, 139.583) |
| | Min, max | 82.3, 222.2 | 55.9, 323.0 |
| Vd (L) after fourth infusion | n | 15 | 12 |
| | Geometric mean (95% CI) | 4.66 (3.910, 5.552) | 5.11 (4.382, 5.966) |
| | Min, max | 2.2, 8.3 | 3.8, 7.9 |
| λz after fourth infusion (1/day) | n | 15 | 12 |
| | Geometric mean (95% CI) | 0.03 (0.024, 0.034) | 0.02 (0.021, 0.028) |
| | Min, max | 0.0, 0.1 | 0.0, 0.0 |
| $t_{1/2}$ after fourth infusion (day) | n | 15 | 12 |
| | Geometric mean (95% CI) | 23.04 (19.865, 26.726) | 28.02 (24.344, 32.243) |
| | Min, max | 13.9, 33.0 | 17.0, 37.5 |

λz = terminal rate constant; AI (expected) = expected accumulation index; $AUC_{0-inf}$ = area under the serum concentration-time curve extrapolated to infinity; $AUC_{extrap}$(%) = area under the serum concentration-time curve percentage extrapolated area; $C_{avg}$ = average concentration; CI = confidence interval; CL = clearance; max = maximum; min = minimum; PK = pharmacokinetic(s); $t_{1/2}$ = apparent terminal half-life; Vd = apparent volume of distribution Anti-KY105 Antibody Titer and Number of Patients with Positive Response Main Study (to Day 113):

The number and percentage of patients with a positive and negative ADA response is summarized in Table 18 (Safety Set).

TABLE 18

Presence of Anti-KY1005 Antibodies (Safety Set) (Main Study)

| | | KY1005 Low Dose | KY1005 High Dose | Placebo |
|---|---|---|---|---|
| Baseline | n | 29 | 30 | 29 |
| | Negative | 28 (96.6%) | 30 (100.0%) | 26 (89.7%) |
| | Positive | 1 (3.4%) | 0 (0.0%) | 3 (10.3%) |
| Day 15 | n | 28 | 27 | 26 |
| | Negative | 24 (85.7%) | 26 (96.3%) | 24 (92.3%) |
| | Positive | 4 (14.3%) | 1 (3.7%) | 2 (7.7%) |
| Day 29 | n | 26 | 27 | 24 |
| | Negative | 22 (84.6%) | 26 (96.3%) | 22 (91.7%) |
| | Positive | 4 (15.4%) | 1 (3.7%) | 2 (8.3%) |
| Day 57 | n | 24 | 23 | 19 |
| | Negative | 15 (62.5%) | 23 (100.0%) | 17 (89.5%) |
| | Positive | 9 (37.5%) | 0 (0.0%) | 2 (10.5%) |
| Day 85 | n | 22 | 23 | 18 |
| | Negative | 13 (59.1%) | 23 (100.0%) | 16 (88.9%) |
| | Positive | 9 (40.9%) | 0 (0.0%) | 2 (11.1%) |
| Day 113 | n | 20 | 22 | 16 |
| | Negative | 10 (50.0%) | 22 (100.0%) | 14 (87.5%) |
| | Positive | 10 (50.0%) | 0 (0.0%) | 2 (12.5%) |

TABLE 18-continued

| Presence of Anti-KY1005 Antibodies (Safety Set) (Main Study) | | | | |
|---|---|---|---|---|
| | | KY1005 Low Dose | KY1005 High Dose | Placebo |
| Early | n | 2 | 4 | 10 |
| termination - | Negative | 2 (100.0%) | 3 (75.0%) | 8 (80.0%) |
| Main study | Positive | 0 (0.0%) | 1 (25.0%) | 2 (20.0%) |

Note:
Positive represents a titre result ≥1.

The presence and endpoint titer of anti-KY1005 ADAs were determined using a solid-phase extraction acid dissociation bioanalytical method with high estimated sensitivity (5.5 ng/mL) and high tolerance to on-board KY1005 drug concentrations (55 ng/mL and 9 ng/mL ADA positive control tolerated up to 100 and 10 μg/mL KY1005, respectively.)

For the Safety Set, anti-KY1005 antibodies (i.e., titer result >1) were detected at baseline for one patient (3.4%) in the KY1005 low dose group (titer of 34.3) and no patients in the KY1005 high dose group (Table 18.) A positive result was also reported at Baseline for three patients (10.3%) in the placebo group, but the recorded titers were low. Anti-KY1005 antibodies were detected in increasing numbers of patients in the KY1005 low dose group over time, while patients in the KY1005 high dose and placebo groups were generally negative. By Day 113, of the patients with available ADA data, anti-KY1005 antibodies were detected for 10 patients (50.0%) in the KY1005 low dose group and no patient in the KY1005 high dose group. For the 10 patients in the KY1005 low dose group with a positive ADA result, the median titer was 11.85 (range: 1.6 to 465.0). A positive result was also reported at Day 113 for two patients (12.5%) in the placebo group, but the recorded titers were low (3.1 and 3.4). No unexpected changes in PK profile were observed in patients with positive ADA. Given that the bioanalytical PK assay format ensured measurement of active drug (i.e., unbound to OX40L), these findings indicated that where present, ADAs were likely to be weakly or non-neutralizing. No adverse events were associated with positive ADA.

Study Extension (from Day 113):

The number and percentage of responders with a positive and negative response is summarized in Table 19. Similar to the trend in the main study, anti-KY1005 antibodies were detected in increasing numbers of responders in the KY1005 low dose group over time, while those in the KY1005 high dose and placebo groups were negative.

At Day 113, of the responders with available ADA data, anti-KY1005 antibodies were detected for 6 patients (50%) in the KY1005 low dose group with a median titer of 7.94 (range: 1.7 to 29.4). By Day 253, 9 out of 11 patients (81.8%) in the KY1005 low dose group were positive for anti-KY1005 antibodies with a median titer of 53.50 (range: 1.5 to 1740).

As observed in the main study, no unexpected changes in the PK profile were observed in patients with a positive ADA result, although the expected low serum concentrations of KY1005 at Day 253 did not aid interpretation at the final timepoint in this regard. No adverse events were associated with positive ADA.

TABLE 19

| Presence of Anti-KY1005 Antibodies (Responders) (Study Extension) | | | | |
|---|---|---|---|---|
| | | KY1005 Low Dose | KY1005 High Dose | Placebo |
| Day 113 | n | 12 | 10 | 2 |
| | Negative | 6 (50%) | 10 (100.0%) | 2 (100.0%) |
| | Positive | 6 (50%) | 0 (0.0%) | 0 (0.0%) |
| Day 169 | n | 12 | 10 | 2 |
| | Negative | 3 (25.0%) | 10 (100.0%) | 2 (100.0%) |
| | Positive | 9 (75.0%) | 0 (0.0%) | 0 (0.0%) |
| Day 253 | n | 11 | 8 | 2 |
| | Negative | 2 (18.2%) | 8 (100.0%) | 2 (100.0%) |
| | Positive | 9 (81.8%) | 0 (0.0%) | 0 (0.0%) |

Note:
Positive represents a titre result ≥1.

Efficacy and Other Evaluations Conclusions

Main Study to Day 113:

Improvements from baseline were observed in the FAS for the primary efficacy endpoint (percentage change in EASI from Baseline to Day 113), with larger reductions observed in the KY1005 treatment groups compared to placebo. The difference versus placebo was nominally statistically significant for the KY1005 low dose group (p=0.009) but not for the high dose group (p=0.072) at Day 113. Treatment differences were observed with both KY1005 low and high dose groups as early as Day 15 vs placebo and maintained to Day 113. Repeat of the primary efficacy analysis for the PPS and for the sensitivity analyses (using EASI stratum as covariate; with rescue medication within the first month and rescue medication-by-treatment as fixed effects) provided similar results to the main analysis.

Nominally statistically significant improvements from baseline in both KY1005 groups compared to placebo were also observed for the following secondary efficacy endpoints vIGA, SCORAD Index, and affected BSA. There were generally no clear differences between the KY1005 low and high dose groups in either the speed of onset or magnitude of responses.

While reductions from Baseline were generally observed for the secondary patient reported outcome efficacy endpoints of POEM total score, and DLQI total score, these were apparent across all treatment groups, including placebo, and there were no clear differences between the groups. The exception however, was the PO-SCORAD, which demonstrated a nominally statistically significant difference for the KY1005 low dose group compared with placebo.

For patients with a baseline NRS of at least 3 and at least 4, the percentage of patients with a best improvement in NRS for pruritus of at least 3 units and at least 4 units, respectively, was higher in the KY1005 high dose group compared to the KY1005 low dose group and the placebo group.

Results for the subgroup of patients in the EASI >21 stratum (severe disease—56 patients) were similar to those observed in the FAS. Results for the EAST 521 stratum (moderate disease—22 patients) were also generally similar to those observed in the FAS, but the low numbers of patients included in this stratum makes it difficult to draw meaningful conclusions as to whether Baseline disease severity has a meaningful impact on response.

Pharmacokinetics $C_{max}$, $AUC_{0-28}$ and $AUC_{0-inf}$ appeared to be approximately dose proportional, and peak concentrations (45 minutes after the start of all infusions) did not appear to increase on repeat dosing. $AUC_{0-28}$ and $C_{min}$ (trough) levels were similar when first (loading) and fourth (third maintenance) dose exposures were compared and there was minimal accumulation after administration of four doses every 28 days.

Serum concentrations of KY1005 increased rapidly following dosing, with a median $t_{max}$ of 0.03 days for both the KY1005 low and high doses. Following each dose, serum concentrations steadily decreased in a biphasic manner. No target mediated drug disposition was apparent.

In general, the mean serum concentration profile for KY1005 was dose proportional, where the 2.5-fold increase in dose attained an approximately 2.5-fold increase in exposure as measured by $C_{max}$ and $AUC_{0-28}$.

Pharmacodynamics

Anti-KY1005 antibodies were detected in increasing numbers of patients in the KY1005 low dose group over time, while patients in the KY1005 high dose and placebo groups were generally negative. By Day 113 in patients with available data, anti-KY1005 antibodies were detected for 10 patients (50.0%) in the KY1005 low dose group and no patient in the KY1005 high dose group. For the 10 patients in the KY1005 low dose group with a positive ADA result, the median titer was 11.85 (range: 1.6 to 465.0).

No unexpected changes in PK profile was observed in patients with positive ADA, indicating that where present, ADAs were likely to be weakly or non-neutralizing.

Study Extension

Efficacy

A total of 24 patients were defined as responders (vIGA 0/1) at Day 113 (12, 10 and 2 patients in the KY1005 low dose, KY1005 high dose and placebo groups, respectively). On average, improvements from baseline were generally sustained throughout the study extension (to Day 253) in this subset of patients across the exploratory endpoints of EASI, vIGA, SCORAD Index, affected BSA, POEM total score, PO-SCORAD Index, DLQI and NRS for pruritus. However, interpretation is difficult, particularly in the placebo group where there were only 2 patients.

Pharmacokinetics

Serum concentrations of KY1005 steadily decreased from Day 113 to the end of study, with an approximately dose proportional relationship observed for $AUC_{0-inf}$. Similar accumulation index calculated after the fourth dose (about 2-fold), and Vd (about 5 L) was observed for the two KY1005 dose groups, and no target mediated drug disposition was apparent. Geometric mean $t_{1/2}$ values were similar for the low (23.04 days) and high (28.02 days) dose groups.

Pharmacodynamics

Anti-KY1005 antibodies were increasingly detected in the KY1005 low dose group over time, while patients in the KY1005 high dose and placebo groups were negative. By Day 253, of those patients who were defined as responders (vIGA 0/1) at Day 113, 9 out of 11 patients (81.8%) in the KY1005 low dose group were positive for anti-KY1005 antibodies with a median titer of 53.50 (range: 1.5 to 1740).

Adverse Events

During the main study (prior to Visit 19), similar numbers of patients experienced at least one TEAE in the KY1005 low dose and placebo groups (18 [62.1%] and 20 [69.0%] patients, respectively), whereas the number was lower in the KY1005 high dose group (14 [46.7%] patients). Likewise, treatment-related TEAEs were reported for similar numbers of patients in the KY1005 low dose and placebo groups (10 [34.5%] and nine [31.0%] patients, respectively), but a lower number in the KY1005 high dose group (six [20.0%] patients).

One patient (3.4%) in the KY1005 low dose group experienced a serious TEAE during the main study, which was considered treatment-related, and one patient (3.3%) in the KY1005 high dose group experienced a treatment-emergent AESI, which was considered unrelated to treatment. Treatment-emergent AEs leading to discontinuation of study treatment were reported for three patients, including two patients in the placebo group and one patient in the KY1005 low dose group during the main study.

For the study extension, percentages were calculated based on the patients who performed at least one visit of the extension study. During the study extension (from Visit 19), similar numbers of patients experienced at least one TEAE in the KY1005 high dose and low dose groups (seven [35.0%] and eight [36.4%] patients, respectively), whereas the number was lower in the placebo group (four [23.5%] patients). Treatment-related TEAEs were reported for two (10.0%) patients in the KY1005 low dose group and no patients in the KY1005 high dose and placebo groups. One patient (5.0%) in the KY1005 low dose group experienced a serious TEAE during the study extension, which was considered unrelated to study treatment. One patient (5.0%) in the KY1005 low dose group experienced a treatment-emergent AESI, which was considered unrelated to study treatment.

At the discretion of the Investigator, patients could be rescued with a prohibited medication or procedure for the treatment of intolerable AD symptoms. Within the first month from Baseline, up to two rescue therapy administrations of up to 3 days with topical therapies were permitted without permanent discontinuation of threatment. Use of any rescue therapies was recorded in the eCRF. Patients who received any systemic rescue treatment with a prohibited medication or procedure from Baseline through Day 113 were to be permanently discontinued from treatment.

Rescue medications within the first month included corticosteroids, dermatological Preparations, administered to three patients in each of the three treatment groups, and other dermatological preparations, administered to one patient in the KY1005 high dose group (Table 20.)

TABLE 20

Summary of Rescue Medications within the First Month Tabulated by ATC Level 2 Group and WHO Preferred Name (SAF)

| ATC Level 2 Group Text | WHO preferred name | KY1005 low dose (n = 29) | KY1005 high dose (n = 30) | Placebo (n = 29) |
|---|---|---|---|---|
| Corticosteroids. Dermatological Preparations | Total | 3 (10.3%) | 3 (10.0%) | 3 (10.3%) |
| | Betamethasone dipropionate | 0 (0.0%) | 0 (0.0%) | 1 (3.4%) |
| | Betamethasone dipropionate:Gentamicin sulfate | 0 (0.0%) | 1 (3.3%) | 0 (0.0%) |

TABLE 20-continued

Summary of Rescue Medications within the First Month Tabulated by ATC Level 2 Group and WHO Preferred Name (SAF)

| ATC Level 2 Group Text | WHO preferred name | KY1005 low dose (n = 29) | KY1005 high dose (n = 30) | Placebo (n = 29) |
|---|---|---|---|---|
| | Clobetasol propionate | 1 (3.4%) | 1 (3.3%) | 0 (0.0%) |
| | Dexamethasone | 0 (0.0%) | 1 (3.3%) | 0 (0.0%) |
| | Methylprednisolone | 0 (0.0%) | 0 (0.0%) | 1 (3.4%) |
| | Methylprednisolone aceponate | 0 (0.0%) | 0 (0.0%) | 1 (3.4%) |
| | Mometasone furoate | 2 (6.9%) | 2 (6.7%) | 1 (3.4%) |
| Other Dermatological Preparations | Total | 0 (0.0%) | 1 (3.3%) | 0 (0.0%) |
| | Tacrolimus | 0 (0.0%) | 1 (3.3%) | 0 (0.0%) |

Rescue Medication: 'During the BDRM it will also be decided which medications will be counted as rescue medications.
Coding: WHO Drug Dictionary Enhanced. 1 SEP. 2018

Conclusions

This Phase IIa, randomized, double-blind, placebo-controlled, parallel group, multicenter study explored the efficacy and safety of KY1005 in adult patients with moderate to severe AD who had a documented history, within 6 months prior to baseline, of either inadequate response to topical treatments or inadvisability of topical treatments. Patients randomized to KY1005 received a loading dose of 500 mg or 200 mg KY1005 followed by three maintenance doses at 50% of the loading dose at 28-day intervals. Patients randomized to the placebo group received four infusions of matching placebo on Days 1, 29, 57 and 85.

A total of 89 patients were randomized in the study, 59 of whom completed the main study (up to Day 113). One patient in the placebo group terminated the study early due to a protocol deviation prior to the administration of treatment. Three patients terminated the study early due to AEs, all of whom were in the placebo group. The remaining reasons for early termination were withdrawal of consent, 'Other' reasons and failure to meet randomization criteria.

Baseline disease characteristics were as expected for a population of patients with moderate to severe AD and were generally well matched across the treatment groups. While the number of patients in the FAS with a vIGA score of 4 (severe) was higher in the placebo group (15 [62.5%]) compared to the KY1005 groups (10 [37.0] and 9 [33.3%] in the low and high dose groups, respectively), there were no other notable differences between treatment groups in baseline disease characteristics, including affected BSA, EASI, SCORAD, and NRS for pruritus.

The primary efficacy endpoint was the percentage change in EASI from Baseline to Day 113. Progressive reductions in EASI score from Baseline to Days 15, 29, 57, 85 and 113 in the FAS were observed across all treatment groups, including placebo. However, greater reductions were observed in the KY1005 groups compared to placebo at all time points. For the Day 113 time point, LSM percentage change (95% CI) from Baseline was −80.12 [−95.55, −64.68] and −69.97 [−85.04, −54.60] for the KY1005 low and high dose groups, respectively, compared to −49.37 [−66.02, −32.72] for placebo. The difference versus placebo was nominally statistically significant for the KY1005 low dose group (p=0.009) but not for the high dose group (p=0.072). Repeat of the primary efficacy analysis for the PPS and for the sensitivity analysis (using EASI stratum as covariate; with rescue mediation within the first month and rescue medication-by-treatment as fixed effects) provided similar result to the main analysis.

Nominally statistically significant improvements from Baseline in both KY1005 groups compared to placebo were also observed for the following secondary efficacy endpoints vIGA, SCORAD Index, and affected BSA. There were generally no clear differences between the KY1005 low and high dose groups in either the speed of onset or magnitude of responses.

While reductions from Baseline were generally observed for the secondary patient reported outcome efficacy endpoints of POEM total score and DLQI total score, these were apparent across all treatment groups, including placebo, and there were no clear differences between the groups. The exception however, was the PO-SCORAD, which demonstrated a nominally statistically significant difference for the KY1005 low dose group compared with placebo.

For patients with a Baseline NRS of at least 3 and at least 4, the percentage of patients with a best improvement in NRS for pruritus of at least 3 units and at least 4 units, respectively was higher in the KY1005 groups compared with the placebo group.

Results for the subgroup of patients in the EASI >21 stratum (severe disease—56 patients) were similar to those observed in the FAS. Results for the EAST 521 stratum (moderate disease-22 patients) were also generally similar to those observed in the FAS, but the low numbers of patients included in this stratum makes it difficult to draw meaningful conclusions as to whether Baseline disease severity has a meaningful impact on response.

A total of 24 patients were defined as responders (vIGA 0/1) at Day 113 (12, 10 and 2 patients in the KY1005 low dose, KY1005 high dose and placebo groups, respectively). On average, improvements from Baseline were generally sustained throughout the study extension (to Day 253) in this subset of patients across the exploratory endpoints of EASI, vIGA, SCORAD Index, affected BSA, POEM total score, PO-SCORAD Index, DLQI and NRS for pruritus. However, where differences were observed it is not possible to determine whether this is due to a true treatment effect or due to the low numbers of patients and the widely overlapping 95% CIs.

Clinically meaningful improvements from Baseline in the KY1005 groups compared to placebo were observed for the majority of the efficacy endpoints, including the primary endpoint (percentage change in EASI from Baseline to Day 113) and the secondary efficacy endpoints of EASI 50, EASI 75 and EASI 90, vIGA, SCORAD Index, affected BSA and PO-SCORAD Index. The differences versus placebo were nominally statistically significant for the KY1005 low dose group for the primary endpoint and PO-SCORAD, and for both KY1005 groups for vIGA, SCORAD, and affected BSA.

Consistent with previous observations, evaluation of PK revealed that serum concentrations of KY1005 increased rapidly following I.V. administration, with a median $t_{max}$ of 0.03 days and an approximately dose proportional relationship for $C_{max}$, $AUC_{0-28}$ and $AUC_{0-inf}$. Following each dose, serum concentrations steadily decreased in a biphasic manner, with estimated $t_{1/2}$ values that were similar for the low and high doses. No target-mediated drug disposition was apparent and there was minimal accumulation after administration of four doses every 28 days. KY1005 was still measurable in serum at 168 days after the final dose, even at the low dose level.

KY1005 was well tolerated following I.V. administration of 500 mg and 200 mg loading doses followed by three maintenance (50%) doses, with no safety concerns identified in this study.

Anti-KY1005 antibodies were detected in increasing numbers of patients in the KY1005 low dose group over time, while patients in the KY1005 high dose and placebo groups were generally negative. By Day 113 in patients with available data, anti-KY1005 antibodies were detected for 10 patients (50.0%) in the KY1005 low dose group and no patient in the KY1005 high dose group. For the 10 patients in the KY1005 low dose group with a positive ADA result, the median titer was 11.85 (range: 1.6 to 465.0). By Day 253, of those patients who were defined as responders (vIGA 0/1) at Day 113, 9 out of 11 patients (81.8%) in the KY1005 low dose group were positive for anti-KY1005 antibodies with a median titer of 53.50 (range: 1.5 to 1740). No unexpected changes in PK profile was observed in patients with positive ADA, indicating that where present, ADAs were likely to be weakly or non-neutralizing. No adverse events were associated with positive ADA.

Repeat dosing of KY1005 was well tolerated during the main study (up to Day 113) and study extension (up to Day 253), with no safety concerns identified in this study. Overall, there were no clear trends in the numbers of patients reporting TEAEs and treatment-related TEAEs, by SOC and PT.

No deaths occurred during the study up to Day 113. One serious TEAE was reported up to Day 113: an event of Infected dermal cyst in a patient in the KY1005 low dose group. This event was considered possibly related to treatment, although the case was confounded by the patient's ongoing medical history of dermal cysts. One treatment-emergent AESI was reported during the study up to Day 113 and one was reported during the study extension post-Day 113. Both events were considered unrelated to treatment. One serious TEAE of 'sudden death' was reported post-Day 113 on study Day 172 (3 months after last of dose of KY1005 low dose); this event was considered unrelated by the investigator.

Treatment-emergent AEs leading to discontinuation (of study treatment and/or the study overall) were reported for four patients. The events in these cases were reflective of exacerbation of the underlying disease leading to withdrawal (two patients; placebo), a report of Drug ineffective leading to withdrawal (placebo) and a mild event of Nasopharyngitis leading to treatment discontinuation (KY1005 low dose).

No clinically relevant trends in clinical laboratory parameters were observed following treatment with KY1005 or placebo, and no safety concerns were raised. Treatment-emergent AEs in the System Organ Class (SOC) of Investigations were reported for broadly similar numbers of patients across the treatment groups. These abnormalities were sporadic findings and there were no clear trends related to treatment. There were no clinically meaningful changes from baseline or differences between treatment groups in vital signs and ECG measurements.

In the study extension, on average improvements from baseline were generally sustained throughout the study extension (to Day 253) in responders (vIGA 0/1 at Day 113) across the exploratory endpoints of EASI, vIGA, SCORAD Index, affected BSA, POEM total score, PO-SCORAD Index, DLQI and NRS for pruritus. KY1005 continued to be well tolerated during follow-up in the study extension (up to Day 253), with no safety concerns identified in this study. The PK profile of KY1005 was as expected in the study extension, and the geometric mean $t_{1/2}$ ranged from 23 to 28 days. KY1005 was still measurable in serum 168 days after the final dose, even at the low dose level.

Example 3: A Phase I, Open-label Study to Assess the Pharmacokinetics of KY1005 after Single Dose Administration by Subcutaneous and Intravenous Route in Healthy Volunteers, ClinicalTrials.qov Identifier: NCT04449939 (KY1005-CTO4)

Primary Objective

To assess the pharmacokinetics (PK) of KY1005 when administered subcutaneously.

Secondary Objectives

To assess the safety & tolerability of KY1005 when administered subcutaneously and intravenously.

To assess the immunogenicity of KY1005.

Primary Endpoints

The following PK parameters of KY1005 after I.V. and S.C. administration were assessed: maximum observed concentration after I.V. or S.C. administration ($C_{max}$); time at which $C_{max}$ is observed ($t_{max}$); area under the concentration time curve from time 0 to last observation ($AUC_{last}$); area under the concentration time curve from time 0 to infinity ($AUC_{inf}$); percentage of $AUC_{inf}$ extrapolated from tlast to infinity (% $AUC_{extrap}$); mean residence time ($MRT_{inf}$); systemic clearance after I.V. infusion (CL); apparent systemic clearance after S.C. injection (CL/F); volume of distribution during the terminal phase after I.V. infusion ($V_z$); apparent volume of distribution after S.C. injection ($V_z$/F); steady-state volume of distribution after I.V. infusion (Vss); weight-normalised Vss and $V_z$; half-life ($t_{1/2}$); and terminal rate constant ($\lambda_z$), dose-normalised $C_{max}$ ($C_{max}$/D) and dose-normalised $AUC_{inf}$ ($AUC_{inf}$/D) following SC and IV administration, and absolute bioavailability (F) calculated as the ratio of $AUC_{inf}$/D after I.V. and S.C. administration.

Secondary Endpoints

Incidence of TEAEs, treatment-emergent serious adverse events (TESAEs) and local injection site reactions.

Vital signs, laboratory safety tests, 12-lead ECG, physical examination.

Anti-KY1005 antibody titer and number of subjects with positive response.

Study Design

Figure 15:
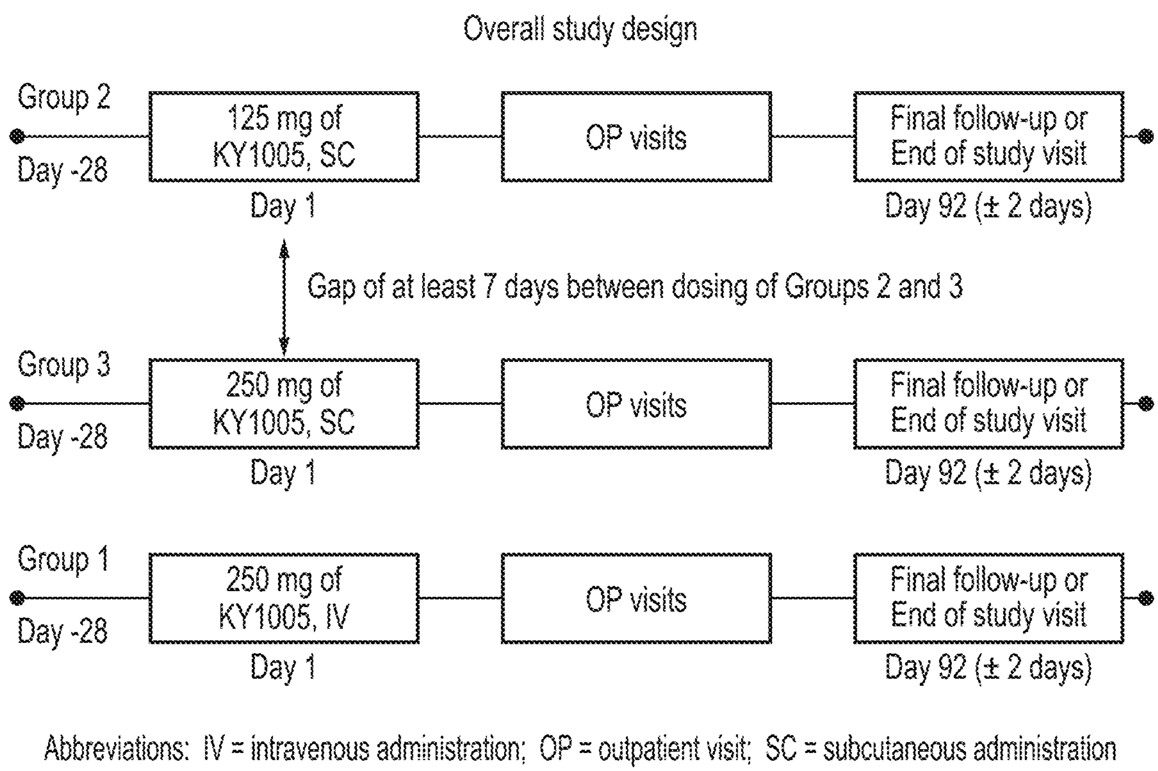
FIG. 15 graphically depicts the overview of study design of Example 3. The study included 3 groups as follows: Comparator Group 1: single dose of 250 mg KY1005, given by IV infusion over 30 min followed by saline flush over 15 min; Group 2: single dose of 125 mg (1 mL) KY1005, given by SC injection into the abdomen; and Group 3: single dose of 250 mg (2 mL) KY1005, given as sequential 2×1 mL SC injections into the abdomen.

This was a Phase 1, single-center, open-label, parallel-group, single-dose study to assess the PK, safety and tolerability of KY1005 after S.C. and I.V. administration in healthy male volunteers. KY1005 administered I.V.was defined as the reference treatment. A schematic diagram of the study design is presented in FIG. 15.

Dosage and Evaluation Groups

Three groups of 8 healthy men were enrolled into the study (Groups 1-3). Subjects for Groups 2 and 3 were recruited before those for Group 1. Each subject had 1 study session in which they received a single dose of KY1005 via S.C. injection(s) or I.V. infusion, as follows.

Comparator Group 1: single dose of 250 mg KY1005, given by I.V. infusion over 30 min followed by saline flush over 15 min.

Group 2: single dose of 125 mg (1 mL) KY1005, given by S.C. injection into the abdomen.

Group 3: single dose of 250 mg (2 mL) KY1005, given as sequential 2×1 mL S.C. injections into the abdomen.

As KY1005 had not been administered to humans by S.C. injection before; there were at least 7 days between dosing of Groups 2 and 3.

Study Visits

All subjects were screened within 28 days before their dose of KY1005.

All subjects received a single dose of KY1005 on Day 1. Subjects who received KY1005 by I.V. infusion (Group 1) were resident on ward from the day before their dose (Day-1) until 24 h after dosing (Day 2). Subjects who received KY1005 by S.C. injection (Groups 2 and 3) were resident on ward from the day before their dose (Day-1) until 96 h after dosing (Day 5). All subjects returned to the ward for 7 outpatient visits after their dose, on Days 8, 15, 22, 29, 36, 57 and 78. They also attended a follow-up visit at about 91 days after their dose (Day 92 i 2 days). The end of the trial was defined as the last visit by the last subject.

Study Assessments

The following assessments were made:

Pharmacokinetic: blood samples for assay of KY1005 were taken before and at frequent time points up to 24 h after dosing (Days 1-2); each morning on Days 3-5 (Groups 2 and 3 only); at each outpatient visit (Days 15-78); and at the final follow-up visit (Day 92).

Safety: laboratory assessments (routine hematology, biochemistry, and urinalysis), physical examination, 12-lead ECG, vital signs, local tolerability, and AEs.

Tolerability: AEs.

Immunogenicity: blood samples for assay of ADA were taken before dosing and at multiple timepoints throughout the study.

Inclusion Criteria

Subjects were eligible for inclusion in the trial if they met the following criteria:

1. Healthy male volunteer, aged 18-45 years at screening (i.e. the time of informed consent).
2. Body weight 60-120 kg, and a body mass index (BMI; Quetelet index) in the range 18.0-30.0 kg/$m^2$ (inclusive).

(Other Inclusion and Exclusion Criteria Available Online at ClinicalTrials.Gov, Identifier: NCT04449939)

Treatments Administered

The dosing schedule is presented in Table 21.

TABLE 21

| Dosing Schedule | | | | |
|---|---|---|---|---|
| Group | Investigational Medicinal Product | Dose | Route of Administration | Frequency and/or Regime |
| 1 | KY1005 | 250 mg | IV | Single dose |
| 2 | KY1005 | 125 mg | SC | Single dose |
| 3 | KY1005 | 250 mg | SC | Single dose given as two 125 mg administrations |

Subjects in Group 1 received a single dose of KY1005 as an I.V. infusion of about 100 mL (250 mg KY1005 in sterile 0.9% saline) over 30 min into a forearm vein, followed by a saline flush over 15 min.

Subjects in Groups 2 and 3 received a single dose of KY1005 by S.C. injection. Subjects in Group 2 received an injection of 1 mL (125 mg KY1005) and subjects in Group 3 received 2 sequential injections of 1 mL each (250 mg KY1005 in total) into the abdomen, given 20-60 min apart.

Identity of Test Product

KY1005 was formulated as a liquid at 125 mg/mL KY1005.

KY1005 was aseptically filled into 2 mL Type 1 clear glass vials with a nominal fill volume of 1 mL, sealed with FluoroTec coated stoppers and crimped with overcaps to ensure container closure integrity. The recommended storage temperature was 2-8° C.

Serum Pharmacokinetics

The concentration of KY1005 in all predose samples was below the limit of quantification (BLQ) (lower limit of quantification (LLQ) was 46.9 ng/mL).

Mean serum concentrations are summarized in Table 22. Mean serum concentrations are plotted against time in FIG. 16A (linear) and FIG. 16B (semi-logarithmic) and FIG. 17A (linear) and FIG. 17B (semi-logarithmic).

TABLE 22

| KY1005 serum concentrations after single intravenous and subcutaneous doses of KY1005: PK concentration population (n = 8 per group) | | | | | | | |
|---|---|---|---|---|---|---|---|
| | Nominal | Arithmetic mean (SD) serum concentrations of KY1005 (ng/mL) | | | | | |
| Study day | timepoint (h) post-dose | 250 mg KY1005 IV (N = 8) | | 250 mg KY1005 SC (N = 8) | | 125 mg KY1005 SC (N = 8) | |
| 1 | Predose | $0^8$ | — | $0^8$ | — | $0^8$ | — |
| | End of infusion* | 88931.34 | (17383.91) | — | — | — | — |
| | 1 | 87854.54 | (14278.25) | 276.79 | (257.837) | $40.69^3$ | (36.480) |
| | 2 | 83639.46 | (9867.235) | 699.91 | (408.109) | $270.58^1$ | (196.077) |
| | 4 | 84028.64 | (11227.33) | 1744.94 | (666.527) | 1054.14 | (713.555) |
| | 8 | 80799.99 | (11512.26) | 4455.90 | (1695.732) | 2414.64 | (1540.815) |
| | 12 | 71815.49 | (11502.46) | 6365.51 | (2445.451) | 3824.13 | (2173.649) |
| 2 | 24 | 65446.84 | (9615.421) | 9640.45 | (3656.326) | 6009.41 | (3049.784) |
| | 48 | — | — | 16524.50 | (6769.445) | 10197.54 | (3741.174) |
| 4 | 72 | — | — | 19988.15 | (6364.779) | 11409.30 | (3279.915) |
| 5 | 96 | — | — | 21833.04 | (6779.306) | 12541.60 | (3544.389) |
| 8 | 168 | 36846.09 | (5063.785) | 25802.99 | (4265.096) | 14222.35 | (2309.279) |
| 15 | — | 31773.21 | (3467.040) | 24750.85 | (4098.516) | 13965.35 | (2664.434) |

TABLE 22-continued

KY1005 serum concentrations after single intravenous and subcutaneous doses of KY1005: PK concentration population (n = 8 per group)

| Study day | Nominal timepoint (h) post-dose | Arithmetic mean (SD) serum concentrations of KY1005 (ng/mL) 250 mg KY1005 IV (N = 8) | | 250 mg KY1005 SC (N = 8) | | 125 mg KY1005 SC (N = 8) | |
|---|---|---|---|---|---|---|---|
| 22 | — | 28372.71 | (4803.550) | 22544.18 | (3854.234) | 12336.64 | (1799.133) |
| 29 | — | 22414.00 | (4822.714) | 19264.55 | (3953.609) | 11243.12 | (1784.189) |
| 36 | — | 20277.83 | (2947.633) | 19584.08 | (3093.818) | 10182.74 | (1377.499) |
| 57 | — | 13714.40 | (3905.523) | 12729.15 | (2723.015) | 6671.20 | (1046.571) |
| 78 | — | 9267.16 | (2170.903) | 9784.15 | (2004.073) | 4354.85 | (999.288) |
| 92 | Follow-up | 7162.31 | (3152.584) | 7748.31 | (2720.715) | 3215.93 | (1036.034) |

*I.V. dosing only.
N: number of subjects receiving treatment;
SD: standard deviation;
Numerical superscripts indicate the number of imputed values.

Figure 17A:
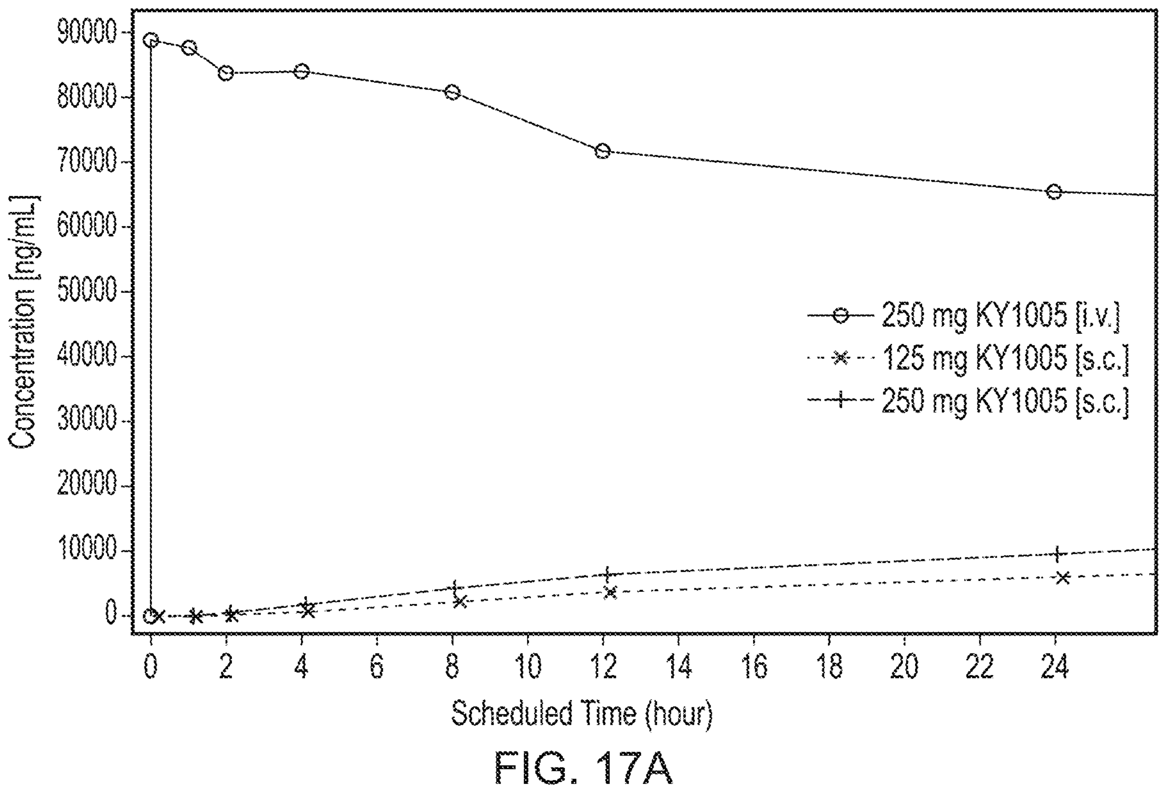
FIG. 17A-17B graphically depicts mean serum concentration time plots of KY1005 up to 24 hours after single intravenous and subcutaneous doses that are linear (FIG. 17A) and semi-logarithmic (FIG. 17B). Absorption via the SC route was slower than seen for the IV administered drug. Single 250 mg KY1005 IV doses rapidly achieved peak serum concentrations at the end of infusion (30 min): mean serum concentration was 88,931 ng/mL; individual subject concentrations at end-infusion ranged from 72,391 to 120,333 ng/mL (with a 1.66-fold ratio between subjects at each extreme).
Figure 17B:
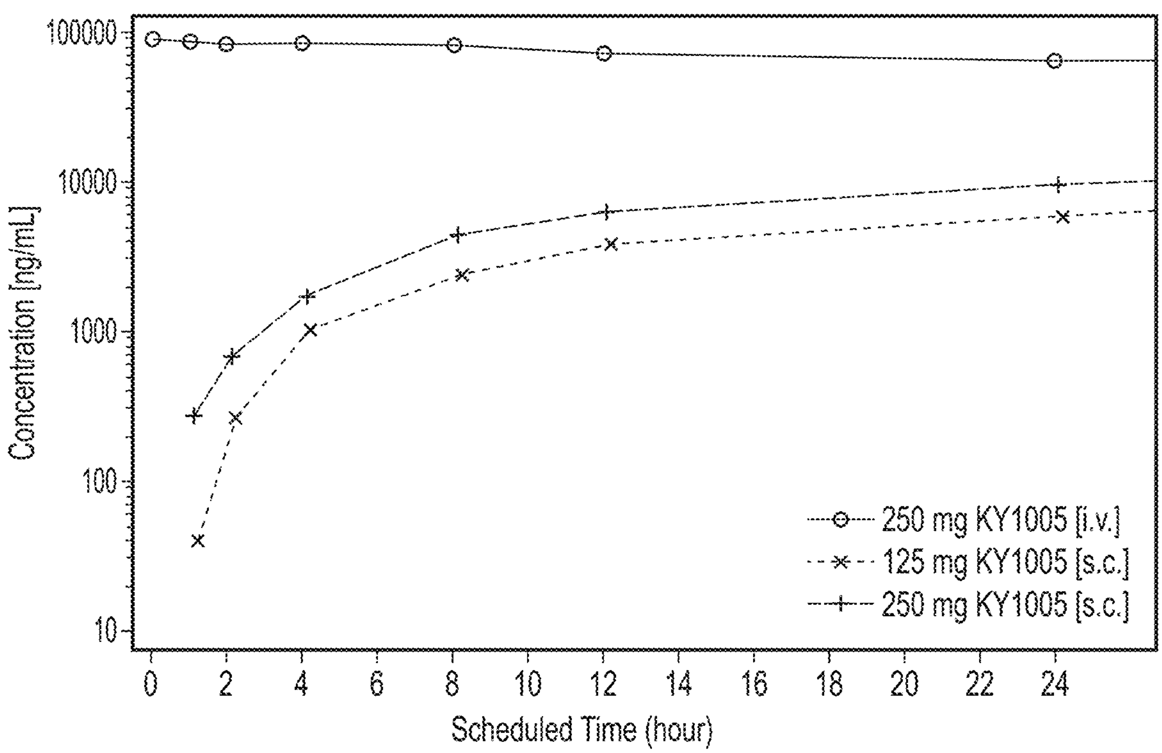

As shown in FIG. 17A (linear) and FIG. 17B (semi-logarithmic), single 250 mg KY1005 I.V. doses rapidly achieved peak serum concentrations at the end of infusion (30 min): mean serum concentration was 88,931 ng/mL; individual subject concentrations at end-infusion ranged from 72,391 to 120,333 ng/mL (with a 1.66 fold ratio between subjects at each extreme). There was high variation in $t_{max}$, which ranged from 0.77 to 8.93 h; 3 subjects (1001, 1004 and 1005) had $t_{max}$ of 8.8, 8.9 and 4.8 h, respectively.

Figure 16A:
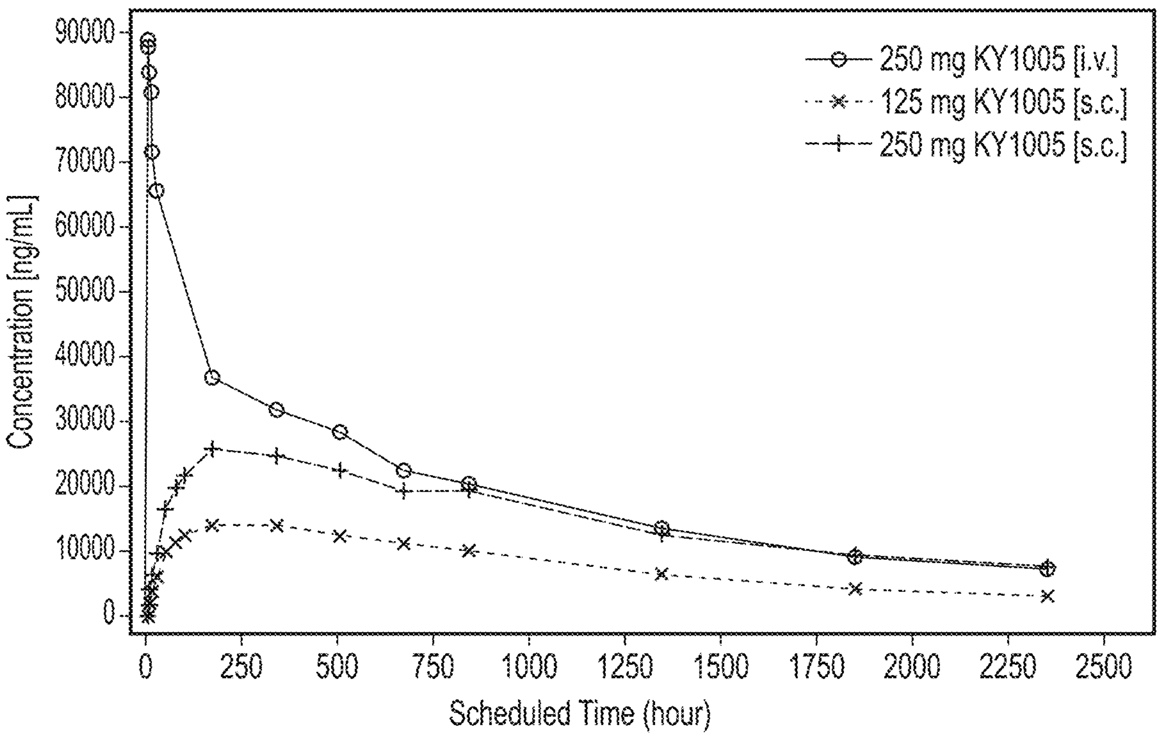
FIG. 16A-16B graphically depicts mean serum concentration time plots of KY1005 up to 92 days after single intravenous and subcutaneous doses that are linear (FIG. 16A) and semi-logarithmic (FIG. 16B). Absorption via the SC route was slower than seen for the IV administered drug: mean serum concentration peaked at 168 h post dose (Day 8) after both 250 mg KY1005 (25,803 ng/mL) and 125 mg (14,222 ng/mL) SC doses. Mean serum concentration after 250 mg IV and SC doses converged at about 20,000 ng/mL on Day 36. After that point, mean serum-concentration time curves for both regimens were closely similar throughout the rest of the sampling period, both falling to about 7,000 ng/mL at Follow-up (Day 92).
Figure 16B:
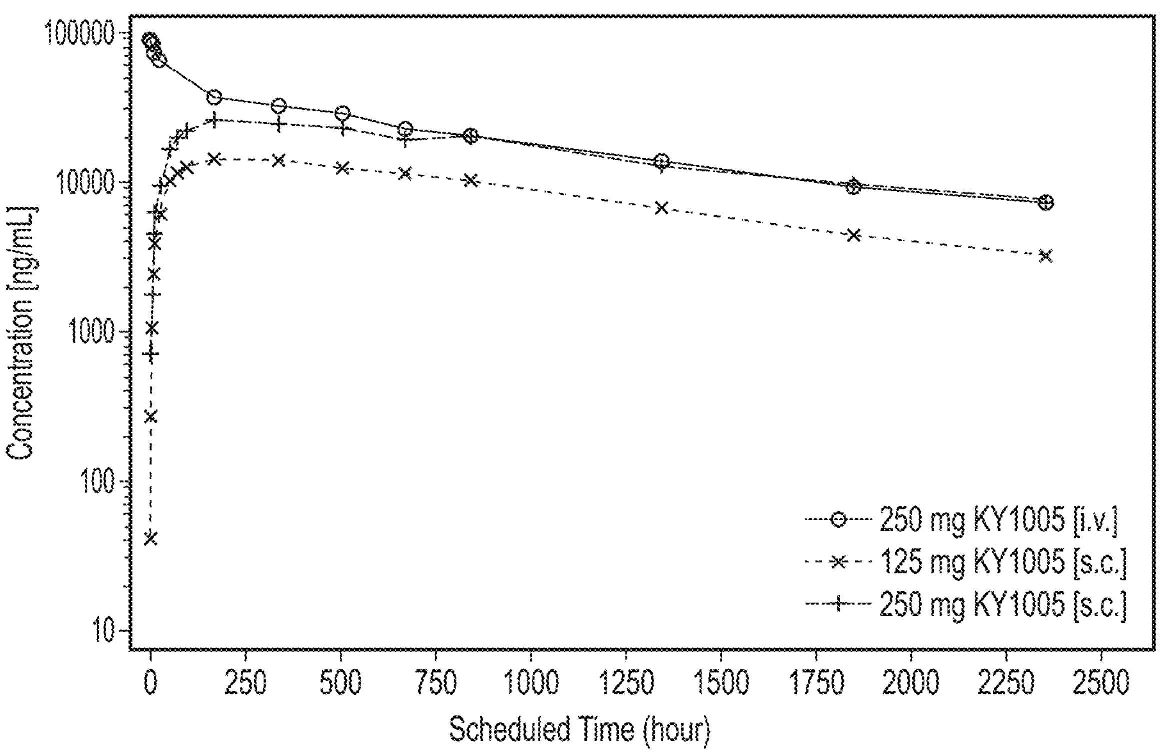

As shown in FIG. 16A (linear) and FIG. 16B (semi-logarithmic), 250 mg KY1005 I.V. showed biphasic elimination. A rapid phase occurred between end of infusion (Day 1) and 168 h (Day 8) after dosing, during which time the mean serum concentration fell from 65,447 to 36,846 ng/mL. That was followed by a slower terminal elimination phase in the rest of the sampling period.

Absorption via the S.C. route was slower than seen for the I.V. administered drug: mean serum concentration peaked at 168 h post dose (Day 8) after both 250 mg KY1005 (25,803 ng/mL) and 125 mg (14,222 ng/mL) S.C. doses. From Day 8 onwards, $t_{max}$ was constrained by 7 to 21-day sampling intervals, which may have contributed to the substantial variation in $t_{max}$ after S.C. dosing: individual $t_{max}$ ranged from 96 (Day 4) to 336 h (Day 15), and 96 (Day 4) to 504 h (Day 22), after 250 mg and 125 mg S.C., respectively; median $t_{max}$ was at the 168-h (Day 8) timepoint.

Mean serum concentration after 250 mg I.V. and S.C. doses converged at about 20,000 ng/mL on Day 36. After that point, mean serum-concentration time curves for both regimens were closely similar throughout the rest of the sampling period, both falling to about 7,000 ng/mL at Follow-up (Day 92). The mean serum-concentration time curve after 125 mg S.C. was similar in profile to that after 250 mg S.C. doses, albeit at about half the concentration.

Serum Parameters

Selected PK parameters of KY1005 are summarized in Table 23.

TABLE 23

Summary of KY1005 serum pharmacokinetic parameters after single intravenous and subcutaneous doses of KY1005: PK parameter population (n = 8 per group)

| KY1005 parameter | | 250 mg KY1005 I.V. (N = 8) | 250 mg KY1005 S.C. (N = 8) | 125 mg KY1005 S.C. (N = 8) |
|---|---|---|---|---|
| $C_{max}$ | geo mean[a] | 90426 | 26130 | 15146 |
| (ng/mL) | 95% CI | (79129, 103336) | (22170, 30798) | (12961, 17700) |
| | Range | 75616-120333 | 17975-33458 | 10005-18351 |
| $C_{max}$/D | geo mean[a] | 362 | 105 | 121 |
| (ng/mL/g) | 95% CI | (317, 413) | (88.7, 123) | (104, 142) |
| | Range | 302-481 | 71.9-134 | 80.0-147 |
| $t_{max}$ | Median | 1.79 | 169 | 170 |
| (h) | Range | 0.767-8.93 | 96.5-337 | 96.0-504 |
| λZ | mean[b] | $0.821 \times 10^{-3}$ | $0.632 \times 10^{-3}$ | $0.915 \times 10^{-3}$ |
| (1/h) | SD (% CVb) | $0.121 \times 10^{-3}$ (14.8) | $0.140 \times 10^{-3}$ (22.2) | $0.305 \times 10^{-3}$ (33.4) |
| | Range | $0.674\text{-}0.981 \times 10^{-3}$ | $0.455\text{-}0.850 \times 10^{-3}$ | $0.673\text{-}1.611 \times 10^{-3}$ |
| $t_{1/2}$ | mean[b] | 861 | 1145 | 813 |
| (h) | SD (% CVb) | 127 (14.7) | 251 (21.9) | 194 (23.9) |
| | Range | 706-1028 | 815-1523 | 430-1029 |
| $AUC_{inf}$ | geo mean[a] | 52.8 | 46.7 | 21.9 |
| (mg · h/mL) | 95% CI | (45.0, 61.9) | (39.1, 55.9) | (18.4, 26.0) |
| | Range | 42.5-70.2 | 35.3-73.2 | 14.7-26.6 |
| $AUC_{inf}$/D | geo mean[a] | 0.21 | 0.19 | 0.18 |
| (mg · h/mL/mg) | 95% CI | (0.18, 0.25) | (0.16, 0.22) | (0.15, 0.21) |
| | Range | 0.17-0.28 | 0.14-0.29 | 0.12-0.21 |
| $AUC_{last}$ | geo mean[a] | 44.5 | 33.9 | 18.1 |
| (mg · h/mL) | 95% CI | (39.4, 50.2) | (29.5, 38.8) | (15.8, 20.7) |
| | Range | 37.7-56.3 | 26.5-45.5 | 12.6-20.4 |

TABLE 23-continued

Summary of KY1005 serum pharmacokinetic parameters after single intravenous and subcutaneous doses of KY1005: PK parameter population (n = 8 per group)

| KY1005 parameter | | 250 mg KY1005 I.V. (N = 8) | 250 mg KY1005 S.C. (N = 8) | 125 mg KY1005 S.C. (N = 8) |
|---|---|---|---|---|
| % $AUC_{extrap}$ | mean[b] | 15.6 | 27.2 | 17.1 |
| (%) | SD (% CVb) | 5.3 (33.9) | 8.1 (29.6) | 6.1 (35.4) |
| | Range | 7.8-22.1 | 15.3-37.8 | 5.7-23.1 |
| $MRT_{inf}$ | geo mean[a] | 1178 | 1674 | 1275 |
| (h) | 95% CI | (1047, 1326) | (1383, 2026) | (1097, 1483) |
| | Range | 1020-1428 | 1164-2234 | 896-1515 |
| Vz/F | mean[b] | — | 8.78 | 6.60 |
| (L) | SD (% CVb) | — | 1.72 (19.5) | 1.28 (19.4) |
| $V_z$ | mean[b] | 5.86 | — | — |
| | SD (% CVb) | 0.698 (11.9) | — | — |
| $V_z$, norm | mean[b] | 0.0773 | — | — |
| (L/kg) | SD (% CVb) | 0.00991 (12.8) | — | — |
| Vss | mean[b] | 5.61 | — | — |
| (L) | SD (% CVb) | 0.624 (11.1) | — | — |
| Vss, norm | mean[b] | 0.0740 | — | — |
| (L/kg) | SD (% CVb) | 0.008951 (12.1) | — | — |
| CL/F | mean[b] | — | 0.005451 | 0.005820 |
| (L/h) | SD (% CVb) | — | 0.001061 (19.5) | 0.001325 (22.8) |
| CL | mean[b] | 0.004807 | — | — |
| (L/h) | SD (% CVb) | 0.000876 (18.2) | — | — |

% $AUC_{extrap}$: percentage of $AUC_{inf}$ extrapolated from last to infinity; % CVb: between-subject coefficient of variance; $C_{max}$: maximum observed concentration; $C_{max}$/D: dose-normalised $C_{max}$; $t_{max}$: time at which $C_{max}$ is observed; $AUC_{0-t}$: area under the concentration time curve from time 0 to last observation; $AUC_{inf}$: area under the concentration time curve from time 0 to infinity; $AUC_{inf}$/D: dose-normalised $AUC_{inf}$; CL: systemic clearance after I.V. infusion; CL/F: apparent systemic clearance after S.C. injection; $V_z$: volume of distribution during the terminal phase after IV infusion; $V_z$/F: apparent volume of distribution after S.C. injection; $V_{ss}$: steady-state volume of distribution after I.V. infusion; $V_{ss, norm}$: body weight-normalised $V_{ss}$; $V_{z,norm}$: body weight-normalised $V_z$; $t_{1/2}$: terminal elimination half-life; $\lambda_Z$: terminal elimination rate constant.
[a]geometric mean;
[b]arithmetic mean.

After 250 mg KY1005 I.V., median $t_{max}$ derived using actual sampling times was 1.79 h, though the true peak concentration, consistent with the PK of monoclonal antibodies, must certainly have been at the end of infusion (30 min); and mean $C_{max}$ occurred at this time. Geometric mean $C_{max}$/D was 362 ng/mg/mL. Absorption of S.C. doses was slow, and yielded lower serum concentrations than did I.V. doses: median $t_{max}$ was 170 and 169 h, and $C_{max}$/D was 121 and 105 ng/mL/mg, after 125 mg and 250 mg S.C., respectively. Variation in $C_{max}$ was low: there was only a 1.59-fold difference between subjects at each extreme after I.V. doses, and 1.86 and 1.83-fold, respectively, after 125 and 250 mg S.C. doses; % CVb was 16.1-19.9 across dosing groups.

Despite the expected differences between I.V. and S.C. administration, dose normalized AUC differed little among dosing groups: geometric mean $AUC_{inf}$/D was 0.21, 0.18 and 0.19 mgh/mL/mg after 250 mg KY1005 I.V., 125 mg S.C., and 250 mg S.C., respectively. Those findings indicate that S.C. doses have a high degree of bioavailability (F was 0.83 and 0.89 for 125 and 250 mg doses, respectively). Variation in $AUC_{inf}$ was low: there was a 1.65-fold difference between subjects at each extreme after 250 mg KY1005 I.V., and 1.81 and 2.07-fold after 125 mg and 250 mg S.C., respectively; % CVb was 19.2-21.6 across dosing groups.

$C_{max}$ and AUC were broadly dose-proportional after S.C. administration of KY1005: geometric mean $C_{max}$ was 15,146 and 26,130 ng/mL, $AUC_{inf}$ was 21.9 and 46.7 mgh/mL, and $AUC_{last}$ was 18.1 and 33.9 mg-h/mL, after 125 mg and 250 mg S.C., respectively, equating to 1.7 to 2.1-fold differences in mean between the 2 dosing groups.

Arithmetic mean $t_{1/2}$ was similar for all dose groups, and ranged from 813 to 1145 h. The close fit of the regression line to the λz plots suggests valid estimation of $t_{1/2}$ for all subjects who received KY1005; arithmetic mean % $AUC_{extrap}$ was 15.6% after 250 mg I.V., 27.2% after 250 mg S.C., and 17.1% after 125 mg S.C.

As with serum concentration, between-subject variation in elimination parameters ($t_{1/2}$ and $\lambda_z$) was low: % CVb was about 14.8% after IV doses, and 21.9-33.4% after S.C. doses.

Geometric mean $MRT_{inf}$ was similar after 250 mg KY1005 I.V. and 125 mg S.C. (1178 and 1275 h, respectively) but about 1.3 to 1.4-fold higher (1674 h) after 250 mg S.C.; % CVb was 14.2-22.0 across dosing groups. Those values are similar to the corresponding ones for $t_{1/2}$.

As a result of the differences in dose-normalized AUC, $V_z$/F and CL/F inevitably differed slightly between S.C. doses: arithmetic mean $V_z$/F was 6.60 and 8.78 L, and CL/F was 0.00582 and 0.00545 L/h, after 125 and 250 mg KY1005 SC, respectively (% CVb 19.4-22.8). After 250 mg KY1005 I.V., $V_z$ and Vss were 5.86 and 5.61 L, and body weight-normalized $V_z$,norm and $V_{ss,norm}$ were 0.0773 and 0.0740 L/kg, respectively (% CVb 11.1-12.8); CL was 0.00481 L/h (% CVb 18.2).

Absolute Bioavailability

Absolute bioavailability of the 2 S.C. dose regimens in the study was assessed for $AUC_{inf}$/D and is summarized in Table 24.

TABLE 24

Summary of the absolute bioavailability analysis of single doses of KY1005 given by subcutaneous administration: PK parameter population (n = 8 per group)

| | Means | | | | |
|---|---|---|---|---|---|
| Parameter | 125 mg KY1005 S.C. | 250 mg KY1005 S.C. | 250 mg KY1005 I.V. | F125 | F250 |
| $AUC_{inf}$/D (ng · h/mL/mg) | 178268 | 190966 | 214740 | 0.83 | 0.89 |

$AUC_{inf}$/D: dose-normalised area under the concentration time curve from time 0 to infinity; $F_{125}$: $AUC_{inf}$/D 125 mg KY1005 S.C./$AUC_{inf}$/D 250 mg KY1005 I.V.; $F_{250}$: $AUC_{inf}$/D 250 mg KY1005 S.C./$AUC_{inf}$/D 250 mg KY1005 I.V.

The absolute bioavailability of KY1005 S.C. doses was similar at each S.C. dose level and was 0.83 after 125 mg S.C. and 0.89 after 250 mg S.C.

Anti-Drug Antibodies

Serum ADA positive results are summarized in Table 25.

TABLE 25

Summary of presence of serum anti-drug antibodies (n = 8 per group)

| Timepoint | 250 mg KY1005 I.V. N = 8 | 250 mg KY1005 S.C. N = 8 | 125 mg KY1005 S.C. N = 8 | All subjects N = 24 |
|---|---|---|---|---|
| | n (%) | | | |
| Predose | 1 (12.5) | 2 (25.0) | — | 3 (12.5) |
| Day 8 | 1 (12.5) | 2 (25.0) | 2 (25.0) | 5 (20.8) |
| Day 15 | 1 (12.5) | 2 (25.0) | 3 (37.5) | 6 (25.0) |
| Day 29 | 3 (37.5) | 3 (37.5) | 4 (50.0) | 10 (41.7) |
| Day 57 | 2 (25.0) | 1 (12.5) | 4 (50.0) | 7 (29.2) |
| Follow-up | 2 (25.0) | 3 (37.5) | 6 (75.0) | 11 (45.8) |

1 subject who received 250 mg KY1005 I.V., and 2 subjects who received 250 mg KY1005 S.C., had low titer positive results for ADA before receiving their doses. Measured titers in these subjects remained largely unchanged or reduced during the course of the study. All subjects who received 125 mg KY1005 S.C. had a negative ADA result before dosing.

Prevalence of KY1005 ADA broadly increased with time: in the total population of 24 subjects, ADA were present in 3 subjects (12.5%) before dosing; 5 subjects (20.8%) at Day 8; 6 subjects (25.0%) at Day 15; 10 subjects (41.7%) at Day 29; 7 subjects (29.2%) at Day 57; and 11 subjects (45.8%) at Follow-up (Day 92).

KY1005 ADA were more prevalent after 125 mg KY1005 S.C. than in the 2 other dosing groups: 6 subjects (75.0%) had ADA at Follow-up after 125 mg S.C., compared with 2 (25.0%) and 3 (37.5%) after 250 mg I.V. and S.C., respectively.

Most ADA were of low, single digit titer score. Only 4 subjects, who each received 125 mg KY1005 S.C., had ADA of titer score 10 at one of their post-dose timepoints, as follows: 3 subjects had a titer score of 20, 10 and 55, respectively, on Day 29 and subject 2007 had a titer score of 87 at follow-up.

No subject who tested positive for ADA had an injection site reaction or a concomitant TEAE. Subject 2007, who had the highest titer score (87 at Follow-up [Day 92], but negative at Day 29), had $AUC_{inf}$ of 14.7 mg.h/mL, the lowest in the dosing group, and about 33% lower than the geometric mean) but his $t_{1/2}$ (719 h) was unremarkable. One subject, who had the second-highest titer score (55 at Day 29, dropping to 2 at Day 57 and <1 at Follow-up [Day 92]), had the second-lowest $AUC_{inf}$ (17.4 mg-h/mL; about 21% lower than the mean) and the shortest $t_{1/2}$ (430 h; about 47% lower than the mean) in the dosing group.

Conclusions

Pharmacokinetics

KY1005 serum concentration peaked at the end of infusion (30 min) with 250 mg I.V., which is consistent with the I.V. infusion of any drug. However, there was high between-subject variation in $t_{max}$ after 250 mg KY1005 I.V., resulting in mean and median $t_{max}$ of 3.55 and 1.79 h, respectively. Serum concentrations of a monoclonal antibody would be expected to fall slowly but progressively after the end of an I.V. infusion. For example, mean serum KY1005 concentrations fell by no more than 5.5% from the end of infusion to 4 h post-dose. Without intending to be bound by scientific theory, observed within-subject variation in serum concentrations may reflect the imprecision of the analytical method rather than true variation in $t_{max}$.

There was biphasic elimination of 250 mg KY1005 I.V.: a rapid phase occurred from 1 to 7 days after dosing, followed by a slower terminal phase.

Absorption via the S.C. route was slower than the I.V. route: mean serum concentration peaked at 168 h post-dose (Day 8) after both 125 mg KY1005 and 250 mg S.C.; there was substantial variation in individual-subject $t_{max}$. Without intending to be bound by scientific theory, this was probably owing to the 7 to 21-day sampling intervals used after Day 8. Dose-normalized $C_{max}$ was about 3 to 3.5-fold higher after 250 mg I.V. than after 250 and 125 mg KY1005 S.C. However, despite those differences, attributable to the different routes of administration, dose normalized absolute bioavailability differed little across dosing groups: 125 and 250 mg KY1005 S.C. yielded 83 and 89% of the $AUC_{inf}/D$ of the 250 mg I.V. dose, respectively.

$C_{max}$ and AUC were broadly dose proportional after KY1005 S.C. administration. Between-subject variability in KY1005 serum concentration was low, as judged by $C_{max}$ and AUC: % CVb was 16.1-21.6 across dosing groups.

Mean serum concentration-time curves showed that elimination of KY1005 after both the I.V. and S.C. dosing was consistent with that expected of a monoclonal antibody. Estimation of $t_{1/2}$ after S.C. doses was good, and variation was low across all dosing groups. Mean $t_{1/2}$ was broadly similar in all dose groups (ranging from 813 to 1145 h). One subject (125 mg KY1005 S.C.) had shorter $t_{1/2}$ (430 h) than did the rest of his dosing group (mean 813 h), which may be consistent with a largely transient ADA response (titre score 55) seen at Day 29. ADA were close to zero however at Day 57 (titre score 2) and 92 (titre score<1) in this individual.

Safety and Tolerability

A secondary objective of the study was to assess the safety and tolerability of KY1005 when administered S.C. and I.V. There were no deaths, SAEs, otherwise significant AEs, or TEAEs leading to withdrawal during the study. All TEAEs were mild or moderate in severity. 250 mg KY1005 I.V. was well tolerated: no subject who received an I.V. dose had a TEAE.

Pharmacodynamics

A secondary objective of the study was to assess the immunogenicity of KY1005.

Prevalence of KY1005 ADAs broadly increased with time, with >40% of subjects across dosing groups testing positive at Day 29 and Follow-up. ADA were most prevalent in the 125 mg KY1005 S.C. dosing group, particularly at Follow-up (Day 92), when 75.0% of subjects tested positive compared with 25.0% and 37.5% after 250 mg I.V. and S.C., respectively. Overall, ADA were more prevalent in the S.C. than I.V. groups.

Most ADA titer scores were low (single digit titers). PK may have been affected by the presence of ADA in 1 subject (125 mg KY1005) who had a titer score of 55 on Day 29 and low $t_{1/2}$ compared with the rest of their dosing group. No subject who tested positive for ADA had an injection site reaction or concomitant TEAE. However, as the sample size in the present study was small, any effect of ADA on the safety, tolerability and PK of KY1005 should be further elucidated in larger studies.

Example 4: Population PK Analysis Study

A population PK analysis, conducted based on data from the first in human (FIH, CT-01, Example 1 hereinabove) study suggested that for dose levels of >=0.15 mg/kg a linear 2-compartmental distribution model was adequate to describe the signature of the observed data. At lower dose levels (0.006 mg/kg-0.05 mg/kg), a saturable elimination term needed to be included into the model to describe the distribution and elimination at low dose levels. The underlying reason of this non-linearity at low doses has its source in the fact that the PK assay measures free antibody rather than total antibody concentration and that the initial apparent elimination of the antibody, when administered at very low doses, is due to binding to its target.

A Phase 2a study (KY1005-CT02, as described in Example 2 above) was conducted in patients with moderate to severe atopic dermatitis and a Phase 1 open-label study was conducted in healthy volunteers (KY1005-CT04, as described in Example 3 above). The present analysis was conducted to characterize the pharmacokinetic in healthy volunteers and atopic dermatitis patients, including the absolute bioavailability for subcutaneous administration. A population pharmacokinetic model was developed to support the dose selection in the upcoming Phase IIb study by simulations.

All studies considered in the population PK analysis are listed in Table 26.

TABLE 26

Overview of the studies included in the population PK analysis

| Study | Indication | Route | Regimen | Dose* | Subjects |
|---|---|---|---|---|---|
| NCT03161288 (KY1005-CT01 Example 1 above) | Healthy Volunteer | Intravenous | Once every 4 weeks (Q4W) | 0.15 mg/kg | 6 |
| | | | | 0.45 mg/kg | 6 |
| | | | | 1.35 mg/kg | 6 |
| | | | | 4 mg/kg | 6 |
| | | | | 12 mg/kg | 6 |
| NCT03754309 (KY1005-CT02 Example 2 above) | Atopic Dermatitis | Intravenous | Q4W | 500 mg | 30 |
| | | | | 200 mg | 29 |
| NCT04449939 (KY1005-CT04 Example 3 above) | Healthy Volunteer | Intravenous | Single Dose | 250 mg | 8 |
| | | Subcutaneous | | 125 mg | 8 |
| | | | | 250 mg | 8 |

*Dose denotes the loading dose. For multiple dose regimens, the follow-up dose was half the loading dose.

The provided source data were used to program one master dataset in the IntiQuan General Dataset Format [IntiQuan GDF] comprising the pooled I.V. studies (KY1005 CT01 [as described in Example 1 above] and KY1005 CT02 [as described in Example 2 above]) and the I.V. +S.C. study KY1005 CT04 [as described in Example 3 above]. The master dataset contained both KY1005 concentration PK and EASI-score PD readouts. The master dataset was employed to derive a modeling datasets for I.V. population PK model building, S.C. population PK model building, and exploratory exposure response analysis.

Based on the master dataset, the population PK analysis dataset was prepared.

The analysis dataset of I.V. and S.C. administration used for the population PK analysis consisted of a total of 1914 serum concentration samples, obtained from 113 subjects. Table 27 provides an overview of PK sample numbers. From the total of 1914 serum PK samples, 118 were below the lower limit of quantification, only 6 of them observed after the first dose. For 95 samples either time or concentration information was missing. Additional 3 records were manually removed. The number of excluded records sum up to 216.

TABLE 27

Summary of available PK observations

| Data | N Subjects | N samples | N BLOQ samples* | N BLOQ samples post first dose* | N missing observations | N total ignored observations | N samples included in analysis |
|---|---|---|---|---|---|---|---|
| KY1005 CT-02 | 59 | 873 | 61 (6.99%) | 2 (0.229%) | 42 (4.81%) | 105 (12%) | 768 (88%) |
| KY1005 CT-04 | 24 | 366 | 28 (7.65%) | 4 (1.09%) | 53 (14.5%) | 81 (22.1%) | 285 (77.9%) |
| KY1005 CT-01 | 30 | 675 | 29 (4.3%) | 0 (0%) | 0 (0%) | 30 (4.44%) | 645 (95.6%) |
| TOTAL | 113 | 1914 | 118 (6.17%) | 6 (0.313%) | 95 (4.96%) | 216 (11.3%) | 1698 (88.7%) |

TABLE 28

| Summary of the available EASI-score observations | | | | |
|---|---|---|---|---|
| Data | N Subjects | N samples | N total ignored observations | N samples included in analysis |
| KY1005 CT-02 | 88 | 574 | 1 (0.174%) | 573 (99.8%) |
| TOTAL | 88 | 574 | 1 (0.174%) | 573 (99.8%) |

The analytical approach was based on principles established in the "Guidance for Industry Population Pharmacokinetics" [FDA 1999, FDA 2019] and "Guidance on Reporting the Results of Population Pharmacokinetic Analyses" [EMEA 2007].

The analysis was performed on the validated IntiQuan computer system [IntiQuan 2020], using a non-linear mixed effects modelling approach with a qualified installation of NONMEM (version 7.4.3—GNU Fortran 95 compiler). The Stochastic Approximation Expectation-Maximization (SAEM) method in NONMEM was used as parameter estimation algorithm with a subsequent importance sampling (IMP) step for refinement of the objective function as suggested in [ICON 2017]. R (version 3.6.3) was used in the analysis for pre- and post-processing of data and model outputs.

Free (unbound) serum concentrations of KY1005 were assessed in blood samples taken during the study using a validated enzyme-linked immunosorbent assay (ELISA) bioanalytical method.

Model building for the population PK analysis was conducted sequentially for I.V. and S.C. administration:

1. First, a population PK model of I.V. administration was developed based on the pooled KY1005-CT01 and KY1005-CT02 I.V. data.
2. Subsequently, the I.V. population PK model was extended by also considering S.C. data from study KY1005-CT04, with a main focus on S.C. absorption parameters (absorption rate and bioavailability).

To assess the time to reach steady state, simulations were performed with a constant infusion rate. The simulation time was 52 weeks. Simulations were inspected by eye to confirm that the simulated PK concentrations had reached the plateau level (steady-state concentration). The time to reach 90% and 95% of the steady-state concentration was determined from the simulated concentration-time courses. Simulations were performed for possible combinations of the relevant covariates (bodyweight, indication, gender) using the corresponding typical population PK model parameters.

To identify a possible efficacy threshold of $C_{min}$, average concentration ($C_{avg}$), or accumulated $C_{avg}$, and to assess the available information in the data to support the potential future development of a PK-PD model, the individual clinical response (EASI-Score relative change from baseline) was plotted over the simulated exposure metrics.

- For each individual with EASI readout, the individual PK parameters were employed to simulate the individual PK profile and derive individual $C_{min}$, $C_{avg}$, accumulated $C_{avg}$ values after 4, 8, 12, and 16 weeks
- Only placebo and individuals treated with 4 doses were included in the analysis. Subjects with missing doses were excluded
- The baseline EASI-Score (EASI0) was defined as the last observed EASI-Score before the start of the treatment
- The relative change of EASI was defined as (EASI-EASI0)/EASI0
- To improve the visibility of the effect, datapoints were binned and the mean and standard deviation was evaluated per bin The final population PK model describing both I.V. and S.C. administration was characterized as follows:

- Linear two-compartmental distribution model with dosing compartment
- Bolus administration into the dosing compartment with bioavailability and lag time to represent S.C. administration
- Zero-order administration into the central compartment to represent I.V. administration
- Linear elimination
- Random effects on all model parameters (variability fixed to 5% CV for Fabs1)
- Proportional error model
- Bodyweight at baseline as a covariate on CL, Vc, and Vp1
- Indication (AD) as a covariate on CL
- Estimated correlations between random effects for Vc, Vp1 and CL The parameter estimates for the final model are reported in Table 29. The reported shrinkage was stratified by route of administration. Terminal half-lives computed for typical healthy volunteers and atopic dermatitis stratified by bodyweight are shown in Table 30.

TABLE 29

| Parameter estimation table of the final I.V. + S.C. population PK model | | | | | |
|---|---|---|---|---|---|
| PARAMETER | VALUE | RSE | SHRINKAGE [ADMIN = SC] | SHRINKAGE [ADMIN = IV] | COMMENT |
| Typical parameters | | | | | |
| Vc | 3.26 | 2.17% | — | — | Central volume (L) |
| Vp1 | 2.43 | 1.77% | — | — | Peripheral volume (L) |
| CL | S | 3.95% | — | — | Clearance (L/day) |
| ka | 0.222 | 15.2% | — | — | Absorption rate (1/day) |
| Fabs1 | 0.779 | 3.11% | — | — | Bioavailability (.) |
| Q1 | 0.626 | 11.7% | — | — | Intercompartmental clearance (L/day) |
| Tlag1 | 0.0387 | 16.3% | — | — | Lag-time for SC administration (days) |
| Inter-individual variability | | | | | |
| omega(Vc) | 0.181 | 9.51% | 40.5% | 2.3% | LogNormal |
| omega(Vp1) | 0.142 | 8.81% | 54.3% | 7.4% | LogNormal |
| omega(CL) | 0.257 | 8.82% | 43.7% | 6.1% | LogNormal |

TABLE 29-continued

| Parameter estimation table of the final I.V. + S.C. population PK model | | | | | |
|---|---|---|---|---|---|
| PARAMETER | VALUE | RSE | SHRINKAGE [ADMIN = SC] | SHRINKAGE [ADMIN = IV] | COMMENT |
| omega(ka) | 0.477 | 30.8% | −1.4% | 100% | LogNormal |
| omega(Fabs1) | 0.05 (FIX) | — | 95.3% | 100% | LogitNormal |
| omega(Q1) | 0.479 | 25.7% | 23.1% | 54.8% | LogNormal |
| omega(Tlag1) | 0.384 | 31.6% | 4.2% | 100% | LogNormal |
| Correlation of random effects | | | | | |
| corr(Vc, Vp1) | 0.926 | 2.02% | — | — | Correlation coefficient |
| corr(Vc, CL) | 0.492 | 24.5% | — | — | Correlation coefficient |
| corr(Vp1, CL) | 0.127 | 132% | — | — | Correlation coefficient |
| Parameter-Covariate relationships | | | | | |
| beta_CL(WT0) | 0.707 | 28.7% | — | — | Bodyweight at baseline in kg on CL (centered around: 75 kg) |
| beta_CL(IND_1) | 0.26 | 4.61% | — | — | Indication AD on CL |
| beta_Vc(WT0) | 0.635 | 24.3% | — | — | Bodyweight at baseline in kg on Vc (centered around: 75 kg) |
| beta_Vp1(WT0) | 0.714 | 17.6% | — | — | Bodyweight at baseline in kg on Vp1 (centered around: 75 kg) |
| Residual Variability | | | | | |
| error_PROP1 | 0.154 | 0.804% | 22.8%* | 5.01%* | Proportional Error (fraction) - Concentration |
| Objective function | 6801 | — | — | — | — |
| AIC | 6843 | — | — | — | — |
| BIC | 6957 | — | — | — | — |

Model: ../Models/62_Modeling_NLME_Cov_IV_SC/MODELCOV01, Significant digits: 3 (Objective function rounded to closest integer value), omega values and error model parameters reported in standard deviation.
Shrinkage was determined for separate groups of subjects stratified by ADMIN (Route of administration).
The objective function was determined using importance sampling (IMP) with settings EONLY = 1 and MAPITER = 0, as suggested in the NONMEM manual.

TABLE 30

| Model-derived terminal half-life stratified by indication and bodyweight | | |
|---|---|---|
| Indication | Body weight | Terminal half-life |
| Healthy Volunteer | 50 kg | 35 days |
| | 75 kg | 34.8 days |
| | 100 kg | 34.8 days |
| | 120 kg | 34.8 days |
| Atopic Dermatitis | 50 kg | 27.2 days |
| | 75 kg | 27.1 days |
| | 100 kg | 27.2 days |
| | 120 kg | 27.2 days |

Half-life determined from terminal slope. Values rounded to 3 significant digits.

Graphical Exploration of the PK Data

Figures 18A, 18B, 18C, 18D:
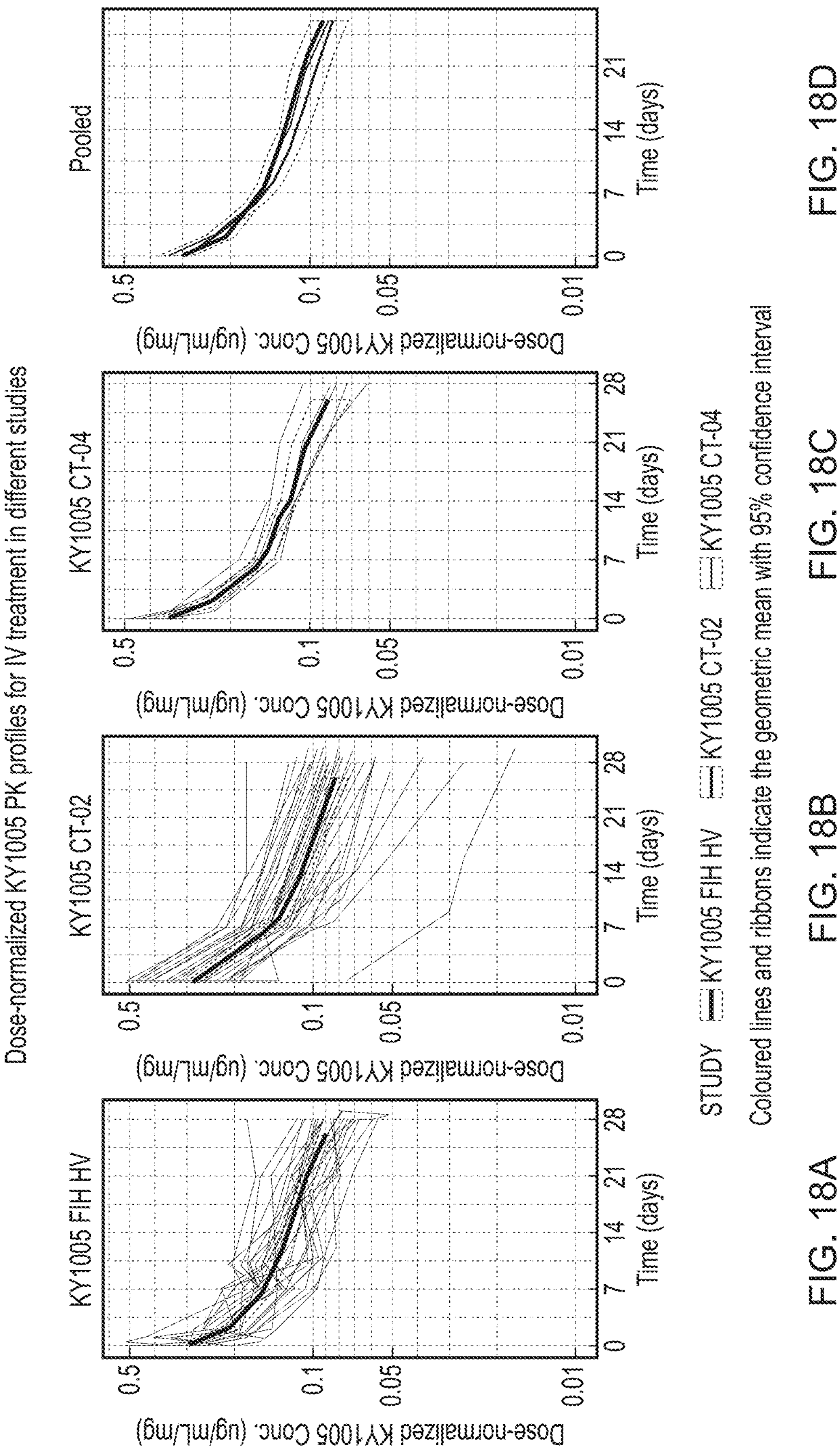
FIG. 18A-18D graphically depicts dose-normalized KY1005 PK profiles for IV treatment in different studies including KY1005 FIH HV CT-01 (FIG. 18A), KY1005 CT-02 (FIG. 18B), and KY1005 CT-04 (FIG. 18C). The three studies are overlayed in different colors in FIG. 18D (CT-01=purple, CT-02=red, CT-04=orange). The dose-normalized IV profiles showed a two-phasic behavior in alignment with the assumed two-compartmental distribution model.
Figure 19:
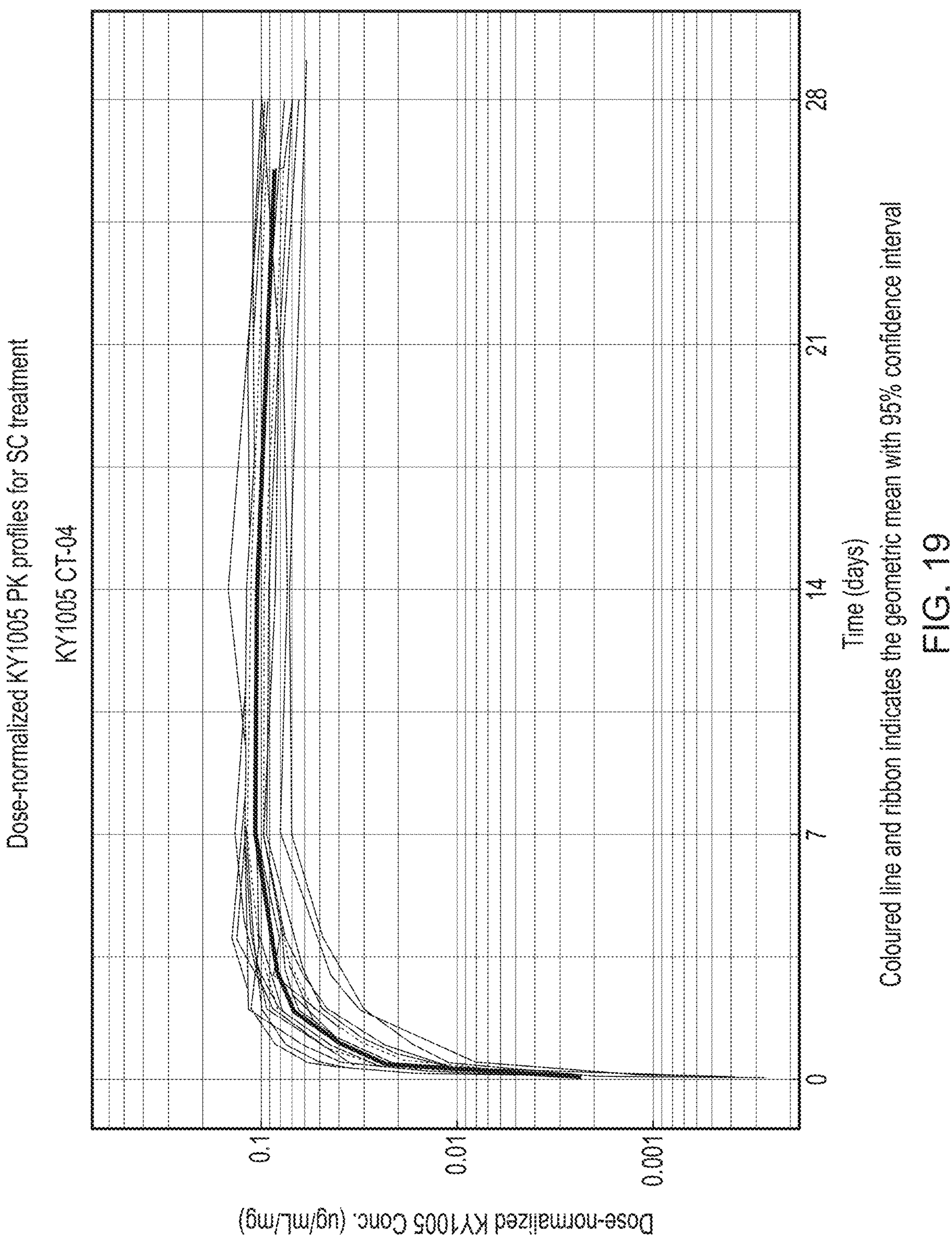
FIG. 19 graphically depicts dose-normalized KY1005 PK profiles for SC treatment for study KY1005 CT-04. The dose-normalized SC profiles were consistent among each other. The profiles were densely sampled during the first day and during the first week. The maximum concentration ($C_{max}$) was reached between 4 and 14 days. The SC profiles after 14 days were much flatter than the IV profiles.
Figure 20A:
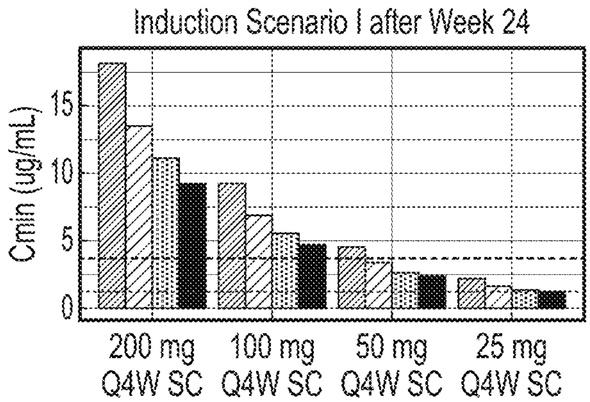
FIG. 20A-20F graphically depict predicted $C_{min}$ at week 24 for induction scenarios I-III (varying doses) and IV-XII (varying regimens).
Figure 20B:
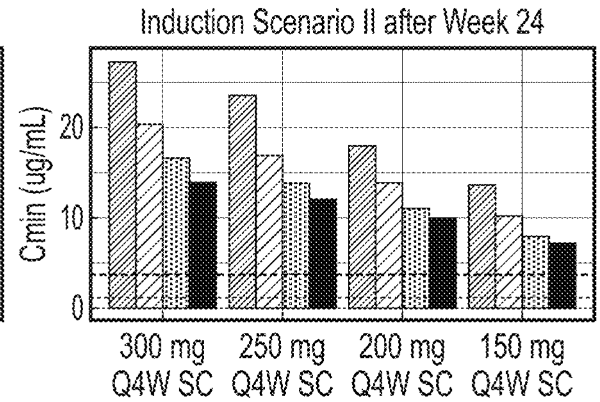
Figure 20C:
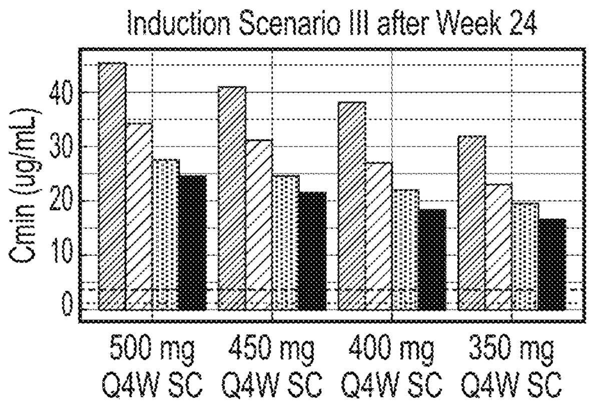
Figure 20D:
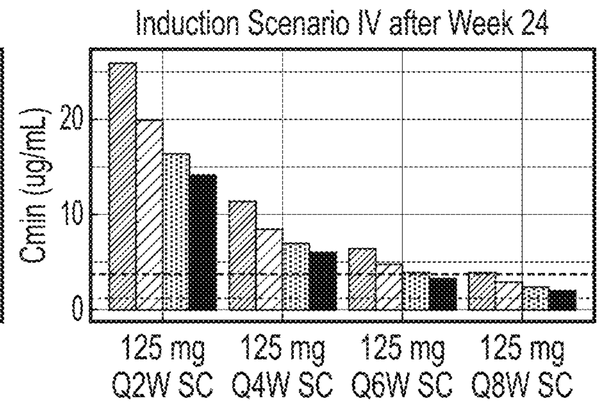
Figure 20E:
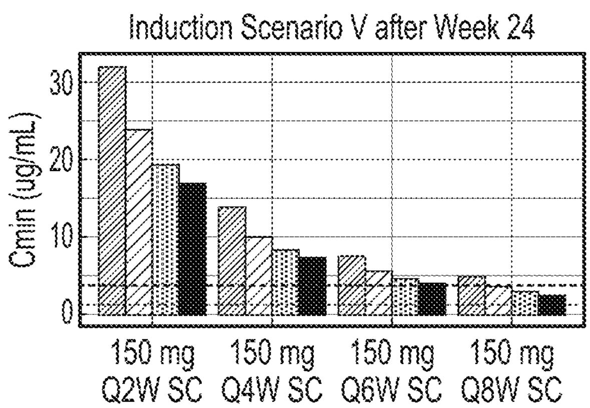
Figure 20F:
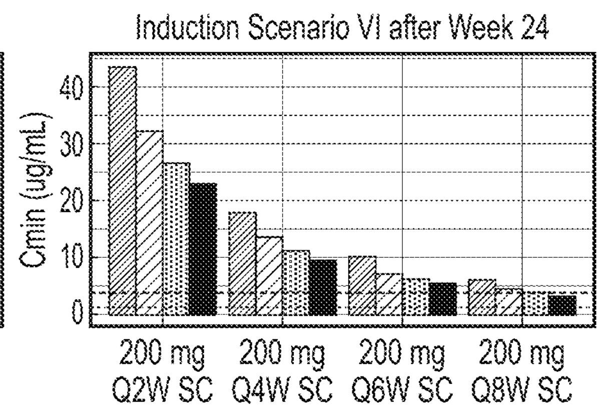
Figure 21A:
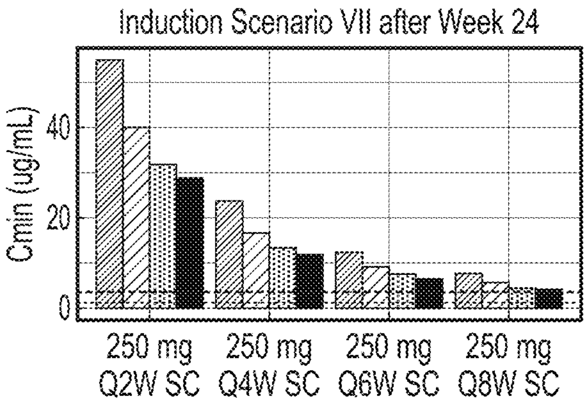
FIG. 21A-21F graphically depicts predicted $C_{min}$ at week 24 for induction scenarios I-III (varying doses) and IV-XII (varying regimens).
Figure 21B:
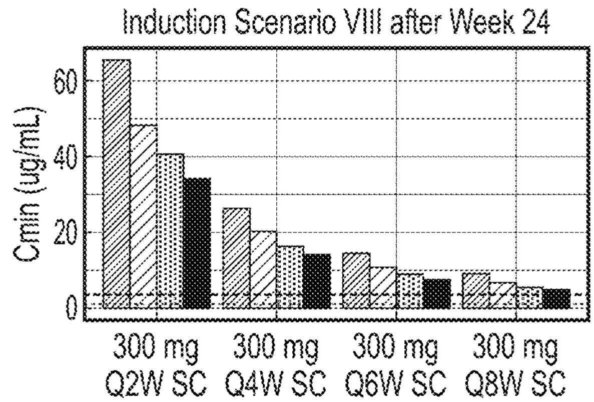
Figure 21C:
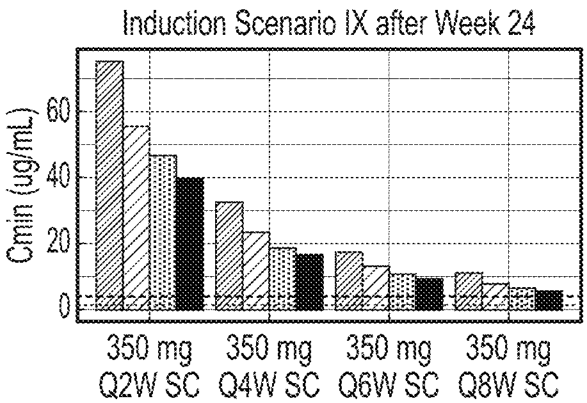
Figure 21D:
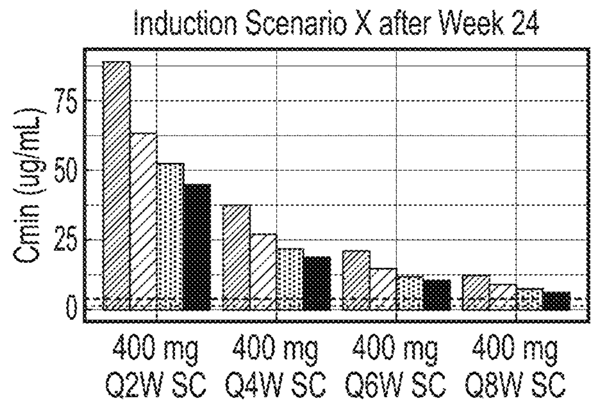
Figure 21E:
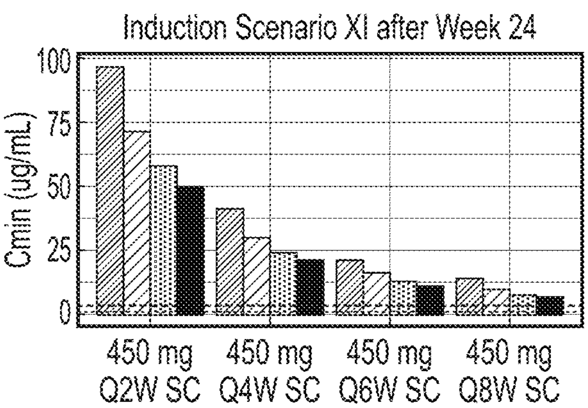
Figure 21F:
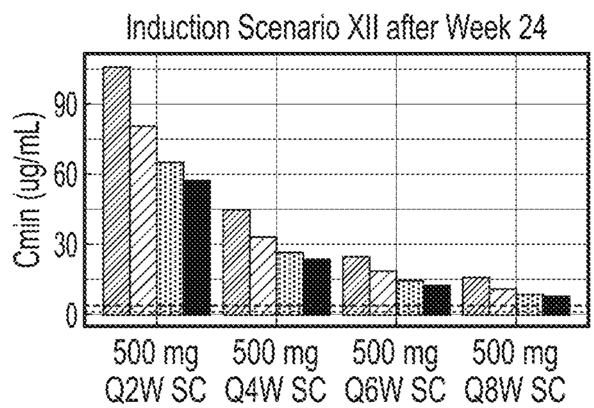

FIG. 18 and FIG. 19 show dose-normalized PK profiles of I.V. and S.C. administration over the first 28 days stratified by study.

The dose-normalized I.V. profiles (FIG. 18) showed a two-phasic behavior in alignment with the assumed two-compartmental distribution model. The profiles appeared to be consistent between the different studies as indicated by the overlay of the mean dose-normalized profiles (LOESS smoothers of the three studies shown in blue in the panels per study were overlayed in different colors in the "Pooled" panel, FIG. 18D). The observed variability between individual PK profiles appeared higher in the patient study (KY1005 CT-02, FIG. 18B) than in the healthy volunteer studies (FIH, KY1005 CT-04, FIG. 18C).

The dose-normalized S.C. profiles (FIG. 19) were consistent among each other. The profiles were densely sampled during the first day and during the first week. The maximum concentration ($C_{max}$) was reached between 4 and 14 days. The profiles after 14 days were much flatter than the I.V. profiles.

None of the individual profiles showed an abrupt increase in clearance at any time during the first 28 days (FIG. 1) or at later time points (data not shown). In conclusion, there was no indication of anti-drug antibodies (ADA) in the observed PK profiles of the different studies.

In KY1005 CT-01 (as described in Example 1 above), a nonlinearity was observed for the lowest dose groups (0.006, 0.018, and 0.05 mg/kg). Since the PK assay measured free KY1005 concentration, this nonlinearity was due to the initial binding of KY1005 to the target upon administration (TMDD). For doses of 0.15 mg/kg and above, KY1005 concentrations were high enough that this nonlinearity was not observed any more.

Simulations of Exposure Metrics Based on the Population PK Model

Figures 22A, 22B, 22C:
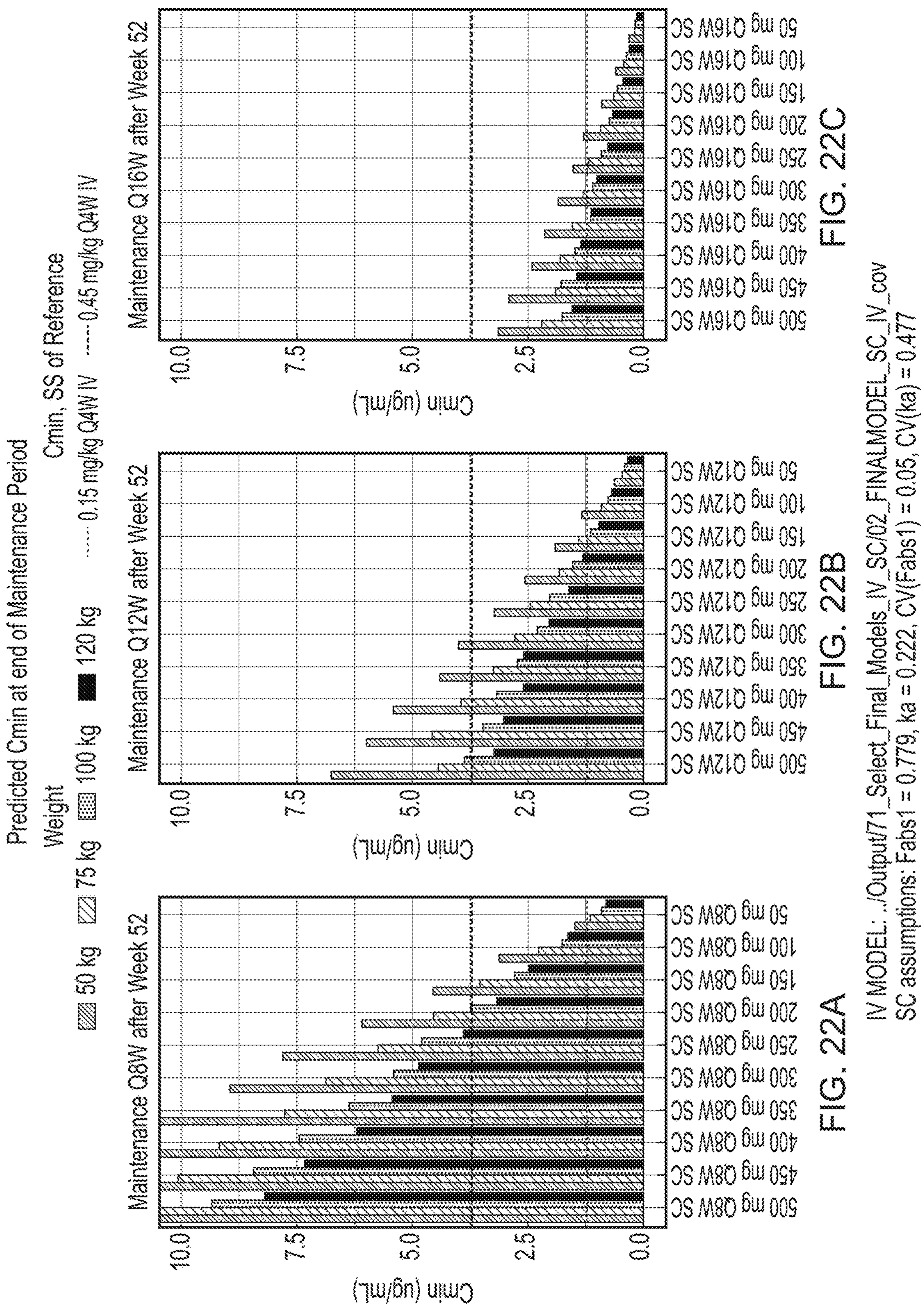
FIG. 22A-22C graphically depicts predicted $C_{min}$ at the end of the maintenance period.
Figure 23A:
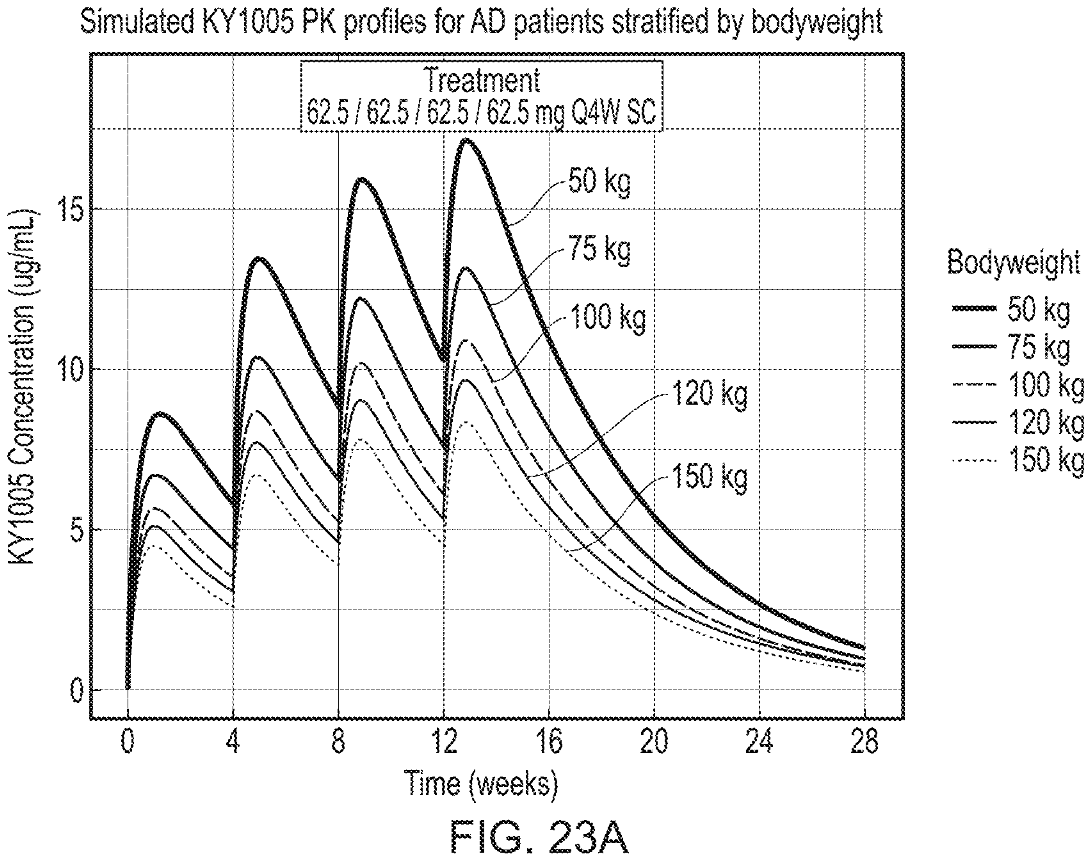
FIG. 23A-23D graphically depicts simulated KY1005 PK profiles for atopic dermatitis (AD) patients stratified by bodyweight. Simulations for bodyweights of 50, 75, 100, 120, and 150 kg are shown.
Figure 23B:
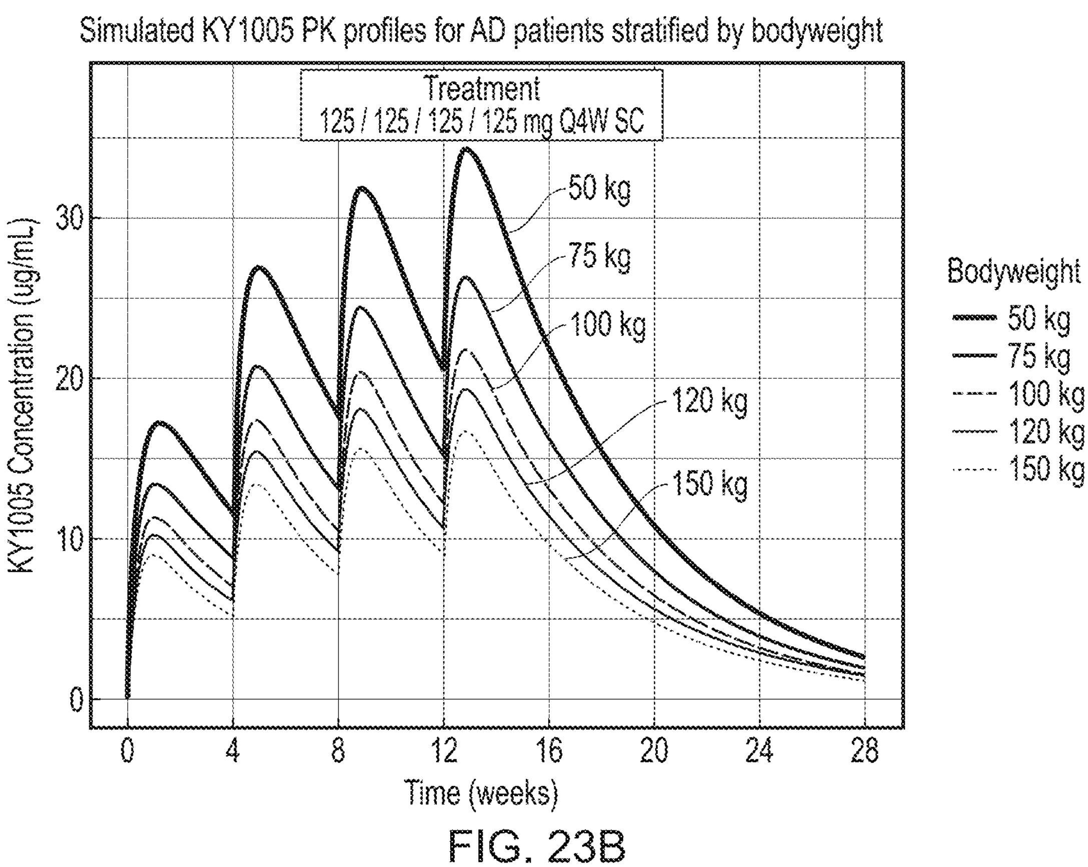
Figure 23C:
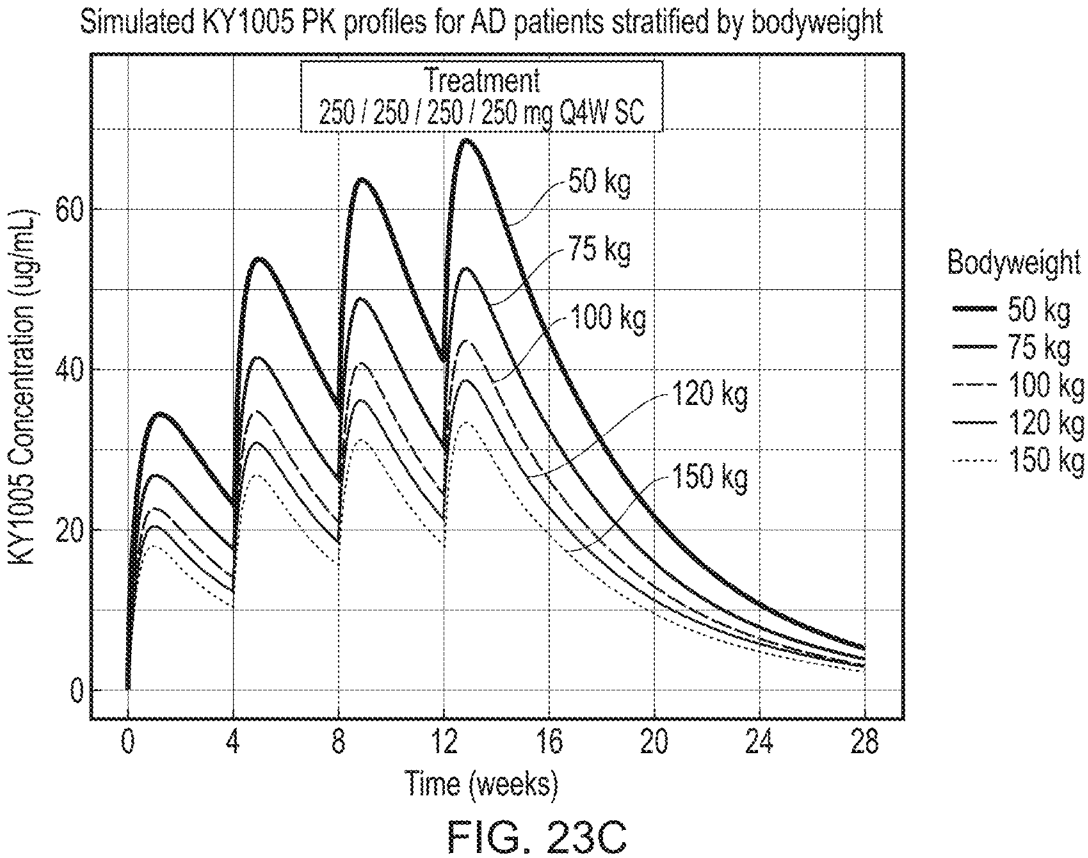
Figure 23D:
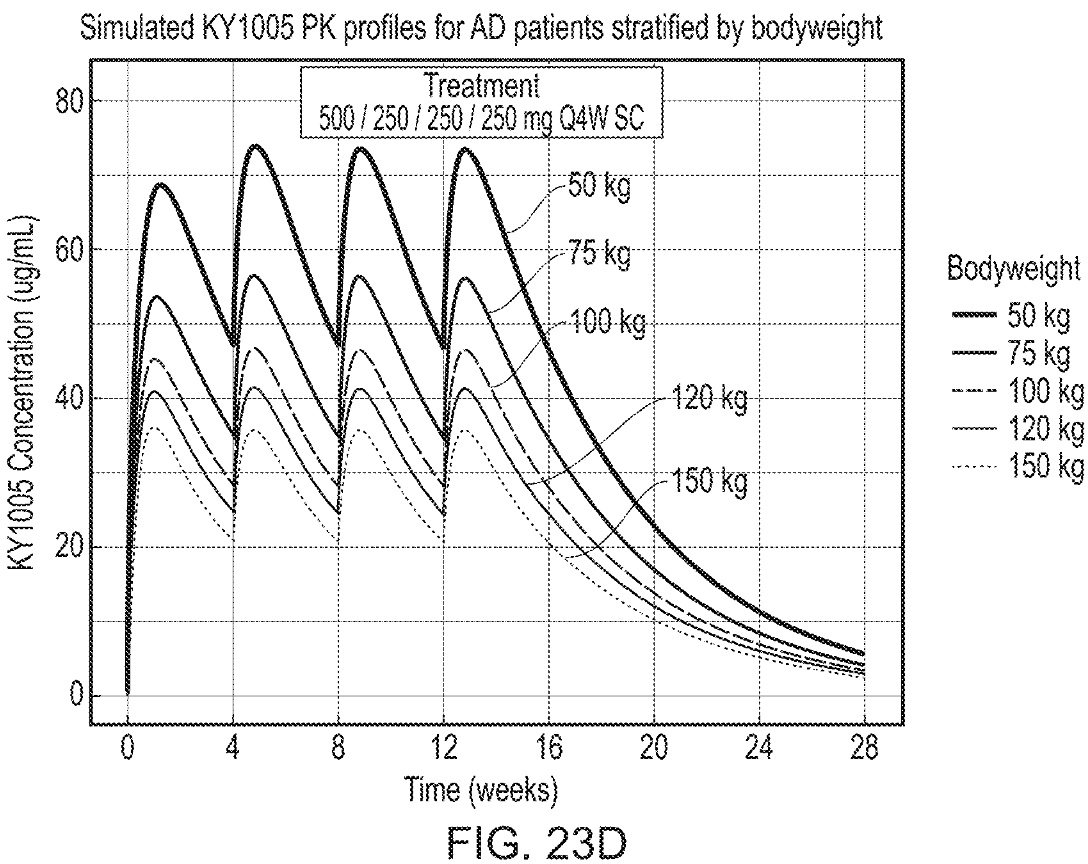
Figure 24A:
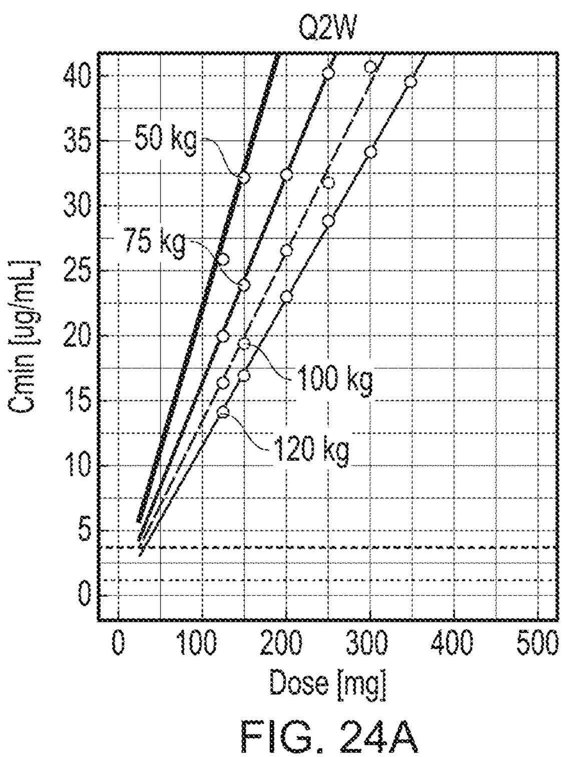
FIG. 24A-24D graphically depicts predicted $C_{min}$ after 24 weeks of induction period. Different regimens (Q2W (FIG. 24A), Q4W (FIG. 24B), Q6W (FIG. 24C), Q8W (FIG. 24D)) were distributed over different panels.
Figure 24B:
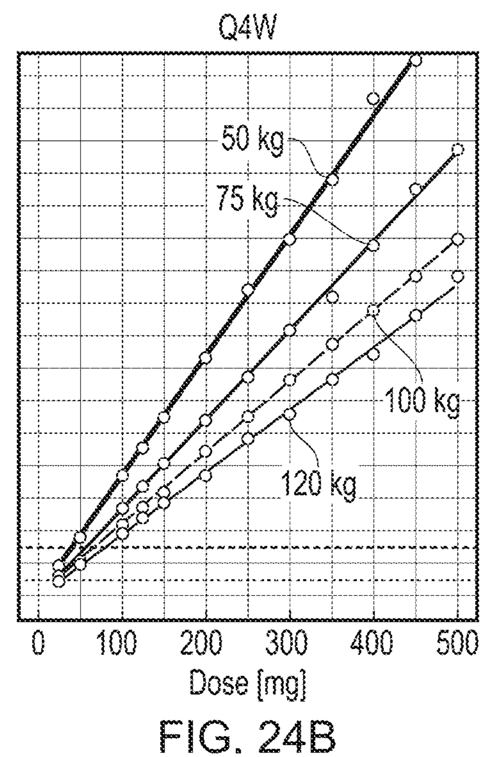
Figure 24C:
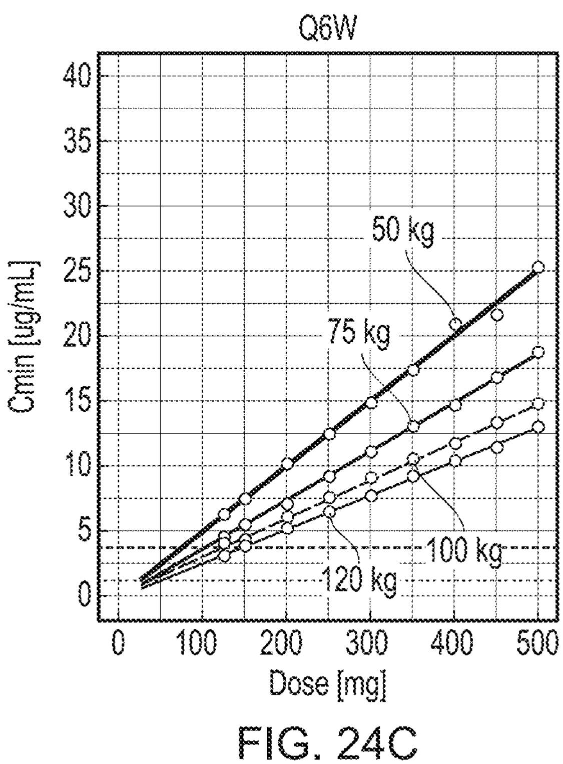
Figure 24D:
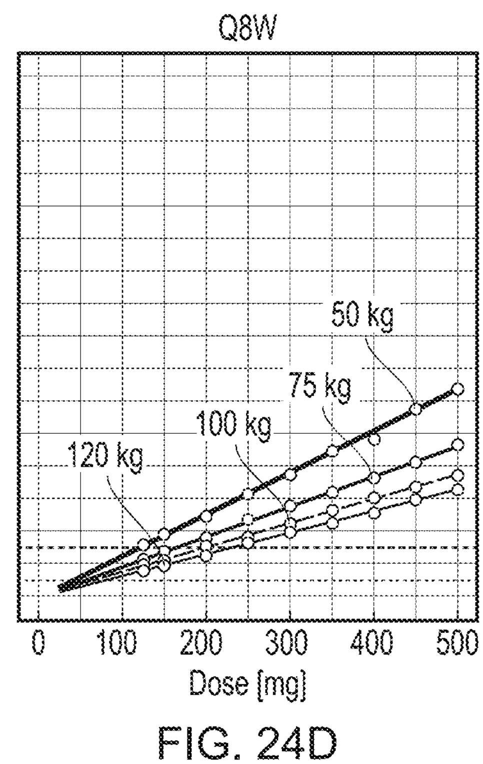

The complete set of simulations is not shown, however simulations included simulations of the induction period with variable dose, simulations of the induction period with variable regimen and simulations of the maintenance period. Summary plots are shown in FIGS. 20-22. Simulated KY1005 PK profiles for selected induction scenarios stratified by body weight are shown in FIG. 23.

Figures 25A, 25B, 25C:
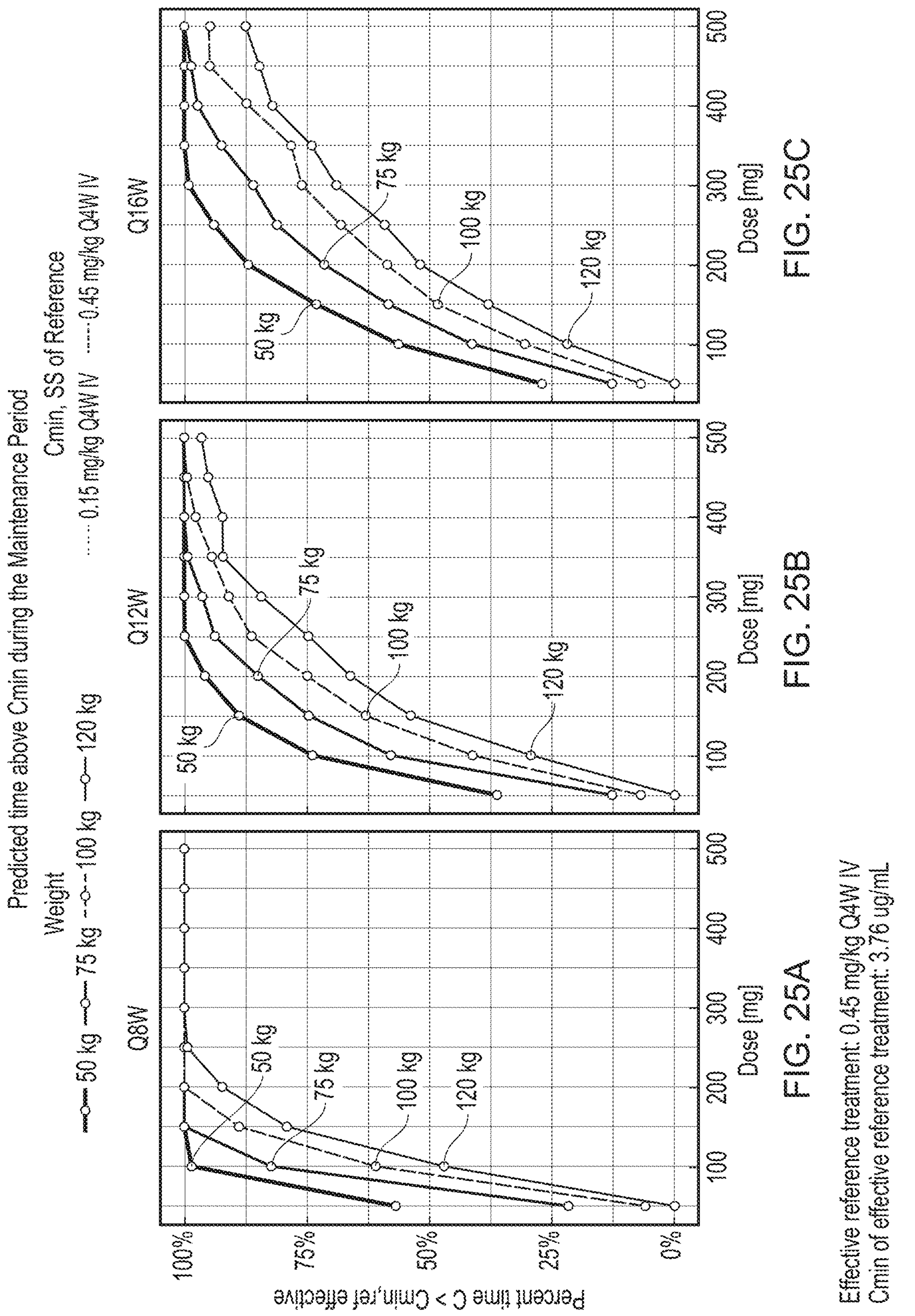
FIG. 25A-25C graphically depicts predicted time above $C_{min}$ during the maintenance period. Different regimens (Q8W (FIG. 25A), Q12W (FIG. 25B), Q16W (FIG. 25C)) were distributed over different panels.

An overall summary of the simulations is shown in FIG. 24 (Induction Period) and FIG. 25 (Maintenance Period). For the induction period (FIG. 24), all simulated $C_{min}$ values at Week 24 were collected and plotted over the dose. Different regimens (Q2W (FIG. 24A), Q4W (FIG. 24B), Q6W (FIG. 24C), Q8W (FIG. 24D)) were distributed over different panels. A similar plot was produced for the Maintenance Period (FIG. 25). The plot shows the percentage of time during the Maintenance Period where the concentration was above the reference $C_{min}$ value. Different regimens (Q8W (FIG. 25A), Q12W (FIG. 25B), Q16W (FIG. 25C)) were distributed over different panels. The dose indicated on the x-axis refers to the loading dose. Subsequent doses were half the loading dose. In particular, all doses during the maintenance period were half of the indicated loading dose.

I.V.+S.C. Population PK Model

To describe S.C. administration, the I.V. population PK model was extended by a dosing compartment, bolus administration into the dosing compartment, and first order absorption from the dosing into the central compartment.

Because the PK profiles for S.C. administration provided several observed samples shortly after the time of administration, it was possible to identify a lag time of approximately one hour for the S.C. bolus administration.

Random effects were considered on all parameters. Based on the pooled KY1005 CT-01 (as described in Example 1 above), KY1005 CT-02 (as described in Example 2 above), and KY1005 CT-04 (as described in Example 3 above) data, it was possible to identify the previously fixed inter-individual variability of Q1. Also, the variability of ka and Tlag1 was identifiable. Individual estimates for Fabs1, however, were highly consistent. Given the low proportion of subjects with SC observations, the inter-individual variability of Fabs1 could not be estimated and was fixed.

The estimated random effects did not indicate new parameter-covariate relationships. Relationships established for the I.V. population PK model were revisited indicating that the impact of female gender on CL was lower than previously estimated. Therefore, besides bodyweight, indication was the only remaining covariate considered in the final population PK model. The higher clearance in patients could possibly be explained by the generally higher target expression in patients, and specifically in skin where KY1005 would distribute to.

Correlations between random effects based on the pooled I.V. +S.C. data were confirmed as established. Further correlations between random effects involving the S.C. population PK model parameters were not considered due to the low proportion of subjects with S.C. observations.

VPCs of I.V. of S.C. administration confirmed the adequacy of the final population PK model. The previously underpredicted observations 168 days after the last dose were better captured by the final population PK model. Because the observed median was at the upper limit of the 95% uncertainty band of the predicted median, the possibility of a potential underprediction of late time points will be further investigated on the basis of new KY1005 CT-02 (as described in Example 2 above) long-term data. VPCs stratified by study did not show indications of inconsistency between the pooled studies. Consequently, the final population PK model was found to be qualified for the conduct of simulations.

Simulations

Simulations were performed for I.V. reference dosing schemes in healthy volunteers and S.C. dosing schemes in patients. Simulations for patients were distinguished by induction period (0 to 24 weeks) and maintenance period (24 to 52 weeks). The main exposure metric of interest for the induction period was the $C_{min}$ after 24 weeks in comparison to the $C_{min}$ of the reference dose. For the maintenance period, the $C_{min}$ after 52 weeks and the time above $C_{min}$ of the reference dose during the maintenance period were the key metrics.

Simulations of the induction period indicated that with a fixed Q4W regimen, the threshold to reach $C_{min}>C_{min,ref}$ was around 50 mg (loading dose, half the loading dose for subsequent doses). This threshold dose would be around 125 mg (loading dose, half the loading dose for subsequent doses) for Q6W and 200 mg for Q8W.

Simulations of the maintenance period indicated that Q8W and Q12W were generally feasible regimens allowing $C_{min}>C_{min,ref}$ after 52 weeks for doses not higher than 500 mg (loading dose, half the loading dose during maintenance period). The Q8W regimen allowed to maintain the $C_{min}$ above the reference $C_{min}$ across all body weights (50 kg to 120 kg) for loading doses higher than 350 mg. For the Q12W regimen, 500 mg loading dose were sufficient to stay above the reference $C_{min}$ for a bodyweight of 50, 75, and 100 kg but not for 120 kg. For the Q16W regimen, the concentration dropped below the reference $C_{min}$ at some time between 24 and 52 weeks for almost all combinations of dose and bodyweight. In particular, for heavy patients (100 and 120 kg) a 100% fraction of time above the reference $C_{min}$ could not be maintained for any of the doses up to 500 mg (loading dose) in the Q16W regimen.

Exploratory Exposure Response Analysis

The exposure response data was highly variable and did not allow to precisely constrain the $C_{min}$ of the half-maximum efficacy ($EC_{50}$). The data suggested that the $EC_{50}$ would be below the $C_{min}$=10 to 20 g/mL region. Thus, the choice of the simulated reference dose of 0.45 mg/mL (loading dose, half the loading dose for subsequent doses) Q4W I.V. leading to $C_{min}$ between 3.3 and 4.2 μg/mL was consistent with the exposure response data.

Conclusions

A population pharmacokinetic model was developed to support the dose selection in the upcoming Phase IIb study by simulations.

The final population pharmacokinetic model adequately describing the dose-concentration relationship was characterized as follows:

- Two-compartmental distribution model with dosing compartment.
- Bolus administration into the dosing compartment with bioavailability and lag time to represent subcutaneous administration.
- Zero-order administration into the central compartment to represent intravenous administration.
- Linear elimination.
- Random effects on all model parameters (inter-individual variability fixed to 5% coefficient of variance for subcutaneous bioavailability).
- Proportional residual error model.
- Bodyweight at baseline as a covariate on clearance, central volume, and peripheral volume.
- Indication (atopic dermatitis) as a covariate on clearance.
- Estimated correlations between random effects for central volume, peripheral volume, and clearance.

The subcutaneous bioavailability was estimated to be 0.779. The 95% confidence interval ranged from 0.731 to 0.827.

The terminal half-life was estimated to be around 35 days for healthy volunteers and around 27 days for atopic dermatitis patients.

Simulations of a virtual patient population treated subcutaneously identified feasible dose and regimen windows exceeding a targeted trough concentration during a 24 week induction period. A prolonged regimen of up to Q12W during maintenance period seemed feasible.

The choice of the simulated reference dose of 0.45 mg/mL (loading dose, half the loading dose for subsequent doses) Q4W intravenously leading to trough concentrations between 3.3 and 4.2 μg/mL was consistent with the analysis of the exposure response data.

Example 5: A Phase IIb. Randomized. Double-blind, Placebo-controlled. Parallel Group, Multicenter Dose Ranging Study of a Subcutaneous Anti-OX40L Monoclonal Antibody (KY1005) in Moderate to Severe Atopic Dermatitis (KY1005-CT05)

Study Purpose

The aim of this study is to characterize the efficacy (including dose/exposure response) and safety of KY1005 across a range of doses/exposures for a maximum duration of 52 weeks in adult patients with moderate-to-severe AD who have had an inadequate response to topical therapies or where topical therapies are not advised. In addition, the durability of response and Pharmacokinetic (PK) characterization following withdrawal from KY1005 from Week 24 will be characterized.

Primary Objective

To characterize the efficacy (including dose/exposure-response) across a range of KY1005 exposures compared to placebo on the signs of AD using the Eczema Area and Severity Index (EASI) in those patients who have who have a documented history, within 6 months prior to baseline, of either inadequate response to topical treatments or inadvisability of topical treatments.

Secondary Objectives

- Asses the safety and tolerability of KY1005.
- The pharmacokinetic profile across a range of KY1005 doses/exposures.
- The response across a range of KY1005 exposures on additional physician assessments of AD activity/severity (EASI-50, EASI-75, EASI-90, EASI-100, Investigator Global Assessment [IGA], SCORAD Index and BSA).
- The response across a range of KY1005 dose/exposures on patient reported AD activity/severity (Atopic dermatitis Control Tool [ADCT], POEM, DLQI, Hospital Anxiety and Depression Scale [HADS], and NRS for pruritus).
- The pharmacodynamic response to KY1005 including but not limited to: the immunogenicity of KY1005, including the anti-KY1005 antibody response.
- The explore the continued clinical response in those patients who achieve ≥EASI-75 or who attain IGA0/1 at Day 169.

Primary Endpoint

- Percentage change in EASI from Baseline to Day 113.

Secondary Endpoints

- Incidence of treatment-emergent adverse events.
- Serum KY1005 concentration assessed throughout the study.
- Percentage change from Baseline in EASI at Day 169.
- Percentage of patients with at least a 75% reduction from Baseline in EASI (EASI-75) at Days 113 and 169.
- Percentage of patients with a response of IGA 0 or 1 and a reduction from Baseline of 2 points at Days 113 and 169.
- Proportion of patients with improvement (reduction) of weekly average of pruritus NRS 4 with a Baseline pruritus NRS of 4 from Baseline to Days 113 and 169.
- Absolute change from Baseline in EASI at Days 15, 29, 57, 85, 113, 141 and 169.
- Percentage change from Baseline in EASI at Days 15, 29, 57, 85 and 141.
- Percentage of patients with at least a 50% reduction from Baseline in EASI (EASI-50) at Days 15, 29, 57, 85, 113, 141 and 169.
- Percentage of patients with at least a 75% reduction from Baseline in EASI (EASI-75) at Days 15, 29, 57, 85, and 141.
- Percentage of patients with at least a 90% reduction from Baseline in EASI (EASI-90) at Days 15, 29, 57, 85, 113, 141 and 169.
- Percentage of patients with at least a 100% reduction from Baseline in EASI (EASI-100) at Days 15, 29, 57, 85, 113, 141 and 169.
- Change in IGA from Baseline to Day 169 and over time.
- Percentage of patients with a response of IGA 0 or 1 and a reduction from Baseline of 2 points at Days 15, 29, 57, 85, and 141.
- Absolute and Percentage in SCORAD Index from Baseline to Day 169 and over time.
- Absolute and Percentage change in affected BSA from Baseline to Day 169 and over time.
- Absolute and Percentage change in POEM, DLQI, ADCT, and HADS from Baseline to Day 169 and over time.
- Absolute and Percentage change in weekly average of pruritus NRS from Baseline to Day 169 and over time.
- Proportion of patients with improvement (reduction) of weekly average of pruritus NRS 3 with a Baseline pruritus NRS of >3 from Baseline to Days 113 and 169.
- The immunogenicity of KY1005, including the anti-KY1005 antibody response.
- Continued assessment of the efficacy endpoints from Day 169 and over time.
- Time to loss of EASI-75, IGA0/2, and EASI-50 in participants randomized to withdrawal post-Week 24.
- Continued assessment of patient reported AD activity/severity endpoints from Day 169 and over time.

Study Design

This is a Phase IIb, randomized, double-blind, placebo-controlled, parallel group, multicenter dose ranging study to characterize the efficacy and safety of S.C. administered KY1005 in adult patients with moderate-to-severe AD who have a documented history, within 6 months prior to baseline, of an inadequate response to, or inadvisability of, topical treatments.

After providing informed consent, patients will be assessed for study eligibility at the Screening Visit. Patients will undergo Screening within 28 days prior to randomization. During the Screening period, treatments for AD will be washed out for at least 7 days prior to baseline (except bland moisturizers). Patients will be required to apply bland moisturizers (emollients) with no additives (e.g., urea) at least twice daily for a minimum of 7 consecutive days before baseline and continue throughout the study.

Up to 350 patients (approximately 70 patients per treatment arm) will be enrolled. Patients who continue to meet the eligibility criteria at Baseline will be randomized to 1 of 5 treatment groups (4 different KY1005 regimens or Placebo) in an equal (1:1:1:1:1) ratio.

From baseline up to Day 169 (Week 24) IMP will be administered at the following dose and intervals:

500 mg loading at baseline (2×2 mL injections of 250 mg) followed 4 weeks later with 250 mg Q4W as 1×2 mL injection;

OR 250 mg (as 1×2 mL injection) plus 1×2 mL Placebo at Baseline followed 4 weeks later with 250 mg Q4W as 1×2 mL injection;

OR 125 mg (as 1×2 mL injection) plus 1×2 mL Placebo at Baseline followed 4 weeks later with 125 mg Q4W as 1×2 mL injection;

OR 62.5 mg (as 1×2 mL injection) plus 1×2 mL placebo at Baseline followed 4 weeks later with 62.5 mg Q4W as 1×2 mL injection;

OR

Placebo given as 2×2 mL injections at Baseline followed 4 weeks later with 1×2 mL Placebo (0 mg).

At baseline, those patients not receiving a KY1005 loading dose will receive both KY1005 and Placebo to maintain the study blind.

The primary analysis will occur when all patients have completed Day 113 (or earlier in the event of termination).

To enable Placebo patients and those patients randomized to the KY1005 62.5 mg Q4W and 125 mg Q4W treatment arms to receive KY1005 at a dose expected to elicit a meaningful clinical response (based on prior clinical evidence), patients who do not achieve greater than or equal to EASI-75 or IGA0/1 at Week 24 will be invited to enroll in the long-term extension (LTE) study where they will receive 250 mg Q4W KY1005.

In those patients who achieve greater than or equal to EASI-75 or who attain IGA0/1 at Week 24, a randomization will occur pre-dose at Day 169 (Week 24). This will occur irrespective of whichever dose group the patient was randomized to at baseline including placebo. Patients will be randomized in a 3:1 manner to be withdrawn from therapy or to continue their pre-Week 24 dose/interval. To maintain the blind, those patients randomized to the Withdrawal arm will receive Placebo Q4W. Those patients who are randomized to the Withdrawal arm who lose their clinical response will be offered the opportunity to be retreated with KY1005 in the LTE study. Loss of clinical response is defined as the first instance of EASI-50 at any point in the study. If loss of clinical response from Week 28 occurs, Investigators will be able to choose to discontinue the patient from KY1005-CT05 or to progress to the LTE study. If loss of response from Week 28 occurs between visits and retreatment with KY1005 is considered appropriate, patients will be permitted to move to the LTE study (subject to meeting the inclusion/exclusion criteria for the LTE) at that time. Waiting until the next scheduled visit will not be required.

At Day 365 (Week 52), patients who have completed the post-Week 24 period will have the opportunity to be considered for enrolment into the LTE protocol. All patients who do not meet the inclusion criteria for the LTE, or where the patient declines to continue participation in the study or subsequent the LTE study, will have an additional 84 days safety follow-up up to Day 449 (Week 64) and then be discharged from the study. The last dose will be given no later than Day 337 and as such safety follow-up will be 112 days following last dose of KY1005.

Skin punch biopsies (5 mm) will be taken in up to approximately one third (30%) of patients who will be enrolled into a skin biopsy sub-study. This will be done at selected sites. Lesional and non-lesional samples will be collected at Baseline with lesional samples requested at Day 113.

Figure 26:
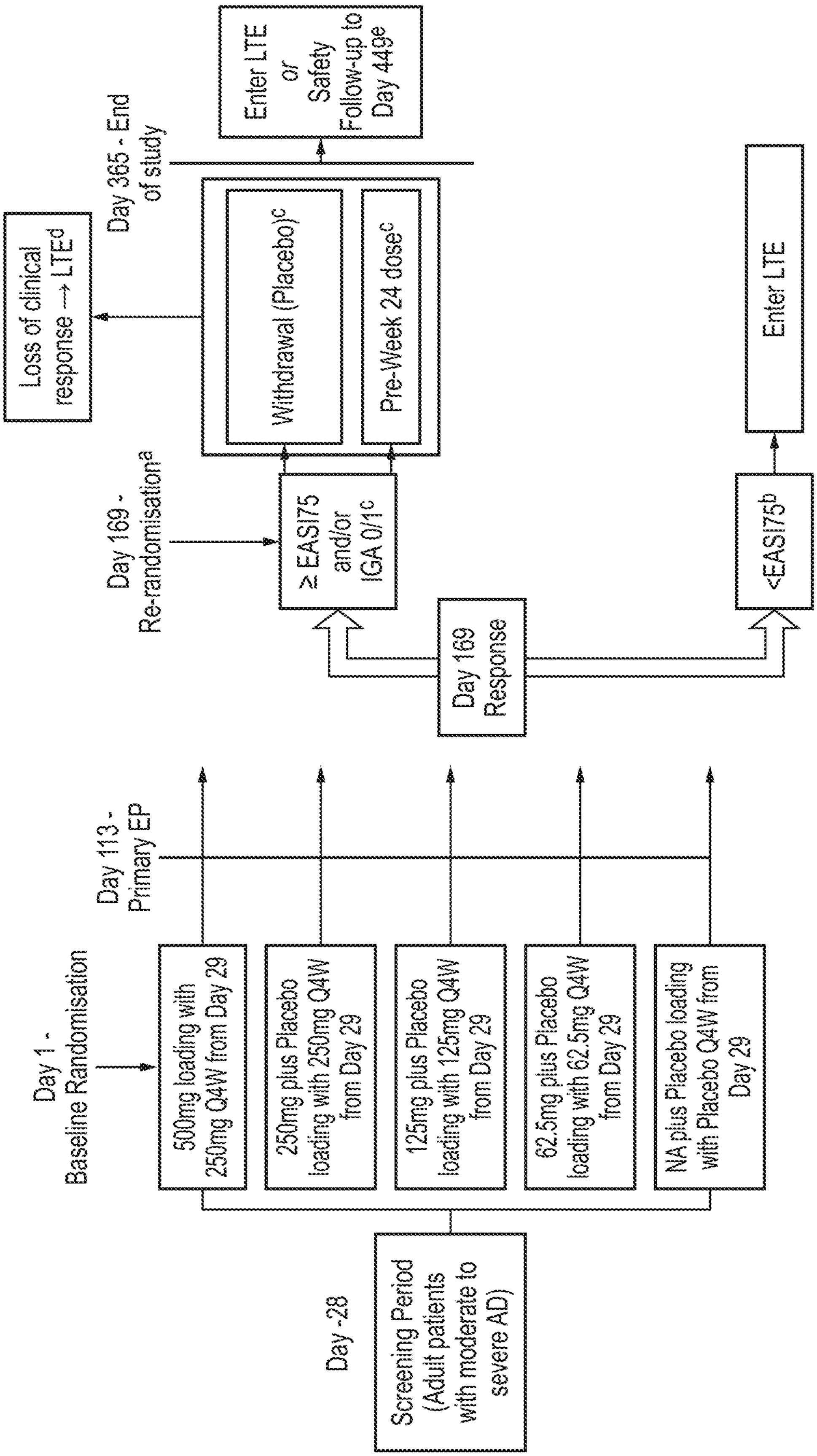
FIG. 26 graphically depicts the overview of study design of Example 5. Four different SC KY1005 dosing regimens will be tested versus placebo. From baseline up to Day 169 (Week 24), KY1005 will be administered at the following doses and intervals; 500 mg loading dose (given as 2×2 mL S.C. administration) followed 28 days later and thereafter with 250 mg every 4 weeks (Q4W) or the following regimens from Baseline: 250 mg Q4W, or 125 mg Q4W or 62.5 mg Q4W or Placebo Q4W.
Figure 27:
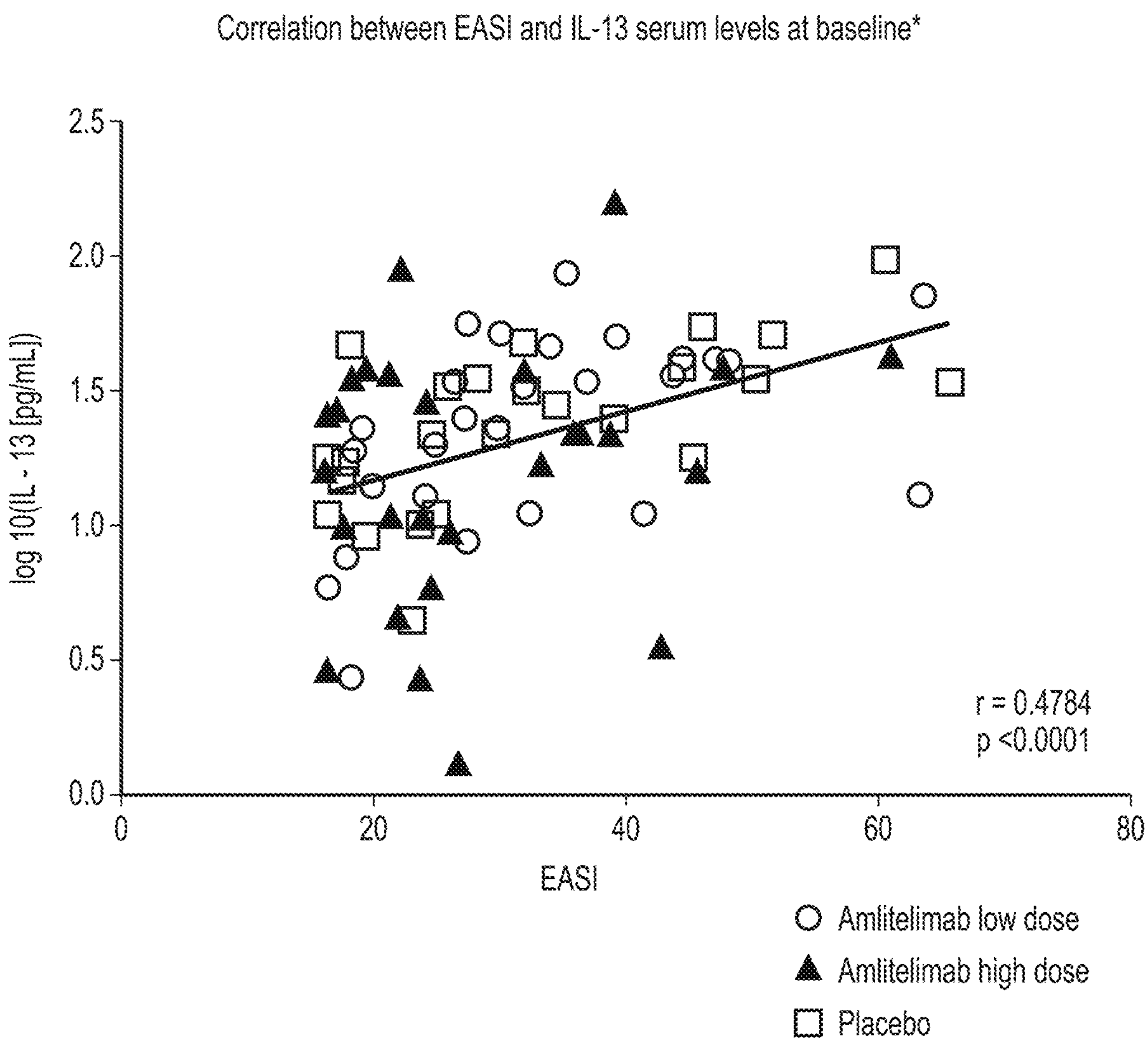
FIG. 27 graphically depicts Correlation between EASI and IL-13 serum levels at baseline. The figure depicts significant correlation of IL-13 levels with severity of disease at BL, as measured by EASI and SCORAD (data not shown). *Linear regression and correlation analysis with r coefficients and p-values based on Spearman correlations (n=77).
Figure 28A:
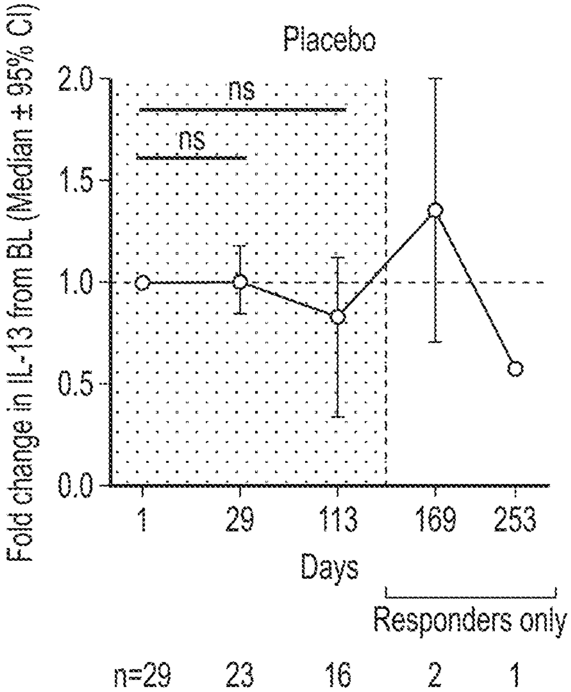
FIG. 28A-28C graphically depict circulating IL-13 over time. Significant decrease in IL-13 serum levels in patients treated with amlitelimab (KY1005 or 2D10), but not placebo, at Day 113. Decrease maintained until Day 253 in responders‡ to amlitelimab, but not to placebo. The sustained reduction in IL-13 serum levels in amlitelimab-treated patients is treatment dependent and strongly indicates that amlitelimab effectively targets immune dysregulation in AD †Repeated-measures two-way ANOVA plus Tukey's multiple comparison test on fold changes in IL-13 compared with BL (Day 1) for patients with complete dataset at Day 113 (placebo, n=15; amlitelimab low dose, n=20; and amlitelimab high dose, n=20). ns $p>0.05$;  $p<0.01$; * $p<0.001$, ****$p<0.0001$. *Decrease maintained in all patients, except for one patient treated with amlitelimab low dose whose IL-13 levels increased at Day 169 compared with BL. AD, atopic dermatitis; BL, baseline; CI, confidence interval; EASI, Eczema Area and Severity Index; IL, interleukin; ns, not significant; SCORAD, SCORing of Atopic Dermatitis.
Figure 28B:
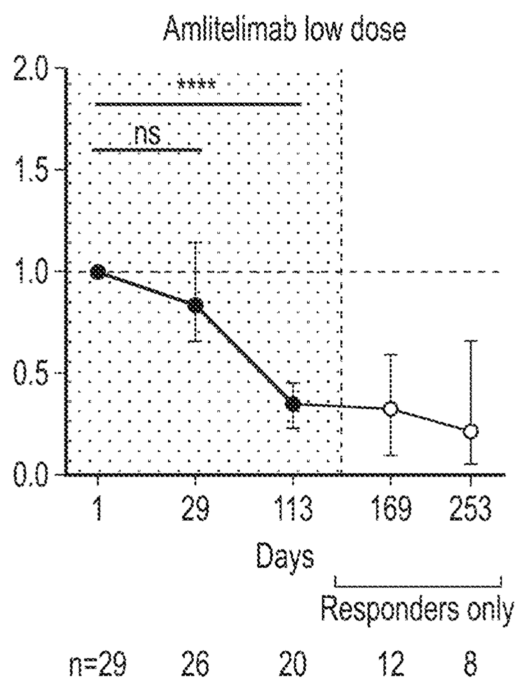
Figure 28C:
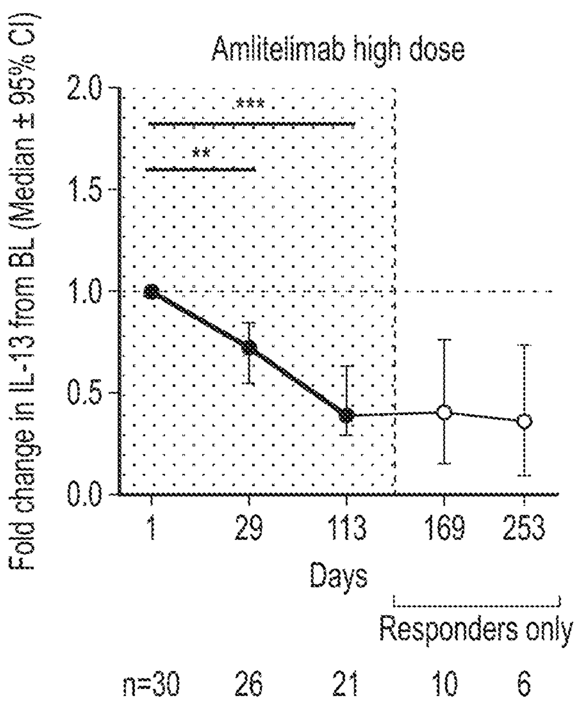
Figure 29A:
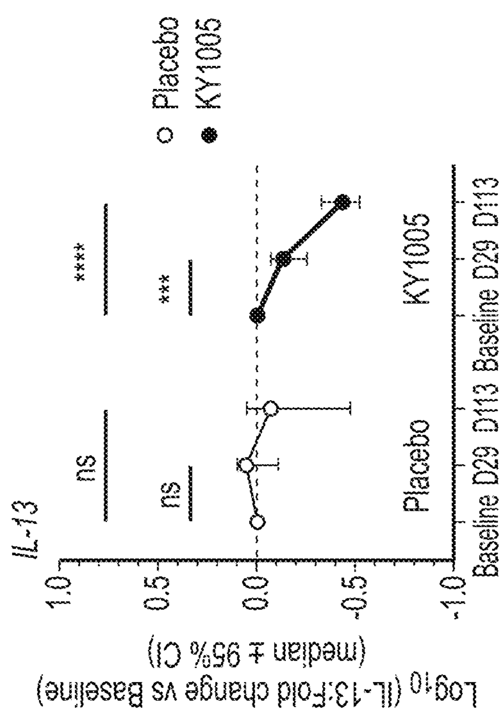
FIG. 29A-29F graphically depict the $\log_{10}$-fold change of biomarkers IL-13 (FIG. 29A-B), IL22 (FIG. 29C-D), and IL-17A (FIG. 29E-F) at Baseline (Day 0), Day 29 and Day 113 in patients administered either KY1005 or placebo (FIG. 29B, FIG. 29D and FIG. 29F further show data for patients administered KY1005 low and KY1005 high doses). Data for IL-13 and IL-22 are from the KY1005 CT02 serum analysis. Data for IL-17A are from the KY1005 CT02 OLINK analysis. ns, not significant; * $P\leq0.05$;  $P\leq0.01$; * $P\leq0.001$; ** P 0.0001. Two-way repeated measures ANOVA; Dunnett's multiple comparisons test.
Figure 29B:
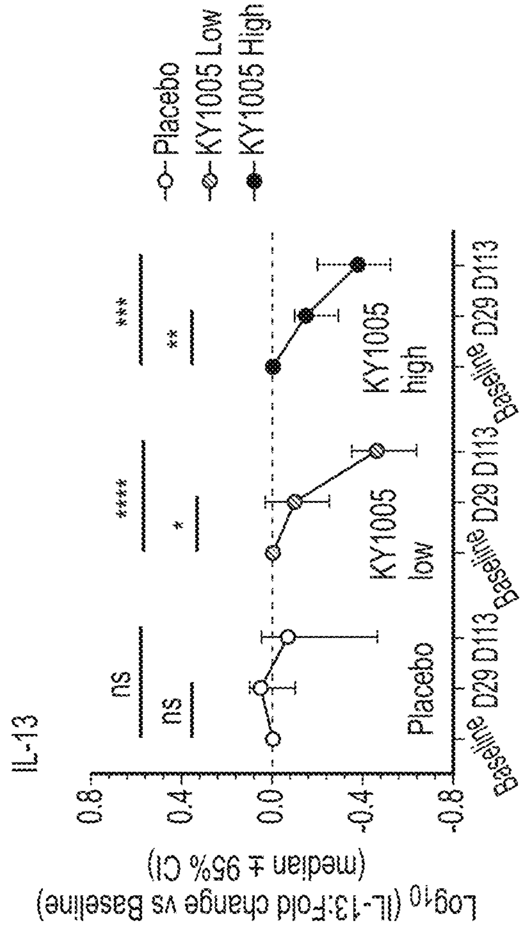
Figure 29C:
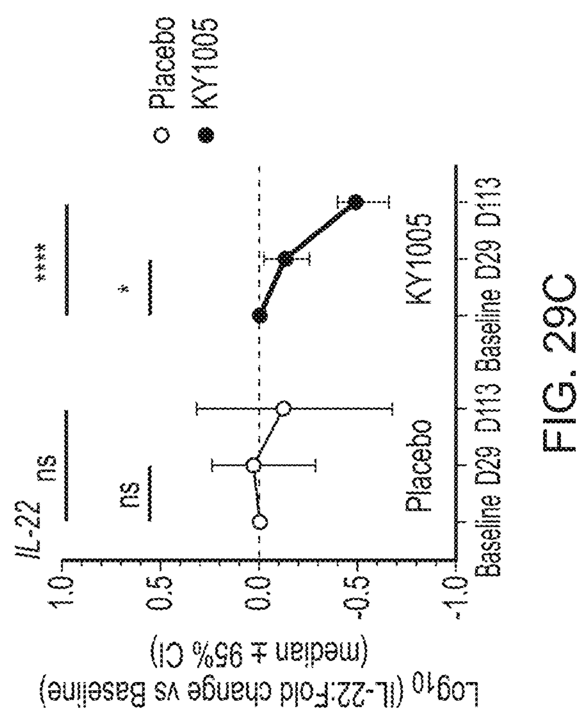
Figure 29D:
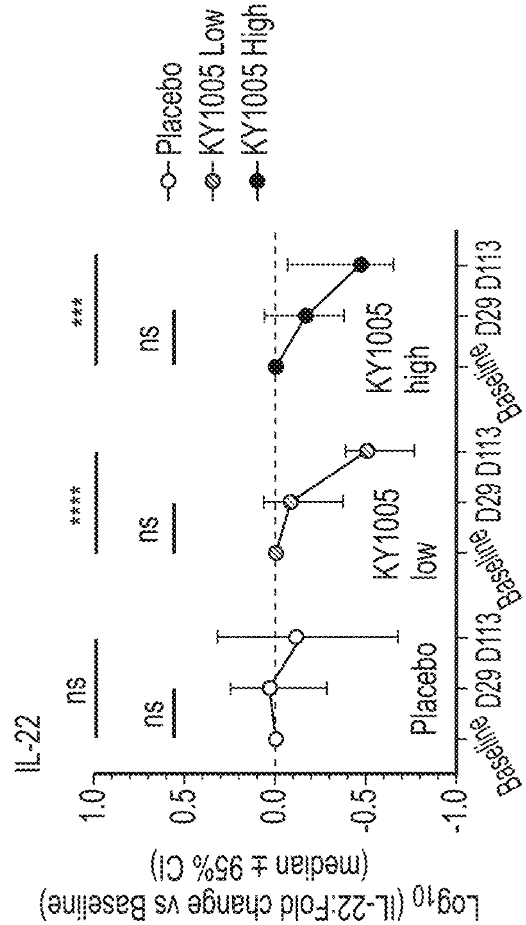
Figure 29F:
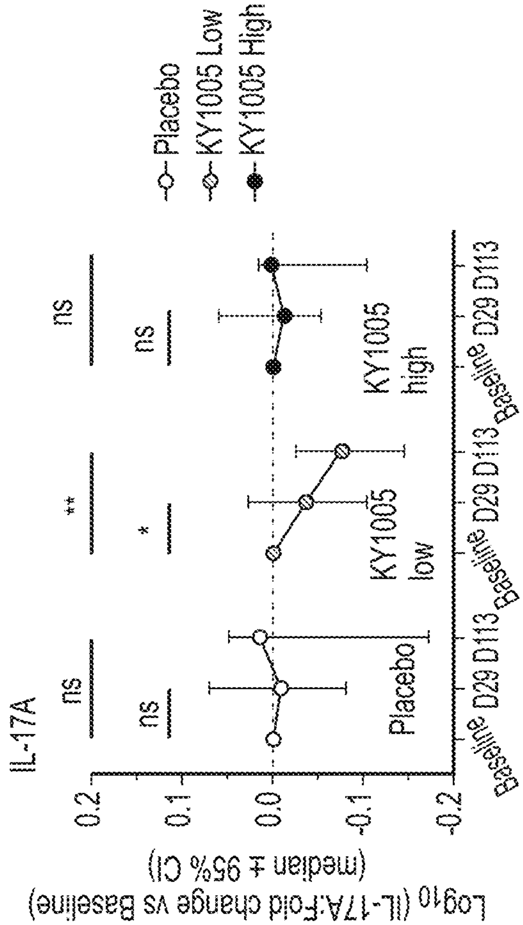
Figure 29E:
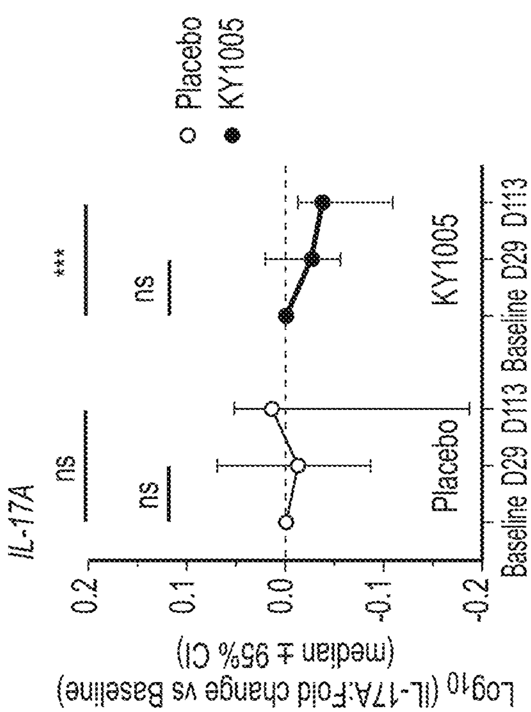
Figure 30:
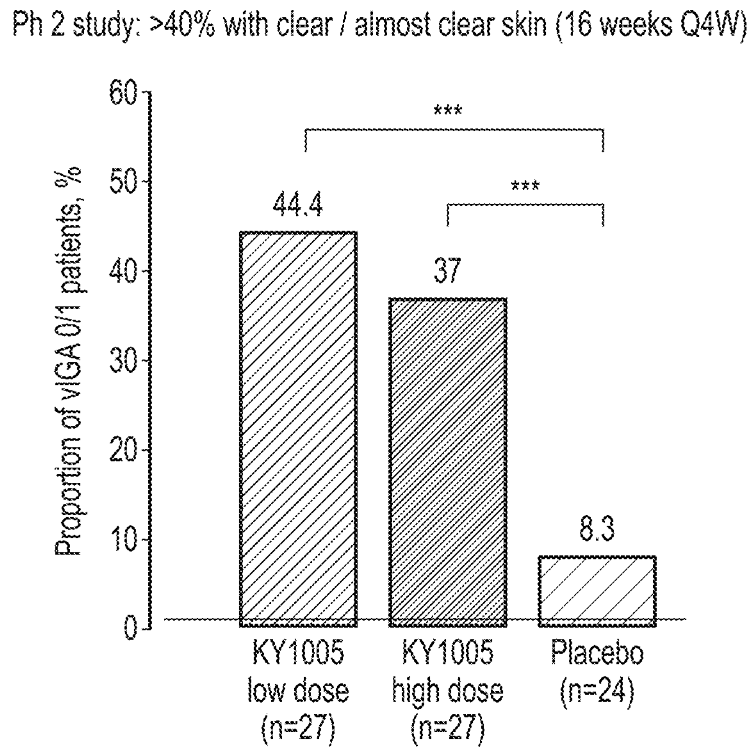
FIG. 30 graphically depicts the proportion of patients achieving a score of 0 or 1 on the Validated Investigator Global Assessment—Atopic Dermatitis (vIGA-AD) scale at 16 weeks of treatment in groups administered either a high dose of KY1005, a low dose of KY1005, or placebo once every four weeks. *$p<0.001$ vs placebo (Cochran-Mantel-Haenszel test), $p<0.001$, *$p<0.05$ vs placebo.

The overall study design is presented in FIG. 26.

Patients and Inclusion Criteria

Up to 350 patients (approximately 70 patients per treatment arm at Baseline) will be randomized.

Patients must fulfill all the following inclusion criteria for entry into the study:

1. Adults (18 to <75 years of age) with AD as defined by the American Academy of Dermatology Consensus Criteria [Eichenfield et al., 2014] for 1 year or longer at Baseline.
2. EASI of 12 or higher at the Screening Visit and 16 or higher at Baseline.
3. IGA of 3 or 4 at Baseline.
4. AD involvement of 10% or more of body surface area (BSA) at Baseline.
5. Baseline worst/maximum pruritus NRS of 4. The baseline weekly average of daily worst/maximum pruritus NRS will be calculated from the 7 consecutive days immediately preceding the Baseline visit. A minimum of 4 daily scores out of the 7 will be required.
6. Documented history, within 6 months prior to Baseline, of either inadequate response or inadvisability of topical treatments.
7. Must have applied a stable dose of topical bland emollient (simple moisturizer, no additives [e.g., urea]) at least twice daily for a minimum of 7 consecutive days before baseline.
8. Able to complete patient questionnaires, including collection of NRS (pruritus) on each of the 7 days prior to baseline. For patients who do not have at least 4 daily scores reported during the 7 days immediately preceding the planned randomization date, randomization should be postponed until this requirement is met, but without exceeding the 28-day maximum duration for screening.
9. For patients at sites selected for skin biopsy collection: (until up to approximately one third (30%) of patients have enrolled to the skin biopsy sub-study), able and willing to provide skin biopsies at required timepoints.

Exclusion Criteria

Patients fulfilling any of the following exclusion criteria will be excluded from the study:

1. Treatment with any of the following prior to first IMP administration (Baseline):

Systemic corticosteroids, and calcineurin inhibitors (tacrolimus and cyclosporin) within 4 weeks;

Leukotriene inhibitors within 4 weeks;

Use of mycophenolate mofetil, azathioprine, methotrexate, cyclosporine, dapsone, intravenous immunoglobulin, Kineret (anakinra), Enbrel (etanercept), or any other immunosuppressant not mentioned in this exclusion criterion within 4 weeks prior to Baseline;

Use of infliximab, adalimumab, golimumab, abatacept, tocilizumab, certolizumab, secukinumab, IFN-γ, janus kinase (JAK) inhibitors, dupilumab, and any other biologic or targeted-synthetic disease modifier drug not mentioned in this exclusion criterion or in the exclusion criterion above, as well as plasmapheresis within 12 weeks prior to baseline;

Use of anti-CD20 drugs such as rituximab, ofatumumab, other long-acting biologics within 6 months prior to baseline (or shorter if there is documented B cell reconstitution for anti-CD20 drugs);

Topical corticosteroids, tacrolimus or pimecrolimus, or topical phosphodiesterase-4 (PDE4) inhibitor within 7 days;

Prescription or non-prescription moisturisers with additives (e.g., urea, filaggrin) within 2 weeks;

Dupilumab (aIL-4Ro) within 3 months;

Any prior use of any anti-OX40, anti-OX40L mAb;

Investigational therapy for the treatment of AD or other conditions within 5 half-lives or the limit of PD effects or 3 months where the $t_{1/2}$ is not known.

2. Weight<40 kg or >150 kg at baseline.

Other inclusion/exclusion criteria as standard for this type of trial will be used.

Investigational Medicinal Product

The IMPs are KY1005 (SAR445229), or matching Placebo.

KY1005 drug product is formulated as a liquid at 125 mg/mL.

KY1005 125 mg/mL drug product is aseptically filled into 2 mL Type 1 clear glass vials with a nominal fill volume of 1 mL, sealed with FluoroTec coated stoppers and crimped with overcaps to ensure container closure integrity.

The matching Placebo is used to dilute KY1005 to the correct dose concentration in a fixed volume to maintain blinding.

Treatment Regimen

Patients may receive study treatment every 4 weeks from Day 1 to Day 337 (Week 48) according to the scheme in FIG. 26.

Patients will initially receive S.C. injections of IMP (Days, 1, 29, 57, 85 and Day 113) ahead of the primary efficacy analysis at Day 113 (Week 16). Treatment will then continue to Day 169 (Week 24). Those patients in the 500 mg loading with 250 mg Q4W treatment arm will receive 2×2 mL 250 mg S.C. injections on Day 1 and commence 250 mg Q4W on Day 29. Those in the remaining treatment arms will receive their assigned KY1005 dose as a 2 mL injection also receive a 2 mL injection of Placebo on Day 1 to maintain the blind and commence their assigned KY1005 or Placebo Q4W dose on Day 29.

Those patients who achieve 2 EASI-75 or who attain IGA0/1 at Week 24 will be re-randomized pre-injection at Day 169 (Week 24) to either the Withdrawal arm (and receive Placebo Q4W) or remain on their pre-Week 24 dose.

TABLE 31

| Treatment Regimens | | | | | | | | |
|---|---|---|---|---|---|---|---|---|
| | Day 1 | | Day 29 to Day 169 | | | Day 169 to Day 365 in patients who achieve ≥ EASI-75 or who attain IGA0/1at Day 169 | | |
| Arm | IMP | Dose (mg) | Frequency | Dose (mg) | Frequency | IMP | Dose (mg) | Frequency |
| 1 | KY1005 | 500 mg (2 × 250 mg) | Q4W | 250 mg | Q4W | KY1005 PBO | 250 mg 0 | Q4W or Q4W |
| 2 | KY1005 | 250 mg plus PBO loading | Q4W | 250 mg | Q4W | KY1005 PBO | 250 mg 0 | Q4W or Q4W |
| 3 | KY1005 | 125 mg plus PBO loading | Q4W | 125 mg | Q4W | KY1005 PBO | 125 mg 0 | Q4W or Q4W |
| 4 | KY1005 | 62.5 mg plus PBO loading | Q4W | 62.5 mg | Q4W | KY1005 PB0 | 62.5 mg 0 | Q4Wor Q4W |
| 5 | Placebo | NA plus PBO loading | Q4W | NA | Q4W | PBO PBO | 0 0 | Q4W or Q4W |

IMP = investigational medicinal product;
PBO = Placebo;
NA = not applicable;
Q4W = every 4 weeks.

All study treatment regimens are presented in Table 31. Randomization will occur pre-injection on Day 1, with re-randomization pre-injection on Day 169 should the patient achieved an ≥EASI75 or attain IGA0/1.

From Day 169 (Week 24) to Day 365 (Week 52) in patients who achieve 2 EASI-75 or who attain IGA0/1 at Week 24 will be randomized 3:1 to either Withdrawal or will continue to receive their pre-Week 24 dosing.

Patients randomized to Withdrawal will receive Placebo Q4W. Those patients not randomized to Withdrawal will continue to receive their pre-Week 24 dose/interval.

Re-randomization from Day 169 will not be uncoded to the team, study sites or patients until after the final Data Base Lock. Those patients who do not achieve 2 EASI-75 or IGA0/1 at Week 24 will have the possibility to enroll into the LTE where they will receive KY1005 250 mg Q4W.

All doses of KY1005 and Placebo will be administered in a 2.0 mL volume. At Baseline, 2×2 mL injections will be given to maintain the integrity of the blind.

Administration of IMP

At the Baseline visit only, 2 S.C. injections will be administered. At all remaining visits, 1 injection will be administered. KY1005 or matching Placebo will be administered as a S.C. injection to the abdomen. If IMP administration to the abdomen is not possible due to the extent of skin involvement, the outer thigh may be selected.

Treatment Duration

All patients treated with KY1005 or matching Placebo will be randomized and begin study treatment on Day 1. The duration of treatment will therefore be up to Day 365 (Week 52), with last dose administered on Day 337 for those patients who achieve 2 EASI-75 or who attain IGA0/1 at Week 24, unless enrolled into the LTE study.

Those patients who do not achieve 2 EASI-75 or IGA0/1 at Week 24 will have the possibility to enter the LTE at Day 169.

Background Therapy

Patients are required to apply a stable dose of a topical bland emollient (simple moisturizer) at least twice daily for a minimum of 7 consecutive days before the baseline visit and to continue with the same emollient at the same dose twice daily throughout their participation in the study.

To permit an adequate assessment of skin dryness, moisturizers should not be applied on area(s) of non-lesional skin, designated as such for assessment purposes, for at least 8 hours before each clinic visit.

Patients are permitted to use any simple bland prescription, over-the-counter or general purchase moisturizer providing it contains no additives, such as corticosteroids or urea (even at low concentrations). Prescription and non-prescription moisturizers with additives (e.g., urea, filaggrin) are not permitted within 2 weeks prior to first IMP administration (Baseline) or during the study.

Efficacy Assessments

The efficacy of KY1005 in the treatment of AD will be assessed using change in EASI, IGA, SCORAD Index and affected BSA. Investigator performed assessments should be carried out by the same assessor on each occasion for an individual patient. Patient reported outcomes will be assessed using the POEM, DLQI, HADS, ADCT and the NRS for pruritus. Patients will be required to use an internet-enabled device (e.g., computer, mobile phone or tablet device) to complete an electronic diary to record the PROs in local languages where validated. Patients should bring their eDiary to visits and review with coordinators. Patients will be encouraged to continue completing diary information until their last visit.

Where possible, the PRO assessments completed at the study site are to be completed by patients prior to the completion of other study assessments and the administration of study drug. The PRO assessments performed with include EASI, v-IGA, SCORAD Index, BSA Involvement of Atopic Dermatitis, POEM, DLQI, and NRS for Pruritus (See Example 2 for a description of these PRO assessments.) Additionally, the ADCT and HADS will be assessed and are described below.

Atopic Dermatitis Control Tool (ADCT)

The ADCT is a validated 6-item instrument with a 7-day recall period to measure AD disease control. The following domains are assessed—overall severity of symptoms, frequency of intense episodes of itching, severity of bother of itching, frequency of sleep impact, severity of daily activities impact, severity of mood or emotions impact. Each item is scored from 0 (none) to 4 (extreme). A total score of 7 or more points (derived by adding item scores) was identified during validation as an optimum threshold to identify patients whose AD is "not in control".

Hospital Anxiety and Depression Scale (HADS)

The HADS is a validated 14-item patient reported outcome measure used to assess states of anxiety and depression over the past week.

Pharmacokinetic Procedures

Blood samples will be withdrawn periodically for KY1005 assay. Pharmacokinetic and ADA samples will be collected from all patients including those receiving Placebo.

Serum concentrations of KY1005 will be assessed from blood samples taken during the study using validated enzyme-linked immunosorbent assay (ELISA) bioanalytical methods. Assay methodologies and procedures will be described in analytical plans to be finalized before the start of sample analysis.

The following PK values will be derived for each patient receiving KY1005 and all KY1005 regimens:

- $C_{max}$ following the first, or any doses where sampling permits. Peak concentrations following any doses where sampling permits.
- $t_{max}$ following the first, or any doses where sampling permits.
- $C_{min}$ following the first, second, third, fourth and any doses where sampling permits.

Anti-Drug Antibody Procedures

Blood samples will be withdrawn periodically for anti-KY1005 antibody assays. Serum titers of anti-KY1005 antibodies will be assessed in blood samples taken during the study using a validated bioanalytical method. Characterization of positive ADA samples, e.g., KY1005 neutralizing capacity, may be performed if required.

Example 6: Treatment with KY1005—a Novel Non-Depleting Anti-OX40Liqand (OX40L) mAb-Reduces IL-13 Serum Levels in a Phase 2a Randomised Placebo-Controlled Trial on Patients with Moderate to Severe Atopic Dermatitis Methods Serum was collected during the trial (Ph2a monotherapy, NCT03754309, Kymab-funded, 16-week, double-blind, RCT). 89 moderate-to-severe AD patients were randomised 1:1:1 to i.v. KY1005 low dose (KY1005-Lo, 200 mg loading/100 mg maintenance Q4W), high dose (KY1005-Hi, 500 mg/250 mg Q4W) or placebo (PBO). Disease severity measurement included EASI. Serum IL-13 levels were determined by single molecule immunoassay (Simoa).

Results

Of 88 subjects who received KY1005, 59 were evaluable at W16. KY1005 was well tolerated with unremarkable safety profile. Mean % change in EASI from baseline (BL) at W16 was −80.1% for KY1005-Lo and −69.9% for KY1005-Hi vs −49.4% for PBO (p=0.009 and 0.072 respectively). No BL difference in IL13 was found between groups. IL-13 levels correlated with disease severity at BL (r=0.4784, p<0.0001). A significant reduction in IL13 levels was observed at W16 in KY1005-treated patients (Lo p<0.0001; Hi p=0.0003) but not PBO (p=0.1558).

Example 7: KY1005-CT02: Analysis of Serum Proteins

Study Summary

IL-22, IL-13, IL-31 and IL-17A were identified to be significantly associated with disease severity as measured using EASI scores. When treatment-induced changes in serum protein levels upon KY1005 and Placebo treatment at Day 113 were assessed, IL-22, IL-13, IL-31 and IL-17A were found to be significantly changed upon KY1005 treatment. IL-22, IL-13, IL-31 and IL-17A were found to be affected by KY1005, but not Placebo treatment, suggesting that these proteins are specifically affected by KY1005.

Study Objective

Olink technology provides the means to assess serum levels of many proteins in parallel using small samples volumes. IL-17A was quantified using Olink. In addition, serum levels of IL-13, IL-22 and IL-31 were analysed using the highly-sensitive Simoa technology. The aim of this study was to identify circulating biomarkers which are affected by KY1005 treatment.

Patient Cohort

Serum samples were collected from all patients enrolled in KY1005-CT02. Serum was collected from all patients at baseline (day 1 of the trial), day 29 and day 113. In the study extension phase, further serum samples were collected at day 169 and day 253 from responders only (=patient who reached a vIGA score of 0 or 1 at the primary endpoint on day 113) For SIMOA analysis, 264 samples in total. Samples collected from 10 patients were only used for analyses independent of clinical scores (EASI, SCORAD, vIGA). 5 samples did not contain enough volume for all assays. All statistical tests were performed on log-transformed data, as IL-13 and IL-22 levels are log-normally distributed.

Serum Collection

At clinical sites, blood was collected by venipuncture into 5 mL SST serum(Gel)-Vacutainer tubes (BD). Immediately after blood collection, the tube was very gently agitated by turning the tube upside-down 8-10 times to ensure dissolution of the anticoagulant. To allow for blood clotting, the tube was left at ambient temperature in an upright position for approximately 30 minutes. The serum(Gel)-Vacutainer was then centrifuged for 10 minutes at 2500 g, ambient temperature in a swing bucket centrifuge if available. At least 300 μL of the supernatant serum were then carefully transferred into each of four 2 mL CryoPure tubes with yellow screw caps using a fresh pipette. Contamination with erythrocytes was strictly avoided. If contamination occurred, the specimen had to be centrifuged again. All aliquots were stored upright in a −80° C. freezer (ensuring a temperature of at least −70° C. or below). Visit specific data was recorded in the storage list for frozen serum specimens, before dry ice shipments to the central laboratory LKF were organised. Samples were stored at LKF and shipped to Olink and Myriad RBM (Simoa) for analysis.

Olink Assay

Serum samples were shipped to Olink on dry ice and stored at −80° C. until tested. Samples were analysed in three batches. Upon thawing, 40 μL of each sample were aliquoted into 96-well plates in a randomised fashion. 1 μL per sample and per panel were then used to quantify the serum levels of proteins using Olink panels.

The Olink reagents are based on Proximity Extension Assay technology, where proteins can be detected by antigen-specific oligonucleotide-labelled antibody probe pairs. A PCR reporter sequence is formed by a proximity-dependent DNA polymerization event. This is then amplified, and subsequently detected and quantified using real-time PCR using the Fluidigm® BioMark™ HID System. The assay is performed in a homogeneous 96-well format without any need for washing steps, using the 96×96 Dynamic Array™ IFC for multiplexing and an IFC loader to load the 96×96 Dynamic Array IFC. Internal controls are added to each sample and include two Immunoassay controls, one Extension control, one Detection control and one external interplate control used to monitor the extension and readout steps and for data normalisation across samples and different runs.

Analysis results are presented as Normalised Protein eXpression (NPX) units on a log 2 scale, which are generated from the extension reaction read-out after normalisation based on internal controls and allow for relative (not absolute) quantitation of serum protein levels.

| PANEL ASSAY | UNIPROT ID | OLINKID |
|---|---|---|
| Olink INFLAMMATION(v.3022) IL-17A | Q16552 | OID00485 |

Simoa Assay

All serum samples were stored at temperatures below −72° C. until tested. Samples were thawed at room temperature, vortexed, spun at 3700×g for 5 minutes for clarification and transferred to a master 96-well plate and diluted to the final required dilution. The assay was processed using Quanterix's fully automated immunoassay platform:

Simoa HD-1/HD-X Analyzer and single molecule array (Simoa) technology. All incubations took place at ambient temperature inside the Simoa HD-1/HD-X analyzer. Capture antibody conjugated paramagnetic beads were incubated with standards, samples, controls, and biotinylated detection antibodies. The beads were then washed and incubated with streptavidin-β-galactosidase (SBG). After the final wash, the beads were loaded into the Simoa Disc with SBG, resorufin β-galactopyranoside. The fluorescence signals were compared to the standard curve and the quantity of target analyte was determined for each sample. The data was interpreted using proprietary software developed by Myriad RBM. For each assay, both calibrators and controls were included on each sample plate. Eight-point calibrators were used to form a standard curve in the first and last column of each plate and controls at 3 concentration levels were run in duplicate. QC for the standard curve, controls, and samples was performed to ensure proper assay performance.

The QHSP-IL-13 Simoa™ ultra-high sensitivity assay was developed by Myriad RBM (MRBM) using Quanterix's fully automated immune assay platform and performed using up to 150 μL of serum following the steps described above. The QHSP-IL-22 Simoa™ ultra-high sensitivity assay was developed by Myriad RBM (MRBM) using Quanterix's fully automated immunoassay platform and performed using up to 100 μL of serum following the steps described above.

The QHSP-IL-31 Simoa™ ultra-high sensitivity assay was developed by Myriad RBM (MRBM) using Quanterix's fully automated immunoassay platform and performed using up to 100 μL of serum following the steps described above (Kit lot number: K15859-QHSP-IL-31). IL-31 levels were quantified in left-over serum samples, only when corresponding baseline samples from the same patient were still available (n=230, with 9 samples excluded due to missing baseline samples).

TABLE 32

| Simoa assay specifications | | | | | | | | |
|---|---|---|---|---|---|---|---|---|
| Assay | N | Unit | Dilution | LDD | LLOQ | LLOQ | Dynamic Range |
| IL-13 | 260 | pg/mL | 1:2 | 0.10 | 0.099 | 500 | 0.099-500 |
| IL-22 | 264 | pg/mL | 1:4 | 0.024 | 0.047 | 120 | 0.024-120 |
| IL-31 | 232 | pg/mL | 1:4 | 0.033 | 0.024 | 400 | 0.024-400 |

Data Analysis

Assay results were obtained from Olink. Simoa data was obtained from Myriad RBM in the form of Excel tables. Patient response information was extracted from the clinical "adrs.xpt" Adam SAS dataset.

Analysis was conducted using the statistical computer language R (version 4.0.2).

Processing and batch normalisation of the Olink data was performed with the OlinkAnalyze R package written by Olink Proteomics. The three spreadsheets of Olink data were loaded into R using the "read_NPX" function. The three resulting data objects were combined, and batch corrected using the "olink_normalization" function. Batch correction used the bridging sample and was performed in a two-step process. Both batch 2 and 3 were separately normalised to batch 1, altering the values of batch 2 and 3 samples. All three batches were then combined into a single dataset. After the initial batch correction, a residual batch effect was observed. An additional batch correction was performed using the limma function "removeBatchEffect" to remove this effect. $Log_2$-transformed Simoa data were analysed alongside Olink data.

Linear models were performed for all time-points up to Day 113 using the base-R function 'Im'. Uniform Manifold Approximation and Projection (UMAP) dimensionality reduction plots were performed with the 'umap' package. All plots were generated using "The Grammar of Graphics" inspired 'ggplot2' data visualisation package.

Results

Numerically greater reductions in serum levels of total IgE, Th2-associated cytokines IL-13 and IL-31 and the Th22-associated cytokine, IL-22 on week 16 compared to baseline were observed in the amlitelimab high and low dose groups compared to the placebo group. In the study extension, treatment-dependent reductions of total IgE, IL-13 and IL-22 up to week 16 were also largely maintained up to week 36 in patients who maintained their vIGA0/1 status 24 weeks after the last amlitelimab dose.

Serum Protein Levels Associated with Clinical Disease Severity

TABLE 33

Significantly different serum protein changes between KY1005 and Placebo

| | | DAY 29 | | DAY 113 | |
|---|---|---|---|---|---|
| ProteinID | Protein | Estimate | Unadj. p | Estimate | Unadj. p |
| Simoa_IL13 | IL13 | −0.50261 | 0.025623 | −0.66645 | 0.103372 |
| Simoa_IL31 | IL31 | −0.38903 | 0.220672 | −1.46837 | 0.018847 |

Differences in the changes in serum protein levels between KY1005-treated and Placebo patients at days 29 and 113 were assessed. Proteins with an unadjusted p-value <0.05 seen in at least one of the two timepoints are displayed in Table 33. Proteins are ordered by the magnitude of difference in protein changes (Estimate) between the Placebo and KY1005 treatment groups at day 29. Proteins decreased in KY1005 compared to Placebo are shown.

Figures 31A, 31B:
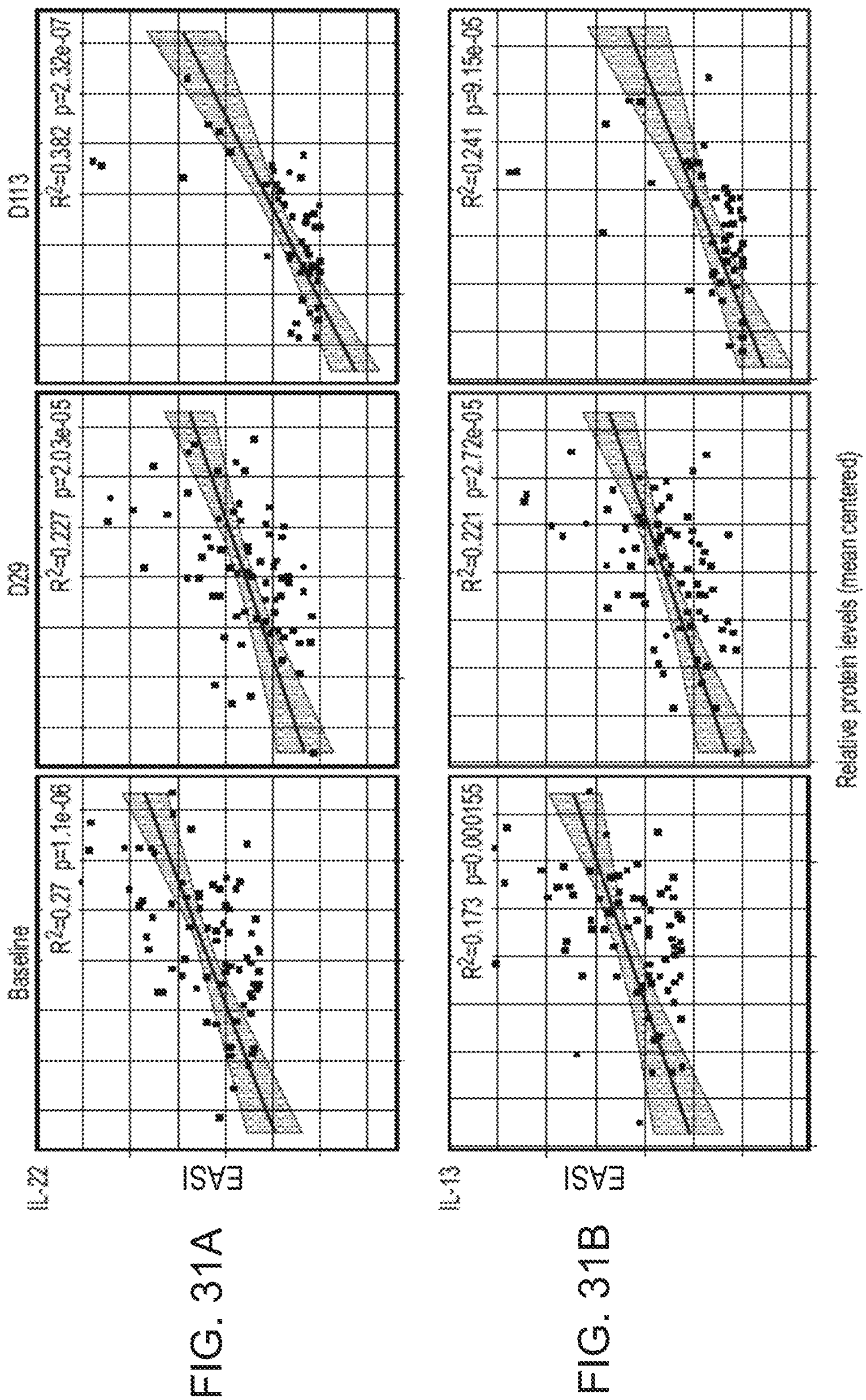
FIG. 31A-31B graphically depicts the relative protein levels of two proteins (IL-22 in FIG. 31A, and IL-13 in FIG. 31B) associated with disease severity. IL-22 and IL-13 protein levels were found to be significantly associated (FDR p-value<0.05) with EASI scores at baseline (first column). This association was also maintained at day 29 and day 113 for both proteins. The coefficient of determination $R^2$ and p-values were calculated using linear models. Each dot represents a patient sample, the blue line represents the linear regression line, the 95% confidence interval is shown in grey.
Figure 32A:
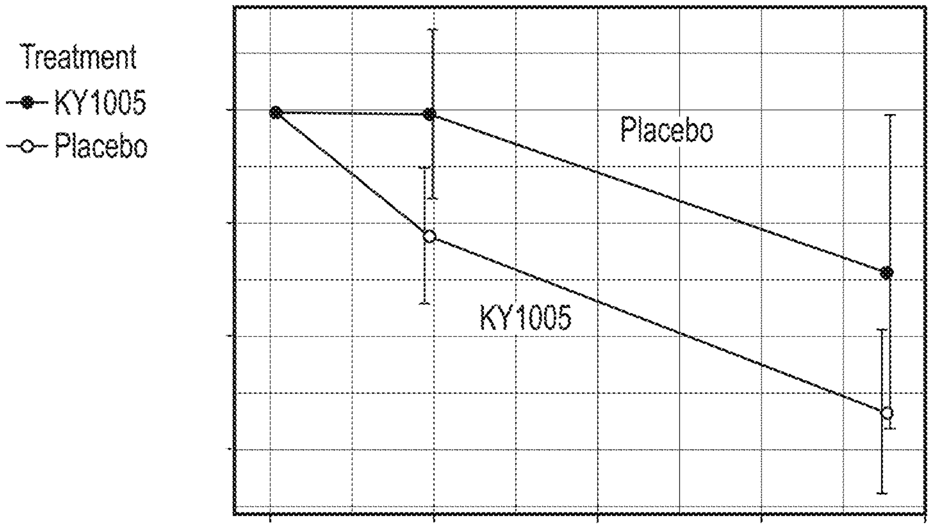
FIG. 32A-32C graphically depicts the levels of IL-13 (FIG. 32A), IL-22 (FIG. 32B), and IL-17A (FIG. 32C), which are significantly reduced at Day 113 upon KY1005 treatment (FDR p-value<0.05). X-axis shows time in days (data points are at days 0, 29 and 113). Y-axis shows $\text{Log}_2$ change from baseline level.
Figure 32B:
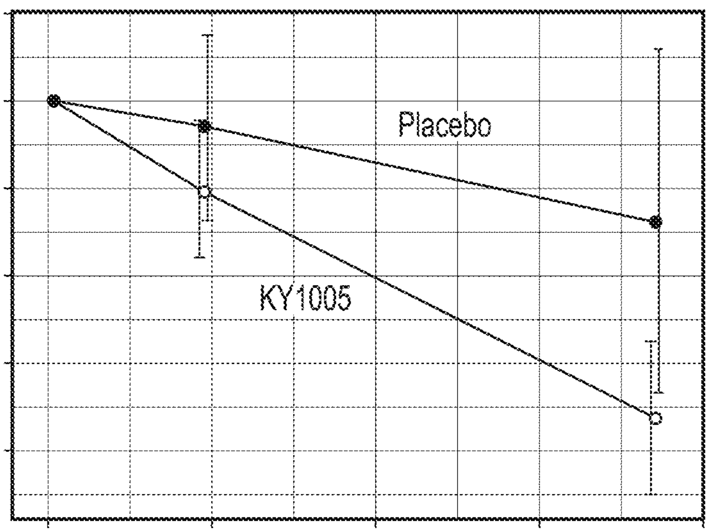
Figure 32C:
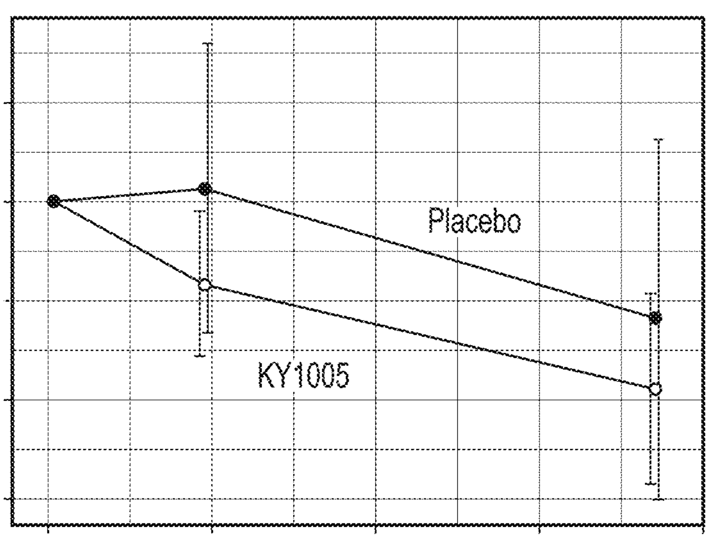
Figure 33A:
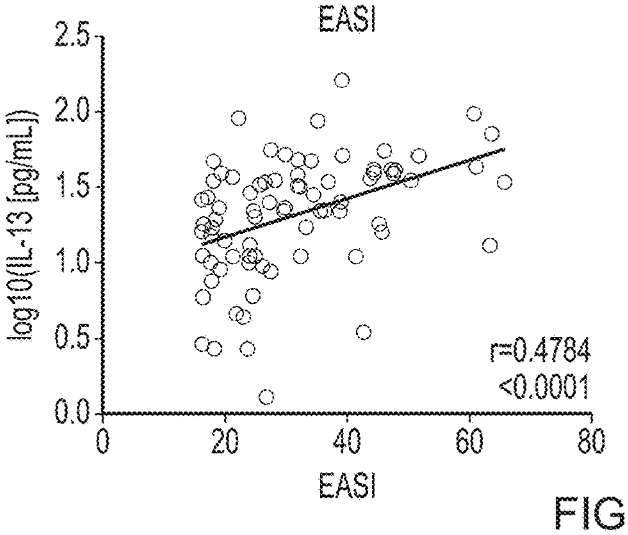
FIG. 33A-33C graphically depicts that IL-13 serum levels at baseline are correlated with disease severity. IL-13 is significantly positively correlated with disease severity as measured by both EASI (FIG. 33A) and SCORAD (FIG. 33B) at baseline. IL-13 baseline levels are not significantly different between treatment groups (FIG. 33C). Spearman correlation of IL-13 and EASI/SCORAD at baseline (n=78). One-Way ANOVA with Tukey's multiple comparisons test.
Figure 33B:
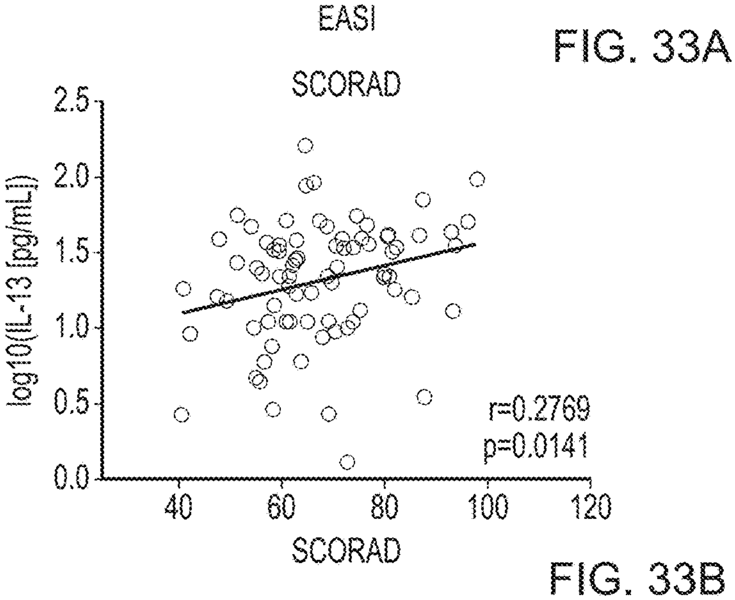
Figure 33C:
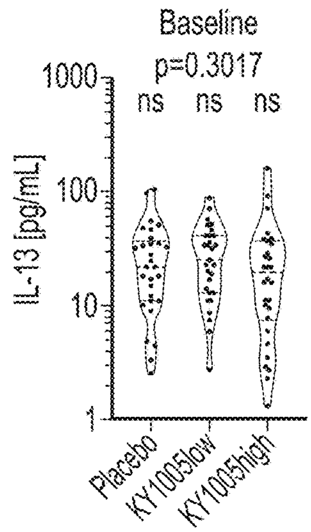
Figure 34:
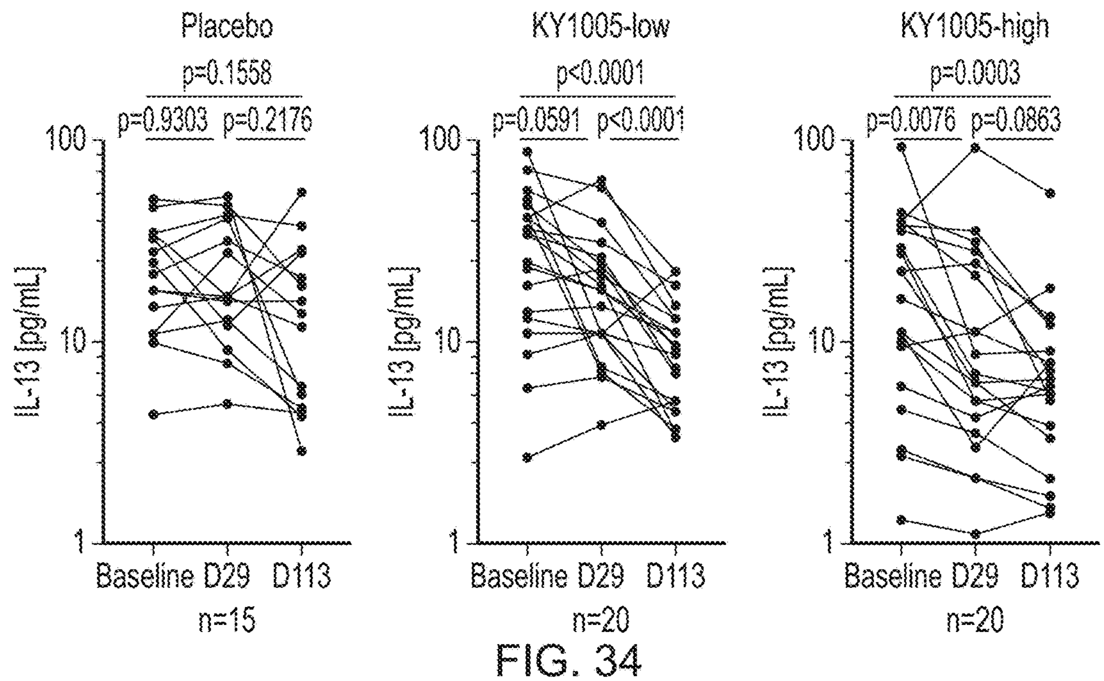
FIG. 34 graphically depicts circulating IL-13 in different treatment groups between baseline and D113. IL-13 levels normalized to Baseline. n=Number of patients with full set of samples up to D113. Two-way ANOVA+Tukey's multiple comparisons test. IL-13 is significantly reduced in KY1005-treated patients (KY1005-low & -high) at D113, but not in Placebo patients.
Figure 35A:
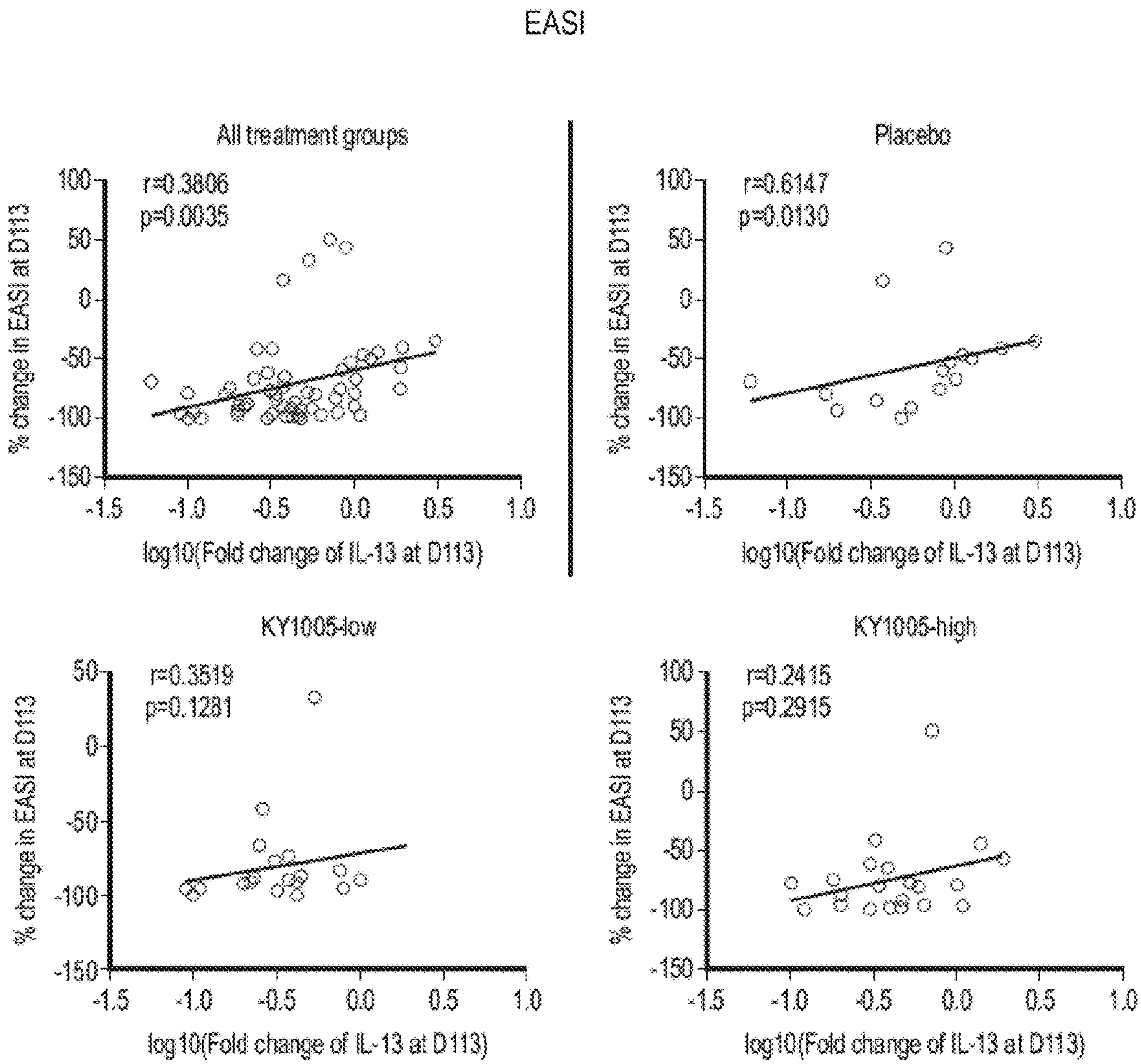
FIG. 35A-35B graphically depicts D113 vs baseline changes in IL-13 levels, illustrating that IL-13 levels are correlated with disease improvement. Only patients with full set of samples up to D113 included (n=58). Spearman correlation of fold change of IL-13 and EASI (FIG. 35A)/SCORAD(FIG. 35B) at D113. Weak correlations between changes in IL-13 and EASI (FIG. 35A) & SCORAD (FIG. 35A) disease improvement at D113.
Figure 35B:
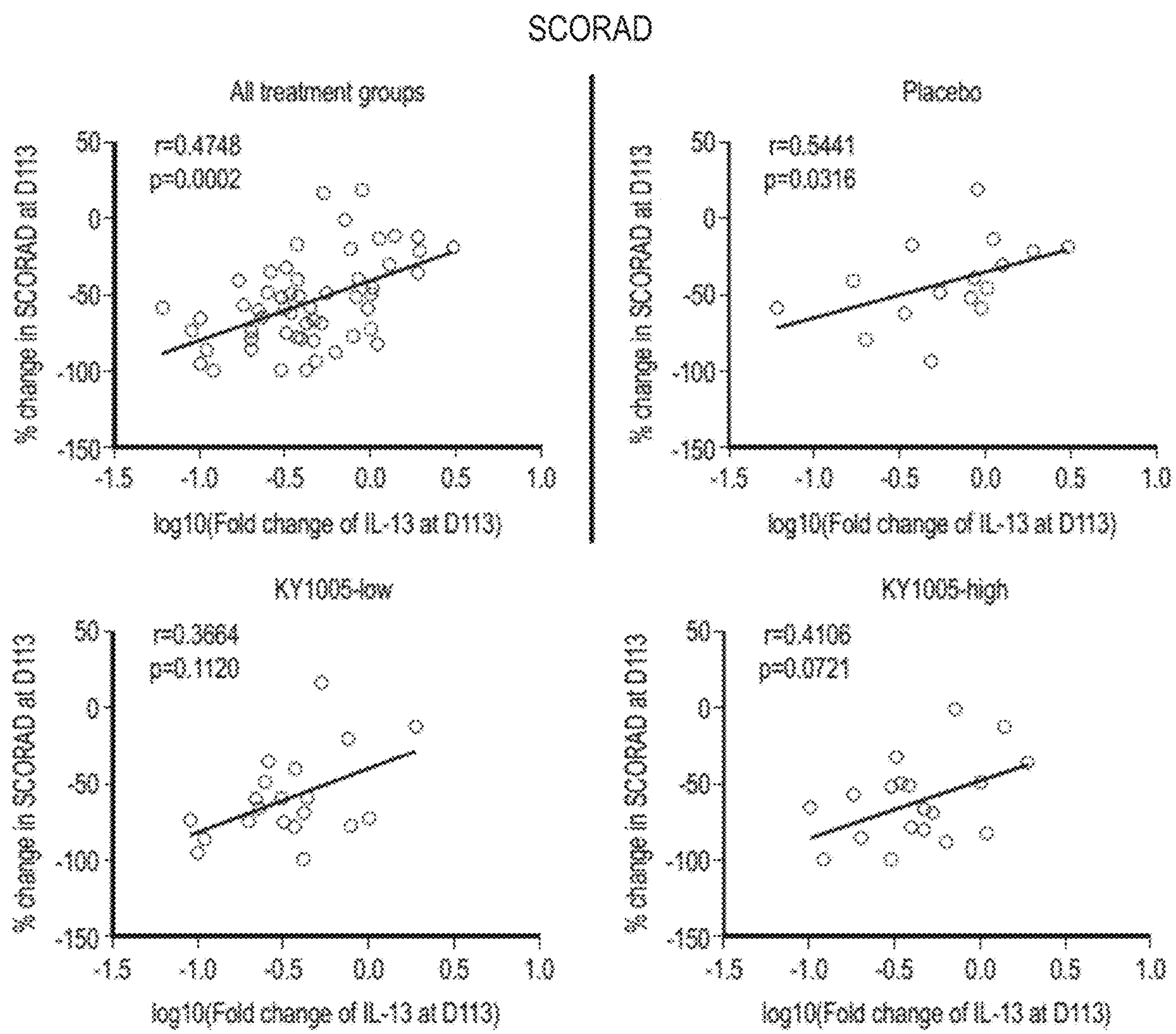
Figure 36:
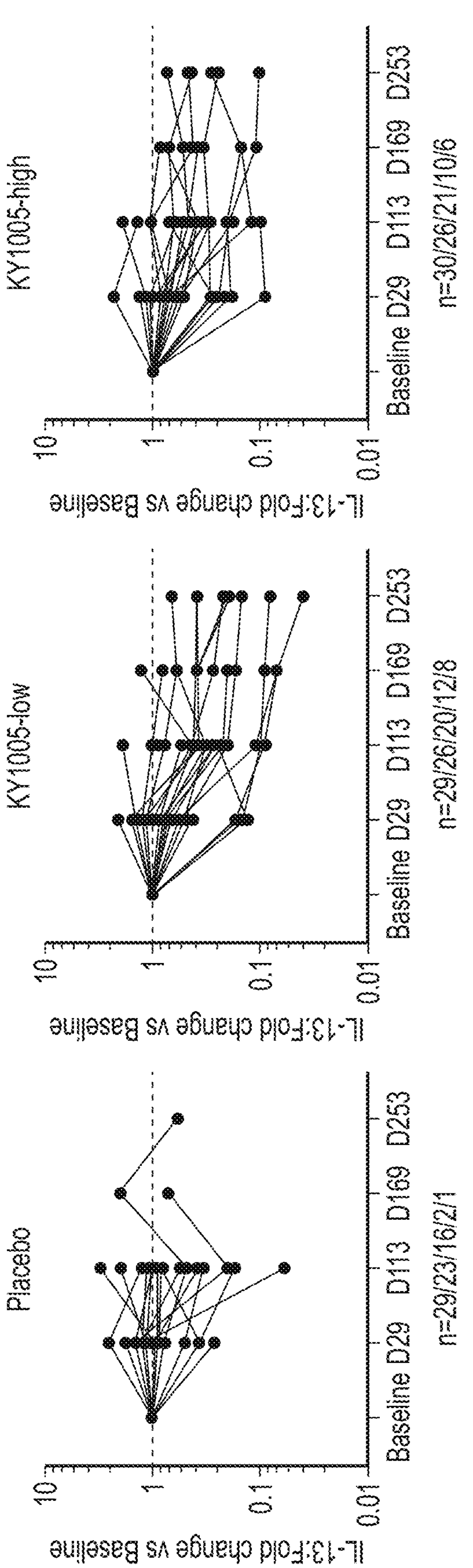
FIG. 36 graphically depicts that IL-13 serum level changes are maintained past D113 in vIGA 0/1 responders. 24 D169 samples and 15 evaluable D253 samples were obtained from 24 patients classified as responder at D113 (vIGA 0-1). In patients classified as responders at D113 (vIGA 0-1), IL-13 serum reduction was prolonged up to D169 and D253 for those treated with KY1005.
Figure 37A:
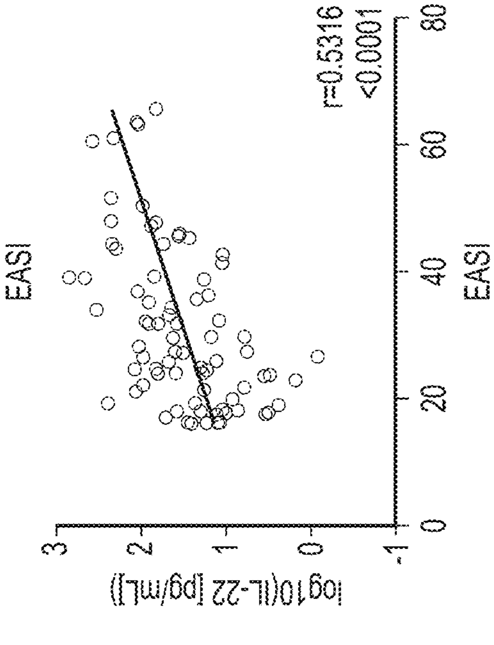
FIG. 37A-37C graphically depicts that IL-22 serum levels at baseline are correlated with disease severity. One-Way ANOVA with Tukey's multiple comparisons test Spearman correlation of IL-22 and EASI/SCORAD at baseline (n=78). IL-22 is significantly correlated with disease severity as measured by both EASI (FIG. 37A) and SCORAD (FIG. 37B) at baseline. IL-22 baseline levels are not significantly different between treatment groups (FIG. 37C).
Figure 37B:
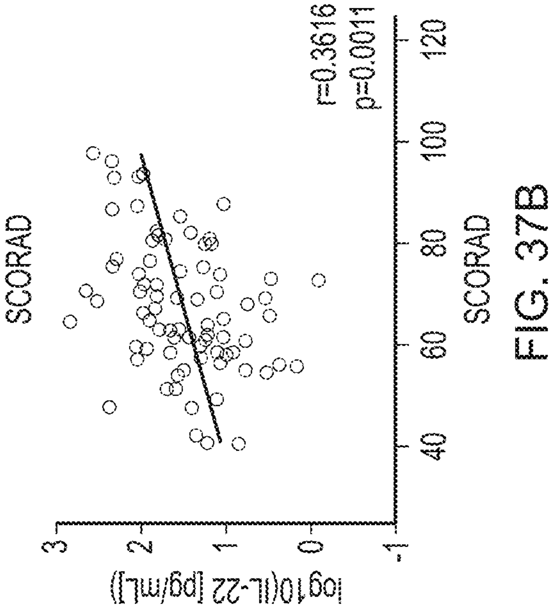
Figure 37C:
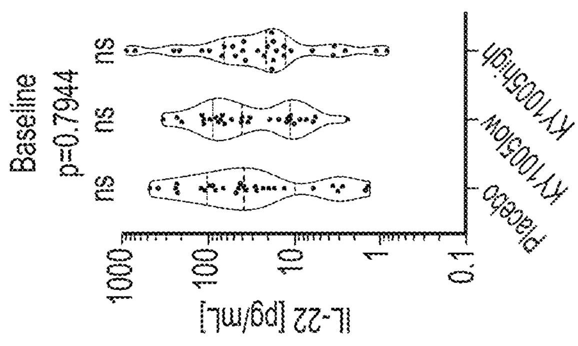
Figure 38:
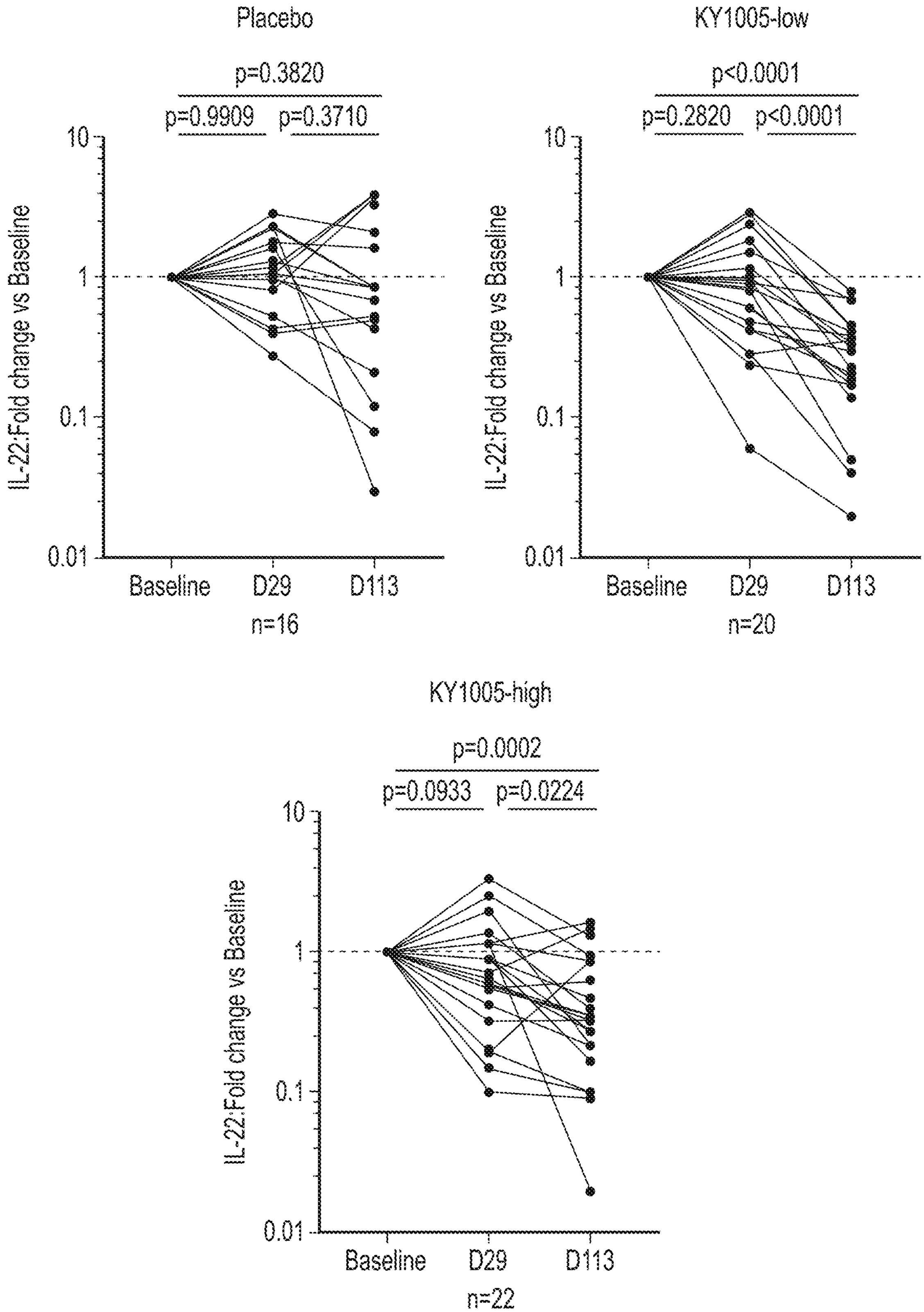
FIG. 38 graphically depicts circulating IL-22 in different treatment groups between baseline and D113. n=Number of patients with full set of samples up to D113. Two-way ANOVA+Tukey's multiple comparisons test. Significant change in IL-22 levels relative to baseline in KY1005-treated patients at D113 (and at D29 in KY1005-high-treated patients), but not in Placebo patients.
Figure 39A:
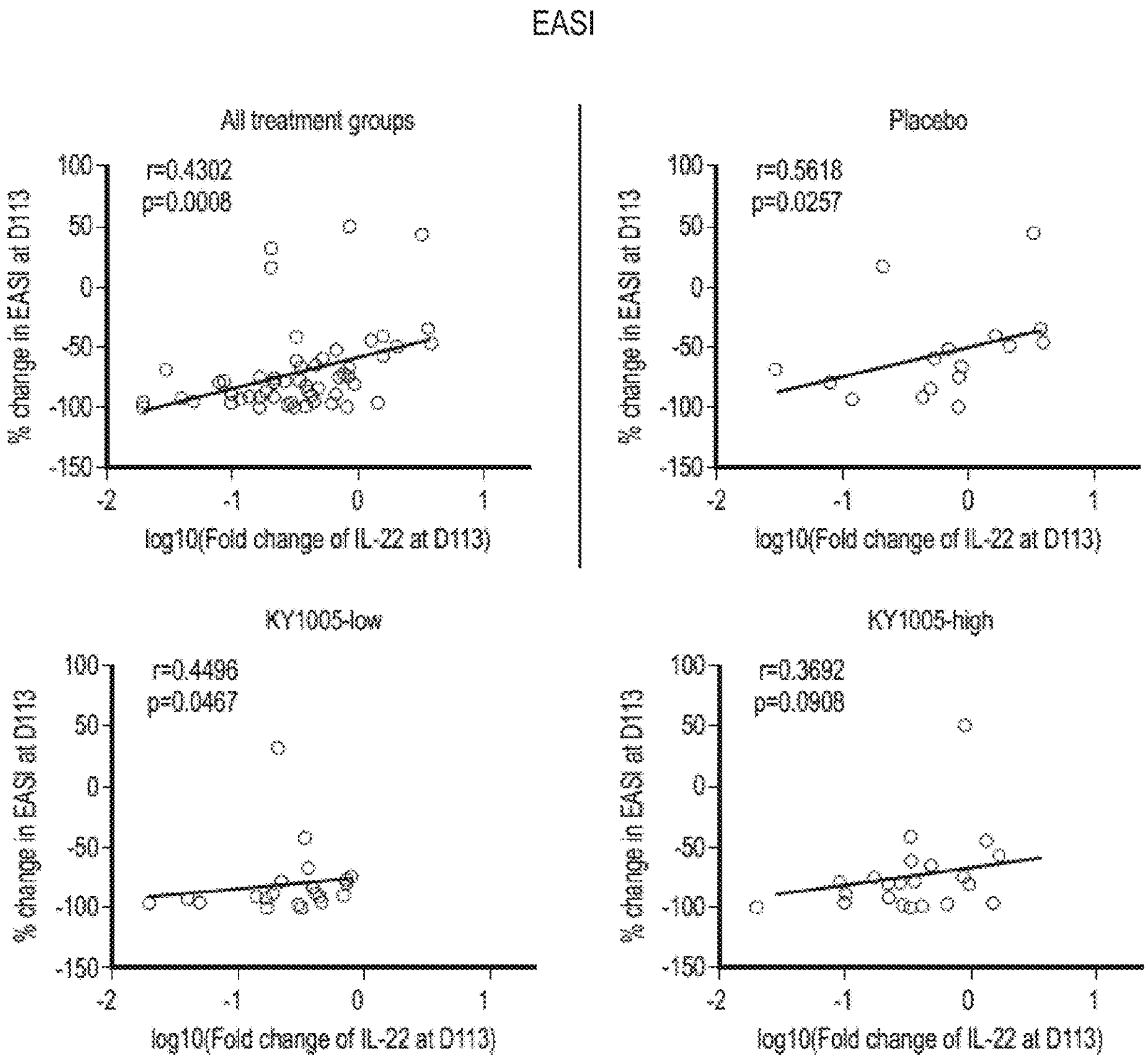
FIG. 39A-39B graphically depicts D113 vs baseline changes in IL-22 levels, illustrating that IL-22 levels are correlated with disease improvement. Only patients with full set of samples up to D113 included (n=58). Spearman correlation of fold change of IL-22 and EASI (FIG. 39A)/SCORAD(FIG. 39B) at D113. Weak correlations between changes in IL-22 and EASI (FIG. 39A) & SCORAD (FIG. 39A) disease improvement at D113.
Figure 39B:
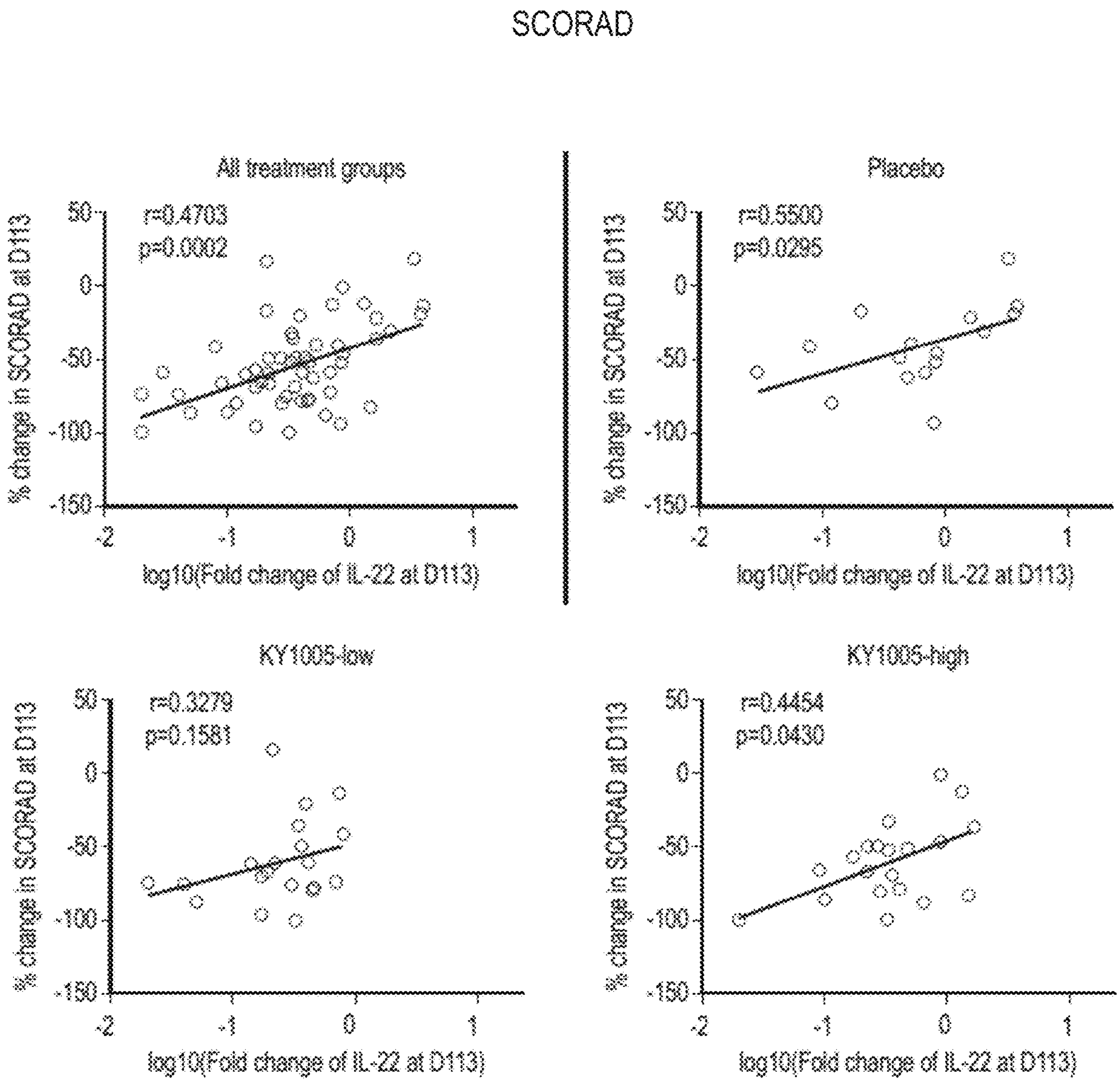
Figure 40:
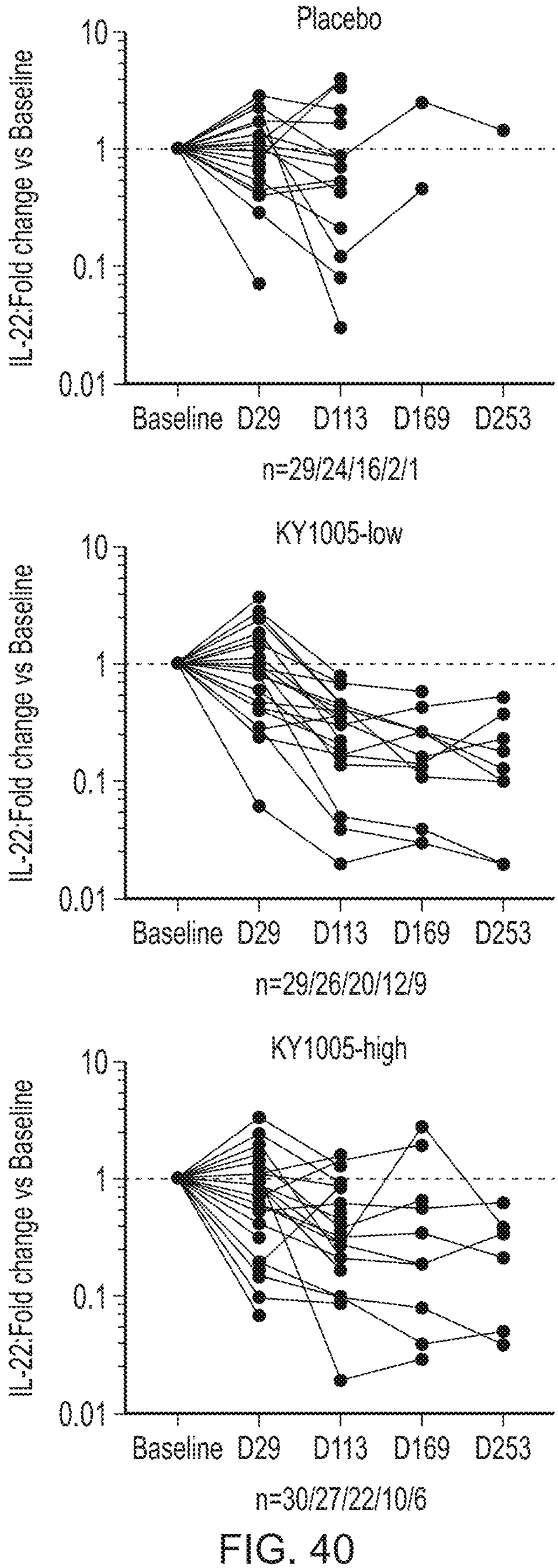
FIG. 40 graphically depicts that IL-22 serum level changes are maintained past D113 in vIGA 0/1 responders. 24 D169 samples and 16 evaluable D253 samples were obtained from 24 patients classified as responder at D113 (vIGA 0-1). In patients classified as responder at D113 (vIGA 0-1), IL-22 serum reduction was prolonged up to D169 and D253 for those treated with KY1005.

FIG. 31A-31B: Proteins associated with disease severity.

IL-22 and IL-13 protein levels were found to be significantly associated (FDR p-value <0.05) with EASI scores at baseline (first column). This association was also maintained at day 29 and day 113. The coefficient of determination R2 and p-values were calculated using linear models. Each dot represents a patient sample, the blue line represents the linear regression line, the 95% confidence interval is shown in grey. Linear modelling was performed between EASI scores and serum protein levels (EASI NPX). Analysis of baseline samples revealed a significant association (FDR p-value <0.05) between baseline EASI scores and serum levels of interleukin (IL)-22 and IL-13 (FIGS. 31A and 31B; Table 34).

When the sample size was increased by including all samples up to Day 113 in the analysis, IL-13, IL-22 and IL-17A were found to be significantly (FDR <0.05) associated with AD disease severity in our cohort (Table 35). Top hits of this second analysis again included IL-22 and IL-13, which were positively correlated with EASI severity scores at all timepoints (FIGS. 31A and 31B).

TABLE 34

IL-13 and IL-22 are associated with disease severity at Baseline

| ProteinID | Protein | Estimate | Unadj P | FDR |
|---|---|---|---|---|
| Simoa_IL22 | IL22 | 3.3603 | 1.10E−06 | 0.000289 |
| Simoa_IL13 | IL13 | 4.092481 | 0.000155 | 0.020401 |

Linear modelling (EASI~NPX) was performed between baseline EASI scores (EASI) and serum protein levels (NPX). Proteins with an FDR p-value < 0.05 are shown.

TABLE 35

IL-13, IL-22 and IL-17A are associated with disease severity at Baseline, Day 29 and Day 113

| ProteinID | Protein | Estimate | Unadj P | FDR |
|---|---|---|---|---|
| Simoa_IL22 | IL22 | 5.930553 | 7.17E−13 | 1.30E−10 |
| Simoa_IL13 | IL13 | 7.79846 | 9.88E−13 | 1.30E−10 |
| OID00485 | IL-17A | 9.815526 | 0.000145 | 0.001529 |

Linear modelling (EASI~NPX + SUBJID) was performed between serum protein levels at Baseline, Day 29 and Day 113 (NPX) and EASI scores at these timepoints (EASI). Proteins with an FDR p-value < 0.05 are shown.

KY1005-Induced Changes in Serum Protein Levels

To further investigate potential treatment effects of KY1005, temporal changes in protein levels at Day 113 from baseline in KY1005-treated patients were analysed. Based on this analysis, it was noted that proteins IL-13, IL-22, IL-17A and IL-31 were significantly changed at D113 upon KY1005 treatment (FDR p-value <0.05; Table 36; FIG. 32A-C and FIG. 42).

TABLE 36

IL-13, IL-22, IL-17A and IL-31 are reduced upon KY1005 and Placebo treatment

| | | | KY1005 | | | Placebo | |
|---|---|---|---|---|---|---|---|
| ProteinID | Protein | Estimate | Unadj P | FDR | Estimate | Unadj P | FDR |
| Simoa_IL13 | IL13 | −1.37953 | 5.70E−10 | 7.52E−08 | −0.71307 | 0.061703 | 0.191642 |
| Simoa_IL22 | IL22 | −1.81296 | 3.82E−10 | 7.52E−08 | −0.69007 | 0.191019 | 0.327462 |
| OID00485 | IL-17A | −0.37636 | 0.000405 | 0.00668 | −0.236 | 0.223961 | 0.353614 |
| Simoa_IL31 | IL31 | −1.78224 | 6.32E−07 | 2.39E−05 | −0.31386 | 0.541913 | 0.656261 |

Statistical analysis of changes in KY1005-treated and Placebo patients at days 29 and 113 compared to baseline were performed. The proteins had changed at Day 113 compared to baseline with an unadj. p-value <0.05 in KY1005 and Placebo patients.

IqE Changes Upon KY1005 Treatment

As part of KY1005-CT02 (NCT03754309), serum levels of immunoglobulins class E (IgEs) were quantified. Serum samples were assayed on a COBAS Modular Analytics E170 using a Elecsys IgE II kit (catalogue number 04827031-190) following the manufacturer's instructions.

IgE levels were homogeneously distributed among the treatment groups, without any significant difference among groups. The plot also confirmed that, as reported in literature, moderate to severe AD patients show higher than normal IgE levels, with ~88% of the patients with IgE levels above 100 IU/mL in our cohort. A weak but significant correlation between IgE levels and EASI score was observed.

IgE levels were plotted at baseline, day 29 and day 113 (primary endpoint) grouped by treatment, in order to compare the two KY1005 doses and placebo. Both KY1005 doses induced a significant decrease in circulating IgE levels at day 113, and for the KY1005 low group, a significant decrease in IgE was already apparent at day 29.

Finally, the persistence of the KY1005-dependent reduction in IgE levels in the follow-up period was assessed (time-points: day 29, 113, 169 and 253) and the raw IgE values for all the available time-points (baseline, day 29, 113, 169 and 253 or baseline, week 4, week 16, week 24 and week 36) were plotted per every treatment arm. As shown in FIG. 41(A), the patients treated with KY1005 showed a persisting reduction in IgE levels achieved during the active period of the trial, and this was evident both when plotting the fold-changes from baseline and the raw IgE values.

In addition, KY1005-treated patients that were considered responders (vIGA 0-1) at Day113 demonstrated a significant reduction in IgE levels (vs baseline) by day 113 which continued to decrease up to day 253. Non-responders also demonstrated a decrease in IgE levels in response to KY1005 at day 113 (albeit less significant than responders). The decrease in IgE levels did not significantly correlate with improved clinical score in the cohort.

Effect of Amlitelimab on Serum Biomarkers (Total IQE. IL-13, IL-22 and IL-31)

Figure 41:
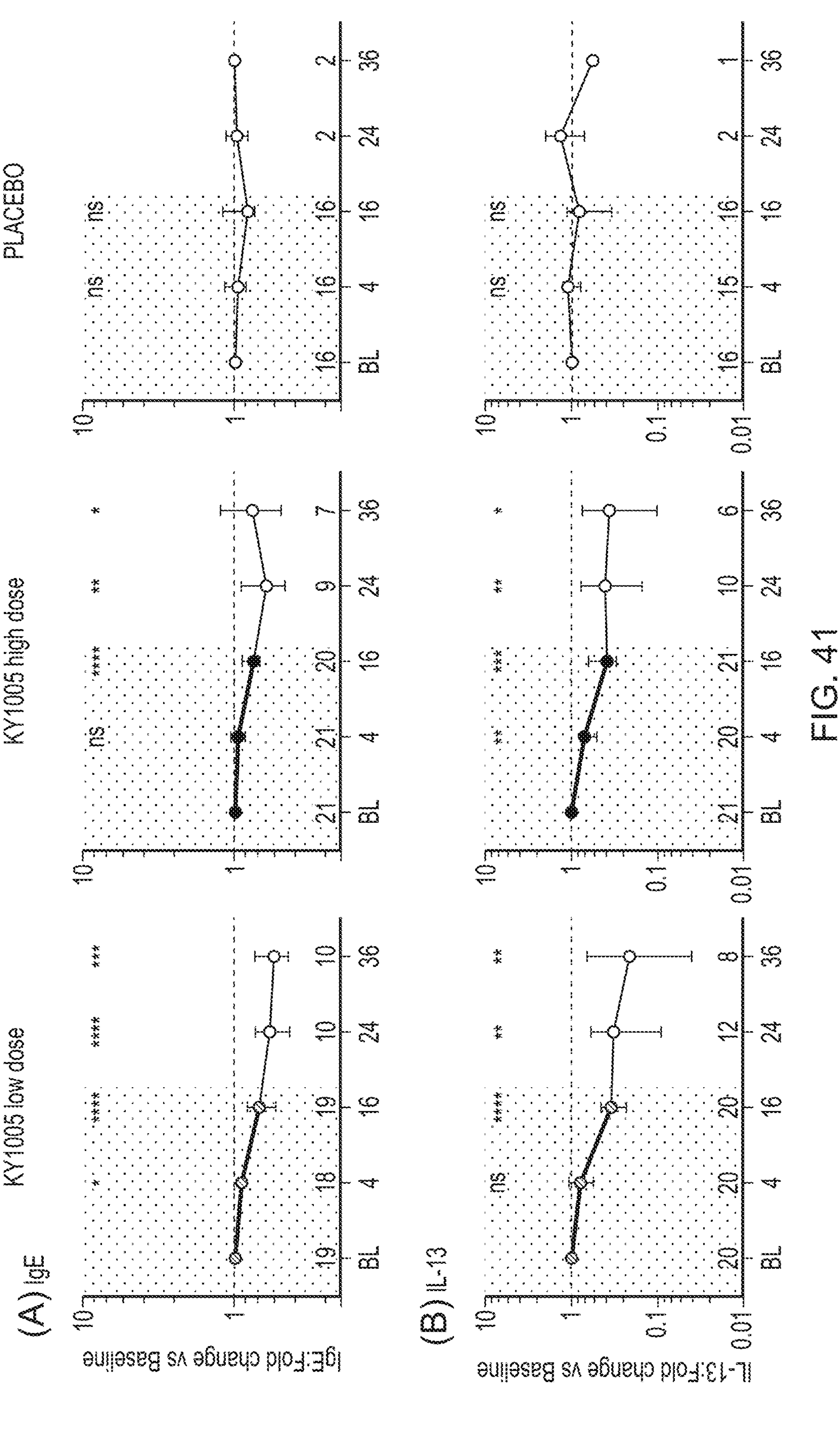
FIG. 41 graphically depicts the effect of Amlitelimab on serum biomarkers (total IgE, IL-13, IL-22 and IL-31). Fold change from baseline in serum (A) IgE, (B) IL-13, (C) IL-22 and (D) IL-31 over time by treatment regimen. Up to week 16, all patients with biomarker data at baseline and week 16 or at least two alternative on-treatment timepoints were included. For the study extension, only patients who achieved vIGA0/1 at week 16 (w16 responders) were included. Post-hoc linear mixed-effects model with Dunnett's multiple comparison test for log 10-transformed fold change from baseline by treatment regimen (ns not significant, * $p<0.05$,  p,0.01, * $p<0.001$, **** $p<0.0001$). Median +95% confidence interval; sample size displayed above x-axis.
Figure 41:
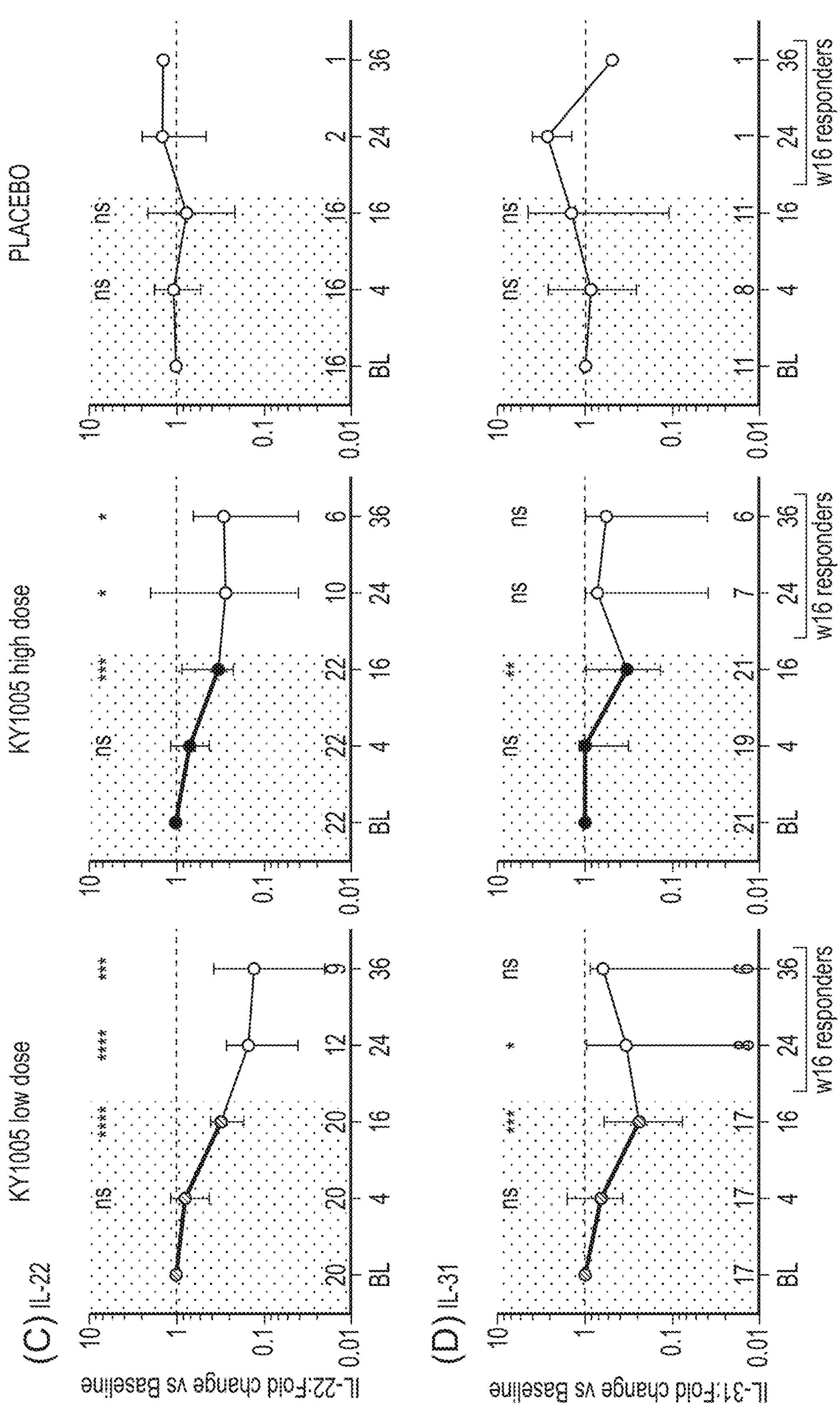
Figure 42:
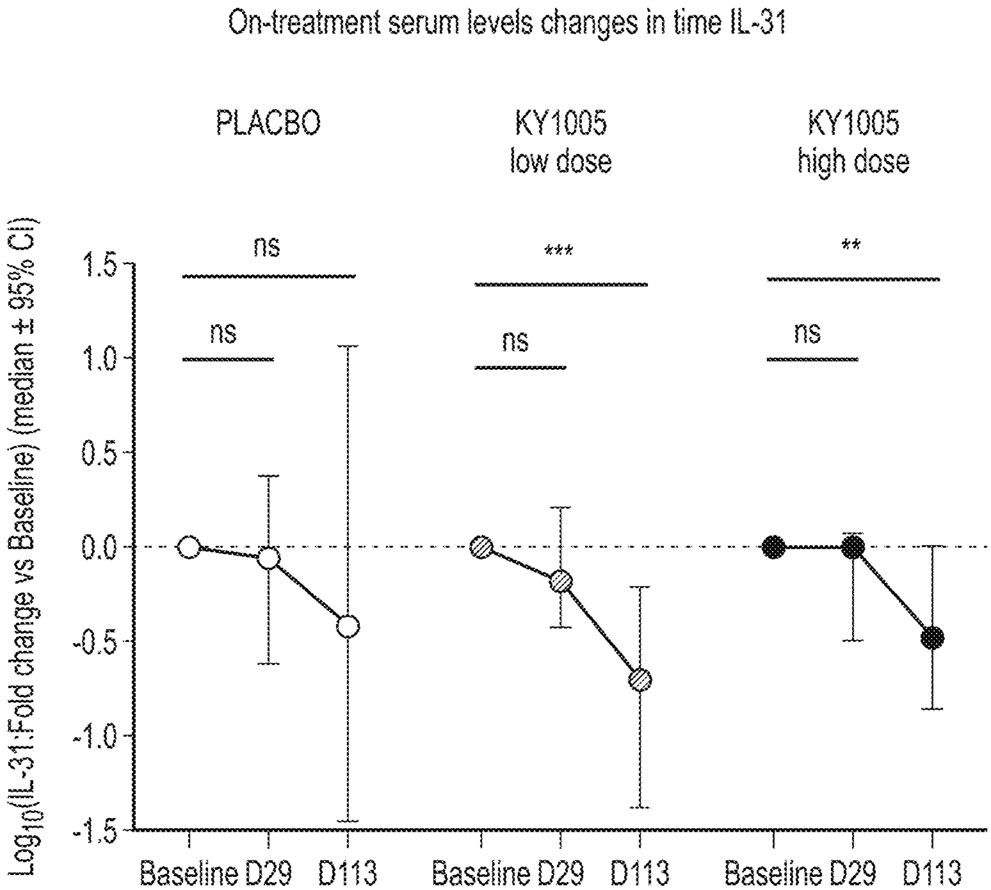
FIG. 42 graphically depicts on-treatment IL-31 serum levels changes in time.

Fold change from baseline in serum (A) IgE, (B) IL-13, (C) IL-22 and (D) IL-31 over time by treatment regimen is shown in FIG. 41. Up to week 16, all patients with biomarker data at baseline and week 16 or at least two alternative on-treatment timepoints were included. For the study extension, only patients who achieved vIGA0/1 at week 16 (w16 responders) were included. Post-hoc linear mixed-effects model with Dunnett's multiple comparison test for log 10-transformed fold change from baseline by treatment regimen (ns not significant, * p<0.05,  p,0.01, * p<0.001, **** p<0.0001). Median+95% confidence interval; sample size displayed above x-axis.

Unlike placebo, KY1005 led to a significant decrease in IgE, IL-13 and IL-22 serum concentrations at D113, which was maintained until D253.

Conclusion

Serum levels of IL-13, IL-22, IL-31 and IL-17A were quantified in all patients at Baseline, Days 29, 113, 169 and 253 using a combination of Olink and Simoa technology.

A significant positive correlation between baseline IL 13 and IL 22 levels and clinical score (EASI/SCORAD) was demonstrated. A positive correlation between the decrease in IL13/IL 22 levels and decrease in clinical score at D 113 was demonstrated. In addition, a significant and specific reduction (vs baseline) in circulating IL 13/IL 22 at D 113 in response to KY 1005 was observed. Levels of IL 13/IL 22 remain low up to D 253 for KY 1005 treated patients.

Correlations between serum markers of AD and AD disease severity could be observed. Using linear modelling of EASI scores with serum protein levels, a significant association between disease severity and up to IL-13, IL-22, IL-17A across multiple time points could be demonstrated. These proteins positively correlated with disease severity not only at baseline, but also at later timepoints. When treatment-induced changes in serum protein levels upon KY1005 and Placebo treatment at Day 113 were assessed IL-13, IL-22 and IL-17A were found to be significantly changed upon KY1005 treatment. These proteins were found to be affected by KY1005, but not Placebo treatment, suggesting that these proteins are specifically affected by KY1005.

KY1005 treatment, both low and high doses, induced a significant drop in IgE levels, which was already observable for both treatments at day 29 (and statistically significant for KY1005 low dose) and was significant for both KY1005 treatment groups at day 113.

In addition, KY1005-treated patients that were considered responders (vIGA 0-1) at Day113 demonstrated a significant reduction in IgE levels (vs baseline) by day 113 which continued to decrease up to day 253. Reduction in IgE levels is associated with KY1005 treatment. IgE levels may serve as a response biomarker to KY1005 treatment.

SEQUENCE LISTING

| SEQ ID NO: | | | |
|---|---|---|---|
| 1 | 10A07 | VH Nucleotide Sequence | GAGCTGCAACTGCTGGACTCTGGGGGAGTCTTGCT ACAGCCGGGGGGCTCCCTGAGACTCTCCTCTGCAG CCTCTGGATTCACCTTTAGCAGTTATATTATGACT TGGGTCCGCCAGGCTCCAGGGAAGGGGCTGGAGTG GGTCTCAGCTATTACTGCTACTGCTGCTGCTACAT ACTACGCAGACTCCATGAAGGGCCGGTTCACCATC TCCAGAGACAATTCCAAGAACACGCTCTATCTGCA GATGAACAGCCTGAGAGTCGAGGACACGGCCCTAT ATTACTGTGCGAAAGATCGGTTAGGTCCGATTACT TTGGTTCGGGGGGGCTATTACTACGGTATGGACCT CTGGGGCCAAGGGACCACGGTCACCGTCTCCTCA |
| 2 | | VH Amino Acid Sequence | EVQLVESGGVLVQPGGSLRLSCAASGFTFSSYIMT WVRQAPGKGLEWVSGISGSGGGTYYADSMKGRFTI SRDNSKNTLYLQMNSLRVEDTAVYYCAKDRLGPIT LVRGGYYYGMDVWGQGTTVTVSS |
| 3 | | HCDR1 Nucleotide Sequence (IMCT) | GGATTCACCTTTAGCAGTTATATT |
| 4 | | HCDR1 Amino Acid Sequence (IMGT) | GFTFSSYI |
| 5 | | HCDR2 Nucleotide Sequence (IMGT) | ATTAGTGGTAGTGGTGGTGGTACA |
| 6 | | HCDR2 Amino Acid Sequence (IMGT) | ISGSGGGT |
| 7 | | HCDR3 Nucleotide Sequence (IMGT) | GCGAAAGATCGGTTAGGTCCGATTACTTTGGTTCG GGGGGGCTATTACTACGGTATGGACGTC |

-continued

| SEQUENCE LISTING | | |
|---|---|---|
| SEQ ID NO: | | |
| 8 | HCDR3 Amino Acid Sequence (IMGT) | AKDRLGPTTLVRGGYYYGMDV |
| 9 | HCDR1 Nucleotide Sequence (KABAT) | AGTTATATTATGACT |
| 10 | HCDR1 Amino Acid Sequence (KABAT) | SYIMT |
| 11 | HCDR2 Nucleotide Sequence (KABAT) | GCTATTAGTGGTACTGGTGGTGGTACATACTACGC AGACTCCATGAAGGGC |
| 12 | HCDR2 Amino Acid Sequence (KABAT) | GISGSGGGTYYADSMKG |
| 13 | HCDR3 Nucleotide Sequence (KABAT) | GATCGGTTAGCTCCGATTACTTTGGTTCGGGGGGG CTATTACTACGGTATGGACCTC |
| 14 | HCDR3 Amino Acid Sequence (KABAT) | DRLGPTTLVRGGYYYGMDV |
| 15 | VL Nucleotide Sequence | GACATCCAGATGACCCACTCTCCATCCTCCCTCTC TGCATCTCTAGGAGACAGAGTCACCATCACTTGCC GGGCAACTCAGAGCATTAGCGACTATTTAAATTGG TATCAGCAGAAACCAGGGAAAGCCCCTAAGTTCCT GATCTATGCTGCATCCAGTTTGCAAAGTGGAGTCC CATCAAGGTTCAGTGGCAGTGGATCTGGGACAGAT TTCACTCTCACCGTCAGCAGTCTGCAACCTGAAGA TTTTGCAACTTACTACTGTCAACAGAGTTACAGTA CCCCTCGGACGTTCGGCCAAGGGACCAGGGTGGAA ATCAAA |
| 16 | VL Amino Acid Sequence | DIQMTQSPSSLSASVGDRVTITCRASQSISDYLNW YQQKPGKAPKFLIYAASSLQSGVPSRFSGSGSGTD FTLTVSSLQPEDFATYYCQQSYSTPRTFGQGTRVE IK |
| 17 | LCDR1 Nucleotide Sequence (IMGT) | CAGAGCATTAGCGACTAT |
| 18 | LCDR1 Amino Acid Sequence (IMGT) | QSISDY |
| 19 | LCDR2 Nucleotide Sequence (IMGT) | GCTGCATCC |
| 20 | LCDR2 Amino Acid Sequence (IMGT) | AAS |
| 21 | LCDR3 Nucleotide Sequence (IMGT) | CAACAGAGTTACAGTACCCCTCGGACG |
| 22 | LCDR3 Amino Acid Sequence (IMGT) | QQSYSTPRT |
| 23 | LCDR1 Nucleotide Sequence (KABAT) | CGGGCAAGTCAGAGCATTAGCGACTATTTAAAT |
| 24 | LCDR1 Amino Acid Sequence (KABAT) | RASQSISDYLN |
| 25 | LCDR2 Nucleotide Sequence (KABAT) | GCTGCATCCAGTTTGCAAAGT |
| 26 | LCDR2 Amino Acid Sequence (KABAT) | AASSLQS |
| 27 | LCDR3 Nucleotide Sequence (KABAT) | CAACAGAGTTACAGTACCCCTCGGACG |
| 28 | LCDR3 Amino Acid Sequence (KABAT) | QQSYSTPRT |

-continued

SEQUENCE LISTING

| SEQ ID NO: | | |
|---|---|---|
| 29 | Heavy Chain Nucleotide Sequence | GAGGTCCAGCTCGTGGAAAGCGGAGGAGTGCTCGT GCAGCCTGGAGGCAGCCTCAGGCTGTCCTGTGCCG CCTCCGGCTTCACCTTCAGCAGCTACATCATGACC TGGGTGAGGCAGGCTCCCGGAAAAGGCCTGGAGTG GGTGTCCGGCATCTCCGGATCCGGAGGAGGCACAT ACTACGCCGACAGCATGAAGGGCCGGTTCACCATC AGCCGGGACAATAGCAAGAATACCCTCTACCTGCA AATGAACAGCCTGCGGGTGGAGGATACCGCCGTGT ACTACTGCGCCAAAGATAGGCTGGGCCCCATTACC CTCGTGAGGGGAGGCTATTACTACGGCATGGATGT GTGGGGCCAGGGCACCACCGTGACAGTGTCCAGCG CCAGCACCAAGGGCCCTTCCGTGTTCCCCCTGGCC CCTTGCAGCAGGAGCACCTCCGAATCCACAGCTGC CCTGGGCTGTCTGGTGAAGGACTACTTTCCCGAGC CCGTGACCGTGAGCTGGAACAGCGGCGCTCTGACA TCCGGCGTCCACACCTTTCCTGCCGTCCTGCAGTC CTCCGGCCTCTACTCCCTGTCCTCCGTGGTGACCG TGCCTAGCTCCTCCCTCGGCACCAAGACCTACACC TGTAACGTGGACCACAAACCCTCCAACACCAAGGT GGACAAACGGGTCGAGA GCAAGTACGGCCCTCCCTGCCCTCCTTGTCCTGCC CCCGAGTTCGAAGGCGGACCCAGCGTGTTCCTGTT CCCTCCTAAGCCCAAGGACACCCTCATGATCAGCC GGACACCCGAGGTGACCTGCGTGGTGGTGGATGTG AGCCAGGAGGACCCTGAGGTCCAGTTCAACTGGTA TGTGGATGGCGTGGAGGTGCACAACGCCAAGACAA AGCCCCGGGAAGAGCAGTTCAACTCCACCTACAGG GTGGTCAGCGTGCTGACCGTGCTGCATCAGGACTG GCTGAACGGCAAGGAGTACAAGTGCAAGGTCAGCA ATAAGGGACTGCCCAGCAGCATCGAGAAGACCATC TCCAAGGCTAAAGGCCAGCCCCGGGAACCTCAGGT GTACACCCTGCCTCCCAGCCAGGAGGAGATGACCA AGAACCAGGTGAGCCTGACCTGCCTGGTGAAGGGA TTCTACCCTTCCGACATCGCCGTGGAGTGGGAGTC CAACGGCCAGCCCGAGAACAATTATAAGACCACCC CTCCCGTCCTCGACAGCGACGGATCCTTCTTTCTG TACTCCAGGCTGACCGTGGATAAGTCCAGGTGGCA GGAAGGCAACGTGTTCAGCTGCTCCGTGATGCACG AGGCCCTGCACAATCACTACACCCAGAAGTCCCTG AGCCTGTCCCTGGGAAAG |
| 30 | Heavy Chain Amino Acid Sequence | EVQLVESGGVLVQPGGSLRLSCAASGFTFSSYIMT WVRQAPGKGLEWVSGISGSGGGTYYADSMKGRFTI SRDNSKNTLYLQMNSLRVEDTAVYYCAKDRLGPIT LVRGGYYYGMDVWGQGTTVTVSSASTKGPSVFPLA PCSRSTSESTAALGCLVKDYFPEPVTVSWNSGALT SGVHTFPAVLQSSGLYSLSSVVTVPSSSLGTKTYT CNVDHKPSNTKVDKRVESKYGPPCPPCPAPEFEGG PSVFLFPPKPKDTLMISRTPEVTCVVVDVSQEDPE VQFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLGK |
| 31 | Light Chain Nucleotide Sequence | GACATCCAGATGACCCAGTCCCCTTCCTCCCTGTC CGCCTCCGTGGGAGACAGGGTGACCATCACCTGCC GGGCCAGCCAGTCCATCAGCGACTACCTGAACTGG TATCAGCAGAAGCCCGGCAAGGCCCCTAAGTTCCT GATCTACGCCGCTTCCTCCCTGCAGTCCGGAGTGC CCAGCAGGTTTTCCGGCTCCGGATCCGGCACCGAC TTCACCCTGACCGTGTCCAGCCTGCAGCCCGAGGA CTTCGCCACCTACTACTGCCAGCAGAGCTACAGCA CCCCCAGGACATTTGGCCAGGGCACCCGGGTGGAG ATCAAGAGGACCGTCGCTGCCCCCTCCGTGTTTAT CTTCCCCCCCAGCGACGAGCAGCTGAAATCCGGCA CCGCCTCCGTGGTCTGCCTGCTGAATAACTTCTAC CCTCGGGAGGCCAAGGTGCAGTGGAAGGTGGACAA CGCCCTGCAGAGCGGAAACTCCCAGGAGAGCGTGA CCGAGCAGGACTCCAAGGACTCCACATACTCCCTG TCCTCCACCCTGACACTGTCCAAGGCCGATTACGA GAAGCACAAGGTGTACGCCTGCGAGGTGACCCACC |

-continued

| SEQUENCE LISTING | | |
|---|---|---|
| SEQ ID NO: | | |
| | | AGGGACTGTCCTCCCCCGTGACCAAGTCCTTCAAC CGGGGCGAGTGC |
| 32 | Light Chain Amino Acid Sequence | DIQMTQSPSSLSASVGDRVTITCRASQSISDYLNW YQQKPGKAPKFLIYAASSLQSGVPSRFSGSGSGTD FTLTVSSLQPEDFATYYCQQSYSTPRTFGQGTRVE IKRTVAAPSVFIFPPSDEQLKSGTASWCLLNNFYP REAKVQWKVDNALQSGNSQESVTEQDSKDSTYSLS STLTLSKADYEKHKVYACEVTHQGLSSPVTKSFNR GEC |
| 33 02D10 | VH Nucleotide Sequence | GAGGTGCAGTTGGTGGAGTCTGGGGGAGGCTTGGT ACAGCCTGGGGGGTCCCTGAGACTCTCCTGTGCAG CCTCTGGATTCACTTTTAGCAACTATGCCATGAAC TGGGTCCGCCAGGCTCCAGGGAAGGGGCTGGAGTG GGTCTCAACTATTAGCGGAAGTGGTGGTGCCACAA GGTATGCAGACTCCGTGAAGGGCCGATTCACCATA TCCAGAGACAATTCCAGGAACACGGTGTATCTGCA AATGAACAGCCTGAGAGTCGAGGACACGGCCGTTT TTTACTGTACGAAAGATCGGCTCATTATGGCTACG GTTCGGGGACCCTATTACTACGGTATGGACGTCTG GGGCCAAGGGACCACGGTCACCGTCTCCTCA |
| 34 | VH Amino Acid Sequence | EVQLVESGGGLVQPGGSLRLSCAASGFTFSNYAMN WVRQAPGKGLEWVSTISGSGGATRYADSVKGRFTI SRDNSRNTVYLQMNSLRVEDTAVFYCTKDRLIMAT VRGPYYYGMDVWGQGTTVTVSS |
| 35 | HCDR1 Nucleotide Sequence (IMGT) | GGATTCACTTTTAGCAACTATGCC |
| 36 | HCDR1 Amino Acid Sequence (IMGT) | GFTFSNYA |
| 37 | HCDR2 Nucleotide Sequence (IMGT) | ATTAGCGGAAGTGGTGGTGCCACA |
| 38 | HCDR2 Amino Acid Sequence (IMGT) | ISGSGGAT |
| 39 | HCDR3 Nucleotide Sequence (IMGT) | ACGAAAGATCGGCTCATTATGGCTACGGTTCGGGG ACCCTATTACTACGGTATGGACGTC |
| 40 | HCDR3 Amino Acid Sequence (IMGT) | TKDRLIMATVRGPYYYGMDV |
| 41 | HCDR1 Nucleotide Sequence (KABAT) | AACTATGCCATGAAC |
| 42 | HCDR1 Amino Acid Sequence (KABAT) | NYAMN |
| 43 | HCDR2 Nucleotide Sequence (KABAT) | ACTATTAGCGGAAGTGGTGGTGCCACAAGGTATGC AGACTCCGTGAAGGGC |
| 44 | HCDR2 Amino Acid Sequence (KABAT) | TISGSGGATRYADSVKG |
| 45 | HCDR3 Nucleotide Sequence (KABAT) | GATCGGCTCATTATGGCTACGGiTTCGGGGACCCT ATTACTACGGTATGGACGTC |
| 46 | HCDR3 Amino Acid Sequence (KABAT) | DRLIMATVRGPYYYGMDV |
| 47 | VL Nucleotide Sequence | GACATCCAGATGACCCAGTCTCCATCCTCCCTGTC TGCATCTGTAGGAGACAGAGTCACCATCACTTGCC GGGCAAGTCAGAGCATTAGCAGCTATTTAAATTGG TATCAGCAGAAACCAGGGAAAGCCCCTAACCTCCT GATCTATGCTGCATCCAGTTTGCAAAGTGGGGTCC CATCAAGGTTCAGTGGCAGTGGATCTGAGACAGAT TTCACTCTCACCATCAGCAGTCTGCAACCTGAAGA TTTTGCAACTTACTACTGTCAACAGAGTCACAGTG |

-continued

| SEQUENCE LISTING | | |
|---|---|---|
| SEQ ID NO: | | |
| | | TCTCATTCACTTTCGGCCCTGGGACCAAAGTGGAT ATCAAA |
| 48 | VL Amino Acid Sequence | DIQMTQSPSSLSASVGDRVTITCRASQSISSYLNW YQQKPGKAPNLLIYAASSLQSGVPSRFSGSGSETD FTLTISSLQPEDFATYYCQQSHSVSFTFGPGTKVD IK |
| 49 | LCDR1 Nucleotide Sequence (IMGT) | CAGAGCATTAGCAGCTAT |
| 50 | LCDR1 Amino Acid Sequence (IMGT) | QSISSY |
| 51 | LCDR2 Nucleotide Sequence (IMGT) | GCTGCATCC |
| 52 | LCDR2 Amino Acid Sequence (IMGT) | AAS |
| 53 | LCDR3 Nucleotide Sequence (IMGT) | CAACAGAGTCACAGTGTCTCATTCACT |
| 54 | LCDR3 Amino Acid Sequence (IMGT) | QQSHSVSFT |
| 55 | LCDR1 Nucleotide Sequence (KABAT) | CGGGCAAGTCAGAGCATTAGCAGCTATTTAAAT |
| 56 | LCDR1 Amino Acid Sequence (KABAT) | RASQSISSYLN |
| 57 | LCDR2 Nucleotide Sequence (KABAT) | GCTGCATCCAGTTTGCAAAGT |
| 58 | LCDR2 Amino Acid Sequence (KABAT) | AASSLQS |
| 59 | LCDR3 Nucleotide Sequence (KABAT) | CAACAGAGTCACAGTGTCTCATTCACT |
| 60 | LCDR3 Amino Acid Sequence (KABAT) | QQSHSVSFT |
| 61 | Heavy Chain Nucleotide Sequence | GAAGTGCAACTGGTGGAGTCCGGAGGAGGCCTGGT GCAGCCTGGAGGAAGCCTGAGGCTGAGCTGTGCCG CCAGCGGCTTCACCTTCAGCAACTACGCCATGAAC TGGGTGAGGCAGGCCCCTGGCAAGGGACTGGAGTG GGTCTCCACCATCAGCGGCTCCGGAGGCGCTACAC GGTACGCCGATAGCGTGAAGGGCCGGTTTACCATT TCCCGGGACAACTCCCGGAACACCGTGTACCTCCA GATGAACAGCCTGAGGGTGGAGGATACCGCCGTGT TCTACTGCACCAAGGACAGGCTGATTATGGCCACC GTGAGGGGACCTTACTACTATGGCATGGATGTGTG GGGCCAGGGCACAACCGTCACCGTGTCCTCCGCCT CCACCAAGGGACCTAGCGTGTTCCCTCTCGCCCCC TGTTCCAGGTCCACAAGCGAGTCCACCGCTGCCCT CGGCTGTCTGGTGAAAGACTACTTTCCCGAGCCCG TGACCGTCTCCTGGAATAGCGGAGCCCTGACCTCC GGCGTGCACACATTTCCCGCCGTGCTGCAGAGCAG CGGACTGTATAGCCTGAGCAGCGTGGTGACCGTGC CCAGCTCCAGCCTCGGCACCAAAACCTACACCTGC AACGTGGACCACAAGCCCTCCAACACCAAGGTGGA CAAGCGGGTGGAGAGCAAGTACGGCCCCCCTTGCC CTCCTTGTCCTGCCCCTGAGTTCGAGGGAGGACCC TCCGTGTTCCTGTTTCCCCCCAAACCCAAGGACAC CCTGATGATCTCCCGGACACCCGAGGTGACCTGTG TGGTCGTGGACGTCAGCCAGGAGGACCCCGAGGTG CAGTTCAACTGGTATGTGGACGGCGTGGAGGTGCA CAATGCCAAAACCAAGCCCAGGGAGGAGCAGTTCA ATTCCACCTACAGGGTGGTGAGCGTGCTGACCGTC CTGCATCAGGATTGGCTGAACGGCAAGGAGTACAA GTGCAAGGTGTCCAACAAGGGACTGCCCAGCTCCA |

-continued

| SEQUENCE LISTING | | | |
|---|---|---|---|
| SEQ ID NO: | | | |
| | | | TCGAGAAGACCATCAGCAAGGCTAAGGGCCAGCCG AGGGAGCCCCAGGTGTATACCCTGCCTCCTAGCCA GGAAGAGATGACCAAGAACCAAGTGTCCCTGACCT GCCTGGTGAAGGGATTCTACCCCTCCGACATCGCC GTGGAGTGGGAGAGCAATGGCCAGCCCGAGAACAA CTACAAAACAACCCCTCCCGTGCTCGATAGCGACG GCAGCTTCTTTCTCTACAGCCGGCTGACAGTGGAC AAGAGCAGGTGGCAGGAGGGCAACGTGTTCTCCTG TTCCGTGATGCACGAGGCCCTGCACAATCACTACA CCCAGAAGAGCCTCTCCCTGTCCCTGGGCAAG |
| 62 | | Heavy Chain Amino Acid Sequence | EVQLVESGGGLVQPGGSLRLSCAASGFTFSNYAMN WVRQAPGKGLEWVSTISGSGGATRYADSVKGRFTI SRDNSRNTVYLQMNSLRVEDTAVFYCTKDRLIMAT VRGPYYYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFEGGP SVFLFPPKPKDTLMISRTPEVTCVWDVSQEDPEVQ FNWYVDGVEVHNAKTKPREEQFNSTYRVVSVLTVL HQDWLNGKEYKCKVSNKGLPSSIEKTISKAKGQPR EPQVYTLPPSQEEMTKNQVSLTCLVKGFYPSDIAV EWESNGQPENNYKTTPPVLDSDGSFFLYSRLTVDK SRWQEGNVFSCSVMHEALHNHYTQKSLSLSLGK |
| 63 | | Light Chain Nucleotide Sequence | GACATCCAGATGACCCAGTCCCCTTCCTCCCTGAG CGCTAGCGTGGGAGATAGGGTGACCATCACCTGCA GGGCCTCCCAAAGCATCTCCTCCTACCTGAACTGG TACCAGCAGAAACCCGGCAAGGCCCCCAACCTGCT GATCTACGCTGCCTCCTCCCTCCAGTCCGGCGTGC CTAGCAGGTTTAGCGGCTCCGGAAGCGAGACCGAC TTCACCCTGACCATCTCCTCCCTGCAGCCCGAGGA CTTCGCCACCTACTACTGCCAGCAATCCCACAGCG TGTCCTTCACCTTCGGCCCCGGCACCAAGGTGGAC ATCAAGAGGACCGTGGCCGCCCCCTCCGTGTTCAT CTTTCCCCCCTCCGATGAACAGCTGAAGAGCGGCA CCGCJAGCGTGGTGTGCCTGCTGAACAACTTCTAC CCCAGGGAGGCCAAGGTGCAGTGGAAGGTGGACAA TGCCCTGCAGTCCGGCAACAGCCAGGAGAGCGTGA CCGAGCAGGACTCCAAGGACAGCACCTACAGCCTG TCCTCCACCCTGACCCTGTCCAAGGCCGACTACGA GAAGCACAAAGTGTACGCCTGCGAAGTGACCCATC AGGGCCTGAGCTCCCCCGTGACCAAGTCCTTTAAC AGGGGCGAGTGC |
| 64 | | Light Chain Amino Acid Sequence | DIQMTQSPSSLSASVGDRVTITCRASQSISSYLNW YQQKPGKAPNLLIYAASSLQSGVPSRFSGSGSEID FILIISSLQPEDFATYYCQQSHSVSFTFGPGTKVD IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| 65 | 09H04 | VH Nucleotide Sequence | CAGGTGCAGCTGGTGGAGTCTGGGGGAGGCTTGGT CAAGCCTGGAGGGTCCCTGAGACTCTCCTGTGCAG CCTCTCGATTCACCCTCAGTGACTACTACATGACC TGGATCCGCCAGGCTCCAGGGAAGGGGCTGGAGTG GGTTTCATACATTAGTAGTAGTGGTAATACCATAT ACTACGCAGACTCTGTGAAGGGCCGATTCACCATC TCCAGGGACAACGCCAAGAACTCACTGTATCTGCA AATGAACAGCCTGAGAGCCGAGGACACGGCCGTGT ATTACTGTGCGAGAGATCTGAGTGGGAGCTACTGG GACTACTACTACGGTATGGACGTCTGGGGCCAAGG GACCACGGTCACCGTCTCCTCA |
| 66 | | VH Amino Acid Sequence | QVQLVESGGGLVKPGGSLRLSCAASRFTLSDYYMT WIRQAPGKGLEWVSYISSSGNTIYYADSVKGRFTI SRDNAKNSLYLQMNSLRAEDTAVYYCARDLSGSYW DYYYGMDVWGQGTTVTVSS |
| 67 | | HCDR1 Nucleotide Sequence (IMGT) | CGATTCACCCTCAGTGACTACTAC |

-continued

SEQUENCE LISTING

| SEQ ID NO: | | |
|---|---|---|
| 68 | HCDR1 Amino Acid Sequence (IMGT) | RFTLSDYY |
| 69 | HCDR2 Nucleotide Sequence (IMGT) | ATTAGTAGTAGTGGTAATACCATA |
| 70 | HCDR2 Amino Acid Sequence (IMGT) | ISSSGNTI |
| 71 | HCDR3 Nucleotide Sequence (IMGT) | GCGAGAGATCTGAGTGGGAGCTACTGGGACTACTA CTACGGTATGGACGTC |
| 72 | HCDR3 Amino Acid Sequence (IMGT) | ARDLSGSYWDYYYGMDV |
| 73 | HCDR1 Nucleotide Sequence (KABAT) | GACTACTACATGACC |
| 74 | HCDR1 Amino Acid Sequence (KABAT) | DYYMT |
| 75 | HCDR2 Nucleotide Sequence (KABAT) | TACATTAGTAGTAGTGGTAATACCATATACTACGC AGACTCTGTGAAGGGC |
| 76 | HCDR2 Amino Acid Sequence (KABAT) | YISSSGNTIYYADSVKG |
| 77 | HCDR3 Nucleotide Sequence (KABAT) | GATCTGAGTGGGAGCTACTGGGACTACTACTACGG TATGGACGTC |
| 78 | HCDR3 Amino Acid Sequence (KABAT) | DLSGSYWDYYYGMDV |
| 79 | VL Nucleotide Sequence | GCCATCCAGTTGACCCAGTCTCCATCCTCCCTGTC TACATCTGTAGGAGACAGAGTCACCATCGCTTGCC GGGCAAGTCAGGGCATTAACAATGCTTTAGCCTGG TATCAGCAGAAACCAGGGAAAGCTCCTAAGCTCCT GATCTATGATGCCTCCAGTTTGGAAAGTGGGGTCC CATCAAGGTTCAGCGGCAGTGGATCTGGGACAGAT TTCACTCTCACCATCAGCAGCCTGCAGCCTGAAGA lTTTGCAACTTATTACTGTCAACAGTTTAATAGTT ACCCTCGGACGTTCGGCCAAGGGACCAAGGTGGAA ATCAAA |
| 80 | VL Amino Acid Sequence | AIQLTQSPSSLSTSVGDRVTIACRASQGINNALAW YQQKPGKAPKLLIYDASSLESGVPSRFSGSGSGTD FTLTISSLQPEDFATYYCQQFNSYPRTFGQGTKVE IK |
| 81 | LCDR1 Nucleotide Sequence (IMGT) | CAGGGCATTAACAATGCT |
| 82 | LCDR1 Amino Acid Sequence (IMGT) | QGINNA |
| 83 | LCDR2 Nucleotide Sequence (IMGT) | GATGCCTCC |
| 84 | LCDR2 Amino Acid Sequence (IMGT) | DAS |
| 85 | LCDR3 Nucleotide Sequence (IMGT) | CAACAGTTTAATAGTTACCCTCGGACG |
| 86 | LCDR3 Amino Acid Sequence (IMGT) | QQFNSYPRT |
| 87 | LCDR1 Nucleotide Sequence (KABAT) | CGGGCAAGTCAGGGCATTAACAATGCTTTAGCC |
| 88 | LCDR1 Amino Acid Sequence (KABAT) | RASQGINNALA |

-continued

SEQUENCE LISTING

| SEQ ID NO: | | |
|---|---|---|
| 89 | LCDR2 Nucleotide Sequence (KABAT) | GATGCCTCCAGTTTGGAAAGT |
| 90 | LCDR2 Amino Acid Sequence (KABAT) | DASSLES |
| 91 | LCDR3 Nucleotide Sequence (KABAT) | CAACAGTTTAATAGTTACCCTCGGACG |
| 92 | LCDR3 Amino Acid Sequence (KABAT) | QQFNSYPRT |
| 93 19H01 | VH Nucleotide Sequence | GAGGTGCAGCTGGTGGAGTCTGGGGGAGGCTTGGTAAAGCCTGGGCBGGTCCCTTAGACTCTCCTGTGCAGCCTCTGGATTCACTTTCAGTAACGCCTGGATGAGCTGGGTCCGCCAGGCTCCAGGGAAGGGGCTGGAGTGGGTTGGCCGTATTAAAAGCAAAACTGAAGGTGGGACAACAGACTACGCTGCACCCGTGAAAGGCAGATTCACCATCTCAAGAGATGATTCAAAAAACACGCTGTATCTGCAAATGAACAGCCTGAAAACCGAGGACACAGCCGTGTATTACTGTACCACAGATTTTCTATGGTTCGGGGAGTTCCCTTTTGACTACTGGGGCCAGGGAACCCTGGTCACCGTCTCCTCA |
| 94 | VH Amino Acid Sequence | EVQLVESGGGLVKPGGSLRLSCAASGFTFSNAWMSWVRQAPGKGLEWVGRIKSKTEGGTTDYAAPVKGRFTISRDDSKNTLYLQMNSLKTEDTAVYYCTTDFLWFGEFPFDYWGQGTLVTVSS |
| 95 | HCDR1 Nucleotide Sequence (IMGT) | GGATTCACTTTCAGTAACGCCTGG |
| 96 | HCDR1 Amino Acid Sequence (IMGT) | GFTFSNAW |
| 97 | HCDR2 Nucleotide Sequence (IMGT) | ATTAAAAGCAAAACTGAAGGTGGGACAACA |
| 98 | HCDR2 Amino Acid Sequence (IMGT) | IKSKTEGGTT |
| 99 | HCDR3 Nucleotide Sequence (IMGT) | ACCACAGATTTTCTATGGTTCGGGGAGTTCCCTTTTGACTAC |
| 100 | HCDR3 Amino Acid Sequence (IMGT) | TTDFLWFGEFPFDY |
| 101 | HCDR1 Nucleotide Sequence (KABAT) | AACGCCTGGATGAGC |
| 102 | HCDR1 Amino Acid Sequence (KABAT) | NAWMS |
| 103 | HCDR2 Nucleotide Sequence (KABAT) | CGTATTAAAAGCAAAACTGAAGGTGGGACAACAGACTACGCTGCACCCGTGAAAGGC |
| 104 | HCDR2 Amino Acid Sequence (KABAT) | RIKSKTEGGTTDYAAPVKG |
| 105 | HCDR3 Nucleotide Sequence (KABAT) | GATTTTCTATGGTTCGGGGAGTTCCCTTTTGACTAC |
| 106 | HCDR3 Amino Acid Sequence (KABAT) | DFLWFGEFPFDY |
| 107 | VL Nucleotide Sequence | GACATCCAGATGACCCAGTCTCCATCCTCCCTGTCTGCATCTGTAGGAGACAGAGTCACCATCACTTGCCGGGCGAGTCAGGGCATTAGCAATTATTTAGCCTGGTATCAGCAGAAACCAGGGAAAATTCCTAAGCTCCTGATCTATGCTGCATCCACTTTGCAATCAGGGGTCCCATCTCGGTTCAGTGGCAGTGGATCTGGGACAGATTTCACTCTCACCATCAGCAGCCTGCAGCCTGAAGATGTTGCAACTTATTACTGTCAAAAGTATAACAGTG |

-continued

| SEQUENCE LISTING | | | | |
|---|---|---|---|---|
| SEQ ID NO: | | | | |
| | | | | CCCCTCGGACGTTCGGCCAAGGGACCAAGGTGGAA ATCAAA |
| 108 | | | VL Amino Acid Sequence | DIQMTQSPSSLSASVGDRVTITCRASQGISNYLAW YQQKPGKIPKLLIYAASTLQSGVPSRFSGSGSGTD FTLTISSLQPEDVATYYCQKYNSAPRTFGQGTKVE IK |
| 109 | | | LCDR1 Nucleotide Sequence (IMGT) | CAGGGCATTAGCAATTAT |
| 110 | | | LCDR1 Amino Acid Sequence (IMGT) | QGISNY |
| 111 | | | LCDR2 Nucleotide Sequence (IMGT) | GCTGCATCC |
| 112 | | | LCDR2 Amino Acid Sequence (IMGT) | AAS |
| 113 | | | LCDR3 Nucleotide Sequence (IMGT) | CAAAAGTATAACAGTGCCCCTCGGACG |
| 114 | | | LCDR3 Amino Acid Sequence (IMGT) | QKYNSAPRT |
| 115 | | | LCDR1 Nucleotide Sequence (KABAT) | CGGGCGAGTCAGGGCATTAGCAATTATTTAGCC |
| 116 | | | LCDR1 Amino Acid Sequence (KABAT) | RASQGISNYLA |
| 117 | | | LCDR2 Nucleotide Sequence (KABAT) | GCTGCATCCACTTTGCAATCA |
| 118 | | | LCDR2 Amino Acid Sequence (KABAT) | AASTLQS |
| 119 | | | LCDR3 Nucleotide Sequence (KABAT) | CAAAAGTATAACAGTGCCCCTCGGACG |
| 120 | | | LCDR3 Amino Acid Sequence (KABAT) | QKYNSAPRT |
| 121 | Human IgG4 heavy chain constant region #1 | IGHG *01 | Heavy Chain Constant Region Nucleotide Sequence | gcttccaccaagggcccatccgtcttcccctggc gccctgctccaggagcacctccgagagcacagccg ccctgggctgcctggtcaaggactacttccccgaa ccggtgacggtgtcgtggaactcaggcgccctgac cagcggcgtgcacaccttcccggctgtcctacagt cctcaggactctactccctcagcagcgtggtgacc gtgccctccagcagcttgggcacgaagacctacac ctgcaacgtagatcacaagcccagcaacaccaagg tggacaagagagttgagtccaaatatggtcccca tgcccatcatgcccagcacctgagttcctgggggg accatcagtcttcctgttccccccaaaacccaagg acactctcatgatctcccggacccctgaggtcacg tgcgtggtggtggacgtgagccaggaagaccccga ggtccagttcaactggtacgtggatggcgtggagg tgcataatgccaagacaaagccgcgggaggagcag ttcaacagcacgtaccgtgtggtcagcgtcctcac cgtcctgcaccaggactggctgaacggcaaggagt acaagtgcaaggtctccaacaaaggcctcccgtcc tccatcgagaaaaccatctccaaagccaaagggca gccccgagagccacaggtgtacaccctgcccccat cccaggaggagatgaccaagaaccaggtcagcctg acctgcctggtcaaaggcttctaccccagcgacat cgccgtggagtgggagagcaatgggcagccggaga acaactacaagaccacgcctcccgtgctggactcc gacggctccttcttcctctacagcaggctaaccgt ggacaagagcaggtggcaggaggggaatgtcttct catgctccgtgatgcatgaggctctgcacaaccac tacacacagaagagcctctccctgtctctgggtaa a |

-continued

SEQUENCE LISTING

| SEQ ID NO: | | | | |
|---|---|---|---|---|
| 122 | | | Heavy Chain Constant Region Amino Acid Sequence | ASTKGPSVFPLAPCSRSTSESTAALGCLVKDYFPE<br>PVTVSWNSGALTSGVHTFPAVLQSSGLYSLSSVVT<br>VPSSSLGTKTYTCNVDHKPSNTKVDKRVESKYGPP<br>CPSCPAPEFLGGPSVFLFPPKPKDTLMISRTPEVT<br>CVVVDVSQEDPEVQFNWYVDGVEVHNAKTKPREEQ<br>FNSTYRVVSVLTVLHQDWLNGKEYKCKVSNKGLPS<br>SIEKTISKAKGQPREPQVYTLPPSQEEMTKNQVSL<br>TCLVKGFYPSDIAVEWESNGQPENNYKTTPPVLDS<br>DGSFFLYSRLTVDKSRWQEGNVFSCSVMHEALHNH<br>YTQKSLSLSLGK |
| 123 | Human IgG4 heavy chain constant region #2 | IGHG *02 | Heavy Chain Constant Region Nucleotide Sequence | gcttccaccaagggcccatccgtcttccccctggc<br>gccctgctccaggagcacctccgagagcacagccg<br>ccctgggctgcctggtcaaggactacttccccgaa<br>ccggtgacggtgtcgtggaactcaggcgccctgac<br>cagcggcgtgcacaccttcccggctgtcctacagt<br>cctcaggactctactccctcagcagcgtggtgacc<br>gtgccctccagcagcttgggcacgaagacctacac<br>ctgcaacgtagatcacaagcccagcaacaccaagg<br>tggacaagagagttgagtccaaatatggtcccccg<br>tgcccatcatgcccagcacctgagttcctgggggg<br>accatcagtcttcctgttccccccaaaacccaagg<br>acactctcatgatctcccggacccctgaggtcacg<br>tgcgtggtggtggacgtgagccaggaagaccccga<br>ggtccagttcaactggtacgtggatggcgtggagg<br>tgcataatgccaagacaaagccgcgggaggagcag<br>ttcaacagcacgtaccgtgtggtcagcgtcctcac<br>cgtcgtgcaccaggactggctgaacggcaaggagt<br>acaagtgcaaggtctccaacaaaggcctcccgtcc<br>tccatcgagaaaaccatctccaaagccaaagggca<br>gccccgagagccacaggtgtacaccctgcccccat<br>cccaggaggagatgaccaagaaccaggtcagcctg<br>acctgcctggtcaaaggcttctaccccagcgacat<br>cgccgtggagtgggagagcaatgggcagccggaga<br>acaactacaagaccacgcctcccgtgctggactcc<br>gacggctccttcttcctctacagcaggctaaccgt<br>ggacaagagcaggtggcaggaggggaatgtcttct<br>catgctccgtgatgcatgaggctctgcacaaccac<br>tacacgcagaagagcctctccctgtctctgggtaa<br>a |
| 124 | | | Heavy Chain Constant Region Amino Acid Sequence | ASTKGPSVFPLAPCSRSTSESTAALGCLVKDYFPE<br>PVTVSWNSGALTSGVHTFPAVLQSSGLYSLSSVVT<br>VPSSSLGTKTYTCNVDHKPSNTKVDKRVESKYGPP<br>CPSCPAPEFLGGPSVFLFPPKPKDTLMISRTPEVT<br>CVWDVSQEDPEVQFNWYVDGVEVHNAKTKPREEQF<br>NSTYRVVSVLTVHQDWLNGKEYKCKVSNKGLPSSI<br>EKTISKAKGQPREPQVYTLPPSQEEMTKNQVSLTC<br>LVKGFYPSDIAVEWESNGQPENNYKTTPPVLDSDG<br>SFFLYSRLTVDKSRWQEGNVFSCSVMHEALHNHYT<br>QKSLSLSLGK |
| 125 | Human IgG4 heavy chain constant region #3 | IGHG *03 | Heavy Chain Constant Region Nucleotide Sequence | gcttccaccaagggcccatccgtcttccccctggc<br>gccctgctccaggagcacctccgagagcacagccg<br>ccctgggctgcctggtcaaggactacttccccgaa<br>ccggtgacggtgtcgtggaactcaggcgccctgac<br>cagcggcgtgcacaccttcccggctgtcctacagt<br>cctcaggactctactccctcagcagcgtggtgacc<br>gtgccctccagcagcttgggcacgaagacctacac<br>ctgcaacgtagatcacaagcccagcaacaccaagg<br>tggacaagagagttgagtccaaatatggtcccccca<br>tgcccatcatgcccagcacctgagttcctgggggg<br>accatcagtcttcctgttccccccaaaacccaagg<br>acactctcatgatctcccggacccctgaggtcacg<br>tgcgtggtggtggacgtgagccaggaagaccccga<br>ggtccagttcaactggtacgtggatggcgtggagg<br>tgcataatgccaagacaaagccgcgggaggagcag<br>ttcaacagcacgtaccgtgtggtcagcgtcctcac<br>cgtcctgcaccaggactggctgaacggcaaggagt<br>acaagtgcaaggtctccaacaaaggcctcccgtcc<br>tccatcgagaaaaccatctccaaagccaaagggca<br>gccccgagagccacaggtgtacaccctgcccccat |

-continued

SEQUENCE LISTING

| SEQ ID NO: | | | |
|---|---|---|---|
| | | | cccaggaggagatgaccaagaaccaggtcagcctg<br>acctgcctggtcaaaggcttctaccccagcgacat<br>cgccgtggagtgggagagcaatgggcagccggaga<br>acaactacaagaccacgcctcccgtgctggactcc<br>gacggctccttcttcctctacagcaagctcaccgt<br>ggacaagagcaggtggcaggaggggaacgtcttct<br>catgctccgtgatgcatgaggctctgcacaaccac<br>tacacgcagaagagcctctccctgtctctgggtaa<br>a |
| 126 | | Heavy Chain Constant Region Amino Acid Sequence | ASTKGPSVFPLAPCSRSTSESTAALGCLVKDYFPE<br>PVTVSWNSGALTSGVHTFPAVLQSSGLYSLSSVVT<br>VPSSSLGTKTYTCNVDHKPSNTKVDKRVESKYGPP<br>CPSCPAPEFLGGPSVFLFPPKPKDTLMISRTPEVT<br>CVVVDVSQEDPEVQFNWYVDGVEVHNAKTKPREEQ<br>FNSTYRVVSVLTVLHQDWLNGKEYKCKVSNKGLPS<br>SIEKTISKAKGQPREPQVYTLPPSQEEMTKNQVSL<br>TCLVKGFYPSDIAVEWESNGQPENNYKTTPPVLDS<br>DGSFFLYSKLTVDKSRWQEGNVFSCSVMHEALHNH<br>YTQKSLSLSLGK |
| 127 | IgG4 heavy chain constant region | Heavy Chain Constant Region Nucleotide Sequence-Synthetic Version A | gcctccaccaagggcccatccgtcttccccctggc<br>gccctgctccaggagcacctccgagagcacggccg<br>ccctgggctgcctggtcaaggactacttccccgaa<br>ccagtgacggtgtcgtggaactcaggcgccctgac<br>cagcggcgtgcacaccttcccggctgtcctacagt<br>cctcaggactctactccctcagcagcgtggtgacc<br>gtgccctccagcagcttgggcacgaagacctacac<br>ctgcaacgtagatcacaagcccagcaacaccaagg<br>tggacaagagagttgagtccaaatatggtccccca<br>tgcccaccatgcccagcgcctgaatttgaggggggg<br>accatcagtcttcctgttccccccaaaacccaagg<br>acactctcatgatctcccggacccctgaggtcacg<br>tgcgtggtggtggacgtgagccaggaagaccccga<br>ggtccagttcaactggtacgtggatggcgtggagg<br>tgcataatgccaagacaaagccgcgggaggagcag<br>ttcaacagcacgtaccgtgtggtcagcgtcctcac<br>cgtcctgcaccaggactggctgaacggcaaggagt<br>acaagtgcaaggtctccaacaaaggcctcccgtca<br>tcgatcgagaaaaccatctccaaagccaaagggca<br>gccccgagagccacaggtgtacaccctgcccccat<br>cccaggaggagatgaccaagaaccaggtcagcctg<br>acctgcctggtcaaaggcttctaccccagcgacat<br>cgccgtggagtgggagagcaatgggcagccggaga<br>acaactacaagaccacgcctcccgtgctggactcc<br>gacggatccttcttcctctacagcaggctaaccgt<br>ggacaagagcaggtggcaggaggggaatgtcttct<br>catgctccgtgatgcatgaggctctgcacaaccac<br>tacacacagaagagcctctccctgtctctgggtaa<br>a |
| 128 | IgG4 heavy chain constant region-IgG4-PE | Heavy Chain Constant Region Amino Acid Sequence-Encoded by Synthetic Version A, B& C | ASTKGPSVFPLAPCSRSTSESTAALGCLVKDYFPE<br>PVTVSWNSGALTSGVHTFPAVLQSSGLYSLSSVVT<br>VPSSSLGTKTYTCNVDHKPSNTKVDKRVESKYGPP<br>CPPCPAPEFEGGPSVFLFPPKPKDTLMISRTPEVT<br>CVVVDVSQEDPEVQFNWYVDGVEVHNAKTKPREEQ<br>FNSTYRVVSVLTVLHQDWLNGKEYKCKVSNKGLPS<br>SIEKTISKAKGQPREPQVYTLPPSQEEMTKNQVSL<br>TCLVKGFYPSDIAVEWESNGQPENNYKTTPPVLDS<br>DGSFFLYSRLTVDKSRWQEGNVFSCSVMHEALHNH<br>YTQKSLSLSLGK |
| 129 | IgG4 heavy chain constant region | Heavy Chain Constant Region Nucleotide Sequence-Synthetic Version B | Gcctccaccaagggacctagcgtgttccctctcgc<br>cccctgttccaggtccacaagcgagtccaccgctg<br>ccctcggctgtctggtgaaagactactttcccgag<br>cccgtgaccgtctcctggaatagcggagccctgac<br>ctccggcgtgcacacatttcccgccgtgctgcaga<br>gcagcggactgtatagcctgagcagcgtggtgacc<br>gtgcccagctccagcctcggcaccaaaacctacac<br>ctgcaacgtggaccacaagccctccaacaccaagg<br>tggacaagcgggtggagagcaagtacggcccccct<br>tgccctccttgtcctgcccctgagttcgagggagg<br>accctccgtgttcctgtttccccccaaacccaagg |

-continued

SEQUENCE LISTING

| SEQ ID NO: | | | |
|---|---|---|---|
| | | | acaccctgatgatctcccggacacccgaggtgacc<br>tgtgtggtcgtggacgtcagccaggaggaccccga<br>ggtgcagttcaactggtatgtggacggcgtggagg<br>tgcacaatgccaaaaccaagcccagggaggagcag<br>ttcaattccacctacagggtggtgagcgtgctgac<br>cgtcctgcatcaggattggctgaacggcaaggagt<br>acaagtgcaaggtgtccaacaagggactgcccagc<br>tccatcgagaagaccatcagcaaggctaagggcca<br>gccgagggagccccaggtgtataccctgcctccta<br>gccaggaagagatgaccaagaaccaagtgtccctg<br>acctgcctggtgaagggattctacccctccgacat<br>cgccgtggagtgggagagcaatggccagcccgaga<br>acaactacaaaacaacccctcccgtgctcgatagc<br>gacggcagcttctttctctacagccggctgacagt<br>ggacaagagcaggtggcaggagggcaacgtgttct<br>cctgttccgtgatgcacgaggccctgcacaatcac<br>tacacccagaagagcctctccctgtccctgggcaa<br>g |
| 130 | IgG4 heavy chain constant region | Heavy Chain Constant Region Nucleotide Sequence-Synthetic Version C | gccagcaccaagggcccttccgtgttcccccctggc<br>cccttgcagcaggagcacctccgaatccacagctg<br>ccctgggctgtctggtgaaggactactttcccgag<br>cccgtgaccgtgagctggaacagcggcgctctgac<br>atccggcgtccacacctttcctgccgtcctgcagt<br>cctccggcctctactccctgtcctccgtggtgacc<br>gtgcctagctcctccctcggcaccaagacctacac<br>ctgtaacgtggaccacaaaccctccaacaccaagg<br>tggacaaacgggtcgagagcaagtacggccctccc<br>tgccctccttgtcctgcccccgagttcgaaggcgg<br>acccagcgtgttcctgttccctcctaagcccaagg<br>acaccctcatgatcagccggacacccgaggtgacc<br>tgcgtggtggtggatgtgagccaggaggaccctga<br>ggtccagttcaactggtatgtggatggcgtggagg<br>tgcacaacgccaagacaaagccccgggaagagcag<br>ttcaactccacctacagggtggtcagcgtgctgac<br>cgtgctgcatcaggactggctgaacggcaaggagt<br>acaagtgcaaggtcagcaataagggactgcccagc<br>agcatcgagaagaccatctccaaggctaaaggcca<br>gccccgggaacctcaggtgtacaccctgcctccca<br>gccaggaggagatgaccaagaaccaggtgagcctg<br>acctgcctggtgaagggattctacccttccgacat<br>cgccgtggagtgggagtccaacggccagcccgaga<br>acaattataagaccacccctcccgtcctcgacagc<br>gacggatccttctttctgtactccaggctgaccgt<br>ggataagtccaggtggcaggaaggcaacgtgttca<br>gctgctccgtgatgcacgaggccctgcacaatcac<br>tacacccagaagtccctgagcctgtccctgggaaa<br>g |
| 131 | IgG4 heavy chain constant region | Heavy Chain Constant Region Nucleotide Sequence-Synthetic Version D | gcctccaccaagggcccatccgtcttcccccctggc<br>gccctgctccaggagcacctccgagagcacggccg<br>ccctgggctgcctggtcaaggactacttccccgaa<br>ccagtgacggtgtcgtggaactcaggcgccctgac<br>cagcggcgtgcacaccttcccggctgtcctacagt<br>cctcaggactctactccctcagcagcgtggtgacc<br>gtgccctccagcagcttgggcacgaagacctacac<br>ctgcaacgtagatcacaagcccagcaacaccaagg<br>tggacaagagagttgagtccaaatatggtcccccca<br>tgcccaccatgcccagcgcctccagttgcgggggg<br>accatcagtcttcctgttcccccaaaacccaagg<br>acactctcatgatctcccggacccctgaggtcacg<br>tgcgtggtggtggacgtgagccaggaagaccccga<br>ggtccagttcaactggtacgtggatggcgtggagg<br>tgcataatgccaagacaaagccgcgggaggagcag<br>ttcaacagcacgtaccgtgtggtcagcgtcctcac<br>cgtcctgcaccaggactggctgaacggcaaggagt<br>acaagtgcaaggtctccaacaaaggcctcccgtca<br>tcgatcgagaaaaccatctccaaagccaaagggca<br>gccccgagagccacaggtgtacaccctgcccccat<br>cccaggaggagatgaccaagaaccaggtcagcctg<br>acctgcctggtcaaaggcttctaccccagcgacat<br>cgccgtggagtgggagagcaatgggcagccggaga<br>acaactacaagaccacgcctcccgtgctggactcc |

-continued

SEQUENCE LISTING

| SEQ ID NO: | | | | |
|---|---|---|---|---|
| | | | | gacggatccttcttcctctacagcaggctaaccgt<br>ggacaagagcaggtggcaggaggggaatgtcttct<br>catgctccgtgatgcatgaggctctgcacaaccac<br>tacacacagaagagcctctccctgtctctgggtaa<br>a |
| 132 | | | Heavy Chain Constant Region Amino Acid Sequence-encoded by Synthetic Version D | ASTKGPSVFPLAPCSRSTSESTAALGCLVKDYFPE<br>PVTVSWNSGALTSGVHTFPAVLQSSGLYSLSSVVT<br>VPSSSLGTKTYTCNVDHKPSNTKVDKRVESKYGPP<br>CPPCPAPPVAGGPSVFLFPPKPKDTLMISRTPEVT<br>CVVVDVSQEDPEVQFNWYVDGVEVHNAKTKPREEQ<br>FNSTYRVVSVLTVLHQDWLNGKEYKCKVSNKGLPS<br>SIEKTISKAKGQPREPQVYTLPPSQEEMTKNQVSL<br>TCLVKGFYPSDIAVEWESNGQPENNYKTTPPVLDS<br>DGSFFLYSRLTVDKSRWQEGNVFSCSVMHEALHNH<br>YTQKSLSLSLGK |
| 133 | Human IgG1 heavy chain constant region | | Heavy Chain Constant Region Nucleotide Sequence | gcctccaccaagggcccatcggtcttccccctggc<br>accctcctccaagagcacctctgggggcacagcgg<br>ccctgggctgcctggtcaaggactacttccccgaa<br>ccggtgacggtgtcgtggaactcaggcgccctgac<br>cagcggcgtgcacaccttcccggctgtcctacagt<br>cctcaggactctactccctcagcagcgtggtgacc<br>gtgccctccagcagcttgggcacccagacctacat<br>ctgcaacgtgaatcacaagcccagcaacaccaagg<br>tggacaagaaagtggagcccaaatcttgtgacaaa<br>actcacacatgcccaccgtgcccagcacctgaact<br>cgcgggggcaccgtcagtcttcctcttccccccaa<br>aacccaaggacaccctcatgatctcccggacccct<br>gaggtcacatgcgtggtggtggacgtgagccacga<br>agaccctgaggtcaagttcaactggtacgtggacg<br>gcgtggaggtgcataatgccaagacaaagccgcgg<br>gaggagcagtacaacagcacgtaccgtgtggtcag<br>cgtcctcaccgtcctgcaccaggactggctgaatg<br>gcaaggagtacaagtgcaaggtctccaacaaagcc<br>ctcccagcccccatcgagaaaaccatctccaaagc<br>caaagggcagccccgagaaccacaggtgtacaccc<br>tgcccccatcccgggatgagctgaccaagaaccag<br>gtcagcctgacctgcctggtcaaaggcttctatcc<br>cagcgacatcgccgtggagtgggagagcaatgggc<br>agccggagaacaactacaagaccacgcctcccgtg<br>ctggactccgacggctccttcttcctctacagcaa<br>gctcaccgtggacaagagcaggtggcagcagggga<br>acgtcttctcatgctccgtgatgcatgaggctctg<br>cacaaccactacacgcagaagagcctctccctgtc<br>tccgggtaaa |
| 134 | | | Heavy Chain Constant Region Amino Acid Sequence | ASTKGPSVFPLAPSSKSTSGGTAALGCLVKDYFPE<br>PVTVSWNSGALTSGVHTFPAVLQSSGLYSLSSVVT<br>VPSSSLGTQTYICNVNHKPSNTKVDKKVEPKSCDK<br>THTCPPCPAPELAGAPSVFLFPPKPKDTLMISRTP<br>EVTCVVVDVSHEDPEVKFNWYVDGVEVHNAKTKPR<br>EEQYNSTYRVVSVLTVLHQDWLNGKEYKCKVSNKA<br>LPAPIEKTISKAKGQPREPQVYTLPPSRDELTKNQ<br>VSLTCLVKGFYPSDIAVEWESNGQPENNYKTTPPV<br>LDSDGSFFLYSKLTVDKSRWQQGNVFSCSVMHEAL<br>HNHYTQKSLSLSPGK |
| 135 | Human Cκ constant region | IGKC *01 | Cκ Light Chain Constant Region Nucleotide Sequence | cgtacggtggccgctccctccgtgttcatcttccc<br>accttccgacgagcagctgaagtccggcaccgctt<br>ctgtcgtgtgcctgctgaacaacttctacccccgc<br>gaggccaaggtgcagtggaaggtggacaacgccct<br>gcagtccggcaactcccaggaatccgtgaccgagc<br>aggactccaaggacagcacctactccctgtcctcc<br>accctgaccctgtccaaggccgactacgagaagca<br>caaggtgtacgcctgcgaagtgacccaccagggcc<br>tgtctagccccgtgaccaagtctttcaaccggggc<br>gagtgt |
| 136 | | | Cκ Light Chain Constant Region Amino Acid Sequence | RTVAAPSVFIFPPSDEQLKSGTASVVCLLNNFYPR<br>EAKVQWKVDNALQSGNSQESVTEQDSKDSTYSLSS<br>TLTLSKADYEKHKVYACEVTHQGLSSPVTKSFNRG<br>EC |

-continued

| SEQUENCE LISTING | | | |
|---|---|---|---|
| SEQ ID NO: | | | |
| 137 Human Cκ constant region | IGKC *02 | Cκ Light Chain Constant Region Nucleotide Sequence | cgaactgtggctgcaccatctgtcttcatcttccc gccatctgatgagcagttgaaatctggaactgcct ctgttgtgtgcctgctgaataacttctatcccaga gaggccaaagtacagtggaaggtggataacgccct ccaatcgggtaactcccaggagagtgtcacagagc aggagagcaaggacagcacctacagcctcagcagc accctgacgctgagcaaagcagactacgagaaaca caaagtctacgccggcgaagtcacccatcagggcc tgagctcgcccgtcacaaagagcttcaacagggga gagtgt |
| 138 | | Cκ Light Chain Constant Region Amino Acid Sequence | RTVAAPSVFIFPPSDEQLKSGTASVVCLLNNFYPR EAKVQWKVDNALQSGNSQESVTEQESKDSTYSLSS TLTLSKADYEKHKVYAGEVTHQGLSSPVTKSFNRG EC |
| 139 Human Cκ constant region | IGKC *03 | Cκ Light Chain Constant Region Nucleotide Sequence | cgaactgtggctgcaccatctgtcttcatcttccc gccatctgatgagcagttgaaatctggaactgcct ctgttgtgtgcctgctgaataacttctatcccaga gaggccaaagtacagcggaaggtggataacgccct ccaatcgggtaactcccaggagagtgtcacagagc aggagagcaaggacagcacctacagcctcagcagc accctgacgctgagcaaagcagactacgagaaaca caaagtctacgcctgcgaagtcacccatcagggcc tgagctcgcccgtcacaaagagcttcaacagggga gagtgt |
| 140 | | Cκ Light Chain Constant Region Amino Acid Sequence | RTVAAPSVFIFPPSDEQLKSGTASVVCLLNNFYPR EAKVQRKVDNALQSGNSQESVTEQESKDSTYSLSS TLTLSKADYEKHKVYACEVTHQGLSSPVTKSFNRG EC |
| 141 Human Cκ constant region | IGKC *04 | Cκ Light Chain Constant Region Nucleotide Sequence | cgaactgtggctgcaccatctgtcttcatcttccc gccatctgatgagcagttgaaatctggaactgcct ctgttgtgtgcctgctgaataacttctatcccaga gaggccaaagtacagtggaaggtggataacgccct ccaatcgggtaactcccaggagagtgtcacagagc aggacagcaaggacagcacctacagcctcagcagc accctgacgctgagcaaagcagactacgagaaaca caaactctacgcctgcgaagtcacccatcagggcc tgagctcgcccgtcacaaagagcttcaacagggga gagtgt |
| 142 | | Cκ Light Chain Constant Region Amino Acid Sequence | RTVAAPSVFIFPPSDEQLKSGTASWCLLNNFYPRE AKVQWKVDNALQSGNSQESVTEQDSKDSTYSLSST LTLSKADYEKHKLYACEVTHQGLSSPVTKSFNRGE C |
| 143 Human Cκ constant region | IGKC *05 | Cκ Light Chain Constant Region Nucleotide Sequence | cgaactgtggctgcaccatctgtcttcatcttccc gccatctgatgagcagttgaaatctggaactgcct ctgttgtgtgcctgctgaataacttctatcccaga gaggccaaagtacagtggaaggtggataacgccct ccaatcgggtaactcccaggagagtgtcacagagc aggacagcaaggacagcacctacagcctcagcaac accctgacgctgagcaaagcagactacgagaaaca caaagtctacgcctgcgaagtcacccatcagggcc tgagctcgcccgtcacaaagagcttcaacagggga gagtgc |
| 144 | | Cκ Light Chain Constant Region Amino Acid Sequence | RTVAAPSVFIFPPSDEQLKSGTASVVCLLNNFYPR EAKVQWKVDNALQSGNSQESVTEQDSKDSTYSLSN TLTLSKADYEKHKVYACEVTHQGLSSPVTKSFNRG EC |
| 145 Human Cλ constant region | IGCλ1 *01 | Cλ Light Chain Constant Region Nucleotide Sequence | cccaaggccaaccccacggtcactctgttcccgcc ctcctctgaggagctccaagccaacaaggccacac tagtgtgtctgatcagtgacttctacccgggagct gtgacagtggcttggaaggcagatggcagccccgt caaggcgggagtggagacgaccaaaccctccaaac agagcaacaacaagtacgcggccagcagctacctg |

-continued

SEQUENCE LISTING

| SEQ ID NO: | | | | |
|---|---|---|---|---|
| | | | | agcctgacgcccgagcagtggaagtcccacagaag<br>ctacagctgccaggtcacgcatgaagggagcaccg<br>tggagaagacagtggcccctacagaatgttca |
| 146 | | | Cλ Light Chain Constant Region Amino Acid Sequence | PKANPTVTLFPPSSEELQANKATLVCLISDFYPGA<br>VTVAWKADGSPVKAGVETTKPSKQSNNKYAASSYL<br>SLTPEQWKSHRSYSCQVTHEGSTVEKTVAPTECS |
| 147 | Human Cλ constant region | IGCλ1 *02 | Cλ Light Chain Constant Region Nucleotide Sequence | ggtcagcccaaggccaaccccactgtcactctgtt<br>cccgccctcctctgaggagctccaagccaacaagg<br>ccacactagtgtgtctgatcagtgacttctacccg<br>ggagctgtgacagtggcctggaaggcagatggcag<br>ccccgtcaaggcgggagtggagaccaccaaaccct<br>ccaaacagagcaacaacaagtacgcggccagcagc<br>tacctgagcctgacgcccgagcagtggaagtccca<br>cagaagctacagctgccaggtcacgcatgaaggga<br>gcaccgtggagaagacagtggcccctacagaatgt<br>tca |
| 148 | | | Cλ Light Chain Constant Region Amino Acid Sequence | GQPKANPTVTLFPPSSEELQANKATLVCLISDFYP<br>GAVTVAWKADGSPVKAGVETTKPSKQSNNKYAASS<br>YLSLTPEQWKSHRSYSCQVTHEGSTVEKTVAPTEC<br>S |
| 149 | Human Cλ constant region | IGCλ2 *01 | Cλ Light Chain Constant Region Nucleotide Sequence-Version A | ggtcagcccaaggccaaccccactgtcactctgtt<br>cccgccctcctctgaggagctccaagccaacaagg<br>ccacactagtgtgtctgatcagtgacttctacccg<br>ggagctgtgacagtggcctggaaggcagatggcag<br>ccccgtcaaggcgggagtggagaccaccaaaccct<br>ccaaacagagcaacaacaagtacgcggccagcagc<br>tacctgagcctgacgcccgagcagtggaagtccca<br>cagaagctacagctgccaggtcacgcatgaaggga<br>gcaccgtggagaagacagtggcccctacagaatgt<br>tca |
| 150 | | | Cλ Light Chain Constant Region Nucleotide Sequence-Version B | ggccagcctaaggccgctccttctgtgaccctgtt<br>ccccccatcctccgaggaactgcaggctaacaagg<br>ccaccctcgtgtgcctgatcagcgacttctaccct<br>ggcgccgtgaccgtggcctggaaggctgatagctc<br>tcctgtgaaggccggcgtggaaaccaccaccccctt<br>ccaagcagtccaacaacaaatacgccgcctcctcc<br>tacctgtccctgacccctgagcagtggaagtccca<br>ccggtcctacagctgccaagtgacccacgagggct<br>ccaccgtggaaaagaccgtggctcctaccgagtgc<br>tcc |
| 151 | | | Cλ Light Chain Constant Region Nucleotide Sequence-Version C | ggccagcctaaagctgcccccagcgtcaccctgtt<br>tcctccctccagcgaggagctccaggccaacaagg<br>ccaccctcgtgtgcctgatctccgacttctatccc<br>ggcgctgtgaccgtggcttggaaagccgactccag<br>ccctgtcaaagccggcgtggagaccaccacaccct<br>ccaagcagtccaacaacaagtacgccgcctccagc<br>tatctctccctgacccctgagcagtggaagtccca<br>ccggtcctactcctgtcaggtgacccacgagggct<br>ccaccgtggaaaagaccgtcgcccccaccgagtgc<br>tcc |
| 152 | | | Cλ Light Chain Constant Region Amino Acid Sequence-Encoded by Version A, B & C | GQPKANPTVTLFPPSSEELQANKATLVCLISDFYP<br>GAVTVAWKADGSPVKAGVETTKPSKQSNNKYAASS<br>YLSLTPEQWKSHRSYSCQVTHEGSTVEKTVAPTEC<br>S |
| 153 | Human Cλ constant region | IGCλ2 *02 | Cλ Light Chain Constant Region Nucleotide Sequence | ggtcagcccaaggctgccccctcggtcactctgtt<br>cccgccctcctctgaggagcttcaagccaacaagg<br>ccacactggtgtgtctcataagtgacttctacccg<br>ggagccgtgacagtggcctggaaggcagatagcag<br>ccccgtcaaggcgggagtggagaccaccacaccct<br>ccaaacaaagcaacaacaagtacgcggccagcagc<br>tatctgagcctgacgcctgagcagtggaagtccca<br>cagaagctacagctgccaggtcacgcatgaaggga<br>gcaccgtggagaagacagtggcccctacagaatgt<br>tca |

-continued

SEQUENCE LISTING

| SEQ ID NO: | | | | |
|---|---|---|---|---|
| 154 | | | Cλ Light Chain Constant Region Amino Acid Sequence | GQPKAAPSVTLFPPSSEELQANKATLVCLISDFYP GAVTVAWKADSSPVKAGVETTTPSKQSNNKYAASS YLSLTPEQWKSHRSYSCQVTHEGSTVEKTVAPTEC S |
| 155 | Human Cλ constant region | IGCλ3 *01 | Cλ Light Chain Constant Region Nucleotide Sequence | cccaaggctgcccccctcggtcactctgttcccacc ctcctctgaggagcttcaagccaacaaggccacac tggtgtgtctcataagtgacttctacccgggagcc gtgacagttgcctggaaggcagatagcagccccgt caaggcgggggtggagaccaccacaccctccaaac aaagcaacaacaagtacgcggccagcagctacctg agcctgacgcctgagcagtggaagtcccacaaaag ctacagctgccaggtcacgcatgaagggagcaccg tggagaagacagttgcccctacggaatgttca |
| 156 | | | Cλ Light Chain Constant Region Amino Acid Sequence | PKAAPSVTLFPPSSEELQANKATLVCLISDFYPGA VTVAWKADSSPVKAGVETTTPSKQSNNKYAASSYL SLTPEQWKSHKSYSCQVTHEGSTVEKTVAPTECS |
| 157 | Human Cλ constant region | IGCλ3 *02 | Cλ Light Chain Constant Region Nucleotide Sequence | ggtcagcccaaggctgcccccctcggtcactctgtt cccaccctcctctgaggagcttcaagccaacaagg ccacactggtgtgtctcataagtgacttctacccg ggccagtgacagttgcctggaaggcagatagcag ccccgtcaaggcgggggtggagaccaccacaccct ccaaacaaagcaacaacaagtacgcggccagcagc tacctgagcctgacgcctgagcagtggaagtccca caaaagctacagctgccaggtcacgcatgaaggga gcaccgtggagaagacagtggcccctacggaatgt tca |
| 158 | | | Cλ Light Chain Constant Region Amino Acid Sequence | GQPKAAPSVTLFPPSSEELQANKATLVCLISDFYP GPVTVAWKADSSPVKAGVETTTPSKQSNNKYAASS YLSLTPEQWKSHKSYSCQVTHEGSTVEKTVAPTEC S |
| 159 | Human Cλ constant region | IGCλ3 *03 | Cλ Light Chain Constant Region Nucleotide Sequence | ggtcagcccaaggctgcccccctcggtcactctgtt cccaccctcctctgaggagcttcaagccaacaagg ccacactggtgtgtctcataagtgacttctacccg ggagccgtgacagtggcctggaaggcagatagcag ccccgtcaaggcgggagtggagaccaccacaccct ccaaacaaagcaacaacaagtacgcggccagcagc tacctgagcctgacgcctgagcagtggaagtccca caaaagctacagctgccaggtcacgcatgaaggga gcaccgtggagaagacagtggcccctacagaatgt tca |
| 160 | | | Cλ Light Chain Constant Region Amino Acid Sequence | GQPKAAPSVTLFPPSSEELQANKATLVCLISDFYP GAVTVAWKADSSPVKAGVETTTPSKQSNNKYAASS YLSLTPEQWKSHKSYSCQVTHEGSTVEKTVAPTEC S |
| 161 | Human Cλ constant region | IGCλ3 *04 | Cλ Light Chain Constant Region Nucleotide Sequence | ggtcagcccaaggctgcccccctcggtcactctgtt cccgccctcctctgaggagcttcaagccaacaagg ccacactggtgtgtctcataagtgacttctacccg ggagccgtgacagtggcctggaaggcagatagcag ccccgtcaaggcgggagtggagaccaccacaccct ccaaacaaagcaacaacaagtacgcggccagcagc tacctgagcctgacgcctgagcagtggaagtccca cagaagctacagctgccaggtcacgcatgaaggga gcaccgtggagaagacagtggcccctacagaatgt tca |
| 162 | | | Cλ Light Chain Constant Region Amino Acid Sequence | GQPKAAPSVTLFPPSSEELQANKATLVCLISDFYP GAVTVAWKADSSPVKAGVETTTPSKQSNNKYAASS YLSLTPEQWKSHRSYSCQVTHEGSTVEKTVAPTEC S |
| 163 | Human Cλ constant region | IGCλ6 *01 | Cλ Light Chain Constant Region Nucleotide Sequence | ggtcagcccaaggctgccccatcggtcactctgtt cccgccctcctctgaggagcttcaagccaacaagg ccacactggtgtgcctgatcagtgacttctacccg ggagctgtgaaagtggcctggaaggcagatggcag ccccgtcaacacgggagtggagaccaccacaccct ccaaacagagcaacaacaagtacgcggccagcagc |

SEQUENCE LISTING

| SEQ ID NO: | | | | |
|---|---|---|---|---|
| | | | | tacctgagcctgacgcctgagcagtggaagtccca cagaagctacagctgccaggtcacgcatgaaggga gcaccgtggagaagacagtggcccctgcagaatgt tca |
| 164 | | | Cλ Light Chain Constant Region Amino Acid Sequence | GQPKAAPSVTLFPPSSEELQANKATLVCLISDFYP GAVKVAWKADGSPVNTGVETTTPSKQSNNKYAASS YLSLTPEQWKSHRSYSCQVTHEGSTVEKTVAPAEC S |
| 165 | Human Cλ constant region | IGCλ7 *02 | Cλ Light Chain Constant Region Nucleotide Sequence | ggtcagcccaaggctgccccatcggtcactctgtt cccaccctcctctgaggagcttcaagccaacaagg ccacactggtgtgtctcgtaagtgacttctacccg ggagccgtgacagtggcctggaaggcagatggcag ccccgtcaaggtgggagtggagaccaccaaaccct ccaaacaaagcaacaacaagtatgcggccagcagc tacctgagcctgacgcccgagcagtggaagtccca cagaagctacagctgccgggtcacgcatgaaggga gcaccgtggagaagacagtggcccctgcagaatgc tct |
| 166 | | | Cλ Light Chain Constant Region Amino Acid Sequence | GQPKAAPSVTLFPPSSEELQANKATLVCLVSDFYP GAVTVAWKADGSPVKVGVETTKPSKQSNNKYAASS YLSLTPEQWKSHRSYSCRVTHEGSTVEKTVAPAEC S |
| 167 | Recombinant Human OX40L (Leader sequence, Isoleucine Zipper and FLAG Sequence Included) | | Nucleotide Sequence | ATGGGCTGGTCCTGCATCATCCTGTTTCTGGTGGC CACCGCCACCGGCGTGCACAGCGATTACAAGGATG ACGACGATAAGCGTATGAAACAGATCGAAGATAAA ATTGAAGAGATCTTGAGCAAAATCTATCATATCGA AAACGAAATTGCGCGTATCAAAAAGCTGATTGGCG AACGTGGCGGrGGCAGCGGrGGCGGTAGCGGCGGT GGCAGCCAGGTGTCCCACCGATACCCCAGGATCCA GTCCATCAAGGTCCAGTTCACCGAGTACAAAAAGG AGAAGGGATTCATCCTGACCTCCCAAAAGGAGGAC GAGATCATGAAGGTGCAAAACAACTCCGTGATCAT CAACTGCGACGGCTTCTACCTGATCTCCCTGAAGG GCTACTTCTCCCAGGAGGTGAACATCTCCCTGCAC TACCAGAAGGACGAGGAGCCCCTGTTCCAGCTGAA GAAGGTGAGGTCCGTGAATTCCCTGATGGTGGCCA GCCTGACCTACAAGGACAAGGTCTACCTGAACGTG ACCACCGACAACACCAGCCTGGACGACTTCCATGT CAACGGCGGCGAGCTGATCCTGATCCATCAGAACC CCGGCGAGTTTTGCGTCCTG |
| 168 | | | Amino Acid Sequence | MGWSCIILFLVATATGVHSDYKDDDDKRMKQIEDK IEEILSKIYHIENEIARIKKLIGERGGGSGGGSGG GSQVSHRYPRIQSIKVQFTEYKKEKGFILTSQKED EIMKVQNNSVIINCDGFYLISLKGYFSQEVNISLH YQKDEEPLFQLKKVRSVNSLMVASLTYKDKVYLNV TTDNTSLDDFHVNGGELILIHQNPGEFCVL |
| 169 | Recombinant Rhesus OX40L (Leader Sequence, FLAG and Isoleucine zipper included) | | Nucleotide Sequence | ATGGGCTGGTCCTGCATCATCCTGTTTCTGGrGGC CACCGCCACCGGCGTGCACAGCGATTACAAGGATG ACGACGATAAGCGTATGAAACAGATCGAAGATAAA ATTGAAGAGATCTTGAGCAAAATCTATCATATCGA AAACGAAATTGCGCGTATCAAAAAGCTGATTGGCG AACGTGGCGGTGGCAGCGGTGGCGGTAGCGGCGGT GGCAGCCAGGTGTCCCACCAATACCCCAGGATCCA GTCCATCAAGGTCCAGTTCACCGAGTACAAAAAGG AGGAGGGATTCATCCTGACCTCCCAAAAGGAGGAC GAGATCATGAAGGTGCAAAACAACTCCGTGATCAT CAACTGCGACGGCTTCTACCTGATCTCCCTGAAGG GCTACTTCTCCCAGGAGGTGAACATCTCCCTGCAC TACCAGAAGGACGAGGAGCCCCTGTTCCAGCTGAA GAAGGTGAGGTCCGTGAATTCCCTGATGGTGGCCA GCCTGACCTACAAGGACAAGGTCTACCTGAACGTG ACCACCGACAACACCAGCCTGGACGACTTCCATGT CAACGGCGGCGAGCTGATCCTGATCCATCAGAACC CCGGCGAGTTTTGCGTCCTG |

-continued

| SEQUENCE LISTING | | |
|---|---|---|
| SEQ ID NO: | | |
| 170 | Amino Acid Sequence | MGWSCIILFLVATATGVHSDYKDDDDKRMKQIEDKIEEILSKIYHIENEIARIKKLIGERGGGSGGGSGGGSQVSHQYPRIQSIKVQFTEYKKEEGFILTSQKEDEIMKVQNNSVIINCDGFYLISLKGYFSQEVNISLHYQKDEEPLFQLKKVRSVNSLMVASLTYKDKVYLNVTTDNTSLDDFHVNGGELILIHQNPGEFCVL |
| 171 Recombinant Human OX40R (Leader Sequence and Human Fc Sequence included) | Nucleotide Sequence | ATGGGCTGGTCCTGCATCATCCTGnTTCTGGTGGCCACCGCCACCGGCGTGCACAGCCTGCATTGCGTGGGCGACACCTATCCCTCCAACGACAGGTGCTGCCACGAGTGCAGGCCTGGAAACGGCATGGTGAGCAGGTGCAGCCGGTCCCAGAATACCGTGTGTAGGCCCTGCGGCCCCGGCTTTTACAACGACGTGGTGTCCTCCAAGCCCTGCAAGCCCTGCACATGGTGCAACCTGCGGTCCGGCAGCGAGAGGAAGCAGCTCTGCACAGCCACCCAGGACACCGTCTGTAGGTGTAGGGCTGGCACCCAGCCTCTGGACTCCTACAAGCCCGGCGTGGATTGTGCTCCTTGCCCTCCCGGCCATTTCTCCCCTGGCGACAACCAGGCTTGCAAGCCCTGGACCAACTGTACCCTGGCCGGCAAGCATACACTGCAGCCTGCTTCCAACTCCTCCGACGCTATCTGCGAGGATAGGGACCCCCCTGCCACACAACCCCAGGAGACACAGGGCCCTCCTGCTAGGCCCATCACAGTCCAACCCACCGAAGCCTGGCCCAGGACATCCCAAGGCCCTTCCACCAGGCCTGTGGAAGTGCCTGGAGGAAGGGCTGTGGCCATTGAAGGTCGTATGGATGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTTCCCTGACCTGTCTCGTGAAAGGCTTCTACCCCTCCGATATCGCCGTGGAATGGGAGTCCAACGGCCAGCCTGAGAACAACTACAAGACCACCCCCCCTCTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCTGA |
| 172 | Amino Acid Sequence | MGWSCIILFLVATATGVHSLHCVGDTYPSNDRCCHECRPGNGMVSRCSRSQNTVCRPCGPGFYNDVVSSKPCKPCTWCNLRSGSERKQLCTATQDTVCRCRAGTQPLDSYKPGVDCAPCPPGHFSPGDNQACKPWTNCTLAGKHTLQPASNSSDAICEDRDPPATQPQETQGPPARPITVQPTEAWPRTSQGPSTRPVEVPGGRAVAIEGRMDEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSP |
| 173 Cell Expressed OX40L (CHO/MEF) (Leader sequence included) | Nucleotide Sequence | ATGGAGAGGGTGCAGCCCCTCGAGGAGAACGTGGGAAACGCCGCCAGGCCTAGGTTCGAGAGGAACAAGCTGCTGCTGGTGGCTTCCGTGATCCAAGGACTCGGCCTGCTGCTCTGCTTCACCTACATCTGCCTCCACTTCAGCGCCCTGCAGGTGTCCCACCGATACCCCAGGATCCAGTCCATCAAGGTCCAGTTCACCGAGTACAAAAAGGAGAAGGGATTCATCCTGACCTCCCAAAAGGAGGACGAGATCATGAAGGTGCAAAACAACTCCGTGATCATCAACTGCGACGGCTTCTACCTGATCTCCCTGAAGGGCTACTTCTCCCAGGAGGTGAACATCTCCCTGCACTACCAGAAGGACGAGGAGCCCCTGTTCCAGC |

-continued

| SEQUENCE LISTING | | |
|---|---|---|
| SEQ ID NO: | | |
| | | TGAAGAAGGTGAGGTCCGTGAATTCCCTGATGGTG GCCAGCCTGACCTACAAGGACAAGGTCTACCTGAA CGTGACCACCGACAACACCAGCCTGGACGACTTCC ATGTCAACGGCGGCGAGCTGATCCTGATCCATCAG AACCCCGGCGAGTTTTGCGTCCTGTAA |
| 174 | Amino Acid Sequence | MERVQPLEENVGNAARPRFERNKLLLVASVIQGLG LLLCFTYICLHFSALQVSHRYPRIQSIKVQFTEYK KEKGFILTSQKEDEIMKVQNNSVIINCDGFYLISL KGYFSQEVNISLHYQKDEEPLFQLKKVRSVNSLMV ASLTYKDKVYLNVTTDNTSLDDFHVNGGELILIHQ NPGEFC |
| 175 Cell Expressed OX40 receptor (HT1080) | Nucleotide Sequence | ATGTGCGTGGGGGCTCGGCGGCTGGGCCGCGGGCC GTGTGCGGCTCTGCTCCTCCTGGGCCTGGGGCTGA GCACCGTGACGGGGCTCCACTGTGTCGGGGACACC TACCCCAGCAACGACCGGTGCTGCCACGAGTGCAG GCCAGGCAACGGGATGGTGAGCCGCTGCAGCCGCT CCCAGAACACGGTGTGCCGTCCGTGCGGGCCGGGC TTCTACAACGACGTGGTCAGCTCCAAGCCGTGCAA GCCCTGCACGTGGTGTAACCTCAGAAGTGGGAGTG AGCGGAAGCAGCTGTGCACGGCCACACAGGACACA GTCTGCCGCTGCCGGGCGGGCACCCAGCCCCTGGA CAGCTACAAGCCTGGAGTTGACTGTGCCCCCTGCC CTCCAGGGCACTTCTCCCCAGGCGACAACCAGGCC TGCAAGCCCTGGACCAACTGCACCTTGGCTGGGAA GCACACCCTGCAGCCGGCCAGCAATAGCTCGGACG CAATCTGTGAGGACAGGGACCCCCCAGCCACGCAG CCCCAGGAGACCCAGGGCCCCCCGGCCAGGCCCAT CACTGTCCAGCCCACTGAAGCCTGGCCCAGAACCT CACAGGGACCCTCCACCCGGCCCGTGGAGGTCCCC GGGGGCCGTGCGGTTGCCGCCATCCTGGGCCTGGG CCTGGTGCTGGGGCTGCTGGGCCCCCTGGCCATCC TGCTGGCCCTGTACCTGCTCCGGAGGGACCAGAGG CTGCCCCCCGATGCCCACAAGCCCCCTGGGGGAGG CAGTTTCCGGACCCCCATCCAAGAGGAGCAGGCCG ACGCCCACTCCACCCTGGCCAAGATCTGA |
| 176 | Amino Acid Sequence | MCVGARRLGRGPCAALLLLGLGLSTVTGLHCVGDT YPSNDRCCHECRPGNGMVSRCSRSQNTVCRPCGPG FYNDVVSSKPCKPCTWCNLRSGSERKQLCTATQDT VCRCRAGTQPLDSYKPGVDCAPCPPGHFSPGDNQA CKPWTNCTLAGKHTLQPASNSSDAICEDRDPPATQ PQETQGPPARPITVQPTEAWPRTSQGPSTRPVEVP GGRAVAAILGLGLVLGLLGPLAILLALYLLRRDQR LPPDAHKPPGGGSFRTPIQEEQADAHSTLAKI |
| 177 OX40L15B07 | Amino Acid Sequence of OX40L15B07 (Seq ID No 179 in WO2011/ 073180, Table A-1) | EVQLVESGGGLVQAGGSLRLSCAASRSIGRLDRMG WYRHRTGEPRELVATITGGSSINYGDFVKGRFTIS IDNAKNTVYLQMNNLKPEDTAVYYCNFNKYVTSRD TWGQGTQVTVSS |
| 178 OX40L01B11 | Amino Acid Sequence of OX40L01B11 (Seq ID No 180 in WO2011/ 073180, Table A-1) | EVQLVESGGGLVQAGGSLRLSCVASGRSFSTYIMG WFRQAPGKEREFVATISRSGITIRSADSVKGRFTI SRDNAKNTVYLQMNSLKPEDTAVYYCAAGPYVEQT LGLYQTLGPWDYWGQGTQVTVSS |
| 179 OX40L01E07 | Amino Acid Sequence of OX40L01E07 (Seq ID No 181 in WO2011/ 073180, Table A-1) | EVQLVESGGGLVQAGGSLRLSCAASGRTFSSIYAK GWFRQAPGKEREFVAAISRSGRSTSYADSVKGRFT ISRDNAKNTVYLQMNSLKPEDTAVYYCAAVGGATT VTASEWDYWGLGTQVTVSS |
| 180 OX40L01E10 | Amino Acid Sequence of OX40L01E10 (Seq ID No 182 in WO2011/ 073180, Table A-1) | EVQLVESGGGLVQAGDSLRLSCAASGLTFSSFAMG WFRQAPGKEREFVAAISRSGYGTSEADSVRDRFII SRDNAKNTVTLHLSRLKPEDTAVYYCAAEHTLGRP SRSQINYLYWGQGTQVTVSS |
| 181 OX40L18E09 | Amino Acid Sequence of OX40L18E09 (Seq ID No 183 in WO2011/ 073180, Table A-1) | EVQLVESGGGLVQAGGSLRLSCAASRNILSLNTMG WYRHAPGKPRELVARISSNSKTDYADSVKGRFTIS RDNAKNTVLLQMNSLKPEDTGVYYCNLNVWRTSSD YWGQGTQVTVSS |

-continued

| SEQUENCE LISTING | | |
|---|---|---|
| SEQ ID NO: | | |
| 182 OX40L19A07 | Amino Acid Sequence of OX40L19A07 (Seq ID No 184 in WO2011/ 073180, Table A-1) | EVQLVESGGGLVQAGGSLRLSCAASGFTLDDYAIA WFRQAPGKEREGVSRIKISNGRTTYAGSVKGRFTI SSDNAKNTVYLQMNSLNAEDTAVYYCAADRSSLLF GSNWDRKARYDYWGQGTQVTVSS |
| 183 OX40L19D08 | Amino Acid Sequence of OX40L19D08 (Seq ID No 185 in WO2011/ 073180, Table A-1) | EVQLVESGGGLVQAGASLRLSCAASGRRFISNYAM GWFRQAPGQERAFVAAISRSGSITYYTDSVKGRFS ISRDYAKSTVYLQMDNLKPEDTAVYYCAADGGAVR DLTTNLPDYWGRGTQVTVSS |
| 184 OX40L075 | Amino Acid Sequence of OX40L075 (Seq ID No 199 in WO2011/ 073180, Table A-2) | EVQLVESGGGLVQPGGSLRLSCAASGRSFSTYIMG WFRQAPGKEREFVATISRSGITTRSADSVKGRFTI SRDNSKNTVYLQMNSLRPEDTAVYYCAAGPYVEQT LGLYQTLGPWDYWGQGTLVTVSS |
| 185 OX40L024 | Amino Acid Sequence of OX40L024 (Seq ID No 200 in WO2011/ 073180, Table A-2) | EVQLVESGGGLVQPGGSLRLSCAASGRTFSSIYAK GWFRQAPGKEREFVAAISRSG RSTSYADSVKG R FTISRD NAKNTVYLQMNSLRPEDTAVYYCAAVGG ATTVTASEWDYWGLGTLVTVSS |
| 186 OX40L025 | Amino Acid Sequence of OX40L025 (Seq ID No 201 in WO2011/ 073180, Table A-2) | EVQLVESGGGLVQPGGSLRLSCAASGRTFSSIYAK GWFRQAPGKEREFVAAISRSG RSTSYADSVKG R FTISRD NSKNTVYLQMNSLRPEDTAVYYCAAVGG ATTVTASEWDYWGLGTLVTVSS |
| 187 OX40L026 | Amino Acid Sequence of OX40L026 (Seq ID No 202 in WO2011/ 073180, Table A-2) | EVQLVESGGGLVQPGGSLRLSCAASGRTFSSIYAK GWFRQAPGKEREFVAAISRSG RSTSYADSVKG R FTISRD NAKNTVYLQMNSLRPEDTAVYYCAAVGG ATTVTASEWDYWGQGTLVTVSS |
| 188 OX40L027 | Amino Acid Sequence of OX40L027 (Seq ID No 203 in WO2011/ 073180, Table A-2) | EVQLVESGGGLVQPGGSLRLSCAASGRTFSSIYAK GWFRQAPGKEREFVAAISRSG RSTSYADSVKG R FTISRDNSKNTVYLQM NSLRPEDTAVYYCAAVGG ATTVTASEWDYWGQGTLVTVSS |
| 189 OX40L028 | Amino Acid Sequence of OX40L028 (Seq ID No 204 in WO2011/ 073180, Table A-2) | DVQLVESGGGLVQPGGSLRLSCAASGRTFSSIYAK GWFRQAPGKEREFVAAISRSG RSTSYADSVKG R FTISRD NAKNTVYLQMNSLRPEDTAVYYCAAVGG ATTVTASEWDYWGLGTLVTVSS |
| 190 OX40L039 | Amino Acid Sequence of OX40L039 (Seq ID No 205 in WO2011/ 073180, Table A-2) | DVQLVESGGGLVQPGGSLRLSCAASGRTFSSIYAK GWFRQAPGKEREFVAAISRSG RSTSYADSVKG R FTISRD NSKNTVYLQMNSLRPEDTAVYYCAAVGG ATTVTASEWDYWGQGTLVTVSS |
| 191 OX40L030 | Amino Acid Sequence of OX40L030 (Seq ID No 206 in WO2011/ 073180, Table A-2) | DVQLVESGGGLVQAGGSLRLSCAASRSIGRLDRMG WYRHRTGEPRELVATITGGSSINYG D FVKG RF TISID NAKNTVYLQM N NLKPEDTAVYYCNFNK YVTSRDTWGQGTQVTVSS |
| 192 OX40L040 | Amino Acid Sequence of OX40L040 (Seq ID No 207 in WO2011/ 073180, Table A-2) | DVQLVESGGGLVQPGGSLRLSCAASRSIGRLDRMG WYRHRTGEPRELVATITGGSSINYG D FVKG RF TISRDNSKNTVYLQM NSLRPEDTAVYYCNFNKYV TSRDTWGQGTLVTVSS |
| 193 OX40L041 | Amino Acid Sequence of OX40L041 (Seq ID No 208 in WO2011/ 073180, Table A-2) | DVQLVESGGGLVQPGGSLRLSCAASRSIGRLDRMG WYRHATGEPRELVATITGGSSINYG D FVKG RF TISRDNSKNTVYLQMNSLRPEDTAVYYCNFNKYVT SRDTWGQGTLVTVSS |
| 194 OX40L042 | Amino Acid Sequence of OX40L042 (Seq ID No 209 in WO2011/ 073180, Table A-2) | DVQLVESGGGLVQPGGSLRLSCAASRSIGRLDRMG WYRHRPGEPRELVATITGGSSINYG D FVKG RF TISRDNSKNTVYLQM NSLRPEDTAVYYCNFNKYV TSRDTWGQGTLVTVSS |
| 195 OX40L043 | Amino Acid Sequence of OX40L043 (Seq ID No 210 in WO2011/ 073180, Table A-2) | DVQLVESGGGLVQPGGSLRLSCAASRSIGRLDRMG WYRHRTGKPRELVATITGGSSINYG D FVKG RF TISRDNSKNTVYLQM NSLRPEDTAVYYCNFNKYV TSRDTWGQGTLVTVSS |

-continued

SEQUENCE LISTING

| SEQ ID NO: | | | |
|---|---|---|---|
| 196 | OX40L044 | Amino Acid Sequence of OX40L044 (Seq ID No 211 in WO2011/ 073180, Table A-2) | DVQLVESGGGLVQPGGSLRLSCAASRSIGRLDRMG WYRHAPGEPRELVATITGGSSINYG D FVKG RF TISRDNSKNTVYLQM NSLRPEDTAVYYCNFN KYVTSRDTWGQGTLVTVSS |
| 197 | OX40L045 | Amino Acid Sequence of OX40L045 (Seq ID No 212 in WO2011/ 073180, Table A-2) | DVQLVESGGGLVQPGGSLRLSCAASRSIGRLDRMG WYRHATGKPRELVATITGGSSINYG D FVKG RF TISRDNSKNTVYLQM NSLRPEDTAVYYCNFNKYV TSRDTWGQGTLVTVSS |
| 198 | OX40L046 | Amino Acid Sequence of OX40L046 (Seq ID No 213 in WO2011/ 073180, Table A-2) | DVQLVESGGGLVQPGGSLRLSCAASRSIGRLDRMG WYRHRPGKPRELVATITGGSSINYG D FVKG RF TISRDNSKNTVYLQM NSLRPEDTAVYYCNFNKYV TSRDTWGQGTLVTVSS |
| 199 | OX40L047 | Amino Acid Sequence of OX40L047 (Seq ID No 214 in WO2011/ 073180, Table A-2) | DVQLVESGGGLVQPGGSLRLSCAASRSIGRLDRMG WYRHAPGKPRELVATITGGSSINYG D FVKG RF TISRDNSKNTVYLQM NSLRPEDTAVYYCNFNKYV TSRDTWGQGTLVTVSS |
| 200 | OX40L048 | Amino Acid Sequence of OX40L048 (Seq ID No 215 in WO2011/ 073180, Table A-2) | DVQLVESGGGLVQPGGSLRLSCAASRSIGRLDRMG WYRHRTGEPRELVATITGGSSINYADFVKG RFTI SRDNSKNTVYLQM NSLRPEDTAVYYCNFNKYVTS RDTWGQGTLVTVSS |
| 201 | OX40L049 | Amino Acid Sequence of OX40L049 (Seq ID No 216 in WO2011/ 073180, Table A-2) | DVQLVESGGGLVQPGGSLRLSCAASRSIGRLDRMG WYRHRTGEPRELVATITGGSSINYG DSVKG RFT ISRDNSKNTVYLQM NSLRPEDTAVYYCNFNKYVT SRDTWGQGTLVTVSS |
| 202 | OX40L050 | Amino Acid Sequence of OX40L050 (Seq ID No 217 in WO2011/ 073180, Table A-2) | DVQLVESGGGLVQPGGSLRLSCAASRSIGRLDRMG WYRHRTGEPRELVATITGGSSINYADSVKG RFTI SRD NSKNTVYLQMN SLRPEDTAVYYCNFNKYVT SRDTWGQGTLVTVSS |
| 203 | OX40L053 | Amino Acid Sequence of OX40L053 (Seq ID No 218 in WO2011/ 073180, Table A-2) | DVQLVESGGGLVQPGGSLRLSCAASRSIGRLDRMG WYRHRTGEPRELVATITGGSSINYGDFVKGRFTIS IDNSKNTVYLQM NSLRPEDTAVYYCNFNKYVTS RDTWGQGTLVTVSS |
| 204 | OX40L054 | Amino Acid Sequence of OX40L054 (Seq ID No 219 in WO2011/ 073180, Table A-2) | DVQLVESGGGLVQPGGSLRLSCAASRSIGRLDRMG WYRHRTGEPRELVATITGGSSINYG D FVKGRFT ISRDNAKNTVYLQM NSLRPEDTAVYYCNFNKYVT SRDTWGQGTLVTVSS |
| 205 | OX40L055 | Amino Acid Sequence of OX40L055 (Seq ID No 220 in WO2011/ 073180, Table A-2) | DVQLVESGGGLVQPGGSLRLSCAASRSIGRLDRMG WYRHRTGEPRELVATITGGSSINYGDFVKGRFTIS RDNSKNTVYLQM NN LRPEDTAVYYCN FNKYVT SRDTWGQGTLVTVSS |
| 206 | OX40L056 | Amino Acid Sequence of OX40L056 (Seq ID No 221 in WO2011/ 073180, Table A-2) | DVQLVESGGGLVQPGGSLRLSCAASRSIGRLDRMG WYRHRPGKPRELVATITGGSSINYADSVKG RFTI SRD NSKNTVYLQMN SLRPEDTAVYYCNFNKYVT SRDTWGQGTLVTVSS |
| 207 | OX40L069 | Amino Acid Sequence of OX40L069 (Seq ID No 222 in WO2011/ 073180, Table A-2) | DVQLVESGGGLVQPGGSLRLSCAASRSIGRLDRMG WYRHRPGKPRELVATITGGSSINYADSVKG RFTI SI DNSKNTVYLQM NSLRPE DTAVYYCNFN KY VTS RDTWGQGTLVTVSS |
| 208 | OX40L070 | Amino Acid Sequence of OX40L070 (Seq ID No 223 in WO2011/073180, Table A-2) | DVQLVESGGGLVQPGGSLRLSCAASRSIGRLDRMG WYRHRPGKPRELVATITGGSSINYADSVKG RFTI SRD NSKNTVYLQM N N LRPEDTAVYYCNFNKY VTSRDTWGQGTLVTVSS |
| 209 | OX40L071 | Amino Acid Sequence of OX40L071 (Seq ID No 224 in WO2011/ 073180, Table A-2) | DVQLVESGGGLVQPGGSLRLSCAASRSIGRLDRMG WYRHRPGKPRELVATITGGSSINYADSVKG RFTI SI DNSKNTVYLQM N N LRPEDTAVYYCNFNKY VTSRDTWGQGTLVTVSS |

-continued

SEQUENCE LISTING

| SEQ ID NO: | | | |
|---|---|---|---|
| 210 | OX40L082 | Amino Acid Sequence of OX40L082 (Seq ID No 225 in WO2011/073180, Table A-2) | EVQLVESGGGLVQPGGSLRLSCAASRSIGRLDRMG WYRHRPGEPRELVATITGGSSINYGDSVKGRFTIS IDNSKNTVYLQM NSLRPEDTAVYYCNFNKYVTS RDTWGQGTLVTVSS |
| 211 | OX40L083 | Amino Acid Sequence of OX40L083 (Seq ID No 226 in WO2011/073180, Table A-2) | EVQLVESGGGLVQPGGSLRLSCAASRSIGRLDRMG WYRHRPGKPRELVATITGGSSINYGDSVKGRFTIS IDNSKNTVYLQMNSLRPEDTAVYYCN FNK YVTS RDTWGQGTLVTVSS |
| 212 | OX40L benchmark antibodγ heavy chain | Amino acid sequence of OX40L benchmark antibodγ heavy chain (Seq ID No: 177 in WO2011/073180, Table A-5) | EVQLLESGGGLVQPGGSLRLSCAASGFTFNSYAMS WVRQAPGKGLEWVSIISGSGGFTYYADSVKGRFTI SRDNSRTTLYLQMNSLRAEDTAVYYCAKDRLVAPG TFDYWGQGALVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPS NTKVDKKVEPKSCDKTHTCPPCPAPELLGGPSVFL FP PKPKDTLM IS RTPEVTCVVVDVSH E D P EVKFNWYVDGVEVHNAKTKPREEQYNSTYRVVSV LTVLHQDWLNG KEYKCKVSN KALPAPI EKTIS KAKGQPREPQVYTLPPSRDELTKNQVSLTCLVKG FYPSDIAVEWESNGQPE N NYKTTPPVLDSDGSF FLYSKLTVD KSRWQQG NVFSCSV M HEALH N HYTQKSLSLSPGK |
| 213 | OX40L benchmark antibody light chain | Amino acid sequence of OX40L benchmark antibody light chain (Seq ID No: 178 in WO2011/073180, Table A-5) | DIQMTQSPSSLSASVGDRVTITCRASQGISSWLAW YQQKPEKAPKSLIYAASSLQSGVPSRFSGSGSGTD FTLTISSLQPEDFATYYCQQYNSYPYTFGQGTKLE IKRTVAAPSVFIFPPSD EQLKSGTASVVCLLN N FY PREAKVQWKVDNALQSG NSQESVTEQDSKDSTYS LSSTLTLSKADYEKH KVYACEVTHQGLSSPVTKS FNRGEC |
| 214 | κ light chain variable region of LC.001 | Amino acid sequence of kappa light chain variable region of LC.001 (Seq ID No: 1 in WO2006/029879) | DIQMTQSPSSLSASVGDRVTITCRASQGISSWLAW YQQKPEKAPKSLIYAASSLQSGVPSRFSGSGSGTD FTLTISSLQPEDFATYYCQQYNSYPYTFGQGTKLE IK |
| 215 | γ heavy chain variable region of LC.001 | Amino acid sequence of γ heavy chain variable region of LC.001 (Seq ID No: 2 in WO2006/029879) | EVQLLESGGGLVQPGGSLRLSCAASGFTFNSYAMS WVRQAPGKGLEWVSIISGSGGFTYYADSVKGRFTI SRDNSRTTLYLQMNSLRAEDTAVYYCAKDRLVAPG TFDYWGQGALVTVSS |
| 216 | κ light chain variable region of LC.005 | Amino acid sequence of kappa light chain variable region of LC.005 (Seq ID No: 3 in WO2006/029879) | EIVLTQSPGTLSLSPGERATLSCRASQSVSSNYLA WYQQKPGQAPRLLIYGASSRATGIPDRFSGSGSGT DFTLTISRLEPEDFAVYYCQQYGSSFTFGPGTKVD IK |
| 217 | γ heavy chain variable region of LC.005 | Amino acid sequence of γ heavy chain variable region of LC.005 (Seq ID No: 4 in WO2006/029879) | QVQLVESGGGVVQPGRSLRLSCAASGFTFSNFGMH WVRQAPGKGLEWVAAIWYDGHDKYYSYYVKGRFTI SRDNSKNTLFLQMNSLRAEDTAVYYCARDSSSWYR YFDYWGQGTLVTVSS |
| 218 | κ light chain variable region of LC.010 | Amino acid sequence of kappa light chain variable region of LC.010 (Seq ID No: 5 in WO2006/029879) | EIVLTQSPGTLSLSPGERATLSCRASQSVSSSYLA WYQQKPGQAPRLLIYGASSRATGIPDRFSGSGSGT DFTLTISRLEPEDFAVYYCQQYGSSFTFGPGTKVD IK |
| 219 | γ heavy chain variable region of LC.010 | Amino acid sequence of γ heavy chain variable region of LC.010 (Seq ID No: 6 in WO2006/029879) | QVQLVESGGGVVQPGRSLRLSCAASGFTFSNFGMH WVRQAPGKGLEWVAAIWYDGHDKYYAYYVKGRFTI SRDNSKNTLFLQMNSLRAEDTAVYYCARDSSSWYR YFDYWGQGTLVTVSS |
| 220 | κ light chain variable region of LC.029 | Amino acid sequence of kappa light chain variable region of LC.029 (Seq ID No: 7 in WO2006/029879) | MLHPLCKVGSHQGSVAVDLGQISLSPSAACSLKIL QLITVNSIIVSLTFGGGTKVEIK |
| 221 | γ heavy chain variable region of LC.029 | Amino acid sequence of γ heavy chain variable region of LC.029 (Seq ID No: 8 in WO2006/029879) | QVQLVESGGGVVQPGRSLRLSCAASGFTFSNFGMH WVRQAPGKGLEWVAAIWYDGHDKYYSYYVKGRFTI SRDNSKNTLFLQMNSLRAEDTAVYYCARDSSSWYR YFDYWGQGTLVTVSS |

-continued

SEQUENCE LISTING

| SEQ ID NO: | | | |
|---|---|---|---|
| 222 | κ light chain variable region of LC.019 | Amino acid sequence of kappa light chain variable region of LC.019 (Seq ID No: 9 in WO2006/029879) | MPPVWKVGSHQGSAAVDLGQISLSPSAACSLKILQLITVNSLIVTLTFGGGTKVEIK |
| 223 | γ heavy chain variable region of LC.019 | Amino acid sequence of γ heavy chain variable region of LC.019 (Seq ID No: 10 in WO2006/029879) | QVQLVESGGGVVQPGRSLRLSCAASGFTFSSYTMHWVRQAPGKGLEWVAVIWYDGSNKYYVDSVKGRFTISRDNSKNTLYLQMNSLRAEDTAVYYCARKNWSFDFWGQGTLVTVSS |
| 224 | κ light chain variable region of LC.033 | Amino acid sequence of kappa light chain variable region of LC.033 (Seq ID No: 11 in WO2006/029879) | EIVLTQSPATLSLSPGERATLSCRASQGVSRYLAWYQQKPGQAPRLLIYDASNRATGIPARVSGSGPGTDFTLTISSLEPEDFAVDYCQQRSNWQYTFGQGTKLEI |
| 225 | γ heavy chain variable region of LC.033 | Amino acid sequence of γ heavy chain variable region of LC.033 (Seq ID No: 12 in WO2006/029879) | QKQLVEFGGGVVQPGRSLRLSCAASGFTFSNYGMHWVRQAPGKGLEWVAVIWNDGSNKYYVDSVKGRFIISRDNSKNTLYLQMNSLRAEDTAVYYCARDRMGIYYYGMDVWGQGTTVTVSS |
| 226 | mutant κ light chain variable region of LC.033 | Amino acid sequence of mutant kappa light chain variable region of LC.033 (Seq ID No: 16 in WO2006/029879) | EIVLTQSPATLSLSPGERATLSCRASQSVSSYLAWYQQKPGQAPRLLIYDASNRATGIPARFSGSGSGTDFTLTISSLEPEDFAVYYCQQRSNWTFGQGTKVE1 |
| 227 | γ heavy chain variable region of LC.059 | Amino acid sequence of γ heavy chain variable region of LC.059 (Seq ID No: 17 in WO2006/029879) | EVQLLESGGGLVQPGGSLRLSCAASGFTFSSYAMNWVRQAPGKGLEWVSIISGSGGFTYYADSVKGRFTISRDNSKNTLYLQMNRLRAEDTAIYFCAKDDIPAAGTFDPWGQGTLVTVSS |
| 228 | κ light chain variable region of LC.060 | Amino acid sequence of kappa light chain variable region of LC.060 (Seq ID No: 18 in WO2006/029879) | AIQLTQSPSSLSASVGDRVTITCRASQGISSALAWYQQKPGKAPKLLIYDVSSLESGVPSRFSGSGSGTDFTLTISSLQPEDFATYYCQQFNSYWTFGQGTKVEIK |
| 229 | γ heavy chain variable region of LC.060 | Amino acid sequence of γ heavy chain variable region of LC.060 (Seq ID No: 19 in WO2006/029879) | EVQLLESGGGLVQPGGSLRLSCAASGFTFSSYAMSWVRQAPGKGLEWVSLISGSGGLTKYADSVKGRFTISRDNSKRTLYLQMNSLRAEDTAVYYCAKDILVTGALDYWGQGTLVTVSS |
| 230 | γ heavy chain variable region of LC.063 | Amino acid sequence of γ heavy chain variable region of LC.063 (Seq ID No: 20 in WO2006/029879) | EVQLLESGGGLVQPGGSLRLSCAASGFTFSSYAMNWVRQAPGKGLEWVSIISGSGGFTYYADSVKGRFTISRDNSKKTLYLQMSRLRAEDTAIYFCAKDDIPAAGTFDPWGQGTLVTVSS |
| 231 | 8E12 light chain variable region | Amino acid sequence of 8E12 light chain variable region (Seq ID No: 13 in U.S. Pat. No. 7,812,133) | DILMTQTPLSLPVSLGDQASISCRSSQSIVHGNGNTYLEWHLQKPGQSPKLLIYRVSNRFSGVPDRFSGSGSGTDFTLKINRVEAEDLGVYYCFQGSHVPYTFGGGTKVEIKR |
| 232 | 8E12 heavy chain variable region | Amino acid sequence of 8E12 heavy chain variable region (Seq ID No: 14 in U.S. Pat. No. 7,812,133) | DIVMTQTPLSLPVSLGDQASMYCRSSQSPVHSNGNTYLHWYLQKPGQSPKLLIYKVSNRFSGVPDRFSGSGSGTDFTLKISRVEAEDLGVYFCSQSTHIPWTFGGGTKVEIKR |
| 233 | 13G5 light chain variable region | Amino acid sequence of 13G5 light chain variable region (Seq ID No: 15 in U.S. Pat. No. 7,812,133) | QVQLQQPGAELVRPGASVkLSCKASGYTFTSYWLNWVKQRPGQGLEWIVMIDPSDSETHYNQVFKDKATLTVDKSSSTAYMQLSSLTSEDSAVYYCIRGRGNFYGGSHAMEYWGQGTLLTVSS |
| 234 | 13G5 heavy chain variable region | Amino acid sequence of 13G5 heavy chain variable region (Seq ID No: 16 in U.S. Pat. No. 7,812,133) | QVQLQQPGAELVKPGTSVKLSCKASGYSFTSYWMHGVRQRPGQGLEWIGEIDPSNGRTNYNEKFKSKATLTVDKSSSTAYIQLSSLTSEDSAVYYCTRERSPRYFDVWGAGTTLTVSS |
| 235 | | HCDR3 motif | VRGXYYY |

IMGT indicates that CDR is determined using IMGT nomenclature;
KABAT indicates that CDR is determined using Kabat nomenclature.
The numbering in the sequence correlation table takes precedence over any inconsistent numbering elsewhere in this text

SEQUENCE LISTING

```
Sequence total quantity: 235
SEQ ID NO: 1            moltype = DNA  length = 384
FEATURE                 Location/Qualifiers
source                  1..384
                        mol_type = other DNA
                        organism = Homo sapiens
SEQUENCE: 1
gaggtgcaac tggtggagtc tgggggagtc ttggtacagc cggggggtc cctgagactc  60
tcctgtgcag cctctggatt cacctttagc agttatatta tgacttgggt ccgccaggct  120
ccagggaagg ggctggagtg ggtctcaggt attagtggta gtggtggtgg tacatactac  180
gcagactcca tgaagggccg gttcaccatc tccagagaca attccaagaa cacgctgtat  240
ctgcagatga acagcctgag agtcgaggac acggccgtat attactgtgc gaaagatcgg  300
ttaggtccga ttactttggt tcgggggggc tattactacg gtatggacgt ctggggccaa  360
gggaccacgg tcaccgtctc ctca                                         384

SEQ ID NO: 2            moltype = AA  length = 128
FEATURE                 Location/Qualifiers
source                  1..128
                        mol_type = protein
                        organism = Homo sapiens
SEQUENCE: 2
EVQLVESGGV LVQPGGSLRL SCAASGFTFS SYIMTWVRQA PGKGLEWVSG ISGSGGGTYY  60
ADSMKGRFTI SRDNSKNTLY LQMNSLRVED TAVYYCAKDR LGPITLVRGG YYYGMDVWGQ  120
GTTVTVSS                                                           128

SEQ ID NO: 3            moltype = DNA  length = 24
FEATURE                 Location/Qualifiers
source                  1..24
                        mol_type = other DNA
                        organism = Homo sapiens
SEQUENCE: 3
ggattcacct ttagcagtta tatt                                         24

SEQ ID NO: 4            moltype = AA  length = 8
FEATURE                 Location/Qualifiers
source                  1..8
                        mol_type = protein
                        organism = Homo sapiens
SEQUENCE: 4
GFTFSSYI                                                           8

SEQ ID NO: 5            moltype = DNA  length = 24
FEATURE                 Location/Qualifiers
source                  1..24
                        mol_type = other DNA
                        organism = Homo sapiens
SEQUENCE: 5
attagtggta gtggtggtgg taca                                         24

SEQ ID NO: 6            moltype = AA  length = 8
FEATURE                 Location/Qualifiers
source                  1..8
                        mol_type = protein
                        organism = Homo sapiens
SEQUENCE: 6
ISGSGGGT                                                           8

SEQ ID NO: 7            moltype = DNA  length = 63
FEATURE                 Location/Qualifiers
source                  1..63
                        mol_type = other DNA
                        organism = Homo sapiens
SEQUENCE: 7
gcgaaagatc ggttaggtcc gattactttg gttcgggggg gctattacta cggtatggac  60
gtc                                                                63

SEQ ID NO: 8            moltype = AA  length = 21
FEATURE                 Location/Qualifiers
source                  1..21
                        mol_type = protein
                        organism = Homo sapiens
SEQUENCE: 8
AKDRLGPITL VRGGYYYGMD V                                            21

SEQ ID NO: 9            moltype = DNA  length = 15
FEATURE                 Location/Qualifiers
source                  1..15
                        mol_type = other DNA
```

```
                       organism = Homo sapiens
SEQUENCE: 9
agttatatta tgact                                                   15

SEQ ID NO: 10          moltype = AA  length = 5
FEATURE                Location/Qualifiers
source                 1..5
                       mol_type = protein
                       organism = Homo sapiens
SEQUENCE: 10
SYIMT                                                              5

SEQ ID NO: 11          moltype = DNA  length = 51
FEATURE                Location/Qualifiers
source                 1..51
                       mol_type = other DNA
                       organism = Homo sapiens
SEQUENCE: 11
ggtattagtg gtagtggtgg tggtacatac tacgcagact ccatgaaggg c           51

SEQ ID NO: 12          moltype = AA  length = 17
FEATURE                Location/Qualifiers
source                 1..17
                       mol_type = protein
                       organism = Homo sapiens
SEQUENCE: 12
GISGSGGGTY YADSMKG                                                 17

SEQ ID NO: 13          moltype = DNA  length = 57
FEATURE                Location/Qualifiers
source                 1..57
                       mol_type = other DNA
                       organism = Homo sapiens
SEQUENCE: 13
gatcggttag gtccgattac tttggttcgg gggggctatt actacggtat ggacgtc     57

SEQ ID NO: 14          moltype = AA  length = 19
FEATURE                Location/Qualifiers
source                 1..19
                       mol_type = protein
                       organism = Homo sapiens
SEQUENCE: 14
DRLGPITLVR GGYYYGMDV                                               19

SEQ ID NO: 15          moltype = DNA  length = 321
FEATURE                Location/Qualifiers
source                 1..321
                       mol_type = other DNA
                       organism = Homo sapiens
SEQUENCE: 15
gacatccaga tgacccagtc tccatcctcc ctgtctgcat ctgtaggaga cagagtcacc  60
atcacttgcc gggcaagtca gagcattagc gactatttaa attggtatca gcagaaacca  120
gggaaagccc ctaagttcct gatctatgct gcatccagtt tgcaaagtgg agtcccatca  180
aggttcagtg gcagtggatc tgggacagat ttcactctca ccgtcagcag tctgcaacct  240
gaagattttg caacttacta ctgtcaacag agttacagta cccctcggac gttcggccaa  300
gggaccaggg tggaaatcaa a                                            321

SEQ ID NO: 16          moltype = AA  length = 107
FEATURE                Location/Qualifiers
source                 1..107
                       mol_type = protein
                       organism = Homo sapiens
SEQUENCE: 16
DIQMTQSPSS LSASVGDRVT ITCRASQSIS DYLNWYQQKP GKAPKFLIYA ASSLQSGVPS  60
RFSGSGSGTD FTLTVSSLQP EDFATYYCQQ SYSTPRTFGQ GTRVEIK                107

SEQ ID NO: 17          moltype = DNA  length = 18
FEATURE                Location/Qualifiers
source                 1..18
                       mol_type = other DNA
                       organism = Homo sapiens
SEQUENCE: 17
cagagcatta gcgactat                                                18

SEQ ID NO: 18          moltype = AA  length = 6
FEATURE                Location/Qualifiers
source                 1..6
                       mol_type = protein
                       organism = Homo sapiens
```

```
SEQUENCE: 18
QSISDY                                                                6

SEQ ID NO: 19          moltype =   length =
SEQUENCE: 19
000

SEQ ID NO: 20          moltype =   length =
SEQUENCE: 20
000

SEQ ID NO: 21          moltype = DNA  length = 27
FEATURE                Location/Qualifiers
source                 1..27
                       mol_type = other DNA
                       organism = Homo sapiens
SEQUENCE: 21
caacagagtt acagtacccc tcggacg                                         27

SEQ ID NO: 22          moltype = AA  length = 9
FEATURE                Location/Qualifiers
source                 1..9
                       mol_type = protein
                       organism = Homo sapiens
SEQUENCE: 22
QQSYSTPRT                                                             9

SEQ ID NO: 23          moltype = DNA  length = 33
FEATURE                Location/Qualifiers
source                 1..33
                       mol_type = other DNA
                       organism = Homo sapiens
SEQUENCE: 23
cgggcaagtc agagcattag cgactattta aat                                  33

SEQ ID NO: 24          moltype = AA  length = 11
FEATURE                Location/Qualifiers
source                 1..11
                       mol_type = protein
                       organism = Homo sapiens
SEQUENCE: 24
RASQSISDYL N                                                          11

SEQ ID NO: 25          moltype = DNA  length = 21
FEATURE                Location/Qualifiers
source                 1..21
                       mol_type = other DNA
                       organism = Homo sapiens
SEQUENCE: 25
gctgcatcca gtttgcaaag t                                               21

SEQ ID NO: 26          moltype = AA  length = 7
FEATURE                Location/Qualifiers
source                 1..7
                       mol_type = protein
                       organism = Homo sapiens
SEQUENCE: 26
AASSLQS                                                               7

SEQ ID NO: 27          moltype = DNA  length = 27
FEATURE                Location/Qualifiers
source                 1..27
                       mol_type = other DNA
                       organism = Homo sapiens
SEQUENCE: 27
caacagagtt acagtacccc tcggacg                                         27

SEQ ID NO: 28          moltype = AA  length = 9
FEATURE                Location/Qualifiers
source                 1..9
                       mol_type = protein
                       organism = Homo sapiens
SEQUENCE: 28
QQSYSTPRT                                                             9

SEQ ID NO: 29          moltype = DNA  length = 1365
FEATURE                Location/Qualifiers
source                 1..1365
                       mol_type = other DNA
```

```
                         organism = Homo sapiens
SEQUENCE: 29
gaggtccagc tcgtggaaag cggaggagtg ctcgtgcagc ctggaggcag cctcaggctg  60
tcctgtgccg cctccggctt caccttcagc agctacatca tgacctgggt gaggcaggct  120
cccggaaaag gcctggagtg ggtgtccggc atctccggat ccggaggagg cacatactac  180
gccgacagca tgaagggccg gttcaccatc agccgggaca atagcaagaa taccctctac  240
ctgcaaatga acagcctgcg ggtggaggat accgccgtgt actactgcgc caaagatagg  300
ctgggcccca ttaccctcgt gaggggaggc tattactacg gcatggatgt gtggggccag  360
ggcaccaccg tgacagtgtc cagcgccagc accaagggcc cttccgtgtt ccccctggcc  420
ccttgcagca ggagcacctc cgaatccaca gctgccctgg gctgtctggt gaaggactac  480
tttcccgagc ccgtgaccgt gagctggaac agcggcgctc tgacatccgg cgtccacacc  540
tttcctgccg tcctgcagtc ctccggcctc tactccctgt cctccgtggt gaccgtgcct  600
agctcctccc tcggcaccaa gacctacacc tgtaacgtgg accacaaacc ctccaacacc  660
aaggtggaca aacgggtcga gagcaagtac ggccctccct gccctccttg tcctgccccc  720
gagttcgaag gcggacccag cgtgttcctg ttccctccta agcccaagga caccctcatg  780
atcagccgga cacccgaggt gacctgcgtg gtggtggatg tgagccagga ggaccctgag  840
gtccagttca actggtatgt ggatggcgtg gaggtgcaca acgccaagac aaagccccgg  900
gaagagcagt tcaactccac ctacagggtg gtcagcgtgc tgaccgtgct gcatcaggac  960
tggctgaacg gcaaggagta caagtgcaag gtcagcaata agggactgcc cagcagcatc  1020
gagaagacca tctccaaggc taaaggccag ccccgggaac ctcaggtgta caccctgcct  1080
cccagccagg aggagatgac caagaaccag gtgagcctga cctgcctggt gaagggattc  1140
tacccttccg acatcgccgt ggagtgggag tccaacggcc agcccgagaa caattataag  1200
accacccctc ccgtcctcga cagcgacgga tccttctttc tgtactccag gctgaccgtg  1260
gataagtcca ggtggcagga aggcaacgtg ttcagctgct ccgtgatgca cgaggccctg  1320
cacaatcact acacccagaa gtccctgagc ctgtccctgg gaaag                 1365

SEQ ID NO: 30            moltype = AA  length = 455
FEATURE                  Location/Qualifiers
source                   1..455
                         mol_type = protein
                         organism = Homo sapiens
SEQUENCE: 30
EVQLVESGGV LVQPGGSLRL SCAASGFTFS SYIMTWVRQA PGKGLEWVSG ISGSGGGTYY  60
ADSMKGRFTI SRDNSKNTLY LQMNSLRVED TAVYYCAKDR LGPITLVRGG YYYGMDVWGQ  120
GTTVTVSSAS TKGPSVFPLA PCSRSTSEST AALGCLVKDY FPEPVTVSWN SGALTSGVHT  180
FPAVLQSSGL YSLSSVVTVP SSSLGTKTYT CNVDHKPSNT KVDKRVESKY GPPCPPCPAP  240
EFEGGPSVFL FPPKPKDTLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVMHEAL HNHYTQKSLS LSLGK                            455

SEQ ID NO: 31            moltype = DNA  length = 642
FEATURE                  Location/Qualifiers
source                   1..642
                         mol_type = other DNA
                         organism = Homo sapiens
SEQUENCE: 31
gacatccaga tgacccagtc cccttcctcc ctgtccgcct ccgtgggaga cagggtgacc  60
atcacctgcc gggccagcca gtccatcagc gactacctga actggtatca gcagaagccc  120
ggcaaggccc ctaagttcct gatctacgcc gcttcctccc tgcagtccgg agtgcccagc  180
aggttttccg gctccggatc cggcaccgac ttcaccctga ccgtgtccag cctgcagccc  240
gaggacttcg ccacctacta ctgccagcag agctacagca cccccaggac atttggccag  300
ggcacccggg tggagatcaa gaggaccgtc gctgccccct ccgtgtttat cttccccccc  360
agcgacgagc agctgaaatc cggcaccgcc tccgtggtct gcctgctgaa taacttctac  420
cctcgggagg ccaaggtgca gtggaaggtg gacaacgccc tgcagagcgg aaactcccag  480
gagagcgtga ccgagcagga ctccaaggac tccacatact ccctgtcctc caccctgaca  540
ctgtccaagg ccgattacga gaagcacaag gtgtacgcct gcgaggtgac ccaccaggga  600
ctgtcctccc ccgtgaccaa gtccttcaac cggggcgagt gc                    642

SEQ ID NO: 32            moltype = AA  length = 214
FEATURE                  Location/Qualifiers
source                   1..214
                         mol_type = protein
                         organism = Homo sapiens
SEQUENCE: 32
DIQMTQSPSS LSASVGDRVT ITCRASQSIS DYLNWYQQKP GKAPKFLIYA ASSLQSGVPS  60
RFSGSGSGTD FTLTVSSLQP EDFATYYCQQ SYSTPRTFGQ GTRVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 33            moltype = DNA  length = 381
FEATURE                  Location/Qualifiers
source                   1..381
                         mol_type = other DNA
                         organism = Homo sapiens
SEQUENCE: 33
gaggtgcagt tggtggagtc tgggggaggc ttggtacagc ctgggggtc cctgagactc  60
tcctgtgcag cctctggatt cactttagc aactatgcca tgaactgggt ccgccaggct  120
ccagggaagg ggctggagtg ggtctcaact attagcggaa gtggtggtgc cacaaggtat  180
```

```
gcagactccg tgaagggccg attcaccata tccagagaca attccaggaa cacggtgtat  240
ctgcaaatga acagcctgag agtcgaggac acggccgttt tttactgtac gaaagatcgg  300
ctcattatgg ctacggttcg gggaccctat tactacggta tggacgtctg ggccaaggg   360
accacggtca ccgtctcctc a                                            381

SEQ ID NO: 34           moltype = AA  length = 127
FEATURE                 Location/Qualifiers
source                  1..127
                        mol_type = protein
                        organism = Homo sapiens
SEQUENCE: 34
EVQLVESGGG LVQPGGSLRL SCAASGFTFS NYAMNWVRQA PGKGLEWVST ISGSGGATRY  60
ADSVKGRFTI SRDNSRNTVY LQMNSLRVED TAVFYCTKDR LIMATVRGPY YYGMDVWGQG  120
TTVTVSS                                                            127

SEQ ID NO: 35           moltype = DNA  length = 24
FEATURE                 Location/Qualifiers
source                  1..24
                        mol_type = other DNA
                        organism = Homo sapiens
SEQUENCE: 35
ggattcactt ttagcaacta tgcc                                         24

SEQ ID NO: 36           moltype = AA  length = 8
FEATURE                 Location/Qualifiers
source                  1..8
                        mol_type = protein
                        organism = Homo sapiens
SEQUENCE: 36
GFTFSNYA                                                           8

SEQ ID NO: 37           moltype = DNA  length = 24
FEATURE                 Location/Qualifiers
source                  1..24
                        mol_type = other DNA
                        organism = Homo sapiens
SEQUENCE: 37
attagcggaa gtggtggtgc caca                                         24

SEQ ID NO: 38           moltype = AA  length = 8
FEATURE                 Location/Qualifiers
source                  1..8
                        mol_type = protein
                        organism = Homo sapiens
SEQUENCE: 38
ISGSGGAT                                                           8

SEQ ID NO: 39           moltype = DNA  length = 60
FEATURE                 Location/Qualifiers
source                  1..60
                        mol_type = other DNA
                        organism = Homo sapiens
SEQUENCE: 39
acgaaagatc ggctcattat ggctacggtt cggggaccct attactacgg tatggacgtc  60

SEQ ID NO: 40           moltype = AA  length = 20
FEATURE                 Location/Qualifiers
source                  1..20
                        mol_type = protein
                        organism = Homo sapiens
SEQUENCE: 40
TKDRLIMATV RGPYYYGMDV                                              20

SEQ ID NO: 41           moltype = DNA  length = 15
FEATURE                 Location/Qualifiers
source                  1..15
                        mol_type = other DNA
                        organism = Homo sapiens
SEQUENCE: 41
aactatgcca tgaac                                                   15

SEQ ID NO: 42           moltype = AA  length = 5
FEATURE                 Location/Qualifiers
source                  1..5
                        mol_type = protein
                        organism = Homo sapiens
SEQUENCE: 42
NYAMN                                                              5
```

```
SEQ ID NO: 43           moltype = DNA  length = 51
FEATURE                 Location/Qualifiers
source                  1..51
                        mol_type = other DNA
                        organism = Homo sapiens
SEQUENCE: 43
actattagcg gaagtggtgg tgccacaagg tatgcagact ccgtgaaggg c          51

SEQ ID NO: 44           moltype = AA  length = 17
FEATURE                 Location/Qualifiers
source                  1..17
                        mol_type = protein
                        organism = Homo sapiens
SEQUENCE: 44
TISGSGGATR YADSVKG                                                17

SEQ ID NO: 45           moltype = DNA  length = 54
FEATURE                 Location/Qualifiers
source                  1..54
                        mol_type = other DNA
                        organism = Homo sapiens
SEQUENCE: 45
gatcggctca ttatggctac ggttcgggga ccctattact acggtatgga cgtc       54

SEQ ID NO: 46           moltype = AA  length = 18
FEATURE                 Location/Qualifiers
source                  1..18
                        mol_type = protein
                        organism = Homo sapiens
SEQUENCE: 46
DRLIMATVRG PYYYGMDV                                               18

SEQ ID NO: 47           moltype = DNA  length = 321
FEATURE                 Location/Qualifiers
source                  1..321
                        mol_type = other DNA
                        organism = Homo sapiens
SEQUENCE: 47
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaacctcct gatctatgct gcatccagtt tgcaaagtgg ggtcccatca  180
aggttcagtg gcagtggatc tgagacagat ttcactctca ccatcagcag tctgcaacct  240
gaagattttg caacttacta ctgtcaacag agtcacagtg tctcattcac tttcggccct  300
gggaccaaag tggatatcaa a                                            321

SEQ ID NO: 48           moltype = AA  length = 107
FEATURE                 Location/Qualifiers
source                  1..107
                        mol_type = protein
                        organism = Homo sapiens
SEQUENCE: 48
DIQMTQSPSS LSASVGDRVT ITCRASQSIS SYLNWYQQKP GKAPNLLIYA ASSLQSGVPS  60
RFSGSGSETD FTLTISSLQP EDFATYYCQQ SHSVSFTFGP GTKVDIK                107

SEQ ID NO: 49           moltype = DNA  length = 18
FEATURE                 Location/Qualifiers
source                  1..18
                        mol_type = other DNA
                        organism = Homo sapiens
SEQUENCE: 49
cagagcatta gcagctat                                               18

SEQ ID NO: 50           moltype = AA  length = 6
FEATURE                 Location/Qualifiers
source                  1..6
                        mol_type = protein
                        organism = Homo sapiens
SEQUENCE: 50
QSISSY                                                            6

SEQ ID NO: 51           moltype =   length =
SEQUENCE: 51
000

SEQ ID NO: 52           moltype =   length =
SEQUENCE: 52
000

SEQ ID NO: 53           moltype = DNA  length = 27
```

```
FEATURE                Location/Qualifiers
source                 1..27
                       mol_type = other DNA
                       organism = Homo sapiens
SEQUENCE: 53
caacagagtc acagtgtctc attcact                                  27

SEQ ID NO: 54          moltype = AA  length = 9
FEATURE                Location/Qualifiers
source                 1..9
                       mol_type = protein
                       organism = Homo sapiens
SEQUENCE: 54
QQSHSVSFT                                                      9

SEQ ID NO: 55          moltype = DNA  length = 33
FEATURE                Location/Qualifiers
source                 1..33
                       mol_type = other DNA
                       organism = Homo sapiens
SEQUENCE: 55
cgggcaagtc agagcattag cagctattta aat                           33

SEQ ID NO: 56          moltype = AA  length = 11
FEATURE                Location/Qualifiers
source                 1..11
                       mol_type = protein
                       organism = Homo sapiens
SEQUENCE: 56
RASQSISSYL N                                                   11

SEQ ID NO: 57          moltype = DNA  length = 21
FEATURE                Location/Qualifiers
source                 1..21
                       mol_type = other DNA
                       organism = Homo sapiens
SEQUENCE: 57
gctgcatcca gtttgcaaag t                                        21

SEQ ID NO: 58          moltype = AA  length = 7
FEATURE                Location/Qualifiers
source                 1..7
                       mol_type = protein
                       organism = Homo sapiens
SEQUENCE: 58
AASSLQS                                                        7

SEQ ID NO: 59          moltype = DNA  length = 27
FEATURE                Location/Qualifiers
source                 1..27
                       mol_type = other DNA
                       organism = Homo sapiens
SEQUENCE: 59
caacagagtc acagtgtctc attcact                                  27

SEQ ID NO: 60          moltype = AA  length = 9
FEATURE                Location/Qualifiers
source                 1..9
                       mol_type = protein
                       organism = Homo sapiens
SEQUENCE: 60
QQSHSVSFT                                                      9

SEQ ID NO: 61          moltype = DNA  length = 1362
FEATURE                Location/Qualifiers
source                 1..1362
                       mol_type = other DNA
                       organism = Homo sapiens
SEQUENCE: 61
gaagtgcaac tggtggagtc cggaggaggc ctggtgcagc ctggaggaag cctgaggctg  60
agctgtgccg ccagcggctt caccttcagc aactacgcca tgaactgggt gaggcaggcc  120
cctggcaagg gactggagtg ggtctccacc atcagcggct ccggaggcgc tacacggtac  180
gccgatagcg tgaagggccg gtttaccatt tcccgggaca actcccggaa caccgtgtac  240
ctccagatga acagcctgag ggtggaggat accgccgtgt tctactgcac caaggacagg  300
ctgattatgg ccaccgtgag gggaccttac tactatggca tggatgtgtg gggccagggc  360
acaaccgtca ccgtgtcctc cgcctccacc aagggaccta gcgtgttccc tctcgccccc  420
tgttccaggt ccacaagcga gtccaccgct gccctcggct gtctggtgaa agactacttt  480
cccgagcccg tgaccgtctc ctggaatagc ggagccctga cctccggcgt gcacacattt  540
cccgccgtgc tgcagagcag cggactgtat agcctgagca gcgtggtgac cgtgcccagc  600
```

-continued

```
tccagcctcg gcaccaaaac ctacacctgc aacgtggacc acaagccctc caacaccaag  660
gtggacaagc gggtggagag caagtacggc ccccccttgcc ctccttgtcc tgcccctgag  720
ttcgagggag gaccctccgt gttcctgttt ccccccaaac ccaaggacac cctgatgatc  780
tcccggacac ccgaggtgac ctgtgtggtc gtggacgtca gccaggagga ccccgaggtg  840
cagttcaact ggtatgtgga cggcgtggag gtgcacaatg ccaaaaccaa gcccagggag  900
gagcagttca attccaccta cagggtggtg agcgtgctga ccgtcctgca tcaggattgg  960
ctgaacggca aggagtacaa gtgcaaggtg tccaacaagg gactgcccag ctccatcgag  1020
aagaccatca gcaaggctaa gggccagccg agggagcccc aggtgtatac cctgcctcct  1080
agccaggaag agatgaccaa gaaccaagtg tccctgacct gcctggtgaa gggattctac  1140
ccctccgaca tcgccgtgga gtgggagagc aatggccagc ccgagaacaa ctacaaaaca  1200
acccctcccg tgctcgatag cgacggcagc ttctttctct acagccggct gacagtggac  1260
aagagcaggt ggcaggaggg caacgtgttc tcctgttccg tgatgcacga ggccctgcac  1320
aatcactaca cccagaagag cctctccctg tccctgggca ag                      1362

SEQ ID NO: 62           moltype = AA  length = 454
FEATURE                 Location/Qualifiers
source                  1..454
                        mol_type = protein
                        organism = Homo sapiens
SEQUENCE: 62
EVQLVESGGG LVQPGGSLRL SCAASGFTFS NYAMNWVRQA PGKGLEWVST ISGSGGATRY  60
ADSVKGRFTI SRDNSRNTVY LQMNSLRVED TAVFYCTKDR LIMATVRGPY YYGMDVWGQG  120
TTVTVSSAST KGPSVFPLAP CSRSTSESTA ALGCLVKDYF PEPVTVSWNS GALTSGVHTF  180
PAVLQSSGLY SLSSVVTVPS SSLGTKTYTC NVDHKPSNTK VDKRVESKYG PPCPPCPAPE  240
FEGGPSVFLF PPKPKDTLMI SRTPEVTCVV VDVSQEDPEV QFNWYVDGVE VHNAKTKPRE  300
EQFNSTYRVV SVLTVLHQDW LNGKEYKCKV SNKGLPSSIE KTISKAKGQP REPQVYTLPP  360
SQEEMTKNQV SLTCLVKGFY PSDIAVEWES NGQPENNYKT TPPVLDSDGS FFLYSRLTVD  420
KSRWQEGNVF SCSVMHEALH NHYTQKSLSL SLGK                              454

SEQ ID NO: 63           moltype = DNA  length = 642
FEATURE                 Location/Qualifiers
source                  1..642
                        mol_type = other DNA
                        organism = Homo sapiens
SEQUENCE: 63
gacatccaga tgacccagtc cccttcctcc ctgagcgcta gcgtgggaga tagggtgacc  60
atcacctgca gggcctccca aagcatctcc tcctacctga actggtacca gcagaaaccc  120
ggcaaggccc ccaacctgct gatctacgct gcctcctccc tccagtccgg cgtgcctagc  180
aggtttagcg gctccggaag cgagaccgac ttcaccctga ccatctcctc cctgcagccc  240
gaggacttcg ccacctacta ctgccagcaa tcccacagcg tgtccttcac cttcggcccc  300
ggcaccaagg tggacatcaa gaggaccgtg gccgccccct ccgtgttcat ctttcccccc  360
tccgatgaac agctgaagag cggcaccgct agcgtggtgt gcctgctgaa caacttctac  420
cccagggagg ccaaggtgca gtggaaggtg gacaatgccc tgcagtccgg caacagccag  480
gagagcgtga ccgagcagga ctccaaggac agcacctaca gcctgtcctc caccctgacc  540
ctgtccaagg ccgactacga gaagcacaaa gtgtacgcct gcgaagtgac ccatcagggc  600
ctgagctccc ccgtgaccaa gtcctttaac aggggcgagt gc                      642

SEQ ID NO: 64           moltype = AA  length = 214
FEATURE                 Location/Qualifiers
source                  1..214
                        mol_type = protein
                        organism = Homo sapiens
SEQUENCE: 64
DIQMTQSPSS LSASVGDRVT ITCRASQSIS SYLNWYQQKP GKAPNLLIYA ASSLQSGVPS  60
RFSGSGSETD FTLTISSLQP EDFATYYCQQ SHSVSFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 65           moltype = DNA  length = 372
FEATURE                 Location/Qualifiers
source                  1..372
                        mol_type = other DNA
                        organism = Homo sapiens
SEQUENCE: 65
caggtgcagc tggtggagtc tgggggaggc ttggtcaagc ctggagggtc cctgagactc  60
tcctgtgcag cctctcgatt caccctcagt gactactaca tgacctggat ccgccaggct  120
ccagggaagg ggctggagtg ggtttcatac attagtagta gtggtaatac catatactac  180
gcagactctg tgaagggccg attcaccatc tccagggaca acgccaagaa ctcactgtat  240
ctgcaaatga acagcctgag agccgaggac acggccgtgt attactgtgc gagagatctg  300
agtgggagct actgggacta ctactacggt atggacgtct ggggccaagg gaccacggtc  360
accgtctcct ca                                                       372

SEQ ID NO: 66           moltype = AA  length = 124
FEATURE                 Location/Qualifiers
source                  1..124
                        mol_type = protein
                        organism = Homo sapiens
SEQUENCE: 66
QVQLVESGGG LVKPGGSLRL SCAASRFTLS DYYMTWIRQA PGKGLEWVSY ISSSGNTIYY  60
```

```
ADSVKGRFTI SRDNAKNSLY LQMNSLRAED TAVYYCARDL SGSYWDYYYG MDVWGQGTTV  120
TVSS                                                              124

SEQ ID NO: 67           moltype = DNA  length = 24
FEATURE                 Location/Qualifiers
source                  1..24
                        mol_type = other DNA
                        organism = Homo sapiens
SEQUENCE: 67
cgattcaccc tcagtgacta ctac                                        24

SEQ ID NO: 68           moltype = AA  length = 8
FEATURE                 Location/Qualifiers
source                  1..8
                        mol_type = protein
                        organism = Homo sapiens
SEQUENCE: 68
RFTLSDYY                                                          8

SEQ ID NO: 69           moltype = DNA  length = 24
FEATURE                 Location/Qualifiers
source                  1..24
                        mol_type = other DNA
                        organism = Homo sapiens
SEQUENCE: 69
attagtagta gtggtaatac cata                                        24

SEQ ID NO: 70           moltype = AA  length = 8
FEATURE                 Location/Qualifiers
source                  1..8
                        mol_type = protein
                        organism = Homo sapiens
SEQUENCE: 70
ISSSGNTI                                                          8

SEQ ID NO: 71           moltype = DNA  length = 51
FEATURE                 Location/Qualifiers
source                  1..51
                        mol_type = other DNA
                        organism = Homo sapiens
SEQUENCE: 71
gcgagagatc tgagtgggag ctactgggac tactactacg gtatggacgt c          51

SEQ ID NO: 72           moltype = AA  length = 17
FEATURE                 Location/Qualifiers
source                  1..17
                        mol_type = protein
                        organism = Homo sapiens
SEQUENCE: 72
ARDLSGSYWD YYYGMDV                                                17

SEQ ID NO: 73           moltype = DNA  length = 15
FEATURE                 Location/Qualifiers
source                  1..15
                        mol_type = other DNA
                        organism = Homo sapiens
SEQUENCE: 73
gactactaca tgacc                                                  15

SEQ ID NO: 74           moltype = AA  length = 5
FEATURE                 Location/Qualifiers
source                  1..5
                        mol_type = protein
                        organism = Homo sapiens
SEQUENCE: 74
DYYMT                                                             5

SEQ ID NO: 75           moltype = DNA  length = 51
FEATURE                 Location/Qualifiers
source                  1..51
                        mol_type = other DNA
                        organism = Homo sapiens
SEQUENCE: 75
tacattagta gtagtggtaa taccatatac tacgcagact ctgtgaaggg c          51

SEQ ID NO: 76           moltype = AA  length = 17
FEATURE                 Location/Qualifiers
source                  1..17
                        mol_type = protein
```

-continued

```
                        organism = Homo sapiens
SEQUENCE: 76
YISSSGNTIY YADSVKG                                                 17

SEQ ID NO: 77           moltype = DNA  length = 45
FEATURE                 Location/Qualifiers
source                  1..45
                        mol_type = other DNA
                        organism = Homo sapiens
SEQUENCE: 77
gatctgagtg ggagctactg ggactactac tacggtatgg acgtc                  45

SEQ ID NO: 78           moltype = AA  length = 15
FEATURE                 Location/Qualifiers
source                  1..15
                        mol_type = protein
                        organism = Homo sapiens
SEQUENCE: 78
DLSGSYWDYY YGMDV                                                   15

SEQ ID NO: 79           moltype = DNA  length = 321
FEATURE                 Location/Qualifiers
source                  1..321
                        mol_type = other DNA
                        organism = Homo sapiens
SEQUENCE: 79
gccatccagt tgacccagtc tccatcctcc ctgtctacat ctgtaggaga cagagtcacc  60
atcgcttgcc gggcaagtca gggcattaac aatgctttag cctggtatca gcagaaacca  120
gggaaagctc ctaagctcct gatctatgat gcctccagtt tggaaagtgg ggtcccatca  180
aggttcagcg gcagtggatc tgggacagat ttcactctca ccatcagcag cctgcagcct  240
gaagattttg caacttatta ctgtcaacag tttaatagtt accctcggac gttcggccaa  300
gggaccaagg tggaaatcaa a                                            321

SEQ ID NO: 80           moltype = AA  length = 107
FEATURE                 Location/Qualifiers
source                  1..107
                        mol_type = protein
                        organism = Homo sapiens
SEQUENCE: 80
AIQLTQSPSS LSTSVGDRVT IACRASQGIN NALAWYQQKP GKAPKLLIYD ASSLESGVPS  60
RFSGSGSGTD FTLTISSLQP EDFATYYCQQ FNSYPRTFGQ GTKVEIK                107

SEQ ID NO: 81           moltype = DNA  length = 18
FEATURE                 Location/Qualifiers
source                  1..18
                        mol_type = other DNA
                        organism = Homo sapiens
SEQUENCE: 81
cagggcatta acaatgct                                                18

SEQ ID NO: 82           moltype = AA  length = 6
FEATURE                 Location/Qualifiers
source                  1..6
                        mol_type = protein
                        organism = Homo sapiens
SEQUENCE: 82
QGINNA                                                             6

SEQ ID NO: 83           moltype =   length =
SEQUENCE: 83
000

SEQ ID NO: 84           moltype =   length =
SEQUENCE: 84
000

SEQ ID NO: 85           moltype = DNA  length = 27
FEATURE                 Location/Qualifiers
source                  1..27
                        mol_type = other DNA
                        organism = Homo sapiens
SEQUENCE: 85
caacagttta atagttaccc tcggacg                                      27

SEQ ID NO: 86           moltype = AA  length = 9
FEATURE                 Location/Qualifiers
source                  1..9
                        mol_type = protein
                        organism = Homo sapiens
```

```
SEQUENCE: 86
QQFNSYPRT                                                     9

SEQ ID NO: 87           moltype = DNA  length = 33
FEATURE                 Location/Qualifiers
source                  1..33
                        mol_type = other DNA
                        organism = Homo sapiens
SEQUENCE: 87
cgggcaagtc agggcattaa caatgcttta gcc                          33

SEQ ID NO: 88           moltype = AA  length = 11
FEATURE                 Location/Qualifiers
source                  1..11
                        mol_type = protein
                        organism = Homo sapiens
SEQUENCE: 88
RASQGINNAL A                                                  11

SEQ ID NO: 89           moltype = DNA  length = 21
FEATURE                 Location/Qualifiers
source                  1..21
                        mol_type = other DNA
                        organism = Homo sapiens
SEQUENCE: 89
gatgcctcca gtttggaaag t                                       21

SEQ ID NO: 90           moltype = AA  length = 7
FEATURE                 Location/Qualifiers
source                  1..7
                        mol_type = protein
                        organism = Homo sapiens
SEQUENCE: 90
DASSLES                                                       7

SEQ ID NO: 91           moltype = DNA  length = 27
FEATURE                 Location/Qualifiers
source                  1..27
                        mol_type = other DNA
                        organism = Homo sapiens
SEQUENCE: 91
caacagttta atagttaccc tcggacg                                 27

SEQ ID NO: 92           moltype = AA  length = 9
FEATURE                 Location/Qualifiers
source                  1..9
                        mol_type = protein
                        organism = Homo sapiens
SEQUENCE: 92
QQFNSYPRT                                                     9

SEQ ID NO: 93           moltype = DNA  length = 369
FEATURE                 Location/Qualifiers
source                  1..369
                        mol_type = other DNA
                        organism = Homo sapiens
SEQUENCE: 93
gaggtgcagc tggtggagtc tgggggaggc ttggtaaagc ctgggggggtc ccttagactc  60
tcctgtgcag cctctggatt cactttcagt aacgcctgga tgagctgggt ccgccaggct  120
ccagggaagg ggctggagtg ggttggccgt attaaaagca aaactgaagg tgggacaaca  180
gactacgctg cacccgtgaa aggcagattc accatctcaa gagatgattc aaaaaacacg  240
ctgtatctgc aaatgaacag cctgaaaacc gaggacacag ccgtgtatta ctgtaccaca  300
gattttctat ggttcgggga gttccctttt gactactggg gccagggaac cctggtcacc  360
gtctcctca                                                     369

SEQ ID NO: 94           moltype = AA  length = 123
FEATURE                 Location/Qualifiers
source                  1..123
                        mol_type = protein
                        organism = Homo sapiens
SEQUENCE: 94
EVQLVESGGG LVKPGGSLRL SCAASGFTFS NAWMSWVRQA PGKGLEWVGR IKSKTEGGTT  60
DYAAPVKGRF TISRDDSKNT LYLQMNSLKT EDTAVYYCTT DFLWFGEFPF DYWGQGTLVT  120
VSS                                                           123

SEQ ID NO: 95           moltype = DNA  length = 24
FEATURE                 Location/Qualifiers
source                  1..24
                        mol_type = other DNA
```

```
                         organism = Homo sapiens
SEQUENCE: 95
ggattcactt tcagtaacgc ctgg                                         24

SEQ ID NO: 96            moltype = AA  length = 8
FEATURE                  Location/Qualifiers
source                   1..8
                         mol_type = protein
                         organism = Homo sapiens
SEQUENCE: 96
GFTFSNAW                                                           8

SEQ ID NO: 97            moltype = DNA  length = 30
FEATURE                  Location/Qualifiers
source                   1..30
                         mol_type = other DNA
                         organism = Homo sapiens
SEQUENCE: 97
attaaaagca aaactgaagg tgggacaaca                                   30

SEQ ID NO: 98            moltype = AA  length = 10
FEATURE                  Location/Qualifiers
source                   1..10
                         mol_type = protein
                         organism = Homo sapiens
SEQUENCE: 98
IKSKTEGGTT                                                         10

SEQ ID NO: 99            moltype = DNA  length = 42
FEATURE                  Location/Qualifiers
source                   1..42
                         mol_type = other DNA
                         organism = Homo sapiens
SEQUENCE: 99
accacagatt ttctatggtt cggggagttc ccttttgact ac                     42

SEQ ID NO: 100           moltype = AA  length = 14
FEATURE                  Location/Qualifiers
source                   1..14
                         mol_type = protein
                         organism = Homo sapiens
SEQUENCE: 100
TTDFLWFGEF PFDY                                                    14

SEQ ID NO: 101           moltype = DNA  length = 15
FEATURE                  Location/Qualifiers
source                   1..15
                         mol_type = other DNA
                         organism = Homo sapiens
SEQUENCE: 101
aacgcctgga tgagc                                                   15

SEQ ID NO: 102           moltype = AA  length = 5
FEATURE                  Location/Qualifiers
source                   1..5
                         mol_type = protein
                         organism = Homo sapiens
SEQUENCE: 102
NAWMS                                                              5

SEQ ID NO: 103           moltype = DNA  length = 57
FEATURE                  Location/Qualifiers
source                   1..57
                         mol_type = other DNA
                         organism = Homo sapiens
SEQUENCE: 103
cgtattaaaa gcaaaactga aggtgggaca acagactacg ctgcacccgt gaaaggc     57

SEQ ID NO: 104           moltype = AA  length = 19
FEATURE                  Location/Qualifiers
source                   1..19
                         mol_type = protein
                         organism = Homo sapiens
SEQUENCE: 104
RIKSKTEGGT TDYAAPVKG                                               19

SEQ ID NO: 105           moltype = DNA  length = 36
FEATURE                  Location/Qualifiers
source                   1..36
```

```
                        mol_type = other DNA
                        organism = Homo sapiens
SEQUENCE: 105
gattttctat ggttcgggga gttccctttt gactac                         36

SEQ ID NO: 106          moltype = AA  length = 12
FEATURE                 Location/Qualifiers
source                  1..12
                        mol_type = protein
                        organism = Homo sapiens
SEQUENCE: 106
DFLWFGEFPF DY                                                   12

SEQ ID NO: 107          moltype = DNA  length = 321
FEATURE                 Location/Qualifiers
source                  1..321
                        mol_type = other DNA
                        organism = Homo sapiens
SEQUENCE: 107
gacatccaga tgacccagtc tccatcctcc ctgtctgcat ctgtaggaga cagagtcacc  60
atcacttgcc gggcgagtca gggcattagc aattatttag cctggtatca gcagaaacca  120
gggaaaattc ctaagctcct gatctatgct gcatccactt tgcaatcagg ggtcccatct  180
cggttcagtg gcagtggatc tgggacagat ttcactctca ccatcagcag cctgcagcct  240
gaagatgttg caacttatta ctgtcaaaag tataacagtg cccctcggac gttcggccaa  300
gggaccaagg tggaaatcaa a                                         321

SEQ ID NO: 108          moltype = AA  length = 107
FEATURE                 Location/Qualifiers
source                  1..107
                        mol_type = protein
                        organism = Homo sapiens
SEQUENCE: 108
DIQMTQSPSS LSASVGDRVT ITCRASQGIS NYLAWYQQKP GKIPKLLIYA ASTLQSGVPS  60
RFSGSGSGTD FTLTISSLQP EDVATYYCQK YNSAPRTFGQ GTKVEIK              107

SEQ ID NO: 109          moltype = DNA  length = 18
FEATURE                 Location/Qualifiers
source                  1..18
                        mol_type = other DNA
                        organism = Homo sapiens
SEQUENCE: 109
cagggcatta gcaattat                                             18

SEQ ID NO: 110          moltype = AA  length = 6
FEATURE                 Location/Qualifiers
source                  1..6
                        mol_type = protein
                        organism = Homo sapiens
SEQUENCE: 110
QGISNY                                                          6

SEQ ID NO: 111          moltype =   length =
SEQUENCE: 111
000

SEQ ID NO: 112          moltype =   length =
SEQUENCE: 112
000

SEQ ID NO: 113          moltype = DNA  length = 27
FEATURE                 Location/Qualifiers
source                  1..27
                        mol_type = other DNA
                        organism = Homo sapiens
SEQUENCE: 113
caaaagtata acagtgcccc tcggacg                                   27

SEQ ID NO: 114          moltype = AA  length = 9
FEATURE                 Location/Qualifiers
source                  1..9
                        mol_type = protein
                        organism = Homo sapiens
SEQUENCE: 114
QKYNSAPRT                                                       9

SEQ ID NO: 115          moltype = DNA  length = 33
FEATURE                 Location/Qualifiers
source                  1..33
                        mol_type = other DNA
```

```
                         organism = Homo sapiens
SEQUENCE: 115
cgggcgagtc agggcattag caattattta gcc                              33

SEQ ID NO: 116           moltype = AA  length = 11
FEATURE                  Location/Qualifiers
source                   1..11
                         mol_type = protein
                         organism = Homo sapiens
SEQUENCE: 116
RASQGISNYL A                                                      11

SEQ ID NO: 117           moltype = DNA  length = 21
FEATURE                  Location/Qualifiers
source                   1..21
                         mol_type = other DNA
                         organism = Homo sapiens
SEQUENCE: 117
gctgcatcca ctttgcaatc a                                           21

SEQ ID NO: 118           moltype = AA  length = 7
FEATURE                  Location/Qualifiers
source                   1..7
                         mol_type = protein
                         organism = Homo sapiens
SEQUENCE: 118
AASTLQS                                                           7

SEQ ID NO: 119           moltype = DNA  length = 27
FEATURE                  Location/Qualifiers
source                   1..27
                         mol_type = other DNA
                         organism = Homo sapiens
SEQUENCE: 119
caaaagtata acagtgcccc tcggacg                                     27

SEQ ID NO: 120           moltype = AA  length = 9
FEATURE                  Location/Qualifiers
source                   1..9
                         mol_type = protein
                         organism = Homo sapiens
SEQUENCE: 120
QKYNSAPRT                                                         9

SEQ ID NO: 121           moltype = DNA  length = 981
FEATURE                  Location/Qualifiers
source                   1..981
                         mol_type = other DNA
                         organism = Homo sapiens
SEQUENCE: 121
gcttccacca agggcccatc cgtcttcccc ctggcgccct gctccaggag cacctccgag  60
agcacagccg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacgaagacc  240
tacacctgca acgtagatca caagcccagc aacaccaagg tggacaagag agttgagtcc  300
aaatatggtc ccccatgccc atcatgccca gcacctgagt tcctgggggg accatcagtc  360
ttcctgttcc ccccaaaacc caaggacact ctcatgatct cccggacccc tgaggtcacg  420
tgcgtggtgg tggacgtgag ccaggaagac cccgaggtcc agttcaactg gtacgtggat  480
ggcgtggagg tgcataatgc caagacaaag ccgcgggagg agcagttcaa cagcacgtac  540
cgtgtggtca gcgtcctcac cgtcctgcac caggactggc tgaacggcaa ggagtacaag  600
tgcaaggtct ccaacaaagg cctcccgtcc tccatcgaga aaaccatctc caaagccaaa  660
gggcagcccc gagagccaca ggtgtacacc ctgcccccat cccaggagga gatgaccaag  720
aaccaggtca gcctgacctg cctggtcaaa ggcttctacc ccagcgacat cgccgtggag  780
tgggagagca atgggcagcc ggagaacaac tacaagacca cgcctcccgt gctggactcc  840
gacggctcct tcttcctcta cagcaggcta accgtggaca agagcaggtg gcaggagggg  900
aatgtcttct catgctccgt gatgcatgag gctctgcaca accactacac acagaagagc  960
ctctccctgt ctctgggtaa a                                           981

SEQ ID NO: 122           moltype = AA  length = 327
FEATURE                  Location/Qualifiers
source                   1..327
                         mol_type = protein
                         organism = Homo sapiens
SEQUENCE: 122
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
```

```
NVFSCSVMHE ALHNHYTQKS LSLSLGK                                327

SEQ ID NO: 123          moltype = DNA  length = 981
FEATURE                 Location/Qualifiers
source                  1..981
                        mol_type = other DNA
                        organism = Homo sapiens
SEQUENCE: 123
gcttccacca agggcccatc cgtcttcccc ctggcgccct gctccaggag cacctccgag  60
agcacagccg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacgaagacc  240
tacacctgca acgtagatca caagcccagc aacaccaagg tggacaagag agttgagtcc  300
aaatatggtc ccccgtgccc atcatgccca gcacctgagt tcctgggggg accatcagtc  360
ttcctgttcc ccccaaaacc caaggacact ctcatgatct cccggacccc tgaggtcacg  420
tgcgtggtgg tggacgtgag ccaggaagac cccgaggtcc agttcaactg gtacgtggat  480
ggcgtggagg tgcataatgc caagacaaag ccgcgggagg agcagttcaa cagcacgtac  540
cgtgtggtca gcgtcctcac cgtcgtgcac caggactggc tgaacggcaa ggagtacaag  600
tgcaaggtct ccaacaaagg cctcccgtcc tccatcgaga aaaccatctc caaagccaaa  660
gggcagcccc gagagccaca ggtgtacacc ctgcccccat cccaggagga gatgaccaag  720
aaccaggtca gcctgacctg cctggtcaaa ggcttctacc ccagcgacat cgccgtggag  780
tgggagagca atgggcagcc ggagaacaac tacaagacca cgcctcccgt gctggactcc  840
gacggctcct tcttcctcta cagcaggcta accgtggaca agagcaggtg gcaggagggg  900
aatgtcttct catgctccgt gatgcatgag gctctgcaca accactacac gcagaagagc  960
ctctccctgt ctctgggtaa a                                      981

SEQ ID NO: 124          moltype = AA  length = 327
FEATURE                 Location/Qualifiers
source                  1..327
                        mol_type = protein
                        organism = Homo sapiens
SEQUENCE: 124
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVVH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                327

SEQ ID NO: 125          moltype = DNA  length = 981
FEATURE                 Location/Qualifiers
source                  1..981
                        mol_type = other DNA
                        organism = Homo sapiens
SEQUENCE: 125
gcttccacca agggcccatc cgtcttcccc ctggcgccct gctccaggag cacctccgag  60
agcacagccg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacgaagacc  240
tacacctgca acgtagatca caagcccagc aacaccaagg tggacaagag agttgagtcc  300
aaatatggtc ccccatgccc atcatgccca gcacctgagt tcctgggggg accatcagtc  360
ttcctgttcc ccccaaaacc caaggacact ctcatgatct cccggacccc tgaggtcacg  420
tgcgtggtgg tggacgtgag ccaggaagac cccgaggtcc agttcaactg gtacgtggat  480
ggcgtggagg tgcataatgc caagacaaag ccgcgggagg agcagttcaa cagcacgtac  540
cgtgtggtca gcgtcctcac cgtcctgcac caggactggc tgaacggcaa ggagtacaag  600
tgcaaggtct ccaacaaagg cctcccgtcc tccatcgaga aaaccatctc caaagccaaa  660
gggcagcccc gagagccaca ggtgtacacc ctgcccccat cccaggagga gatgaccaag  720
aaccaggtca gcctgacctg cctggtcaaa ggcttctacc ccagcgacat cgccgtggag  780
tgggagagca atgggcagcc ggagaacaac tacaagacca cgcctcccgt gctggactcc  840
gacggctcct tcttcctcta cagcaagctc accgtggaca agagcaggtg gcaggagggg  900
aacgtcttct catgctccgt gatgcatgag gctctgcaca accactacac gcagaagagc  960
ctctccctgt ctctgggtaa a                                      981

SEQ ID NO: 126          moltype = AA  length = 327
FEATURE                 Location/Qualifiers
source                  1..327
                        mol_type = protein
                        organism = Homo sapiens
SEQUENCE: 126
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSKL TVDKSRWQEG  300
NVFSCSVMHE ALHNHYTQKS LSLSLGK                                327

SEQ ID NO: 127          moltype = DNA  length = 981
FEATURE                 Location/Qualifiers
source                  1..981
```

```
                         mol_type = other DNA
                         organism = Homo sapiens
SEQUENCE: 127
gcctccacca agggcccatc cgtcttcccc ctggcgccct gctccaggag cacctccgag  60
agcacggccg ccctgggctg cctggtcaag gactacttcc ccgaaccagt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacgaagacc  240
tacacctgca acgtagatca caagcccagc aacaccaagg tggacaagag agttgagtcc  300
aaatatggtc ccccatgccc accatgccca gcgcctgaat ttgagggggg accatcagtc  360
ttcctgttcc ccccaaaacc caaggacact ctcatgatct cccggacccc tgaggtcacg  420
tgcgtggtgg tggacgtgag ccaggaagac cccgaggtcc agttcaactg gtacgtggat  480
ggcgtggagg tgcataatgc caagacaaag ccgcgggagg agcagttcaa cagcacgtac  540
cgtgtggtca gcgtcctcac cgtcctgcac caggactggc tgaacggcaa ggagtacaag  600
tgcaaggtct ccaacaaagg cctcccgtca tcgatcgaga aaaccatctc caaagccaaa  660
gggcagcccc gagagccaca ggtgtacacc ctgcccccat cccaggagga gatgaccaag  720
aaccaggtca gcctgacctg cctggtcaaa ggcttctacc ccagcgacat cgccgtggag  780
tgggagagca atgggcagcc ggagaacaac tacaagacca cgcctcccgt gctggactcc  840
gacggatcct tcttcctcta cagcaggcta accgtggaca agagcaggtg gcaggagggg  900
aatgtcttct catgctccgt gatgcatgag gctctgcaca accactacac acagaagagc  960
ctctccctgt ctctgggtaa a                                            981

SEQ ID NO: 128           moltype = AA  length = 327
FEATURE                  Location/Qualifiers
source                   1..327
                         mol_type = protein
                         organism = Homo sapiens
SEQUENCE: 128
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFEGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 129           moltype = DNA  length = 981
FEATURE                  Location/Qualifiers
source                   1..981
                         mol_type = other DNA
                         organism = Homo sapiens
SEQUENCE: 129
gcctccacca agggacctag cgtgttccct ctcgcccccct gttccaggtc cacaagcgag  60
tccaccgctg ccctcggctg tctggtgaaa gactactttc ccgagcccgt gaccgtctcc  120
tggaatagcg gagccctgac ctccggcgtg cacacatttc ccgccgtgct gcagagcagc  180
ggactgtata gcctgagcag cgtggtgacc gtgcccagct ccagcctcgg caccaaaacc  240
tacacctgca acgtggacca caagccctcc aacaccaagg tggacaagcg ggtggagagc  300
aagtacggcc cccccttgccc tccttgtcct gcccctgagt tcgagggagg accctccgtg  360
ttcctgtttc cccccaaacc caaggacacc ctgatgatct cccggacacc cgaggtgacc  420
tgtgtggtcg tggacgtcag ccaggaggac cccgaggtgc agttcaactg gtatgtggac  480
ggcgtggagg tgcacaatgc caaaaccaag cccagggagg agcagttcaa ttccacctac  540
agggtggtga gcgtgctgac cgtcctgcat caggattggc tgaacggcaa ggagtacaag  600
tgcaaggtgt ccaacaaggg actgcccagc tccatcgaga agaccatcag caaggctaag  660
ggccagccga gggagcccca ggtgtatacc ctgcctccta gccaggaaga gatgaccaag  720
aaccaagtgt ccctgacctg cctggtgaag ggattctacc cctccgacat cgccgtggag  780
tgggagagca atggccagcc cgagaacaac tacaaaacaa cccctcccgt gctcgatagc  840
gacggcagct tctttctcta cagccggctg acagtggaca agagcaggtg gcaggagggc  900
aacgtgttct cctgttccgt gatgcacgag gccctgcaca atcactacac ccagaagagc  960
ctctccctgt ccctgggcaa g                                            981

SEQ ID NO: 130           moltype = DNA  length = 981
FEATURE                  Location/Qualifiers
source                   1..981
                         mol_type = other DNA
                         organism = Homo sapiens
SEQUENCE: 130
gccagcacca agggcccttc cgtgttcccc ctggcccctt gcagcaggag cacctccgaa  60
tccacagctg ccctgggctg tctggtgaag gactactttc ccgagcccgt gaccgtgagc  120
tggaacagcg gcgctctgac atccggcgtc cacacctttc ctgccgtcct gcagtcctcc  180
ggcctctact ccctgtcctc cgtggtgacc gtgcctagct cctccctcgg caccaagacc  240
tacacctgta acgtggacca caaaccctcc aacaccaagg tggacaaacg ggtcgagagc  300
aagtacggcc ctccctgccc tccttgtcct gcccccgagt tcgaaggcgg acccagcgtg  360
ttcctgttcc ctcctaagcc caaggacacc ctcatgatca gccggacacc cgaggtgacc  420
tgcgtggtgg tggatgtgag ccaggaggac cctgaggtcc agttcaactg gtatgtggat  480
ggcgtggagg tgcacaacgc caagacaaag ccccgggaag agcagttcaa ctccacctac  540
agggtggtca gcgtgctgac cgtgctgcat caggactggc tgaacggcaa ggagtacaag  600
tgcaaggtca gcaataaggg actgcccagc agcatcgaga agaccatctc caaggctaaa  660
ggccagcccc gggaacctca ggtgtacacc ctgcctccca gccaggagga gatgaccaag  720
aaccaggtga gcctgacctg cctggtgaag ggattctacc cttccgacat cgccgtggag  780
tgggagtcca acggccagcc cgagaacaat tataagacca cccctcccgt cctcgacagc  840
gacggatcct tctttctgta ctccaggctg accgtggata agtccaggtg gcaggaaggc  900
```

```
aacgtgttca gctgctccgt gatgcacgag gccctgcaca atcactacac ccagaagtcc  960
ctgagcctgt ccctgggaaa g                                            981

SEQ ID NO: 131         moltype = DNA  length = 981
FEATURE                Location/Qualifiers
source                 1..981
                       mol_type = other DNA
                       organism = Homo sapiens
SEQUENCE: 131
gcctccacca agggcccatc cgtcttcccc ctggcgccct gctccaggag cacctccgag  60
agcacggccg ccctgggctg cctggtcaag gactacttcc ccgaaccagt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacgaagacc  240
tacacctgca acgtagatca caagcccagc aacaccaagg tggacaagag agttgagtcc  300
aaatatggtc ccccatgccc accatgccca gcgcctccag ttgcgggggg accatcagtc  360
ttcctgttcc ccccaaaacc caaggacact ctcatgatct cccggacccc tgaggtcacg  420
tgcgtggtgg tggacgtgag ccaggaagac cccgaggtcc agttcaactg gtacgtggat  480
ggcgtggagg tgcataatgc caagacaaag ccgcgggagg agcagttcaa cagcacgtac  540
cgtgtggtca gcgtcctcac cgtcctgcac caggactggc tgaacggcaa ggagtacaag  600
tgcaaggtct ccaacaaagg cctcccgtca tcgatcgaga aaaccatctc caaagccaaa  660
gggcagcccc gagagccaca ggtgtacacc ctgcccccat cccaggagga gatgaccaag  720
aaccaggtca gcctgacctg cctggtcaaa ggcttctacc ccagcgacat cgccgtggag  780
tgggagagca atgggcagcc ggagaacaac tacaagacca cgcctcccgt gctggactcc  840
gacggatcct tcttcctcta cagcaggcta accgtggaca agagcaggtg gcaggagggg  900
aatgtcttct catgctccgt gatgcatgag gctctgcaca accactacac acagaagagc  960
ctctccctgt ctctgggtaa a                                            981

SEQ ID NO: 132         moltype = AA  length = 327
FEATURE                Location/Qualifiers
source                 1..327
                       mol_type = protein
                       organism = Homo sapiens
SEQUENCE: 132
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APPVAGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 133         moltype = DNA  length = 990
FEATURE                Location/Qualifiers
source                 1..990
                       mol_type = other DNA
                       organism = Homo sapiens
SEQUENCE: 133
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agtggagccc  300
aaatcttgtg acaaaactca cacatgccca ccgtgcccag cacctgaact cgcgggggca  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggatgag  720
ctgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 134         moltype = AA  length = 330
FEATURE                Location/Qualifiers
source                 1..330
                       mol_type = protein
                       organism = Homo sapiens
SEQUENCE: 134
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 135         moltype = DNA  length = 321
FEATURE                Location/Qualifiers
```

```
source                  1..321
                        mol_type = other DNA
                        organism = Homo sapiens
SEQUENCE: 135
cgtacggtgg ccgctccctc cgtgttcatc ttcccacctt ccgacgagca gctgaagtcc  60
ggcaccgctt ctgtcgtgtg cctgctgaac aacttctacc cccgcgaggc caaggtgcag  120
tggaaggtgg acaacgccct gcagtccggc aactcccagg aatccgtgac cgagcaggac  180
tccaaggaca gcacctactc cctgtcctcc accctgaccc tgtccaaggc cgactacgag  240
aagcacaagg tgtacgcctg cgaagtgacc caccagggcc tgtctagccc cgtgaccaag  300
tctttcaacc ggggcgagtg t                                             321

SEQ ID NO: 136          moltype = AA  length = 107
FEATURE                 Location/Qualifiers
source                  1..107
                        mol_type = protein
                        organism = Homo sapiens
SEQUENCE: 136
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                 107

SEQ ID NO: 137          moltype = DNA  length = 321
FEATURE                 Location/Qualifiers
source                  1..321
                        mol_type = other DNA
                        organism = Homo sapiens
SEQUENCE: 137
cgaactgtgg ctgcaccatc tgtcttcatc ttcccgccat ctgatgagca gttgaaatct  60
ggaactgcct ctgttgtgtg cctgctgaat aacttctatc ccagagaggc caaagtacag  120
tggaaggtgg ataacgccct ccaatcgggt aactcccagg agagtgtcac agagcaggag  180
agcaaggaca gcacctacag cctcagcagc accctgacgc tgagcaaagc agactacgag  240
aaacacaaag tctacgccgg cgaagtcacc catcagggcc tgagctcgcc cgtcacaaag  300
agcttcaaca ggggagagtg t                                             321

SEQ ID NO: 138          moltype = AA  length = 107
FEATURE                 Location/Qualifiers
source                  1..107
                        mol_type = protein
                        organism = Homo sapiens
SEQUENCE: 138
RTVAAPSVFI FPPSDEQLKS GTASVVCLLN NFYPREAKVQ WKVDNALQSG NSQESVTEQE  60
SKDSTYSLSS TLTLSKADYE KHKVYAGEVT HQGLSSPVTK SFNRGEC                 107

SEQ ID NO: 139          moltype = DNA  length = 321
FEATURE                 Location/Qualifiers
source                  1..321
                        mol_type = other DNA
                        organism = Homo sapiens
SEQUENCE: 139
cgaactgtgg ctgcaccatc tgtcttcatc ttcccgccat ctgatgagca gttgaaatct  60
ggaactgcct ctgttgtgtg cctgctgaat aacttctatc ccagagaggc caaagtacag  120
cggaaggtgg ataacgccct ccaatcgggt aactcccagg agagtgtcac agagcaggag  180
agcaaggaca gcacctacag cctcagcagc accctgacgc tgagcaaagc agactacgag  240
aaacacaaag tctacgcctg cgaagtcacc catcagggcc tgagctcgcc cgtcacaaag  300
agcttcaaca ggggagagtg t                                             321

SEQ ID NO: 140          moltype = AA  length = 107
FEATURE                 Location/Qualifiers
source                  1..107
                        mol_type = protein
                        organism = Homo sapiens
SEQUENCE: 140
RTVAAPSVFI FPPSDEQLKS GTASVVCLLN NFYPREAKVQ RKVDNALQSG NSQESVTEQE  60
SKDSTYSLSS TLTLSKADYE KHKVYACEVT HQGLSSPVTK SFNRGEC                 107

SEQ ID NO: 141          moltype = DNA  length = 321
FEATURE                 Location/Qualifiers
source                  1..321
                        mol_type = other DNA
                        organism = Homo sapiens
SEQUENCE: 141
cgaactgtgg ctgcaccatc tgtcttcatc ttcccgccat ctgatgagca gttgaaatct  60
ggaactgcct ctgttgtgtg cctgctgaat aacttctatc ccagagaggc caaagtacag  120
tggaaggtgg ataacgccct ccaatcgggt aactcccagg agagtgtcac agagcaggac  180
agcaaggaca gcacctacag cctcagcagc accctgacgc tgagcaaagc agactacgag  240
aaacacaaac tctacgcctg cgaagtcacc catcagggcc tgagctcgcc cgtcacaaag  300
agcttcaaca ggggagagtg t                                             321

SEQ ID NO: 142          moltype = AA  length = 107
FEATURE                 Location/Qualifiers
```

```
source                  1..107
                        mol_type = protein
                        organism = Homo sapiens
SEQUENCE: 142
RTVAAPSVFI FPPSDEQLKS GTASVVCLLN NFYPREAKVQ WKVDNALQSG NSQESVTEQD  60
SKDSTYSLSS TLTLSKADYE KHKLYACEVT HQGLSSPVTK SFNRGEC                107

SEQ ID NO: 143          moltype = DNA  length = 321
FEATURE                 Location/Qualifiers
source                  1..321
                        mol_type = other DNA
                        organism = Homo sapiens
SEQUENCE: 143
cgaactgtgg ctgcaccatc tgtcttcatc ttcccgccat ctgatgagca gttgaaatct  60
ggaactgcct ctgttgtgtg cctgctgaat aacttctatc ccagagaggc caaagtacag  120
tggaaggtgg ataacgccct ccaatcgggt aactcccagg agagtgtcac agagcaggac  180
agcaaggaca gcacctacag cctcagcaac accctgacgc tgagcaaagc agactacgag  240
aaacacaaag tctacgcctg cgaagtcacc catcagggcc tgagctcgcc cgtcacaaag  300
agcttcaaca ggggagagtg c                                            321

SEQ ID NO: 144          moltype = AA  length = 107
FEATURE                 Location/Qualifiers
source                  1..107
                        mol_type = protein
                        organism = Homo sapiens
SEQUENCE: 144
RTVAAPSVFI FPPSDEQLKS GTASVVCLLN NFYPREAKVQ WKVDNALQSG NSQESVTEQD  60
SKDSTYSLSN TLTLSKADYE KHKVYACEVT HQGLSSPVTK SFNRGEC                107

SEQ ID NO: 145          moltype = DNA  length = 312
FEATURE                 Location/Qualifiers
source                  1..312
                        mol_type = other DNA
                        organism = Homo sapiens
SEQUENCE: 145
cccaaggcca accccacggt cactctgttc ccgccctcct ctgaggagct ccaagccaac  60
aaggccacac tagtgtgtct gatcagtgac ttctacccgg gagctgtgac agtggcttgg  120
aaggcagatg gcagccccgt caaggcggga gtggagacga ccaaaccctc caaacagagc  180
aacaacaagt acgcggccag cagctacctg agcctgacgc ccgagcagtg gaagtcccac  240
agaagctaca gctgccaggt cacgcatgaa gggagcaccg tggagaagac agtggcccct  300
acagaatgtt ca                                                      312

SEQ ID NO: 146          moltype = AA  length = 104
FEATURE                 Location/Qualifiers
source                  1..104
                        mol_type = protein
                        organism = Homo sapiens
SEQUENCE: 146
PKANPTVTLF PPSSEELQAN KATLVCLISD FYPGAVTVAW KADGSPVKAG VETTKPSKQS  60
NNKYAASSYL SLTPEQWKSH RSYSCQVTHE GSTVEKTVAP TECS                   104

SEQ ID NO: 147          moltype = DNA  length = 318
FEATURE                 Location/Qualifiers
source                  1..318
                        mol_type = other DNA
                        organism = Homo sapiens
SEQUENCE: 147
ggtcagccca aggccaaccc cactgtcact ctgttcccgc cctcctctga ggagctccaa  60
gccaacaagg ccacactagt gtgtctgatc agtgacttct acccgggagc tgtgacagtg  120
gcctggaagg cagatggcag ccccgtcaag gcgggagtgg agaccaccaa accctccaaa  180
cagagcaaca acaagtacgc ggccagcagc tacctgagcc tgacgcccga gcagtggaag  240
tcccacagaa gctacagctg ccaggtcacg catgaaggga gcaccgtgga gaagacagtg  300
gcccctacag aatgttca                                                318

SEQ ID NO: 148          moltype = AA  length = 106
FEATURE                 Location/Qualifiers
source                  1..106
                        mol_type = protein
                        organism = Homo sapiens
SEQUENCE: 148
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 149          moltype = DNA  length = 318
FEATURE                 Location/Qualifiers
source                  1..318
                        mol_type = other DNA
                        organism = Homo sapiens
SEQUENCE: 149
```

```
ggtcagccca aggccaaccc cactgtcact ctgttcccgc cctcctctga ggagctccaa  60
gccaacaagg ccacactagt gtgtctgatc agtgacttct acccgggagc tgtgacagtg  120
gcctggaagg cagatggcag ccccgtcaag gcgggagtgg agaccaccaa accctccaaa  180
cagagcaaca acaagtacgc ggccagcagc tacctgagcc tgacgcccga gcagtggaag  240
tcccacagaa gctacagctg ccaggtcacg catgaaggga gcaccgtgga gaagacagtg  300
gcccctacag aatgttca                                                318

SEQ ID NO: 150          moltype = DNA  length = 318
FEATURE                 Location/Qualifiers
source                  1..318
                        mol_type = other DNA
                        organism = Homo sapiens
SEQUENCE: 150
ggccagccta aggccgctcc ttctgtgacc ctgttccccc catcctccga ggaactgcag  60
gctaacaagg ccaccctcgt gtgcctgatc agcgacttct accctggcgc cgtgaccgtg  120
gcctggaagg ctgatagctc tcctgtgaag gccggcgtgg aaaccaccac cccttccaag  180
cagtccaaca acaaatacgc cgcctcctcc tacctgtccc tgacccctga gcagtggaag  240
tcccaccggt cctacagctg ccaagtgacc cacgagggct ccaccgtgga aaagaccgtg  300
gctcctaccg agtgctcc                                                318

SEQ ID NO: 151          moltype = DNA  length = 318
FEATURE                 Location/Qualifiers
source                  1..318
                        mol_type = other DNA
                        organism = Homo sapiens
SEQUENCE: 151
ggccagccta aagctgcccc cagcgtcacc ctgtttcctc cctccagcga ggagctccag  60
gccaacaagg ccaccctcgt gtgcctgatc tccgacttct atcccggcgc tgtgaccgtg  120
gcttggaaag ccgactccag ccctgtcaaa gccggcgtgg agaccaccac accctccaag  180
cagtccaaca acaagtacgc cgcctccagc tatctctccc tgacccctga gcagtggaag  240
tcccaccggt cctactcctg tcaggtgacc cacgagggct ccaccgtgga aaagaccgtc  300
gcccccaccg agtgctcc                                                318

SEQ ID NO: 152          moltype = AA  length = 106
FEATURE                 Location/Qualifiers
source                  1..106
                        mol_type = protein
                        organism = Homo sapiens
SEQUENCE: 152
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 153          moltype = DNA  length = 318
FEATURE                 Location/Qualifiers
source                  1..318
                        mol_type = other DNA
                        organism = Homo sapiens
SEQUENCE: 153
ggtcagccca aggctgcccc ctcggtcact ctgttcccgc cctcctctga ggagcttcaa  60
gccaacaagg ccacactggt gtgtctcata agtgacttct acccgggagc cgtgacagtg  120
gcctggaagg cagatagcag ccccgtcaag gcgggagtgg agaccaccac accctccaaa  180
caaagcaaca acaagtacgc ggccagcagc tatctgagcc tgacgcctga gcagtggaag  240
tcccacagaa gctacagctg ccaggtcacg catgaaggga gcaccgtgga gaagacagtg  300
gcccctacag aatgttca                                                318

SEQ ID NO: 154          moltype = AA  length = 106
FEATURE                 Location/Qualifiers
source                  1..106
                        mol_type = protein
                        organism = Homo sapiens
SEQUENCE: 154
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 155          moltype = DNA  length = 312
FEATURE                 Location/Qualifiers
source                  1..312
                        mol_type = other DNA
                        organism = Homo sapiens
SEQUENCE: 155
cccaaggctg ccccctcggt cactctgttc ccaccctcct ctgaggagct tcaagccaac  60
aaggccacac tggtgtgtct cataagtgac ttctacccgg gagccgtgac agttgcctgg  120
aaggcagata gcagccccgt caaggcgggg gtggagacca ccacaccctc caaacaaagc  180
aacaacaagt acgcggccag cagctacctg agcctgacgc ctgagcagtg gaagtcccac  240
aaaagctaca gctgccaggt cacgcatgaa gggagcaccg tggagaagac agttgcccct  300
acggaatgtt ca                                                      312

SEQ ID NO: 156          moltype = AA  length = 104
FEATURE                 Location/Qualifiers
```

```
source                  1..104
                        mol_type = protein
                        organism = Homo sapiens
SEQUENCE: 156
PKAAPSVTLF PPSSEELQAN KATLVCLISD FYPGAVTVAW KADSSPVKAG VETTTPSKQS  60
NNKYAASSYL SLTPEQWKSH KSYSCQVTHE GSTVEKTVAP TECS                  104

SEQ ID NO: 157          moltype = DNA  length = 318
FEATURE                 Location/Qualifiers
source                  1..318
                        mol_type = other DNA
                        organism = Homo sapiens
SEQUENCE: 157
ggtcagccca aggctgcccc ctcggtcact ctgttcccac cctcctctga ggagcttcaa  60
gccaacaagg ccacactggt gtgtctcata agtgacttct acccggggcc agtgacagtt  120
gcctggaagg cagatagcag ccccgtcaag gcgggggtgg agaccaccac accctccaaa  180
caaagcaaca acaagtacgc ggccagcagc tacctgagcc tgacgcctga gcagtggaag  240
tcccacaaaa gctacagctg ccaggtcacg catgaaggga gcaccgtgga gaagacagtg  300
gcccctacgg aatgttca                                                318

SEQ ID NO: 158          moltype = AA  length = 106
FEATURE                 Location/Qualifiers
source                  1..106
                        mol_type = protein
                        organism = Homo sapiens
SEQUENCE: 158
GQPKAAPSVT LFPPSSEELQ ANKATLVCLI SDFYPGPVTV AWKADSSPVK AGVETTTPSK  60
QSNNKYAASS YLSLTPEQWK SHKSYSCQVT HEGSTVEKTV APTECS                106

SEQ ID NO: 159          moltype = DNA  length = 318
FEATURE                 Location/Qualifiers
source                  1..318
                        mol_type = other DNA
                        organism = Homo sapiens
SEQUENCE: 159
ggtcagccca aggctgcccc ctcggtcact ctgttcccac cctcctctga ggagcttcaa  60
gccaacaagg ccacactggt gtgtctcata agtgacttct acccgggagc cgtgacagtg  120
gcctggaagg cagatagcag ccccgtcaag gcgggagtgg agaccaccac accctccaaa  180
caaagcaaca acaagtacgc ggccagcagc tacctgagcc tgacgcctga gcagtggaag  240
tcccacaaaa gctacagctg ccaggtcacg catgaaggga gcaccgtgga gaagacagtg  300
gcccctacag aatgttca                                                318

SEQ ID NO: 160          moltype = AA  length = 106
FEATURE                 Location/Qualifiers
source                  1..106
                        mol_type = protein
                        organism = Homo sapiens
SEQUENCE: 160
GQPKAAPSVT LFPPSSEELQ ANKATLVCLI SDFYPGAVTV AWKADSSPVK AGVETTTPSK  60
QSNNKYAASS YLSLTPEQWK SHKSYSCQVT HEGSTVEKTV APTECS                106

SEQ ID NO: 161          moltype = DNA  length = 318
FEATURE                 Location/Qualifiers
source                  1..318
                        mol_type = other DNA
                        organism = Homo sapiens
SEQUENCE: 161
ggtcagccca aggctgcccc ctcggtcact ctgttcccgc cctcctctga ggagcttcaa  60
gccaacaagg ccacactggt gtgtctcata agtgacttct acccgggagc cgtgacagtg  120
gcctggaagg cagatagcag ccccgtcaag gcgggagtgg agaccaccac accctccaaa  180
caaagcaaca acaagtacgc ggccagcagc tacctgagcc tgacgcctga gcagtggaag  240
tcccacagaa gctacagctg ccaggtcacg catgaaggga gcaccgtgga gaagacagtg  300
gcccctacag aatgttca                                                318

SEQ ID NO: 162          moltype = AA  length = 106
FEATURE                 Location/Qualifiers
source                  1..106
                        mol_type = protein
                        organism = Homo sapiens
SEQUENCE: 162
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                106

SEQ ID NO: 163          moltype = DNA  length = 318
FEATURE                 Location/Qualifiers
source                  1..318
                        mol_type = other DNA
                        organism = Homo sapiens
SEQUENCE: 163
```

```
ggtcagccca aggctgcccc atcggtcact ctgttcccgc cctcctctga ggagcttcaa  60
gccaacaagg ccacactggt gtgcctgatc agtgacttct acccgggagc tgtgaaagtg  120
gcctggaagg cagatggcag ccccgtcaac acgggagtgg agaccaccac accctccaaa  180
cagagcaaca acaagtacgc ggccagcagc tacctgagcc tgacgcctga gcagtggaag  240
tcccacagaa gctacagctg ccaggtcacg catgaaggga gcaccgtgga gaagacagtg  300
gcccctgcag aatgttca                                                  318

SEQ ID NO: 164          moltype = AA  length = 106
FEATURE                 Location/Qualifiers
source                  1..106
                        mol_type = protein
                        organism = Homo sapiens
SEQUENCE: 164
GQPKAAPSVT LFPPSSEELQ ANKATLVCLI SDFYPGAVKV AWKADGSPVN TGVETTTPSK  60
QSNNKYAASS YLSLTPEQWK SHRSYSCQVT HEGSTVEKTV APAECS                   106

SEQ ID NO: 165          moltype = DNA  length = 318
FEATURE                 Location/Qualifiers
source                  1..318
                        mol_type = other DNA
                        organism = Homo sapiens
SEQUENCE: 165
ggtcagccca aggctgcccc atcggtcact ctgttcccac cctcctctga ggagcttcaa  60
gccaacaagg ccacactggt gtgtctcgta agtgacttct acccgggagc cgtgacagtg  120
gcctggaagg cagatggcag ccccgtcaag gtgggagtgg agaccaccaa accctccaaa  180
caaagcaaca acaagtatgc ggccagcagc tacctgagcc tgacgcccga gcagtggaag  240
tcccacagaa gctacagctg ccgggtcacg catgaaggga gcaccgtgga gaagacagtg  300
gcccctgcag aatgctct                                                  318

SEQ ID NO: 166          moltype = AA  length = 106
FEATURE                 Location/Qualifiers
source                  1..106
                        mol_type = protein
                        organism = Homo sapiens
SEQUENCE: 166
GQPKAAPSVT LFPPSSEELQ ANKATLVCLV SDFYPGAVTV AWKADGSPVK VGVETTKPSK  60
QSNNKYAASS YLSLTPEQWK SHRSYSCRVT HEGSTVEKTV APAECS                   106

SEQ ID NO: 167          moltype = DNA  length = 615
FEATURE                 Location/Qualifiers
source                  1..615
                        mol_type = other DNA
                        organism = Homo sapiens
SEQUENCE: 167
atgggctggt cctgcatcat cctgtttctg gtggccaccg ccaccggcgt gcacagcgat  60
tacaaggatg acgacgataa gcgtatgaaa cagatcgaag ataaaattga agagatcttg  120
agcaaaatct atcatatcga aaacgaaatt gcgcgtatca aaaagctgat tggcgaacgt  180
ggcggtggca gcggtggcgg tagcggcggt ggcagccagg tgtcccaccg ataccccagg  240
atccagtcca tcaaggtcca gttcaccgag tacaaaaagg agaagggatt catcctgacc  300
tcccaaaagg aggacgagat catgaaggtg caaaacaact ccgtgatcat caactgcgac  360
ggcttctacc tgatctccct gaagggctac ttctcccagg aggtgaacat ctccctgcac  420
taccagaagg acgaggagcc cctgttccag ctgaagaagg tgaggtccgt gaattccctg  480
atggtggcca gcctgaccta caaggacaag gtctacctga acgtgaccac cgacaacacc  540
agcctggacg acttccatgt caacggcggc gagctgatcc tgatccatca gaaccccggc  600
gagttttgcg tcctg                                                     615

SEQ ID NO: 168          moltype = AA  length = 205
FEATURE                 Location/Qualifiers
source                  1..205
                        mol_type = protein
                        organism = Homo sapiens
SEQUENCE: 168
MGWSCIILFL VATATGVHSD YKDDDDKRMK QIEDKIEEIL SKIYHIENEI ARIKKLIGER  60
GGGSGGGSGG GSQVSHRYPR IQSIKVQFTE YKKEKGFILT SQKEDEIMKV QNNSVIINCD  120
GFYLISLKGY FSQEVNISLH YQKDEEPLFQ LKKVRSVNSL MVASLTYKDK VYLNVTTDNT  180
SLDDFHVNGG ELILIHQNPG EFCVL                                          205

SEQ ID NO: 169          moltype = DNA  length = 615
FEATURE                 Location/Qualifiers
source                  1..615
                        mol_type = other DNA
                        organism = Homo sapiens
SEQUENCE: 169
atgggctggt cctgcatcat cctgtttctg gtggccaccg ccaccggcgt gcacagcgat  60
tacaaggatg acgacgataa gcgtatgaaa cagatcgaag ataaaattga agagatcttg  120
agcaaaatct atcatatcga aaacgaaatt gcgcgtatca aaaagctgat tggcgaacgt  180
ggcggtggca gcggtggcgg tagcggcggt ggcagccagg tgtcccacca ataccccagg  240
atccagtcca tcaaggtcca gttcaccgag tacaaaaagg aggagggatt catcctgacc  300
tcccaaaagg aggacgagat catgaaggtg caaaacaact ccgtgatcat caactgcgac  360
```

```
ggcttctacc tgatctccct gaagggctac ttctcccagg aggtgaacat ctccctgcac  420
taccagaagg acgaggagcc cctgttccag ctgaagaagg tgaggtccgt gaattccctg  480
atggtggcca gcctgaccta caaggacaag gtctacctga acgtgaccac cgacaacacc  540
agcctggacg acttccatgt caacggcggc gagctgatcc tgatccatca gaaccccggc  600
gagttttgcg tcctg                                                    615

SEQ ID NO: 170          moltype = AA  length = 205
FEATURE                 Location/Qualifiers
source                  1..205
                        mol_type = protein
                        organism = Homo sapiens
SEQUENCE: 170
MGWSCIILFL VATATGVHSD YKDDDDKRMK QIEDKIEEIL SKIYHIENEI ARIKKLIGER  60
GGGSGGGSGG GSQVSHQYPR IQSIKVQFTE YKKEEGFILT SQKEDEIMKV QNNSVIINCD  120
GFYLISLKGY FSQEVNISLH YQKDEEPLFQ LKKVRSVNSL MVASLTYKDK VYLNVTTDNT  180
SLDDFHVNGG ELILIHQNPG EFCVL                                         205

SEQ ID NO: 171          moltype = DNA  length = 1332
FEATURE                 Location/Qualifiers
source                  1..1332
                        mol_type = other DNA
                        organism = Homo sapiens
SEQUENCE: 171
atgggctggt cctgcatcat cctgtttctg gtggccaccg ccaccggcgt gcacagcctg  60
cattgcgtgg gcgacaccta tccctccaac gacaggtgct gccacgagtg caggcctgga  120
aacggcatgg tgagcaggtg cagccggtcc cagaataccg tgtgtaggcc ctgcggcccc  180
ggcttttaca acgacgtggt gtcctccaag ccctgcaagc cctgcacatg gtgcaacctg  240
cggtccggca gcgagaggaa gcagctctgc acagccaccc aggacaccgt ctgtaggtgt  300
agggctggca cccagcctct ggactcctac aagcccggcg tggattgtgc tccttgccct  360
cccggccatt tctcccctgg cgacaaccag gcttgcaagc cctggaccaa ctgtaccctg  420
gccggcaagc atacactgca gcctgcttcc aactcctccg acgctatctg cgaggatagg  480
gacccccctg ccacacaacc ccaggagaca cagggccctc ctgctaggcc catcacagtc  540
caacccaccg aagcctggcc caggacatcc caaggccctt ccaccaggcc tgtggaagtg  600
cctggaggaa gggctgtggc cattgaaggt cgtatggatg aacccaagtc ctgcgacaag  660
acccacacct gtccccottg tcctgcccct gaactgctgg gcggaccttc cgtgttcctg  720
ttcccccccaa agcccaagga caccctgatg atctcccgga cccccgaagt gacctgcgtg  780
gtggtggatg tgtcccacga ggaccctgaa gtgaagttca attggtacgt ggacggcgtg  840
gaagtgcaca acgccaagac caagcctaga gaggaacagt acaactccac ctaccgggtg  900
gtgtccgtgc tgaccgtgct gcaccaggat tggctgaacg gcaaagagta caagtgcaag  960
gtgtccaaca aggccctgcc tgcccccatc gaaaagacca tctccaaggc caagggccag  1020
ccccgggaac cccaggtgta cacactgccc cctagcaggg acgagctgac caagaaccag  1080
gtgtccctga cctgtctcgt gaaaggcttc taccccctccg atatcgccgt ggaatgggag  1140
tccaacggcc agcctgagaa caactacaag accacccccc ctgtgctgga ctccgacggc  1200
tcattcttcc tgtacagcaa gctgacagtg gacaagtccc ggtggcagca gggcaacgtg  1260
ttctcctgct ccgtgatgca cgaggccctg cacaaccact acacccagaa gtccctgtcc  1320
ctgagcccct ga                                                       1332

SEQ ID NO: 172          moltype = AA  length = 443
FEATURE                 Location/Qualifiers
source                  1..443
                        mol_type = protein
                        organism = Homo sapiens
SEQUENCE: 172
MGWSCIILFL VATATGVHSL HCVGDTYPSN DRCCHECRPG NGMVSRCSRS QNTVCRPCGP  60
GFYNDVVSSK PCKPCTWCNL RSGSERKQLC TATQDTVCRC RAGTQPLDSY KPGVDCAPCP  120
PGHFSPGDNQ ACKPWTNCTL AGKHTLQPAS NSSDAICEDR DPPATQPQET QGPPARPITV  180
QPTEAWPRTS QGPSTRPVEV PGGRAVAIEG RMDEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSP                                           443

SEQ ID NO: 173          moltype = DNA  length = 552
FEATURE                 Location/Qualifiers
source                  1..552
                        mol_type = other DNA
                        organism = Homo sapiens
SEQUENCE: 173
atggagaggg tgcagcccct cgaggagaac gtgggaaacg ccgccaggcc taggttcgag  60
aggaacaagc tgctgctggt ggcttccgtg atccaaggac tcggcctgct gctctgcttc  120
acctacatct gcctccactt cagcgccctg caggtgtccc accgataccc caggatccag  180
tccatcaagg tccagttcac cgagtacaaa aaggagaagg gattcatcct gacctcccaa  240
aaggaggacg agatcatgaa ggtgcaaaac aactccgtga tcatcaactg cgacggcttc  300
tacctgatct ccctgaaggg ctacttctcc caggaggtga acatctccct gcactaccag  360
aaggacgagg agcccctgtt ccagctgaag aaggtgaggt ccgtgaattc cctgatggtg  420
gccagcctga cctacaagga caaggtctac ctgaacgtga ccaccgacaa caccagcctg  480
gacgacttcc atgtcaacgg cggcgagctg atcctgatcc atcagaaccc cggcgagttt  540
tgcgtcctgt aa                                                       552
```

-continued

```
SEQ ID NO: 174          moltype = AA  length = 181
FEATURE                 Location/Qualifiers
source                  1..181
                        mol_type = protein
                        organism = Homo sapiens
SEQUENCE: 174
MERVQPLEEN VGNAARPRFE RNKLLLVASV IQGLGLLLCF TYICLHFSAL QVSHRYPRIQ  60
SIKVQFTEYK KEKGFILTSQ KEDEIMKVQN NSVIINCDGF YLISLKGYFS QEVNISLHYQ  120
KDEEPLFQLK KVRSVNSLMV ASLTYKDKVY LNVTTDNTSL DDFHVNGGEL ILIHQNPGEF  180
C                                                                  181

SEQ ID NO: 175          moltype = DNA  length = 834
FEATURE                 Location/Qualifiers
source                  1..834
                        mol_type = other DNA
                        organism = Homo sapiens
SEQUENCE: 175
atgtgcgtgg gggctcggcg gctgggccgc gggccgtgtg cggctctgct cctcctgggc  60
ctggggctga gcaccgtgac ggggctccac tgtgtcgggg acacctaccc cagcaacgac  120
cggtgctgcc acgagtgcag gccaggcaac gggatggtga gccgctgcag ccgctcccag  180
aacacggtgt gccgtccgtg cgggccgggc ttctacaacg acgtggtcag ctccaagccg  240
tgcaagccct gcacgtggtg taacctcaga agtgggagtg agcggaagca gctgtgcacg  300
gccacacagg acacagtctg ccgctgccgg gcgggcaccc agcccctgga cagctacaag  360
cctggagttg actgtgcccc ctgccctcca gggcacttct ccccaggcga caaccaggcc  420
tgcaagccct ggaccaactg caccttggct gggaagcaca ccctgcagcc ggccagcaat  480
agctcggacg caatctgtga ggacagggac cccccagcca cgcagcccca ggagacccag  540
ggccccccgg ccaggcccat cactgtccag cccactgaag cctggcccag aacctcacag  600
ggaccctcca cccggcccgt ggaggtcccc gggggccgtg cggttgccgc catcctgggc  660
ctgggcctgg tgctggggct gctgggcccc ctggccatcc tgctggccct gtacctgctc  720
cggagggacc agaggctgcc ccccgatgcc cacaagcccc ctgggggagg cagtttccgg  780
acccccatcc aagaggagca ggccgacgcc cactccaccc tggccaagat ctga        834

SEQ ID NO: 176          moltype = AA  length = 277
FEATURE                 Location/Qualifiers
source                  1..277
                        mol_type = protein
                        organism = Homo sapiens
SEQUENCE: 176
MCVGARRLGR GPCAALLLLG LGLSTVTGLH CVGDTYPSND RCCHECRPGN GMVSRCSRSQ  60
NTVCRPCGPG FYNDVVSSKP CKPCTWCNLR SGSERKQLCT ATQDTVCRCR AGTQPLDSYK  120
PGVDCAPCPP GHFSPGDNQA CKPWTNCTLA GKHTLQPASN SSDAICEDRD PPATQPQETQ  180
GPPARPITVQ PTEAWPRTSQ GPSTRPVEVP GGRAVAAILG LGLVLGLLGP LAILLALYLL  240
RRDQRLPPDA HKPPGGGSFR TPIQEEQADA HSTLAKI                           277

SEQ ID NO: 177          moltype = AA  length = 117
FEATURE                 Location/Qualifiers
source                  1..117
                        mol_type = protein
                        organism = Homo sapiens
SEQUENCE: 177
EVQLVESGGG LVQAGGSLRL SCAASRSIGR LDRMGWYRHR TGEPRELVAT ITGGSSINYG  60
DFVKGRFTIS IDNAKNTVYL QMNNLKPEDT AVYYCNFNKY VTSRDTWGQG TQVTVSS     117

SEQ ID NO: 178          moltype = AA  length = 128
FEATURE                 Location/Qualifiers
source                  1..128
                        mol_type = protein
                        organism = Homo sapiens
SEQUENCE: 178
EVQLVESGGG LVQAGGSLRL SCVASGRSFS TYIMGWFRQA PGKEREFVAT ISRSGITIRS  60
ADSVKGRFTI SRDNAKNTVY LQMNSLKPED TAVYYCAAGP YVEQTLGLYQ TLGPWDYWGQ  120
GTQVTVSS                                                           128

SEQ ID NO: 179          moltype = AA  length = 124
FEATURE                 Location/Qualifiers
source                  1..124
                        mol_type = protein
                        organism = Homo sapiens
SEQUENCE: 179
EVQLVESGGG LVQAGGSLRL SCAASGRTFS SIYAKGWFRQ APGKEREFVA AISRSGRSTS  60
YADSVKGRFT ISRDNAKNTV YLQMNSLKPE DTAVYYCAAV GGATTVTASE WDYWGLGTQV  120
TVSS                                                               124

SEQ ID NO: 180          moltype = AA  length = 125
FEATURE                 Location/Qualifiers
source                  1..125
                        mol_type = protein
                        organism = Homo sapiens
SEQUENCE: 180
```

-continued

```
EVQLVESGGG LVQAGDSLRL SCAASGLTFS SFAMGWFRQA PGKEREFVAA ISRSGYGTSE  60
ADSVRDRFII SRDNAKNTVT LHLSRLKPED TAVYYCAAEH TLGRPSRSQI NYLYWGQGTQ  120
VTVSS                                                             125

SEQ ID NO: 181          moltype = AA  length = 117
FEATURE                 Location/Qualifiers
source                  1..117
                        mol_type = protein
                        organism = Homo sapiens
SEQUENCE: 181
EVQLVESGGG LVQAGGSLRL SCAASRNILS LNTMGWYRHA PGKPRELVAR ISSNSKTDYA  60
DSVKGRFTIS RDNAKNTVLL QMNSLKPEDT GVYYCNLNVW RTSSDYWGQG TQVTVSS     117

SEQ ID NO: 182          moltype = AA  length = 128
FEATURE                 Location/Qualifiers
source                  1..128
                        mol_type = protein
                        organism = Homo sapiens
SEQUENCE: 182
EVQLVESGGG LVQAGGSLRL SCAASGFTLD DYAIAWFRQA PGKEREGVSR IKISNGRTTY  60
AGSVKGRFTI SSDNAKNTVY LQMNSLNAED TAVYYCAADR SSLLFGSNWD RKARYDYWGQ  120
GTQVTVSS                                                          128

SEQ ID NO: 183          moltype = AA  length = 125
FEATURE                 Location/Qualifiers
source                  1..125
                        mol_type = protein
                        organism = Homo sapiens
SEQUENCE: 183
EVQLVESGGG LVQAGASLRL SCAASGRRFI SNYAMGWFRQ APGQERAFVA AISRSGSITY  60
YTDSVKGRFS ISRDYAKSTV YLQMDNLKPE DTAVYYCAAD GGAVRDLTTN LPDYWGRGTQ  120
VTVSS                                                             125

SEQ ID NO: 184          moltype = AA  length = 128
FEATURE                 Location/Qualifiers
source                  1..128
                        mol_type = protein
                        organism = Homo sapiens
SEQUENCE: 184
EVQLVESGGG LVQPGGSLRL SCAASGRSFS TYIMGWFRQA PGKEREFVAT ISRSGITTRS  60
ADSVKGRFTI SRDNSKNTVY LQMNSLRPED TAVYYCAAGP YVEQTLGLYQ TLGPWDYWGQ  120
GTLVTVSS                                                          128

SEQ ID NO: 185          moltype = AA  length = 124
FEATURE                 Location/Qualifiers
source                  1..124
                        mol_type = protein
                        organism = Homo sapiens
SEQUENCE: 185
EVQLVESGGG LVQPGGSLRL SCAASGRTFS SIYAKGWFRQ APGKEREFVA AISRSGRSTS  60
YADSVKGRFT ISRDNAKNTV YLQMNSLRPE DTAVYYCAAV GGATTVTASE WDYWGLGTLV  120
TVSS                                                              124

SEQ ID NO: 186          moltype = AA  length = 124
FEATURE                 Location/Qualifiers
source                  1..124
                        mol_type = protein
                        organism = Homo sapiens
SEQUENCE: 186
EVQLVESGGG LVQPGGSLRL SCAASGRTFS SIYAKGWFRQ APGKEREFVA AISRSGRSTS  60
YADSVKGRFT ISRDNSKNTV YLQMNSLRPE DTAVYYCAAV GGATTVTASE WDYWGLGTLV  120
TVSS                                                              124

SEQ ID NO: 187          moltype = AA  length = 124
FEATURE                 Location/Qualifiers
source                  1..124
                        mol_type = protein
                        organism = Homo sapiens
SEQUENCE: 187
EVQLVESGGG LVQPGGSLRL SCAASGRTFS SIYAKGWFRQ APGKEREFVA AISRSGRSTS  60
YADSVKGRFT ISRDNAKNTV YLQMNSLRPE DTAVYYCAAV GGATTVTASE WDYWGQGTLV  120
TVSS                                                              124

SEQ ID NO: 188          moltype = AA  length = 124
FEATURE                 Location/Qualifiers
source                  1..124
                        mol_type = protein
                        organism = Homo sapiens
SEQUENCE: 188
```

```
EVQLVESGGG LVQPGGSLRL SCAASGRTFS SIYAKGWFRQ APGKEREFVA AISRSGRSTS  60
YADSVKGRFT ISRDNSKNTV YLQMNSLRPE DTAVYYCAAV GGATTVTASE WDYWGQGTLV  120
TVSS                                                               124

SEQ ID NO: 189         moltype = AA  length = 124
FEATURE                Location/Qualifiers
source                 1..124
                       mol_type = protein
                       organism = Homo sapiens
SEQUENCE: 189
DVQLVESGGG LVQPGGSLRL SCAASGRTFS SIYAKGWFRQ APGKEREFVA AISRSGRSTS  60
YADSVKGRFT ISRDNAKNTV YLQMNSLRPE DTAVYYCAAV GGATTVTASE WDYWGLGTLV  120
TVSS                                                               124

SEQ ID NO: 190         moltype = AA  length = 124
FEATURE                Location/Qualifiers
source                 1..124
                       mol_type = protein
                       organism = Homo sapiens
SEQUENCE: 190
DVQLVESGGG LVQPGGSLRL SCAASGRTFS SIYAKGWFRQ APGKEREFVA AISRSGRSTS  60
YADSVKGRFT ISRDNSKNTV YLQMNSLRPE DTAVYYCAAV GGATTVTASE WDYWGQGTLV  120
TVSS                                                               124

SEQ ID NO: 191         moltype = AA  length = 117
FEATURE                Location/Qualifiers
source                 1..117
                       mol_type = protein
                       organism = Homo sapiens
SEQUENCE: 191
DVQLVESGGG LVQAGGSLRL SCAASRSIGR LDRMGWYRHR TGEPRELVAT ITGGSSINYG  60
DFVKGRFTIS IDNAKNTVYL QMNNLKPEDT AVYYCNFNKY VTSRDTWGQG TQVTVSS     117

SEQ ID NO: 192         moltype = AA  length = 117
FEATURE                Location/Qualifiers
source                 1..117
                       mol_type = protein
                       organism = Homo sapiens
SEQUENCE: 192
DVQLVESGGG LVQPGGSLRL SCAASRSIGR LDRMGWYRHR TGEPRELVAT ITGGSSINYG  60
DFVKGRFTIS RDNSKNTVYL QMNSLRPEDT AVYYCNFNKY VTSRDTWGQG TLVTVSS     117

SEQ ID NO: 193         moltype = AA  length = 117
FEATURE                Location/Qualifiers
source                 1..117
                       mol_type = protein
                       organism = Homo sapiens
SEQUENCE: 193
DVQLVESGGG LVQPGGSLRL SCAASRSIGR LDRMGWYRHA TGEPRELVAT ITGGSSINYG  60
DFVKGRFTIS RDNSKNTVYL QMNSLRPEDT AVYYCNFNKY VTSRDTWGQG TLVTVSS     117

SEQ ID NO: 194         moltype = AA  length = 117
FEATURE                Location/Qualifiers
source                 1..117
                       mol_type = protein
                       organism = Homo sapiens
SEQUENCE: 194
DVQLVESGGG LVQPGGSLRL SCAASRSIGR LDRMGWYRHR PGEPRELVAT ITGGSSINYG  60
DFVKGRFTIS RDNSKNTVYL QMNSLRPEDT AVYYCNFNKY VTSRDTWGQG TLVTVSS     117

SEQ ID NO: 195         moltype = AA  length = 117
FEATURE                Location/Qualifiers
source                 1..117
                       mol_type = protein
                       organism = Homo sapiens
SEQUENCE: 195
DVQLVESGGG LVQPGGSLRL SCAASRSIGR LDRMGWYRHR TGKPRELVAT ITGGSSINYG  60
DFVKGRFTIS RDNSKNTVYL QMNSLRPEDT AVYYCNFNKY VTSRDTWGQG TLVTVSS     117

SEQ ID NO: 196         moltype = AA  length = 117
FEATURE                Location/Qualifiers
source                 1..117
                       mol_type = protein
                       organism = Homo sapiens
SEQUENCE: 196
DVQLVESGGG LVQPGGSLRL SCAASRSIGR LDRMGWYRHA PGEPRELVAT ITGGSSINYG  60
DFVKGRFTIS RDNSKNTVYL QMNSLRPEDT AVYYCNFNKY VTSRDTWGQG TLVTVSS     117

SEQ ID NO: 197         moltype = AA  length = 117
```

```
FEATURE                Location/Qualifiers
source                 1..117
                       mol_type = protein
                       organism = Homo sapiens
SEQUENCE: 197
DVQLVESGGG LVQPGGSLRL SCAASRSIGR LDRMGWYRHA TGKPRELVAT ITGGSSINYG  60
DFVKGRFTIS RDNSKNTVYL QMNSLRPEDT AVYYCNFNKY VTSRDTWGQG TLVTVSS     117

SEQ ID NO: 198         moltype = AA  length = 117
FEATURE                Location/Qualifiers
source                 1..117
                       mol_type = protein
                       organism = Homo sapiens
SEQUENCE: 198
DVQLVESGGG LVQPGGSLRL SCAASRSIGR LDRMGWYRHR PGKPRELVAT ITGGSSINYG  60
DFVKGRFTIS RDNSKNTVYL QMNSLRPEDT AVYYCNFNKY VTSRDTWGQG TLVTVSS     117

SEQ ID NO: 199         moltype = AA  length = 117
FEATURE                Location/Qualifiers
source                 1..117
                       mol_type = protein
                       organism = Homo sapiens
SEQUENCE: 199
DVQLVESGGG LVQPGGSLRL SCAASRSIGR LDRMGWYRHA PGKPRELVAT ITGGSSINYG  60
DFVKGRFTIS RDNSKNTVYL QMNSLRPEDT AVYYCNFNKY VTSRDTWGQG TLVTVSS     117

SEQ ID NO: 200         moltype = AA  length = 117
FEATURE                Location/Qualifiers
source                 1..117
                       mol_type = protein
                       organism = Homo sapiens
SEQUENCE: 200
DVQLVESGGG LVQPGGSLRL SCAASRSIGR LDRMGWYRHR TGEPRELVAT ITGGSSINYA  60
DFVKGRFTIS RDNSKNTVYL QMNSLRPEDT AVYYCNFNKY VTSRDTWGQG TLVTVSS     117

SEQ ID NO: 201         moltype = AA  length = 117
FEATURE                Location/Qualifiers
source                 1..117
                       mol_type = protein
                       organism = Homo sapiens
SEQUENCE: 201
DVQLVESGGG LVQPGGSLRL SCAASRSIGR LDRMGWYRHR TGEPRELVAT ITGGSSINYG  60
DSVKGRFTIS RDNSKNTVYL QMNSLRPEDT AVYYCNFNKY VTSRDTWGQG TLVTVSS     117

SEQ ID NO: 202         moltype = AA  length = 117
FEATURE                Location/Qualifiers
source                 1..117
                       mol_type = protein
                       organism = Homo sapiens
SEQUENCE: 202
DVQLVESGGG LVQPGGSLRL SCAASRSIGR LDRMGWYRHR TGEPRELVAT ITGGSSINYA  60
DSVKGRFTIS RDNSKNTVYL QMNSLRPEDT AVYYCNFNKY VTSRDTWGQG TLVTVSS     117

SEQ ID NO: 203         moltype = AA  length = 117
FEATURE                Location/Qualifiers
source                 1..117
                       mol_type = protein
                       organism = Homo sapiens
SEQUENCE: 203
DVQLVESGGG LVQPGGSLRL SCAASRSIGR LDRMGWYRHR TGEPRELVAT ITGGSSINYG  60
DFVKGRFTIS IDNSKNTVYL QMNSLRPEDT AVYYCNFNKY VTSRDTWGQG TLVTVSS     117

SEQ ID NO: 204         moltype = AA  length = 117
FEATURE                Location/Qualifiers
source                 1..117
                       mol_type = protein
                       organism = Homo sapiens
SEQUENCE: 204
DVQLVESGGG LVQPGGSLRL SCAASRSIGR LDRMGWYRHR TGEPRELVAT ITGGSSINYG  60
DFVKGRFTIS RDNAKNTVYL QMNSLRPEDT AVYYCNFNKY VTSRDTWGQG TLVTVSS     117

SEQ ID NO: 205         moltype = AA  length = 117
FEATURE                Location/Qualifiers
source                 1..117
                       mol_type = protein
                       organism = Homo sapiens
SEQUENCE: 205
DVQLVESGGG LVQPGGSLRL SCAASRSIGR LDRMGWYRHR TGEPRELVAT ITGGSSINYG  60
DFVKGRFTIS RDNSKNTVYL QMNNLRPEDT AVYYCNFNKY VTSRDTWGQG TLVTVSS     117
```

```
SEQ ID NO: 206          moltype = AA  length = 117
FEATURE                 Location/Qualifiers
source                  1..117
                        mol_type = protein
                        organism = Homo sapiens
SEQUENCE: 206
DVQLVESGGG LVQPGGSLRL SCAASRSIGR LDRMGWYRHR PGKPRELVAT ITGGSSINYA  60
DSVKGRFTIS RDNSKNTVYL QMNSLRPEDT AVYYCNFNKY VTSRDTWGQG TLVTVSS     117

SEQ ID NO: 207          moltype = AA  length = 117
FEATURE                 Location/Qualifiers
source                  1..117
                        mol_type = protein
                        organism = Homo sapiens
SEQUENCE: 207
DVQLVESGGG LVQPGGSLRL SCAASRSIGR LDRMGWYRHR PGKPRELVAT ITGGSSINYA  60
DSVKGRFTIS IDNSKNTVYL QMNSLRPEDT AVYYCNFNKY VTSRDTWGQG TLVTVSS     117

SEQ ID NO: 208          moltype = AA  length = 117
FEATURE                 Location/Qualifiers
source                  1..117
                        mol_type = protein
                        organism = Homo sapiens
SEQUENCE: 208
DVQLVESGGG LVQPGGSLRL SCAASRSIGR LDRMGWYRHR PGKPRELVAT ITGGSSINYA  60
DSVKGRFTIS RDNSKNTVYL QMNNLRPEDT AVYYCNFNKY VTSRDTWGQG TLVTVSS     117

SEQ ID NO: 209          moltype = AA  length = 117
FEATURE                 Location/Qualifiers
source                  1..117
                        mol_type = protein
                        organism = Homo sapiens
SEQUENCE: 209
DVQLVESGGG LVQPGGSLRL SCAASRSIGR LDRMGWYRHR PGKPRELVAT ITGGSSINYA  60
DSVKGRFTIS IDNSKNTVYL QMNNLRPEDT AVYYCNFNKY VTSRDTWGQG TLVTVSS     117

SEQ ID NO: 210          moltype = AA  length = 117
FEATURE                 Location/Qualifiers
source                  1..117
                        mol_type = protein
                        organism = Homo sapiens
SEQUENCE: 210
EVQLVESGGG LVQPGGSLRL SCAASRSIGR LDRMGWYRHR PGEPRELVAT ITGGSSINYG  60
DSVKGRFTIS IDNSKNTVYL QMNSLRPEDT AVYYCNFNKY VTSRDTWGQG TLVTVSS     117

SEQ ID NO: 211          moltype = AA  length = 117
FEATURE                 Location/Qualifiers
source                  1..117
                        mol_type = protein
                        organism = Homo sapiens
SEQUENCE: 211
EVQLVESGGG LVQPGGSLRL SCAASRSIGR LDRMGWYRHR PGKPRELVAT ITGGSSINYG  60
DSVKGRFTIS IDNSKNTVYL QMNSLRPEDT AVYYCNFNKY VTSRDTWGQG TLVTVSS     117

SEQ ID NO: 212          moltype = AA  length = 450
FEATURE                 Location/Qualifiers
source                  1..450
                        mol_type = protein
                        organism = Homo sapiens
SEQUENCE: 212
EVQLLESGGG LVQPGGSLRL SCAASGFTFN SYAMSWVRQA PGKGLEWVSL ISGSGGFTYY  60
ADSVKGRFTI SRDNSRTTLY LQMNSLRAED TAVYYCAKDR LVAPGTFDYW GQGALVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 213          moltype = AA  length = 214
FEATURE                 Location/Qualifiers
source                  1..214
                        mol_type = protein
                        organism = Homo sapiens
SEQUENCE: 213
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
```

```
LSKADYEKHK VYACEVTHQG LSSPVTKSFN RGEC                          214

SEQ ID NO: 214          moltype = AA  length = 107
FEATURE                 Location/Qualifiers
source                  1..107
                        mol_type = protein
                        organism = Homo sapiens
SEQUENCE: 214
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK            107

SEQ ID NO: 215          moltype = AA  length = 120
FEATURE                 Location/Qualifiers
source                  1..120
                        mol_type = protein
                        organism = Homo sapiens
SEQUENCE: 215
EVQLLESGGG LVQPGGSLRL SCAASGFTFN SYAMSWVRQA PGKGLEWVSI ISGSGGFTYY  60
ADSVKGRFTI SRDNSRTTLY LQMNSLRAED TAVYYCAKDR LVAPGTFDYW GQGALVTVSS  120

SEQ ID NO: 216          moltype = AA  length = 107
FEATURE                 Location/Qualifiers
source                  1..107
                        mol_type = protein
                        organism = Homo sapiens
SEQUENCE: 216
EIVLTQSPGT LSLSPGERAT LSCRASQSVS SNYLAWYQQK PGQAPRLLIY GASSRATGIP  60
DRFSGSGSGT DFTLTISRLE PEDFAVYYCQ QYGSSFTFGP GTKVDIK            107

SEQ ID NO: 217          moltype = AA  length = 120
FEATURE                 Location/Qualifiers
source                  1..120
                        mol_type = protein
                        organism = Homo sapiens
SEQUENCE: 217
QVQLVESGGG VVQPGRSLRL SCAASGFTFS NFGMHWVRQA PGKGLEWVAA IWYDGHDKYY  60
SYYVKGRFTI SRDNSKNTLF LQMNSLRAED TAVYYCARDS SSWYRYFDYW GQGTLVTVSS  120

SEQ ID NO: 218          moltype = AA  length = 107
FEATURE                 Location/Qualifiers
source                  1..107
                        mol_type = protein
                        organism = Homo sapiens
SEQUENCE: 218
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSFTFGP GTKVDIK            107

SEQ ID NO: 219          moltype = AA  length = 120
FEATURE                 Location/Qualifiers
source                  1..120
                        mol_type = protein
                        organism = Homo sapiens
SEQUENCE: 219
QVQLVESGGG VVQPGRSLRL SCAASGFTFS NFGMHWVRQA PGKGLEWVAA IWYDGHDKYY  60
AYYVKGRFTI SRDNSKNTLF LQMNSLRAED TAVYYCARDS SSWYRYFDYW GQGTLVTVSS  120

SEQ ID NO: 220          moltype = AA  length = 58
FEATURE                 Location/Qualifiers
source                  1..58
                        mol_type = protein
                        organism = Homo sapiens
SEQUENCE: 220
MLHPLCKVGS HQGSVAVDLG QISLSPSAAC SLKILQLITV NSIIVSLTFG GGTKVEIK    58

SEQ ID NO: 221          moltype = AA  length = 120
FEATURE                 Location/Qualifiers
source                  1..120
                        mol_type = protein
                        organism = Homo sapiens
SEQUENCE: 221
QVQLVESGGG VVQPGRSLRL SCAASGFTFS NFGMHWVRQA PGKGLEWVAA IWYDGHDKYY  60
SYYVKGRFTI SRDNSKNTLF LQMNSLRAED TAVYYCARDS SSWYRYFDYW GQGTLVTVSS  120

SEQ ID NO: 222          moltype = AA  length = 57
FEATURE                 Location/Qualifiers
source                  1..57
                        mol_type = protein
                        organism = Homo sapiens
SEQUENCE: 222
```

-continued

```
MPPVWKVGSH QGSAAVDLGQ ISLSPSAACS LKILQLITVN SLIVTLTFGG GTKVEIK     57

SEQ ID NO: 223          moltype = AA  length = 116
FEATURE                 Location/Qualifiers
source                  1..116
                        mol_type = protein
                        organism = Homo sapiens
SEQUENCE: 223
QVQLVESGGG VVQPGRSLRL SCAASGFTFS SYTMHWVRQA PGKGLEWVAV IWYDGSNKYY  60
VDSVKGRFTI SRDNSKNTLY LQMNSLRAED TAVYYCARKN WSFDFWGQGT LVTVSS      116

SEQ ID NO: 224          moltype = AA  length = 106
FEATURE                 Location/Qualifiers
source                  1..106
                        mol_type = protein
                        organism = Homo sapiens
SEQUENCE: 224
EIVLTQSPAT LSLSPGERAT LSCRASQGVS RYLAWYQQKP GQAPRLLIYD ASNRATGIPA  60
RVSGSGPGTD FTLTISSLEP EDFAVDYCQQ RSNWQYTFGQ GTKLEI                 106

SEQ ID NO: 225          moltype = AA  length = 121
FEATURE                 Location/Qualifiers
source                  1..121
                        mol_type = protein
                        organism = Homo sapiens
SEQUENCE: 225
QKQLVEFGGG VVQPGRSLRL SCAASGFTFS NYGMHWVRQA PGKGLEWVAV IWNDGSNKYY  60
VDSVKGRFII SRDNSKNTLY LQMNSLRAED TAVYYCARDR MGIYYYGMDV WGQGTTVTVS  120
S                                                                  121

SEQ ID NO: 226          moltype = AA  length = 104
FEATURE                 Location/Qualifiers
source                  1..104
                        mol_type = protein
                        organism = Homo sapiens
SEQUENCE: 226
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWTFGQGT KVEI                   104

SEQ ID NO: 227          moltype = AA  length = 120
FEATURE                 Location/Qualifiers
source                  1..120
                        mol_type = protein
                        organism = Homo sapiens
SEQUENCE: 227
EVQLLESGGG LVQPGGSLRL SCAASGFTFS SYAMNWVRQA PGKGLEWVSI ISGSGGFTYY  60
ADSVKGRFTI SRDNSKNTLY LQMNRLRAED TAIYFCAKDD IPAAGTFDPW GQGTLVTVSS  120

SEQ ID NO: 228          moltype = AA  length = 106
FEATURE                 Location/Qualifiers
source                  1..106
                        mol_type = protein
                        organism = Homo sapiens
SEQUENCE: 228
AIQLTQSPSS LSASVGDRVT ITCRASQGIS SALAWYQQKP GKAPKLLIYD VSSLESGVPS  60
RFSGSGSGTD FTLTISSLQP EDFATYYCQQ FNSYWTFGQG TKVEIK                 106

SEQ ID NO: 229          moltype = AA  length = 119
FEATURE                 Location/Qualifiers
source                  1..119
                        mol_type = protein
                        organism = Homo sapiens
SEQUENCE: 229
EVQLLESGGG LVQPGGSLRL SCAASGFTFS SYAMSWVRQA PGKGLEWVSL ISGSGGLTKY  60
ADSVKGRFTI SRDNSKRTLY LQMNSLRAED TAVYYCAKDI LVTGALDYWG QGTLVTVSS   119

SEQ ID NO: 230          moltype = AA  length = 120
FEATURE                 Location/Qualifiers
source                  1..120
                        mol_type = protein
                        organism = Homo sapiens
SEQUENCE: 230
EVQLLESGGG LVQPGGSLRL SCAASGFTFS SYAMNWVRQA PGKGLEWVSI ISGSGGFTYY  60
ADSVKGRFTI SRDNSKKTLY LQMSRLRAED TAIYFCAKDD IPAAGTFDPW GQGTLVTVSS  120

SEQ ID NO: 231          moltype = AA  length = 113
FEATURE                 Location/Qualifiers
source                  1..113
                        mol_type = protein
```

-continued

```
                        organism = Homo sapiens
SEQUENCE: 231
DILMTQTPLS LPVSLGDQAS ISCRSSQSIV HGNGNTYLEW HLQKPGQSPK LLIYRVSNRF  60
SGVPDRFSGS GSGTDFTLKI NRVEAEDLGV YYCFQGSHVP YTFGGGTKVE IKR         113

SEQ ID NO: 232          moltype = AA  length = 113
FEATURE                 Location/Qualifiers
source                  1..113
                        mol_type = protein
                        organism = Homo sapiens
SEQUENCE: 232
DIVMTQTPLS LPVSLGDQAS MYCRSSQSPV HSNGNTYLHW YLQKPGQSPK LLIYKVSNRF  60
SGVPDRFSGS GSGTDFTLKI SRVEAEDLGV YFCSQSTHIP WTFGGGTKVE IKR         113

SEQ ID NO: 233          moltype = AA  length = 123
FEATURE                 Location/Qualifiers
source                  1..123
                        mol_type = protein
                        organism = Homo sapiens
SEQUENCE: 233
QVQLQQPGAE LVRPGASVKL SCKASGYTFT SYWLNWVKQR PGQGLEWIVM IDPSDSETHY  60
NQVFKDKATL TVDKSSSTAY MQLSSLTSED SAVYYCIRGR GNFYGGSHAM EYWGQGTLLT  120
VSS                                                                123

SEQ ID NO: 234          moltype = AA  length = 118
FEATURE                 Location/Qualifiers
source                  1..118
                        mol_type = protein
                        organism = Homo sapiens
SEQUENCE: 234
QVQLQQPGAE LVKPGTSVKL SCKASGYSFT SYWMHGVRQR PGQGLEWIGE IDPSNGRTNY  60
NEKFKSKATL TVDKSSSTAY IQLSSLTSED SAVYYCTRER SPRYFDVWGA GTTLTVSS    118

SEQ ID NO: 235          moltype = AA  length = 7
FEATURE                 Location/Qualifiers
SITE                    4
                        note = MISC_FEATURE - wherein X is any amino acid
source                  1..7
                        mol_type = protein
                        organism = Homo sapiens
SEQUENCE: 235
VRGXYYY                                                            7
```

The invention claimed is:

1. A method of treating atopic dermatitis (AD) in a human subject comprising administering to the subject a therapeutically effective amount of an anti-OX40L antibody, or antigen-binding fragment thereof, wherein the antibody or antigen-binding fragment thereof comprises:

(a) the HCDR1 amino acid sequence of SEQ ID NO: 42;

(b) the HCDR2 amino acid sequence of SEQ ID NO: 44;

(c) the HCDR3 amino acid sequence of SEQ ID NO: 46;

(d) the LCDR1 amino acid sequence of SEQ ID NO: 56;

(e) the LCDR2 amino acid sequence of SEQ ID NO: 58; and (f) the LCDR3 amino acid sequence of SEQ ID NO: 60, wherein the antibody or antigen-binding fragment thereof is administered subcutaneously as a fixed dose during a maintenance phase at a frequency of every 12 weeks (Q12W).

2. The method according to claim 1, wherein the antibody or antigen-binding fragment thereof is a disease modifying drug optionally wherein after administering the disease modifying drug, the subject achieves an IGA-AD score of 0 or 1 for at least six months.

3. The method according to claim 1, wherein:

each dose of the antibody or antigen-binding fragment thereof is between about 20 mg and about 1000 mg; or each dose of the antibody or antigen-binding fragment thereof is about 62.5 mg, about 125 mg, about 150 mg, about 250 mg, or about 500 mg.

4. The method of claim 1, wherein:

(a) the minimum blood serum concentration reached by the antibody or fragment thereof between any two injections ($C_{min}$) is at least 2.5 μg/ml, 2.6 μg/ml, at least 2.7 μg/ml, at least 2.8 μg/ml, at least 2.9 μg/ml, at least 3 μg/ml, at least 3.1 μg/ml, at least 3.2 μg/ml, at least 3.3 μg/ml, at least 3.4 μg/ml, at least 3.5 μg/ml, at least 3.6 μg/ml, at least 3.7 μg/ml, at least 3.8 μg/ml, at least 3.9 μg/ml, at least 4 μg/ml, at least 4.1 μg/ml, at least 4.2 μg/ml, at least 4.3 μg/ml, at least 4.4 μg/ml, at least 4.5 μg/ml, at least 4.6 μg/ml, at least 4.7 μg/ml, at least 4.8 μg/ml, at least 4.9 μg/ml, at least 5 μg/ml, at least 5.1 μg/ml, at least 5.2 μg/ml, at least 5.3 μg/ml, at least 5.4 μg/ml, at least 5.5 μg/ml, at least 5.6 μg/ml, at least 5.7 μg/ml, at least 5.8 μg/ml, at least 5.9 μg/ml, at least 6 μg/ml, at least 6.5 μg/ml, at least 7 μg/ml, at least 7.5 μg/ml, at least 8 μg/ml, at least 8.5 μg/ml, at least 9 μg/ml, at least 9.5 μg/ml, at least 10 μg/ml, at least 11 μg/ml, at least 12 μg/ml, at least 13 μg/ml, at least 14 μg/ml, at least 15 μg/ml, at least 16 μg/ml, at least 17 μg/ml, at least 18 μg/ml, at least 19 μg/ml, at least 20 μg/ml, at least 25 μg/ml, at least 30 μg/ml, at least 35 μg/ml, at least 40 μg/ml, at least 50 μg/ml, at least 60

μg/ml, at least 70 μg/ml, at least 80 μg/ml, at least 90 μg/ml, or at least 100 μg/ml; or (b) the maximum blood serum concentration reached by antibody or fragment thereof after administration of an injection and prior to administration of a subsequent injection ($C_{max}$) is at least 1.5 μg/ml, at least 2 μg/ml, at least 5 μg/ml, at least 10 μg/ml, at least 20 μg/ml, at least 30 μg/ml, at least 40 μg/ml, at least 50 μg/ml, at least 60 μg/ml, at least 70 μg/ml, at least 80 μg/ml, at least 90 μg/ml, at least 100 μg/ml, at least 150 μg/ml, at least 200 μg/ml, at least 300 μg/ml or at least 550 μg/ml; or (c) blood serum concentrations of the antibody or fragment thereof during treatment range between about 4 g/mL and about 15 g/mL; or (d) blood serum concentrations of the antibody or fragment thereof during treatment range between about 20 g/mL and about 45 g/mL; or (e) blood serum concentrations of the antibody or fragment thereof during treatment range between about 5 g/mL and about 23 g/mL; or (f) blood serum concentrations of the-antibody or fragment thereof during treatment are about 10 g/mL or below 10 g/mL; or (g) the antibody or fragment thereof is administered via injection and the area under the serum concentration-time curve (AUC extrapolated to infinity [$AUC_{0-inf}$]) following a first injection is from around 100,000 ng/ml*day to around 4,500,000 ng/ml*day or around 1,000,000 ng/ml*day to around 3,800,000 ng/ml*day.

5. The method of claim 1, further comprising an induction phase.

6. The method of claim 5, wherein:

each dose of the antibody or fragment thereof administered during the induction phase is about 500 mg, about 250 mg, about 125 mg or about 62.5 mg, optionally wherein each dose administered during the induction phase is at a frequency of every 4 weeks (Q4W); or each dose of the antibody or fragment thereof administered during the maintenance phase is about 500 mg, about 250 mg, about 125 mg or about 62.5 mg.

7. The method of claim 5, wherein each dose of the antibody or fragment thereof administered during the induction phase is about 500 mg, and each dose of the antibody or antigen-binding fragment thereof administered during the maintenance phase is about 250 mg.

8. The method of claim 5, wherein each dose of the antibody or fragment thereof administered during the induction phase is about 250 mg, and each dose of the antibody or antigen-binding fragment thereof administered during the maintenance phase is about 250 mg.

9. The method of claim 5, wherein each dose administered during the induction phase is at a frequency of every 4 weeks (Q4W).

10. The method of claim 1, wherein:

(a) the antibody or fragment thereof exhibits one or more pharmacokinetic properties selected from the group consisting of:

(i) a rate of clearance (CL) of about 0.05 to about 0.18 L/day;

(ii) an absorption constant ($k_a$) of about 0.11 to about 0.33 L/day;

(iii) a volume of central compartment volume (Vc) of about 1.6 to about 5.0 L;

(iv) a second (peripheral compartment) volume (Vp1) of about 1.2 to about 3.6 L;

(v) a rate of clearance from the central compartment to the second compartment (Q) of about 0.31 to about 0.93 L/day; and (vi) a bioavailability (Fabs1) of about 0.6 to about 1.0; or (b) the subject is at least 18 years of age and/or less than 75 years of age; or (c) the atopic dermatitis is moderate-to-severe atopic dermatitis; or (d) the atopic dermatitis is moderate-to-severe atopic dermatitis and wherein the subject is a patient candidate for systemic therapy; or (e) the atopic dermatitis is moderate-to-severe atopic dermatitis and wherein the subject is a patient whose disease is not adequately controlled with topical prescription therapies or a patient for whom topical prescription therapies are not advisable; or (f) the atopic dermatitis is resistant, non-responsive, or inadequately responsive to treatment by either topical corticosteroids and/or systemic therapies; or (g) either topical corticosteroids and/or systemic therapies are not advisable for the subject; or (h) the subject has had an inadequate response to, was intolerant to, or is refractory to one or more topical corticosteroids.

11. The method of claim 10, wherein the atopic dermatitis is moderate-to-severe atopic dermatitis.

12. The method of claim 10, wherein the subject is a patient whose disease is not adequately controlled with topical prescription therapies or is a patient for whom topical prescription therapies are not advisable.

13. The method of claim 10, wherein the atopic dermatitis is not adequately controlled in a patient with systemic therapies or wherein systemic therapies are not advisable for a patient.

14. The method according to claim 1, further comprising administering a therapeutically effective amount of one or more topical corticosteroids.

15. The method of claim 14, wherein the topical corticosteroid is selected from the group consisting of betamethasone dipropionate, clobetasol propionate, dexamethasone, methylprednisolone, methylprednisolone aceponate, mometasone furoate, diflorasone diacetate, halobetasol propionate, amcinonide, augmented betamethasone dipropionate, fluocinonide, halcinonide, triamcinolone acetonide, betamethasone valerate, clocortolone pivalate, desoximetasone, fluocinolone acetonide, flurandrenolide, fluticasone propionate, hydrocortisone butyrate, hydrocortisone probutate, hydrocortisone valerate, prednicarbate, alclometasone dipropionate, desonide, hydrocortisone, and hydrocortisone acetate.

16. The method of claim 1, wherein the administration of the anti-OX40L antibody, or antigen-binding fragment thereof results in at least one improvement selected from the group consisting of:

a. a decrease from baseline in validated investigator global assessment atopic dermatitis (vIGA-AD) score of at least 2 points;

b. achieving clear or almost clear skin (vIGA-AD 0/1) from baseline;

c. a decrease from baseline in eczema area and severity index (EASI) score of at least 50%;

d. a decrease from baseline in EASI score of at least 75%;

e. achieving EASI-75;

f. achieving EASI-90;

g. achieving an improvement of at least 3 points in pruritus numerical rating scale, (NRS) score;

h. achieving an improvement of at least 4 points in pruritus NRS score, i. a decrease from baseline in SCORAD (SCORing Atopic Dermatitis) index score of at least 50%, j. a decrease from baseline in SCORAD index score of at least 55%;

k. a decrease from baseline in affected BSA (Body Surface Area) score of at least 60%; and l. a decrease from baseline in affected BSA score of at least 70%.

17. The method of claim 1, wherein:

(a) the atopic dermatitis has been assessed by determining a baseline EASI score; or (b) the atopic dermatitis has been assessed by determining a baseline EASI score and wherein the post-administration EASI score is maintained, without additional administration of the anti-OX40L antibody, or antigen-binding fragment thereof, for:

(i) at least 2 months, at least 3 months, at least 4 months, at least 5 months, or at least 6 months after administration of the last injection; or (ii) at least about 4, 8, 15, 22, 25, 29, 36, 43, 50, 57, 64, 71, 85, 113, 169, or 253 days; or (c) the atopic dermatitis has been assessed by determining a baseline EASI score and wherein the post-administration EASI is determined at least around 113 days after administering a first injection of the antibody or fragment thereof and wherein the post-administration EASI is EASI50, EASI75, EASI90 or EASI100; or (d) the atopic dermatitis has been assessed by determining a baseline EASI score and wherein the post-administration EASI is determined at least around 169 days after administering a first injection of the antibody or fragment thereof and wherein the post-administration EASI is EASI50, EASI75, EASI90 or EASI100; or (e) the atopic dermatitis has been assessed by determining a baseline EASI score and wherein the post-administration EASI is determined at least around 253 days after administering a first injection of the antibody or fragment thereof and wherein the post-administration EASI a is EASI50, EASI75, EASI90 or EASI100; or (f) the atopic dermatitis has been assessed by determining a baseline EASI score and wherein the atopic dermatitis is treated as evidenced by a reduction in the EASI score by at least 40% after the third injection as a treatment dose and wherein the reduction in EASI score is persistent for at least 2 months, at least 3 months, at least 4 months, at least 5 months, or at least 6 months after administration of the last injection as a treatment dose.

18. The method of claim 1, wherein the atopic dermatitis has been assessed by determining a baseline vIGA-AD score, and wherein:

(a) the post-administration vIGA-AD score is 0 or 1; or (b) the post-administration vIGA-AD score is maintained, without additional administration of the anti-OX40L antibody, or antigen-binding fragment thereof, for:

(i) at least 2 months, at least 3 months, at least 4 months, at least 5 months, or at least 6 months after administration of the last injection; or (ii) at least about 4, 8, 15, 22, 25, 29, 36, 43, 50, 57, 64, 71, 85, 113, 169 or 253 days; or (c) the post-administration vIGA-AD is determined at least around 113 days after administering a first injection of the antibody or fragment thereof and wherein the post-administration vIGA-AD AD is:

(i) a vIGA-AD score of 0 or 1, and/or (ii) reduced at least 2 points relative to the baseline vIGA-AD score; or (d) the post-administration vIGA-AD is determined at least around 169 days after administering a first injection of the antibody or fragment thereof and wherein the post-administration vIGA-AD is:

(i) a vIGA-AD score of 0 or 1, and/or (ii) reduced at least 2 points relative to the baseline vIGA-AD score; or (e) the post-administration vIGA-AD is determined at least around 253 days after administering a first injection of the antibody or fragment thereof and wherein the post-administration vIGA-AD is:

(i) A vIGA-AD score of 0 or 1, and/or (ii) reduced at least 2 points relative to the baseline vIGA-AD score; or (f) the atopic dermatitis is treated as evidenced by a reduction in the vIGA-AD score by at least 2 points after the third injection as a treatment dose and wherein the reduction in vIGA-AD score is persistent for at least 2 months, at least 3 months, at least 4 months, at least 5 months, or at least 6 months after administration of the last injection as a treatment dose.

19. The method of claim 1, wherein the anti-OX40L antibody or antigen-binding fragment thereof comprises the heavy chain variable (VH) domain of SEQ ID NO: 34; or the anti-OX40L antibody or antigen-binding fragment thereof comprises the light chain variable (VL) domain of SEQ ID NO: 48; or the anti-OX40L antibody or antigen-binding fragment thereof comprises the VH domain of SEQ ID NO: 34 and the VL domain of SEQ ID NO: 48.

20. The method of claim 1, wherein the subject is classified as a Th2 AD patient and/or a non-Th2 AD patient; or comprising selecting a subject having atopic dermatitis.

21. The method of claim 1, further comprising administering an initial dose of about 500 mg and one or more secondary doses of about 250 mg each, wherein each of the initial dose and the one or more secondary doses are administered prior to the maintenance phase.

22. The method of claim 21, wherein each dose of the antibody or antigen-binding fragment thereof administered during the maintenance phase is about 250 mg.

23. The method of claim 1, wherein a decrease of serum levels of one or more of IL-13, IL-22, IL-17A, IL-31 and IgE are achieved.

24. The method of claim 1, wherein the anti-OX40L antibody or antigen-binding fragment thereof comprises the heavy chain of SEQ ID NO: 62 and the light chain of SEQ ID NO: 64.

25. The method of claim 1, wherein the anti-OX40L antibody is amlitelimab.

26. The method of claim 1, wherein the anti-OX40L antibody or antigen-binding fragment thereof is administered using a prefilled syringe, a pen delivery device or an autoinjector delivery device.

27. The method of claim 1, wherein each dose of the antibody or antigen-binding fragment thereof administered during the maintenance phase is about 250 mg.

28. The method of claim 1, wherein each dose of the antibody or antigen-binding fragment thereof administered during the maintenance phase is about 150 mg.

29. The method of claim 1, wherein each dose of the antibody or antigen-binding fragment thereof administered during the maintenance phase is about 125 mg.

30. The method of claim 1, wherein each dose of the antibody or antigen-binding fragment thereof administered during the maintenance phase is about 62.5 mg.

31. The method of claim 1, wherein the anti-OX40L antibody or antigen-binding fragment thereof comprises the heavy chain variable (VH) domain of SEQ ID NO: 34 and the light chain variable (VL) domain of SEQ ID NO: 48.

32. The method of claim 1, wherein the subject is 12 years of age to 18 years of age.

33. The method of claim 1, wherein the subject is at least 18 years of age.

34. The method of claim 1, wherein the subject has previously received a systemic therapy.

35. The method of claim 1, wherein the subject has not previously received a systemic therapy.

36. A method of treating moderate-to-severe atopic dermatitis (AD) in a subject in need thereof, comprising administering to the subject a therapeutically effective amount of an anti-OX40L antibody or antigen-binding fragment thereof, wherein the anti-OX40L antibody or antigen-binding fragment thereof comprises three heavy chain complementary determining region (CDR) sequences comprising SEQ ID NOs: 42, 44, and 46, respectively, and three light chain CDR sequences comprising SEQ ID NOs: 56, 58, and 60, respectively, wherein the antibody or antigen-binding fragment thereof is administered subcutaneously as a fixed dose during a maintenance phase at a frequency of every 12 weeks (Q12W).

37. The method of claim 36, wherein the subject achieves a decrease from baseline in eczema area and severity index (EASI) score of at least a 75% reduction (EASI-75), or a decrease from baseline in EASI score of at least a 90% reduction (EASI-90).

38. The method of claim 36, wherein the subject achieves a decrease from baseline in SCORing Atopic Dermatitis (SCORAD) index score of at least 50%, or wherein the subject achieves a decrease from baseline in SCORAD index score of at least 55%.

39. The method of claim 36, wherein the anti-OX40L antibody or antigen-binding fragment thereof comprises a heavy chain variable region (HCVR) comprising the amino acid sequence of SEQ ID NO: 34, and a light chain variable region (LCVR) comprising the amino acid sequence of SEQ ID NO: 48.

40. The method of claim 39, wherein the antibody is amlitelimab.

41. The method of claim 36, further comprising one or more induction doses.

42. The method of claim 36, wherein a decrease of serum levels of one or more of IL-13, IL-22, IL-17A, IL-31 and IgE are achieved.

43. The method of claim 36, wherein the anti OX40L antibody or antigen-binding fragment thereof comprises the heavy chain of SEQ ID NO: 62 and the light chain of SEQ ID NO: 64.

44. The method of claim 36, further comprising administering an initial dose of about 500 mg and one or more secondary doses of about 250 mg each, wherein each of the initial dose and the one or more secondary doses are administered prior to the maintenance phase.

45. The method of claim 36, further comprising administering to the subject one or more topical corticosteroids.

46. The method of claim 36, wherein the subject is 12 years of age to 18 years of age.

47. The method of claim 36, wherein the subject is at least 18 years of age.

48. The method of claim 36, wherein the subject is a patient whose disease is not adequately controlled with topical prescription therapies or is a patient for whom topical prescription therapies are not advisable.

49. The method of claim 36, wherein the atopic dermatitis is not adequately controlled in a patient with systemic therapies or wherein systemic therapies are not advisable for a patient.

50. The method of claim 36, wherein the subject has previously received a systemic therapy.

51. The method of claim 36, wherein the subject has not previously received a systemic therapy.

52. A method of treating atopic dermatitis (AD) in a human subject comprising administering to the subject an anti-OX40L antibody or antigen-binding fragment thereof, wherein the antibody or antigen-binding fragment thereof comprises:

(a) the HCDR1 amino acid sequence of SEQ ID NO: 42;

(b) the HCDR2 amino acid sequence of SEQ ID NO: 44;

(c) the HCDR3 amino acid sequence of SEQ ID NO: 46;

(d) the LCDR1 amino acid sequence of SEQ ID NO: 56;

(e) the LCDR2 amino acid sequence of SEQ ID NO: 58; and (f) the LCDR3 amino acid sequence of SEQ ID NO: 60;

wherein the antibody or antigen-binding fragment thereof is administered subcutaneously as a fixed dose of 250 mg; 150 mg; 125 mg; or 62.5 mg during a maintenance phase at a frequency of every 12 weeks (Q12W).

* * * * *